(12) United States Patent
Drummond et al.

(10) Patent No.: US 12,064,479 B2
(45) Date of Patent: Aug. 20, 2024

(54) LIPID NANOPARTICLES FOR DELIVERY OF NUCLEIC ACIDS AND METHODS OF USE THEREOF

(71) Applicant: Akagera Medicines, Inc., Boxford, MA (US)

(72) Inventors: Daryl C. Drummond, Lincoln, MA (US); Dmitri B. Kirpotin, San Francisco, CA (US); Mark E. Hayes, Mill Valley, CA (US); Alexander Koshkaryev, Norwood, MA (US); Ross B. Fulton, Southborough, MA (US)

(73) Assignee: Akagera Medicines, Inc., Boxford, MA (US)

( * ) Notice: Subject to any disclaimer, the term of this patent is extended or adjusted under 35 U.S.C. 154(b) by 0 days.

(21) Appl. No.: 18/324,097

(22) Filed: May 25, 2023

(65) Prior Publication Data
US 2023/0381303 A1    Nov. 30, 2023

Related U.S. Application Data

(60) Provisional application No. 63/346,197, filed on May 26, 2022, provisional application No. 63/345,823, filed on May 25, 2022.

(51) Int. Cl.
| | | |
|---|---|---|
| A61K 39/395 | (2006.01) | |
| A61K 39/215 | (2006.01) | |
| A61K 39/385 | (2006.01) | |
| A61K 47/24 | (2006.01) | |
| A61K 47/28 | (2006.01) | |
| A61K 47/69 | (2017.01) | |

(52) U.S. Cl.
CPC .......... *A61K 39/385* (2013.01); *A61K 39/215* (2013.01); *A61K 47/24* (2013.01); *A61K 47/28* (2013.01); *A61K 47/6929* (2017.08); *A61K 47/6935* (2017.08)

(58) Field of Classification Search
None
See application file for complete search history.

(56) References Cited

U.S. PATENT DOCUMENTS

| | | |
|---|---|---|
| 4,394,448 A | 7/1983 | Szoka, Jr. et al. |
| 4,438,052 A | 3/1984 | Weder et al. |
| 4,515,736 A | 5/1985 | Deamer |
| 4,598,051 A | 7/1986 | Papahadjopoulos et al. |
| 4,897,355 A | 1/1990 | Eppstein et al. |
| 5,013,556 A | 5/1991 | Woodle et al. |
| 5,171,678 A | 12/1992 | Behr et al. |
| 5,208,036 A | 5/1993 | Eppstein et al. |
| 5,225,212 A | 7/1993 | Martin et al. |
| 5,264,618 A | 11/1993 | Feigner et al. |
| 5,279,833 A | 1/1994 | Rose |
| 5,283,185 A | 2/1994 | Epand et al. |
| 5,316,771 A | 5/1994 | Barenholz et al. |
| 5,320,906 A | 6/1994 | Eley et al. |
| 5,334,761 A | 8/1994 | Gebeyehu et al. |
| 5,545,412 A | 8/1996 | Eppstein et al. |
| 5,578,475 A | 11/1996 | Jessee |
| 5,627,159 A | 5/1997 | Shih et al. |
| 5,641,662 A | 6/1997 | Debs et al. |
| 5,656,743 A | 8/1997 | Busch et al. |
| 5,674,908 A | 10/1997 | Haces et al. |
| 5,703,055 A | 12/1997 | Feigner et al. |
| 5,705,385 A | 1/1998 | Bally et al. |
| 5,736,392 A | 4/1998 | Hawley-Nelson et al. |
| 5,800,833 A | 9/1998 | Hope et al. |
| 5,820,873 A | 10/1998 | Choi et al. |
| 5,877,220 A | 3/1999 | Schwartz et al. |
| 5,885,613 A | 3/1999 | Holland et al. |
| 5,958,901 A | 9/1999 | Dwyer et al. |
| 5,976,567 A | 11/1999 | Wheeler et al. |
| 5,981,501 A | 11/1999 | Wheeler et al. |
| 6,020,202 A | 2/2000 | Jessee |
| 6,020,526 A | 2/2000 | Schwartz et al. |
| 6,034,135 A | 3/2000 | Schwartz et al. |
| 6,051,429 A | 4/2000 | Hawley-Nelson et al. |
| 6,075,012 A | 6/2000 | Gebeyehu et al. |
| 6,110,491 A | 8/2000 | Kirpotin |
| 6,165,501 A | 12/2000 | Tirosh et al. |
| 6,172,049 B1 | 1/2001 | Dwyer et al. |
| 6,251,939 B1 | 6/2001 | Schwartz et al. |
| 6,284,267 B1 | 9/2001 | Aneja |
| 6,287,591 B1 | 9/2001 | Semple et al. |
| 6,339,173 B1 | 1/2002 | Schwartz et al. |
| 6,376,248 B1 | 4/2002 | Hawley-Nelson et al. |

(Continued)

FOREIGN PATENT DOCUMENTS

| | | |
|---|---|---|
| CA | 2 271 582 | 11/1989 |
| CA | 2 309 727 | 4/1999 |

(Continued)

OTHER PUBLICATIONS

Akinc et al., "Development of Lipidoid—siRNA Formulations for Systemic Delivery to the Liver" Molecular Therapy, vol. 17, No. 5, pp. 872-879, May 2009.

(Continued)

*Primary Examiner* — Yunsoo Kim
(74) *Attorney, Agent, or Firm* — Greenberg Traurig, LLP; David J. Dykeman; Natalie Salem

(57) ABSTRACT

The present disclosure provides for improved compositions of ionizable lipid nanoparticles for the delivery of therapeutic nucleic acids to cells. Anionic phospholipids, including phosphatidylserine and phosphatidylglycerol are included in the lipid nanoparticles to increase the transfection efficiency in human dendritic cells. The further incorporation of mono-unsaturated alkyl chain analogs in dimethylaminopropyl-dioxolane or heterocyclic ketal ionizable lipids in the formulation demonstrated high levels of transfection in human dendritic cells, compared to other ionizable lipids in the same family, and demonstrated good stability to oxidative damage. Finally, the use of an ammonium salt of phosphatidylserine allows for the efficient production of PS-targeted LNPs.

28 Claims, 58 Drawing Sheets

Specification includes a Sequence Listing.

(56) References Cited

U.S. PATENT DOCUMENTS

| | | |
|---|---|---|
| 6,534,484 B1 | 3/2003 | Wheeler et al. |
| 6,586,410 B1 | 7/2003 | Wheeler et al. |
| 6,638,529 B2 | 10/2003 | Schwartz et al. |
| 6,649,780 B1 | 11/2003 | Eibl et al. |
| 6,671,393 B2 | 12/2003 | Hays et al. |
| 6,689,779 B2 | 2/2004 | Lee et al. |
| 6,696,424 B1 | 2/2004 | Wheeler |
| 6,815,432 B2 | 11/2004 | Wheeler et al. |
| 6,858,224 B2 | 2/2005 | Wheeler et al. |
| 7,074,596 B2 | 7/2006 | Darzynkiewicz |
| 7,166,745 B1 | 1/2007 | Chu et al. |
| 7,422,902 B1 | 9/2008 | Wheeler et al. |
| 7,462,615 B2 | 12/2008 | Guedat et al. |
| 7,479,573 B2 | 1/2009 | Chu et al. |
| 7,601,872 B2 | 10/2009 | Chu et al. |
| 7,687,070 B2 | 3/2010 | Gebeyehu et al. |
| 7,744,921 B2 | 6/2010 | Tardi et al. |
| 7,745,651 B2 | 6/2010 | Heyes et al. |
| 7,799,565 B2 | 9/2010 | Maclachlan et al. |
| 7,803,397 B2 | 9/2010 | Heyes et al. |
| 7,807,815 B2 | 10/2010 | Maclachlan et al. |
| 7,816,379 B2 | 10/2010 | Rhee et al. |
| 7,838,658 B2 | 11/2010 | Maclachlan et al. |
| 7,901,708 B2 | 3/2011 | Maclachlan et al. |
| 7,915,450 B2 | 3/2011 | Chu et al. |
| 7,982,027 B2 | 7/2011 | MacLachlan et al. |
| 8,021,686 B2 | 9/2011 | Semple et al. |
| 8,058,068 B2 | 11/2011 | Hawley-Nelson et al. |
| 8,058,069 B2 | 11/2011 | Yaworski et al. |
| 8,101,741 B2 | 1/2012 | Maclachlan et al. |
| 8,147,867 B2 | 4/2012 | Hong et al. |
| 8,158,827 B2 | 4/2012 | Chu et al. |
| 8,188,263 B2 | 5/2012 | Maclachlan et al. |
| 8,227,443 B2 | 7/2012 | Maclachlan et al. |
| 8,278,036 B2 | 10/2012 | Kariko et al. |
| 8,283,333 B2 | 10/2012 | Yaworski et al. |
| 8,349,360 B2 | 1/2013 | Bally et al. |
| 8,455,455 B1 | 6/2013 | Robbins et al. |
| 8,492,359 B2 | 7/2013 | Yaworski et al. |
| 8,513,403 B2 | 8/2013 | Maclachlan et al. |
| 8,569,256 B2 | 10/2013 | Heyes et al. |
| 8,598,333 B2 | 12/2013 | Maclachlan et al. |
| 8,822,668 B2 | 9/2014 | Yaworski et al. |
| 9,061,063 B2 | 6/2015 | Maier et al. |
| 9,139,554 B2 | 9/2015 | Hope et al. |
| 9,220,683 B2 | 12/2015 | Manoharan et al. |
| 9,364,435 B2 | 6/2016 | Yaworski et al. |
| 9,404,127 B2 | 8/2016 | Yaworski et al. |
| 9,504,651 B2 | 11/2016 | MacLachlan et al. |
| 9,549,939 B2 | 1/2017 | Weers |
| 9,657,295 B2 | 5/2017 | Schrum et al. |
| 9,764,036 B2 | 9/2017 | Manoharan et al. |
| 10,072,057 B2 | 9/2018 | Hoge et al. |
| 10,221,127 B2 | 3/2019 | Du et al. |
| 10,369,226 B2 | 8/2019 | Maier et al. |
| 10,632,191 B2 | 4/2020 | Reed et al. |
| 10,653,780 B2 | 5/2020 | Hope et al. |
| 11,071,784 B2 | 7/2021 | Maier et al. |
| 11,141,378 B2 | 10/2021 | Yaworski et al. |
| 11,246,933 B1 | 2/2022 | Maier et al. |
| 11,591,544 B2 | 2/2023 | Drummond et al. |
| 2001/0048940 A1 | 12/2001 | Tousignant et al. |
| 2003/0069173 A1 | 4/2003 | Hawley-Nelson et al. |
| 2003/0072794 A1 | 4/2003 | Boulikas |
| 2003/0077829 A1 | 4/2003 | Maclachlan |
| 2003/0143732 A1 | 7/2003 | Fosnaugh et al. |
| 2004/0009126 A1 | 1/2004 | Pilkiewicz et al. |
| 2004/0063654 A1 | 4/2004 | Davis et al. |
| 2004/0142892 A1 | 7/2004 | Finn et al. |
| 2004/0253723 A1 | 12/2004 | Tachas et al. |
| 2004/0258651 A1 | 12/2004 | Pascaly et al. |
| 2004/0258652 A1 | 12/2004 | Pascaly et al. |
| 2004/0259247 A1 | 12/2004 | Tuschl et al. |
| 2005/0000030 A1 | 1/2005 | Dupont et al. |
| 2005/0064595 A1 | 3/2005 | Maclachlan et al. |
| 2005/0118253 A1 | 6/2005 | Maclachlan et al. |
| 2005/0187218 A1 | 8/2005 | Marinier et al. |
| 2005/0260757 A1 | 11/2005 | Gebeyehu et al. |
| 2006/0008519 A1 | 1/2006 | Davidsen et al. |
| 2006/0008910 A1 | 1/2006 | Maclachlan et al. |
| 2006/0083780 A1* | 4/2006 | Heyes .................. A61P 31/00 |
| | | 435/458 |
| 2006/0147514 A1 | 7/2006 | Gebeyehu et al. |
| 2006/0228406 A1 | 10/2006 | Chiou et al. |
| 2006/0240093 A1 | 10/2006 | Maclachlan et al. |
| 2007/0042031 A1 | 2/2007 | Maclachlan et al. |
| 2007/0148220 A1 | 6/2007 | Muller et al. |
| 2007/0202598 A1 | 8/2007 | Chu et al. |
| 2007/0202600 A1 | 8/2007 | Chu et al. |
| 2008/0021071 A1 | 1/2008 | Gravestock et al. |
| 2009/0023729 A1 | 1/2009 | Nakamura et al. |
| 2009/0143583 A1 | 6/2009 | Chu et al. |
| 2009/0291131 A1 | 11/2009 | Maclachlan et al. |
| 2010/0130588 A1 | 5/2010 | Yaworski et al. |
| 2010/0159593 A1 | 6/2010 | Chu et al. |
| 2010/0192814 A1 | 8/2010 | Herzog et al. |
| 2011/0060032 A1 | 3/2011 | MacLachlan et al. |
| 2011/0262527 A1 | 10/2011 | Heyes et al. |
| 2012/0058188 A1 | 3/2012 | Maclachlan et al. |
| 2012/0095075 A1 | 4/2012 | Manoharan et al. |
| 2012/0136073 A1 | 5/2012 | Zhiwei et al. |
| 2012/0183581 A1 | 7/2012 | Yaworski et al. |
| 2012/0238747 A1 | 9/2012 | Chu et al. |
| 2012/0276209 A1 | 11/2012 | Cullis et al. |
| 2014/0065228 A1 | 3/2014 | Yaworski et al. |
| 2016/0317676 A1 | 11/2016 | Hope et al. |
| 2018/0064807 A1 | 3/2018 | Manoharan et al. |
| 2018/0125985 A1 | 5/2018 | Manoharan |
| 2018/0170866 A1 | 6/2018 | Payne et al. |
| 2018/0369143 A1 | 12/2018 | Bally et al. |
| 2019/0083593 A1 | 3/2019 | Sahin et al. |
| 2019/0262448 A1 | 8/2019 | Brito et al. |
| 2020/0078345 A1 | 3/2020 | Rhee et al. |
| 2020/0206362 A1 | 7/2020 | Besin et al. |
| 2020/0254086 A1 | 8/2020 | Hoge et al. |
| 2020/0282060 A1 | 9/2020 | Heyes et al. |
| 2020/0289638 A1 | 9/2020 | Ciaramella et al. |
| 2021/0290756 A1 | 9/2021 | Sullivan et al. |
| 2021/0323914 A1 | 10/2021 | Payne et al. |
| 2022/0105187 A1 | 4/2022 | Maier et al. |
| 2022/0111053 A1 | 4/2022 | Maier et al. |
| 2022/0162521 A1 | 5/2022 | Drummond et al. |
| 2022/0175928 A1 | 6/2022 | Maier et al. |
| 2022/0175929 A1 | 6/2022 | Maier et al. |
| 2022/0175930 A1 | 6/2022 | Maier et al. |
| 2022/0411394 A1 | 12/2022 | Drummond et al. |
| 2023/0126953 A1 | 4/2023 | Drummond et al. |

FOREIGN PATENT DOCUMENTS

| | | |
|---|---|---|
| CA | 2 330 741 | 11/1999 |
| CA | 2 397 016 | 7/2001 |
| EP | 2 350 043 | 3/2014 |
| JP | 03-126211 | 5/1991 |
| JP | 2002525063 | 8/2002 |
| JP | 2003524349 | 2/2003 |
| JP | 2005-202085 | 7/2005 |
| JP | 2006-080560 | 3/2006 |
| JP | 2009-051827 | 3/2009 |
| JP | 2009-051828 | 3/2009 |
| WO | WO1990001405 | 2/1990 |
| WO | WO1991016024 | 10/1991 |
| WO | WO1993005162 | 3/1993 |
| WO | WO1993012240 | 6/1993 |
| WO | WO1993012756 | 7/1993 |
| WO | WO1993024640 | 12/1993 |
| WO | WO1993025673 | 12/1993 |
| WO | WO1995002698 | 1/1995 |
| WO | WO1995018863 | 7/1995 |
| WO | WO1995035301 | 12/1995 |
| WO | WO1996002655 | 2/1996 |
| WO | WO1996010390 | 4/1996 |
| WO | WO1996040964 | 12/1996 |
| WO | WO1996041873 | 12/1996 |

(56) References Cited

FOREIGN PATENT DOCUMENTS

| | | |
|---|---|---|
| WO | WO1998051285 | 11/1998 |
| WO | WO2000003683 | 1/2000 |
| WO | WO2000015820 | 3/2000 |
| WO | WO2000062813 | 10/2000 |
| WO | WO2001005374 | 1/2001 |
| WO | WO2001005873 | 1/2001 |
| WO | WO2001075164 | 10/2001 |
| WO | WO2001093836 | 12/2001 |
| WO | WO2002020492 | 3/2002 |
| WO | WO2002034236 | 5/2002 |
| WO | WO2002040614 | 5/2002 |
| WO | WO2002087541 | 11/2002 |
| WO | WO2003097805 | 11/2003 |
| WO | WO2004039409 | 5/2004 |
| WO | WO2004041752 | 5/2004 |
| WO | WO2004065546 | 8/2004 |
| WO | WO2004072069 | 8/2004 |
| WO | WO2004087117 | 10/2004 |
| WO | WO2004110499 | 12/2004 |
| WO | WO2005007196 | 1/2005 |
| WO | WO2005026372 | 3/2005 |
| WO | WO2005035764 | 4/2005 |
| WO | WO2005115992 | 12/2005 |
| WO | WO2005120152 | 12/2005 |
| WO | WO2006002538 | 1/2006 |
| WO | WO2006053430 | 5/2006 |
| WO | WO2006124687 | 11/2006 |
| WO | WO2007015877 | 2/2007 |
| WO | WO2007036366 | 4/2007 |
| WO | WO2007048046 | 4/2007 |
| WO | WO2007056861 | 5/2007 |
| WO | WO2007066200 | 6/2007 |
| WO | WO2007088999 | 8/2007 |
| WO | WO2007116922 | 10/2007 |
| WO | WO2008038136 | 4/2008 |
| WO | WO2008127714 | 4/2008 |
| WO | WO2088037635 | 4/2008 |
| WO | WO2008064317 | 5/2008 |
| WO | WO2008064318 | 5/2008 |
| WO | WO2008091681 | 7/2008 |
| WO | WO2008101029 | 8/2008 |
| WO | WO2008101905 | 8/2008 |
| WO | WO2009024221 | 2/2009 |
| WO | WO2009025983 | 2/2009 |
| WO | WO2009086558 | 7/2009 |
| WO | WO2009103064 | 8/2009 |
| WO | WO2009105782 | 8/2009 |
| WO | WO2009111658 | 9/2009 |
| WO | WO2009114763 | 9/2009 |
| WO | WO2009132131 | 10/2009 |
| WO | WO2009156535 | 12/2009 |
| WO | WO2010006432 | 1/2010 |
| WO | WO2010042877 | 4/2010 |
| WO | WO2010048228 | 4/2010 |
| WO | WO2010048536 | 4/2010 |
| WO | WO2010054406 | 5/2010 |
| WO | WO2010074327 | 7/2010 |
| WO | WO2010088537 | 8/2010 |
| WO | WO2010105209 | 9/2010 |
| WO | WO2010129709 | 11/2010 |
| WO | WO2010138652 | 12/2010 |
| WO | WO2010138659 | 12/2010 |
| WO | WO2010138685 | 12/2010 |
| WO | WO2010138695 | 12/2010 |
| WO | WO2010138706 | 12/2010 |
| WO | WO2010138758 | 12/2010 |
| WO | WO2010148422 | 12/2010 |
| WO | WO2011000106 | 1/2011 |
| WO | WO2011000107 | 1/2011 |
| WO | WO2011000108 | 1/2011 |
| WO | WO2011011447 | 1/2011 |
| WO | WO2011017548 | 1/2011 |
| WO | WO2011021218 | 2/2011 |
| WO | WO2011045415 | 4/2011 |
| WO | WO2011066651 | 6/2011 |
| WO | WO2011079315 | 6/2011 |
| WO | WO2011103189 | 8/2011 |
| WO | WO2011140627 | 11/2011 |
| WO | WO2021123332 | 6/2012 |
| WO | 2013149140 A1 | 10/2013 |
| WO | WO2014089239 | 6/2014 |
| WO | WO2015130584 | 9/2015 |
| WO | WO2016176330 | 3/2016 |
| WO | WO2016118697 | 7/2016 |
| WO | WO2017066964 | 4/2017 |
| WO | WO2017112865 | 6/2017 |
| WO | WO2017173054 | 10/2017 |
| WO | 2017201346 A1 | 11/2017 |
| WO | WO2017218704 | 12/2017 |
| WO | WO2018064755 | 4/2018 |
| WO | WO2018075592 | 4/2018 |
| WO | WO2018078053 | 5/2018 |
| WO | WO2018081480 | 5/2018 |
| WO | WO2018081638 | 5/2018 |
| WO | WO2018089540 | 5/2018 |
| WO | WO2018119514 | 7/2018 |
| WO | WO2018126084 | 7/2018 |
| WO | WO2018170306 | 9/2018 |
| WO | WO2018170336 | 9/2018 |
| WO | WO2018200613 | 11/2018 |
| WO | WO2018208856 | 11/2018 |
| WO | WO2018213789 | 11/2018 |
| WO | WO2018232120 | 12/2018 |
| WO | WO2018232357 | 12/2018 |
| WO | WO2019046809 | 3/2019 |
| WO | WO2019051289 | 3/2019 |
| WO | WO2019067992 | 4/2019 |
| WO | WO2019089828 | 5/2019 |
| WO | WO2019126593 | 6/2019 |
| WO | WO2019141814 | 7/2019 |
| WO | WO2019147749 | 8/2019 |
| WO | WO2019200171 | 10/2019 |
| WO | WO2019202035 | 10/2019 |
| WO | WO2019210394 | 11/2019 |
| WO | WO2020028133 | 2/2020 |
| WO | WO2020056304 | 3/2020 |
| WO | WO2020061332 | 3/2020 |
| WO | WO2020061367 | 3/2020 |
| WO | WO2020061457 | 3/2020 |
| WO | WO2020069169 | 4/2020 |
| WO | WO2020069718 | 4/2020 |
| WO | WO2020070040 | 4/2020 |
| WO | WO2020077007 | 4/2020 |
| WO | WO2020123300 | 6/2020 |
| WO | WO2020160397 | 8/2020 |
| WO | WO2020191103 | 9/2020 |
| WO | WO2020198697 | 10/2020 |
| WO | WO2020198706 | 10/2020 |
| WO | WO2020201383 | 10/2020 |
| WO | WO2020205644 | 10/2020 |
| WO | WO2020210901 | 10/2020 |
| WO | WO2020219941 | 10/2020 |
| WO | WO2020227510 | 11/2020 |
| WO | WO2020252589 | 12/2020 |
| WO | WO2020263985 | 12/2020 |
| WO | WO2021000041 | 1/2021 |
| WO | WO2021016430 | 1/2021 |
| WO | WO2021022173 | 2/2021 |
| WO | WO2021026358 | 2/2021 |
| WO | WO2021030701 | 2/2021 |
| WO | WO2021046265 | 3/2021 |
| WO | WO2021050986 | 3/2021 |
| WO | WO2021055833 | 3/2021 |
| WO | WO2021055835 | 3/2021 |
| WO | WO2021055849 | 3/2021 |
| WO | WO2021076805 | 4/2021 |
| WO | WO2021077066 | 4/2021 |
| WO | WO2021077067 | 4/2021 |
| WO | WO2021102411 | 5/2021 |
| WO | WO2021142336 | 7/2021 |
| WO | WO2021148511 | 7/2021 |
| WO | WO2021155274 | 8/2021 |
| WO | WO2021156267 | 8/2021 |
| WO | WO2021159130 | 8/2021 |

(56) References Cited

FOREIGN PATENT DOCUMENTS

| WO | WO2021178510 | 9/2021 |
|---|---|---|
| WO | WO2021178725 | 9/2021 |
| WO | WO2021183563 | 9/2021 |
| WO | WO2021191265 | 9/2021 |
| WO | WO2021195529 | 9/2021 |
| WO | WO2021198157 | 10/2021 |
| WO | WO2021207020 | 10/2021 |
| WO | WO2021207710 | 10/2021 |
| WO | WO2021207712 | 10/2021 |
| WO | WO2021214204 | 10/2021 |
| WO | WO2021222287 | 11/2021 |
| WO | WO2021222801 | 11/2021 |
| WO | WO2021231901 | 11/2021 |
| WO | WO2022115645 | 6/2022 |
| WO | 20232305878 A2 | 11/2023 |

OTHER PUBLICATIONS

Allen et al., "Pharmacokinetics and Anti-Tumor Activity of Vincristine Encapsulated in Sterically Stabilized Liposomes", Int. J. Cancer, vol. 62, No. 2, pp. 199-204, Jul. 17, 1995.

Anderluzzi et al., "Investigating the Impact of Delivery System Design on the Efficacy of Self-Amplifying RNA Vaccines," Vaccines, vol. 8, No. 2, pp. 212-233, May 8, 2020.

Anderson et al., "Safety and Immunogenicity of SARS-CoV-2 mRNA-1273 Vaccine in Older Adults," New England Journal of Medicine, vol. 383, No. 25, pp. 2427-2438, Sep. 29, 2020.

Arpicco et al., "Preparation and Characterization of Novel Cationic Lipids Developed for Gene Transfection," Proceed. Int'l Symp. Control. Rel. Bioact. Mater. (Controlled Release Society, Inc.), 1999, vol. 26, pp. 759-760.

Arpicco et al., "Synthesis, characterization and transfection activity of new saturated and unsaturated cationic lipids," IL Farmaco, vol. 59, No. 11, pp. 869-878, Nov. 2004.

Ballas et al., "Liposomes bearing a quaternary ammonium detergent as an efficient vehicle for functional transfer of TMV-RNA into plant protoplasts," Biochimica et Biophysica Acta, vol. 939, No. 1, pp. 8-18, Mar. 22, 1988.

Barinaga, M., "Step Taken Toward Improved Vectors for Gene Transfer," Science, vol. 266, Issue 5189, pp. 1326-1327, Nov. 25, 1994.

Bass, "The Short Answer," Nature, vol. 411, No. 6836, pp. 428-429, May 24, 2001.

Beale et al., "Gene Silencing Nucleic Acids Designed by Scanning Arrays: Anti-EGFR Activity of siRNA, Ribozyme and DNA Enzymes Targeting a Single Hybridization-accessible Region using the Same Delivery System," Journal of Drug Targeting, vol. 11, No. 7, pp. 449-456, Aug. 1, 2003.

Behr, J.-P., "Synthetic Gene-Transfer Vectors," Acc. Chem. Res., vol. 26, No. 5, pp. 274-278, May 1, 1993.

Birkkholz et al., "Targeting of DEC-205 on Human Dendritic Cells Results in Efficient MHC Class II-Restricted Antigen Presentation," Blood, vol. 116, No. 13, pp. 2277-2286, Sep. 2010.

Bloom et al., "Self-Amplifying RNA Vaccines for Infectious Diseases," Gene Therapy, vol. 28, pp. 117-129, Oct. 22, 2020.

Bonifaz et al., "In Vivo Targeting of Antigens to Maturing Dendritic Cells via the DEC-205 Receptor Improves T Cell Vaccination," J. Exp. Med., vol. 199, No. 6, pp. 815-824, Mar. 15, 2004.

Brigham et al., "Rapid Communication: In vivo Transfection of Murine Lungs with a Functioning Prokaryotic Gene Using a Liposome Vehicle," The American Journal of the Medical Sciences, vol. 298, No. 4, pp. 278-281, Oct. 1, 1989.

Brummelkamp et al., "A System for Stable Expression of Short Interfering RNAs in Mammalian Cells," Science, vol. 296, No. 5567, pp. 550-553, Mar. 21, 2002.

Cevc, G., "How Membrane Chain-Melting Phase-Transition Temperature is Affected by the Lipid Chain Asymmetry and Degree of Unsaturation: An Effective Chain-Length Model," Biochemistry, vol. 30, No. 29, pp. 7186-7193, Jul. 23, 1991.

Chonn et al., "Recent Advances in Liposomal Drug-Delivery Systems," Current Opinion in Biotechnology, vol. 6, No. 6, pp. 698-708, Jan. 1, 1995.

Check, "RNA to the Rescue", Nature, vol. 425:10-12 (2003), https://222.nature.com/articles/425010a.

Chung et al., "COVID-19 Vaccine Frontrunners and Their Nanotechnology Design," ACS Nano, vol. 14, No. 10, pp. 12522-12537, Oct. 2020.

Corbett et al., "Evaluation of the mRNA-1273 Vaccine Against SARS-CoV-2 in Nonhuman Primates", New England Journal of Medicine, vol. 383, Issue 16, pp. 1544-1555, Jul. 28, 2020.

Corbett et al., "SARS-CoV-2 mRNA Vaccine Development Enabled by Prototype Pathogen Preparedness" bioRvix.org Jun. 11, 2020, https://www.biorxiv.org/content/10.1101/2020.06.11.145920v1.full.

Cortesi et al., "Effect of cationic liposome composition on in vitro cytotoxicity and protective effect on carried DNA," International Journal of Pharmaceutics, vol. 139, No. 1-2, pp. 69-78, Aug. 9, 1996.

COVID-19 Vaccinations in the United States, CDC (last visited Feb. 25, 2022) https://covid.cdc.gov/covid-data-tracker/#vaccinations_vacc-total-admin-rate-total.

Cross, Ryan, "Without These Lipid Shells, There Would be no mRNA Vaccines for COVID-19", Chemical & Engineering News, Mar. 6, 2021, https://cen.acs.org/pharmaceuticals/drugdelivery/Without-lipid-shells-mRNA-vaccines/99/i8.

Cruz et al., "Targeting Nanoparticles fo CD40, DEC-205 or CD11c Molecules on Dendritic Cells for Efficient CD8+ T Cell Response: A Comparative Study," Journal of Controlled Release, vol. 192, pp. 209-218 (2004).

Crystal, R., "Transfer of Genes to Humans: Early Lessons and Obstacles to Success," Science, vol. 270, No. 5235, pp. 404-410, Oct. 20, 1995.

Culver K., "The First Human Gene Therapy Experiment," Gene Therapy: A Handbook for Physicians, pp. 33-40, 1994.

Delaware Environmental Public Health Tracking Network, Vaccine Tracker, https:/myhealthycommunity.dhss.delaware.gove/locations/state/vaccine-tracker.

Dhodapkar et al., "Induction of Antigen-Specific Immunity with a Vaccine Targeting NY-ESO-1 to the Dendritic Cell Receptor DEC-205," Sci. Transl. Med., vol. 6(232), pp. 1-22, Apr. 16, 2014.

Dolgin, "Startups Set Off New Wave of mRNA Therapeutics," Nature Biotechnology, vol. 39, No. 9, pp. 1029-1031, Sep. 2021.

Dolgin, "The Tangled History of MRNA Vaccines," Nature, vol. 597, pp. 318-324, Sep. 16, 2021.

Duzgunes, N., "Membrane Fusion," Subcellular Biochemistry, vol. 11, pp. 195-286, 1985.

Dwarki et al., "Cationic Liposome-Mediated RNA Transfection," Methods in Enzymology, vol. 217, pp. 644-654, 1993.

Elbashir, et al., "Duplexes of 21-nucleotide RNAs Mediate RNA Interference in Cultured Mammalian Cells," Nature, vol. 411, No. 6836, pp. 494-498, May 2001.

Enoch et al., "Formation and Properties of 1000-A-Diameter, Single-Bilayer Phospholipid Vesicles," Proc. Natl. Acad. Sci., vol. 76, No. 1, pp. 145-149, Jan. 1, 1979.

Fadok et al., "Apoptosis: Giving Phosphatidylserine Recognition an Assist—With a Twist", Curr Biol. vol. 13, No. 16, pp. R655-R657, Aug. 19, 2003.

Fahey et al., "A Comprehensive Classification System for Lipids," J. Lipid Res. vol. 46, No. 5, pp. 839-861, May 1, 2005.

Felgner et al., "Cationic Lipid-Mediated Transfection in Mammalian Cells: 'Lipofection,'" J. Tiss. Cult. Meth., vol. 15, No. 2, pp. 63-68, Jun. 1, 1993.

Felgner et al., "Enhanced Gene Delivery and Mechanism Studies with a Novel Series of Cationic Lipid Formulations," The Journal of Biological Chemistry, vol. 269, No. 4, pp. 2550-2561, Jan. 28, 1994.

Felgner et al., "Lipofection: A Highly Efficient, Lipid-Mediated DNA-Transfection Procedure," Proc. Natl. Acad. Sci. vol. 84, No. 21, pp. 7413-7417, Nov. 1, 1987.

Felgner et al., "Cationic Liposome Mediated Transfection," Proc. West. Pharmacol. Soc., vol. 32, pp. 115-121, 1989.

(56) References Cited

OTHER PUBLICATIONS

Filion et al., "Toxicity and Immunomodulatory Activity of Liposomal Vectors Formulated with Cationic Lipids Toward Immune Effector Cells," Biochim Biophys Acta. vol. 1329, No. 2, pp. 345-356, Oct. 23, 1997.
Fossom et al., "Targeting Antigens to Different Receptors on Conventional Type 1 Dendritic Cells Impacts the Immune Response," J. Immnol., vol. 205, pp. 661-673, Jun. 26, 2020.
Gao, X., et al., "A Novel Cationic Liposome Reagent for Efficient Transfection of Mammalian Cells," Biochem. Biophys. Res. Comm., vol. 179, No. 1, pp. 280-285, Aug. 30, 1991.
Gauthier et al., "Quantification of Surface GalNAc Ligands Decorating Nanostructured Lipid Carriers by UPLC-ELSD," J Mol Sci. vol. 20, No. 22, pp. 5669-5684, Nov. 12, 2019.
Gershon, H., et al., "Mode of Formation and Structural Feature of DNA-Cationic Liposome Complexes Used forTransfection," Biochemistry, vol. 32, No. 28, pp. 7143-7151, Jul. 1, 1993.
Global Newswire, retrieved from http://globalnewswire.com on Feb. 27, 2013, Tekmira sues Alnylam Pharmaceuticals for repeated misuse of tradesecrets and confidential information, Mar. 16, 2011, pp. 1-3.
Guy-Caffey et al., "Novel Polyaminolipids Enhance the Cellular Uptake of Oligonucleotides," The Journal of Biological Chemistry, vol. 270, No. 52, pp. 31391-31396, Dec. 29, 1995.
Hassett et al., "Optimization of Lipid Nanoparticles for Intramuscular Administration of mRNA Vaccines", Molecular Therapy: Nucleic Acids, vol. 15, Issue 1, pp. 1-11, Apr. 2019.
Hawley-Nelson et al., "LipofectAmine™ Reagent: A New, Higher Efficiency Polycationic Liposome Transfection Reagent," Focus, vol. 15, No. 3, pp. 73-79, 1993.
Heinz et al., "Distinguishing Features of Current COVID-19 Vaccines: Knowns and Unknowns of Antigen Presentation and Modes of Action," npj Vaccines, vol. 6, No. 1, pp. 1-13, Aug. 16, 2021.
Heyes et al., "Cationic lipid saturation influences intracellular delivery of encapsulated nucleic acids," Journal of Controlled Release, 2005, vol. 107, pp. 276-287.
Heyes et al., "Synthesis of novel cationic lipids: effect of structural modification on the efficiency of gene transfer," J. Med. Chem., vol. 45, No. 1, pp. 99-114, Jan. 3, 2002.
Hoge, Stephen, "Turns Out, Designing a COVID Vaccine Was Easy", UCSF Alumni, https://alumni.ucsf.edu/stories/stephen-hoge.
Hou et al., "Lipid Nanoparticles for mRNA Delivery", Nature, vol. 6, pp. 1078-1094, Dec. 2021.
Huang et al., "Thiocholesterol-Based Lipids for Ordered Assembly of Bioresponsive Gene Carriers," Molecular Therapy, vol. 11, No. 3, pp. 409-417, Mar. 2005.
Hyde, S., et al., "Correction of the Ion Transport Defect in Cystic Fibrosis Transgenic Mice by Gene Therapy," Nature, vol. 362, pp. 250-255, Mar. 18, 1993.
Jackson et al., "An mRNA Vaccine Against SARS-CoV-2—Preliminary Report," New Engl. J. Med., vol. 383, No. 20, pp. 1920-1931, Nov. 12, 2020.
Jayaraman et al., "Maximizing the Potency of siRNA Lipid Nanoparticles for Hepatic Gene Silencing In Vivo**," Angew. Chem. Int. Ed., vol. 51, No. 34, pp. 8529-8533, Aug. 20, 2012.
Jiang, L., et al., "Comparison of protein precipitation methods for sample preparation prior to proteomic analysis," Journal of Chromatography A, vol. 1023, No. 2, pp. 317-320, Jan. 16, 2004.
Juliano et al., "The Effect of Particle Size and Charge on the Clearance Rates of Liposomes and Liposome Encapsulated Drugs," Biochem. Biophys. Res. Commun., vol. 63, No. 3, pp. 651-658, Apr. 7, 1975.
Keough, K., "Influence of Chain Unsaturation and Chain Position on Thermotropism and Intermolecular Interactions in Membranes," Biochem. Soc. Transactions, vol. 18, No. 5, pp. 835-837, 1990.
Krichevsky et al., "RNAi Functions in Cultured Mammalian Neurons," PNAS, vol. 99, No. 18, pp. 11926-11929, Sep. 3, 2002.
Lawrence et al. "The formation, characterization and stability of non-ionic surfactant vesicles," S.T.P. Pharma Sciences, vol. 6, No. 1, pp. 49-60, 1996.
Lawrence et al., "Synthesis and Aggregation Properties of Dialkyl Polyoxyethylene Glycerol Ethers," Chemistry and Physics of Lipids, vol. 82, No. 2, pp. 89-100, Aug. 19, 1996.
Legendre et al., "Delivery of Plasmid DNA into Mammalian Cell Lines Using pH-Sensitive Liposomes: Comparison with Cationic Liposomes," Pharm. Res., vol. 9, No. 10, pp. 1235-1242, Oct. 9, 1992.
Leventis et al., "Interactions of mammalian cells with lipid dispersions containing novel metabolizable cationic amphiphiles," Biochem. Biophys. Acta, vol. 1023, No. 1, pp. 124-132, Mar. 30, 1990.
Li et al., "A Review on Phospholipids and Their Main Applications in Drug Delivery Systems," Asian J. Pharm. Sci. vol. 10, pp. 81-98, 2015.
Liu et al., "Cationic Liposome-Mediated Intravenous Gene Delivery", J. Biol. Chem., vol. 270, No. 42, pp. 24864-24870, Oct. 20, 1995.
Loh, Tim, "Lipids are Delivering the Vaccine Revolution", Bloomberg, Mar. 6, 2021, https://www.bloomberg.com/news/newsletters/2021-03-06/lipids-are-delivering-the-vaccine-revolution.
LoPresti et al., "The Replacement of Helper Lipids with Charged Alternatives in Lipid Nanoparticles Facilitates Targeted mRNA Delvery to the Spleen and Lungs" Journal of Controlled Release, vol. 345, pp. 819-831, May 1, 2022.
Lotter et al., "Incorporation of Phosphatidylserine Improves Efficiency of Lipid Based Gene Delivery Systems" European Journal of Pharmaceutics and Biopharmaceutics, vol. 172, pp. 134-143, Mar. 2022.
Lotter et al., "Incorporation of Phosphatidylserine Improves Efficiency of Lipid Based Gene Delivery Systems" Supporting Information Document.
Luozhong et al., "Phosphatidylserine Lipid Nanoparticles Promote Systemic RNA Delivery to Secondary Lymphoid Organs" Nano Letters, vol. 22, No. 20, pp. 8304-8311, Oct. 4, 2022. https://doi.org/10.1021/acs.nanolett.2c03234.
Maloy et al., "Intralymphatic Immunization Enhances DNA Vaccination," Proc Natl Acad Sci USA, vol., No. 6, pp. 3299-3033, Mar. 13, 2001.
Marshall, E., "Gene Therapy's Growing Pains," Science, vol. 269, No. 5227, pp. 1050-1055, Aug. 25, 1995.
Murahashi et al., "Synthesis and Evaluation of Neoglycolipid for Liposome Modification," Biol. Pharm. Bull., vol. 20, No. 6, pp. 704-707, Jun. 15, 1997.
Nellis et al., "Preclinical Manufacture of an Anti-HER2 scFv-PEG-DSPE, Liposome-Inserting Conjugate. 1. Gram-Scale Production and Purification," Biotechnol Prog., vol. 21, pp. 205-220, Jan. 2005.
Nellis et al., "Preclinical Manufacture of Anti-HER2 Liposome-Inserting, scFv-PEG-Lipid Conjugate. 2. Conjugate Micelle Identity, Purity, Stability, and Potency Analysis," Biotechnol Prog., vol. 21, pp. 221-232, Jan. 2005.
Offutt-Powell et al., "Delaware's My Healthy Community Data Platform: At the Intersection of Public Health Informatics and Epidemiology" Delaware Journal of Public Health, vol. 7, No. 3, p. 58, Jul. 2021.
Orkin, S., et al., NIH Report, Report and Recommendations of the Panel to Assess the NIH Investment in Research on Gene Therapy, vol. 7, Dec. 7, 1995.
Pardi, et al., "MRNA Vaccines—A New Era in Vaccinology," Nat. Rev. Drug Discov. vol. 17, No. 4, pp. 261-279, Apr. 19, 2018.
Parr et al., "Factors Influencing the Retention and Chemical Stability of Polly (Ethylene Glycol)-Lipid Conjugates Incorporated into Large Unilamellar Vesicles," Biochimica et Biophysica Acta, vol. 1195, No. 1, pp. 21-30, Oct. 12, 1994.
Paul, C., et al., "Effective Expression of Small Interfering RNA in Human Cells," Nature Biotech., vol. 20, No. 5, pp. 505-508, May 2002.
Press Release, Moderna and Baxter Announce Agreement for Fill/Finish Manufacturing of the Moderna COVID-19 Vaccine in the U.S. https://investors.modernatx.com/news-releases/news-release-details/baxter-biopharma-solutions-and-moderna-announce-agreement.
Press Release, Moderna and Lonza Announce Worldwide Strategic Collaboration to Manufacture Moderna's Vaccine (mRNA-1273) Against Novel Coronavirus (May 1, 2020), https://investors.modernatx.

(56) References Cited

OTHER PUBLICATIONS com/news-releases/news-release-details/moderna-and-lonza-announce-worldwide-strategic-collaboration.

Press Release, Moderna Announces Initiation of Rolling Submission of Biologics License Application (BLA) with U.S. FDA for the Moderna COVID-19 Vaccine (Jun. 1, 2021) https://investors.modernatx.com/news-releases/news-release-details/moderna-announces-initiation-rolling-submission-biologics.

Press Release, Moderna Receives Full U.S. FDA Approval for COVID 19 Vaccine Spikevax 2022.

Press Release, Moderna, Moderna Reports Fourth Quarter and Fiscal Year 2021 Financial Results and Provides Business Updates, Feb. 24, 2022, https://investors.modernatx.com/news/news-details/2022/Moderna-Reports-Fourth-Quarter-and-Fiscal-Year-2021-Financial-Results-and-Provides-Business-Updates/default.aspx.

Press Release, Moderna, Vaccine Exports from U.S. Accelerate as Moderna Ships Abroad, Bloomberg.com, May 20, 2021, https://www.bloomberg.com/news/articles/2021-05-20/moderna-starts-shipping-vaccine-from-us-boosting-shot-exports.

Puyal, C., et al., "A New Cationic Liposome Encapsulating Genetic Material: A Potential Delivery System for Polynucleotides," Eur. J. Biochem., vol. 228, No. 3, pp. 697-703, Mar. 1995.

Regalado, Antonio, "None of Us Were Ready to Manufacture Genetic Vaccines for a Billion People", MIT Technology Review, Dec. 17, 2020, https://www.technologyreview.com/2020/12/17/1014989/moderna-vaccine-availability-stephane-bancel-ceo/.

Sabnis et al., "A Novel Amino Lipid Series for mRNA Delivery: Improved Endosomal Escape and Sustained Pharmacology and Safety in Non-Human Primates," Molecular Ther., vol. 26, No. 6, pp. 1509-1519, Jun. 2018.

Sahin et al., "Personalized RNA Mutanome Vaccines Mobilize Poly-Specific Therapeutic Immunity Against Cancer," Nature, vol. 547, pp. 222-240, Jul. 13, 2017.

Sawada et al., "Microemulsions in Supercritical CO2 Utilizing the Polyethyleneglycol Dialkylglycerol and Their Use for the Solubilization of Hydrophiles," Dyes and Pigments, vol. 65, No. 1, pp. 67-74, Apr. 1, 2005.

Semple et al., "Rational Design of Cationic Lipids for siRNA Delivery," Nature Biotechnology, vol. 28, No. 2, pp. 172-178, Feb. 2010.

Sharma, et al., "A Review of the Progress and Challenges of Developing a Vaccine for COVID-19," Frontiers in Immunology, vol. 11, pp. 1-17, Oct. 2020.

Shin, et al. "Acid-Triggered Release via dePEGylation of DOPE Liposomes Containing Acid-Labile Vinyl Ether PEG-lipids," Journal of Controlled Release, vol. 91, No. 1-2, pp. 187-200, Aug. 28, 2003.

Shirley et al., "Amikacin Liposome Inhalation Suspension: A Review in Mycobacterium avium Complex Lung Disease", Drugs, vol. 79, No. 5, pp. 555-562, Apr. 2019.

Shurin, et al., "Recognition of Live Phosphatidylserine-Labeled Tumor Cells by Dendritic Cells: A Novel Approach to Immunotherapy of Skin Cancer," Cancer Res. vol. 69, No. 6, pp. 2487-2496, Mar. 15, 2009.

Song et al., "Characterization of the Inhibitory Effect of PEG-lipid Conjugates on the Intracellular Delivery of Plasmid and Antisense DNA Mediated by Cationic Lipid Liposomes," Biochimica et Biophysica Acta, vol. 1558, No. 1, pp. 1-13, Jan. 2, 2002.

Sorensen, et al., "Gene Silencing by Systemic Delivery of Synthetic siRNAs in Adult Mice", J. Biol. Chem., vol. 327, No. 4, pp. 761-766, Apr. 4, 2003.

Spagnou, S., et al., "Lipidic Carriers of siRNA: Differences in the Formulation, Cellular Uptake, and Delivery with Plasmid DNA," Biochemistry, vol. 43, No. 42, pp. 13348-13356, Oct. 26, 2004.

Stamatatos, L., et al., "Interactions of Cationic Lipid Vesicles with Negatively Charged Phospholipid Vesicles and Biological Membranes," Biochemistry, vol. 27, No. 11, pp. 3917-3925, May 1, 1988.

Swadling et al., "Pre-Existing Polymerase-Specific T Cells Expand in Abortive Seronegative SARS-CoV2," Nature, vol. 601, pp. 110-142, Jan. 6, 2022.

Szoka, F., et al., "Comparative Properties and Methods of Preparation of Lipid Vesicles (Liposomes)," Ann. Rev. Biophys. Bioeng., vol. 9, No. 1, pp. 467-508, Jun. 1980.

Szoka et al., "Procedure for preparation of liposomes with large internal aqueous space and high capture by reverse-phase evaporation," Proc. Natl. Acad. Sci., vol. 75, No. 9, pp. 4194-4198, Sep. 1, 1978.

Tada, et al., "Comparison of Neutralizing Antibody Titers Elicited by mRNA and Adenoviral Vector Vaccine Against SARS-CoV-2 Variants," Biorxiv, Jan. 2021.

Templeton, "Cationic Liposome-mediated Gene Delivery In vivo", Bioscience Reports, vol. 22, No. 2, pp. 283-295, Apr. 2002.

Vanderwoude, I., et al., "Parameters influencing the introduction of plasmid DNA into cells by the use of synthetic amphiphiles as a carrier system," Biochimica et Biophysica Acta, vol. 1240, No. 1, pp. 34-40, Nov. 22, 1995.

Vardi, Nathan, "Moderna's Mysterious Coronavirus Vaccine Delivery System", Forbes.com, Jul. 29, 2020, www.forbes.com/sites/nathanvardi/2020/7/29/modernas-mysterious-coronavirus-vaccine-delivery-system/.

Walsh, et al., "Safety and Immunogenicity of Two RNA-Based Covid-19 Vaccine Candidates," N. Engl. J. Med., vol. 383, No. 25, pp. 2439-2450, Dec. 17, 2020.

Wheeler, et al., "Stabilized Plasmid-lipid Particles: Constructions and Characterization," Gene Therapy, vol. 6, No. 2, pp. 271-281, Feb. 5, 1999.

Wilson, R., et al., "Counterion-Induced Condensation of Deoxyribonucleic Acid," A Light-Scattering Study, Biochemistry, vol. 18, No. 11, pp. 2192-2196, May 1, 1979.

Woodle, M.C., et al., "Versatility in lipid compositions showing prolonged circulation with sterically stabilized liposomes," Biochimica et Biophysica Acta, vol. 1105, pp. 193-200, Apr. 13, 1992.

Yu et al., "RNA Drugs and RNA Targets for Small Molecules: Principles, Progress, and Challenges," Pharmacological Reviews, vol. 72, pp. 862-898, Oct. 2020.

Zhu, N., et al., "Systemic Gene Expression After Intravenous DNA Delivery into Adult Mice," Science, vol. 261, No. 5118, pp. 209-211, Jul. 9, 1993.

Hauser et al., "Crystallization of Phosphatidylserine Bilayers Induced by Lithium," The Journal of Biological Chemistry, vol. 256, No. 22, pp. 11377-11380, Nov. 25, 1981.

International Search Report in International Application No. PCT/US2023/067517 mailed Nov. 14, 2023.

\* cited by examiner

FIG. 3A (Example 12)
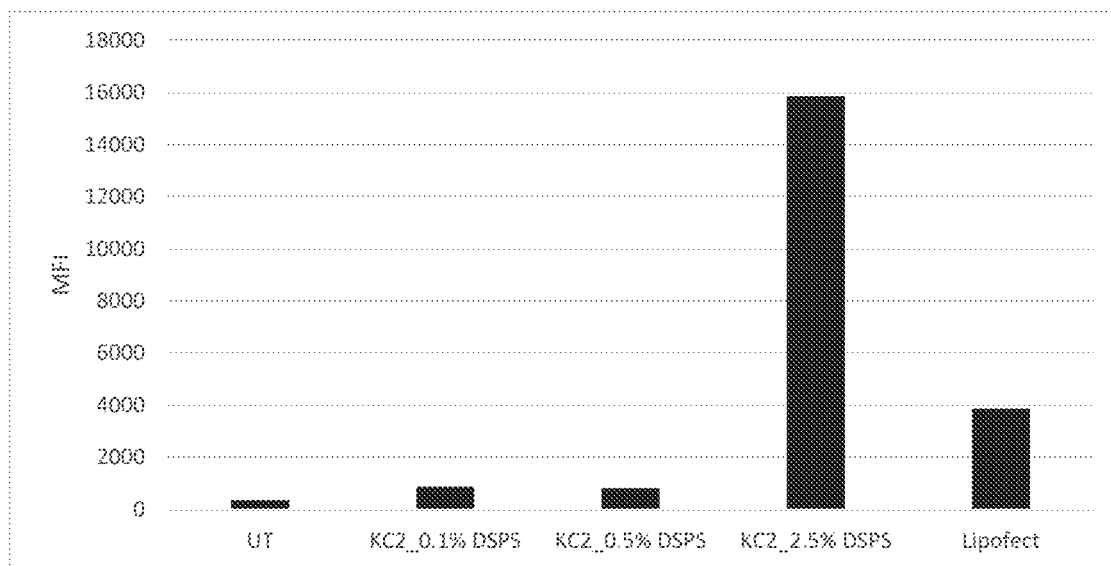
FIG. 3B (Example 12)
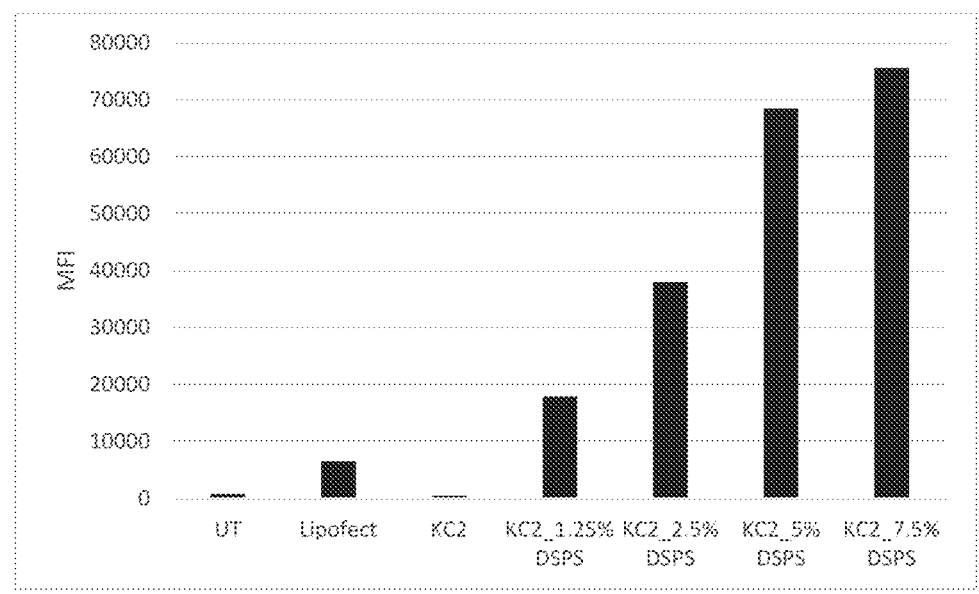

FIG. 3C (Example 12)
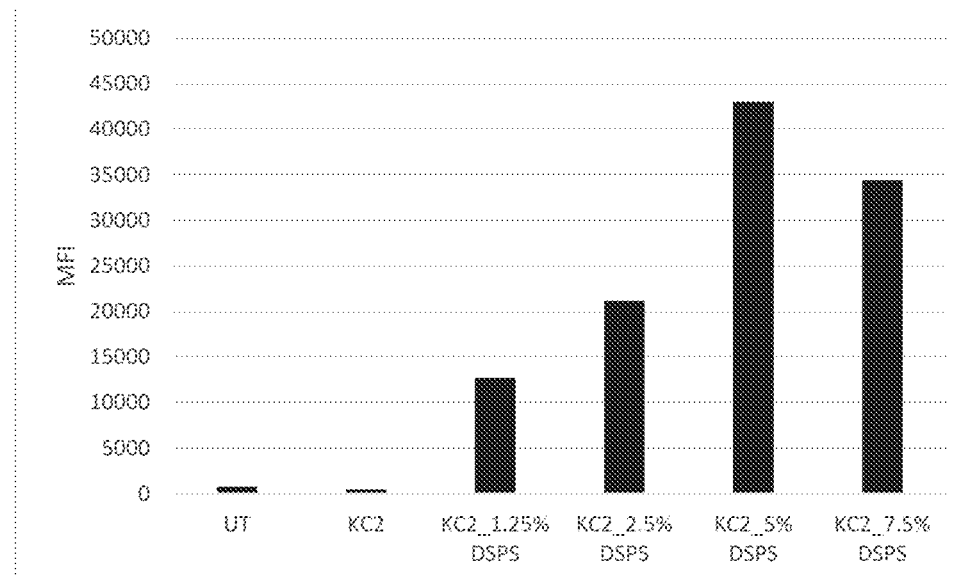
FIG. 3D (Example 12)
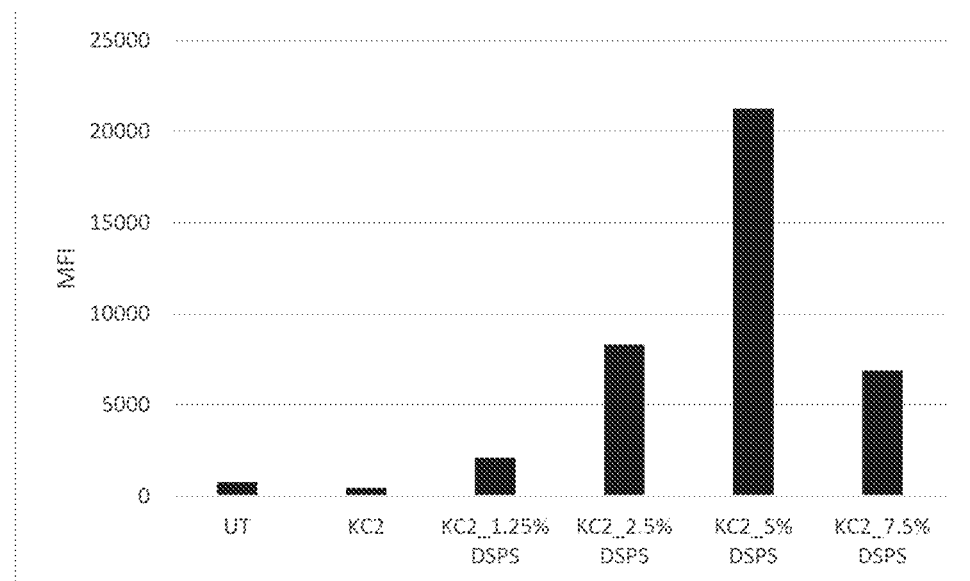

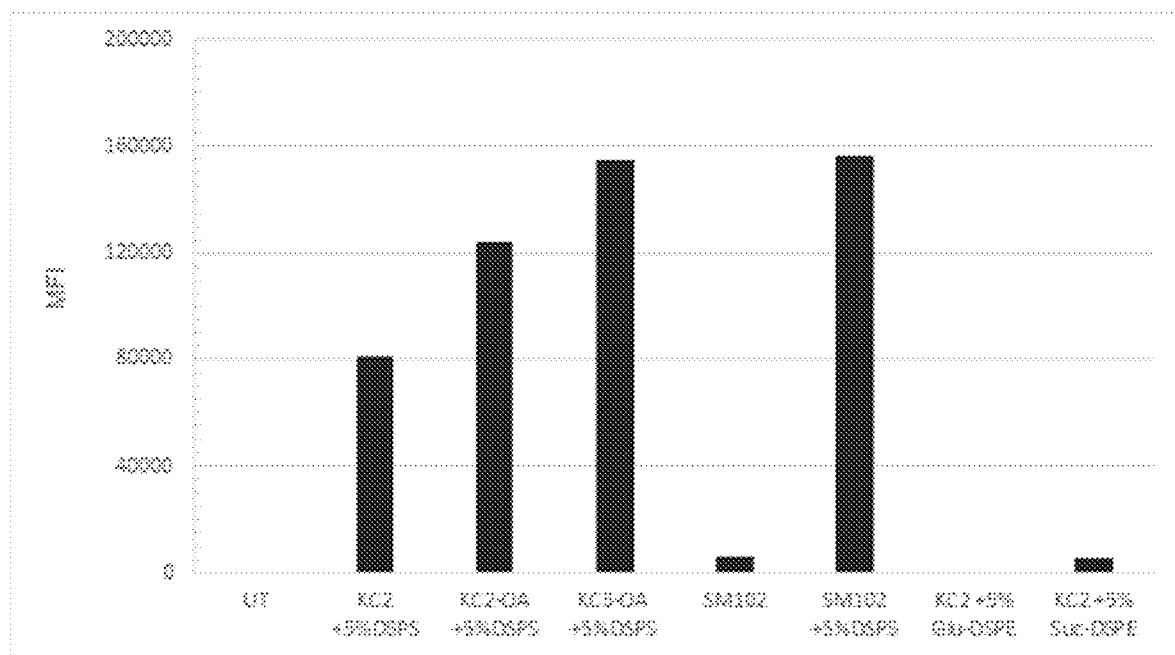
FIG. 4 (Example 13) – SM102 comparison with KC series

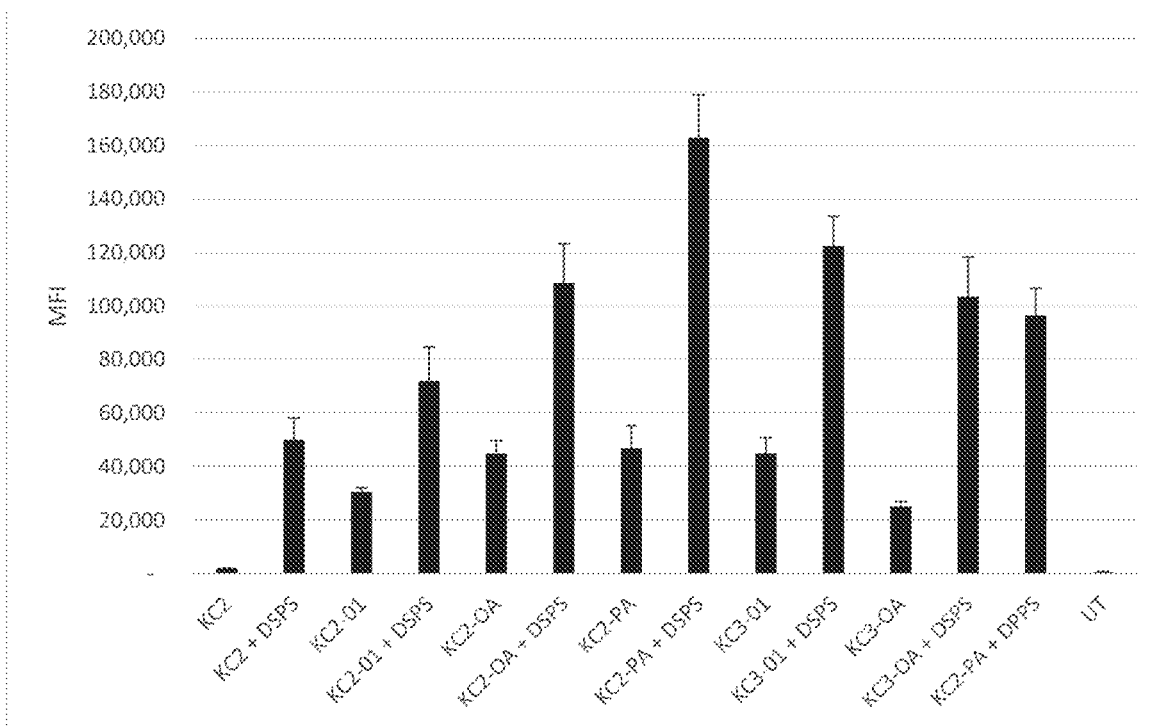
FIG. 5 (Example 14) – PS targeting KC series

FIG. 6A (Example 15)
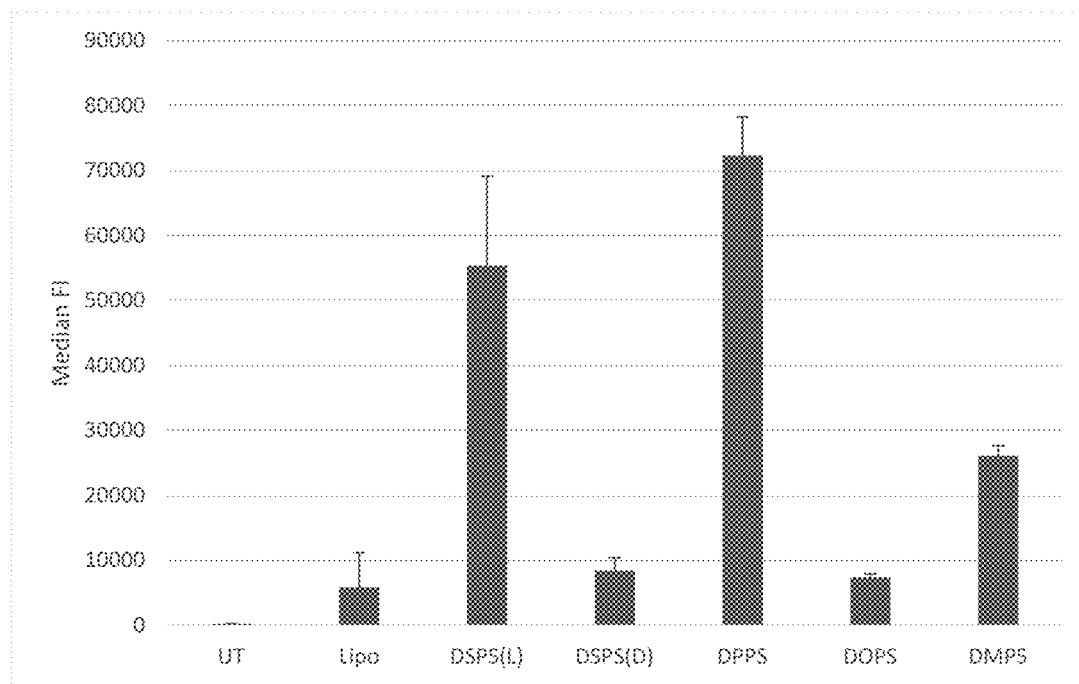
FIG. 6B (Example 15)
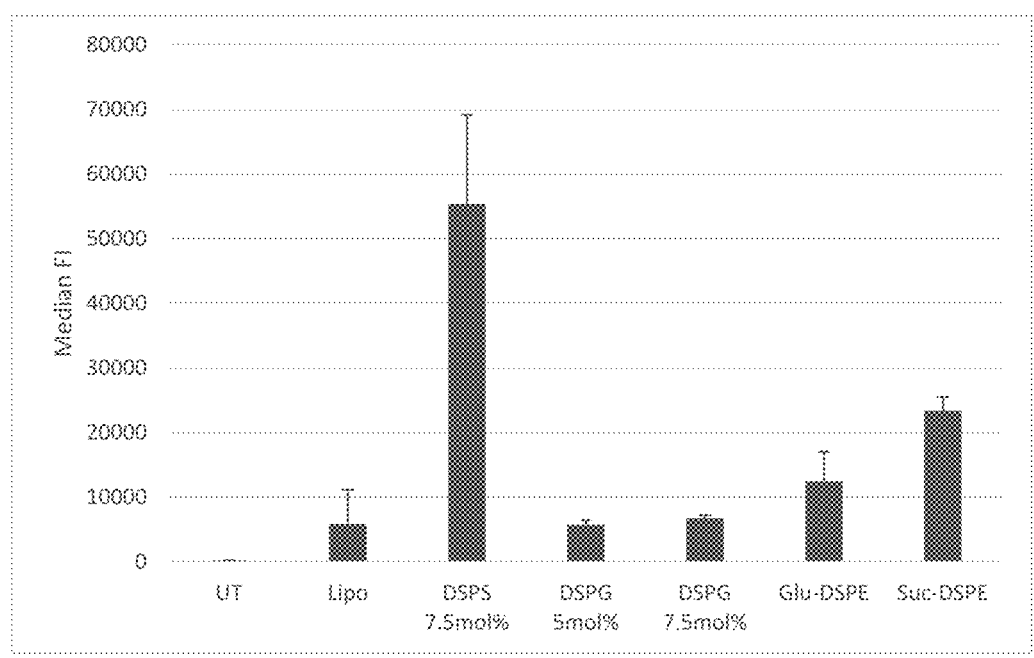

FIG. 7 (Example 16)
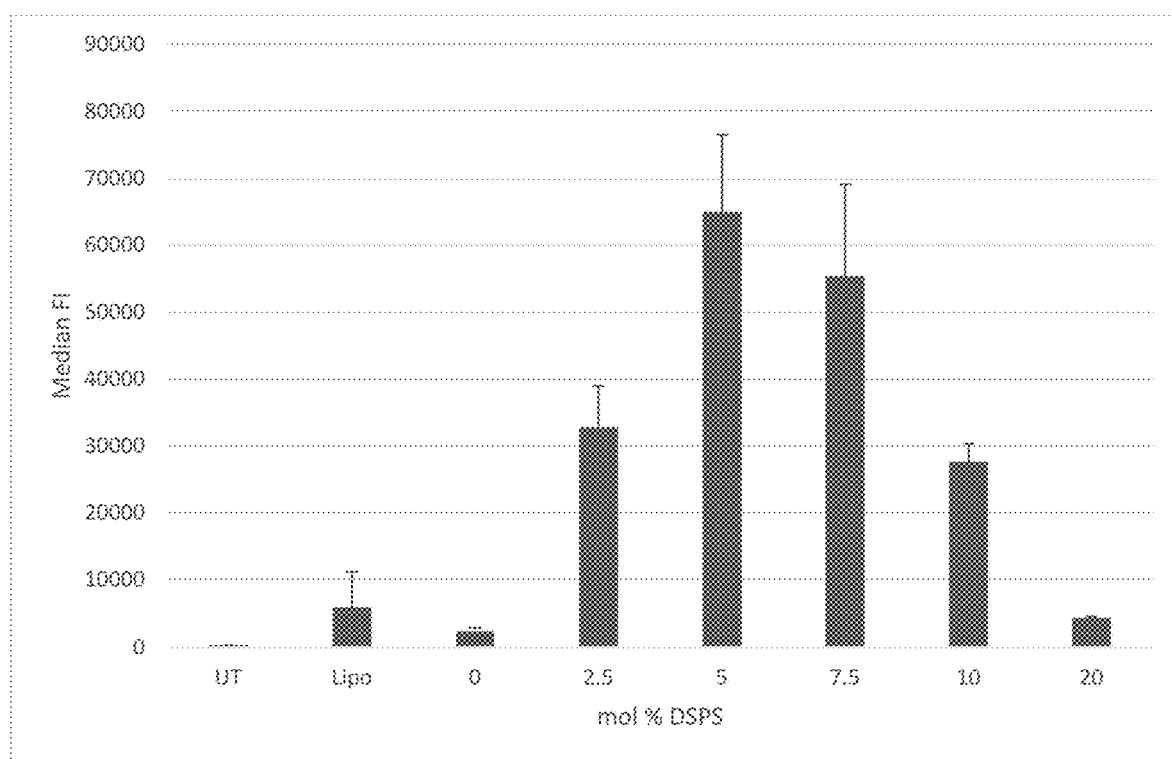

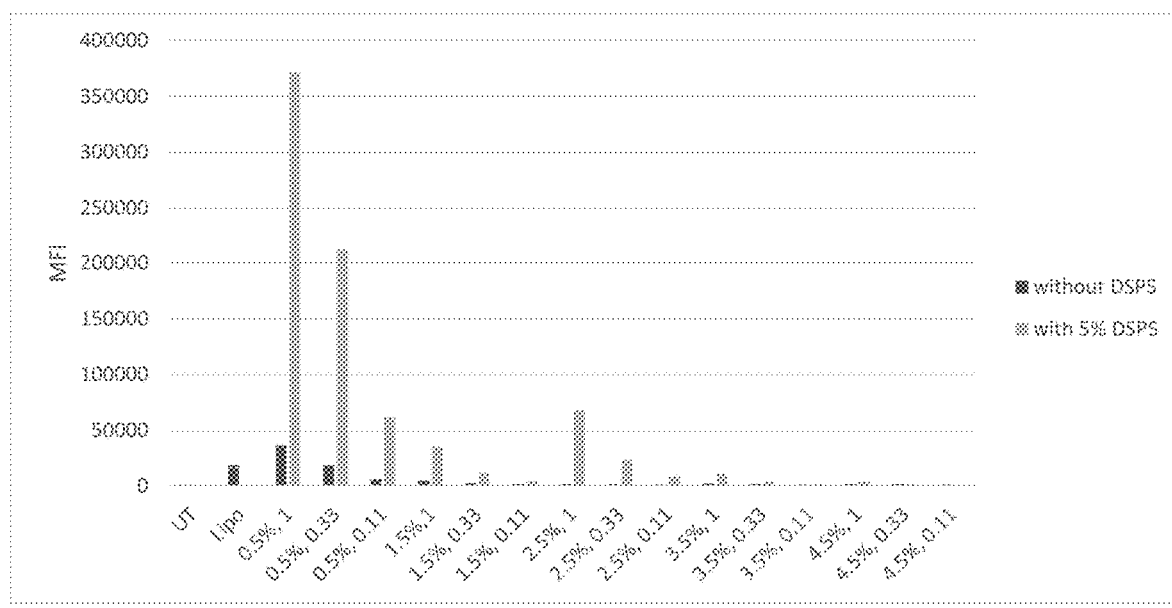
FIG. 8 (Example 17)

FIG. 9A (Example 18)
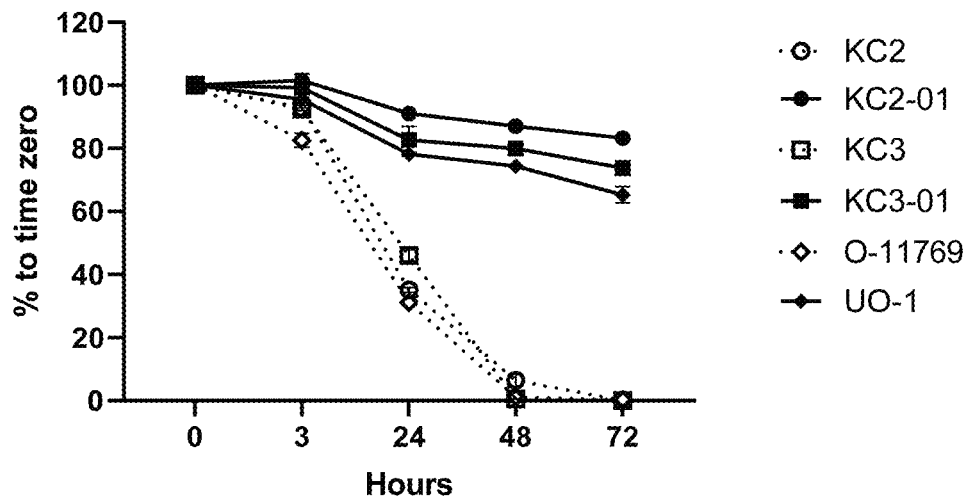
FIG. 9B (Example 18)
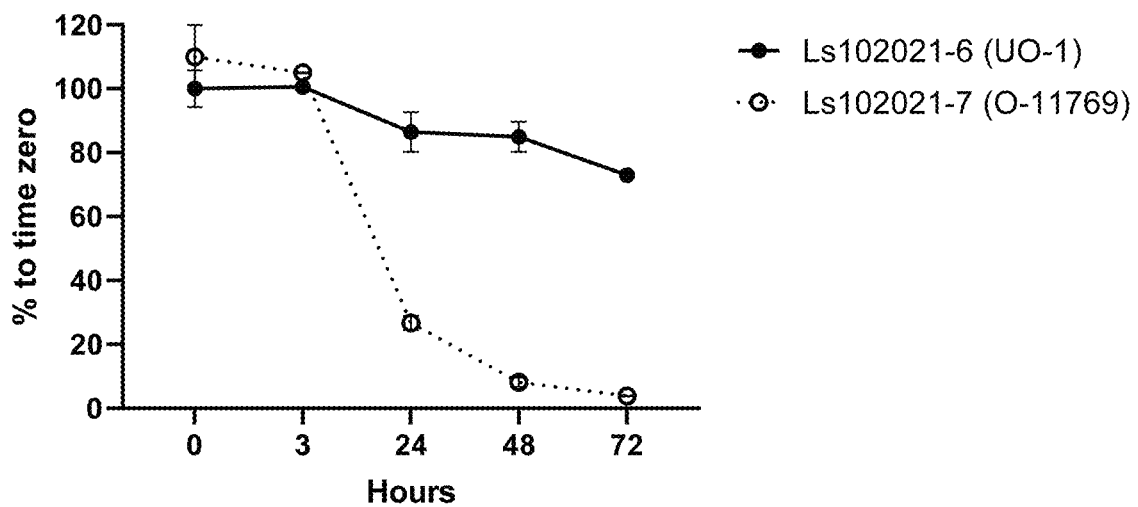

FIG. 10A (Example 19)
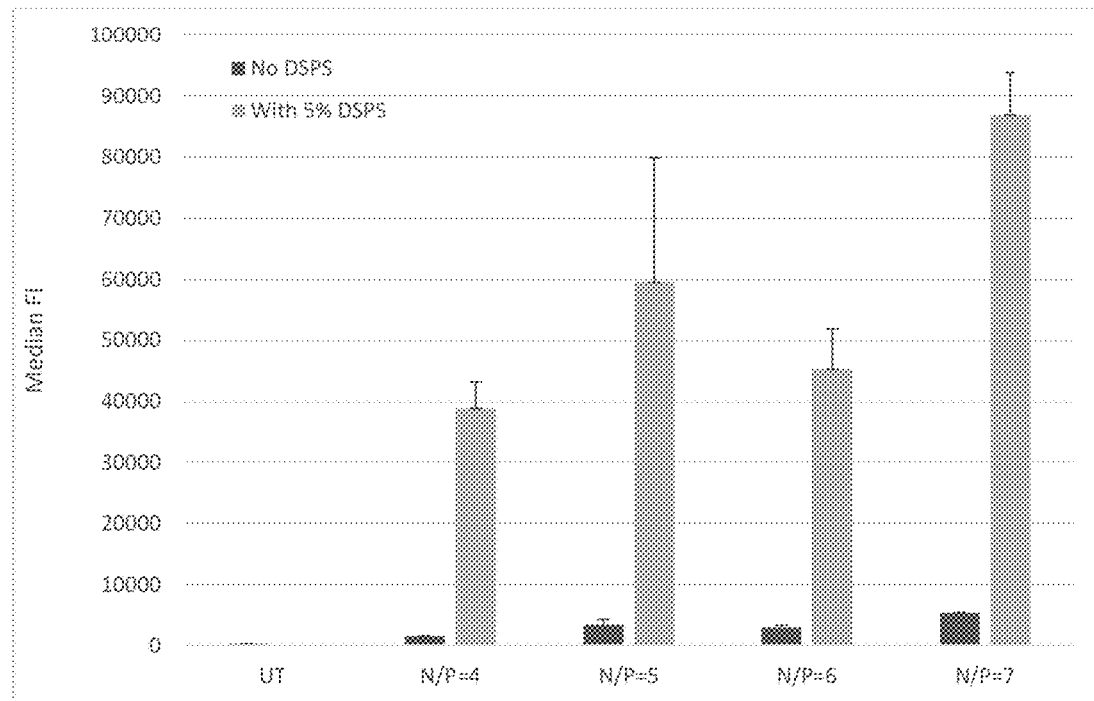
FIG. 10B (Example 19)
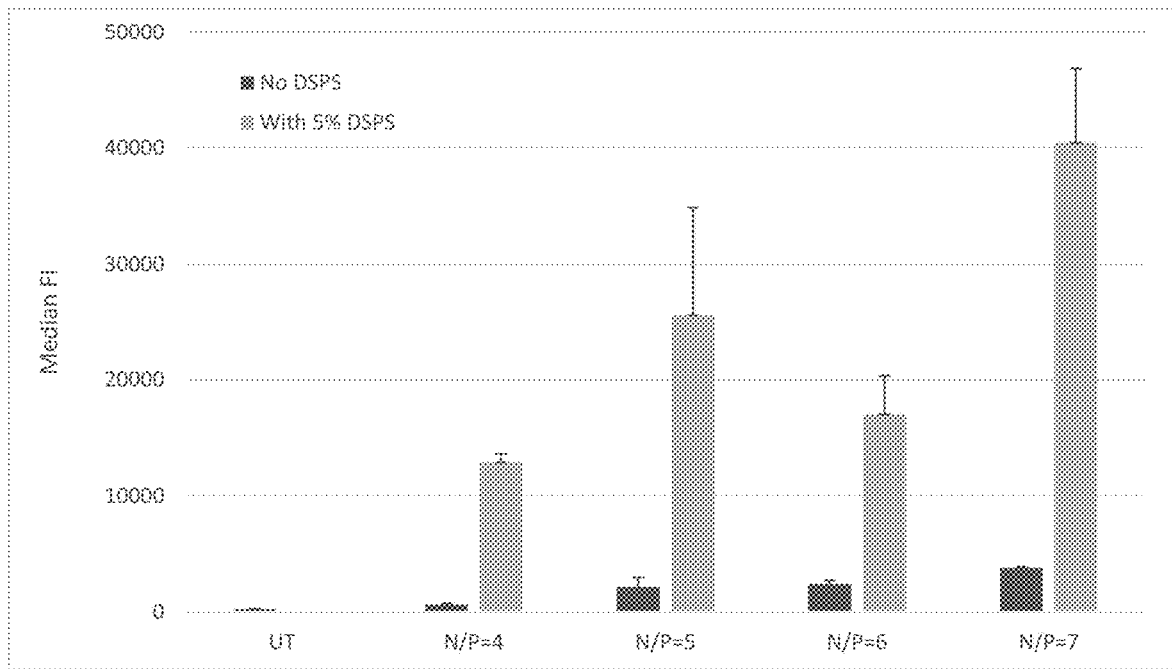

FIG. 11 (Example 20)
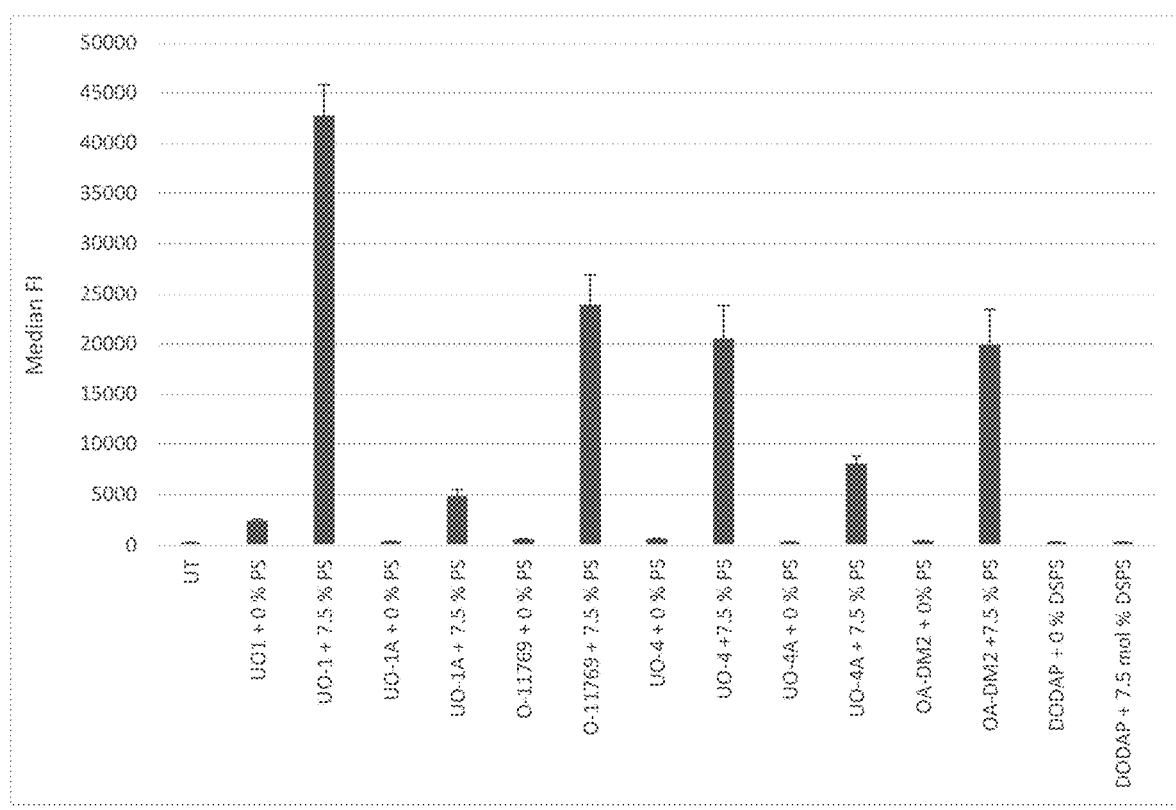

FIG. 12 (Example 21)
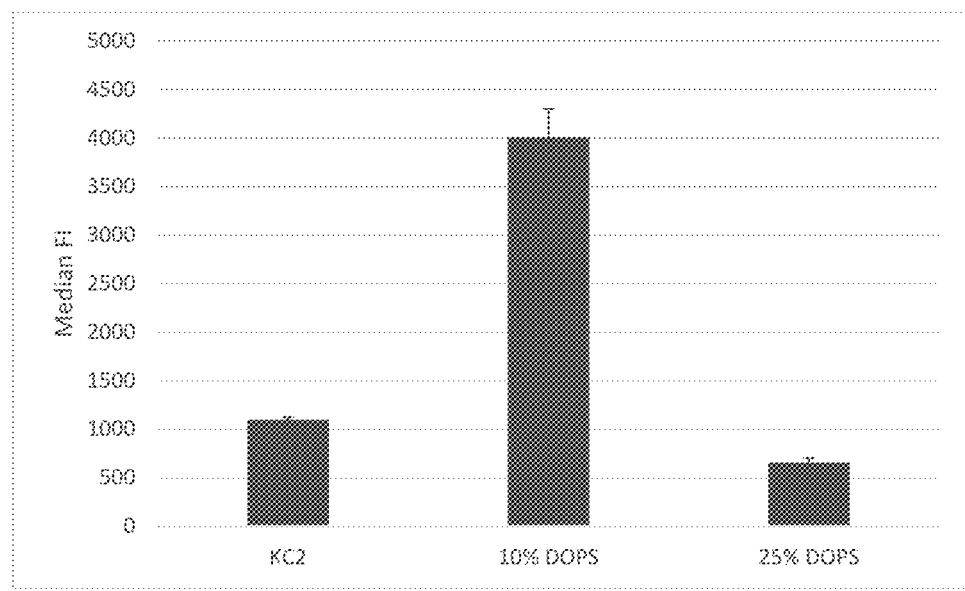

FIG. 13A (Example 22)

mVRN029 (SEQ ID NO: 2)

```
GGGAATAAACTAGTATTCTTCTGGTCCCCACAGACTCAGAGAGAACCCGCCACCATGTTCGTGTTCCTGG
TGCTGCTGCCTCTGGTGTCCAGCCAGTGTGTGAACCTGACCACCAGAACACAGCTGCCTCCAGCCTACAC
CAACAGCTTTACCAGAGGCGTGTACTACCCCGACAAGGTGTTCAGATCCAGCGTGCTGCACTCTACCCAG
GACCTGTTCCTGCCTTTCTTCAGCAACGTGACCTGGTTCCACGCCATCCACGTGTCCGGCACCAATGGCA
CCAAGAGATTCGACAACCCCGTGCTGCCCTTCAACGACGGGGTGTACTTTGCCAGCACCGAGAAGTCCAA
CATCATCAGAGGCTGGATCTTCGGCACCACACTGGACAGCAAGACCCAGAGCCTGCTGATCGTGAACAAC
GCCACCAACGTGGTCATCAAAGTGTGCGAGTTCCAGTTCTGCAACGACCCCTTCCTGGGCGTCTACTACC
ACAAGAACAACAAGAGCTGGATGGAAAGCGAGTTCCGGGTGTACAGCAGCGCCAACAACTGCACCTTCGA
GTACGTGTCCCAGCCTTTCCTGATGGACCTGGAAGGCAAGCAGGGCAACTTCAAGAACCTGCGCGAGTTC
GTGTTTAAGAACATCGACGGCTACTTCAAGATCTACAGCAAGCACACCCTATCAACCTCGTGCGGGATC
TGCCTCAGGGCTTCTCTGCTCTGGAACCCCTGGTGGATCTGCCCATCGGCATCAACATCACCCGGTTTCA
GACACTGCTGGCCCTGCACAGAAGCTACCTGACACCTGGCGATAGCAGCAGCGGATGGACAGCTGGTGCC
GCCGCTTACTATGTGGGCTACCTGCAGCCTAGAACCTTCCTGCTGAAGTACAACGAGAACGGCACCATCA
CCGACGCCGTGGATTGTGCTCTGGATCCTCTGAGCGAGACAAAGTGCACCCTGAAGTCCTTCACCGTGGA
AAAGGGCATCTACCAGACCAGCAACTTCCGGGTGCAGCCCACCGAATCCATCGTGCGGTTCCCCAATATC
ACCAATCTGTGCCCCTTCGGCGAGGTGTTCAATGCCACCAGATTCGCCTCTGTGTACGCCTGGAACCGGA
AGCGGATCAGCAATTGCGTGGCCGACTACTCCGTGCTGTACAACTCCGCCAGCTTCAGCACCTTCAAGTG
CTACGGCGTGTCCCCTACCAAGCTGAACGACCTGTGCTTCACAAACGTGTACGCCGACAGCTTCGTGATC
CGGGGAGATGAAGTGCGGCAGATTGCCCCTGGACAGACAGGCAAGATCGCCGACTACAACTACAAGCTGC
CCGACGACTTCACCGGCTGTGTGATTGCCTGGAACAGCAACAACCTGGACTCCAAAGTCGGCGGCAACTA
CAATTACCTGTACCGGCTGTTCCGGAAGTCCAATCTGAAGCCCTTCGAGCGGGACATCTCCACCGAGATC
TATCAGGCCGGCAGCACCCCTTGTAACGGCGTGGAAGGCTTCAACTGCTACTTCCCACTGCAGTCCTACG
GCTTTCAGCCCACAAATGGCGTGGGCTATCAGCCCTACAGAGTGGTGGTGCTGAGCTTCGAACTGCTGCA
TGCCCCTGCCACAGTGTGCGGCCCTAAGAAAAGCACCAATCTCGTGAAGAACAAATGCGTGAACTTCAAC
TTCAACGGCCTGACCGGCACCGGCGTGCTGACAGAGAGCAACAAGAAGTTCCTGCCATTCCAGCAGTTTG
GCCGGGATATCGCCGATACCACAGACGCCGTTAGAGATCCCCAGACACTGGAAATCCTGGACATCACCCC
TTGCAGCTTCGGCGGAGTGTCTGTGATCACCCCTGGCACCAACACCAGCAATCAGGTGGCAGTGCTGTAC
CAGGACGTGAACTGTACCGAAGTGCCCGTGGCCATTCACGCCGATCAGCTGACACCTACATGGCGGGTGT
ACTCCACCGGCAGCAATGTGTTTCAGACCAGAGCCGGCTGTCTGATCGGAGCCGAGCACGTGAACAATAG
CTACGAGTGCGACATCCCCATCGGCGCTGGAATCTGCGCCAGCTACCAGACACAGACAAACAGCCCTCGG
AGAGCCAGAAGCGTGGCCAGCCAGAGCATCATTGCCTACACAATGTCTCTGGGCGCCGAGAACAGCGTGG
CCTACTCCAACAACTCTATCGCTATCCCCACCAACTTCACCATCAGCGTGACCACAGAGATCCTGCCTGT
GTCCATGACCAAGACCAGCGTGGACTGCACCATGTACATCTGCGGCGATTCCACCGAGTGCTCCAACCTG
CTGCTGCAGTACGGCAGCTTCTGCACCCAGCTGAATAGAGCCCTGACAGGGATCGCCGTGGAACAGGACA
AGAACACCCAAGAGGTGTTCGCCCAAGTGAAGCAGATCTACAAGACCCCTCCTATCAAGGACTTCGGCGG
CTTCAATTTCAGCCAGATTCTGCCCGATCCTAGCAAGCCCAGCAAGCGGAGCTTCATCGAGGACCTGCTG
TTCAACAAAGTGACACTGGCCGACGCCGGCTTCATCAAGCAGTATGGCGATTGTCTGGGCGACATTGCCG
CCAGGGATCTGATTTGCGCCCAGAAGTTTAACGGACTGACAGTGCTGCCTCCTCTGCTGACCGATGAGAT
GATCGCCCAGTACACATCTGCCCTGCTGGCCGGCACAATCACAAGCGGCTGGACATTTGGAGCAGGCGCC
GCTCTGCAGATCCCCTTTGCTATGCAGATGGCCTACCGGTTCAACGGCATCGGAGTGACCCAGAATGTGC
TGTACGAGAACCAGAAGCTGATCGCCAACCAGTTCAACAGCGCCATCGGCAAGATCCAGGACAGCCTGAG
CAGCACAGCAAGCGCCCTGGGAAAGCTGCAGGACGTGGTCAACCAGAATGCCCAGGCACTGAACACCCTG
GTCAAGCAGCTGTCCTCCAACTTCGGCGCCATCAGCTCTGTGCTGAACGATATCCTGAGCAGACTGGACC
CTCCTGAGGCCGAGGTGCAGATCGACAGACTGATCACAGGCAGACTGCAGAGCCTCCAGACATACGTGAC
CCAGCAGCTGATCAGAGCCGCCGAGATTAGAGCCTCTGCCAATCTGGCCGCCACCAAGATGTCTGAGTGT
GTGCTGGGCCAGAGCAAGAGAGTGGACTTTTGCGGCAAGGGCTACCACCTGATGAGCTTCCCTCAGTCTG
CCCCTCACGGCGTGGTGTTTCTGCACGTGACATATGTGCCCGCTCAAGAGAAGAATTTCACCACCGCTCC
```

FIG. 13A (Example 22) Continued

```
AGCCATCTGCCACGACGGCAAAGCCCACTTTCCTAGAGAAGGCGTGTTCGTGTCCAACGGCACCCATTGG
TTCGTGACACAGCGGAACTTCTACGAGCCCCAGATCATCACCACCGACAACACCTTCGTGTCTGGCAACT
GCGACGTCGTGATCGGCATTGTGAACAATACCGTGTACGACCCTCTGCAGCCCGAGCTGGACAGCTTCAA
AGAGGAACTGGACAAGTACTTTAAGAACCACACAAGCCCCGACGTGGACCTGGGCGATATCAGCGGAATC
AATGCCAGCGTCGTGAACATCCAGAAAGAGATCGACCGGCTGAACGAGGTGGCCAAGAATCTGAACGAGA
GCCTGATCGACCTGCAAGAACTGGGGAAGTACGAGCAGTACATCAAGTGGCCCTGGTACATCTGGCTGGG
CTTTATCGCCGGACTGATTGCCATCGTGATGGTCACAATCATGCTGTGTTGCATGACCAGCTGCTGTAGC
TGCCTGAAGGGCTGTTGTAGCTGTGGCAGCTGCTGCAAGTTCGACGAGGACGATTCTGAGCCCGTGCTGA
AGGGCGTGAAACTGCACTACACATGATGACTCGAGCTGGTACTGCATGCACGCAATGCTAGCTGCCCCTT
TCCCGTCCTGGGTACCCCGAGTCTCCCCCGACCTCGGGTCCCAGGTATGCTCCCACCTCCACCTGCCCCA
CTCACCACCTCTGCTAGTTCCAGACACCTCCCAAGCACGCAGCAATGCAGCTCAAAACGCTTAGCCTAGC
CACACCCCACGGGAAACAGCAGTGATTAACCTTTAGCAATAAACGAAAGTTTAACTAAGCTATACTAAC
CCCAGGGTTGGTCAATTTCGTGCCAGCCACACCCTGGAGCTAGCAGCGGCCGCGGCCGCAAAAAAAAAA
AAAAAAAAAAAAAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAA
```

FIG. 13B (Example 22)
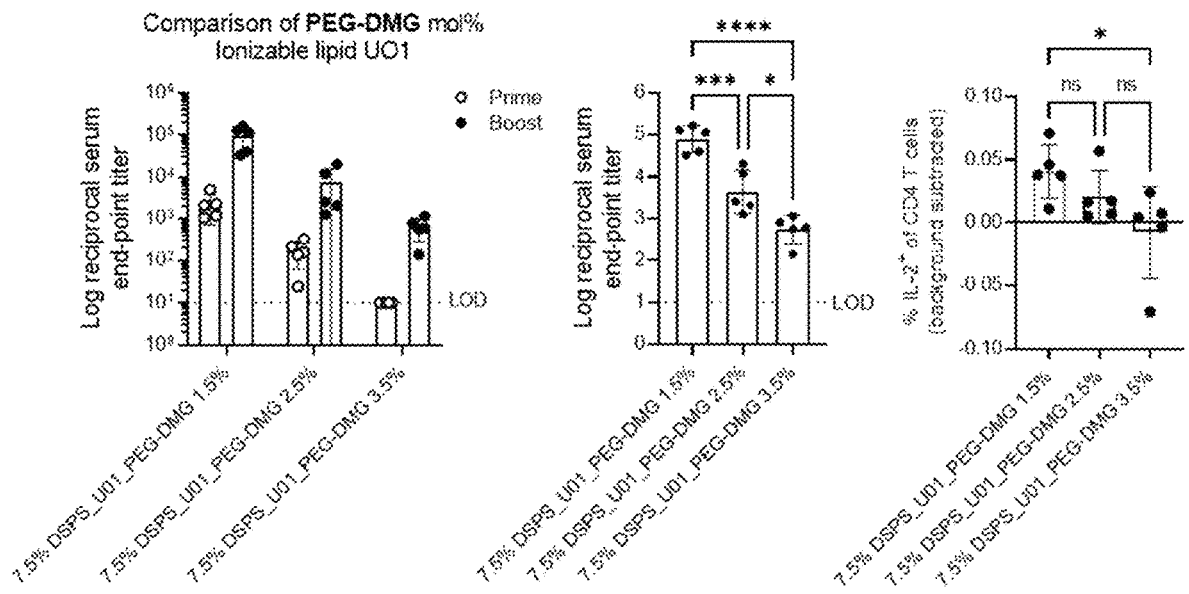
FIG. 13C (Example 22)
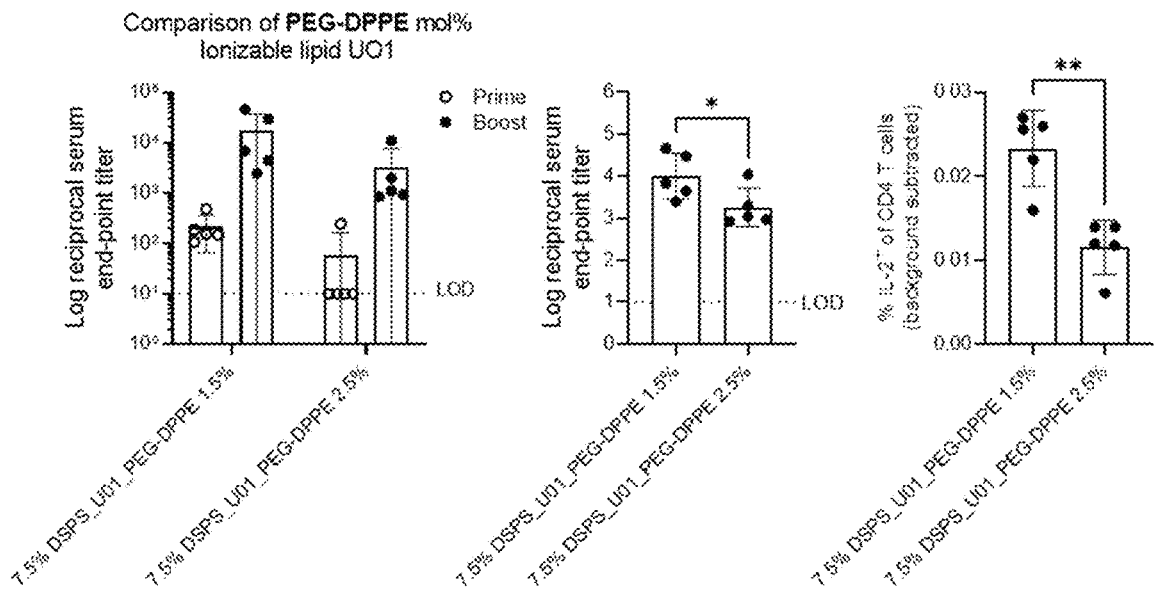

FIG. 13D (Example 22).
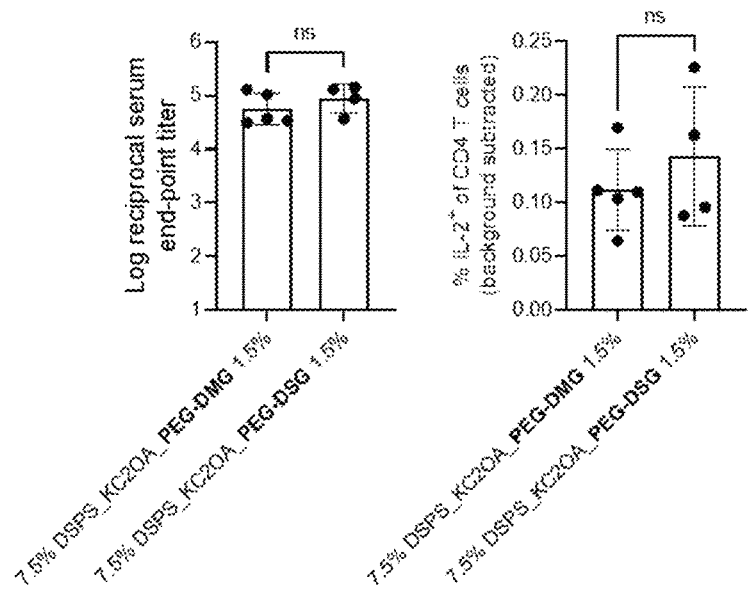
FIG. 13E (Example 22).
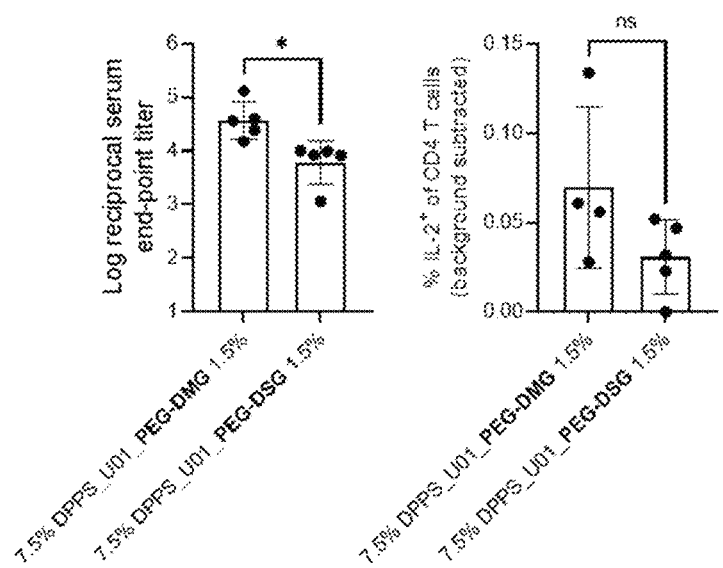

FIG. 13F (Example 22).
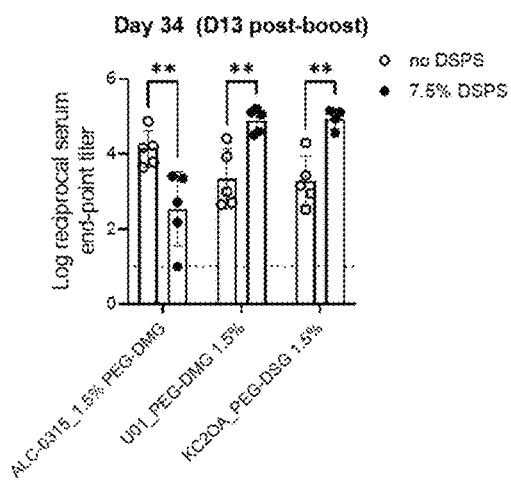
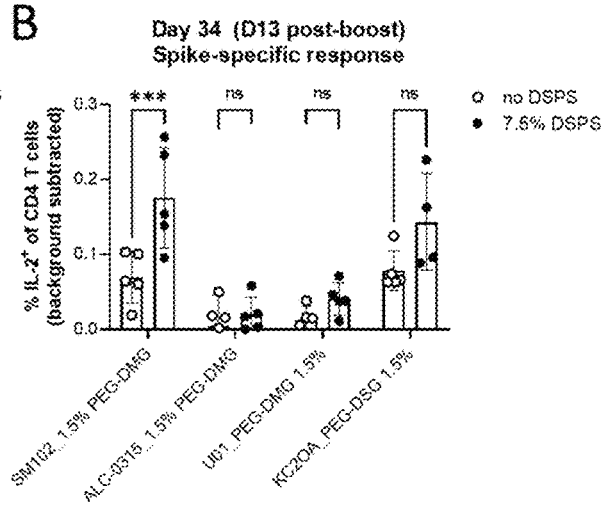
FIG. 13G (Example 22).
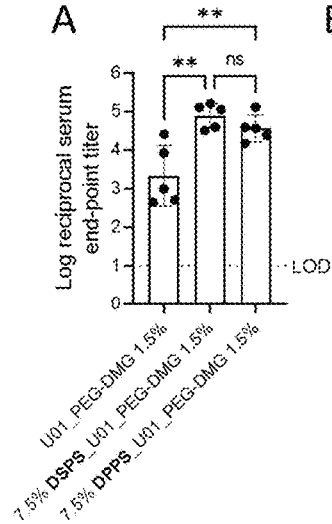
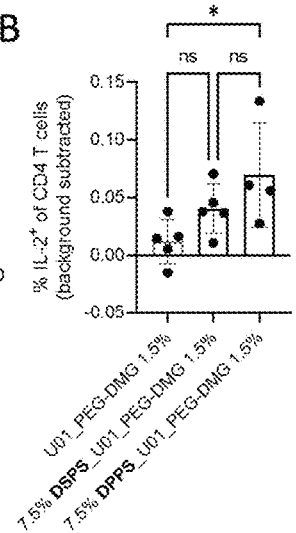

FIG. 14A (Example 23).
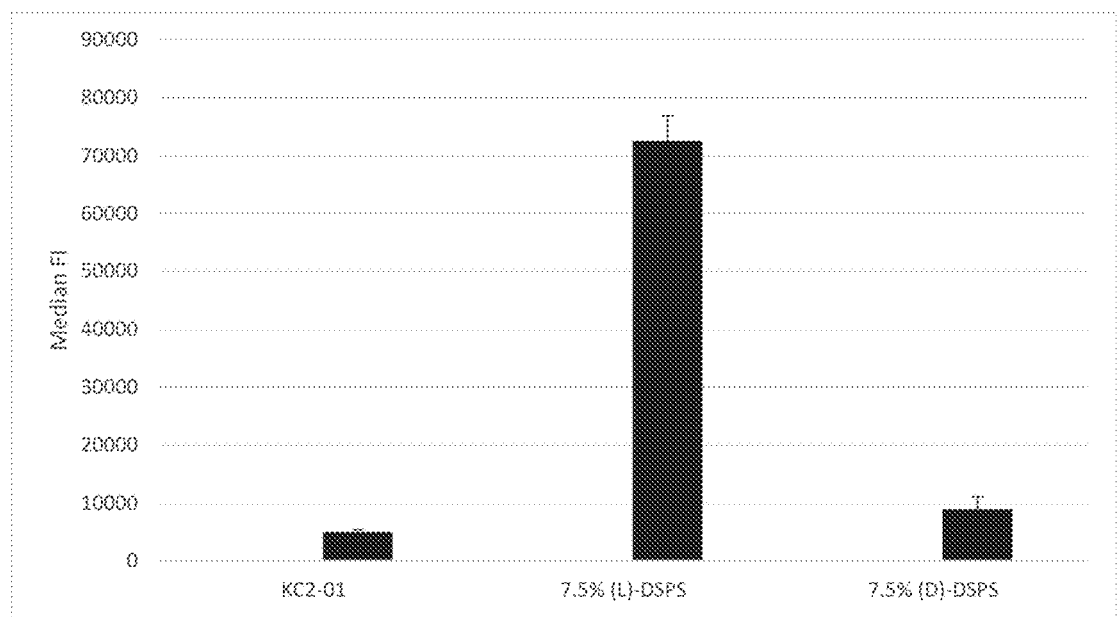
FIG. 14B (Example 23).
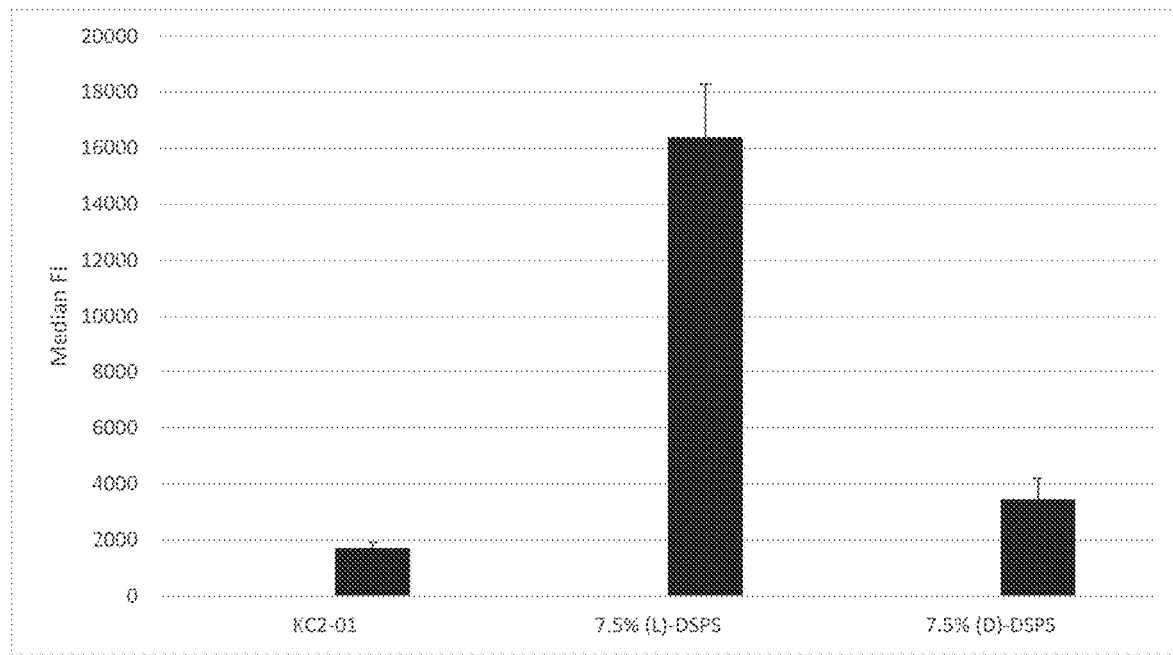

FIG. 15 (Example 24).
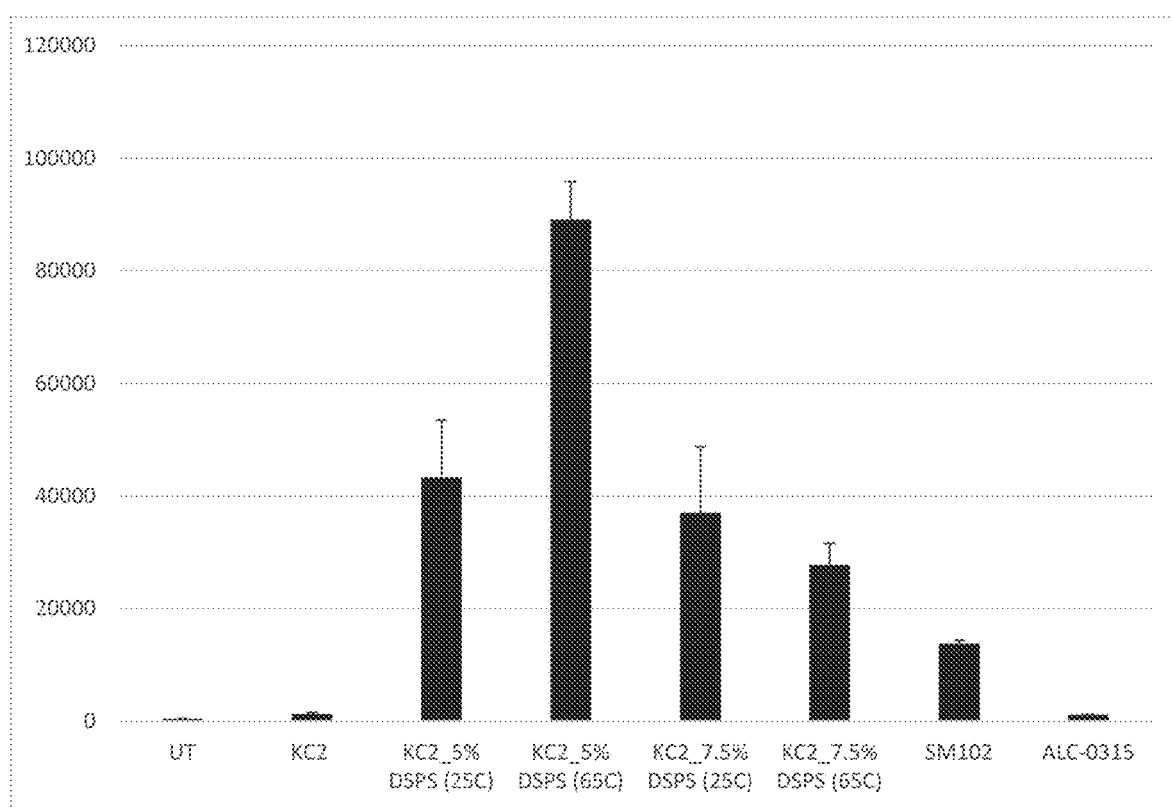

FIG. 16 (Example 25)
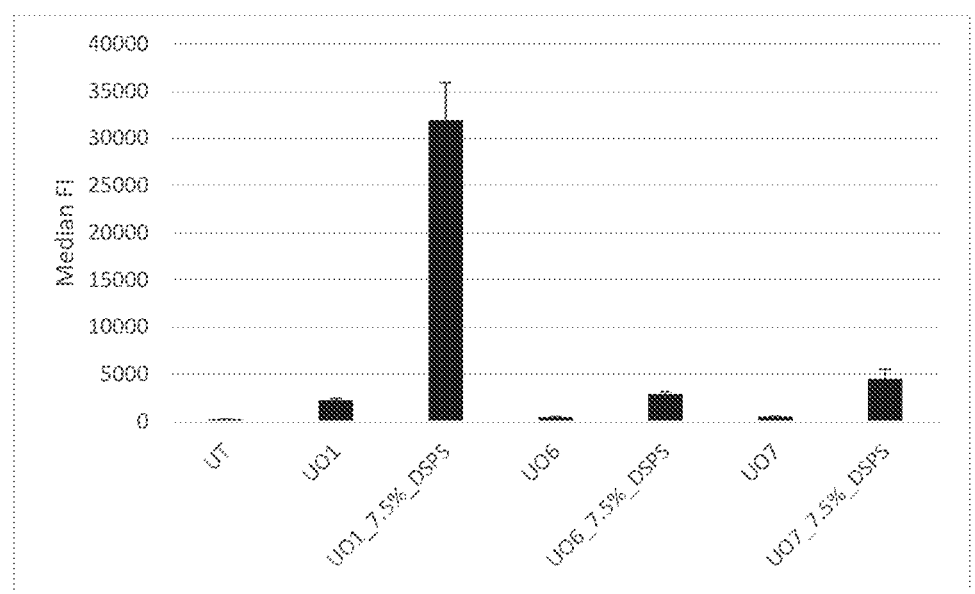

FIG. 17 (Example 26)
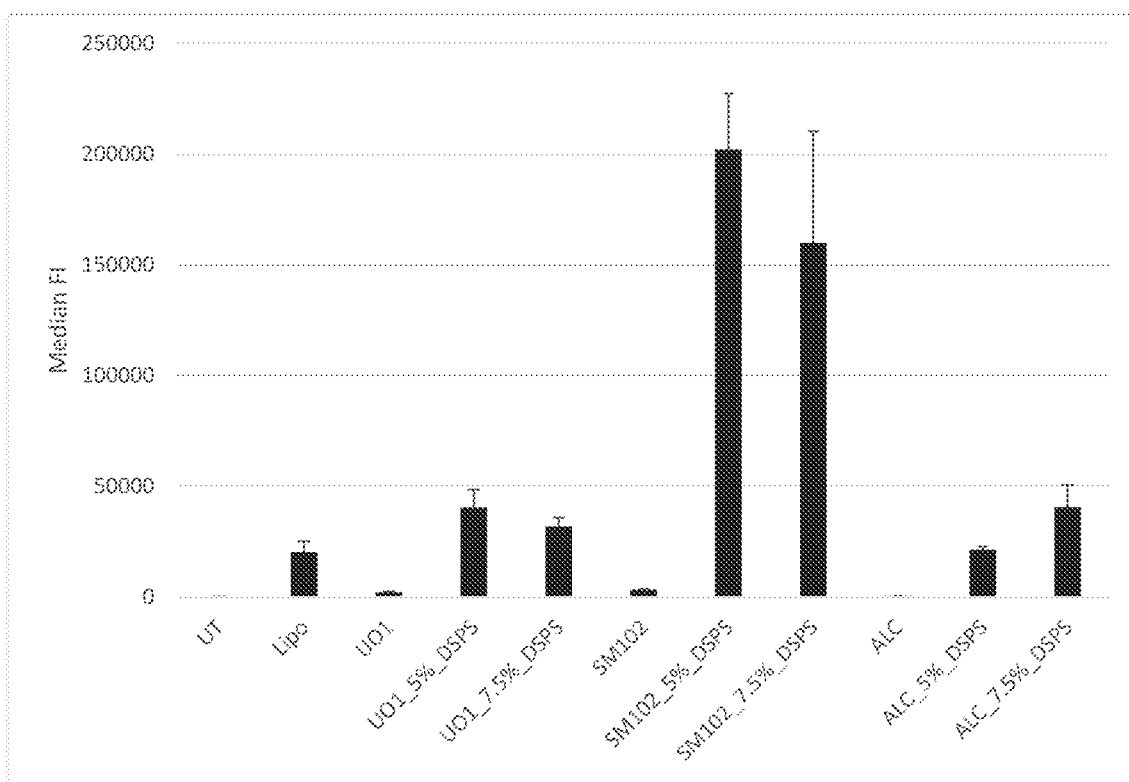

FIG. 18 (Example 29)
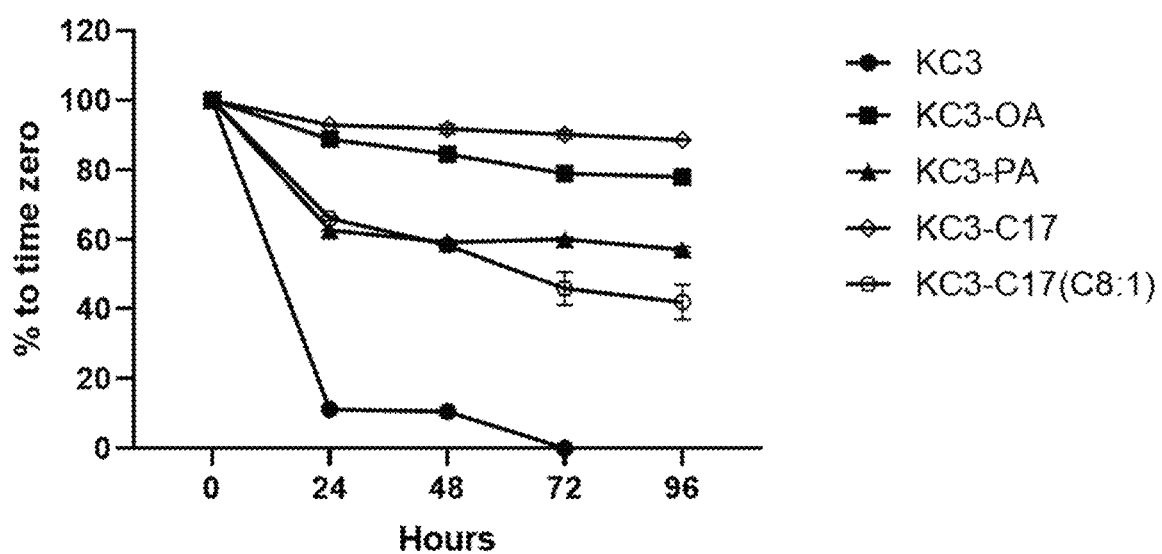

FIG. 19 (Example 30)
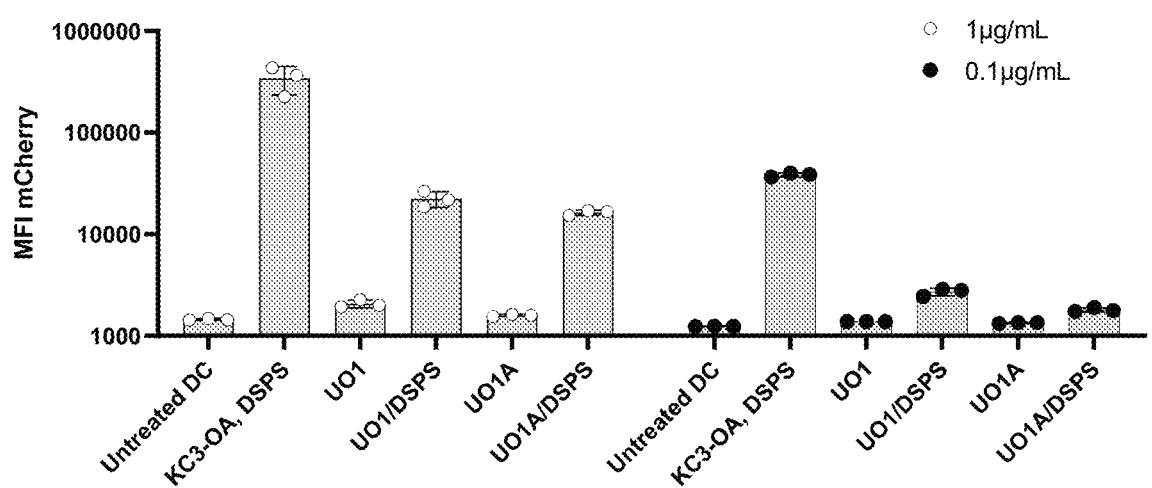

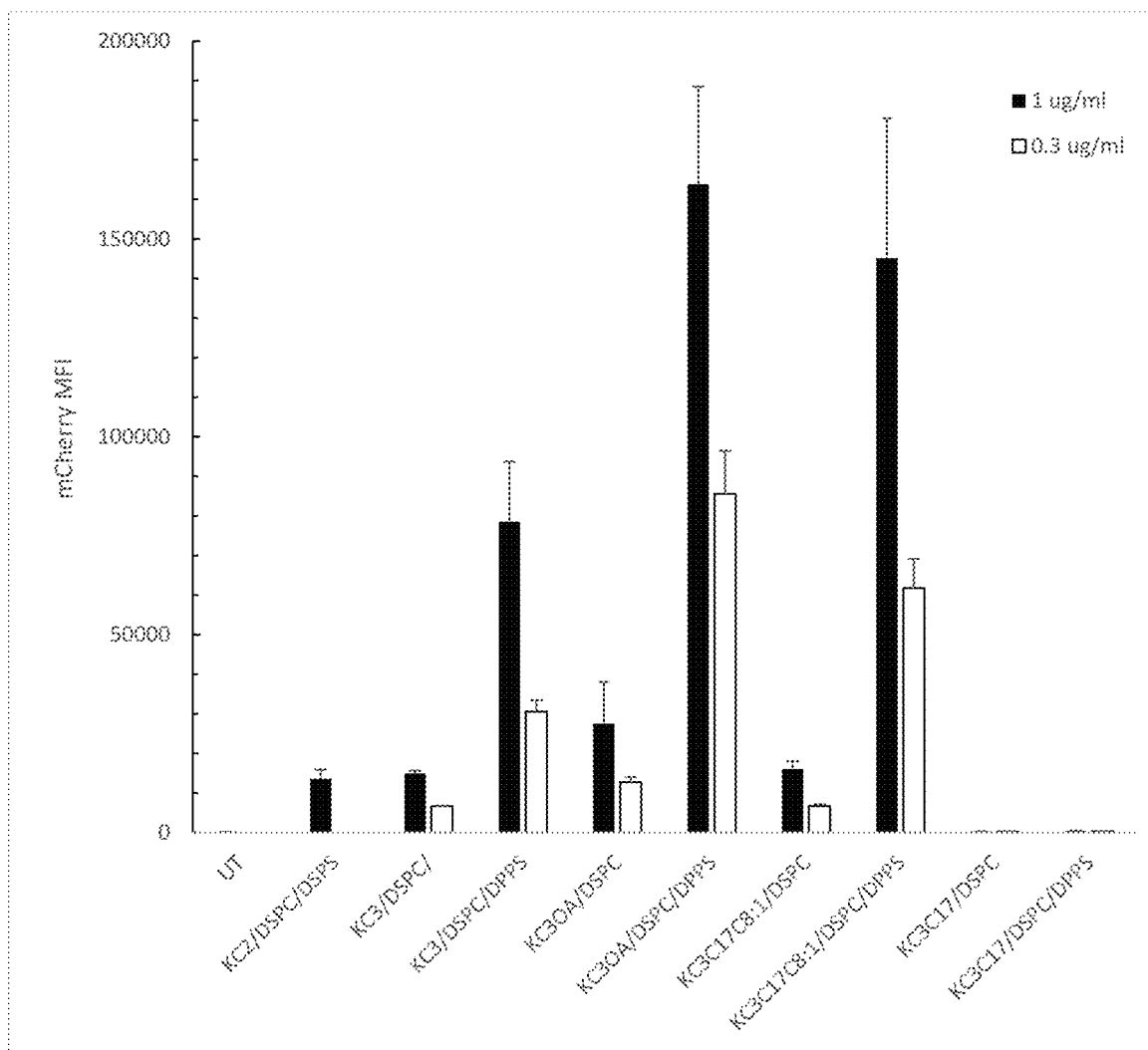
FIG. 20 (Example 31)

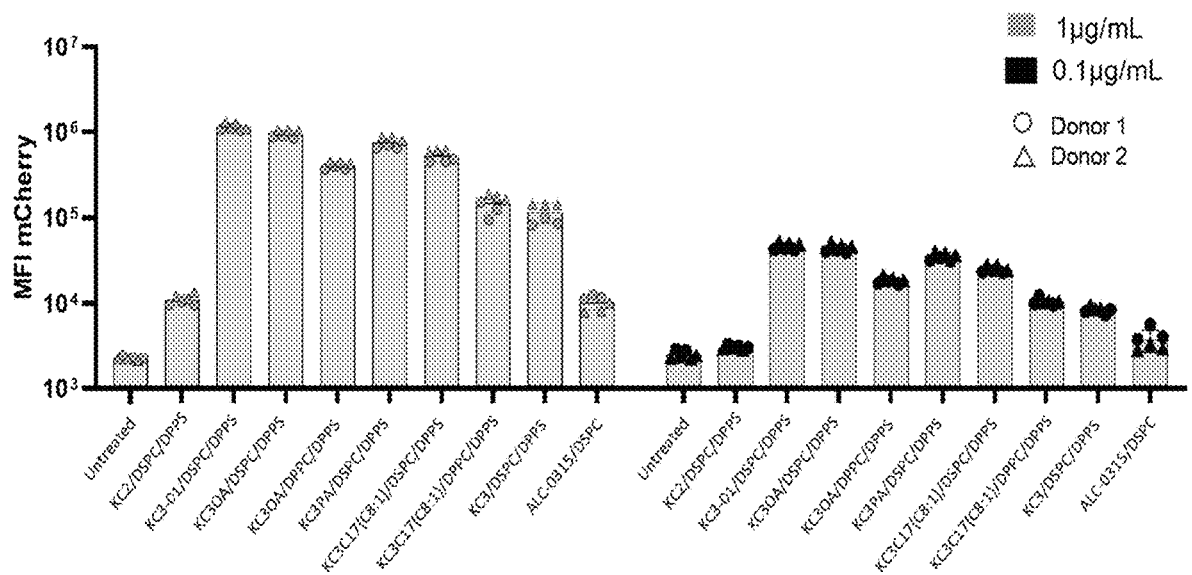
FIG. 21 (Example32)

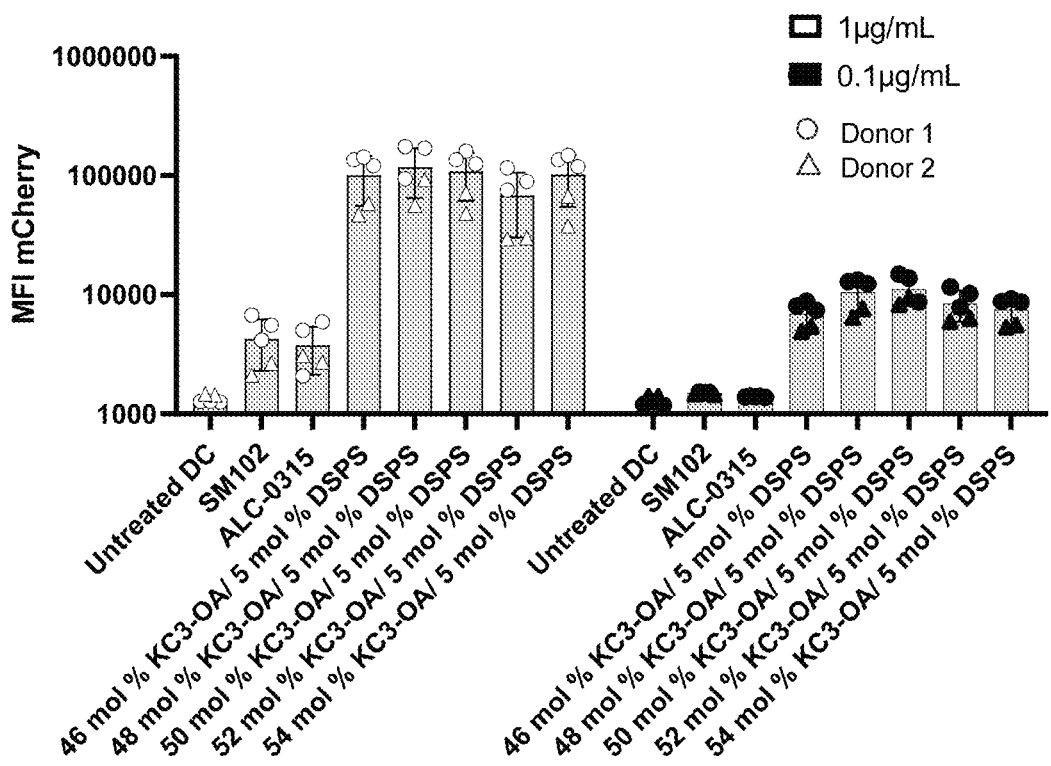
FIG. 22 (Example 33)

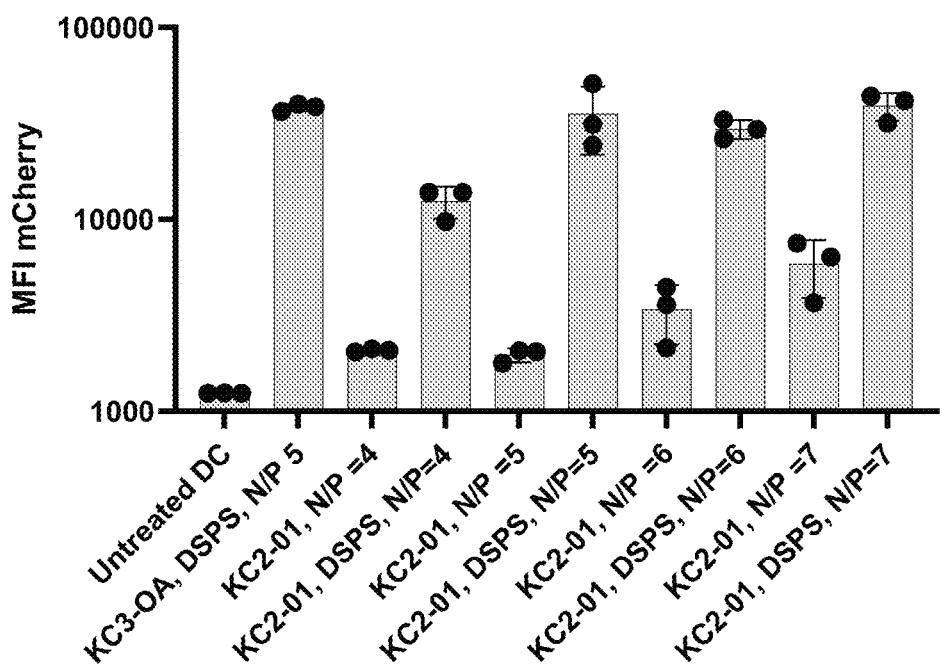
FIG. 23 (Example 34)

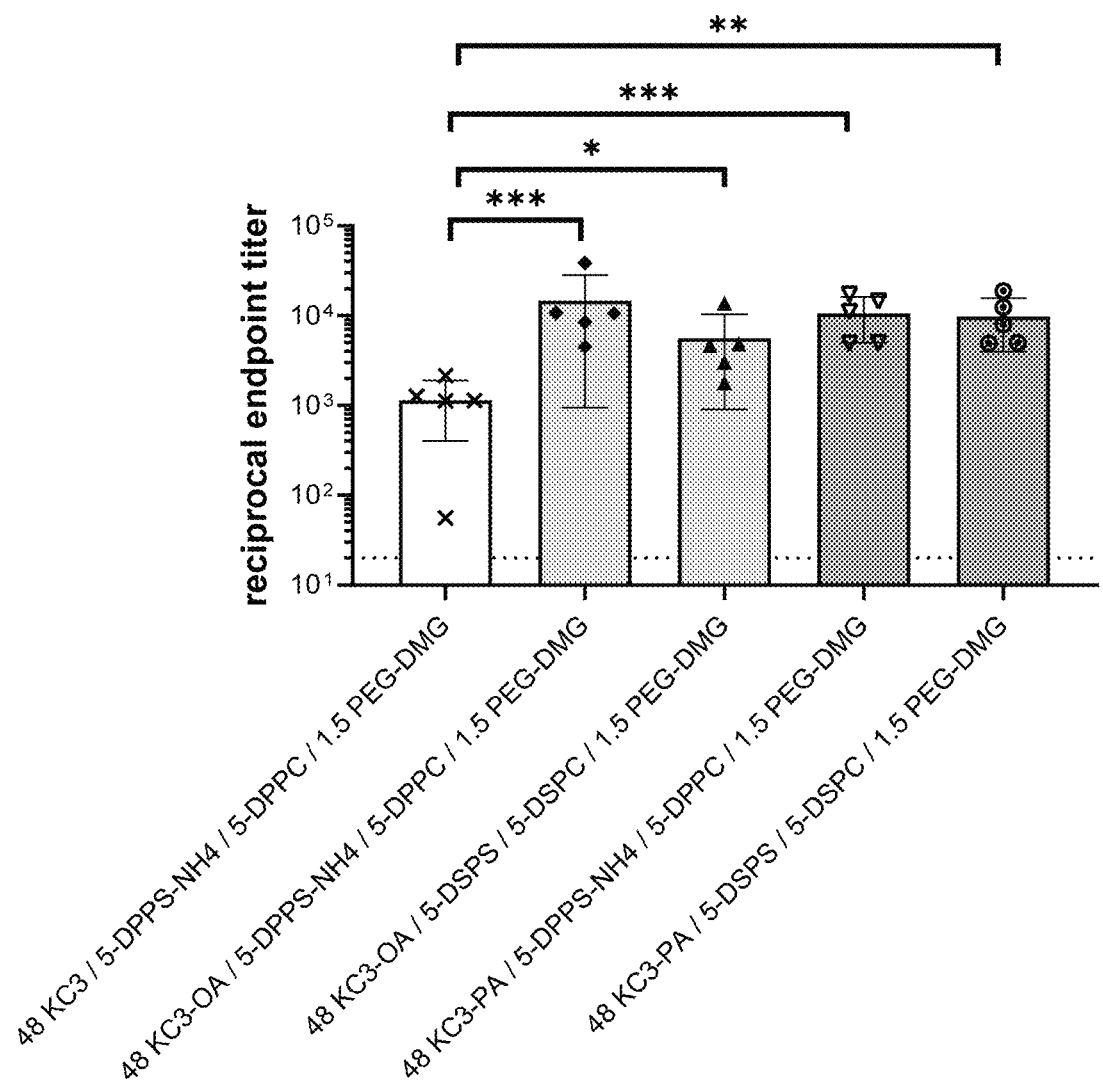
FIG. 24A (Example 35)

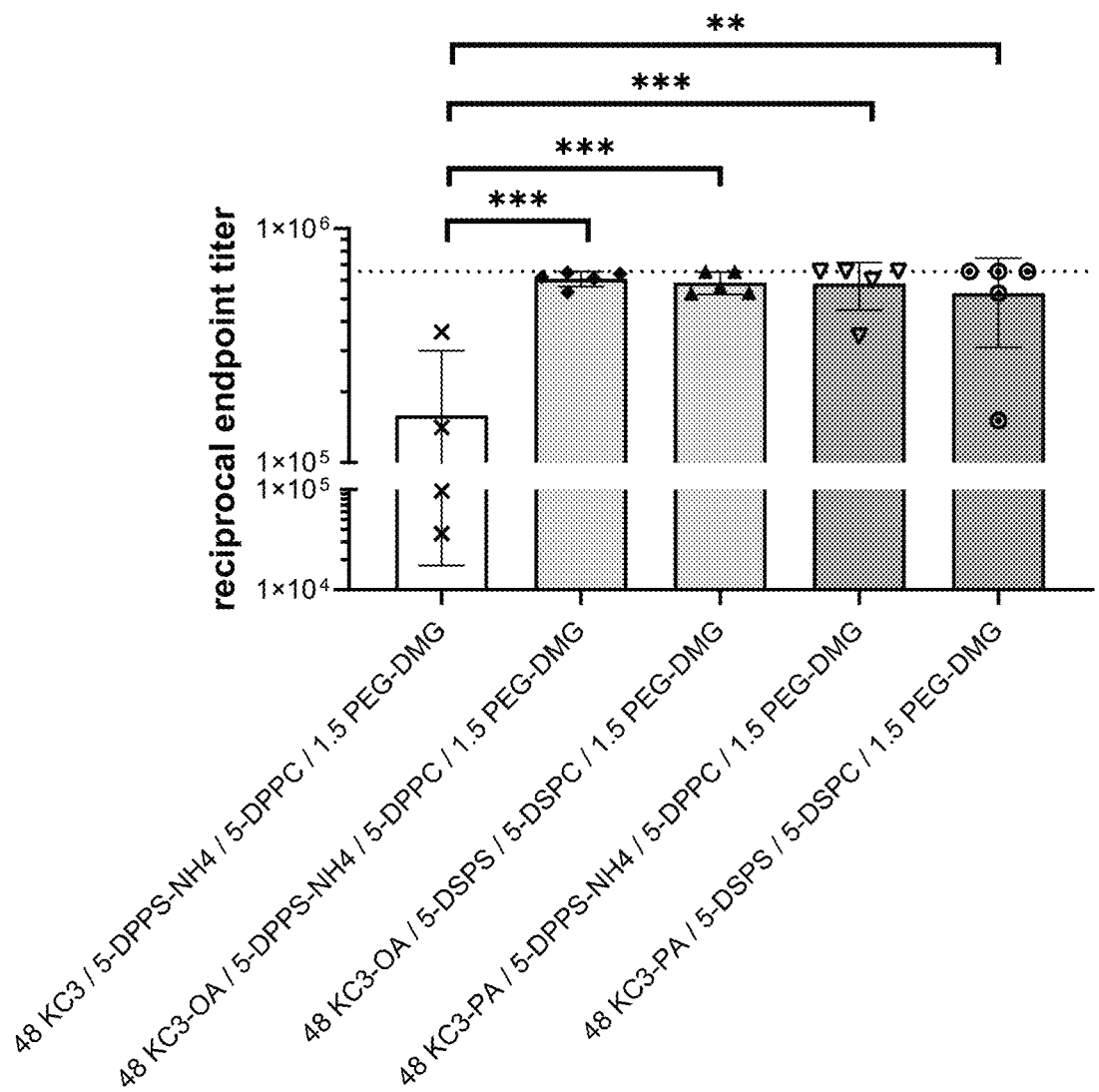
FIG. 24B (Example 35)

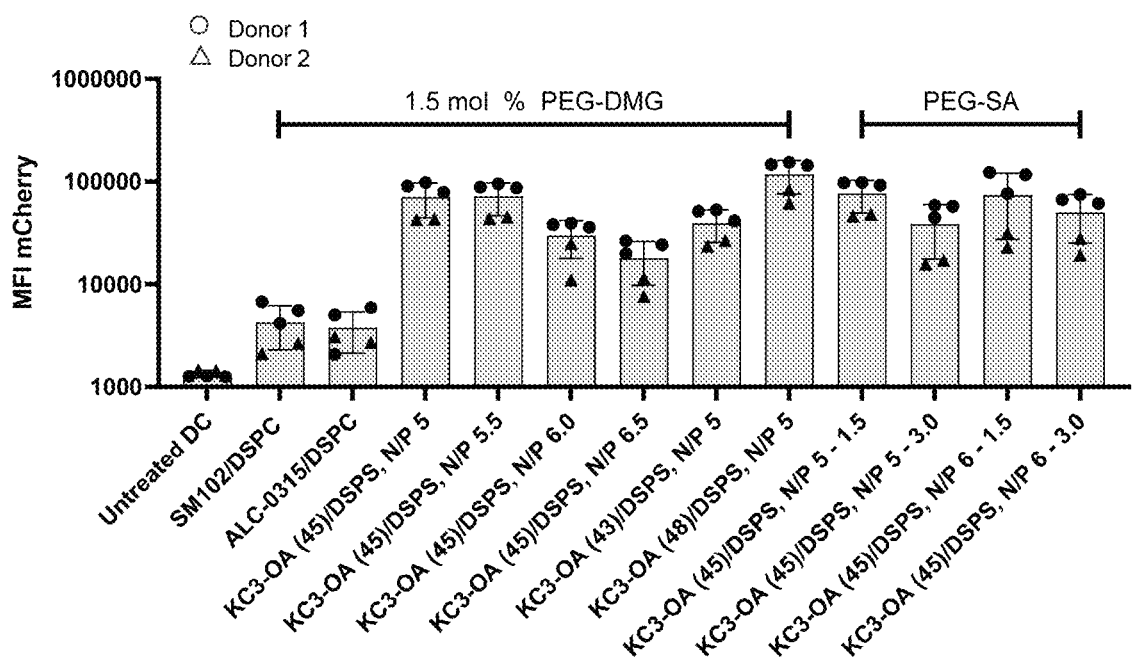
FIG. 25A (Example 38)

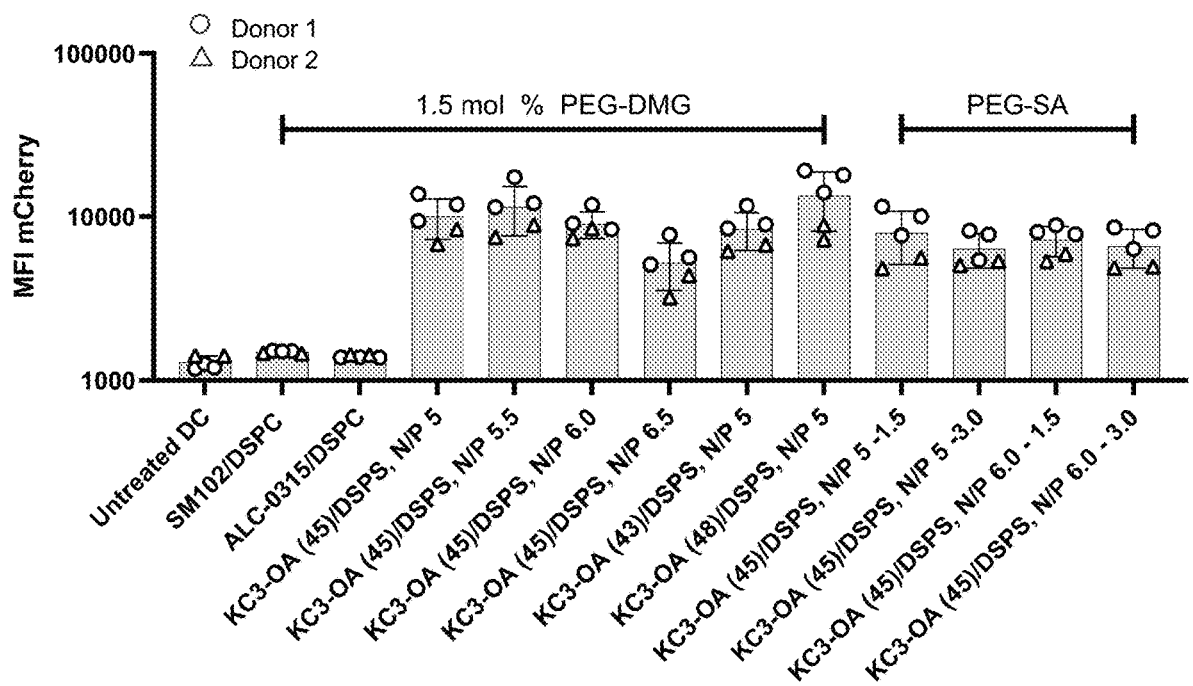
FIG. 25B (Example 38) – MS 148-152

FIG. 26A (Example 39)
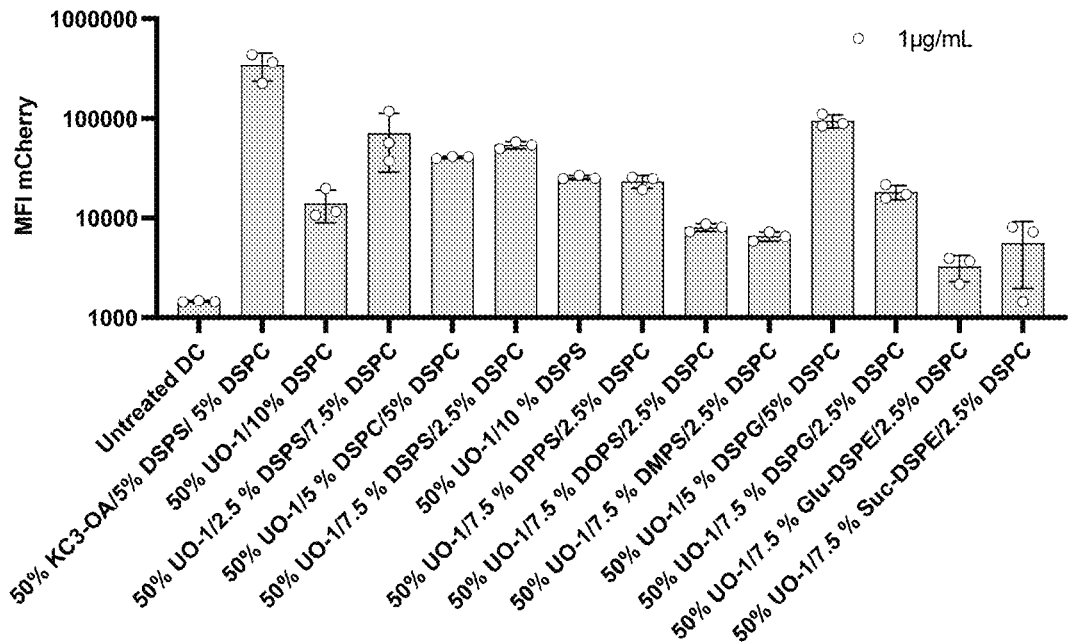
FIG. 26B (Example 39)
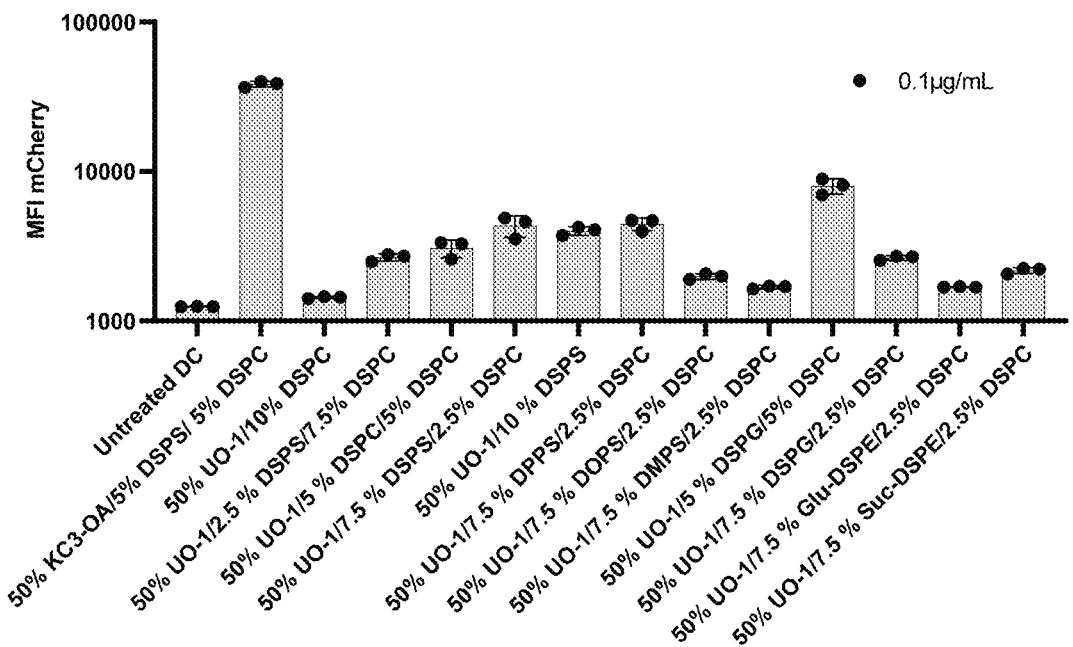

FIG. 27A (Example 40)
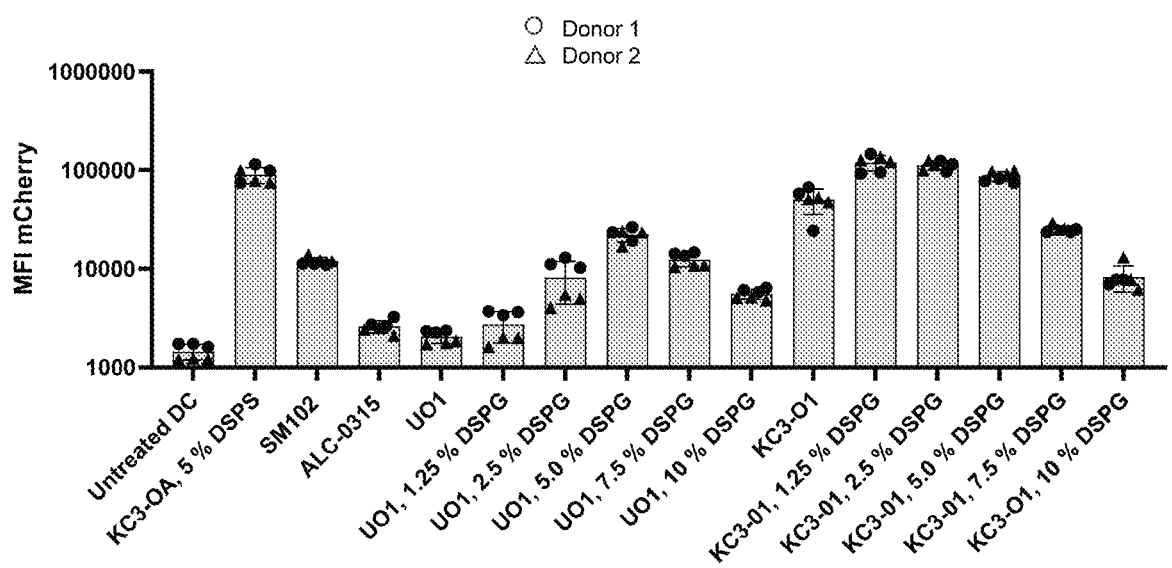
FIG. 27B (Example 40)
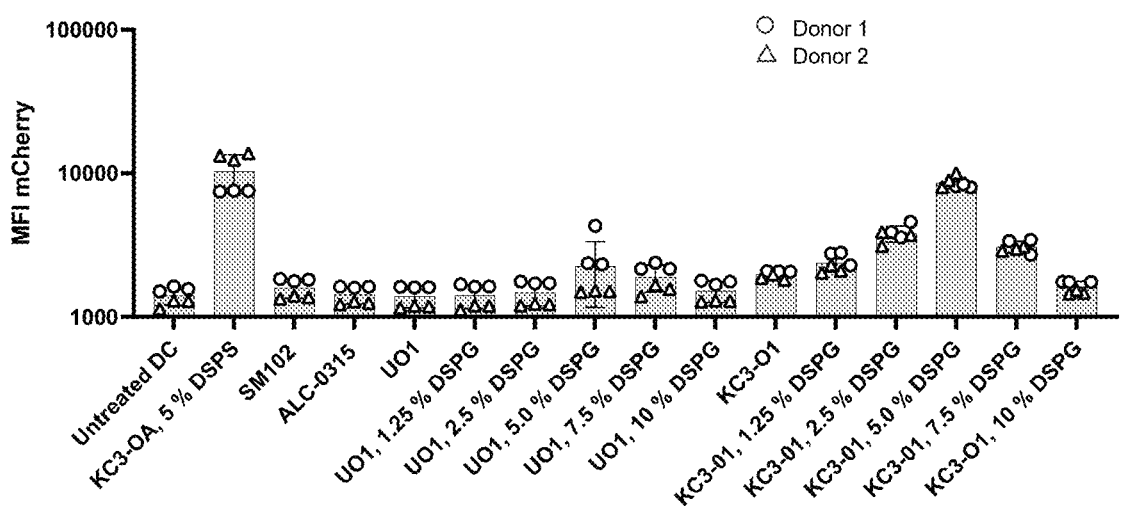

FIG. 28 (Example 42)
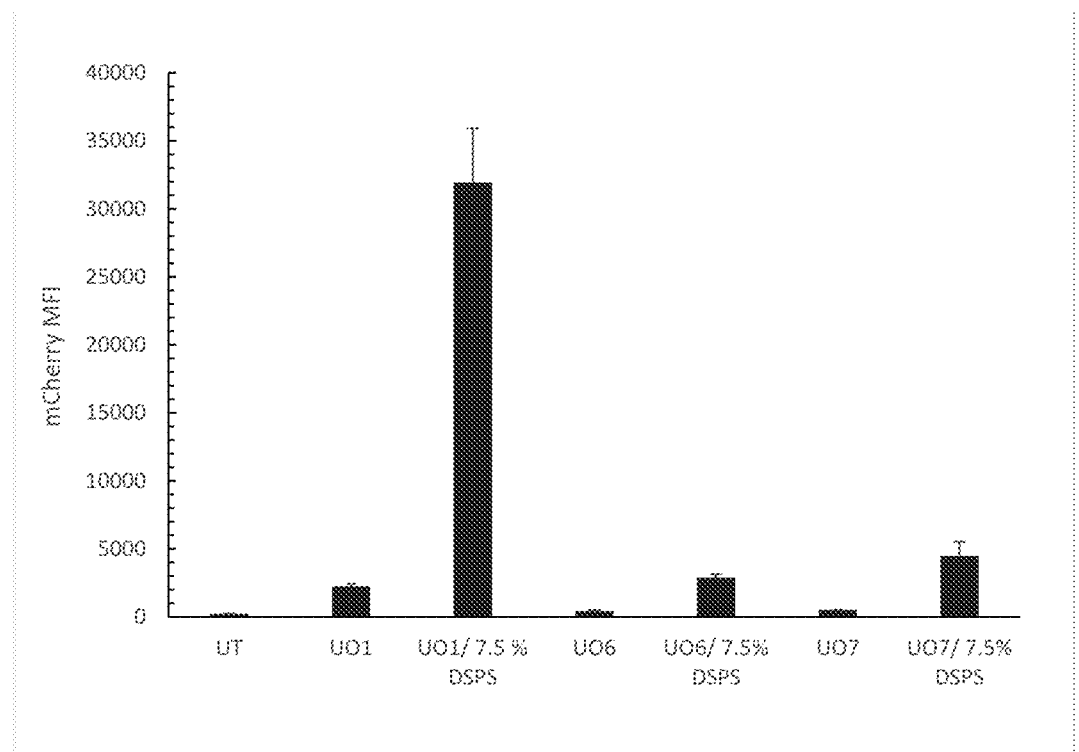

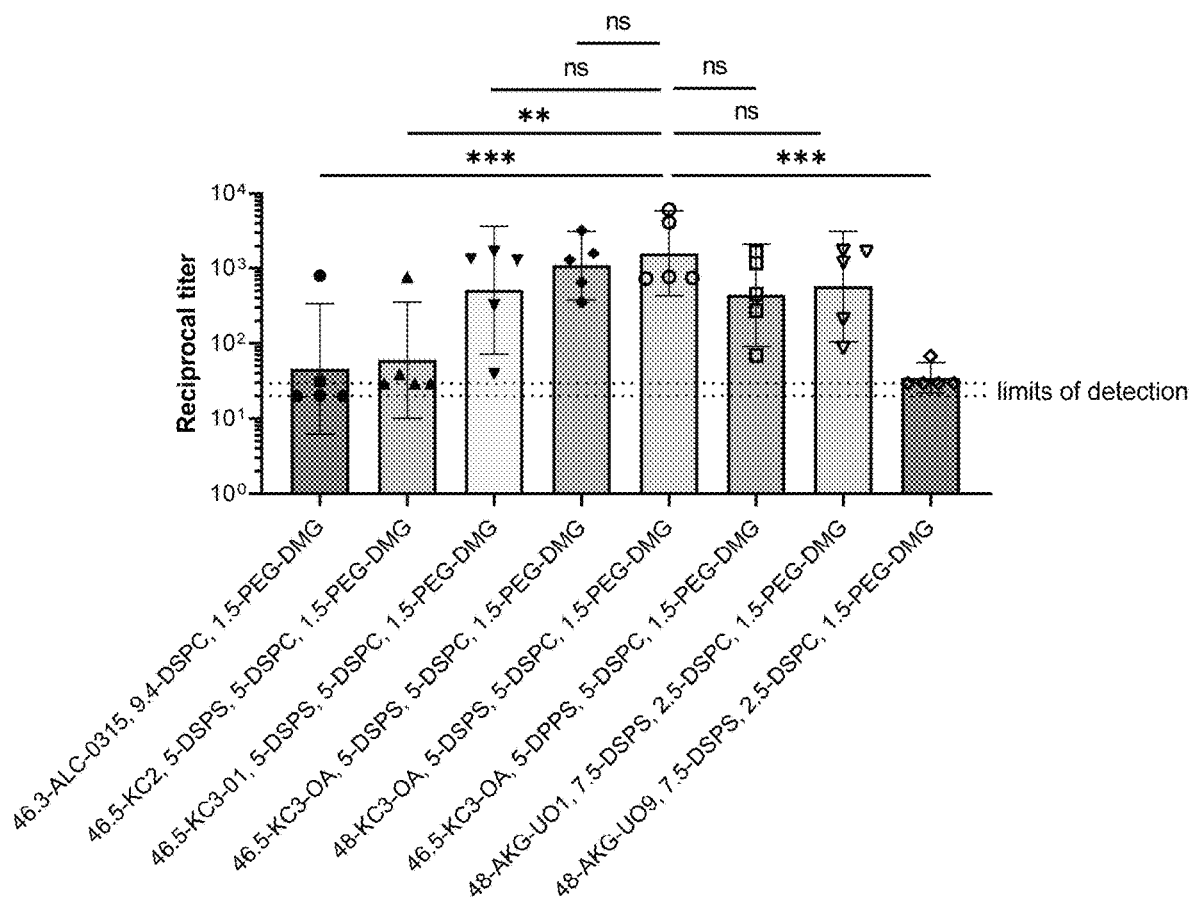
FIG. 29 (Example 43)

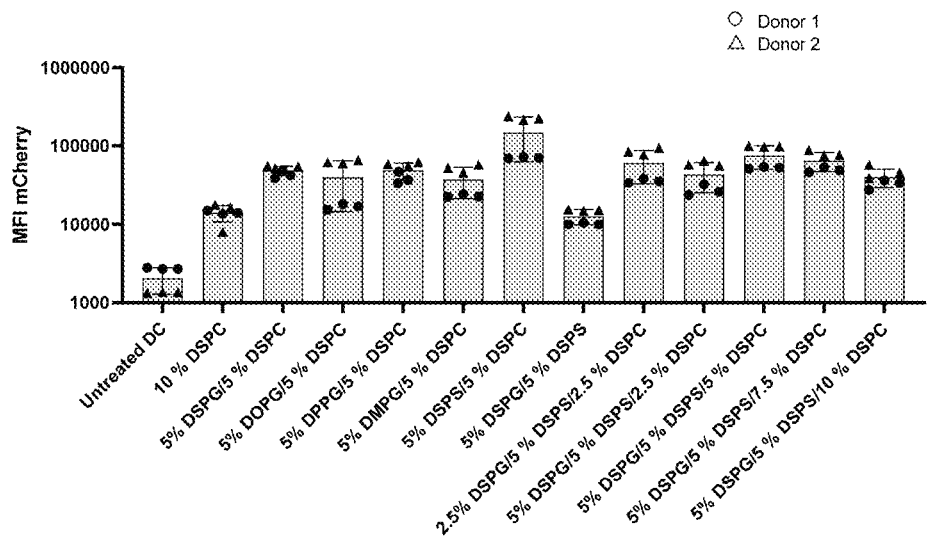
FIG. 30A (Example 44)
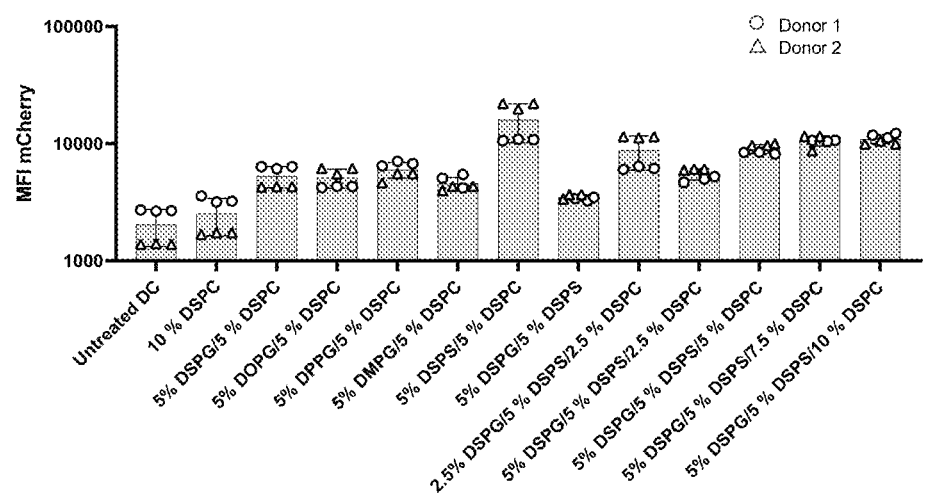
FIG. 30B (Example 44)

FIG. 31 (Example 45)
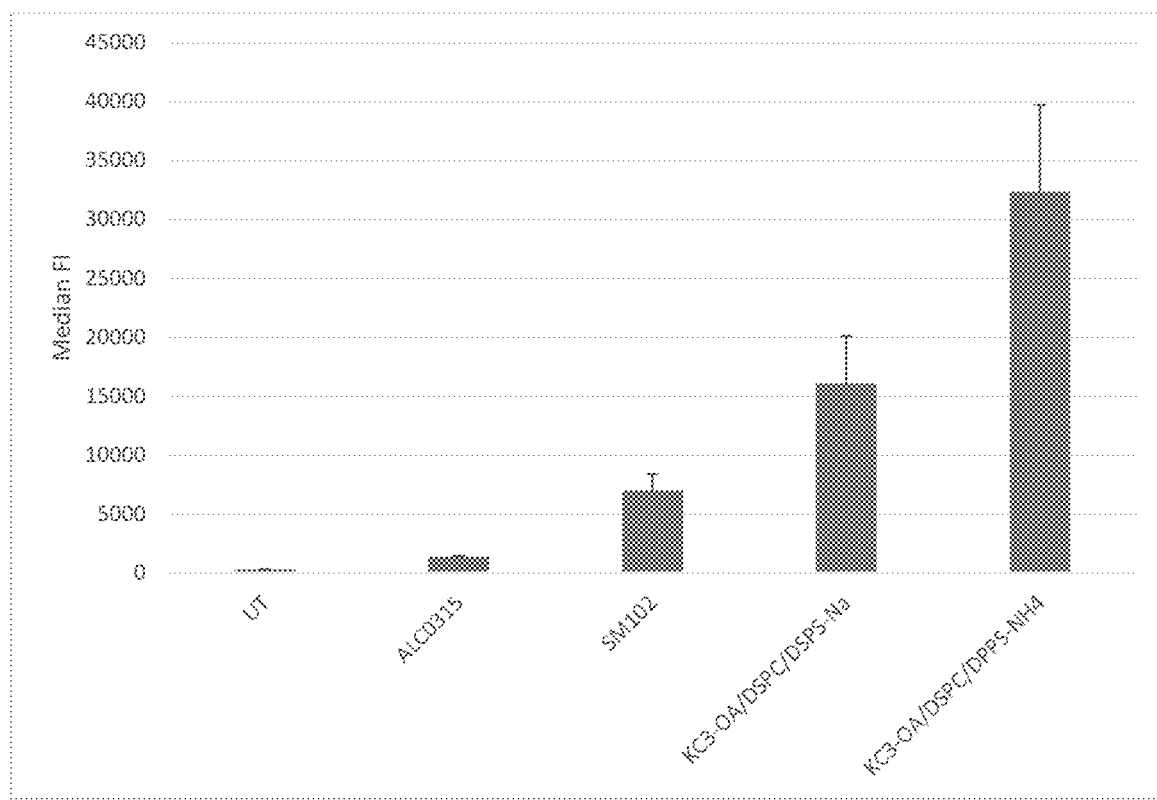

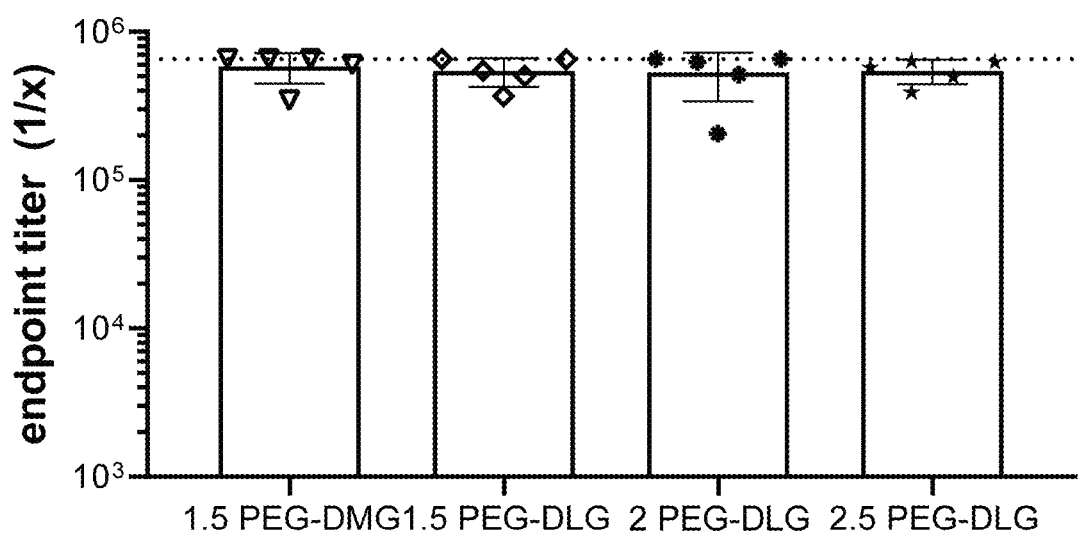
FIG. 40 (After boost)

FIG. 41A (all KC3-OA/5 % DPPS and 1 ug dose)
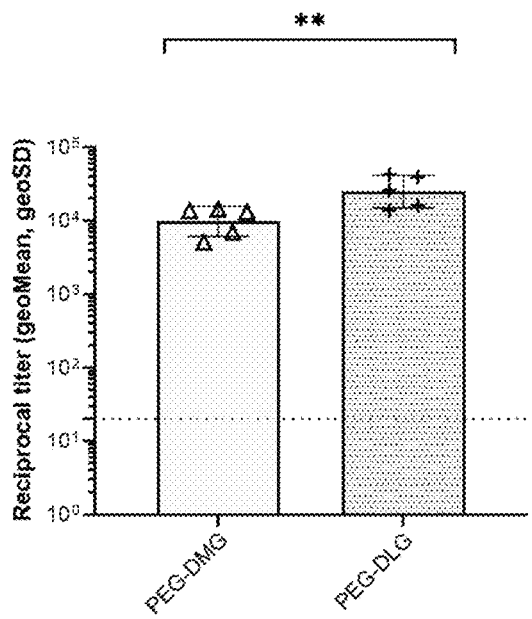
FIG. 41B (2 weeks post boost)
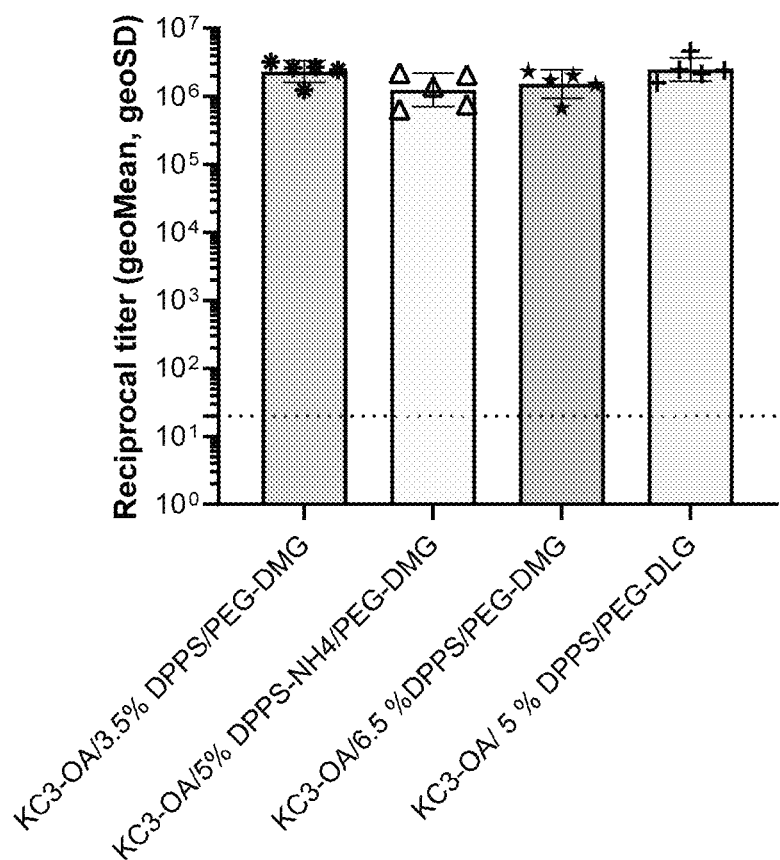

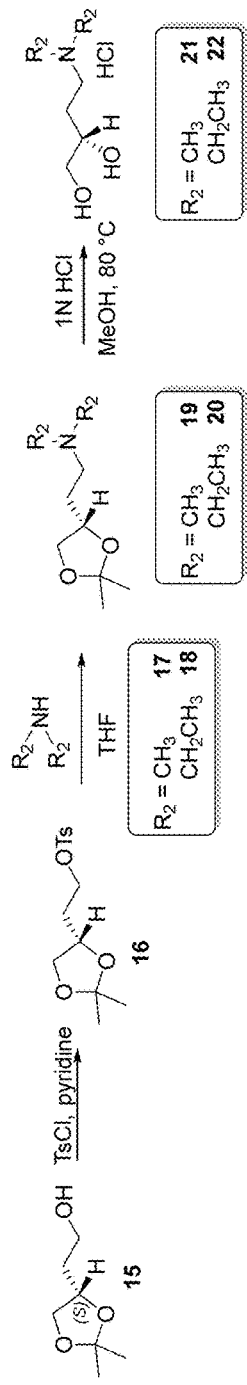
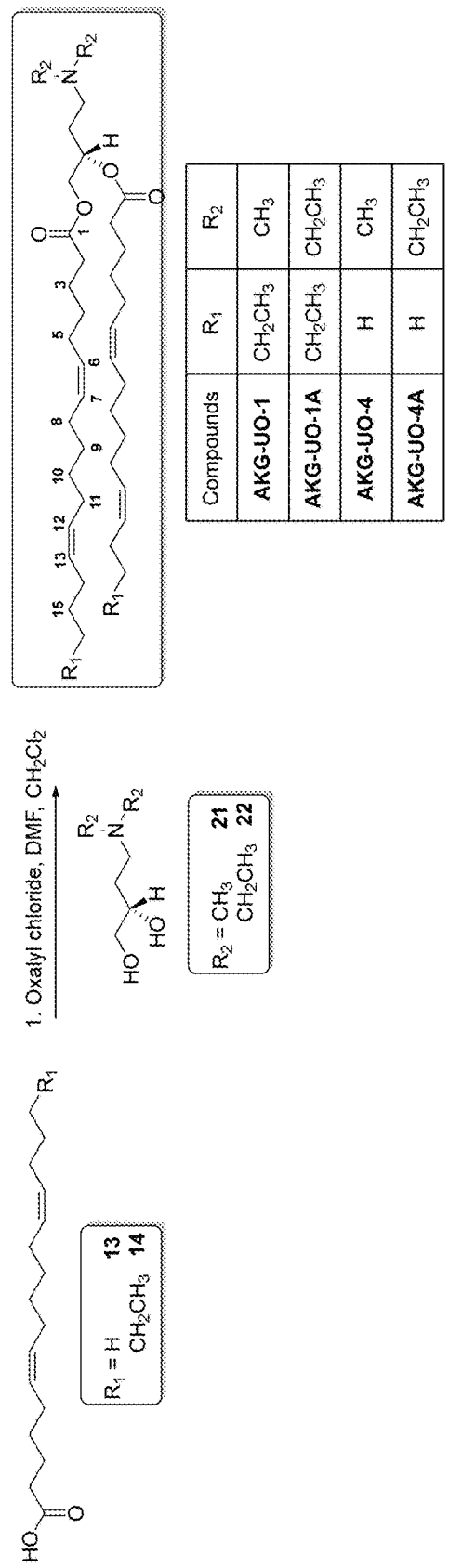
FIG. 47B

LIPID NANOPARTICLES FOR DELIVERY OF NUCLEIC ACIDS AND METHODS OF USE THEREOF

RELATED APPLICATIONS

This patent application claims the benefit of and priority to U.S. Provisional Patent Application No. 63/345,823, filed on May 25, 2022, and to U.S. Provisional Patent Application No. 63/346,197, filed on May 26, 2022, the entire contents of each of which are hereby incorporated herein by reference in their entireties.

REFERENCE TO SEQUENCE LISTING

This specification includes a sequence listing submitted herewith, which includes the file entitled 191016-010502.xml having the following size: 17,585 bytes which was created May 24, 2023, the contents of which are incorporated by reference herein.

FIELD

The present disclosure relates to cationic ionizable lipids and lipid nanoparticles (LNP). In some embodiments, a LNP comprising one or more cationic ionizable lipid(s) is useful for delivery of a nucleic acid compound, for dendritic cell targeting or methods of using these LNP compositions as vaccines. In some embodiments, a LNP can comprise bioreducible ionizable cationic lipids or unconjugated polyolefinic ionizable cationic lipids.

BACKGROUND

Lipid nanoparticles (LNP) are used for the delivery of therapeutic nucleic acids to cells. For example, LNP pharmaceutical compositions are employed in vaccines to deliver mRNA therapeutics. LNP formulations typically include an ionizable cationic lipid (ICL). However, it is known in the art that certain ICL compounds are undesirably sensitive to oxidation during storage. Therefore, there is a need for improved ICL compounds with improved stability to oxidative degradation while in storage, while also providing desired transfection activity or potency in cells when incorporated in a LNP with a therapeutic agent such as a nucleic acid.

LNP compositions, including stable nucleic acid lipid particle (SNALP) compositions, are useful for delivery of nucleic acid therapies for various infectious diseases. Infectious diseases such as tuberculosis, HIV/AIDS, malaria, and COVID-19 represent significant challenges to human health. Mycobacteria, for example, is a genus of bacteria responsible for tuberculosis (TB). According to the World Health Organization, worldwide, TB is one of the top 10 causes of death and the leading cause of death from a single infectious agent. Despite current best efforts, there have been significant challenges in the development of effective vaccines for the prevention of many infectious diseases. New efforts in the identification of individual or combinations of antigenic peptides has helped improved the efficiency of vaccines. Nonetheless, significant opportunities remain in the engineering of adjuvants to help efficiently deliver and present these antigenic sequences to professional antigen presenting cells, like dendritic cells. mRNA coding for antigenic peptides or proteins combined with ionizable cationic lipid nanoparticles represent a particularly promising strategy in the development of a vaccine. There is a need for safe and effective therapies comprising LNP pharmaceutical compositions for delivery of mRNA for treatment and prevention of various diseases, including vaccine compositions.

SUMMARY

Aspects of the disclosure relate to a lipid nanoparticle (LNP) vaccine composition comprising: (a) a nucleic acid; (b) an ionizable cationic lipid at a N/P ratio of 3 to 8 relative to the nucleic acid wherein the ionizable lipid has the chemical structure:

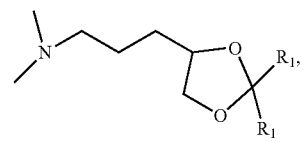

wherein $R_1$ is alkyl group of $C_{15}$-$C_{19}$ containing one or two olefins, and wherein the ionizable cationic lipid is present in the LNP vaccine composition in a total amount of 40-65 mol % of the total lipid content of the LNP composition, and the ionizable cationic lipid is optionally selected from the group DLin-KC3-DMA, KC3-01, KC3-OA, KC3-PA, KC3-C17 (8:1), KC3-C15 (C8:1) Compound 3 (Table 1A), Compound 8 (Table 1A); (c) a sterol in a total amount of 25-mol % of the total lipid content of the LNP composition; (d) one or more phospholipids in a total amount of phospholipids of 5-25 mol % of the total lipid content of the LNP composition; and (e) a conjugated lipid in a total amount of 0.5-2.5 mol % of the total lipid content of the LNP composition.

In some embodiments, the one or more phospholipids comprises a phosphatidylserine (PS) lipid in a total amount of 2.5-10 mol % of the total lipid content of the LNP composition. In some embodiments, the PS-lipid is DSPS or DPPS.

In some embodiments, the second phospholipid is selected from the group consisting of: DSPC, HSPC, DPPC, and sphingomyelin.

In some embodiments, the ionizable cationic lipid comprises either monounsaturated alkyl chains or di-unsaturated alkyl chains, wherein the olefins are separated by at least two methylene groups.

In some embodiments, the ionizable cationic lipid is selected from the group consisting of: KC3-01, KC3-OA, KC3-PA, KC3-C17 (8:1), KC3-C15 (C8:1), and Compound 8 (Table 1A).

In some embodiments, the composition has an N/P ratio of 5-6 relative to the nucleic acid.

In some embodiments, the nucleic acid is an RNA. In some embodiments, the nucleic acid is mRNA. In some embodiments, the nucleic acid is a chemically modified RNA. In some embodiments, the nucleic acid is modified with N-methylpseudouridine.

Other aspects of the disclosure relate to a lipid nanoparticle (LNP) composition comprising: (a) a nucleic acid; (b) an ionizable cationic lipid at a N/P ratio of 3 to 8 relative to the nucleic acid wherein the ionizable lipid has the chemical structure:

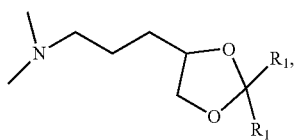

wherein $R_1$ is alkyl group of $C_{15}$-$C_{19}$ containing one or two olefins, and wherein the ionizable cationic lipid is present in the LNP composition in a total amount of 40-65 mol % of the total lipid content of the LNP composition, and the ionizable cationic lipid is optionally selected from the group Compound 3 (Table 1A), Compound 8 (Table 1A), DLin-KC3-DMA, KC3-01, KC3-OA, KC3-PA, KC3-C17 (8:1), and KC3-C15 (C8:1); (c) a sterol in a total amount of 25-45 mol % of the total lipid content of the LNP composition; (d) one or more phospholipids in a total amount of phospholipids of 5-25 mol % of the total lipid content of the LNP composition, and comprising a dipalmitoylphosphatidylserine (DPPS) lipid in a total amount of 2.5-10 mol % of the total lipid content of the LNP composition; and (e) a conjugated lipid in a total amount of 0.5-2.5 mol % of the total lipid content of the LNP composition.

In some embodiments, a second phospholipid is selected from the group consisting of: DSPC, HSPC, and sphingomyelin.

In some embodiments, the ionizable cationic lipid is at an N/P ratio of 5-6 relative to the nucleic acid.

In some embodiments, the ionizable cationic lipid contains either two monounsaturated alkyl chains or two di-unsaturated alkyl chains, and wherein the olefins are separated by at least two methylene groups.

In some embodiments, the ionizable cationic lipid is selected from the group KC3-01, KC3-OA, KC3-PA, KC3-C17 (8:1), KC3-C15 (C8:1), and Compound 8 (Table 1A).

In some embodiments, the ionizable cationic lipid is 3-((S)-2,2-di((Z)-octadec-9-en-1-yl)-1,3-dioxolan-4-yl)-N,N-dimethylpropan-1-amine (KC3-OA).

In some embodiments, the nucleic acid is an mRNA. In some embodiments, the mRNA is chemically modified with N-methylpseudouridine.

Aspects of the disclosure relate to a nucleic acid lipid nanoparticle (LNP) composition comprising: (a) a nucleic acid; (b) an ionizable cationic lipid at a N/P ratio of 3 to 8 relative to the nucleic acid in a total amount of 40-65 mol % of the total lipid content of the LNP composition; (c) a sterol in a total amount of 25-45 mol % of the total lipid content of the LNP composition; (d) one or more phospholipids in a total amount of phospholipids of 5-25 mol % of the total lipid content of the LNP composition; and (e) a conjugated lipid in a total amount of 0.5-2.5 mol % of the total lipid content of the LNP composition comprising a PEG-lipid having a poly(ethylene glycol) chain terminally attached to a linking moiety and two hydrocarbon chains terminally attached to the same linking moiety, wherein the hydrocarbon chains are saturated $C_{12}$-chains independently selected from n-dodecyl (lauryl) group and n-dodecanoyl (lauroyl) group. In some embodiments, the linking moiety is glyceryl group, N-oxycarbonyl glycerophoshoryl ethanolaminocarbonyl group, oxycarbonylamide group, or oxyacetamide group. In some embodiments, the poly(ethyene glycol) chain is methoxy-poly(ethyene glycol) with an average molecular weight of 2000. In some embodiments, the PEG-lipid is mPEG-1,2-dilauroylglycerol (PEG-DLG), mPEG-1,2-dilaurylglycerol (PEG-DLG), PEG-1,2-dilaurylglycerol, PEG-DLPE, PEG-oxycarbonyl-N,N-didodecylamide, or mPEG-N,N-didodecylacetamide.

In some embodiments, the LNP has the z-average particle size of 60-150 nm and is freeze-thaw stable.

In some embodiments, the one or more phospholipids comprise a phosphatidylserine (PS) lipid in a total amount of 2.5-10 mol % of the total lipid content of the LNP composition, and wherein the LNP composition comprises a phosphatidylserine (PS) lipid in a total amount of 2.5-mol % of the total lipid content of the LNP composition.

Aspects of the disclosure relate to a nucleic acid lipid nanoparticle (LNP) human vaccine composition comprising: (a) a nucleic acid; (b) an ionizable cationic lipid at a N/P ratio of 3 to 8 relative to the nucleic acid in a total amount of 40-65 mol % of the total lipid content of the LNP composition; (c) a sterol in a total amount of 25-45 mol % of the total lipid content of the LNP composition; (d) one or more phospholipids in a total amount of phospholipids of 5-25 mol % of the total lipid content of the LNP composition, and comprising a phosphatidylglycerol (PG) in a total amount of 1.0-10 mol % of the total lipid content of the LNP composition; and (e) a conjugated lipid in a total amount of 0.5-2.5 mol % of the total lipid content of the LNP composition.

In some embodiments, the ionizable cationic lipid is selected from the group consisting of: KC3-01, KC3-OA, KC3-PA, KC3-C17 (8:1), KC3-C15 (C8:1), and Compound 8 (Table 1A). In some embodiments, the sterol is cholesterol; and the phosphatidylglycerol (PG) is an anionic phospholipid selected from the group consisting of: distearoylphosphatidylglycerol (DSPG) and dipalmitoyphosphatidylglycerol (DPPG).

In some embodiments, the nucleic acid is mRNA and the ionizable cationic lipid is present at a N/P ratio of 4 to 7 relative to the nucleic acid.

In some embodiments, the conjugated lipid is selected from PEG-DMG, PEG-DLG, and PEG-DLPE.

In some embodiments, the one or more phospholipids comprise a phospholipid selected from the group consisting of: distearoylphosphatidylcholine (DSPC) and hydrogenated soy phosphatidylcholine (HSPC).

Aspects of the disclosure relate to a method of making a nucleic acid delivery composition comprising lipids wherein the lipids comprise phosphatidylserine, the method comprising a step of dissolving the phosphatidylserine in ethanol wherein the phosphatidylserine is in the form of an ammonium salt of the phosphatidylserine.

In some embodiments, the phosphatidylserine is DPPS. In some embodiments, the phosphatidylserine is dissolved in ethanol to the concentration of more than 0.2 mM. In some embodiments, the ammonium salt is a salt comprising an ammonium selected from the group consisting of: ammonium, alkyammonium, dialkylammonium, trialkylammonium, and tetraalkylammonium. In some embodiments, the ammonium form selected from the group consisting of: ammonia, dimethylamine, diethylamine, triethylamine, trimethylamine, 2-(dimethyamino)ethanol, diethanolamine, 2-(diethyamino)ethanol, ethanolamine, ethylenediamine, N-methyl-glucamine, imidazole, histidine, lysine, arginine, 4-(2-hydroxyethyl)-morpholine, piperazine, 1-(2-hydroxyethyl)-pyrrolidine, triethanolamine, or tromethamine (tris (hydroxymethyl)aminomethane).

Aspects of the disclosure relate to a method for delivery of a nucleic acid into cells comprising the step of: contacting the lipid nanoparticle (LNP) with the cells, wherein the cells are human dendritic cells, wherein the LNP composition was obtained by a process of aspects of the disclosure.

In some embodiments, the LNP comprises an ionizable cationic lipid of the disclosure.

In some embodiments, the cells are in a human or animal subject. In some embodiments, the LNP is administered to the subject intramuscularly, subcutaneously, intradermally, or topically.

Aspects of the disclosure relate to an LNP composition comprising: (a) a nucleic acid, wherein the nucleic acid is an mRNA; (b) a cholesterol sterol in a total amount of 25-40 mol % of the total lipid content of the LNP composition; (c) an ionizable cationic lipid having a N/P ratio of 3 to 8 relative to the nucleic acid in a total amount of 40-65 mol % of the total lipid content of the LNP composition; (d) one or more phospholipids in a total amount of phospholipids of 5-25 mol % of the total lipid content of the LNP composition, the one or more phospholipids are selected from the group consisting of (i) an ammonium salt of dipalmitoylphosphatidyl-L-serine ((L-serine)DPPS) lipid in a total amount of 2.5-10 mol % of the total lipid content of the LNP composition; and (ii) a distearoylphosphatidylcholine (DSPC) phospholipid in a total amount of 5-25 mol % of the total lipid content of the LNP composition; and (e) a PEG-containing conjugated lipid in a total amount of 0.5-2.5 mol % of the total lipid content of the LNP composition.

Aspects of the disclosure relate to a method for administering a nucleic acid to a subject in need thereof comprising administering a nucleic acid lipid nanoparticle (LNP) composition to a human subject, the nucleic acid LNP composition comprising: (a) a nucleic acid; (b) an ionizable cationic lipid at a N/P ratio of 3 to 8 relative to the nucleic acid in a total amount of 40-65 mol % of the total lipid content of the LNP composition; (c) a sterol in a total amount of 25-45 mol % of the total lipid content of the LNP composition; (d) one or more phospholipids in a total amount of phospholipids of 5-25 mol % of the total lipid content of the LNP composition, and comprising a phosphatidylglycerol (PG) in a total amount of 1.0-10 mol % of the total lipid content of the LNP composition; and (e) a conjugated lipid in a total amount of 0.5-2.5 mol % of the total lipid content of the LNP composition.

Aspects of the disclosure relate to a nucleic acid lipid nanoparticle (LNP) composition comprising: (a) a nucleic acid; (b) an ionizable cationic lipid at a N/P ratio of 3 to 8 relative to the nucleic acid in a total amount of 40-65 mol % of the total lipid content of the LNP composition; (c) a sterol in a total amount of 25-45 mol % of the total lipid content of the LNP composition; (d) one or more phospholipids in a total amount of phospholipids of 5-25 mol % of the total lipid content of the LNP composition, and comprising a phosphatidylserine (PS) lipid in a total amount of 2.5-10 mol % of the total lipid content of the LNP composition; and (e) a conjugated lipid in a total amount of 0.5-2.5 mol % of the total lipid content of the LNP composition. In some embodiments, the nucleic acid is mRNA; the ionizable cationic lipid is present in the LNP composition at a N/P ratio of 4 to 7 relative to the nucleic acid; the sterol is cholesterol; and the conjugated lipid is a PEG-containing conjugated lipid.

In some embodiments, the one or more phospholipids comprise at least two phospholipids having mismatched acyl chain lengths.

In some embodiments, the phosphatidylserine (PS) lipid is dipalmitoylphosphatidyl-L-serine ((L-serine)DPPS).

In some embodiments, the one or more phospholipids comprise a phospholipid selected from the group consisting of: distearoylphosphatidylcholine (DSPC) and hydrogenated soy phosphatidylcholine (HSPC). In some embodiments, the one or more phospholipids consist of distearoylphosphatidylcholine (DSPC) and dipalmitoylphosphatidyl-L-serine ((L-serine)DPPS). In some embodiments, the PEG-containing conjugated lipid is PEG(2000)-dimyristoylglycerol (PEG-DMG).

Aspects of the disclosure relate to an LNP composition wherein the ionizable lipid has the chemical structure:

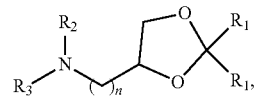

wherein $R_1$ is

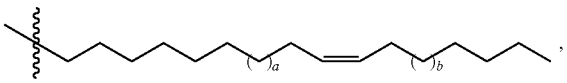

wherein a is 0 or 1; b is 1, 2, 3 or 4, provided the sum a+b is 1, 2, 3 or 4;

$R_2$ and $R_3$ are each independently ($C_1$-$C_4$) alkyl optionally substituted with hydroxyl; and n is an integer equal to 2, 3 or 4.

In some embodiments, $R_2$ and $R_3$ are each methyl; and n is 3 or 4.

In some embodiments, the ionizable cationic lipid is one or more compounds selected from the group consisting of: KC3-OA, KC3-PA, KC3-C17 (8:1), and KC3-C15 (C8:1). In some embodiments, the ionizable cationic lipid is KC3-PA. In some embodiments, the ionizable cationic lipid is KC3-OA. In some embodiments, the ionizable cationic lipid is KC3-C17 (C8:1). Aspects of the disclosure relate to an ionizable cationic lipid selected from the group consisting of KC3-PA, KC3-C17 (8:1), and KC3-C15 (C8:1).

Aspects of the disclosure relate to a nucleic acid lipid nanoparticle (LNP) composition comprising: (a) a nucleic acid; (b) an ionizable cationic lipid at a N/P ratio of 3 to 8 relative to the nucleic acid in a total amount of 40-65 mol % of the total lipid content of the LNP composition; (c) a sterol in a total amount of 25-45 mol % of the total lipid content of the LNP composition; (d) one or more phospholipids in a total amount of phospholipids of 5-25 mol % of the total lipid content of the LNP composition, and comprising a phosphatidylserine (PS) lipid in a total amount of 2.5-10 mol % of the total lipid content of the LNP composition; and (d) a conjugated lipid in a total amount of 0.5-2.5 mol % of the total lipid content of the LNP composition.

In some embodiments, the sterol is cholesterol. In some embodiments, the one or more phospholipids comprise phospholipids having mismatched acyl chain lengths. In some embodiments, the PS lipid is dipalmitoylphosphatidyl-L-serine ((L-serine)DPPS). In some embodiments, the one or more phospholipids comprise a phospholipid selected from the group consisting of: distearoylphosphatidylcholine (DSPC) and hydrogenated soy phosphatidylcholine (HSPC). In some embodiments, the one or more phospholipids comprise distearoylphosphatidylcholine (DSPC) and the phosphatidylserine (PS). In some embodiments, the ionizable cationic lipid is 3-((S)-2,2-di((Z)-octadec-9-en-1-yl)-1,3-dioxolan-4-yl)-N,N-dimethylpropan-1-amine (KC3-OA). In some embodiments, the ionizable cationic lipid is 3-((S)-2, 2-di((Z)-octadec-9-en-1-yl)-1,3-dioxolan-4-yl)-N,N-dimethylpropan-1-amine (KC3-OA). In some embodiments, the one or more phospholipids consist of distearoylphosphatidylcholine (DSPC) and dipalmitoylphosphatidyl-L-serine ((L-serine)DPPS), and the phosphatidylserine (PS) is (L-Serine)DPPS.

In some embodiments, the conjugated lipid is a PEG-containing conjugated lipid, and wherein the PEG-containing conjugated lipid is selected from the group consisting of: PEG(2000)-dimyristoylglycerol (PEG-DMG), 1,2-dilauroyl-sn-glycero-3-phosphoethanolamine-N-[methoxy(polyethylene glycol)-2000] (PEG-DLPE), and PEG(2000)-dilauroylglycerol (PEG-DLG).

In some embodiments, the nucleic acid is mRNA; the one or more phospholipids comprise phosphatidylserine (PS) and one or more phospholipids selected from the group consisting of: distearoylphosphatidylcholine (DSPC), hydrogenated soy phosphatidylcholine (HSPC), and dipalmitoylphosphatidyl-L-serine ((L-serine)DPPS); and the conjugated lipid comprises a polyethylene glycol (PEG). In some embodiments, the conjugated lipid is PEG(2000)-dimyristoylglycerol (PEG-DMG). In some embodiments, the ionizable cationic lipid is 3-((S)-2,2-di((Z)-octadec-9-en-1-yl)-1,3-dioxolan-4-yl)-N,N-dimethylpropan-1-amine (KC3-OA). In some embodiments, the one or more phospholipids consist of distearoylphosphatidylcholine (DSPC) and dipalmitoylphosphatidyl-L-serine ((L-serine)DPPS).

In some embodiments, the dipalmitoylphosphatidyl-L-serine ((L-serine)DPPS) is an ammonium salt of (L-Serine) DPPS.

In some embodiments, (a) the nucleic acid is mRNA; (b) the sterol is a cholesterol sterol in a total amount of 25-45 mol % of the total lipid content of the LNP composition; (c) the ionizable cationic lipid is at a N/P ratio of 3 to 8 relative to the nucleic acid in a total amount of 40-65 mol % of the total lipid content of the LNP composition; (d) the one or more phospholipids is in a total amount of phospholipids of 5-25 mol % of the total lipid content of the LNP composition, the one or more phospholipids consisting of: (i)dipalmitoylphosphatidyl-L-serine ((L-serine)DPPS) lipid in a total amount of 2.5-10 mol % of the total lipid content of the LNP composition; and (ii) a distearoylphosphatidylcholine (DSPC) phospholipid in a total amount of 5-25 mol % of the total lipid content of the LNP composition; (e) the conjugated lipid is a PEG-containing conjugated lipid in a total amount of 0.5-2.5 mol % of the total lipid content of the LNP composition. In some embodiments, the PEG-containing conjugated lipid is selected from the group consisting of: PEG(2000)-dimyristoylglycerol (PEG-DMG), 1,2-dilauroyl-sn-glycero-3-phosphoethanolamine-N-[methoxy(polyethylene glycol)-2000] (PEG-DLPE), and PEG(2000)-dilauroylglycerol (PEG-DLG).

Aspects of the disclosure relate to a nucleic acid lipid nanoparticle (LNP) human vaccine composition comprising: (a) a nucleic acid; (b) an ionizable cationic lipid at a N/P ratio of 3 to 8 relative to the nucleic acid in a total amount of 40-65 mol % of the total lipid content of the LNP composition; (c) a sterol in a total amount of 25-45 mol % of the total lipid content of the LNP composition; (d) one or more phospholipids in a total amount of phospholipids of 5-25 mol % of the total lipid content of the LNP composition, and comprising a phosphatidylglycerol (PG) in a total amount of 1.0-10 mol % of the total lipid content of the LNP composition; and (e) a conjugated lipid in a total amount of 0.5-2.5 mol % of the total lipid content of the LNP composition.

In some embodiments, the sterol is cholesterol; and the phosphatidylglycerol (PG) is an anionic phospholipid selected from the group consisting of: distearoylphosphatidylglycerol (DSPG) and dipalmitoyphosphatidylglycerol (DPPG).

In some embodiments, the nucleic acid is mRNA and the ionizable cationic lipid is present at a N/P ratio of 4 to 7 relative to the nucleic acid.

Aspects of the disclosure relate to a nucleic acid lipid nanoparticle (LNP) composition comprising an ionizable cationic lipid in a total amount of 40-65 mol % of the total lipid content of the LNP composition, wherein the ionizable cationic lipid is selected from the group consisting of:

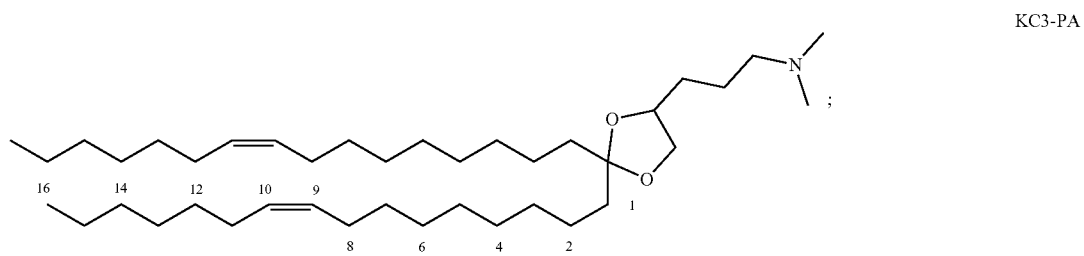

KC3-PA

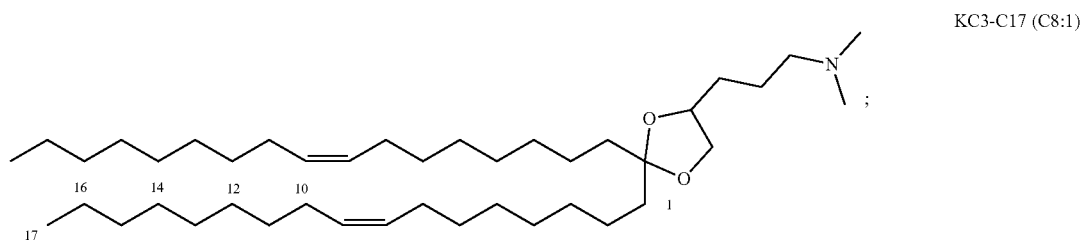

KC3-C17 (C8:1)

-continued

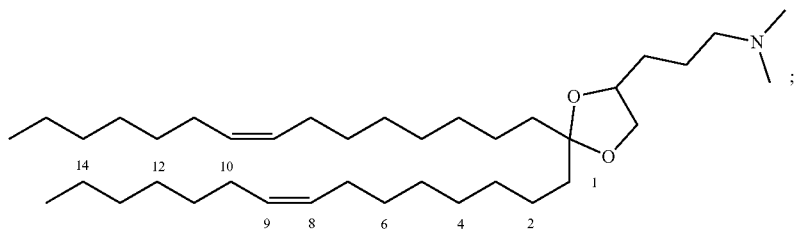

KC3-C15 (C8:1)

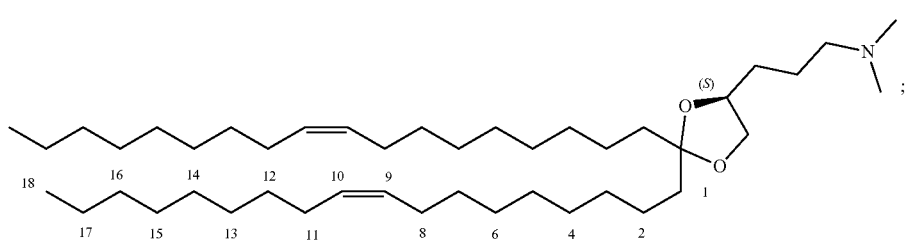

AKG-KC3-OA

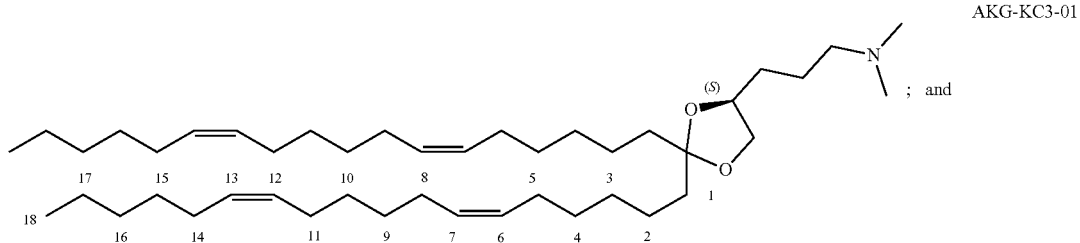

AKG-KC3-O1 ; and

Aspects of the disclosure relate to a nucleic acid lipid nanoparticle (LNP) composition comprising: (a) a nucleic acid; (b) an ionizable cationic lipid at a N/P ratio of 3 to 8 relative to the nucleic acid in a total amount of 40-65 mol % of the total lipid content of the LNP composition; (c) a sterol in a total amount of 25-45 mol % of the total lipid content of the LNP composition; (d) one or more phospholipids in a total amount of phospholipids of 5-25 mol % of the total lipid content of the LNP composition; and (d) a conjugated lipid in a total amount of 0.5-2.5 mol % of the total lipid content of the LNP composition, wherein the conjugated lipid which is a PEG-lipid having a poly(ethylene glycol) chain terminally attached to a linking moiety and two hydrocarbon chains terminally attached to the same linking moiety, wherein the two hydrocarbon chains are saturated $C_{12}$-chains independently selected from n-dodecyl (lauryl) group and n-dodecanoyl (lauroyl) group.

In some embodiments, the linking moiety is a glyceryl group, N-oxycarbonyl glycerophoshoryl ethanolaminocarbonyl group, oxycarbonylamide group, or oxyacetamide group. In some embodiments, the poly(ethyene glycol) chain is methoxy-poly(ethyene glycol) with an average molecular weight of 2000. In some embodiments, the PEG-lipid is mPEG-1,2-dilauroylglycerol (PEG-DLG), mPEG-1,2-dilaurylglycerol (PEG-DLG), PEG-1,2-dilaurylglycerol, PEG-DLPE, PEG-oxycarbonyl-N,N-didodecylamide, or mPEG-N,N-didodecylacetamide.

BRIEF DESCRIPTION OF THE DRAWINGS

FIG. 3A Impact of DSPS inclusion from 0-2.5 mol % on transfection efficiency of dendritic cells (MutuDC1940) using mCherry mRNA LNPs formulated with DLin-KC2-DMA as the ionizable cationic lipid. ICL was kept at 50 mol %, cholesterol at 38.5 mol %, PEG-DMG at 1.5 mol % and the DSPS content varied. Inclusion of DSPS was made by reducing the DSPC content by the same mol % of DSPS that was added. Cells were incubated with each formulation at a concentration of 1 ug mRNA/mL for 24 h. UT sample corresponds to cells where no LNPs were added. Lipofect refers to Lipofectamine treated sample.

FIG. 3B Impact of DSPS inclusion from 0-7.5 mol % on transfection efficiency of dendritic cells (MutuDC1940) using mCherry mRNA LNPs formulated with DLin-KC2-DMA as the ionizable cationic lipid. ICL was kept at 50 mol %, cholesterol at 38.5 mol %, PEG-DMG at 1.5 mol % and the DSPS content varied. Inclusion of DSPS was made by reducing the DSPC content by the same mol % of DSPS that was added. Cells were incubated with each formulation at a concentration of 1 ug mRNA/mL for 24 h. UT sample corresponds to cells where no LNPs were added. Lipofect refers to Lipofectamine treated sample.

FIG. 3C Impact of DSPS inclusion from 0-7.5 mol % on transfection efficiency of dendritic cells (MutuDC1940) using mCherry mRNA LNPs formulated with DLin-KC2-DMA as the ionizable cationic lipid. ICL was kept at 50 mol %, cholesterol at 38.5 mol %, PEG-DMG at 1.5 mol % and the DSPS content varied. Inclusion of DSPS was made by reducing the DSPC content by the same mol % of DSPS that was added. Cells were incubated with each formulation at a concentration of 0.3 ug mRNA/mL for 24 h. UT sample corresponds to where no LNPs were added.

FIG. 3D Impact of DSPS inclusion from 0-7.5 mol % on transfection efficiency of dendritic cells (MutuDC1940) using mCherry mRNA LNPs formulated with DLin-KC2-DMA as the ionizable cationic lipid. ICL was kept at 50 mol %, cholesterol at 38.5 mol %, PEG-DMG at 1.5 mol % and the DSPS content varied. Inclusion of DSPS was made by reducing the DSPC content by the same mol % of DSPS that was added Cells were incubated with each formulation at a concentration of 0.1 ug mRNA/mL for 24 h. UT sample corresponds to cells where no LNPs were added.

FIG. 4 Transfection of murine dendritic cells (MutuDC1940) using LNPs containing various ICLs (KC2, KC2-OA, KC3-OA, and SM-102) and 5 mol % DSPS, and comparison to LNPs using Glu-DSPE or Suc-DSPE rather than DSPS. UT sample corresponds to cells where no LNPs were added.

FIG. 5 DSPS or DPPS increase mCherry LNP transfection with KC2, KC2-01, KC2-PA, KC3-01, and KC3-OA comprising ICLs. UT sample corresponds to cells where no LNPs were added.

FIG. 6A Comparison of various chemical forms of phosphatidylserine with AKG-UO-1 containing LNPs in transfecting murine dendritic cells. UT sample corresponds to cells where no LNPs were added. Lipo refers to Lipofectamine MessengerMax (ThermoFisher) used according to manufacturer's instructions at the same dosage level as the LNPs.

FIG. 6B Comparison of DSPS to other negatively charged phospholipids in transfecting murine dendritic cells using AKG-UO1 containing LNPs. UT sample corresponds to cells where no LNPs were added. Lipo refers to Lipofectamine MessengerMax (ThermoFisher) used according to manufacturer's instructions at the same dosage level as the LNPs.

FIG. 7 Impact of DSPS concentration in AUG-UO-1 containing LNPs on transfection of dendritic cells. UT sample corresponds to cells where no LNPs were added.

FIG. 8 Impact of PEG-DMG concentration in AUG-UO-1 containing LNPs with and without 5 mol % DSPS on transfection of dendritic cells. The Y-axis shows the % PEG used in the composition followed by the concentration of mRNA added to the cells (0.11, 0.33, or 1 µg/mL). UT sample corresponds to cells where no LNPs were added.

FIG. 9A Oxidative degradation of lipid suspensions of ICLs with a single methylene between two olefins (KC2, KC3, and O-11769) and those with four methylenes between the two olefins (KC2-01, KC3-01, and UO-1).

FIG. 9B Oxidative degradation of liposomes containing O-11769, an ICL with a single methylene between two olefins liposomes containing UO-1, an ICL with four methylenes between the two olefins.

FIG. 10A Effect of N/P on mCherry expression of KC2-01 containing LNPs at 1 µg/ml in murine dendritic cells. UT sample corresponds to cells where no LNPs were added.

FIG. 10B Effect of N/P on mCherry expression of KC2-01 containing LNPs at 0.33 µg/ml in murine dendritic cells. UT sample corresponds to cells where no LNPs were added.

FIG. 11 Transfection efficiency of LNPs with and without DSPS (7.5 mol %) and containing different ionizable cationic lipids. UT sample corresponds to cells where no LNPs were added.

FIG. 12 Transfection efficiency of LNP formulations containing various concentrations of DOPS (0, 10, and 25 mol % as % of total lipid) and mCherry mRNA in murine dendritic cells.

FIG. 13A mRNA sequence of VRN-029, a SARS-COV2 spike protein generating sequence.

FIG. 13B The effect of PEG-DMG (C14) concentration (mol %) on LNP vaccine immunogenicity. Total anti-spike antibody titers and CD4 responses from mice immunized with mRNA-LNPs using 7.5% DSPS and the ionizable lipid UO1 with increasing mol % of PEG-DMG. The middle graph shows day 34 endpoint antibody titers. The right graph shows the corresponding CD4 T cell responses.

FIG. 13C The effect of PEG-DPPE (C16) concentration (mol %) on LNP vaccine immunogenicity. Total anti-spike antibody titers from mice immunized with mRNA-LNPs using 7.5% DSPS and the ionizable lipid UO1 with increasing mol % of PEG-DPPE. The middle graph shows day 34 endpoint antibody titers. The mol % of PEG-DPPE inversely impacted antibody levels. The right graph shows the corresponding CD4 T cell responses.

FIG. 13D Total anti-spike antibody titers and CD4 responses from mice immunized with mRNA-LNPs using 7.5% DSPS and the ionizable lipid KC20A with either 1.5 mol % PEG-DMG (14C) or PEG-DSG (18C). The left graph shows day 34 endpoint antibody titers. The right graph shows the corresponding CD4 T cell responses.

FIG. 13E Total anti-spike antibody titers and CD4 responses from mice immunized with mRNA-LNPs using 7.5% DSPS and the ionizable lipid UO1 with either 1.5 mol % PEG-DMG (14C) or PEG-DSG (18C). The left graph shows day 34 endpoint antibody titers. The right graph shows the corresponding CD4 T cell responses.

FIG. 13F Effect of phosphatidylserine incorporation in mRNA-LNP immunogenicity. Total anti-spike antibody titers (A) and spike-specific CD4 T cell responses from mice immunized with mRNA-LNPs using various ionizable lipids and PEG-lipids plus/minus 7.5 mol % DSPS Antibody data were log-transformed and analyzed using two-way ANOVA with a Sidak's multiple comparison test. CD4 T cell data were analyzed using a REML mixed-effects model with a Sidak's multiple comparison test.

FIG. 13G Effect of phosphatidylserine lipid tail (DPPS vs DSPS) composition on mRNA-LNP priming of B (Panel A) and T cell (Panel B) responses. Antibody data were log-transformed prior to analysis. Data were analyzed using one-way ANOVA with a Tukey's multiple comparison test.

FIG. 14A Comparison of the mCherry expression of KC2-01 LNPs, 7.5 mol % DSPS (D isomer) and DSPS (L isomer) at 1 µg/mL mRNA for 24 h.

FIG. 14B Comparison of the mCherry expression of KC2-01 LNPs, 7.5 mol % DSPS (D isomer) and DSPS (L isomer) at 0.33 µg/mL mRNA for 24 h.

FIG. 15 Comparison of the mCherry expression of KC2 LNPs, with 5 and 7.5 mol % DSPS (L-isomer) to LNPs prepared with SM-102 or ALC-0315 at 1 µg/mL mRNA for 24 h. The Y-axis is mean fluorescence intensity (MFI). UT sample corresponds to cells where no LNPs were added.

FIG. 16 Comparison of the mCherry expression of UO1, UO6 and UO7 formulations alone, or with added 7.5 mol % D-isomer of DSPS, at 1 µg/mL mRNA for 24 h. UT sample corresponds to cells where no LNPs were added.

FIG. 17 Comparison of the mCherry expression of UO1, SM102, ALC-0315 formulations alone, or with added DSPS, at 1 µg/mL mRNA for 24 h. Lipo refers to Lipofectamine MessengerMax (ThermoFisher) used according to manufacturer's instructions at the same dosage level as the LNPs. UT sample corresponds to cells where no LNPs were added.

FIG. 18 Oxidative degradation of liposomes containing KC3 (DLin-KC3-DMA), a polyunsaturated ICL with a single methylene between two olefins, to liposomes containing ICLs with monounsaturated alkyl chains (KC3-OA, KC3-PA, or KC3-C17(C8:1)) and the fully saturated ICL, KC3-C17. Effect of hydrogen peroxide on the stability of individual ionizable cationic lipids measured by CAD-HPLC.

FIG. 19 Comparison of the mCherry expression of UO1, UO1A, and KC3-OA LNP formulations alone, or with added DSPS, at 0.1 and 1 μg/mL mRNA for 24 h in human dendritic cells. Untreated DC sample corresponds to human dendritic cells where no LNPs were added.

FIG. 20 Comparison of the mCherry expression in murine dendritic cells of LNPs containing the polyunsaturated KC3, the monounsaturated KC3-OA, KC3-PA, or KC3C17(C8:1), and the fully saturated KC3C17, all with or without DPPS ($NH_4^+$ salt), at 0.3 or 1 μg/mL mRNA for 24 h. UT sample corresponds to cells where no LNPs were added.

FIG. 21 Comparison of the mCherry expression in human dendritic cells of LNPs containing the polyunsaturated KC2 or KC3 with a single methylene between two olefins, polyunsaturated KC3-01 with four methylenes between two olefins, monounsaturated KC3-OA, KC3-PA, or KC3C17 (C8:1), and ALC-0315, all with except ALC-0315 with DPPS ($NH_4^+$ salt), at 0.1 or 1 μg/mL mRNA for 24 h. Untreated samples correspond to cells where no LNPs were added.

FIG. 22 Comparison of the mCherry expression of LNP formulations with 5 mol % DSPS and 46-54 mol % of KC3-OA to ALC-0315 and SM-102 LNP controls, at 0.1 and 1 μg/mL mRNA for 24 h in human dendritic cells. Untreated DC sample corresponds to human dendritic cells where no LNPs were added.

FIG. 23 Comparison of the mCherry expression of LNP formulations with 0 or 5 mol % DSPS and 50 mol % KC2-01 at N/P ratios of 4-7, at 0.1 μg/mL mRNA for 24 h in human dendritic cells. These were also compared to LNPs containing KC3-OA and 5 mol % DSPS at N/P of 5. Untreated DC sample corresponds to human dendritic cells where no LNPs were added.

FIG. 24A Comparison of polyunsaturated KC3 with monounsaturated KC3-OA and KC3-PA containing LNP formulations on vaccine immunogenicity. Total anti-spike antibody titers from mice immunized with mRNA-LNPs using 5 mol % DSPS or DPPS-targeted LNPs containing either KC3, KC3-OA, or KC3-PA. For KC3-OA and KC3-PA LNPs, each formulation was also evaluated with either the C16 DPPC or C18 DSPC neutral phosphatidylcholine component. All LNPs contained 1.5 mol % of PEG-DMG. The graph shows day 21 endpoint antibody titers after the initial prime injection of 1 μg mRNA per mouse.

FIG. 24B Comparison of polyunsaturated KC3 with monounsaturated KC3-OA and KC3-PA containing LNP formulations on vaccine immunogenicity. Total anti-spike antibody titers from mice immunized with mRNA-LNPs using 5 mol % DSPS or DPPS-targeted LNPs containing either KC3, KC3-OA, or KC3-PA. For KC3-OA and KC3-PA LNPs, each formulation was also evaluated with either the C16 DPPC or C18 DSPC neutral phosphatidylcholine component. All LNPs contained 1.5 mol % of PEG-DMG. The graph shows day 34 endpoint antibody titers after the prime then boost on day 21 of 1 μg mRNA per mouse.

FIG. 25A Comparison of the mCherry expression of LNP formulations with 5 mol % DSPS and 43-48 mol % of KC3-OA to ALC-0315 and SM-102 LNP controls, at 1 μg/mL mRNA for 24 h in human dendritic cells KC3-OA LNPs prepared at 45 mol % KC3-OA and 5 mol % DSPS of total lipid were also compared at N/P ratios of 5, 5.5, 6.0, and 6.5. Finally, LNPs with mol % KC3-OA at N/P of 5 and 6 were evaluated with PEG-SA, at either 1 or 3 mol %, in place of 1.5 mol % PEG-DMG. Untreated DC sample corresponds to human dendritic cells where no LNPs were added.

FIG. 25B Comparison of the mCherry expression of LNP formulations with 5 mol % DSPS and 43-48 mol % of KC3-OA to ALC-0315 and SM-102 LNP controls, at 0.1 μg/mL mRNA for 24 h in human dendritic cells KC3-OA LNPs prepared at 45 mol % KC3-OA and 5 mol % DSPS of total lipid were also compared at N/P ratios of 5, 5.5, 6.0, and 6.5. Finally, LNPs with 45 mol % KC3-OA at N/P of 5 and 6 were evaluated with PEG-SA, at either 1 or 3 mol %, in place of 1.5 mol % PEG-DMG. Untreated DC sample corresponds to human dendritic cells where no LNPs were added.

FIG. 26A Comparison of the mCherry expression of 50 mol % UO-1 containing LNP formulations with 7.5 mol % of various anionic phospholipids in human dendritic cells following incubation for 24 h at 1 μg/mL mRNA. All LNPs included 2.5 mol % of DSPC, 50 mol % of UO-1, and 1.5 mol % of PEG-DMG. The anionic phospholipids included the phosphatidylserines, DOPS, DSPS, DPPS, and DMPS, distearoylphosphatidylglycerol (DSPG), and N-glutaryl-distearoylphophatidylethanolamine (Glu-DSPE) and N-succinyl-distearoylphophatidylethanolamine (Suc-DSPE) and were included at 7.5 mol %, except for DSPG was compared at both 5 and 7.5 mol %.

FIG. 26B Comparison of the mCherry expression of 50 mol % UO-1 containing LNP formulations with 7.5 mol % of various anionic phospholipids in human dendritic cells following incubation for 24 h at 0.1 μg/mL mRNA. All LNPs included 2.5 mol % of DSPC, 50 mol % of UO-1, and 1.5 mol % of PEG-DMG. The anionic phospholipids included the phosphatidylserines, DOPS, DSPS, DPPS, and DMPS, distearoylphosphatidylglycerol (DSPG), and N-glutaryl-distearoylphophatidylethanolamine (Glu-DSPE) and N-succinyl-distearoylphophatidylethanolamine (Suc-DSPE) and were included at 7.5 mol %, except for DSPG was compared at both 5 and 7.5 mol %.

FIG. 27A Comparison of the mCherry expression of UO-1 or KC3-01 containing LNP formulations with 0-10 mol % of DSPG in human dendritic cells following incubation for 24 h at 1 μg/mL mRNA. ALC-0315 and SM-102 LNPs controls were also included at 1 μg/mL mRNA and untreated DC sample corresponds to human dendritic cells where no LNPs were added.

FIG. 27B Comparison of the mCherry expression of UO-1 or KC3-01 containing LNP formulations with 0-10 mol % of DSPG in human dendritic cells following incubation for 24 h at 0.1 μg/mL mRNA. ALC-0315 and SM-102 LNPs controls were also included at 0.1 μg/mL mRNA and untreated DC sample corresponds to human dendritic cells where no LNPs were added.

FIG. 28 Comparison of the mCherry expression in murine dendritic cells of LNPs containing UO1, UO6, or UO7 with 7.5 mol % DSPS after incubation at 1 μg/mL mRNA for 24 h. UT sample corresponds to cells where no LNPs were added.

FIG. 29 Comparison of dilinoleyl KC2, monounsaturated KC3-OA, and four methylene interrupted poly unsaturated ICLs (KC3-01, AKG-UO1, and AKG-UO9) containing LNP formulations on vaccine immunogenicity. ALC-0315 containing LNPs were included as a control. All LNPs contained 1.5 mol % of PEG-DMG. Total anti-spike antibody titers from mice immunized with mRNA-LNPs were determined on day 21 after the initial prime injection of 1 μg mRNA per mouse on day 1.

FIG. 30A Comparison of the mCherry expression of 48 mol % KC3-OA containing LNP formulations with 5 mol % of various anionic phospholipids in human dendritic cells following incubation for 24 h at 1 μg/mL mRNA. All LNPs included 2.5 mol % of DSPC, 50 mol % of UO-1, and 1.5 mol % of PEG-DMG. The anionic phospholipids included the phosphatidylglycerols, DOPG, DSPG, DPPG, and DMPG, as well as DSPS. In some LNPs, the DSPG and DSPS were combined either alone or together with DSPC. Two donors were used to produce human dendritic cells in this study and untreated DC sample corresponds to human dendritic cells where no LNPs were added.

FIG. 30B Comparison of the mCherry expression of 48 mol % KC3-OA containing LNP formulations with 5 mol % of various anionic phospholipids in human dendritic cells following incubation for 24 h at 0.1 μg/mL mRNA. All LNPs included 2.5 mol % of DSPC, 50 mol % of UO-1, and 1.5 mol % of PEG-DMG. The anionic phospholipids included the phosphatidylglycerols, DOPG, DSPG, DPPG, and DMPG, as well as DSPS. In some LNPs, the DSPG and DSPS were combined either alone or together with DSPC. Two donors were used to produce human dendritic cells in this study and untreated DC sample corresponds to human dendritic cells where no LNPs were added.

FIG. 31 Comparison of the mCherry expression in murine dendritic cells of LNPs containing KC3-OA LNPs with either 5 mol % DSPS (Na$^+$ salt) or 5 mol % DPPS (NH$_4^+$ salt) after incubation at 1 μg/mL mRNA for 24 h. ALC-0315 and SM-102 LNPs controls were also included at 1 μg/mL mRNA. UT sample corresponds to cells where no LNPs were added.

FIG. 40. Anti-SARS-COV-2 spike protein antibody titers in the sera of Balb/C mice immunized with the VRN029 spike mRNA formulated in KC3-PA/DSPC/DPPS-NH$_4$/Chol/PEG-lipid LNPs containing PRG-DMG or PEG-DLG (N=5) (Example 51). The sera were collected 2 weeks post boost dose (day 35 post prime dose) of 1 μg mRNA/mouse.

The titers were determined using 4× background as an endpoint of ELISA test. The bars represent geometric mean titers across the groups, the error intervals are standard deviations of the log transformed data, the markers show individual animal titers. The numbers at the PEG-lipid designation are mol % of the PEG-lipid relative to the LNP total lipid. The dotted line shows the upper limit of detection in the titer assay.

FIG. 41A. Anti-SARS-COV-2 spike protein antibody titers in the sera of Balb/C mice immunized with the VRN029 spike mRNA formulated in KC3-OA/DSPC/DPPS-NH$_4$/Chol/PEG-lipid LNPs containing PEG-DMG or PEG-DLG (N=5) (Example 52). The sera were collected 3 weeks post prime mRNA-LNP dose of 1 μg mRNA/mouse. The titers were determined using 4× background as an endpoint of ELISA test. The bars represent geometric mean titers across the groups, the error intervals are standard deviations of the log transformed data, the markers show individual animal titers. The difference between the groups is statistically significant. The dotted line shows the lower limit of detection in the titer assay.

FIG. 41B. Anti-SARS-COV-2 spike protein antibody titers in the sera of Balb/C mice immunized with the VRN029 spike mRNA formulated in KC3-OA/DSPC/DPPS-NH$_4$/Chol/PEG-lipid LNPs containing various amounts of DPPS and either PEG-DMG or PEG-DLG (N=5) (Example 52). The sera were collected 2 weeks after the boost mRNA-LNP dose of 1 μg mRNA/mouse administered 3 weeks after the prime. The titers were determined using 4× background as an endpoint of ELISA test. The bars represent geometric mean titers across the groups, the error intervals are standard deviations of the log transformed data, the markers show individual animal titers The dotted line shows the lower limit of detection in the titer assay. "%" signifies the mol % of the lipid component relative to the total LNP lipid.

Figure 42:
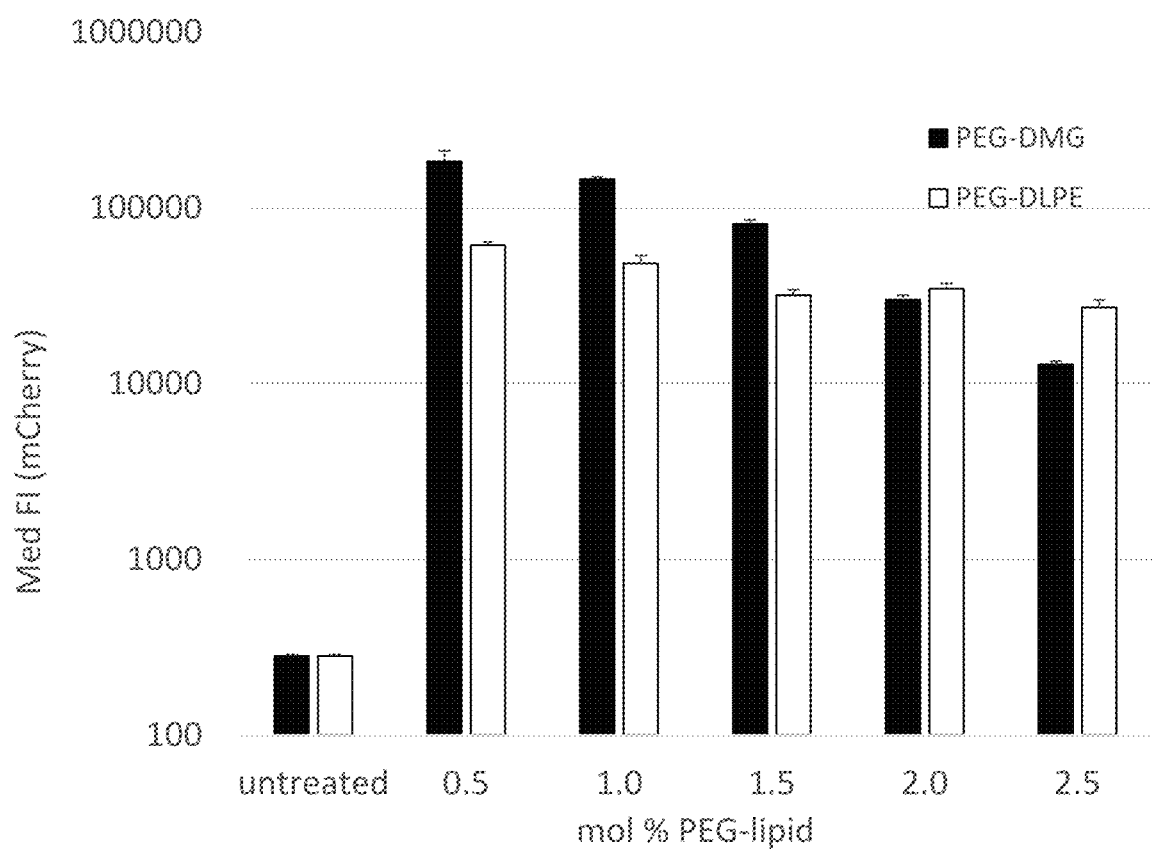

FIG. 42. Expression of mCherry mRNA delivered to human PBMC-derived dendritic cells by KC3OA/DSPC/DPPS-NH$_4$/Chol/PEG-lipid LNPs prepared with various amounts of PEG-DMG or PEG-DLPE (Example 53). The expression was quantified by flow cytometry of mCherry fluorescence 24 hours after transfection with LNPs at 0.3 μg/mL mRNA. The bars show average median cell fluorescence intensity of the replicates. Error intervals are standard deviation. Mol % PEG-lipid refers to the mol % relative to the total LNP lipid.

Figure 43A:
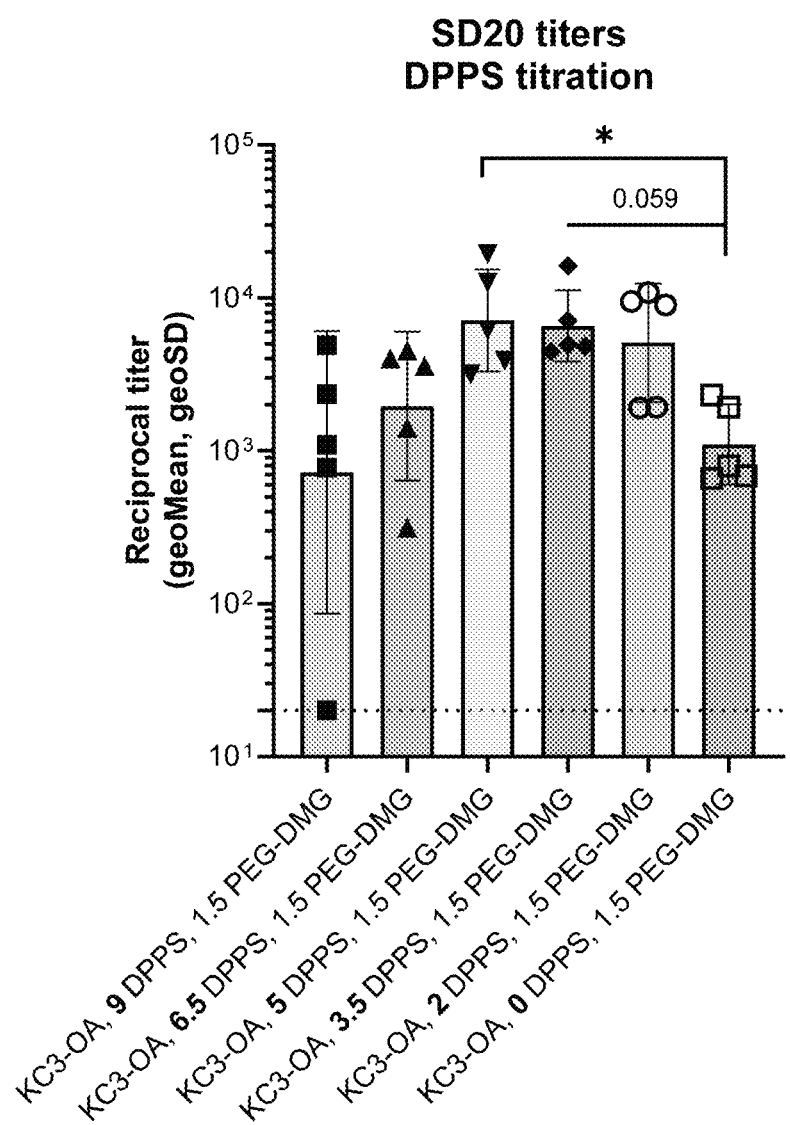

FIG. 43A. Anti-SARS-COV-2 spike protein antibody titers in the sera of Balb/C mice immunized with the VRN029 spike mRNA formulated in KC3-OA/DSPC/DPPS-NH$_4$/Chol/PEG-DMG LNPs containing various amounts of DPPS (N=5) (Example 54). The sera were collected on Day 20 after the prime mRNA dose of 0.3 μg mRNA/mouse. The titers were determined using 4× background as an endpoint of ELISA test. The bars represent geometric mean titers across the groups, the error intervals are standard deviations of the log transformed data, the markers show individual animal titers. The asterisk denotes statistical significance of the difference between the groups at p=0.05. The groups with p value of 0.059 are also shown. The dotted line shows the lower limit of detection in the titer assay. The numbers at the LNP lipid composition labels are mol % of respective components relative to the total LNP lipid.

Figure 43B:
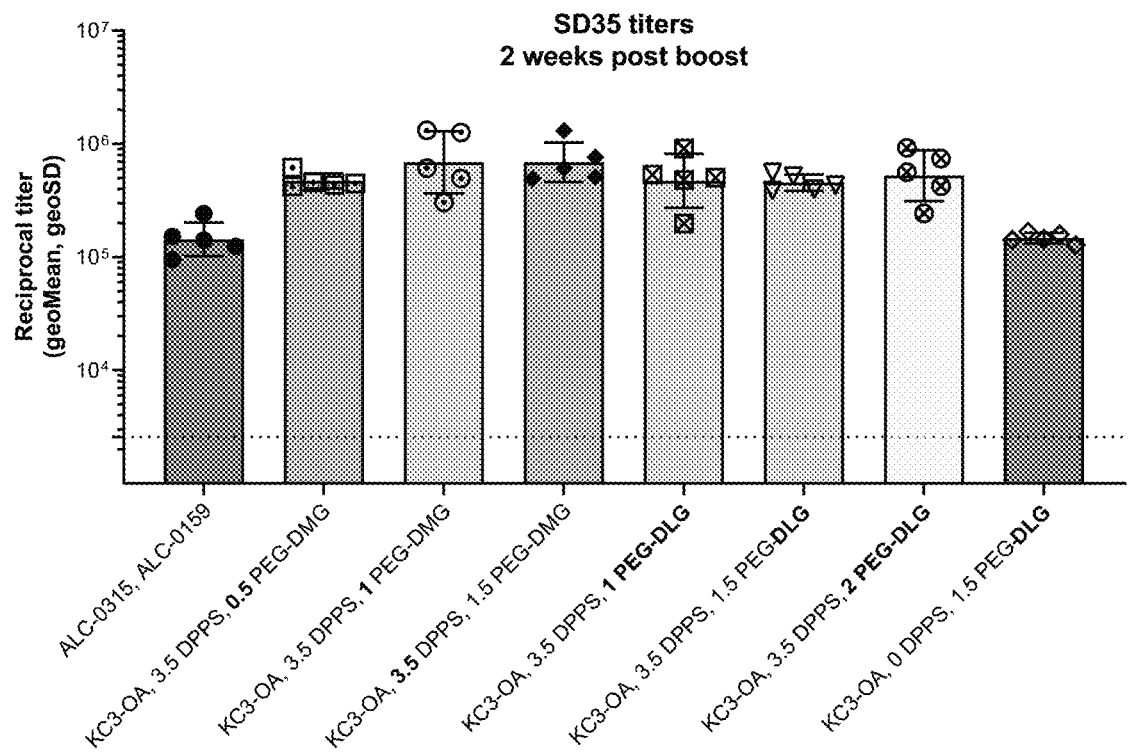

FIG. 43B. Anti-SARS-COV-2 spike protein antibody titers in the sera of Balb/C mice immunized with the VRN029 spike mRNA formulated in KC3-OA/DSPC/DPPS-NH$_4$/Chol/PEG-lipid LNPs containing various amounts of PEG-DMG or PEG-DLG, and of the ALC-0315-based nontargeted LNP formulation (N=5) (Example 54). The sera were collected at 2 weeks after the boost injection made at 3 weeks following the prime mRNA-LNP dose of 0.3 μg mRNA/mouse. The titers were determined using 4× background as an endpoint of ELISA test. The bars represent geometric mean titers across the groups, the error intervals are standard deviations of the log transformed data, the markers show individual animal titers. The dotted line shows the lower limit of detection in the titer assay. The numbers at the LNP lipid composition labels are mol % of respective components relative to the total LNP lipid.

Figure 43C:
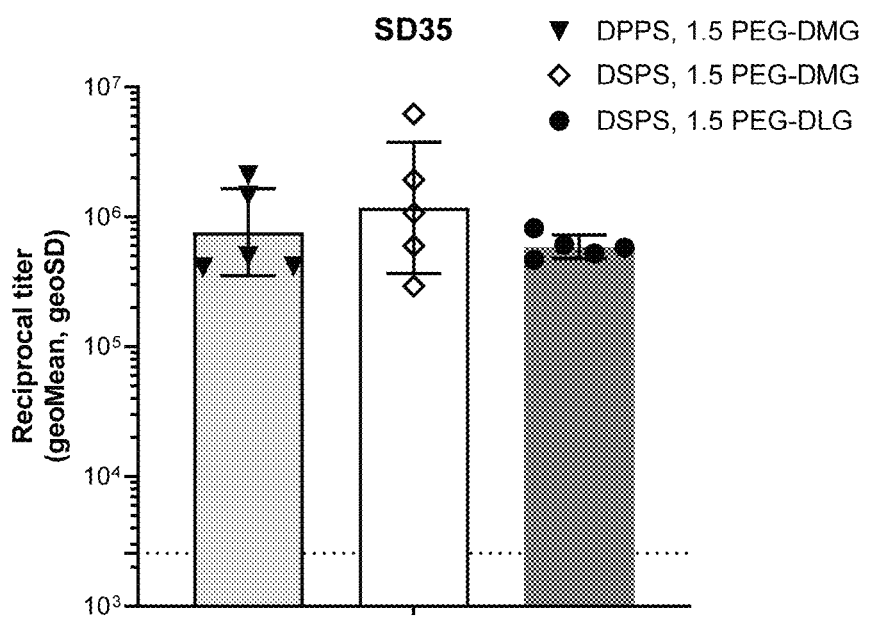

FIG. 43C. Anti-SARS-COV-2 spike protein antibody titers in the sera of Balb/C mice immunized with the VRN029 spike mRNA formulated in KC3-OA/DSPC/PS/Chol/PEG-lipid LNPs containing DSPS-Na or DPPS-NH$_4$ as a PS component at 5 mol % relative to the total LNP lipid, and PEG-DMG or PEG-DLG as a PEG-lipid component at 1.5 mol % relative to the total LNP lipid (N=5) (Example 54). The sera were collected at 2 weeks after the boost injection made at 3 weeks following the prime mRNA-LNP dose of 0.3 μg mRNA/mouse (Day 35 post prime). The titers were determined using 4× background as an endpoint of ELISA test. The bars represent geometric mean titers across the groups, the error intervals are standard deviations of the log transformed data, the markers show individual animal titers. The dotted line shows the lower limit of detection in the titer assay. The numbers at the LNP lipid composition labels are mol % of PEG-lipid relative to the total LNP lipid.

Figure 44:
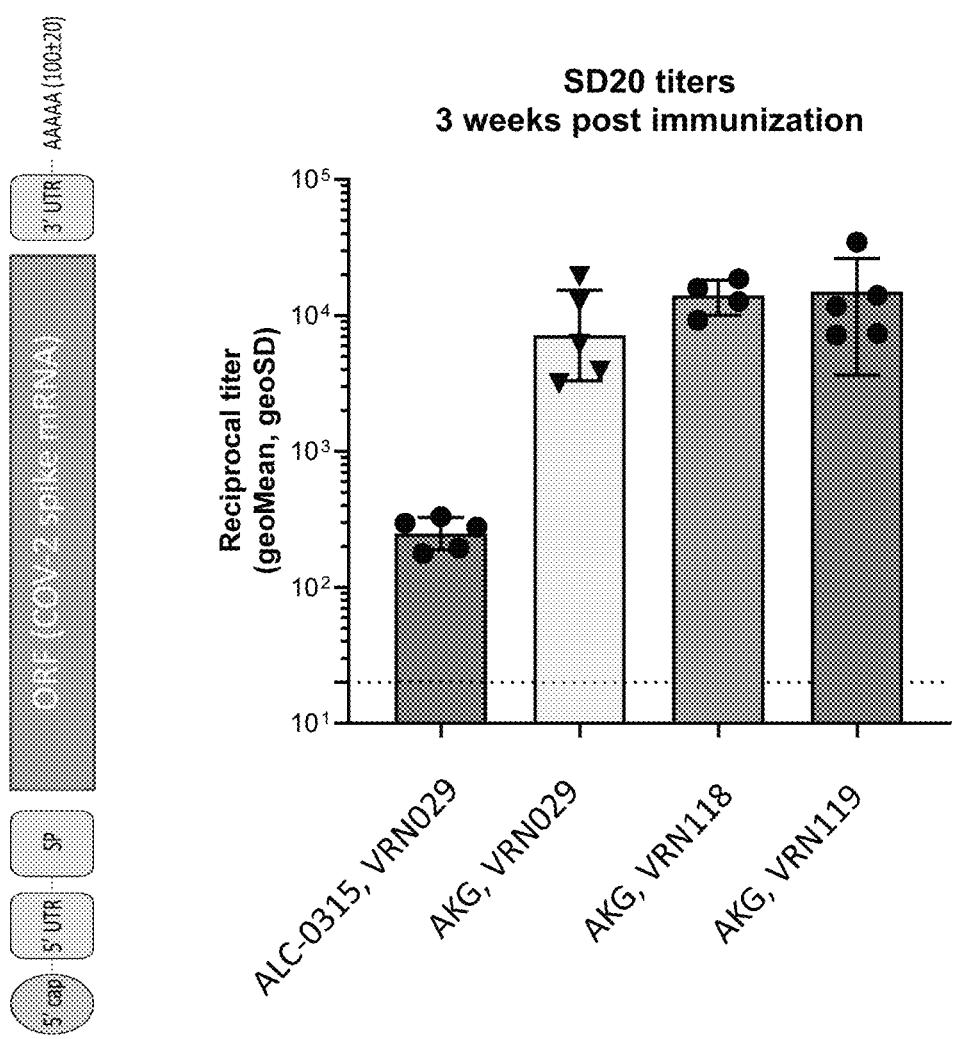

FIG. 44. Anti-SARS-COV-2 spike protein antibody titers in the sera of Balb/C mice immunized with various SARS-COV-2 spike mRNA (VRN029, VRN118, VRN119) formulated in KC3-OA/DSPC/DPPS-NH$_4$/Chol/PEG-DMG LNPs or ALC-0315 LNPs (N=5) (Example 55). The sera were collected on Day 20 after the prime mRNA-LNP dose of 0.3 μg mRNA/mouse. The titers were determined using 4× background as an endpoint of ELISA test. The bars represent geometric mean titers across the groups, the error intervals are standard deviations of the log transformed data, the markers show individual animal titers. The dotted line shows the lower limit of detection in the titer assay.

Figure 45A:
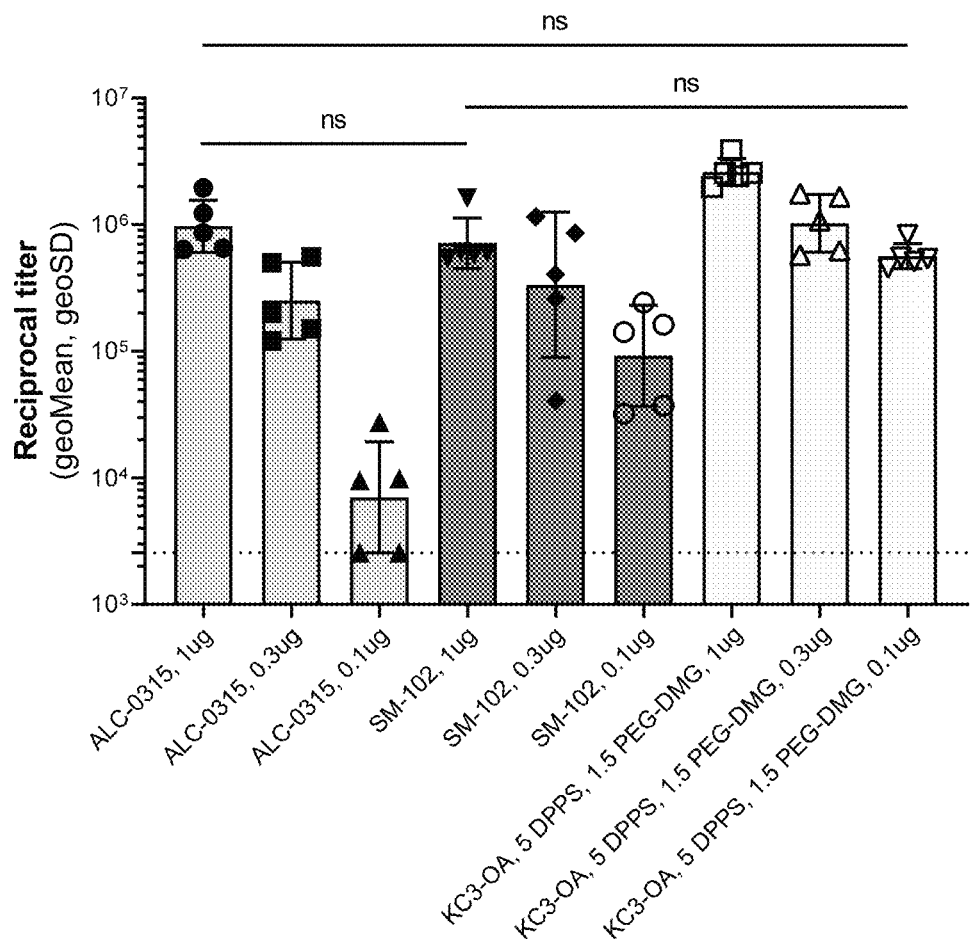

FIG. 45A. Anti-SARS-COV-2 spike protein antibody titers in the sera of Balb/C mice immunized with the VRN029 spike mRNA formulated in ALC-0315-based LNP, SM-102-based LNP, or KC3-OA/DSPC/DPPS-NH$_4$/Chol/PEG-DMG LNPs (N=5) (Example 56). The sera were collected at 2 weeks after the boost injection made at 3 weeks following the prime mRNA-LNP dose of 0.1, 0.3, or 1.0 μg mRNA/mouse (Day 35 post prime). The titers were determined using 4× background as an endpoint of ELISA test. The bars represent geometric mean titers across the groups, the error intervals are standard deviations of the log transformed data, the markers show individual animal titers. The dotted line shows the lower limit of detection in the titer assay. The numbers at the LNP lipid composition labels are mol % of PEG-lipid relative to the total LNP lipid.

Figure 45B:
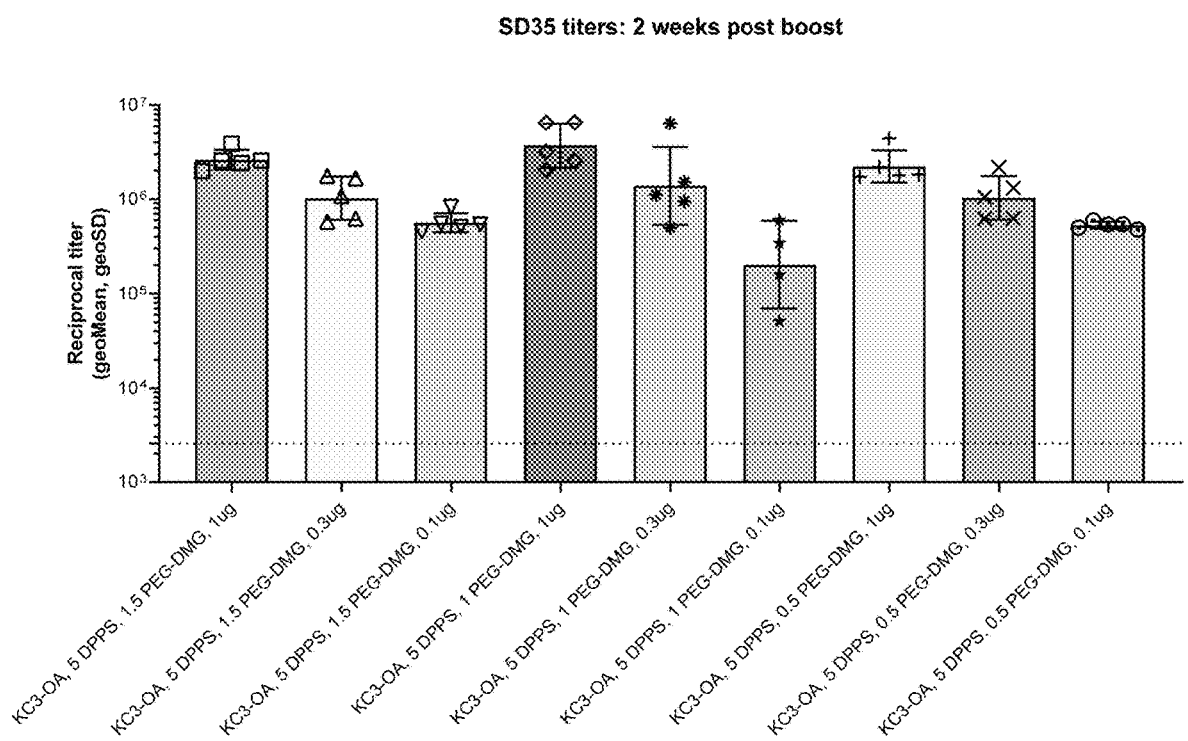

FIG. 45B. Anti-SARS-COV-2 spike protein antibody titers in the sera of Balb/C mice immunized with the VRN029 spike mRNA formulated in KC3-OA/DSPC/DPPS-NH$_4$/Chol/PEG-DMG LNPs with different amounts of PEG-DMG and administered at different doses (N=5) (Example 56). The sera were collected at 2 weeks after the boost injection made at 3 weeks following the prime mRNA-LNP dose of 0.1, 0.3, or 1.0 μg mRNA/mouse (Day 35 post prime). The titers were determined using 4× background as an endpoint of ELISA test. The bars represent geometric mean titers across the groups, the error intervals are standard deviations of the log transformed data, the markers show individual animal titers. The dotted line shows the lower limit of detection in the titer assay. The numbers at the LNP lipid composition labels are mol % of the corresponding lipid components relative to the total LNP lipid.

Figure 46A:
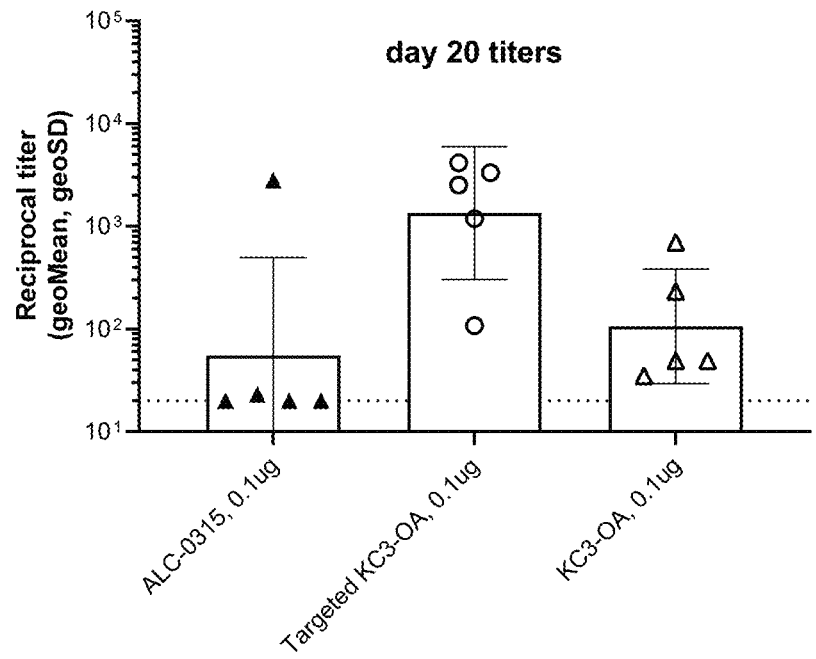

FIG. 46A. Anti-SARS-COV-2 spike protein antibody titers in the sera of Balb/C mice immunized with the VRN029 spike mRNA formulated in KC3-OA/DSPC/DPPS-NH$_4$/Chol/PEG-DMG (targeted KC3-OA) LNPs, KC3-OA/DSPC/Chol/PEG-DMG (non-targeted, KC3-OA) LNPs, or ALC-0315 LNPs (Example 57). The sera were collected at Day 20 following the prime mRNA-LNP dose of 0.1 μg mRNA/mouse. The titers were determined using 4× background as an endpoint of ELISA test. The bars represent geometric mean titers across the groups, the error intervals are standard deviations of the log transformed data, the markers show individual animal titers. The dotted line shows the lower limit of detection in the titer assay.

Figure 46B:
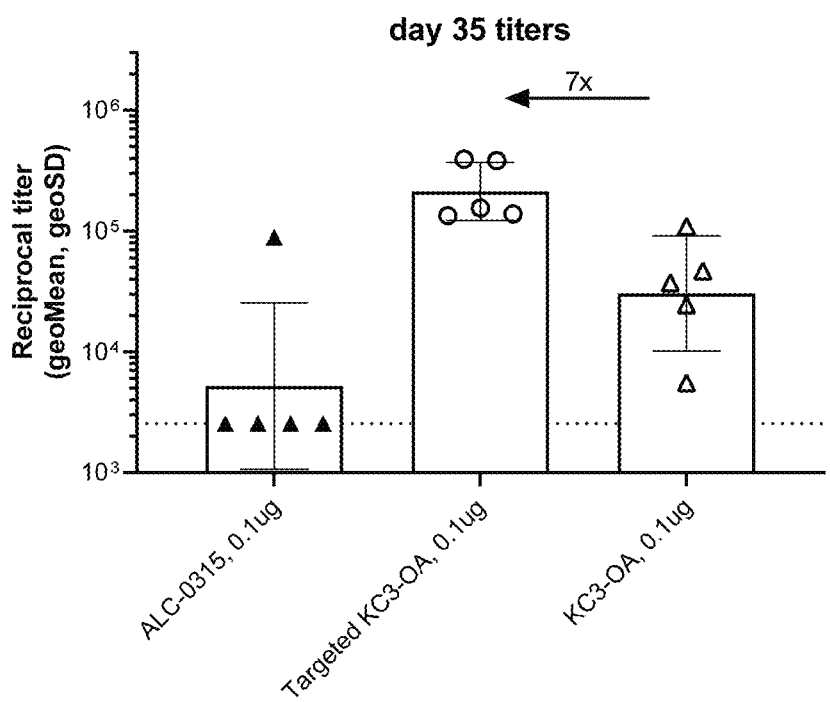

FIG. 46B. Anti-SARS-COV-2 spike protein antibody titers in the sera of Balb/C mice immunized with the VRN029 spike mRNA formulated in KC3-OA/DSPC/DPPS-NH$_4$/Chol/PEG-DMG (targeted KC3-OA) LNPs, KC3-OA/DSPC/Chol/PEG-DMG (non-targeted, KC3-OA) LNPs, or ALC-0315 LNPs (Example 57). The sera were collected at 2 weeks after the boost injection made at 3 weeks following the prime mRNA-LNP dose of 0.1 μg mRNA/mouse (Day 35 post prime). The titers were determined using 4× background as an endpoint of ELISA test. The bars represent geometric mean titers across the groups, the error intervals are standard deviations of the log transformed data, the markers show individual animal titers. The dotted line shows the lower limit of detection in the titer assay.

Figure 47A:
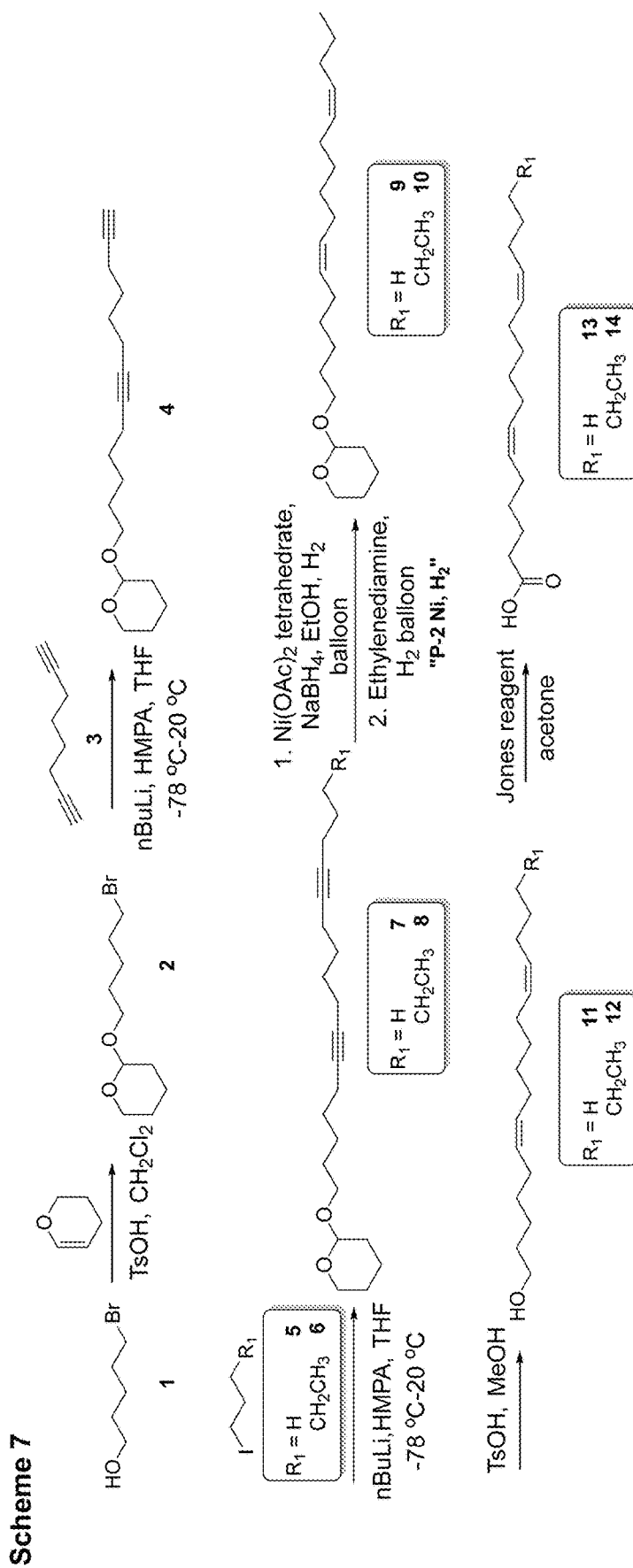

FIG. 47A and FIG. 47B. Synthetic schemes for UO-1 series of ionizable cationic lipids.

Figure 48:
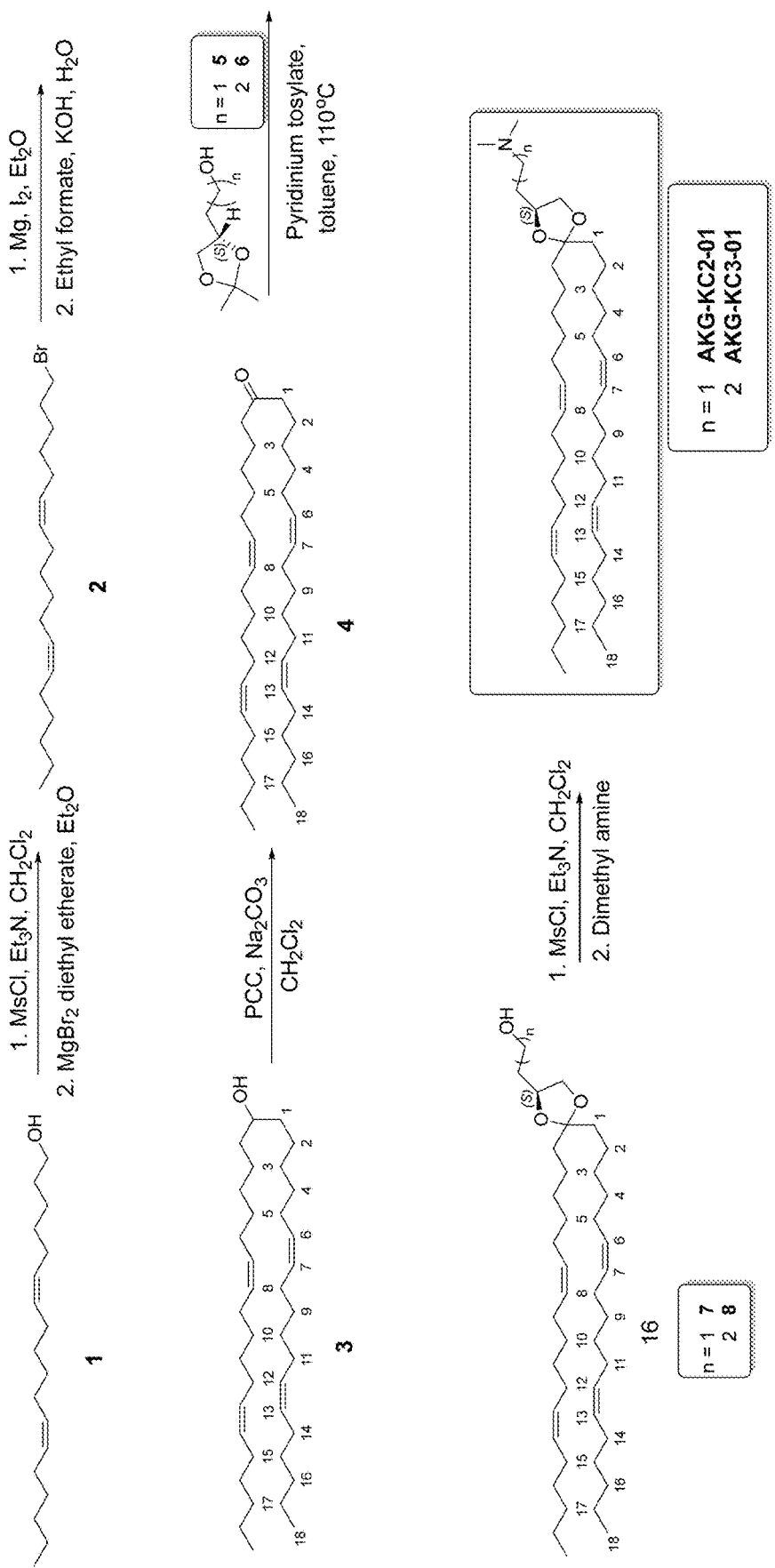

FIG. 48 Synthetic scheme for KC2-01 and KC3-01 ionizable cationic lipids.

Figure 49:
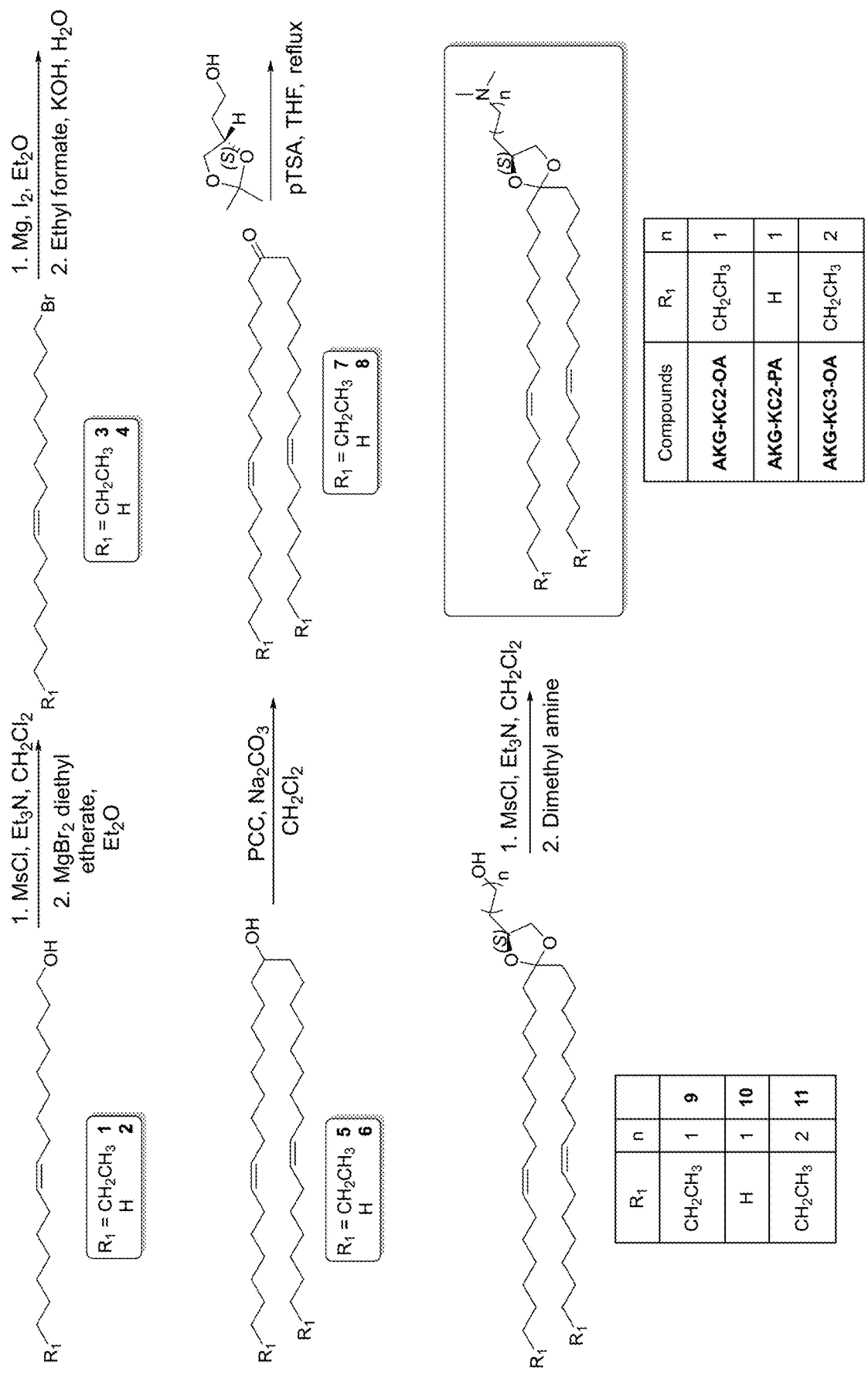

FIG. 49. Synthetic scheme for monounsaturated KC2-OA, KC2-PA, and KC3-OA ionizable cationic lipids.

Figure 50:
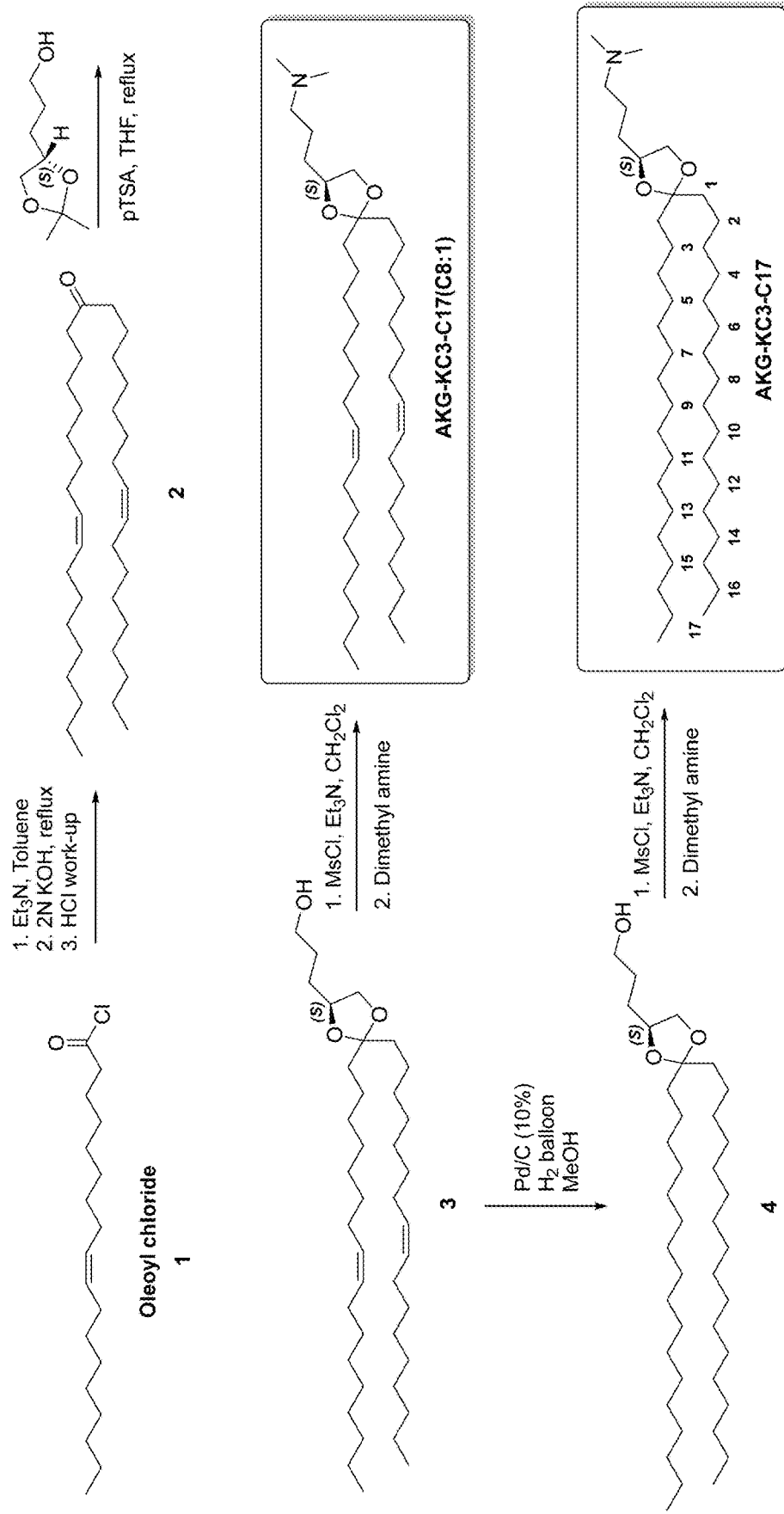

FIG. 50. Synthetic scheme for monounsaturated KC3-C17(C8:1) and fully unsaturated KC3-C17 ionizable cationic lipids.

Figure 51:
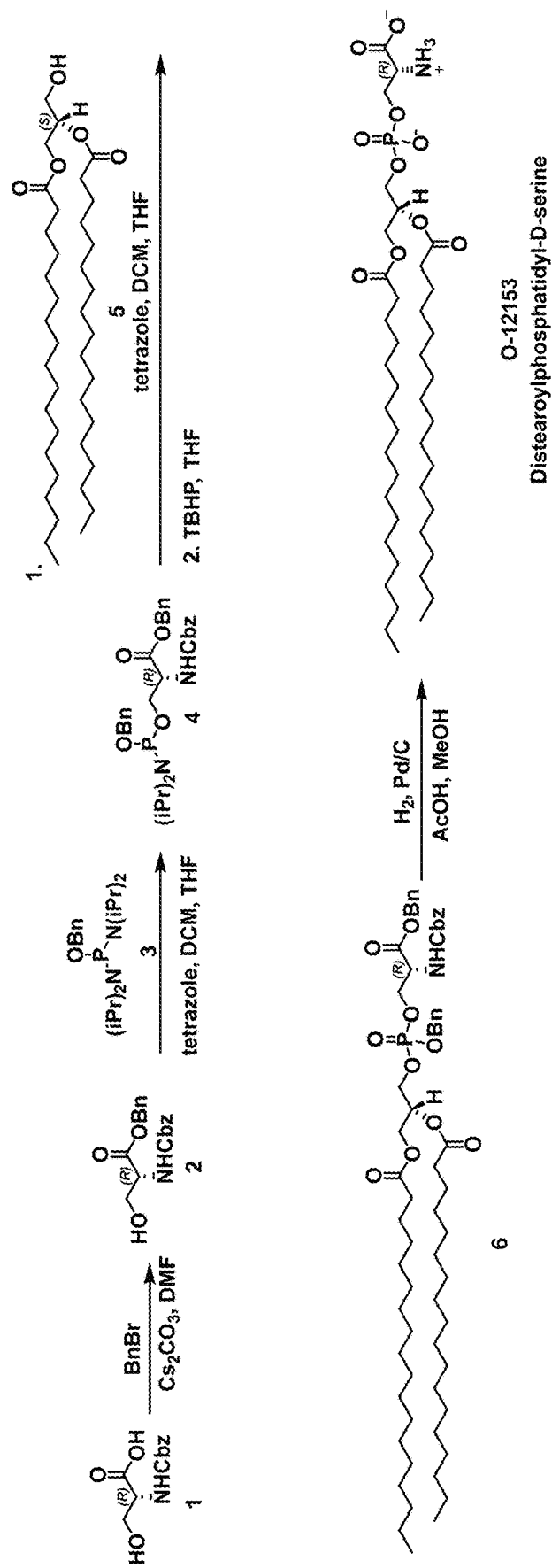

FIG. 51 Synthetic scheme for distearoylphophatidyl-D-serine.

DETAILED DESCRIPTION

It is to be understood that both the foregoing general description and the following detailed description are exemplary and explanatory only and are not restrictive of the compositions and methods of the present disclosure.

Liposomal nanoparticle (LNP) compositions can comprise an ionizable lipid, a sterol, and one or more phospholipids. In some embodiments, the LNP compositions further comprise a nucleic acid such as mRNA for administration in a pharmaceutical composition such as a vaccine. In some embodiments, the LNP compositions optionally further comprise a conjugated lipid.

Figure 1:
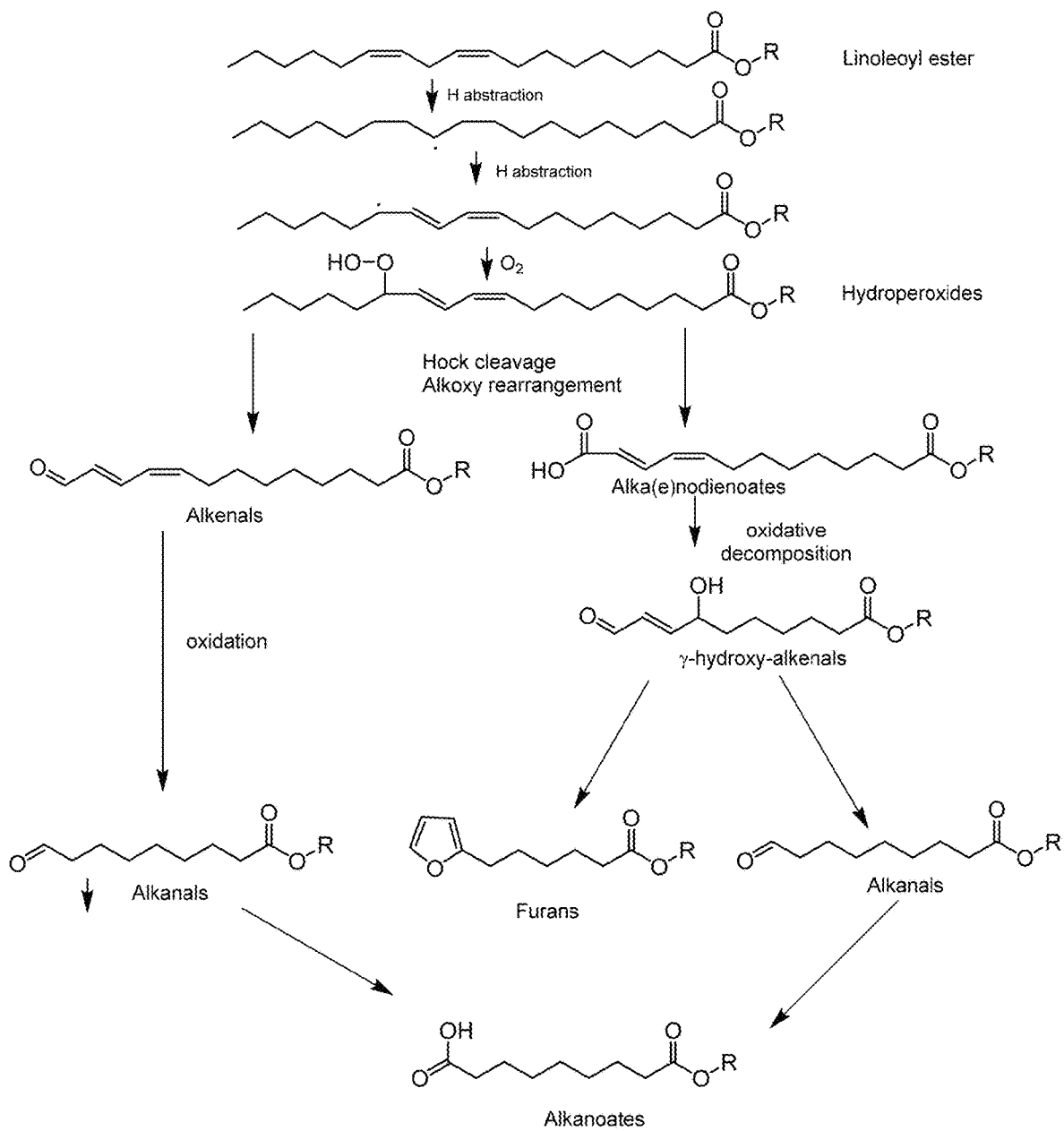
FIG. 1 is a depiction of the oxidative degradation mechanisms of lipid esters of linoleic acid containing conjugated multiple unsaturations that are particularly sensitive to oxidation.

Lipid Nanoparticle (LNP) compositions comprising mRNA include Stabilized Nucleic Acid Lipid Particles (SNALP) used as a vehicle for the systemic delivery of mRNA or other nucleic acid therapeutics. SNALP compositions include cationic lipids such as MC3 or KC2, comprising a protonatable tertiary amine head group joined to a pair of linear 18 carbon aliphatic chains containing a pair of carbon-carbon double bonds separated by a single methylene group (e.g., linoleic acid). However, while the structure of these hydrocarbon chains, each containing a pair of double bonds separated by a single methylene group, imparts desirable biological properties to the SNALP compositions, this chemical sub-structure also results in the undesired problem of increased sensitivity of the compound to oxidative degradation. For example, FIG. 1 is a depiction of the oxidative degradation mechanisms of lipid esters of linoleic acid containing conjugated multiple unsaturations that are particularly sensitive to oxidation. What is needed are novel cationic lipids suitable for use in a SNALP composition, but having enhanced resistance to oxidative degradation.

Disclosed herein are compounds, compositions and methods related to the treatment of bacterial infections. As used herein, the term "compound", "drug" and "active agent" are used interchangeably. Some aspects of the disclosure relate to novel ionizable lipids or bioreducible ionizable lipids. These lipids are cationic (i.e. positively charged) at acidic pH, such as encountered intracellularly following endocytosis or phagocytosis by a cell. The same lipids, and compositions containing them, are near neutral in charge when present at pH 7.4. These lipids may also have a single olefin group present in their alkyl or acyl groups.

Some aspects of the disclosure relate to the process for the synthesis of the novel ionizable lipids.

Other aspects relate to compositions comprising lipidic nanoparticles comprising ionizable cationic lipid, the lipidic nanoparticles containing nucleic acids. In some embodiments, nucleic acids are encapsulated into the lipidic nanoparticles.

Aspects of the disclosure provide for improved compositions of ionizable lipid nanoparticles for the delivery of therapeutic nucleic acids to cells. Anionic phospholipids, including phosphatidylserine and phosphatidylglycerol are included in the lipid nanoparticles to increase the transfection efficiency in dendritic cells. The further incorporation of ionizable lipids in an LNP formulation with gem di-substitution of mono-unsaturated alkyl chains (single olefin) on 2-position of 1,3-dioxolane or ketal demonstrated high levels of transfection in human dendritic cells, compared to other ionizable lipids in the same family, and demonstrated good stability to oxidative damage.

Definitions

For convenience, certain terms employed in the specification, examples, and appended claims are collected here. Unless defined otherwise, all technical and scientific terms used herein have the same meaning as commonly understood by one of ordinary skill in the art to which this disclosure belongs.

As used herein, the following terms and phrases are intended to have the following meanings:

The articles "a" and "an" are used herein to refer to one or to more than one (i.e., to at least one) of the grammatical object of the article. By way of example, "an element" means one element or more than one element.

As used herein the term "comprising" or "comprises" is used in reference to compositions, methods, and respective component(s) thereof, that are present in a given embodiment, yet open to the inclusion of unspecified elements.

As used herein the term "consisting essentially of" refers to those elements required for a given embodiment. The term permits the presence of additional elements that do not materially affect the basic and novel or functional characteristic(s) of that embodiment of the disclosure.

The term "consisting of" refers to compositions, methods, and respective components thereof as described herein, which are exclusive of any element not recited in that description of the embodiment.

The term "comprising" when used in the specification includes "consisting of" and "consisting essentially of".

If it is referred to "as mentioned above" or "mentioned above", "supra" within the description it is referred to any of the disclosures made within the specification in any of the preceding pages.

If it is referred to "as mentioned herein", "described herein", "provided herein," or "as mentioned in the present text," or "stated herein" within the description it is referred to any of the disclosures made within the specification in any of the preceding or subsequent pages.

As used herein, the term "about" means acceptable variations within 20%, within 10% and within 5% of the stated value. In certain embodiments, "about" can mean a variation of +/−1%, 2%, 3%, 4%, 5%, 10% or 20%.

The term "effective amount" as used herein with respect to a compound or the composition means the amount of active compound (also referred herein as active agent or drug) sufficient to cause a bactericidal or bacteriostatic effect. In some embodiments, the effective amount is a "therapeutically effective amount" meaning the amount of active compound that is sufficient alleviate the symptoms of the bacterial infection being treated.

The term "subject" (or, alternatively, "patient") as used herein refers to an animal, preferably a mammal, most preferably a human that receives either prophylactic or therapeutic treatment.

The term "administration" or "administering" as used herein includes all means of introducing the compounds or the pharmaceutical compositions to the subject in need thereof, including but not limited to, oral, intravenous, intramuscular, intraperitoneal, subcutaneous, transdermal, inhalation, buccal, ocular, sublingual, vaginal, rectal and the like. Administration of the compound or the composition is suitably parenteral. For example, the compounds or the composition can be preferentially administered intravenously, but can also be administered intraperitoneally or via inhalation like is currently used in the clinic for liposomal amikacin in the treatment of *Mycobacterium avium* (see Shirley et al., Amikacin Liposome Inhalation Suspension: A Review in *Mycobacterium avium* Complex Lung Disease. Drugs. 2019 April; 79(5):555-562)

The terms "treat," "treating," and "treatment," as used herein, refer to therapeutic or preventative measures such as those described herein.

The term "pharmaceutically acceptable salt" refers to a relatively non-toxic, inorganic or organic acid addition salt of a compound of the present disclosure which salt possesses the desired pharmacological activity.

The term "alkyl" means saturated carbon chains having from one to twenty carbon atoms which may be linear or branched or combinations thereof, unless the carbon chain is defined otherwise. Examples of alkyl groups include methyl, ethyl, propyl, isopropyl, butyl, see- and tert-butyl, pentyl, hexyl, heptyl, octyl, and the like. Unless stated otherwise specifically in the specification, an alkyl group is optionally substituted.

The term "phosphatidylserine", with any of it's acyl chain compositions, refers to the L-isomer of serine in the headgroup unless specified in a particular example.

The term "lipid conjugate" refers to a conjugated lipid that inhibits aggregation of lipid particles. Such lipid conjugates include, but are not limited to, polysarcosine (see e.g. WO2021191265A1 which is herein incorporated by reference in its entirety for all purposes), polyamide oligomers (e.g., ATTA-lipid conjugates), PEG-lipid conjugates, such as PEG coupled to dialkyloxypropyls, PEG coupled to diacylglycerols, PEG coupled to cholesterol, PEG coupled to phosphatidylethanolamines, PEG conjugated to ceramides (see, e.g., U.S. Pat. No. 5,885,613, the disclosure of which is herein incorporated by reference in its entirety for all purposes), cationic PEG lipids, and mixtures thereof. PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In preferred embodiments, non-ester containing linker moieties are used.

The abbreviations for the ionizable cationic lipids may be truncated in the Examples from that used in the Tables, for example, AKG-UO-1 or AKG-KC2-01 may be referred to as UO1 or KC2-01.

The abbreviation UT used in various studies refers to untreated samples.

The term "lipidic nanoparticle", or "LNP", refers to particles having a diameter of from about 5 to 500 nm. In some embodiments, the lipid nanoparticle comprises one or more active agents. In some embodiments, the lipid nanoparticle comprises a nucleic acid. In some embodiments, the nucleic acid is condensed in the interior of the nanoparticle with a cationic lipid, polymer, or polyvalent small molecule and an external lipid coat that interacts with the biological milieu. Due to the repulsive forces between phosphate groups, nucleic acids are naturally stiff polymers and prefer elongated configurations. In the cell, to cope with volume constraints DNA can pack itself in the appropriate solution conditions with the help of ions and other molecules. Usually, DNA condensation is defined as the collapse of extended DNA chains into compact, orderly particles containing only one or a few molecules. By binding to phosphate groups, cationic lipidic can condense DNA by neutralizing the phosphate charges and allow close packing.

In some embodiments, the active agent is encapsulated into the LNP. In some embodiments, the active agent can be an anionic compounds, for example, but not limited to DNA, RNA, natural and synthetic oligonucleotides (including antisense oligonucleotides, interfering RNA and small interfering RNA), nucleoprotein, peptide, nucleic acid, ribozyme, DNA-containing nucleoprotein, such as an intact or partially deproteinated viral particles (virions), oligomeric and polymeric anionic compounds other than DNA (for example, acid polysaccharides and glycoproteins)). In some embodiments, the active agent can be intermixed with an adjuvant.

In a LNP vaccine product, the active agent is generally contained in the interior of the LNP. In some embodiments, the active agent comprises a nucleic acid. Typically, water soluble nucleic acids are condensed with cationic lipids or polycationic polymers in the interior of the particle and the surface of the particle is enriched in neutral lipids or PEG-lipid derivatives. Additional ionizable cationic lipid may also be at the surface and respond to acidification in the environment by becoming positively charged, facilitating endosomal escape.

Ionizable lipids can have different properties or functions with respect to LNPs. Due to the pKa of the amino group, the lipid molecules can become positively charged in acidic conditions. Under these conditions, lipid molecules can electrostatically bind to the phosphate groups of the nucleic acid which allows the formation of LNPs and the entrapment of the nucleic acid. In some embodiments, the pKa can be low enough that it renders the LNP substantially neutral in surface charge in biological fluids, such as blood, which are at physiological pH values. High LNP surface charge is associated with toxicity, rapid clearance from the circulation by the fixed and free macrophages, hemolytic toxicities, including immune activation (Filion et al Biochim Biophys Acta. 1997 Oct. 23; 1329(2):345-56).

In some embodiments, pKa can be high enough that the ionizable cationic lipid can adopt a positively charged form at acidic endosomal pH values. This way, the cationic lipids can combine with endogenous endosomal anionic lipids to promote membrane lytic nonbilayer structures such as the hexagonal HII phase, resulting in more efficient intracellular delivery. In some embodiments, the pKa ranges between 6.2-6.5. For example, the pKa can be about 6.2, about 6.3, about 6.4, about 6.5. Unsaturated tails also contribute to the lipids' ability to adopt nonbilayer structures. (Jayaraman et al., Angew Chem Int Ed Engl. 2012 Aug. 20; 51(34):8529-33).

Release of nucleic acids from LNP formulations, among other characteristics such as liposomal clearance and circulation half-life, can be modified by the presence of polyethylene glycol and/or sterols (e.g., cholesterol) or other potential additives in the LNP, as well as the overall chemical structure, including pKa of any ionizable cationic lipid included as part of the formulation.

The term "bioreducible" refers to compounds that undergo accelerated degradation due to the cleavage of disulfide linkages in a reductive environment. Unlike other nucleic acid therapeutics such as siRNA, the success of mRNA-based therapies depends on the availability of a safe and efficient delivery vehicle that encapsulates the mRNA. mRNA is fragile and needs a protective coating for it to remain active until it reaches its target site. mRNA containing LNPs are a promising vaccine option for Covid-19 immunity (Jackson et al., Preliminary Report. N Engl J Med. 2020 Nov. 12; 383(20):1920-1931). The efficiency and tolerability of LNPs has been attributed to the amino lipid and unlike many biomaterial applications that may have a required service lifetime of weeks or months, functional LNP mediated delivery of mRNA occurs within hours obviating the need for persistent lipids. Indeed in applications where chronic dosing is required this will be especially important. It has been demonstrated that LNPs enter cells via endocytosis and accumulate in endolysosomal compartments. The ionizable cationic lipid (ICL) is able to effectively deliver mRNA to the cytosol after endocytosis while being susceptible to enzymatic hydrolysis in late endosomes/lysosomes by lipases or hydrolysis triggered by the reductive environment of the lysosome allowing complete biodegradation. The extracellular space is a relatively oxidative environment, while the intracellular space is a reductive one, allowing a disulfide linked molecule to remain intact in the extracellular space but be rapidly reduced once internalized (Huang et al., Mol Ther. 2005 March; 11(3): 409-17, 2005). Some embodiments, provide bioreducible disulfide linked ICL molecules (see compounds 29-36, Table 2) that are stable in LNP formulation and while in circulation but undergo cleavage in the reductive environment of the lysosome. Such compounds and compositions can facilitate rapid biological destruction of the lipids and can prevent potentially toxic accumulation of ICL lipids (as observed in rats with DLin-MC3-DMA (Sabins et al., Mol Ther. 2018 Jun. 6; 26(6):1509-1519).

The terms "encapsulation" and "entrapped," as used herein, refer to the incorporation or association of the mRNA, DNA, siRNA or other nucleic acid pharmaceutical agent in or with a lipidic nanoparticle. As used herein, the term "encapsulated" refers to complete encapsulation or partial encapsulation. A siRNA may be capable of selectively knocking down or down regulating expression of a gene of interest. For example, an siRNA could be selected to silence a gene associated with a particular disease, disorder, or condition upon administration to a subject in need thereof of a nanoparticle composition including the siRNA. A siRNA may comprise a sequence that is complementary to an mRNA sequence that encodes a gene or protein of interest.

The term "mol %" with regard to cholesterol refers to the molar amount of cholesterol relative to the sum of the molar amounts of cholesterol and non-PEGylated phospholipid expressed in percentage points. For example, "55 mol. % cholesterol" in a liposome containing cholesterol and HSPC refers to the composition of 55 mol. parts of cholesterol per 45 mol. parts of HSPC.

The term "mol %" with regard to PEG-lipid refers to the ratio of the molar amount of PEG-lipid and non-PEGylated phospholipid expressed in percentage points. For example, "5 mol. % PEG-DSPE" in a LNP containing HSPC and PEG-DSPE refers to the composition having 5 mol. parts of PEG-DSPE per 100 mol. parts of HSPC.

In some embodiments, "mol %" with regard to cholesterol refers to the molar amount of cholesterol relative to the sum of the molar amounts of total lipid expressed in percentage points. For example, "40.5 mol % cholesterol" in an LNP composition containing cholesterol, an ICL, DSPC, PS, cholesterol, and PEG-DMG refers to the composition of 40.5 mol. parts of cholesterol per 59.5 mol. parts of the ICL, DSPC, PS, and PEG-DMG components combined.

In some embodiments, "mol %" with regard to conjugated lipid refers to the ratio of the molar amount of conjugated lipid expressed in percentage points. For example, "1.5 mol % PEG-DMG" in an LNP containing cholesterol, an ICL, DSPC, PS, cholesterol, and PEG-DMG refers to the composition of 1.5 mol. parts of PEG-DMG per 98.5 mol. parts of the combined ICL, DSPC, PS, and cholesterol components.

In some embodiments, "mol %" with regard to the PS lipid refers to the ratio of the molar amount of PS lipid expressed in percentage points. For example, "5 mol % DPPS" in an LNP containing cholesterol, an ICL, DSPC, DPPS, cholesterol, and PEG-DMG refers to the composition of 5 mol. parts of PEG-DMG per 95 mol. parts of the combined ICL, DSPC, PEG-DMG, and cholesterol components.

In some embodiments, "mol %" with regard to ICL refers to the ratio of the molar amount of ICL expressed in percentage points. For example, "48 mol % PEG-DMG" in an LNP containing cholesterol, KC3-OA (e.g., an example of an ICL), DSPC, PS, cholesterol, and PEG-DMG refers to the composition of 48 mol. parts of the ICL per 52 mol. parts of the combined PEG-DMG, DSPC, PS, and cholesterol components.

As used herein, the term "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Various aspects and embodiments are described in further detail in the following subsections.

Ionizable Cationic Lipids

Provided herein are compounds useful in the preparation of lipid nanoparticle (LNP) compositions.

In some embodiments, a lipid nanoparticle (LNP) composition comprises an ionizable cationic lipid having the chemical structure of Formula (I):

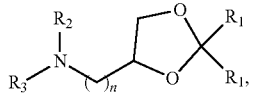
(I)

wherein $R_1$ is

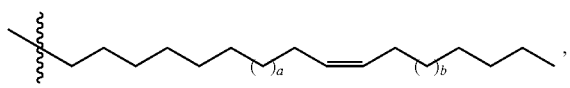

wherein a is 0 or 1; b is 1, 2, 3 or 4, provided the sum a+b is 1, 2, 3 or 4;

$R_2$ and $R_3$ are each independently ($C_1$-$C_4$) alkyl optionally substituted with hydroxyl; and n is an integer equal to 2, 3 or 4.

In some embodiments, a lipid nanoparticle (LNP) composition comprises an ionizable cationic lipid having the chemical structure of Formula (I), wherein the total length of the $R_1$ hydrocarbon chain is $C_{15}$-$C_{18}$. In some embodiments, the total length of the $R_1$ hydrocarbon chain is $C_{16}$-$C_{18}$. In some embodiments, the total length of the $R_1$ hydrocarbon chain is $C_{16}$ or $C_{18}$.

In some embodiments, a lipid nanoparticle (LNP) composition comprises an ionizable cationic lipid having the chemical structure of Formula (I), wherein a is 0 and b is 1, 2, 3 or 4. In some embodiments, a lipid nanoparticle (LNP) composition comprises an ionizable cationic lipid having the chemical structure of Formula (I), wherein a is 0 and b is 1 or 3. In some embodiments, a lipid nanoparticle (LNP) composition comprises an ionizable cationic lipid having the chemical structure of Formula (I), wherein a is 0 and b is 1. In some embodiments, a lipid nanoparticle (LNP) composition comprises an ionizable cationic lipid having the chemical structure of Formula (1), wherein a is 0 and b is 3.

In some embodiments, a lipid nanoparticle (LNP) composition comprises an ionizable cationic lipid having the chemical structure of Formula (I), wherein a is 1 and b is 1, 2, 3 or 4. In some embodiments, a lipid nanoparticle (LNP) composition comprises an ionizable cationic lipid having the chemical structure of Formula (I), wherein a is 1 and b is 1 or 3. In some embodiments, a lipid nanoparticle (LNP) composition comprises an ionizable cationic lipid having the chemical structure of Formula (I), wherein a is 1 and b is 1. In some embodiments, a lipid nanoparticle (LNP) composition comprises an ionizable cationic lipid having the chemical structure of Formula (I), wherein a is 1 and b is 3.

In some embodiments, a lipid nanoparticle (LNP) composition comprises an ionizable cationic lipid having the chemical structure of Formula (I), wherein $R_{10}$ and $R_{12}$ are the same. In some embodiments, a lipid nanoparticle (LNP) composition comprises an ionizable cationic lipid having the chemical structure of Formula (I), wherein $R_{10}$ and $R_{12}$ are each ($C_1$-$C_4$)alkyl optionally substituted with hydroxyl. In some embodiments, a lipid nanoparticle (LNP) composition comprises an ionizable cationic lipid having the chemical structure of Formula (I), wherein $R_{10}$ and $R_{12}$ are each ($C_1$-$C_4$)alkyl. In some embodiments, a lipid nanoparticle (LNP) composition comprises an ionizable cationic lipid having the chemical structure of Formula (I), wherein $R_{10}$ and $R_{12}$ are each methyl. In some embodiments, a lipid nanoparticle (LNP) composition comprises an ionizable cationic lipid having the chemical structure of Formula (I), wherein $R_{10}$ and $R_{12}$ are each ethyl. In some embodiments, a lipid nanoparticle (LNP) composition comprises an ionizable cationic lipid having the chemical structure of Formula (I), wherein $R_{10}$ and $R_{12}$ are each independently selected from methyl or ethyl. In some embodiments, a lipid nanoparticle (LNP) composition comprises an ionizable cationic lipid having the chemical structure of Formula (I), wherein $R_{10}$ and $R_{12}$ are each independently selected from methyl, ethyl, —($CH_2$)($CH_2$)OH, and —($CH_2$)$_2$($CH_2$)OH.

In some embodiments, a lipid nanoparticle (LNP) composition comprises an ionizable cationic lipid having the chemical structure of Formula (I), wherein a is 0 or 1; b is 1, 2, 3 or 4, provided the sum a+b is 1, 2, 3 or 4; $R_2$ and $R_3$ are each methyl; and n is an integer equal to 2, 3 or 4. In some embodiments, a lipid nanoparticle (LNP) composition comprises an ionizable cationic lipid having the chemical structure of Formula (I), wherein a is 0 or 1; b is 1, 2, 3 or 4, provided the sum a+b is 1, 2, 3 or 4; $R_2$ and $R_3$ are each methyl; and n is an integer equal to 2 or 3. In some embodiments, a lipid nanoparticle (LNP) composition comprises an ionizable cationic lipid having the chemical structure of Formula (I), wherein a is 0 or 1; b is 1, 2, 3 or 4, provided the sum a+b is 1, 2, 3 or 4; $R_2$ and $R_3$ are each methyl; and n is an integer equal to 2. In some embodiments, a lipid nanoparticle (LNP) composition comprises an ionizable cationic lipid having the chemical structure of Formula (I), wherein a is 0 or 1; b is 1, 2, 3 or 4, provided the sum a+b is 1, 2, 3 or 4; $R_2$ and $R_3$ are each methyl; and n is an integer equal to 3.

In some embodiments, an ionizable cationic lipid comprises the chemical structure of Formula (II):

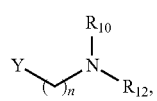
(II)

or a pharmaceutically acceptable salt thereof, wherein
Y is

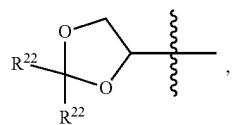

n is an integer 2, 3 or 4;
$R^{22}$ is a hydrocarbon chain with a single olefin and a total length of $C_{15}$-$C_{18}$; and
each of $R_{10}$ and $R_{12}$ is independently ($C_1$-$C_4$)alkyl optionally substituted with hydroxyl.

In some aspects, $R^{22}$ in Formula (II) is a polyene hydrocarbon chain of Formula A.

In some aspects, $R_{10}$ and $R_{12}$ in Formula (II) are each independently selected from methyl, ethyl, propyl, —($CH_2$)($CH_2$)OH, and —($CH_2$)$_2$($CH_2$)OH. In some aspects, $R_{10}$ and $R_{12}$ are each independently methyl in Formula (II). In some aspects, $R_{10}$ and $R_{12}$ are each independently ethyl in Formula (II). In some aspects, at least one of $R_{10}$ and $R_{12}$ is n-propyl optionally substituted with hydroxyl in Formula (II). In some aspects, $R_{10}$ is methyl and $R_{12}$ is selected from methyl, ethyl, —$(CH_2)(CH_2)OH$, and —$(CH_2)_2(CH_2)OH$ in Formula (II). In some aspects, $R_{10}$ is methyl and $R_{12}$ is selected from —$(CH_2)(CH_2)OH$, and —$(CH_2)_2(CH_2)OH$ in Formula (II). In some aspects, $R_{10}$ is methyl and $R_{12}$ is selected from —$(CH_2)(CH_2)OH$, and —$(CH_2)_2(CH_2)OH$ in a compound comprising the chemical structure of Formula (II). In some aspects, $R_{10}$ and $R_{12}$ are independently selected from methyl or ethyl, optionally substituted with one or more hydroxyl in Formula (II). In some aspects, one or both of $R_{10}$ and $R_{12}$ in Formula (II) are —$(CH_2)(CH_2)OH$, or —$(CH_2)_2(CH_2)OH$ in Formula (II). In some aspects, $R_{10}$ is methyl and $R_{12}$ is methyl or ethyl substituted with hydroxyl in Formula (II). In some aspects, one or both of $R_{10}$ in Formula (II) is methyl and $R_{12}$ is —$(CH_2)(CH_2)OH$ in Formula (II). In some aspects, one or both of $R_{10}$ in Formula (II) is methyl and $R_{12}$ is —$(CH_2)_2(CH_2)OH$ in Formula (II).

In some embodiments, the compounds have the structure of the compounds listed in the tables below. Table 1A and Table 1B show examples of cationic lipids. Table 2 shows examples of bioreducible cationic lipids.

Table 1A. Exemplary Cationic Lipids

TABLE 1A

Exemplary cationic lipids

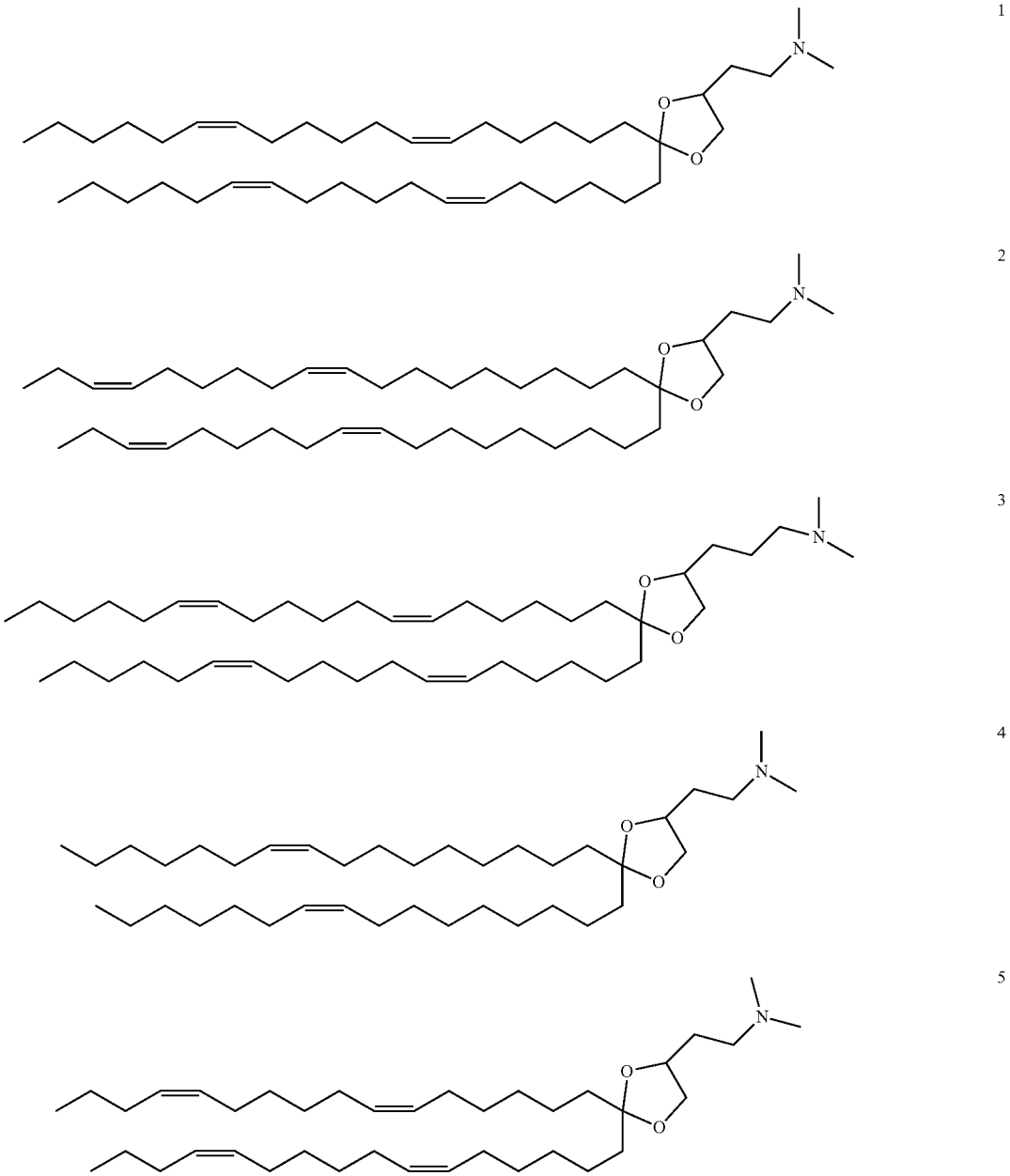

TABLE 1A-continued
Exemplary cationic lipids
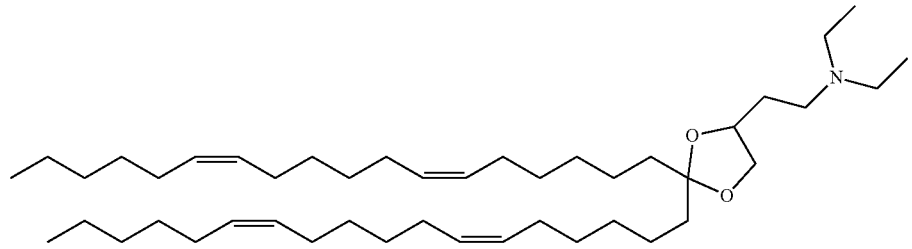 [SMILES: CCCCC/C=C\CCCC/C=C\CCCCCC1(CCCCC/C=C\CCCC/C=C\CCCCC)OCC(CCN(CC)CC)O1]
6
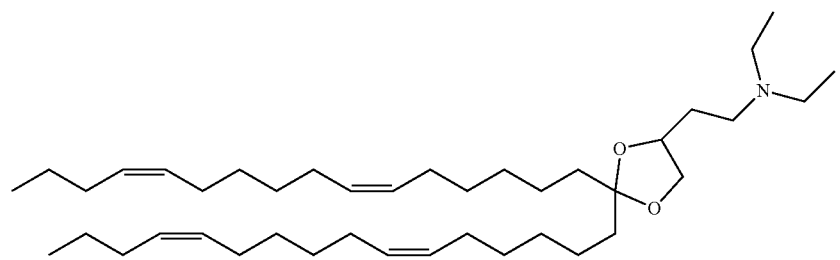 [SMILES: CCC/C=C\CCCC/C=C\CCCCCC1(CCCCC/C=C\CCCC/C=C\CCC)OCC(CCN(CC)CC)O1]
7
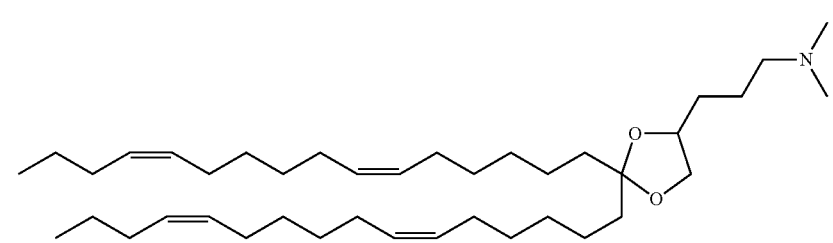 [SMILES: CCC/C=C\CCCC/C=C\CCCCCC1(CCCCC/C=C\CCCC/C=C\CCC)OCC(CCCN(C)C)O1]
8
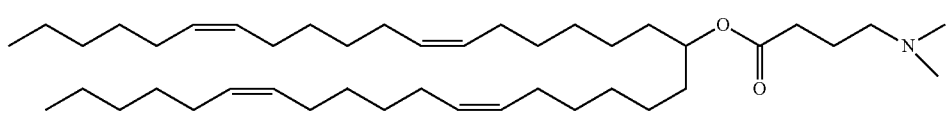 [SMILES: CCCCC/C=C\CCCC/C=C\CCCCCC(CCCCC/C=C\CCCC/C=C\CCCCC)OC(=O)CCCN(C)C]
9
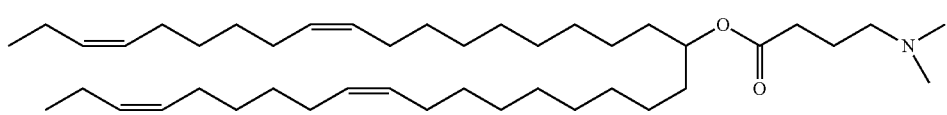 [SMILES: CC/C=C\CCCC/C=C\CCCCCCCCC(CCCCCCCC/C=C\CCCC/C=C\CC)OC(=O)CCCN(C)C]
10
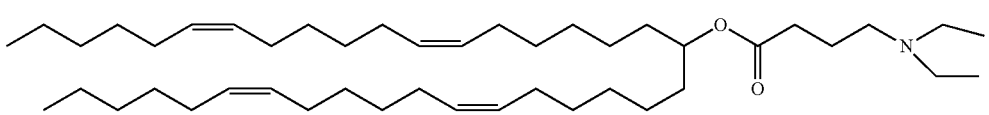 [SMILES: CCCCC/C=C\CCCC/C=C\CCCCCC(CCCCC/C=C\CCCC/C=C\CCCCC)OC(=O)CCCN(CC)CC]
11
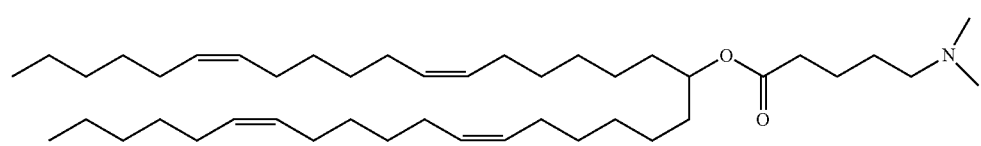 [SMILES: CCCCC/C=C\CCCC/C=C\CCCCCC(CCCCC/C=C\CCCC/C=C\CCCCC)OC(=O)CCCCN(C)C]
12
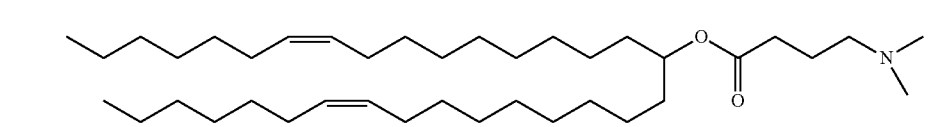 [SMILES: CCCCCC/C=C\CCCCCCCCC(CCCCCCCC/C=C\CCCCCC)OC(=O)CCCN(C)C]
13
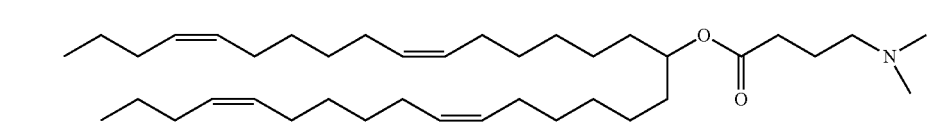 [SMILES: CCC/C=C\CCCC/C=C\CCCCCC(CCCCC/C=C\CCCC/C=C\CCC)OC(=O)CCCN(C)C]
14

TABLE 1A-continued
Exemplary cationic lipids
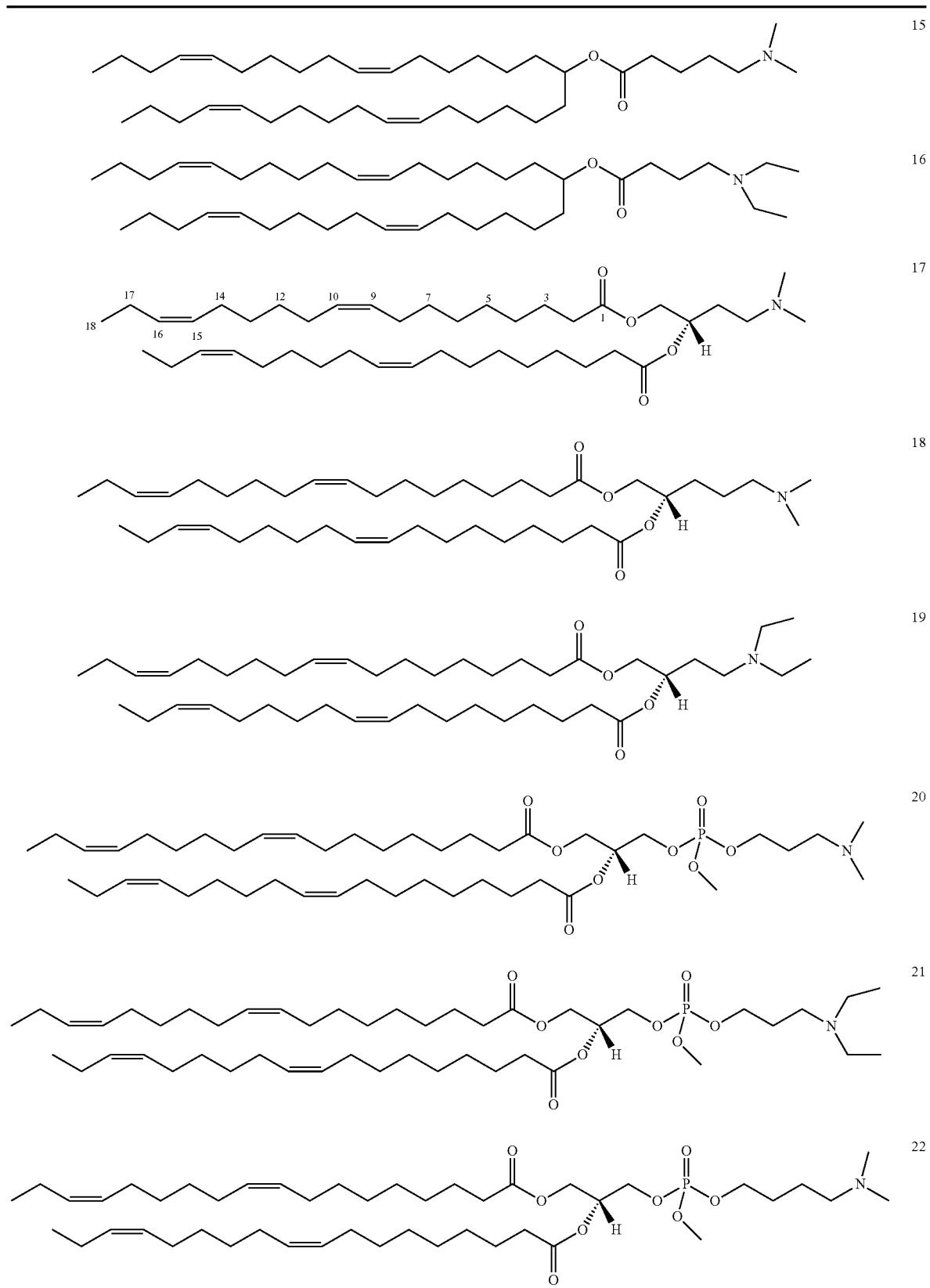

TABLE 1A-continued

Exemplary cationic lipids (Structures 23–28 shown with fatty acid diester backbones bearing dimethylamino, diethylamino, and phosphate-containing head groups.)

TABLE 1B

Additional Exemplary cationic lipids

AKG-UO-6

TABLE 1B-continued
Additional Exemplary cationic lipids
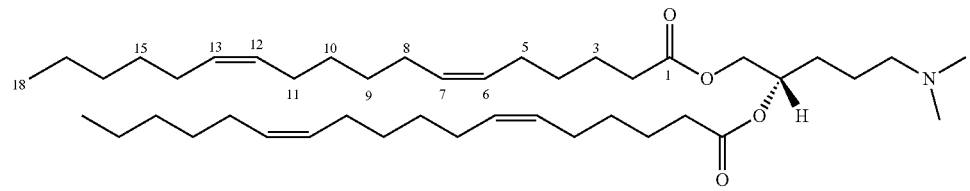 [SMILES: CCCCC/C=C\CCCC/C=C\CCCCC(=O)OC[C@H](CCCN(C)C)OC(=O)CCCC/C=C\CCCC/C=C\CCCCC]
AKG-UO-7
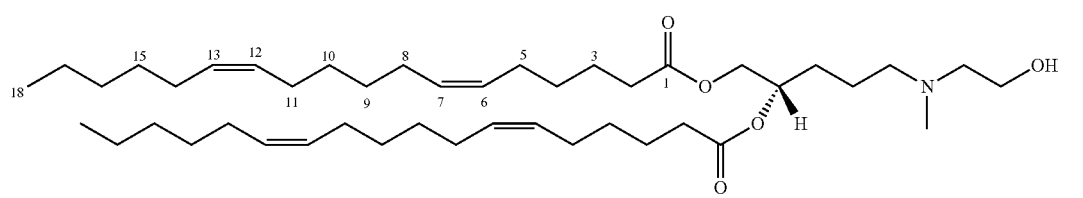 [SMILES: CCCCC/C=C\CCCC/C=C\CCCCC(=O)OC[C@H](CCCN(C)CCO)OC(=O)CCCC/C=C\CCCC/C=C\CCCCC]
AKG-UO-8
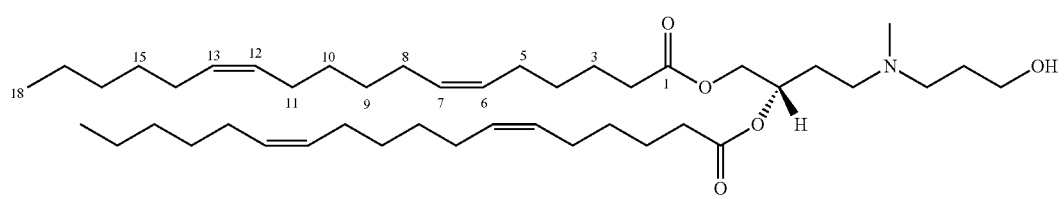 [SMILES: CCCCC/C=C\CCCC/C=C\CCCCC(=O)OC[C@H](CCN(C)CCCO)OC(=O)CCCC/C=C\CCCC/C=C\CCCCC]
AKG-UO-9
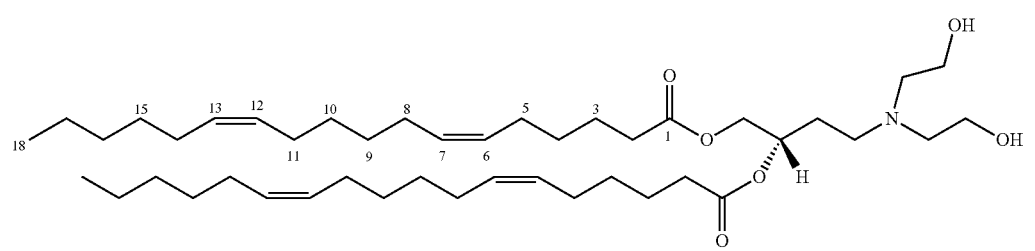 [SMILES: CCCCC/C=C\CCCC/C=C\CCCCC(=O)OC[C@H](CCN(CCO)CCO)OC(=O)CCCC/C=C\CCCC/C=C\CCCCC]
AKG-UO-10
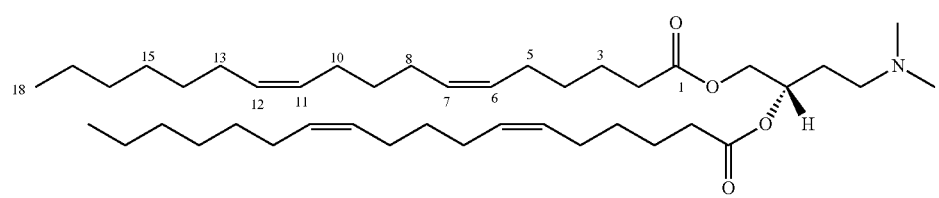 [SMILES: CCCCCC/C=C\CCC/C=C\CCCCC(=O)OC[C@H](CCN(C)C)OC(=O)CCCC/C=C\CCC/C=C\CCCCCC]
AKG-UO-1A
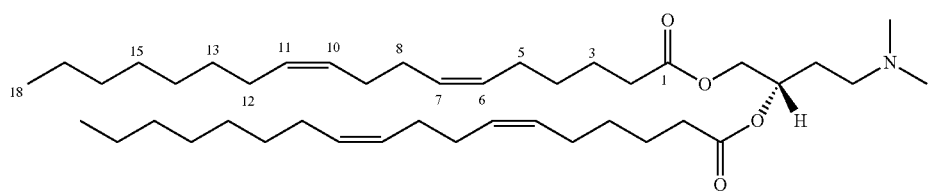 [SMILES: CCCCCCC/C=C\CC/C=C\CCCCC(=O)OC[C@H](CCN(C)C)OC(=O)CCCC/C=C\CC/C=C\CCCCCCC]
AKG-UO-1B TABLE 2
Exemplary bioreducible cationic lipids
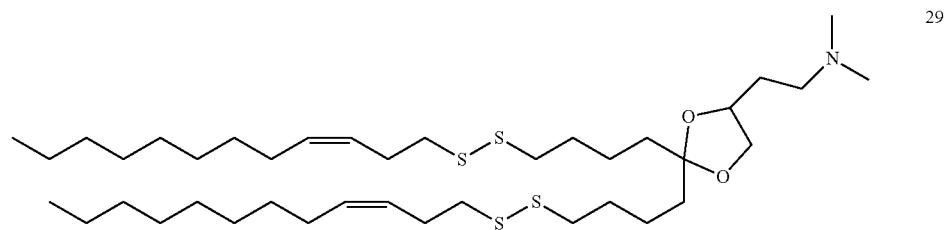
29
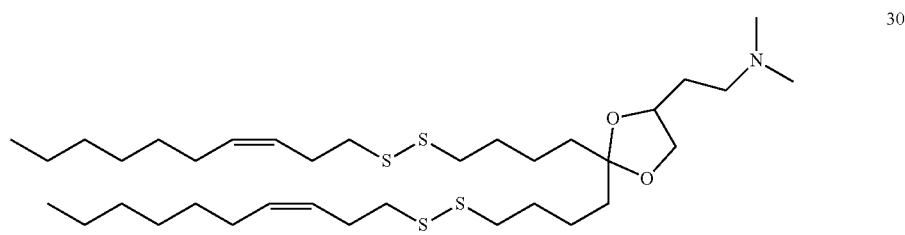
30
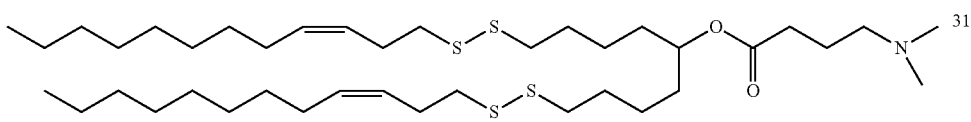
31
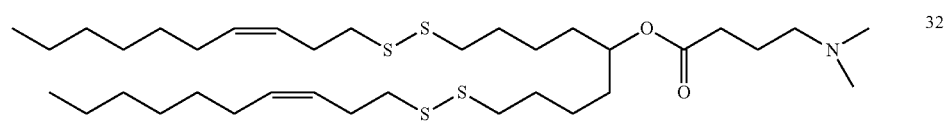
32
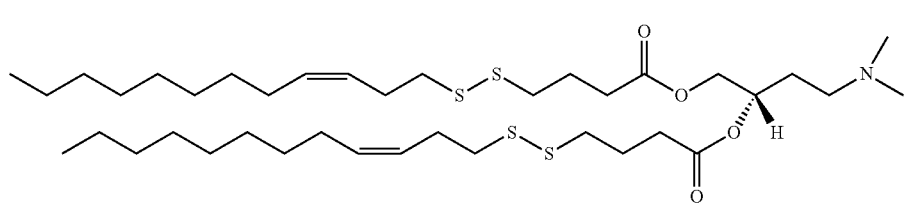 [SMILES: CCCCCCCC/C=C\CCSSCCCC(=O)OC[C@H](CCN(C)C)OC(=O)CCCSSCC/C=C\CCCCCCCC]
33
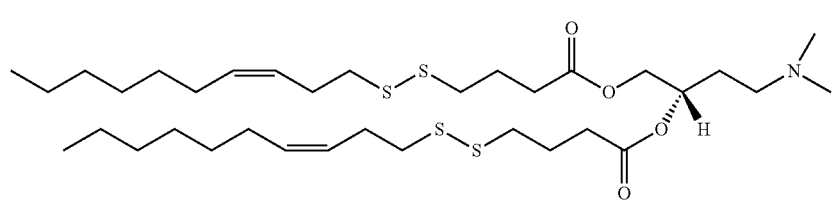 [SMILES: CCCCCC/C=C\CCSSCCCC(=O)OC[C@H](CCN(C)C)OC(=O)CCCSSCC/C=C\CCCCCC]
34
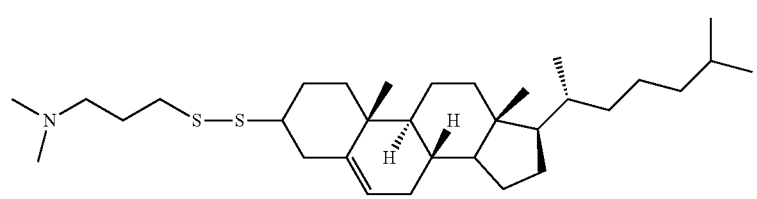
35
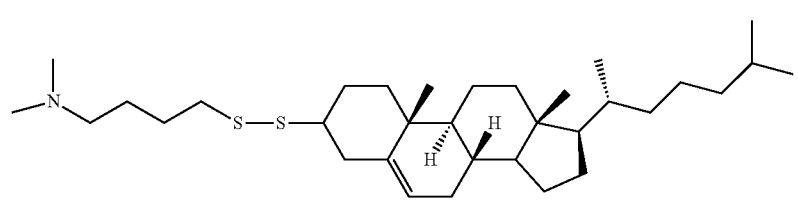
36

TABLE 2-continued

Exemplary bioreducible cationic lipids

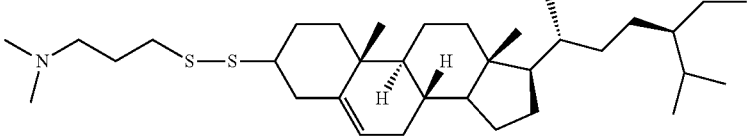

37

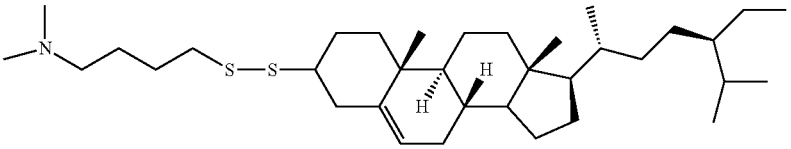

38

In some embodiments, the ionizable lipid encapsulate the nucleic acid. In some embodiments, the ionizable lipid encapsulate the nucleic acid in a LNP formulation. In some embodiments, the nucleic acid is a siRNA molecule. In some embodiments, the nucleic acid is a mRNA molecule. In some embodiments, the nucleic acid is a DNA molecule.

In some embodiments, compositions further comprising ligands, such as antibody conjugates, directed against cell surface receptors to target lipid nanoparticles in a highly specific manner to dendritic cells are provided. In some embodiments, the composition further comprises a targeting ligand, wherein the targeting ligand is oriented to the outside of the nanoparticle. In some embodiments, the targeting ligand is an antibody.

In some embodiments, the lipidic nanoparticles are in an aqueous medium.

In some embodiments, the nucleic acid is entrapped in the lipidic nanoparticle with a compound disclosed herein, including compounds of Formula I, II, III, IV-B, V-A-1 or combinations thereof, wherein the nucleic acid is either RNA or DNA. In some embodiments, the nucleic acid is entrapped in the lipidic nanoparticle with a compound disclosed herein, including compounds of disclosed herein or combinations thereof, wherein the nucleic acid is either RNA or DNA. In some embodiments, the nucleic acid is mRNA. In some embodiments, the nucleic acid is siRNA. In some embodiments, the nucleic acid is DNA.

In some embodiments, the lipidic nanoparticle comprises a membrane comprising phosphatidylcholine and a sterol. In some embodiments, the sterol is cholesterol. In some embodiments, the lipidic nanoparticle comprises a membrane comprising phosphatidylcholine, ionizable cationic lipid (ICL). In some embodiments, the ICL have a structure of Formula I, II, III, IV-B, V-A-1, and cholesterol, wherein the membrane separates the inside of the lipidic nanoparticles from the aqueous medium. In some embodiment, the ICL have a structure as shown in Table 1A and Table 2. In some embodiment, the ICL have a structure as shown in Table 1B. In some embodiments, the phosphatidylcholine is distearoylphosphatidylcholine (DSPC) or hydrogenated soy phosphatidylcholine (HSPC). In some embodiments, the ionizable cationic lipid to cholesterol molar ratios is from about 65:35 to 40:60. In some embodiments, the ICL to cholesterol molar ratio is from about 60:40 to about 45:55.

In some embodiments, the phosphatidylcholine to cholesterol molar ratio is from about 1:5 to about 1:2.

In some embodiments, the membrane further comprises a polymer-conjugated lipid.

In some embodiments, the lipidic nanoparticle comprises ICL, DSPC, cholesterol and polymer-conjugated lipid in a about 49.5:10.3:39.6:2.5 molar ratio.

In some embodiments, the polymer-conjugated lipid is PEG(2000)-dimyristoylglycerol (PEG-DMG) or PEG(Mol. weight 2,000)-dimyristoylphosphatidylethanolamine (PEG-DMPE).

In some embodiments the percentage of oxidative degradation products for the ionizable lipid is less than 50% of that for a DLin-KC2-DMA or DLin-MC3-DMA control formulation.

In some embodiments, the composition is a liquid pharmaceutical formulation for parenteral administration.

In some embodiments, the composition is a liquid pharmaceutical formulation for subcutaneous, intramuscular, or intradermal administration.

In some embodiments, the composition is in the form of a lyophilized powder, that is subsequently reconstituted with aqueous medium prior to administration.

Other aspects of the disclosure relate to a method of preventing a bacterial or viral infection, the method comprising administering to a subject in need thereof an effective amount of the composition provided herein to elicit an immune response. Some embodiments provide methods of vaccinating a subject in need thereof, the method comprising administering the composition comprising a nucleic acid encoding an antigenic protein.

In some embodiments, the composition is administered subcutaneously, intramuscularly, or intradermally.

In some embodiments, the bacterial infection is *Mycobacterium tuberculosis* infection. In some embodiments, the bacterial infection is a form of nontuberculosis *Mycobacterium*.

In some embodiments, the viral infection is a coronavirus. In some embodiments, the coronavirus is SARS-CoV, MERS-CoV or SARS-CoV-2

In some embodiments, the viral infection is HIV/AIDs.

In some embodiments, the lipidic nanoparticle is administered parenterally.

In some embodiments, the lipidic nanoparticle composition is administered as part of a single injection.

The present disclosure features a lipid nanoparticle comprising nucleic acids such as DNA, mRNA, siRNA, antisense oligonucleotides, CRISPR components such as a guide RNA (gRNA or sgRNA) and a CRISPR-associated endonuclease (Cas protein) and a lipid. Exemplary lipids include ionizable cationic lipids (ICLs), phospholipids, sterol lipids, alkylene glycol lipids (e.g., polyethylene glycol lipids), sphingolipids, glycerolipids, glycerophospholipids, prenol lipids, saccharolipids, fatty acids, and polyketides. In some embodiments, the LNP comprises a single type of lipid. In some embodiments, the LNP comprises a plurality (e.g., two or more) of lipids. An LNP may comprise one or more of an ionizable cationic lipid, a phospholipid, a sterol, or an alkylene glycol lipid (e.g., a polyethylene glycol lipid).

In an embodiment, the LNP comprises an ionizable cationic lipid. As used herein "ionizable cationic lipid", "ionizable lipid" and "ICL" are used interchangeably. An ICL is a lipid that comprises an ionizable moiety capable of bearing a charge (e.g., a positive charge e.g., a cationic lipid) under certain conditions (e.g., at a certain pH range, e.g., under physiological conditions). The ionizable moiety may comprise an amine, and preferably a substituted amine. An ionizable lipid may be a cationic lipid or an anionic lipid. In addition to an ionizable moiety, an ionizable lipid may contain an alkyl or alkenyl group, e.g., greater than six carbon atoms in length (e.g., greater than about 8 carbons, 10 carbons, 12 carbons, 14 carbons, 16 carbons, 18 carbons, 20 carbons or more in length). Additional ionizable lipids that may be included in an LNP described herein are disclosed in Jayaraman et al. (*Angew. Chem. Int. Ed.* 51:8529-8533 (2012)), Semple et al. Nature Biotechnol. 28:172-176 (2010)), and U.S. Pat. Nos. 8,710,200 and 8,754,062, each of which is incorporated herein by reference in its entirety.

In some embodiments, an LNP further comprises an ionizable lipid having a structure of Formula (IV-A), or a pharmaceutically acceptable salt thereof,

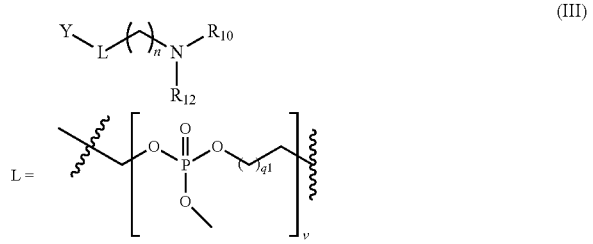

(III)

wherein each of $R_{10}$ and $R_{12}$ is independently $(C_1\text{-}C_4)$alkyl optionally substituted with hydroxyl; v is 0 or 1; q1 is 1 or 2; Y is

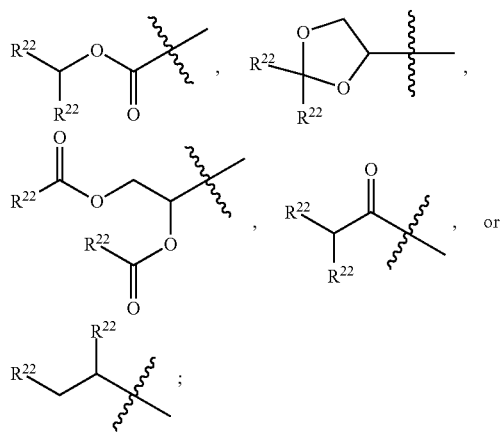

$R^{22}$ is

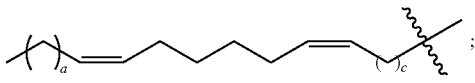

a is 1, 2, 3, 4 or 5; and c is 4, 5, 6, 7 or 8.

In some embodiments, v equals 0 for compounds of Formula (III). In some embodiments, v equals 1 for compounds of Formula (III). In some embodiments, v equals 1 and q1 equals 1 for compounds of Formula (III). In some embodiments, v equals 1 and q1 equals 2 for compounds of Formula (III).

In some embodiments, the sum of a and c is 6, 7, 8 or 9 in $R^{22}$ for compounds of Formula (III). In some embodiments, the sum of a and c is 6 in $R^{22}$ for compounds of Formula (III). In some embodiments, the sum of a and c is 7 in $R^{22}$ for compounds of Formula (III). In some embodiments, the sum of a and c is 9 in $R^{22}$ for compounds of Formula (III).

In some embodiments, v equals 0 and the sum of a and c is 6, 7, 8 or 9 in $R^{22}$ for compounds of Formula (III). In some embodiments, v equals 0 and the sum of a and c is 6 in $R^{22}$ for compounds of Formula (IV-B). In some embodiments, v equals 0 and the sum of a and c is 7 in $R^{22}$ for compounds of Formula (III). In some embodiments, v equals 0 and the sum of a and c is 9 in $R^{22}$ for compounds of Formula (III).

In some embodiments, $R_{10}$ and $R_{12}$ are independently selected from methyl, ethyl, —$(CH_2)(CH_2)OH$, and —$(CH_2)_2(CH_2)OH$ for compounds of Formula (III). In some embodiments, $R_{10}$ and $R_{12}$ are each methyl and the sum of a and c is 6, 7, 8 or 9 in $R^{22}$ for compounds of Formula (III). In some embodiments, $R_{10}$ and $R_{12}$ are each methyl, v is 0 and the sum of a and c is 6, 7, 8 or 9 in $R^{22}$ for compounds of Formula (III).

In some embodiments, v equals 0 and $R_{22}$ is

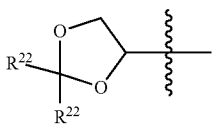

for compounds of Formula (IV-B). In some embodiments, v equals 0 and $R^{22}$ is

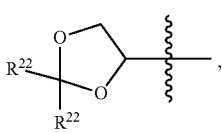

and the sum of a and c is 7 or 9 for compounds of Formula (III). In some embodiments, v equals 0 and $R^{22}$ is

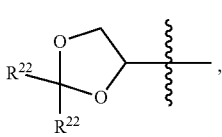

and a is 4 and c is 5 for compounds of Formula (III). In some embodiments, v equals 0 and $R^{22}$ is

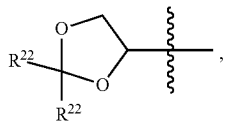

and a is 1 and c is 8 for compounds of Formula (III). In some embodiments, v equals 0 and $R^{22}$ is

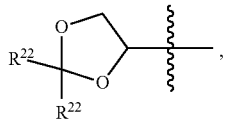

and a is 2 and c is 5 for compounds of Formula (III).

An LNP may comprise an ionizable lipid at a concentration greater than about 0.1 mol %, e.g., of the total lipid content of the LNP. In an embodiment, the LNP comprises an ionizable lipid at a concentration of greater than about 1 mol %, about 2 mol %, about 4 mol %, about 8 mol %, about mol %, about 40 mol %, about 50 mol %, about 60 mol %, about 80 mol %, e.g., of the total lipid content of the LNP. In an embodiment, the LNP comprises an ionizable lipid at a concentration of greater than about 20 mol %, about 40 mol %, or about 50 mol %. In an embodiment, the LNP comprises an ionizable lipid at a concentration between about 1 mol % to about 95 mol %, e.g., of the total lipid content of the LNP. In an embodiment, the LNP comprises an ionizable lipid at a concentration between about 2 mol % to about 90 mol %, about 4 mol % to about 80 mol %, about mol % to about 70 mol %, about 20 mol % to about 60 mol %, about 40 mol % to about 55 mol %, e.g., of the total lipid content of the LNP. In an embodiment, the LNP comprises an ionizable lipid at a concentration between about 20 mol % to about 60 mol %. In an embodiment, the LNP comprises an ionizable lipid at a concentration between about 40 mol % to about 55 mol %.

In an embodiment, the LNP comprises a phospholipid. A phospholipid is a lipid that comprises a phosphate group and at least one alkyl, alkenyl, or heteroalkyl chain. A phospholipid may be naturally occurring or non-naturally occurring (e.g., a synthetic phospholipid). A phospholipid may comprise an amine, amide, ester, carboxyl, choline, hydroxyl, acetal, ether, carbohydrate, sterol, or a glycerol. In some embodiments, a phospholipid may comprise a phosphocholine, phosphosphingolipid, or a plasmalogen. Exemplary phospholipids include 1,2-dioleoyl-sn-glycero-3-phosphocholine (DOPC), 1,2-dipalmitoyl-sn-glycero-3-phosphocholine (DPPC), 1,2-dioleoyl-sn-glycero-3-phosphoethanolamine (DOPE), 1,2-distearoyl-sn-glycero-3-phosphocholine (DSPC), hydrogenated soy phosphatidylcholine (HSPC), 1,2-dilauroyl-sn-glycero-3-phosphocholine (DLPC), 1,2-dimyristoyl-sn-glycero-3-phosphocholine (DMPC), 1,2-distearoyl-sn-glycero-3-phosphoethanolamine (DSPE), 1-myristoyl-2-oleoyl-sn-glycero-3-phosphocholine (MOPC), 1,2-diarachidonoyl-sn-glycero-3-phosphocholine (DAPC), 1-palmitoyl-2-linoleoyl-sn-glycero-3-phosphatidylcholine (PLPC), 1-palmitoyl-2-oleoyl-glycero-3-phosphocholine (POPC), 1-stearoyl-2-myristoyl-sn-glycero-3-phosphocholine (SMPC), 1-palmitoyl-2-myristoyl-sn-glycero-3-phosphocholine (PMPC), bis(monoacylglycerol)phosphate (BMP), L-α-phosphatidylcholine, 1,2-Diheptadecanoyl-sn-glycero-3-phosphorylcholine (DHDPC), and 1-stearoyl-2-arachidonoyl-sn-glycero-3-phosphocholine (SAPC). Additional phospholipids that may be included in an LNP described herein are disclosed in Li, J. et al. (*Asian J. Pharm. Sci.* 10:81-98 (2015)), which is incorporated herein by reference in its entirety.

In some embodiments, the phospholipid is 1,2-distearoyl-sn-glycero-3-phosphocholine (DSPC). In some embodiments, the phospholipid is 1,2-dioleoyl-sn-glycero-3-phosphocholine (DOPC). In some embodiments, the phospholipid is 1,2-dipalmitoyl-sn-glycero-3-phosphocholine (DPPC). In some embodiments, the phospholipid is 1,2-dioleoyl-sn-glycero-3-phosphoethanolamine (DOPE).

Incorporation of Phosphatidylserine

The LNP (e.g., as described herein) may comprise one or more of the following components: (i) Ionizable cationic lipid (ICL) containing a C16 alkyl or C16 alkenyl group or C18 alkyl or C18 alkenyl group at a concentration between about 1 mol % to about 95 mol % (or any value therebetween, e.g. about 20 mol % to about 80 mol %); (ii) A phospholipid at a concentration between 0.1 mol % to about 20 mol % (or any value there between, e.g. between about 2.5 mol % to about 10 mol %) where the phospholipid also contains C16 or C18 alkyl or alkenyl groups; (iii) cholesterol at a concentration between about 1 mol % to about 95 mol % (or any value therebetween, e.g. about 20 mol % to about 80 mol %); (iv) a phosphatidylserine (PS) or phosphatidylglycerol (PG) added to the LNP lipid formulation at a concentration between about 0.5 mol % to about 20 mol %, about 2.5 mol % to about 10 mol %, about 4 mol % to about 8 mol %, or any value therebetween of the total lipid content of the LNP, and (v) a polyethyleneglycol (PEG)-2000-containing lipid (e.g., DPG-PEG2000, DPPE-PEG2000, DMPE-PEG2000, DMG-PEG2000) at a concentration between about 0.1 mol % to about 5 mol % (or any value therebetween, e.g. between about 1 mol % to about 2.5 mol %). In some embodiments, the LNP comprises two of (i)-(v). In some embodiments, the LNP comprises three of (i)-(v). In some embodiments, the LNP comprises four of (i)-(v). In some embodiments, the LNP comprises each of (i)-(v). In some embodiments, the LNP comprises (i) and (ii). In some embodiments, the LNP comprises (i) and (iii). In some embodiments, the LNP comprises (i) and (v). In some embodiments, the LNP comprises (ii) and (iii). In some embodiments, the LNP comprises (ii) and (v). In some embodiments, the LNP comprises (iii) and (iv). In some embodiments, the LNP comprises (iii) and (v). In some embodiments, the LNP comprises (i), (ii), and (iii). In some embodiments, the LNP comprises (i), (ii), and (v). In some embodiments, the LNP comprises (ii), (iii), and (v). In some embodiments, the LNP comprises (ii), (iii), (iv) and (v). In an embodiment, the LNP consists or consists essentially of four of (i)-(v). In an embodiment, the LNP consists or consists essentially of each of (i)-(v). In some embodiments, the LNP consists or consists essentially of (i) and (ii). In some embodiments, the LNP consists or consists essentially of (i) and (iii). In some embodiments, the LNP consists or consists essentially of (i) and (v). In some embodiments, the LNP consists or consists essentially of (ii) and (iii). In some embodiments, the LNP comprises (ii) and (v). In some embodiments, the LNP consists or consists essentially of (iii) and (iv). In some embodiments, the LNP consists or consists essentially of (iii) and (v). In some embodiments, the LNP consists or consists essentially of (i), (ii), and (iii). In some embodiments, the LNP consists or consists essentially of (i), (ii), and (v). In some embodiments, the LNP comprises (ii), (iii), and (v). In some embodiments, the LNP consists or consists essentially of (ii), (iii), (iv) and (v).

An LNP may comprise a phospholipid at a concentration greater than about 0.1 mol %, e.g., of the total lipid content of the LNP. In an embodiment, the LNP comprises a phospholipid at a concentration of greater than about 0.5 mol %, about 1 mol %, about 1.5 mol %, about 2 mol %, about 3 mol %, about 4 mol %, about 5 mol %, about 6 mol %, about 8 mol %, about 10 mol %, about 12 mol %, about 15 mol %, about 20 mol %, about 50 mol %, e.g., of the total lipid content of the LNP. In an embodiment, the LNP comprises a phospholipid at a concentration of greater than about 1 mol %, about 5 mol %, or about 10 mol %. In an embodiment, the LNP comprises a phospholipid at a concentration between about 0.1 mol % to about 50 mol %, e.g., of the total lipid content of the LNP. In an embodiment, the LNP comprises a phospholipid at a concentration between about 0.5 mol % to about 40 mol %, about 1 mol % to about 30 mol %, about 5 mol % to about 25 mol %, about 10 mol % to about 20 mol %, about 10 mol % to about 15 mol %, or about 15 mol % to about 20 mol %, e.g., of the total lipid content of the LNP. In an embodiment, the LNP comprises a phospholipid at a concentration between about 5 mol % to about 25 mol %. In an embodiment, the LNP comprises a phospholipid at a concentration between about 10 mol % to 20 mol %.

In an embodiment, the LNP comprises a sterol or ionizable sterol molecule. A sterol is a lipid that comprises a polycyclic structure and an optionally a hydroxyl or ether substituent, and may be naturally occurring or non-naturally occurring (e.g., a synthetic sterol). Sterols may comprise no double bonds, a single double bond, or multiple double bonds. Sterols may further comprise an alkyl, alkenyl, halo, ester, ketone, hydroxyl, amine, polyether, carbohydrate, or cyclic moiety. An exemplary listing of sterols includes cholesterol, dehydroergosterol, ergosterol, campesterol, β-sitosterol, stigmasterol, lanosterol, dihydrolanosterol, desmosterol, brassicasterol, lathosterol, zymosterol, 7-dehydrodesmosterol, avenasterol, campestanol, lupeol, and cycloartenol. In some embodiments, the sterol comprises cholesterol, dehydroergosterol, ergosterol, campesterol, β-sitosterol, or stigmasterol. Additional sterols that may be included in an LNP described herein are disclosed in Fahy, E. et al. (*J. Lipid. Res.* 46:839-862 (2005)).

Ionizable Sterols

In some embodiments, an LNP comprises a sterol. In some embodiments, the sterol is cholesterol. In some embodiments, the sterol is dehydroergosterol. In some embodiments, the sterol is ergosterol. In some embodiments, the sterol is campesterol. In some embodiments, the sterol is β-sitosterol. In some embodiments, the sterol is stigmasterol. In some embodiments, the sterol is a corticosteroid. (e.g., corticosterone, hydrocortisone, cortisone, or aldosterone).

In some embodiments, the ionizable lipid can be a branched ionizable lipid selected from ALC-0315 and SM-102:

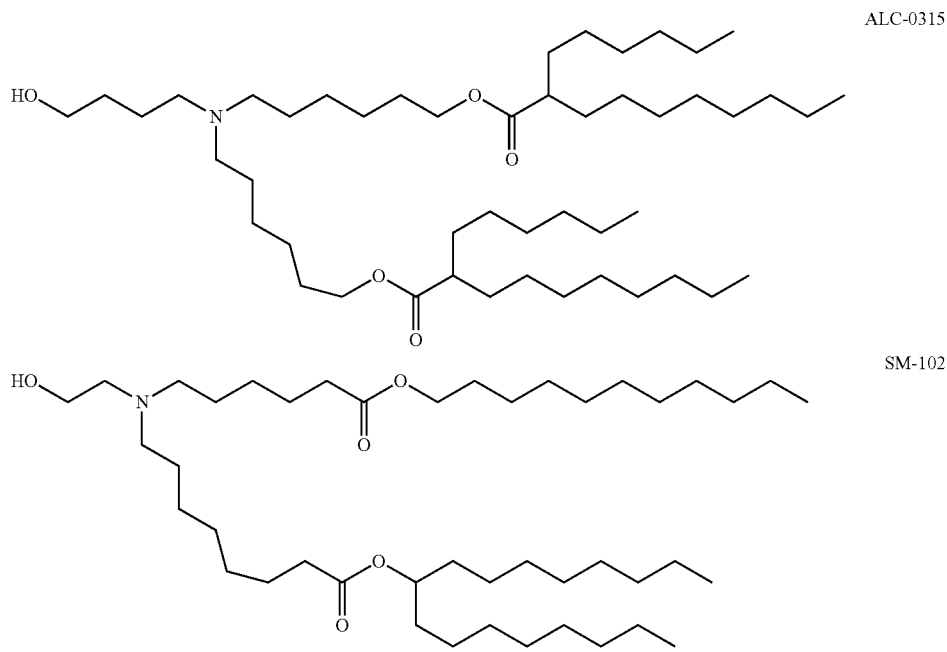

An LNP may comprise a sterol at a concentration greater than about 0.1 mol %, e.g., of the total lipid content of the LNP. In an embodiment, the LNP comprises a sterol at a concentration greater than about 0.5 mol %, about 1 mol %, about 5 mol %, about 10 mol %, about 15 mol %, about mol %, about 25 mol %, about 35 mol %, about 40 mol %, about 45 mol %, about 50 mol %, about 55 mol %, about 60 mol %, about 65 mol %, or about 70 mol %, e.g., of the total lipid content of the LNP. In an embodiment, the LNP comprises a sterol at a concentration greater than about 10 mol %, about 15 mol %, about 20 mol %, or about 25 mol %. In an embodiment, the LNP comprises a sterol at a concentration between about 1 mol % to about 95 mol %, e.g., of the total lipid content of the LNP. In an embodiment, the LNP comprises a sterol at a concentration between about 5 mol % to about 90 mol %, about 10 mol % to about 85 mol %, about 20 mol % to about 80 mol %, about 20 mol % to about 60 mol %, about 20 mol % to about 50 mol %, or about 20 mol % to 40 mol %, e.g., of the total lipid content of the LNP. In an embodiment, the LNP comprises a sterol at a concentration between about 20 mol % to about 50 mol %. In an embodiment, the LNP comprises a sterol at a concentration between about 30 mol % to about 60 mol %.

In some embodiments, the LNP comprises an alkylene glycol-containing lipid. An alkylene glycol-containing lipid is a lipid that comprises at least one alkylene glycol moiety, for example, a methylene glycol or an ethylene glycol moiety. In some embodiments, the alkylene glycol-containing lipid comprises a polyethylene glycol (PEG). An alkylene glycol-containing lipid may be a PEG-containing lipid. Polymer-conjugated lipids may include poly(ethylene glycol)-conjugated (pegylated)phospholipids (PEG-lipids) such as PEG(Mol. weight 2,000) methoxy-poly(ethylene glycol)-1,2-distearoyl-sn-glycerol (PEG-DSG), PEG(Mol. weight 2,000) methoxy-poly(ethylene glycol)-1,2-palmitoyl-sn-glycerol (PEG-DPG), PEG(Mol. weight 2,000) 1,2-distearoyl-sn-glycero-3-phosphoethanolamine-N-[methoxy (polyethylene glycol)-2000](PEG-DSPE) or N-palmitoyl-sphingosine-1-{succinyl[methoxy(polyethylene glycol) 2000]}(PEG-ceramide). The molecular weight of the PEG portion in the PEG-lipid component can also vary from 500-10,000 g/mol, from 1,500-6000 g/mol, but is preferably about 2,000 MW. Other polymers used for conjugation to a lipid anchors may include poly(2-methyl-2-oxazoline) (PMOZ), poly(2-ethyl-2-oxazoline) (PEOZ), poly-N-vinylpyrrolidone (PVP), polyglycerol, poly(hydroxyethyl L-asparagine) (PHEA), and poly(hydroxyethyl L-glutamine) (PHEG).

A PEG-containing lipid may further comprise an amine, amide, ester, carboxyl, phosphate, choline, hydroxyl, acetal, ether, heterocycle, or carbohydrate. PEG-containing lipids may comprise at least one alkyl or alkenyl group, e.g., greater than six carbon atoms in length (e.g., greater than about 8 carbons, 10 carbons, 12 carbons, 14 carbons, 16 carbons, 18 carbons, 20 carbons or more in length), e.g., in addition to a PEG moiety. In an embodiment, a PEG-containing lipid comprises a PEG moiety comprising at least 20 PEG monomers, e.g., at least 30 PEG monomers, 40 PEG monomers, 45 PEG monomers, 50 PEG monomers, 100 PEG monomers, 200 PEG monomers, 300 PEG monomers, 500 PEG monomers, 1000 PEG monomers, or 2000 PEG monomers. Exemplary PEG-containing lipids include PEG-DMG (e.g., DMG-PEG2k), PEG-c-DMG, PEG-DSG, PEG-DPG, PEG-DSPE, PEG-DMPE, PEG-DPPE, PEG-DOPE, and PEG-DLPE. In some embodiments, the PEG-lipids include PEG-DMG (e.g., DMG-PEG2k), PEG-c-DMG, PEG-DSG, and PEG-DPG. Additional PEG-lipids that may be included in an LNP described herein are disclosed in Fahy, E. et al. (*J. Lipid. Res.* 46:839-862 (2005) which is incorporated herein by reference in its entirety.

In some embodiments, the PEG-lipid is PEG-DMG (e.g., DMG-PEG2k). In some embodiments, the PEG-lipid is α-(3'-{[1,2-di(myristyloxy)propanoxy]carbonylamino}propyl)-ω-methoxy, polyoxyethylene (PEG-c-DMG). In some embodiments, the PEG-lipid is PEG-DSG. In some embodiments, the PEG-lipid is PEG-DPG.

An LNP may comprise an alkylene glycol-containing lipid at a concentration greater than about 0.1 mol %, e.g., of the total lipid content of the LNP. In an embodiment, the LNP comprises an alkylene glycol-containing lipid at a concentration of greater than about 0.5 mol %, about 1 mol %, about 1.5 mol %, about 2 mol %, about 3 mol %, about 4 mol %, about 5 mol %, about 6 mol %, about 8 mol %, about 10 mol %, about 12 mol %, about 15 mol %, about 20 mol %, about 50 mol %, e.g., of the total lipid content of the LNP. In an embodiment, the LNP comprises an alkylene glycol-containing lipid at a concentration of greater than about 1 mol %, about 4 mol %, or about 6 mol %. In an embodiment, the LNP comprises an alkylene glycol-containing lipid at a concentration between about 0.1 mol % to about 50 mol %, e.g., of the total lipid content of the LNP. In an embodiment, the LNP comprises an alkylene glycol-containing lipid at a concentration between about 0.5 mol % to about 40 mol %, about 1 mol % to about 35 mol %, about 1.5 mol % to about mol %, about 2 mol % to about 25 mol %, about 2.5 mol % to about 20%, about 3 mol % to about mol %, about 3.5 mol % to about 10 mol %, or about 4 mol % to 9 mol %, e.g., of the total lipid content of the LNP. In an embodiment, the LNP comprises an alkylene glycol-containing lipid at a concentration between about 3.5 mol % to about 10 mol %. In an embodiment, the LNP comprises an alkylene glycol-containing lipid at a concentration between about 4 mol % to 9 mol %.

In some embodiments, the LNP comprises at least two types of lipids. In an embodiment, the LNP comprises two of an ionizable lipid, a phospholipid, a sterol, and an alkylene glycol-containing lipid. In some embodiments, the LNP comprises at least three types of lipids. In an embodiment, the LNP comprises three of an ionizable lipid, a phospholipid, a sterol, and an alkylene glycol-containing lipid. In some embodiments, the LNP comprises at least four types of lipids. In an embodiment, the LNP comprises each of an ionizable lipid, a phospholipid, a sterol, and an alkylene glycol-containing lipid.

The LNP (e.g., as described herein) may comprise one or more of the following components: (i) an ionizable cationic lipid at a concentration between about 1 mol % to about 95 mol % (e.g. about 20 mol % to about 80 mol %); (ii) a phospholipid at a concentration between 0.1 mol % to about 50 mol % (e.g. between about 2.5 mol % to about 20 mol %); (iii) a sterol at a concentration between about 1 mol % to about 95 mol % (e.g. about 20 mol % to about 80 mol %); and (iv) a PEG-containing lipid at a concentration between about 0.1 mol % to about 50 mol % (e.g. between about 2.5 mol % to about 20 mol %). In some embodiments, the LNP comprises one of (i)-(iv). In some embodiments, the LNP comprises two of (i)-(iv). In some embodiments, the LNP comprises three of (i)-(iv). In some embodiments, the LNP comprises each of (i)-(iv). In some embodiments, the LNP comprises (i) and (ii). In some embodiments, the LNP comprises (i) and (iii). In some embodiments, the LNP comprises (i) and (iv). In some embodiments, the LNP comprises (ii) and (iii). In some embodiments, the LNP comprises (ii) and (iv). In some embodiments, the LNP comprises (iii) and (iv). In some embodiments, the LNP comprises (i), (ii), and (iii). In some embodiments, the LNP comprises (i), (ii), and (iv). In some embodiments, the LNP comprises (ii), (iii), and (iv).

The LNP (e.g., as described herein) may comprise one or more of the following components: (i) Ionizable cationic lipid (ICL) at a concentration between about 1 mol % to about 95 mol % (e.g. about 20 mol % to about 80 mol %); (ii) DSPC at a concentration between 0.1 mol % to about 50 mol % (e.g. between about 2.5 mol % to about 20 mol %); (iii) cholesterol at a concentration between about 1 mol % to about 95 mol % (e.g. about 20 mol % to about 80 mol %); and (iv) DMG-PEG2k at a concentration between about 0.1 mol % to about 50 mol % (e.g. between about 2.5 mol % to about 20 mol %). In some embodiments, the LNP comprises two of (i)-(iv). In some embodiments, the LNP comprises three of (i)-(iv). In some embodiments, the LNP comprises each of (i)-(iv). In some embodiments, the LNP comprises (i) and (ii). In some embodiments, the LNP comprises (i) and (iii). In some embodiments, the LNP comprises (i) and (iv). In some embodiments, the LNP comprises (ii) and (iii). In some embodiments, the LNP comprises (ii) and (iv). In some embodiments, the LNP comprises (iii) and (iv). In some embodiments, the LNP comprises (iii) and (iv). In some embodiments, the LNP comprises (i), (ii), and (iii). In some embodiments, the LNP comprises (i), (ii), and (iv). In some embodiments, the LNP comprises (ii), (iii), and (iv).

In an embodiment, the LNP comprises a ratio of ionizable lipid to phospholipid of about 50:1 to about 1:1 (e.g., 40:1, 32:3, 6:1, 7:1, 5:1, 24:5, 26:5, 10:3, 15:2, 16:7, 18:1, 3:1, 3:2, or 1:1). In an embodiment, the LNP comprises a ratio of ionizable lipid to phospholipid of about 15:2. In an embodiment, the LNP comprises a ratio of ionizable lipid to phospholipid of about 5:1. In an embodiment, the LNP comprises a ratio of ionizable lipid to a sterol of about 10:1 to about 1:10 (e.g., 9:1, 8:1, 8:7, 7:1, 7:5, 7:3, 6:1, 6:5, 5:1, 5:3, 4:1, 4:3, 3:1, 2:1, 1:1, 1:2, 1:3, 3:4, 1:4, 3:5, 1:5, 4:5, 1:6, 5:6, 7:6, 7:8, or 8:9). In an embodiment, the LNP comprises a ratio of ionizable lipid to an alkylene-containing lipid of about 1:10 to about 10:1 (e.g., 1:9, 1:8, 7:8, 7:1, 7:5, 7:3, 6:1, 6:5, 5:1, 5:3, 4:1, 4:3, 3:1, 2:1, 1:1, 1:2, 1:3, 3:4, 1:4, 3:5, 1:5, 4:5, 1:6, 5:6, 7:6, 7:8, or 8:9). In an embodiment, the LNP comprises a ratio of phospholipid to an alkylene-containing lipid of about 10:1 to about 1:10 (e.g., 9:1, 8:1, 8:7, 7:1, 7:5, 7:3, 6:1, 6:5, 5:1, 5:3, 4:1, 4:3, 3:1, 2:1, 1:1, 1:2, 1:3, 3:4, 1:4, 3:5, 1:5, 4:5, 1:6, 5:6, 7:6, 7:8, or 8:9). In an embodiment, the LNP comprises a ratio of a sterol to an alkylene-containing lipid of about 50:1 to about 1:1 (e.g., 40:1, 32:3, 6:1, 7:1, 5:1, 24:1, 22:1, 20:1, 22:5, 24:5, 26:5, 10:3, 15:2, 16:7, 18:1, 3:1, 3:2, or 1:1).

In some embodiments, a LNP (e.g., described herein) comprises two of an ionizable lipid, a phospholipid, a sterol, and an alkylene glycol-containing lipid (e.g., PEG-containing lipid). In another embodiment, a LNP (e.g., described herein) comprises three of an ionizable lipid, a phospholipid, a sterol, and an alkylene glycol-containing lipid (e.g., PEG-containing lipid). In some embodiments, LNP (e.g., described herein) comprises each of an ionizable lipid, a phospholipid, a sterol, and an alkylene glycol-containing lipid (e.g., PEG-containing lipid).

In some embodiments, an LNP described herein has a diameter between 5 and 500 nm, e.g., between 10 and 400 nm, 20 and 350 nm, 25 and 325 nm, 30 and 300 nm, 50 and 250 nm, 60 and 200 nm, 75 and 190 nm, 80 and 180 nm, 100 and 200 nm, 200 and 300 nm, and 150 and 250 nm. The diameter of an LNP may be determined by any method known in the art, for example, dynamic light scattering, transmission electron microscopy (TEM) or scanning electron microscopy (SEM). In some embodiments, an LNP has a diameter between 50 and 100 nm, between 70 and 100 nm, and between 80 and 100 nm. In an embodiment, an LNP has a diameter of about 90 nm. In some embodiments, an LNP described herein has a diameter greater than about nm. In some embodiments, an LNP has a diameter greater than about 35 nm, about 40 nm, about 45 nm, about 50 nm, about 60 nm, about 70 nm, about 80 nm, about 90 nm, about 100 nm, about 120 nm, about 140 nm, about 160 nm, about 180 nm, about 200 nm, about 225 nm, about 250 nm, about 275 nm or about 300 nm. In an embodiment, an LNP has a diameter greater than about 70 nm. In an embodiment, an LNP has a diameter greater than about 90 nm. In an embodiment, an LNP has a diameter greater than about 180 nm.

In some embodiments, a plurality of LNPs described herein has an average diameter ranging from about 40 nm to about 180 nm. In some embodiments, a plurality of LNPs described herein has an average diameter from about 50 nm to about 150 nm. In some embodiments, a plurality of LNPs described herein has an average diameter from about 50 nm to about 120 nm.

In some embodiments, a plurality of LNPs described herein has an average diameter from about 60 nm to about 120 nm. In some embodiments, a plurality of LNPs has an average diameter of about 40 nm, about 45 nm, about 50 nm, about 60 nm, about 70 nm, about 80 nm, about 90 nm, about 100 nm, about 120 nm, about 140 nm, about 160 nm, about 180 nm In some embodiments, a nanoparticle or plurality of nanoparticles described herein has an average neutral to negative surface charge of less than −100 mv, for example, less than −90 mv, −80 mv, −70 mv, −60 mv, −50 mv, −40 mv, −30 mv, and −20 mv. In some embodiments, a nanoparticle or plurality of nanoparticles has a neutral to negative surface charge of between −100 mv and 100 my, between −75 mv to 0, or between −50 mv and −10 mv.

In some embodiments, at least 5% (e.g., at least 10%, at least 15%, at least 20%, at least 25%, at least 30%, at least 40%, at least 50%, at least 60%, at least 70%, at least 80%, at least 90%, at least 95%, or at least 99%) of the nanoparticles of a plurality of nanoparticles have an average neutral to negative surface charge of less than −100 mv. In some embodiments, a nanoparticle or plurality of nanoparticles has an average surface charge of between −20 mv to +20, between −10 my and +10 mv, or between −5 mv and +5 mv at pH 7.4. LNPs that are neutral in charge have improved pharmacokinetics and biological performance compared to cationic LNPs.

Making Lipid Nanoparticles (LNPs)

The method of making an LNP can comprise mixing a first solution with a second solution. Mixing can be achieved using standard liquid mixing techniques, such as propellor mixing, vortexing solutions or preferably through microfluidic mixing or high efficiency T-mixing. In some embodiments, the first solution comprises a lipid or a plurality of lipids and a nucleic acid, where all components are solubilized, in water/solvent system. The solvent may be any water miscible solvent (e.g., ethanol, methanol, isopropanol, acetonitrile, dimethylformamide, dimethylsulfoxide, dioxane or tetrahydrofuran). In some embodiments, the first solution comprises a small percentage of water or pH buffered water. The first solution may comprise up to at least 60% by volume of water, e.g., up to at least about 0.05%, 0.1%, 0.5%, 1%, 2%, 3%, 4%, 5%, 10%, 15%, 20%, 25%, 30%, 35%, 40%, 45%, 50%, 55% or 60% by volume of water. In an embodiment, the first solution comprises between about 0.05% and 60% by volume of water, e.g., between about 0.05% and 50%, about 0.05% and 40%, or about 5% and 20% by volume of water.

In some embodiments, the first solution comprises a single type of lipid, for example, an ionizable lipid, a phospholipid, a sterol, or a PEG-containing lipid. In some embodiments, the first solution comprises a plurality of lipids. In some embodiments, the plurality comprises an ionizable lipid, a phospholipid, a sterol, or a PEG-containing lipid. In some embodiments, the plurality of lipids comprise cholesterol, 1,2-distearoyl-sn-glycero-3-phosphocholine (DSPC), 1,2-dimyristoyl-rac-glycero-3-methylpolyoxyethylene2000 (DMG-PEG2k) or α-(3'-{[1,2-di(myristyloxy)propanoxy] carbonylamino}propyl)-ω-methoxy, polyoxyethylene (PEG2000-C-DMG), and an ionizable lipid. The plurality of lipids may exist in any ratio. In an embodiment, the plurality of lipids comprises an ionizable lipid or sterol, a phospholipid, a sterol, a PEG-containing lipid of the above lipids or a combination thereof in a particular ratio (e.g., a ratio described herein).

In some embodiments, the second solution is water. In some embodiments, the second solution is an aqueous buffer with a pH between 3-6 (e.g., a pH of about 3, about 4, about 5, or about 6). The second solution may comprise a load component, e.g., a nucleic acid (e.g., mRNA). The second solution may comprise a small percentage of water-miscible organic solvent. The second solution may comprise up to at least 60% by volume of at least one water miscible organic solvent, e.g., up to at least about 0.05%, 0.1%, 0.5%, 1%, 2%, 3%, 4%, 5%, 6%, 7%, 8%, 9%, 10%, 15%, 20%, 25%, 30%, 35%, 40%, 45%, 50%, 55%, 60% or any percent therebetween by volume of at least one organic solvent (e.g., a water miscible organic solvent). In an embodiment, the second solution comprises between about 0.05% and 60% by volume of organic solvent, e.g., between about 0.05% and 50%, about 0.05% and 40%, or about 5% and 20% by volume of organic solvent (e.g., a water miscible organic solvent). The aqueous buffer solution can be an aqueous solution of citrate buffer. In some embodiments, the aqueous buffer solution is a citrate buffer solution with a pH between 4-6 (e.g., a pH of about 4, about 5, or about 6). In an embodiment, the aqueous buffer solution is a citrate buffer solution with a pH of about 6.

In some embodiments, the solution comprising a mixture of the first and second solutions comprising the LNP suspension can be diluted. In some embodiments, the pH of the solution comprising a mixture of the first and second solutions comprising the LNP suspension can be adjusted. Dilution or adjustment of the pH of the LNP suspension can be achieved with the addition of water, acid, base or aqueous buffer. In some embodiments, no dilution or adjustment of the pH of the LNP suspension is carried out. In some embodiments, both dilution and adjustment of the pH of the LNP suspension is carried out.

In some embodiments, excess reagents, solvents, unencapsulated nucleic acid maybe removed from the LNP suspension by tangential flow filtration (TFF) (e.g., diafiltration). The organic solvent (e.g., ethanol) and buffer may also be removed from the LNP suspension with TFF. In some embodiments, the LNP suspension is subjected to dialysis and not TFF. In some embodiments, the LNP suspension is subjected to TFF and not dialysis. In some embodiments, the LNP suspension is subjected to both dialysis and TFF.

In one aspect, the present disclosure features a method comprising treating a sample of LNPs comprising nucleic acid, with a fluid comprising a detergent (e.g., Triton X-100, or anionic detergents (such as, but not limited to, sodium dodecyl sulfate (SDS), or non-ionic detergent, such as but not limited to β-octylglucoside, or Zwittergent 3-14) for a period of time suitable to degrade the lipid layer and thereby release the encapsulated and/or entrapped nucleic acid(s). In an embodiment, the method further comprises analyzing the sample for the presence, absence, and/or amount of the released nucleic acid(s).

LNP Comprising Ligands

Some aspects of the disclosure relate to LNP comprising a ligand (also referred herein as targeting ligand) having a binding specificity for a cell surface antigen, wherein the binding of the ligand to the antigen induces the internalization of the ligand. Some embodiments relate to compositions comprising LNP comprising a ligand as described herein.

LNP targeting can also accomplished by adding lipids to the formulation. For example, phosphatidylserine is known to redistribute to the external surface of the plasma membrane during apoptosis and is a molecular cue for phagocytotic cell attraction (Fadok et al. Curr Biol. 2003 Aug. 19; 13(16):R655-7). Phosphatidylserine (PS) and phosphatidylglycerol (PG) are recognized by dendritic cells and can induce uptake and activation of dendritic cells LNP targeting can also accomplished by adding certain anionic phospholipids to the formulation (Table 3A). For example, phosphatidylserine is known to redistribute to the external surface of the plasma membrane during apoptosis and is a molecular cue for phagocytotic cell attraction (Fadok et al. Curr Biol. 2003 Aug. 19; 13(16):R655-7). Phosphatidylserine (PS) and phosphatidylglycerol (PG) are recognized by dendritic cells and can induce uptake and activation of dendritic cells (Caronni et al., Nat Comm. 2021 Apr. 14; 12: 2237-2253; Ischihashi et al., PLOS One 2013). Although anionic phospholipids have been used previously in the context of liposomes, their inclusion in lipidic nanoparticles that include condensed nucleic acids is unexpected since anionic headgroups may compete for binding sites of the ionizable cationic lipids with the phosphate backbone of mRNA, may inhibit intracellular escape by altering the surface charge, or may result in aggregation of LNPs during formation or storage.

TABLE 3A

Anionic Phospholipid Targeting Moieties

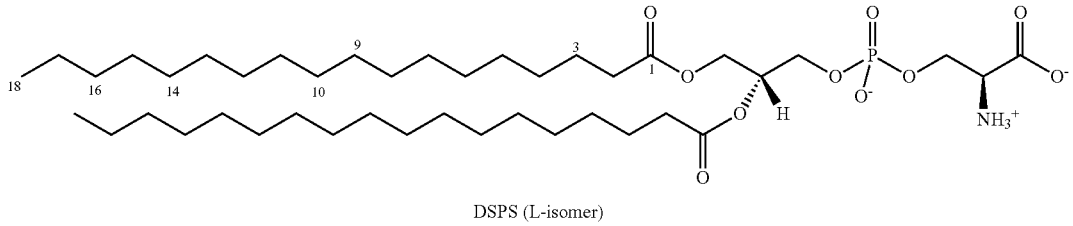 [SMILES: CCCCCCCCCCCCCCCCCC(=O)OC[C@H](COP(=O)([O-])OC[C@H]([NH3+])C(=O)[O-])OC(=O)CCCCCCCCCCCCCCCCC]

DSPS (L-isomer)

TABLE 3A-continued
Anionic Phospholipid Targeting Moieties
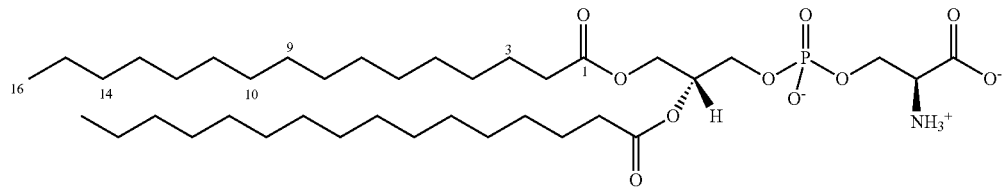
DPPS (L-isomer)
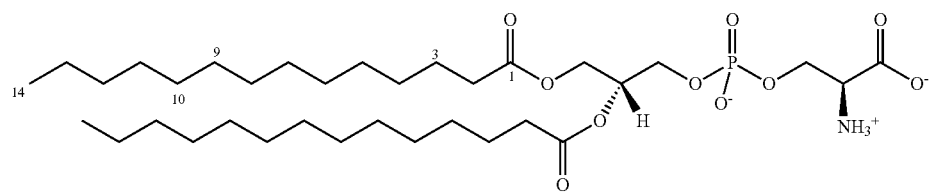
DMPS (L-isomer)
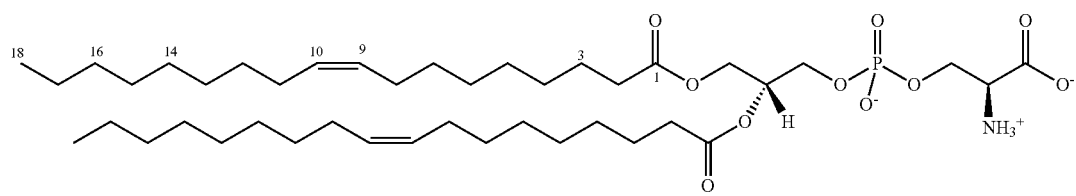
DOPS (L-isomer)
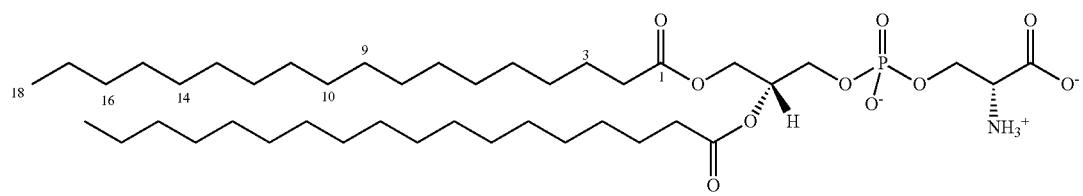
DSPS (D-isomer)
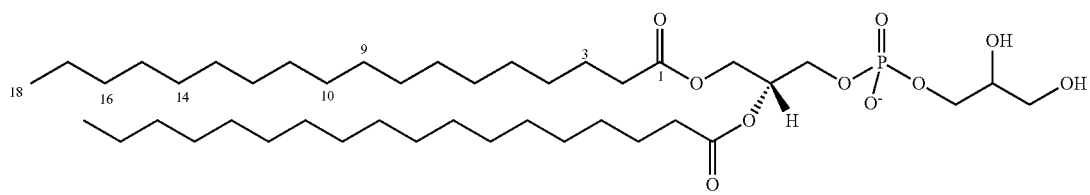
DSPG
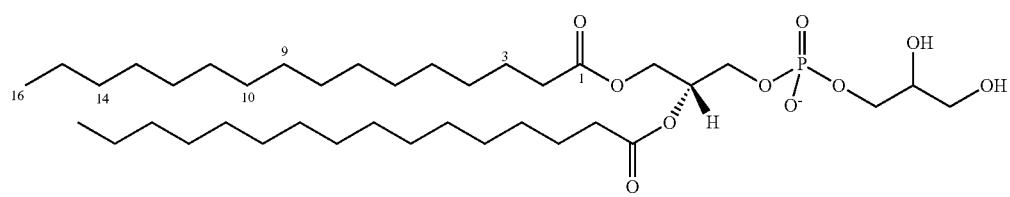
DPPG TABLE 3A-continued
Anionic Phospholipid Targeting Moieties
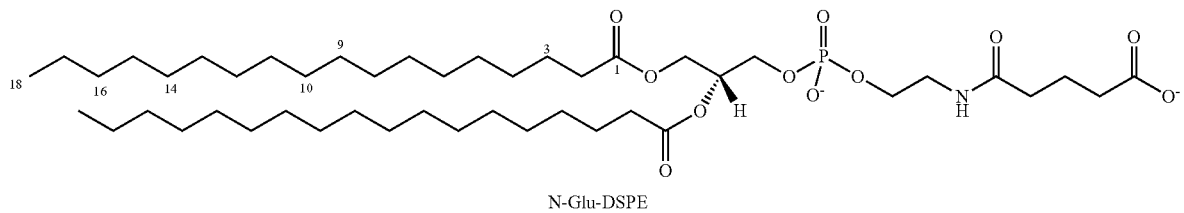 [SMILES: CCCCCCCCCCCCCCCCCC(=O)OC[C@H](COP(=O)([O-])OCCNC(=O)CCCC(=O)[O-])OC(=O)CCCCCCCCCCCCCCCCC]
N-Glu-DSPE
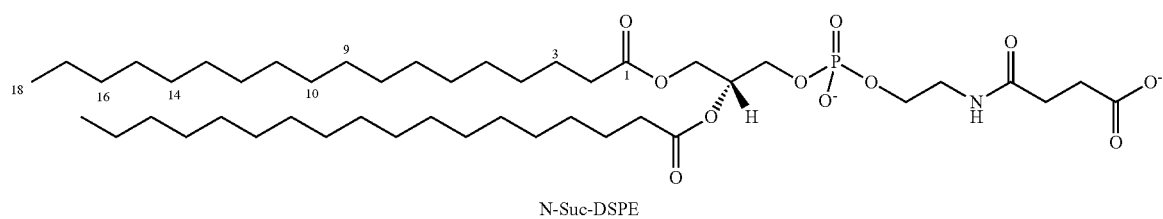 [SMILES: CCCCCCCCCCCCCCCCCC(=O)OC[C@H](COP(=O)([O-])OCCNC(=O)CCC(=O)[O-])OC(=O)CCCCCCCCCCCCCCCCC]
N-Suc-DSPE
TABLE 3B
Phosphatidylserine Targeting Moieties
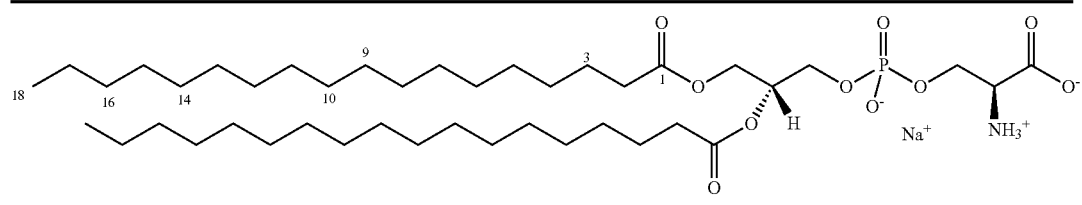
DSPS (L-isomer) - sodium salt
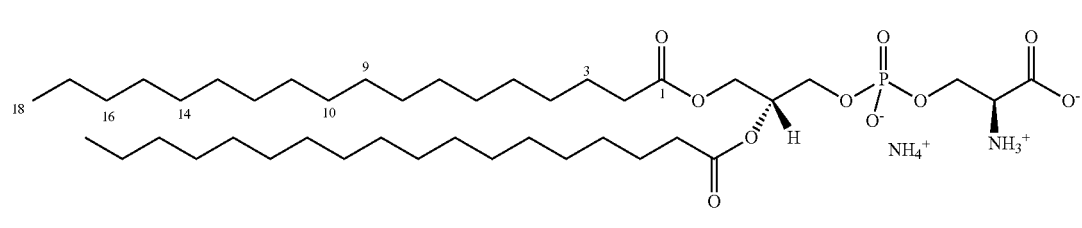
DSPS (L-isomer) - ammonium salt
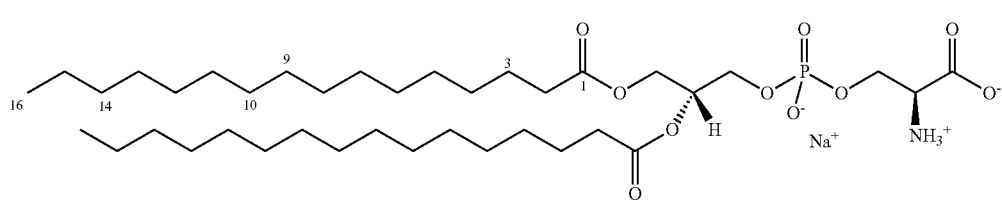
DPPS (L-isomer) - sodium salt
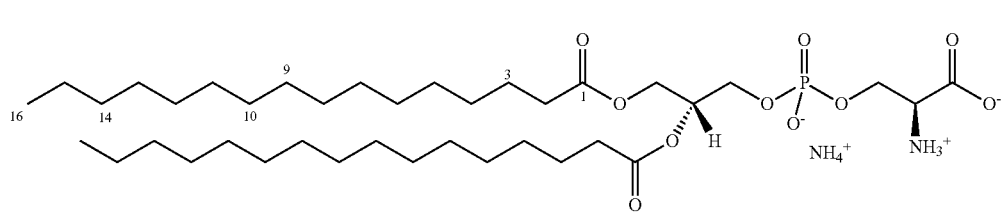
DPPS (L-isomer) - ammonium salt In some embodiments, the anionic targeting ligands are selected from the group, phosphatidylserine (PS), phoshatidylglycerol (PG), N-glutaryl-phosphatidylethanolamine (N-glu-PE), or N-succinyl-phosphatidylethanolamine (N-Suc-PE). In one embodiment, the anionic phospholipid used is phosphatidylserine. In another embodiment, the phosphatidylserine contains the L-isomer of serine. In another embodiment, the acyl chains for the phosphatidylserine are fully saturated, such as the case for dimyristoylphosphatidyl-L-serine (DMPS), dipalmitoylphosphatidyl-L-serine (DPPS), or distearoylphosphatidyl-L-serine (DSPS). In a preferred embodiment, the PS used is the L-isomer of either DPPS or DSPS. The phosphatidylserine may also contain an asymmetric acyl chain composition, for example where one acyl chain is stearic acid and another is palmitic acid.

In some embodiments, the anionic phospholipid is selected from a group other than phosphatidylserine. In some embodiments, these non PS anionic phospholipids include phosphatidylglycerol (PG), phosphatidic acid (PA), N-glutaryl-phosphatidylethanolamine (N-Glu-PE), N-succinyl-phosphatidylethanolamine (N-Suc-PE), and cardiolipin. In one embodiment, these anionic phospholipids include saturated acyl chains of 16 or 18 carbons such as distearoylphosphatidylglycerol (DSPG), dipalmitoyphosphatidylglycerol (DPPG), N-succinyl-distearoylphosphatidylethanolamine (N-Suc-DSPE), N-glutaryl-distearoylphosphatidylethanolamine (N-Glu-DSPE), distearoylphosphatidic acid (DSPA), and cardiolipin.

TABLE 3C

Nonphosphatidylserine anionic phospholipids

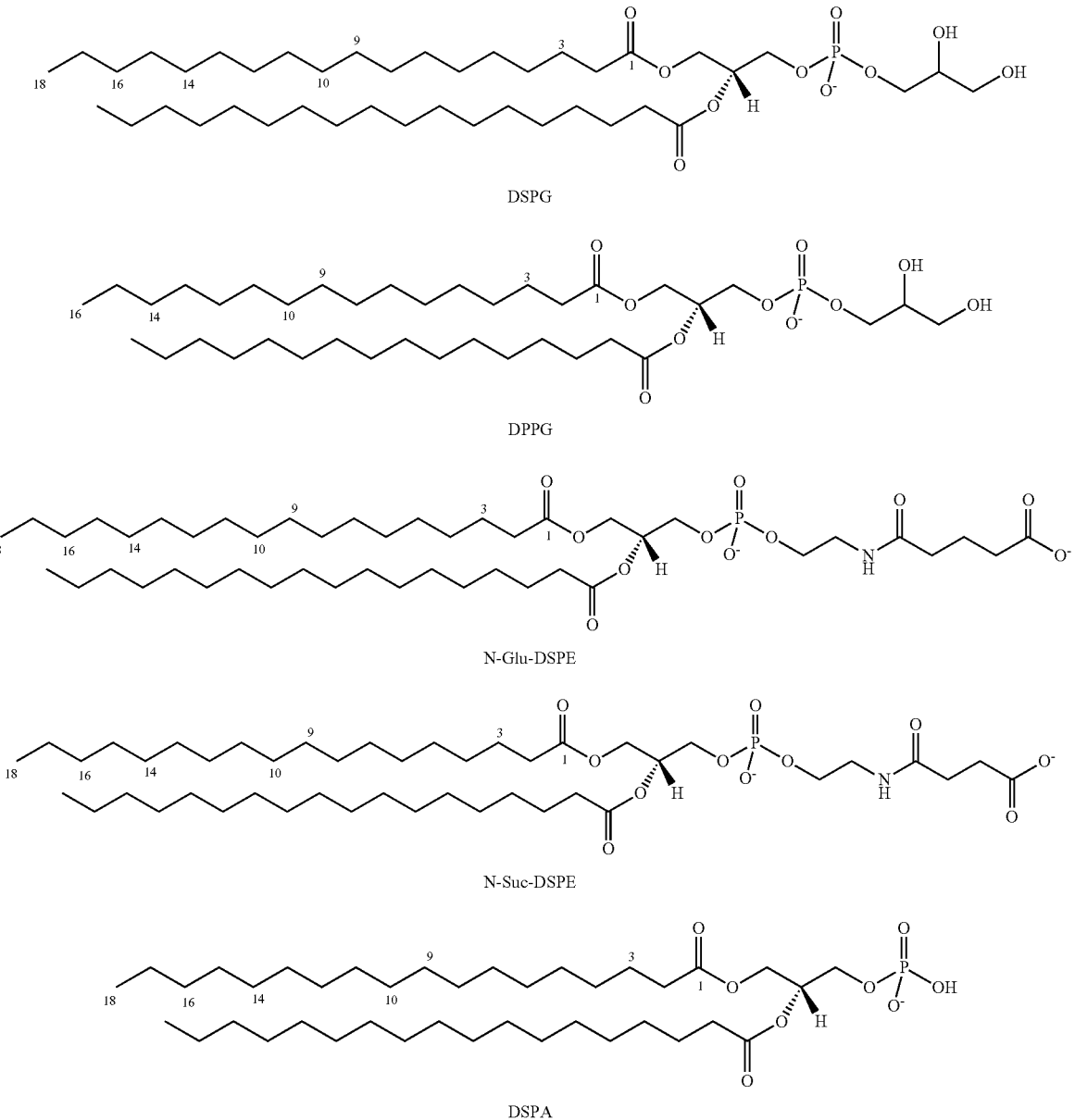

TABLE 3C-continued

Nonphosphatidylserine anionic phospholipids

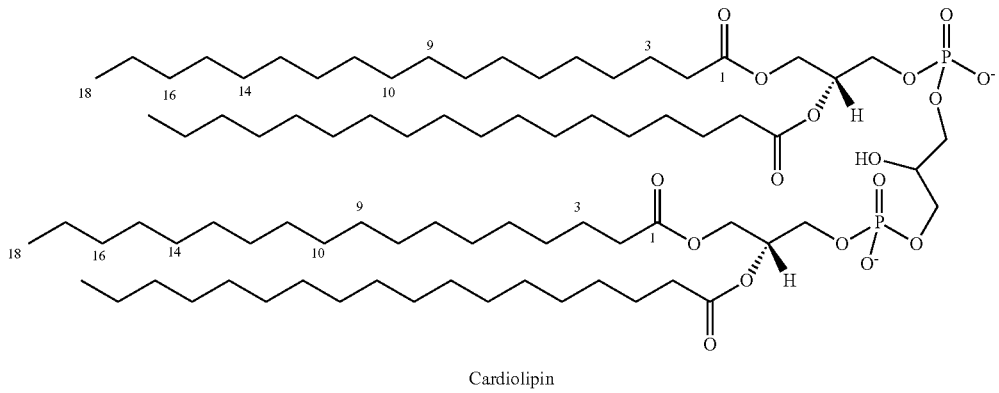 [SMILES: CCCCCCCCCCCCCCCCCC(=O)OC[C@H](COP(=O)([O-])OCC(O)COP(=O)([O-])OC[C@@H](COC(=O)CCCCCCCCCCCCCCCCC)OC(=O)CCCCCCCCCCCCCCCCC)OC(=O)CCCCCCCCCCCCCCCCC]

Cardiolipin

In some embodiments, the anionic phospholipid used is phosphatidylglycerol. In another embodiment, the acyl chains for the phosphatidylglycerol are fully saturated, such as the case for dimyristoylphosphatidylglycerol (DMPG), dipalmitoylphosphatidylglycerol (DPPG), or distearoylphosphatidylglycerol (DSPG). In a preferred embodiment, the PG used is either DPPS or DSPS. The phosphatidylglycerol may also contain an asymmetric acyl chain composition, for example where one acyl chain is stearic acid and another is palmitic acid.

In some embodiments, the salt form of phosphatidylglycerol or phosphatidylserine is highly soluble in ethanol. In some embodiments, the salt form of phosphatidylserine is highly soluble in ethanol. In some embodiments it is soluble at greater than 0.5 mg/ml, greater than 1 mg/mL, greater than 5 mg/mL, greater than 10 mg/mL, or greater than 20 mg/mL. In some embodiments the salt form of phosphatidylglycerol or phosphatidylserine is soluble is at least 0.3 mM, at least 0.4 mM, at least 0.5 mM, at least 0.6 mM, or at least 0.8 mM, as determined by a shake flask method in 200 proof ethanol, at the temperature of 22° C. of less. In some embodiments, the salt is an ammonium salt. In one embodiment, the phosphatidylserine is added to the LNP lipids in the form of ammonium or a substituted ammonium salt. Substituted ammonium salt can be mono-, di-. tri-, or tetraalkylammonium having alkyl groups with one to six, one to four, one to three, one, two, or three carbon atoms each. One or more alkyl groups can be n-alkyl, or branched alkyl groups (such as, for example, isopropyl groups), or form a ring (such as for example, cyclohexyl group). An alkyl group and the nitrogen ammonium atom may form a heterocyclic ring. The substituted ammonium salt may be also formed by an alkylenediamine. Tris(hydroxymethyl)aminomethane and triethanolamine can also be used as the amine bases to form PS salts. In some embodiments, the amine is chosen from ammonia, dimethylamine, diethylamine, triethylamine, trimethylamine, 2-(dimethyamino)ethanol, diethanolamine, 2-(diethyamino)ethanol, ethanolamine, ethylenediamine, N-methyl-glucamine, imidazole, histidine, lysine, arginine, 4-(2-hydroxyethyl)-morpholine, piperazine, 1-(2-hydroxyethyl)-pyrrolidine, triethanolamine, and tromethamine (tris(hydroxymethyl)aminomethane), In some embodiments, this targeting lipid is an ammonium salt of DPPS.

TABLE 3D

Ammonium and sodium salt forms of dipalmitoyl- or distearoyl-phosphatidyl serine.

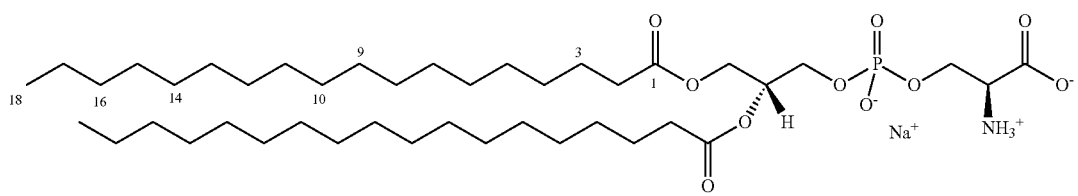

DSPS (L-isomer) - sodium salt

TABLE 3D-continued

Ammonium and sodium salt forms of dipalmitoyl- or distearoyl-phosphatidyl serine.

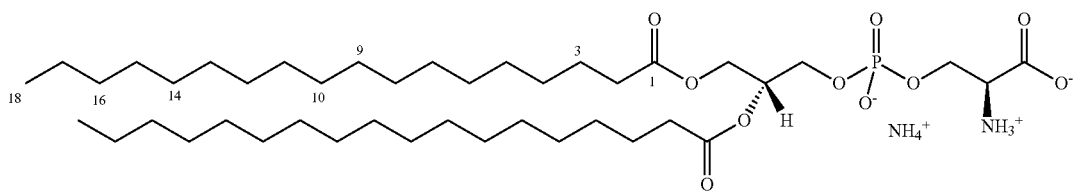

DSPS (L-isomer) - ammonium salt

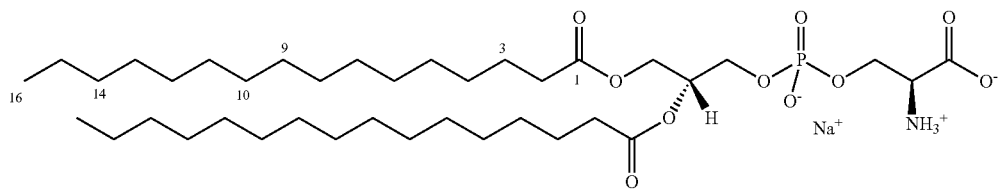

DPPS (L-isomer) - sodium salt

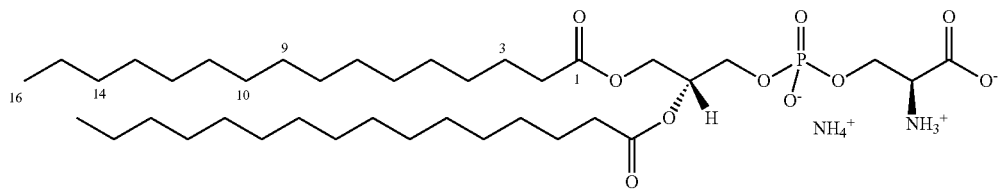

DPPS (L-isomer) - ammonium salt

To obtain phosphatidylserine in the form of ammonium or substituted ammonium salt, any method known in the art may be used. In one embodiment, a sodium salt of phosphatidylserine (PS) is dissolved in a monophase system of chloroform, methanol, and water, containing a chloride salt of ammonium or substituted ammonium (a Bligh-Dyer monophase), and the system is brought to the two-phase state by adding extra methanol and/or water containing the ammonium or substituted ammonium chloride. The chloroform-rich phase, containing the PS, is separated, and the process is repeated. Finally, the chloroform-rich phase is washed with water to remove excess chloride, and the ammonium (substituted ammonium) salt of PS is obtained by evaporation of the chloroform-rich phase. Optionally, the obtained ammonium or substituted ammonium salt of PS is vacuum dried or dissolved in cyclohexane and lyophilized. In another embodiment, the PS as a sodium or potassium salt is dissolved in a water-immiscible organic solvent, such as chloroform or a chloroform-methanol mixture, and washed with diluted aqueous solution of an acid, such as HCl, to obtain a free acid form of the PS, which is then neutralized with ammonium hydroxide or substituted amine in free base form. In yet another embodiment, the organic solution of PS as a sodium or potassium salt is treated with a cation-exchange resin in the ammonium of substituted ammonium form. In yet another embodiment, the PS is prepared in the form of a calcium or magnesium salt and treated with ammonium or substituted ammonium salt of a chelator, such as EDTA, or with ammonium or substituted ammonium phosphate, in the presence of an organic solvent, causing displacement of calcium or magnesium ion in the form of a chelate or a yet less soluble phosphate, which is separated, e.g., by filtration, while ammonium or substituted ammonium salt of PS is left in the organic (e.g., ethanol) solution.

In one embodiment, PS or PG are added to the LNP lipid formulation at a concentration between about 0.1 mol % to about 20 mol %, about 0.1 mol % to about 10 mol %, about 0.1 mol % to about 5 mol %, about 0.5 mol % to about 20 mol %, about 0.5 mol % to about 10 mol %, about 0.5 mol % to about 5 mol %, about 1 mol % to about 20 mol %, about 1 mol % to about 10 mol %, or about 1 mol % to about 5 mol %, of the total lipid content of the LNP. In one embodiment, the PS is added to the LNP lipid formulation at a concentration between about 1 mol % to about 20 mol %, about 2.5 mol % to about 10 mol %, about 3 mol % to about 9 mol %, or about 4 mol % to about 8 mol %, of the total lipid content of the LNP.

In one embodiment the PS or PG lipid is included in the LNP composition comprising ionizable cationic lipids known in the art, including DODAP, AKG-OA-DM2, O-11769, DLin-MC3-DMA, DLin-KC2-DMA, DLin-KC3-DMA, ALC-0315, and SM-102.

In another embodiment the PS lipid is included in the LNP composition comprising ICLs of Formula I, II, III, IV-B, V-A-1, combinations thereof or pharmaceutically salts thereof. In another embodiment the PS lipid is included in the LNP composition using N/P ratios between 3 and 8, between 4 and 7, or between 5 and 6.

In some aspects, a method of delivering a nucleic acid to a cell is provided, the method comprising: contacting the cell with a composition comprising an LNP comprising a ligand (also referred herein as targeting ligand) having a binding specificity for a cell surface antigen, wherein the binding of the ligand to the antigen induces the internalization of the ligand. In some embodiments, the targeting ligand can be, but is not limited to, an internalizing antibody, or a fragment thereof, a small molecule conjugates or glycoconjugates. In some embodiments, the binding of the targeting ligand to a specific cell surface antigen induces the internalization of the LNP with the targeting ligand attached by a cell expressing at least 100,000 or at least 1,000,000 molecules of the antigen when contacted and incubated with the cell under internalizing conditions.

TABLE 4

Exemplary dialkyl and branched ionizable cationic lipids

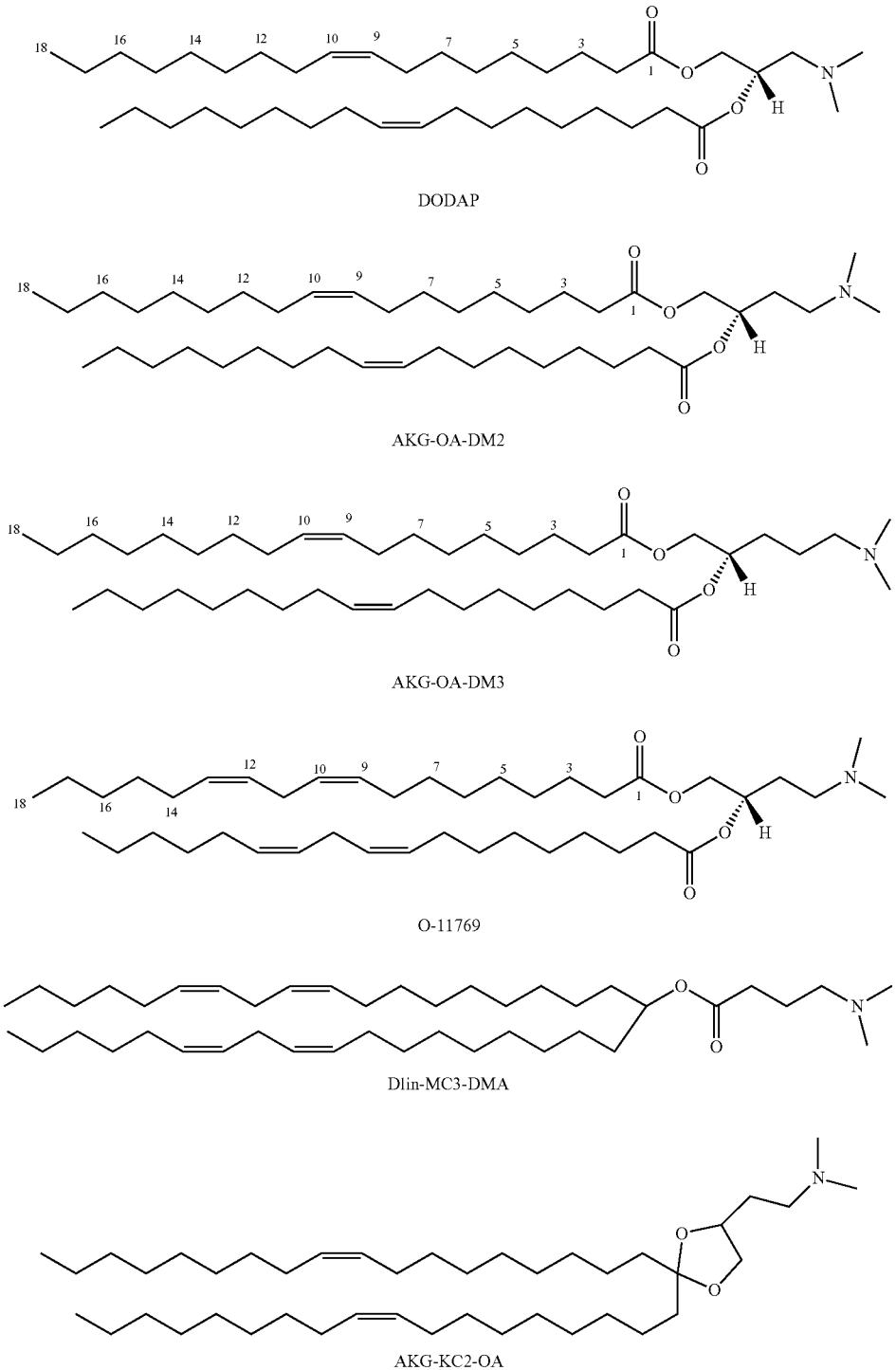

TABLE 4-continued
Exemplary dialkyl and branched ionizable cationic lipids
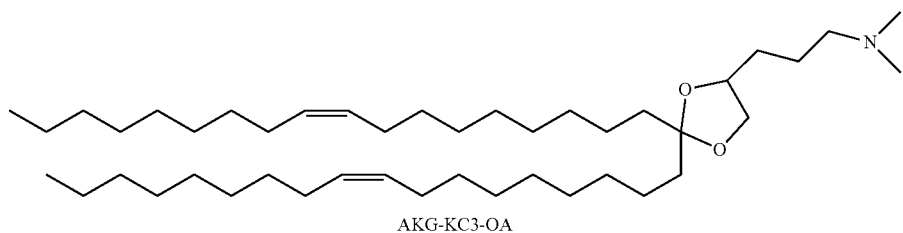 [SMILES: CCCCCCCC/C=C\CCCCCCCCC1(CCCCCCCC/C=C\CCCCCCCC)OCC(CCCN(C)C)O1]
AKG-KC3-OA
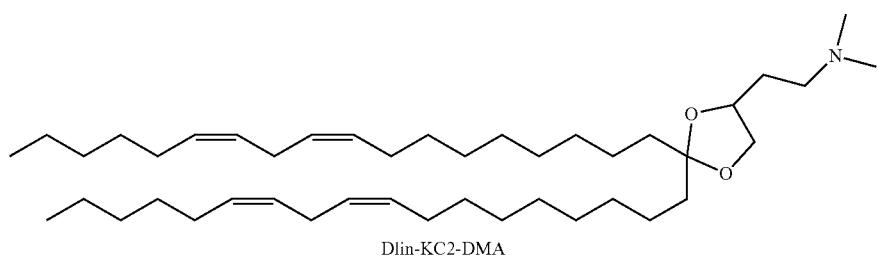 [SMILES: CCCCC/C=C\C/C=C\CCCCCCCCC1(CCCCCCCC/C=C\C/C=C\CCCCC)OCC(CCN(C)C)O1]
Dlin-KC2-DMA
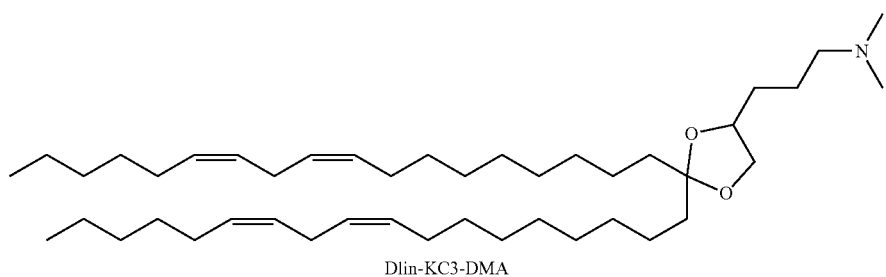 [SMILES: CCCCC/C=C\C/C=C\CCCCCCCCC1(CCCCCCCC/C=C\C/C=C\CCCCC)OCC(CCCN(C)C)O1]
Dlin-KC3-DMA
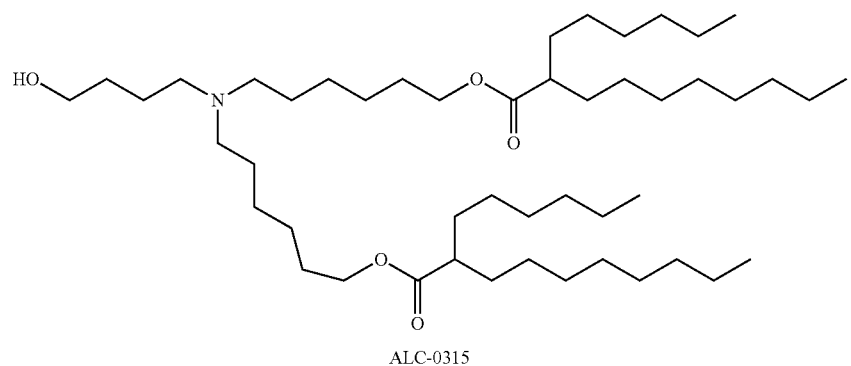 [SMILES: CCCCCCCCC(CCCCCC)C(=O)OCCCCCCN(CCCCO)CCCCCCOC(=O)C(CCCCCC)CCCCCCCC]
ALC-0315
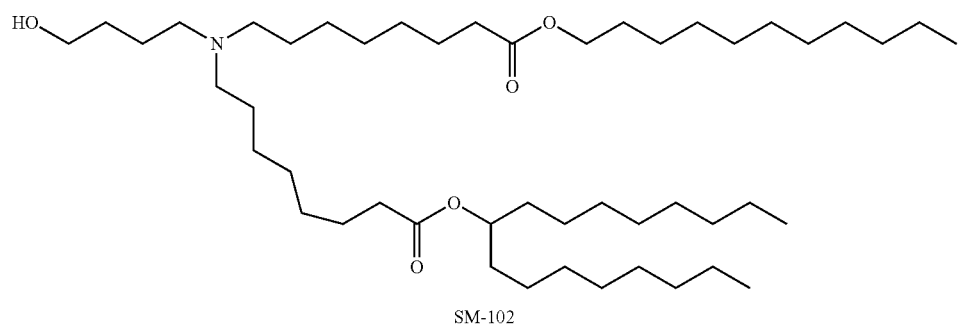 [SMILES: CCCCCCCCCCCOC(=O)CCCCCCCN(CCCCO)CCCCCCCC(=O)OC(CCCCCCCC)CCCCCCCC]
SM-102

Compositions

In some embodiments, a lipidic nanoparticle composition comprises lipids and nucleic acids, the lipidic nanoparticles comprising a compound of Formula I, II, III, IV-B, V-A-1, combinations thereof or pharmaceutically acceptable salts thereof.

Other aspects of the disclosure relate to the use of these ionizable lipids or lipidic nanoparticles compositions comprising ionizable lipids in vaccines for the prevention of infectious diseases or cancer. In some embodiments, the infectious disease can be a bacterial or a viral infection. In some embodiments, the compositions described herein can be used to prevent infections related to tuberculosis, HIV/AIDS, malaria, or coronavirus-related infections such as COVID-19. In other embodiments, the infection is influenza, hepatitis B, hepatitis C, Dengue, human papillomavirus (HPV), norovirus, mumps, measles, Meningococcal disease, pneuomococcal disease, polio, rotovirus, respiratory syncytial virus (RSV), rubella, shingles/herpes zoster virus, tetanus, or whooping cough.

In some embodiments, the compounds and compositions described herein may promote efficient uptake and transfection of target cells, including tissue macrophages and dendritic cells. The efficient delivery nucleic acids coding for antigen specific for infectious viruses or bacteria, and subsequent presentation of that antigen to elicit the desired immune response to protect against corresponding infections is a result. In some embodiments, the nucleic acid can be a synthetic nucleic acid (e.g., engineered codon optimized mRNA) encoding an epitope of coronavirus such as SARS-CoV, MERS-CoV or SARS-CoV-2. In some embodiments the nucleic acid can be a synthetic nucleic acid (e.g. engineered codon optimized mRNA) encoding the S-protein (spike protein) or a fragment thereof of coronavirus such as SARS-CoV, MERS-CoV or SARS-CoV-2.

In some embodiments, the vaccine is used for the prevention *Mycobacterium* infections. In some embodiments, the vaccine can be used for the prevention of tuberculosis, nontuberculous mycobacteria (NTM), nontuberculosis lung disease, leprosy, *Mycobacterium avium-intracellulare*, *Mycobacterium kansasii*, *Mycobacterium marinum*, *Mycobacterium ulcerans*, *Mycobacterium chelonae*, *Mycobacterium fortuitum*, *Mycobacterium abscessus* and other infectious diseases such as those caused by coronaviruses (SARS-CoV-2, Covid-19; SARS-CoV, SARS; MERS-CoV; HCoV-229E; HCoV-NL63; HCoV-OC43; HCoV-HKU1), chikungunya, dengue, diphtheria, Ebola, EV-D68, influenza (flu), hepatitis viruses (including HAV, HBV, HCV, HDV, HEV and GB virus C), *Haemophilus influenzae* type B (Hib), Hendra virus, HIV/AIDS, human metapneumovirus (hMPV), Human Papillomaviruses (HPV), Lassa, Lyme, malaria, Marburg, measles, meningococcal disease, mumps, Nipah virus, norovirus, parainfluenza virus (PIV), plague, pneumococcal disease, polio, respiratory syncytial virus (RSV), Rocky Mountain spotted fever, rotavirus, rubella (German Measles), varicella zoster virus (chickenpox, shingles), smallpox, tetanus (Lockjaw), West Nile, whooping cough (Pertussis) and zika In some embodiments, the composition further comprises a pharmaceutical excipient.

In some embodiments, the lipidic nanoparticles are in an aqueous medium.

In some embodiments, the nucleic acid is entrapped in the lipidic nanoparticle with an ionizable cationic lipid compound provided herein or combinations thereof, wherein the nucleic acid is either RNA or DNA. In some embodiments, the nucleic acid is mRNA. In some embodiments, the nucleic acid is siRNA. In some embodiments, the nucleic acid is DNA.

In some embodiments, the lipidic nanoparticle comprises a membrane comprising phosphatidylcholine and a sterol. In some embodiments, the sterol is cholesterol. In some embodiments, the lipidic nanoparticle comprises a membrane comprising phosphatidylcholine, ionizable cationic lipid (ICL). In some embodiments, the ICL have a structure of Formula I, and cholesterol, wherein the membrane separates the inside of the lipidic nanoparticles from the aqueous medium. In some embodiment, the ICL have a structure as shown in Table 1A and Table 2. In some embodiment, the ICL have a structure as shown in Table 1B. In some embodiments, the phosphatidylcholine is distearoylphosphatidylcholine (DSPC) or hydrogenated soy phosphatidylcholine (HSPC). In some embodiments, the ionizable cationic lipid to cholesterol molar ratios is from about 65:35 to 40:60. In some embodiments, the ICL to cholesterol molar ratio is from about 60:40 to about 45:55.

In some embodiments, the phosphatidylcholine to cholesterol molar ratio is from about 1:5 to about 1:2.

In some embodiments, the membrane further comprises a polymer-conjugated lipid.

In some embodiments, the lipidic nanoparticle comprises ICL, DSPC, cholesterol and polymer-conjugated lipid in a about 49.5:10.3:39.6:2.5 molar ratio.

In some embodiments, the polymer-conjugated lipid is PEG(2000)-dimyristoylglycerol (PEG-DMG) or PEG(Mol. weight 2,000)-dimyristoylphosphatidylethanolamine (PEG-DMPE).

The compositions of this disclosure may be administered by various routes, for example, to effect systemic delivery via intravenous, parenteral, intraperitoneal, or topical routes. The compositions maybe administered intravenously, subcutaneously, or intraperitoneally to a subject.

In some embodiments, the disclosure provides methods for in vivo delivery of nucleic acids to a subject.

In some embodiments, the composition is a liquid pharmaceutical formulation for parenteral administration.

In some embodiments, the composition is a liquid pharmaceutical formulation for subcutaneous, intramuscular, or intradermal administration.

In some embodiments, the composition is in the form of a lyophilized powder, that is subsequently reconstituted with aqueous medium prior to administration.

In some embodiments, a lipid nanoparticle (LNP) composition comprises an ionizable cationic lipid having the chemical structure of Formula (I):

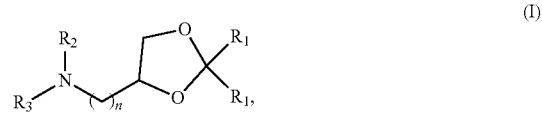

(I)

wherein $R_1$ is

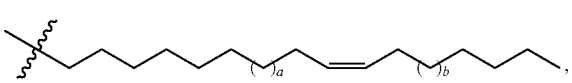

wherein a is 0 or 1; b is 1, 2, 3 or 4, provided the sum a+b is 1, 2, 3 or 4;

$R_2$ and $R_3$ are each independently ($C_1$-$C_4$) alkyl optionally substituted with hydroxyl; and n is an integer equal to 2, 3 or 4.

wherein a and b of the two $R_1$ hydrocarbon chains are the same or different, or one of the two $R_1$ hydrocarbon chains is a saturated $C_{12}$-$C_{18}$ alkyl.

In some embodiments, ionizable cationic lipid compositions are provided. In some embodiments, a lipid nanoparticle (LNP) composition comprises an ionizable cationic lipid having the chemical structure of Formula (I-A):

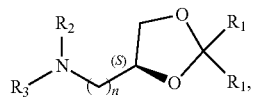

(I-A)

wherein $R_1$ is

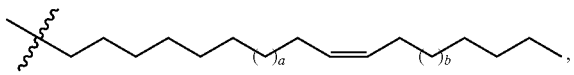

wherein a is 0 or 1; b is 1, 2, 3 or 4, provided the sum a+b is 1, 2, 3 or 4;

$R_2$ and $R_3$ are each independently ($C_1$-$C_4$) alkyl optionally substituted with hydroxyl; and n is an integer equal to 2, 3 or 4.

In some embodiments, a and b of the two $R_1$ hydrocarbon chains are the same.

In some embodiments, a and b of the two $R_1$ hydrocarbon chains are different.

In some embodiments, one of the two $R_1$ hydrocarbon chains is a saturated $C_{12}$-$C_{18}$ alkyl.

In some embodiments, ionizable cationic lipid compositions are provided. In some embodiments, a lipid nanoparticle (LNP) composition comprises an ionizable cationic lipid having the chemical structure of Formula (I-A):

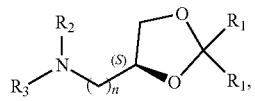

(I-A)

wherein $R_1$ is

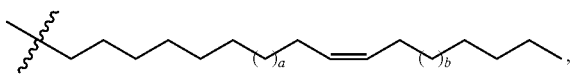

wherein a is 0 or 1; b is 1, 2, 3 or 4, provided the sum a+b is 1, 2, 3 or 4;

$R_2$ and $R_3$ are each methyl; and n is an integer equal to 3.

In some embodiments, a and b of the two $R_1$ hydrocarbon chains are the same.

In some embodiments, a and b of the two $R_1$ hydrocarbon chains are different.

In some embodiments, one of the two $R_1$ hydrocarbon chains is a saturated $C_{12}$-$C_{18}$ alkyl.

In some embodiments, ionizable cationic lipid compositions are provided. In some embodiments, a lipid nanoparticle (LNP) composition comprises an ionizable cationic lipid having the chemical structure of Formula (I-A):

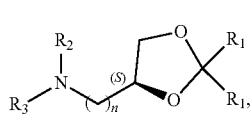

(I-A)

wherein
$R_1$ is a saturated $C_{15}$-$C_{18}$ hydrocarbon chain,
$R_2$ and $R_3$ are each methyl; and
n is an integer equal to 3.

In some embodiments, a and b of the two $R_1$ hydrocarbon chains are the same.

In some embodiments, a and b of the two $R_1$ hydrocarbon chains are different.

In some embodiments, one of the two $R_1$ hydrocarbon chains is a saturated C12-Cis alkyl.

METHODS OF USE

Targeting of Dendritic Cells

Dendritic cells (DCs) are specialized antigen-presenting cells that play a central role in initiating and regulating adaptive immunity. Owing to their potent antigen (Ag) presentation capacity and ability to generate distinct T-cell responses, efficient and specific delivery of Ags to DCs is the cornerstone for generating Ag-specific effector and memory cells against tumors or pathogens.

Dendritic cells can be generated from human blood monocytes by adding granulocyte-macrophage colony-stimulating factor (GM-CSF), IL-4, and IFN-gamma to differentiate monocyte-derived DC in vitro. Cells in culture exhibit both dendritic and veiled morphologies, the former being adherent, and the latter suspended. Phenotypically, they are CD1a−/dim, CD11a+, CD11b++, CD11c+, CD14dim/−, CD16a−/dim, CD18+, CD32dim/−, CD33+, CD40+, CD45RO+, CD50+, CD54+, CD64−/dim, CD68+, CD71+, CD80dim, CD86+/++, MHC class I++/, HLA-DR++/, HLA-DP+, and HLA-DQ (Geiseler et al. Dev Immunol. 1998; 6(1-2):25-39).

Alternatively, human primary blood dendritic cell lines have been developed and are commercially available from Creative Biolabs.

CD8+ T cells can produce IL2, IFN-γ, and TNF, cytokines that are known to have critical functions during *Mycobacterium tuberculosis* infection. Importantly, CD8+ T cells have cytolytic functions to kill *Mycobacterium tuberculosis*-infected cells via granule-mediated function (via perforin, granzymes, and granulysin) or Fas-Fas ligand interaction to induce apoptosis. In humans, CD8+ T cell can produce granulysin, which can kill *Mycobacterium tuberculosis* directly. Therefore, it is anticipated that antigen generating mRNA LNPs delivered to DC will stimulate a CD8+ T cell response to fight against *Mycobacterium tuberculosis* infection.

CD8+ T cells are able to recognize *M. tuberculosis* specific antigens (as peptides) presented by classical and non-classical MHC molecules. Classically restricted CD8+ T cells have been identified that recognize antigens presented by antigen presenting cells in the context of classical MHC Ia (HLA-A, -B, -C) molecules. Non-classically restricted CD8+ T cells include those CD8+ T cells that are capable of recognizing Mg antigen in the context of HLA-E molecules (non-MHC 1a), glycolipids associated with group 1 CD1 molecules and MHC I-related molecules (MR1) such as mucosal associated invariant T cells (MAIT). Finally, γδ T cells represent a separate population of CD8 (and CD4) T cells that have both innate and adaptive functions in response to *Mycobacterium tuberculosis* infection. CD8+ T cells have been shown to play direct functions in response to *Mycobacterium tuberculosis* infection but they also play important roles in orchestrating many different functions in the overall host immune response (e.g., interaction to provide optimal CD4 T cell function)

In one embodiment, LNPs can be added to cultured human dendritic cells at an appropriate concentration, (e.g. 1-5 µg/mL mRNA). After some time to allow for cellular uptake and antigen expression, human T cells (HemaCare) can be added, and the cell culture media is sampled at various times for INF-γ by Elisa (R&D Systems, DIF50C). Alternatively, the cells can be analyzed by flow cytometry for CD8+ marker or intracellular INFγ production (PE anti-human IFN-γ antibody, Biolegend).

In one embodiment, LNPs can be administered into a subject at a dose of 0.01-5 mg/kg mRNA by any route of administration outlined above. According to some embodiments, a proportion of LNPs are taken up DC cells, while most will accumulate in the liver and spleen. The DC cells can express the antigenic peptide, process it for MHC I presentation and travel to the lymph node for presentation to naïve T cells inducing an education of memory T-cells towards the antigen.

In one embodiment, LNPs that have been modified with a targeting ligand such as anti-DEC205-PEG-DSPE can be administered into a subject at a dose of 0.01-5 mg/kg mRNA. According to some embodiments, a higher proportion of LNPs can be taken up DC cells, allowing for increased production of antigenic peptide compared to non-targeted LNP and a more efficient vaccination against the pathogen. Additional targeting ligands for dendritic cells include, but are not limited to, CLEC9A, CLEC4A, XCR1, CD141, and HLD-DR. For example, assessing the CD8+ reactivity to the in vivo produced antigen could be accomplished by measuring INFγ plasma levels by species specific IFN-gamma Quantikine ELISA Kits from R&D Systems.

In some embodiments, LNP compositions provide desirable pharmacokinetic properties such as extended plasma half-life and stable encapsulation of mRNA. The plasma half-life can be measured as the percentage of the injected dose (ID) remaining in blood after 6 or 24 hours following injection intravenously in immunocompetent mice. The stability of the encapsulation of mRNA over 24 hours in plasma can be determined by changes in the mRNA-to-lipid ratio (mRNA/L ratio) following iv administration in mice. In some embodiments, the percentage of encapsulated mRNA remaining in blood is greater than 20%, preferably greater than 30%, and most preferably greater than 40% of the injected dose at 6 hours. The percent retained in blood after 24 h is preferably greater than 10%, and more preferably greater than 20% of the injected dose.

Disclosed herein are methods for preventing mycobacteria infection, such as *Mycobacterium tuberculosis*, or gram positive bacteria, such as methicillin-resistant *Staphylococcus aureus* (MRSA). Additional mycobacteria and gram positive bacteria include, but are not limited to, *Mycobacterium avium* complex, *Mycobacterium leprae*, *Mycobacterium gordonae*, *Mycobacterium abscessus*, *Mycobacterium abscessus*, *Mycobacterium mucogenicum*, streptococci, vancomycin-resistant enterococci (VRE), *Staphylococcus pneumoniae, Enterococcus faecium, Streptococcus agalactiae, Streptococcus pneumoniae, Streptococcus pyogenes*, the *viridans* group streptococci, *Listeria monocytogenes, Nocardia*, and *Corynebacterium*.

Administration of a vaccine for inducing a second immune response may provide MHC class II-presented epitopes that are capable of eliciting a CD4+ helper T cell response against cells expressing antigens from which the MHC presented epitopes are derived. Alternatively or additionally, administration of a vaccine for inducing a second immune response may provide MHC class I-presented epitopes that are capable of eliciting a CD8+ T cell response against cells expressing antigens from which the MHC presented epitopes are derived. Furthermore, administration of a vaccine for inducing a second immune response may provide one or more neo-epitopes (including known neo epitopes) as well as one or more epitopes not containing cancer specific somatic mutations but being expressed by cancer cells and preferably inducing an immune response against cancer cells, preferably a cancer specific immune response. In one embodiment, administration of a vaccine for inducing a second immune response provides neo-epitopes that are MHC class II-presented epitopes and/or are capable of eliciting a CD4+ helper T cell response against cells expressing antigens from which the MHC presented epitopes are derived as well as epitopes not containing cancer-specific somatic mutations that are MHC class I-presented epitopes and/or are capable of eliciting a CD8+ T cell response against cells expressing antigens from which the MHC presented epitopes are derived. In one embodiment, the epitopes do not contain cancer-specific somatic mutations.

A "cellular immune response", a "cellular response", a "cellular response against an antigen" or a similar term is meant to include a cellular response directed to cells characterized by presentation of an antigen with class I or class II MHC. The cellular response relates to cells called T cells or T-lymphocytes which act as either "helper cells" or "killer cells". The helper T cells (also termed CD4+ T cells) play a central role by regulating the immune response and the killer cells (also termed cytotoxic T cells, cytolytic T cells, CD8+ T cells or CTLS) kill diseased cells such as cancer cells, preventing the production of more diseased cells. In preferred embodiments, the present disclosure involves the stimulation of an anti-*Mycobacterium tuberculosis* CTL response against the *Mycobacterium* expressing one or more expressed antigens and preferably presenting such expressed antigens with class I MHC.

An "antigen" according to the disclosure covers any substance that will elicit an immune response. In particular, an "antigen" relates to any substance, preferably a peptide or protein, that reacts specifically with antibodies or T-lymphocytes (T cells). As used herein, the term "antigen" comprises any molecule which comprises at least one epitope. Preferably, an antigen in the context of the present disclosure is a molecule which, optionally after processing, induces an immune reaction, which is preferably specific for the antigen (including cells expressing the antigen). According to the present disclosure, any suitable antigen may be used, which is a candidate for an immune reaction, wherein the immune reaction is preferably a cellular immune reaction. In the context of the embodiments of the present disclosure, the antigen is preferably presented by a cell, preferably by an antigen presenting cell which includes a diseased cell, in particular a cancer cell, in the context of MHC molecules, which results in an immune reaction against the antigen. An antigen is preferably a product which corresponds to or is derived from a naturally occurring antigen. Such naturally occurring antigens may include tumor antigens.

As used herein, an "antigen peptide" relates to a portion or fragment of an antigen which is capable of stimulating an immune response, preferably a cellular response against the antigen or cells characterized by expression of the antigen and preferably by presentation of the antigen such as diseased cells, in particular cancer cells. Preferably, an antigen peptide is capable of stimulating a cellular response against a cell characterized by presentation of an antigen with class I MHC and preferably is capable of stimulating an antigen-responsive cytotoxic T-lymphocyte (CTL). Preferably, the antigen peptides according to the disclosure are MHC class I and/or class II presented peptides or can be processed to produce MHC class I and/or class II presented peptides. Preferably, the antigen peptides comprise an amino acid sequence substantially corresponding to the amino acid sequence of a fragment of an antigen. Preferably, said fragment of an antigen is an MHC class I and/or class II presented peptide. Preferably, an antigen peptide according to the disclosure comprises an amino acid sequence substantially corresponding to the amino acid sequence of such fragment and is processed to produce such fragment, i.e., an MHC class I and/or class II presented peptide derived from an antigen. If a peptide is to be presented directly, i.e., without processing, in particular without cleavage, it has a length which is suitable for binding to an MHC molecule, in particular a class I MHC molecule, and preferably is 7-20 amino acids in length, more preferably 7-12 amino acids in length, more preferably 8-11 amino acids in length, in particular 9 or 10 amino acids in length.

The main types of professional antigen-presenting cells are dendritic cells, which have the broadest range of antigen presentation, and are probably the most important antigen-presenting cells, macrophages, B-cells, and certain activated epithelial cells. Dendritic cells (DCs) are leukocyte populations that present antigens captured in peripheral tissues to T cells via both MHC class II and I antigen presentation pathways. It is well known that dendritic cells are potent inducers of immune responses and the activation of these cells is a critical step for the induction of antitumoral immunity. Dendritic cells are conveniently categorized as "immature" and "mature" cells, which can be used as a simple way to discriminate between two well characterized phenotypes.

However, this nomenclature should not be construed to exclude all possible intermediate stages of differentiation. Immature dendritic cells are characterized as anti gen presenting cells with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g. CD54 and CD11) and costimulatory molecules (e.g., CD40, CD80, CD86 and 4-1 BB). Dendritic cell maturation is referred to as the status of dendritic cell activation at which such antigen-presenting dendritic cells lead to T cell priming, while presentation by immature dendritic cells results in tolerance. Dendritic cell maturation is chiefly caused by biomolecules with microbial features detected by innate receptors (bacterial DNA, viral RNA, endotoxin, etc), pro-inflammatory cytokines (TNF, IL-1, IFNs), ligation of CD40 on the dendritic cell surface by CD40L, and substances released from cells undergoing stressful cell death. The dendritic cells can be derived by culturing bone marrow cells in vitro with cytokines, such as granulocyte-macrophage colony-stimulating factor (GM CSF) and tumor necrosis factor alpha. Non-professional antigen-presenting cells do not constitutively express the MHC class II proteins required for interaction with naive T cells; these are expressed only upon stimulation of the non-professional antigen-presenting cells by certain cytokines such as IFNγ. "Antigen presenting cells" can be loaded with MHC class I presented peptides by transducing the cells with nucleic acid, preferably mRNA, encoding a peptide or polypeptide comprising the peptide to be presented, e.g. a nucleic acid encoding the antigen.

In some embodiments, a pharmaceutical composition comprising a gene delivery vehicle that targets a dendritic or other antigen presenting cell may be administered to a patient, resulting in transfection that occurs in vivo. As used herein, a "nucleic acid" is a deoxyribonucleic acid (DNA) or ribonucleic acid (RNA), more preferably RNA, most preferably in vitro transcribed RNA (IVT RNA) or synthetic RNA. Nucleic acids include according to the disclosure genomic DNA, cDNA, mRNA, recombinantly produced and chemically synthesized molecules. According to the disclosure, a nucleic acid may be present as a single-stranded or double-stranded and linear or covalently circularly closed molecule. A nucleic acid can, according to the disclosure, be isolated. The term "isolated nucleic acid" means, according to the disclosure, that the nucleic acid (i) was amplified in vitro, for example via polymerase chain reaction (PCR), (ii) was produced recombinantly by cloning, (iii) was purified, for example, by cleavage and separation by gel electrophoresis, or (iv) was synthesized, for example, by chemical synthesis. A nucleic can be employed for introduction into, i.e. transfection of cells, in particular, in the form of RNA which can be prepared by in vitro transcription from a DNA template. The RNA can moreover be modified before application by stabilizing sequences, capping, and polyadenylation.

As used herein, the term "RNA" relates to a molecule which comprises ribonucleotide residues and preferably being entirely or substantially composed of ribonucleotide residues. "Ribonucleotide" relates to a nucleotide with a hydroxyl group at the 2'-position of a B-D-ribofuranosyl group. The term "RNA" comprises double-stranded RNA, single-stranded RNA, isolated RNA such as partially or completely purified RNA, essentially pure RNA, synthetic RNA, and recombinantly generated RNA such as modified RNA which differs from naturally occurring RNA by addition, deletion, substitution and/or alteration of one or more nucleotides. Such alterations can include addition of non-nucleotide material, such as to the end (s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

As used herein, the term "RNA" includes and preferably relates to "mRNA". The term "mRNA" means "messenger-RNA" and relates to a "transcript" which is generated by using a DNA template and encodes a peptide or polypeptide. Typically, an mRNA comprises a 5'-UTR, a protein coding region, and a 3'-UTR. mRNA only possesses limited half-life in cells and in vitro. In the context of the present disclosure, mRNA may be generated by in vitro transcription from a DNA template. The term "modification" in the context of the RNA used in the present disclosure includes any modification of an RNA which is not naturally present in said RNA. In one embodiment of the disclosure, the RNA used according to the disclosure does not have uncapped 5'-triphosphates. Removal of such uncapped 5'-triphosphates can be achieved by treating RNA with a phosphatase. The RNA according to the disclosure may have modified ribonucleotides in order to increase its stability and/or decrease cytotoxicity. For example, in one embodiment, in the RNA used according to the disclosure 5-methylcytidine is substituted partially or completely, preferably completely, for cytidine. Alternatively or additionally, in one embodiment, in the RNA used according to the disclosure pseudouridine is substituted partially or completely, preferably completely, for uridine.

In one embodiment, the term "modification" relates to providing an RNA with a 5-cap or 5'-cap analog. The term "5-cap" refers to a cap structure found on the 5'-end of an mRNA molecule and generally consists of a guanosine nucleotide connected to the mRNA via an unusual 5' to 5 triphosphate linkage. In one embodiment, this guanosine is methylated at the 7-position. The term "conventional 5'-cap" refers to a naturally occurring RNA 5'-cap, preferably to the 7-methylguanosine cap (m'G). as used herein, the term "5'-cap" includes a 5'-cap analog that resembles the RNA cap structure and is modified to possess the ability to stabilize RNA and/or enhance translation of RNA if attached thereto, preferably in vivo and/or in a cell.

According to the disclosure, the stability and translation efficiency of RNA may be modified as required. For example, RNA may be stabilized and its translation increased by one or more modifications having a stabilizing effects and/or increasing translation efficiency of RNA. Such modifications are described, for example, in PCT/EP2006/009448 incorporated herein by reference. In order to increase expression of the RNA used according to the present disclosure, it may be modified within the coding region, i.e. the sequence encoding the expressed peptide or protein, preferably without altering the sequence of the expressed peptide or protein, so as to increase the GC content to increase mRNA stability and to perform a codon optimization and, thus, enhance translation in cells.

Aspects of the disclosure relate to a method of preventing a bacterial or viral infection, the method comprising administering to a subject in need thereof an effective amount of the composition provided herein to elicit an immune response.

Aspects of the disclosure provide methods of vaccinating a subject comprising administering to the subject a single dosage of the compositions described herein comprising a nucleic acid (e.g. mRNA) encoding an polypeptide in an effective amount to vaccinate the subject.

In some embodiments, the nucleic acid is formulated within a cationic lipidic nanoparticle. In some embodiments, the lipidic nanoparticle composition is administered as a single injection.

In some embodiments, the bacterial infection is *Mycobacterium tuberculosis* infection.

In some embodiments, the viral infection is a coronavirus. In some embodiments, the coronavirus is SARS-CoV, MERS-CoV or SARS-CoV-2

In some embodiments, the viral infection is HIV/AIDS.

In some embodiments, the lipidic nanoparticle is administered parenterally.

In general, administration to a patient by intradermal injection is possible. However, injection may also be carried out intranodally into a lymph node (Maloy et al. (2001), Proc Natl Acad Sci USA 98:3299-3033). The resulting cells present the complex of interest and are recognized by autologous cytotoxic T lymphocytes which then propagate.

In some embodiments, the compositions are administered by inhalation. In some embodiments, the composition is formulated as nasal spray, and/or aerosol Actual dosage levels of the active agents in the pharmaceutical compositions disclosed herein may be varied so as to obtain an amount of the active agent which is effective to achieve the desired therapeutic response for a particular patient, composition, and mode of administration, without being toxic to the patient.

"Parenteral" as used herein in the context of administration means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The phrases "parenteral administration" and "administered parenterally" as used herein refer to modes of administration other than enteral (i.e., via the digestive tract) and topical administration, usually by injection or infusion, and includes, without limitation, intravenous, intramuscular, intraarterial, intrathecal, intracapsular, intraorbital, intracardiac, intradermal, intraperitoneal, transtracheal, subcutaneous, subcuticular, intraarticular, inhalation, subcapsular, subarachnoid, respiratory mucosal, intraspinal, epidural and intrasternal injection and infusion. Intravenous injection and infusion are often (but not exclusively) used for liposomal drug administration.

Dosage regimens can be adjusted to provide the optimum desired response (e.g., a therapeutic response). For example, one or more doses may be administered over time or the dose may be proportionally reduced or increased as indicated by the exigencies of the therapeutic situation.

In some embodiments, the dose comprises between 0.01 to 5 mg/kg of nucleic acid. In some embodiments, the dose comprises between 0.01 to 5 mg/kg of mRNA. In some embodiments, the dose comprises between 0.01 to 3 mg/kg of nucleic acid. In some embodiments, the dose comprises between 0.01 to 3 mg/kg of mRNA. In some embodiments, the dose comprises between 0.01 to 1 mg/kg of nucleic acid. In some embodiments, the dose comprises between 0.01 to 1 mg/kg of mRNA. In some embodiments, the dose comprises between 0.01 to 0.5 mg/kg of nucleic acid. In some embodiments, the dose comprises between 0.01 to 0.5 mg/kg of mRNA. In some embodiments, the dose comprises between 0.01 to 1 mg/kg of mRNA. In some embodiments, the dose comprises between 0.01 to 0.1 mg/kg of nucleic acid. In some embodiments, the dose comprises between 0.01 to 0.05 mg/kg of mRNA. In some embodiments, the dose comprises between 0.01 to 0.1 mg/kg of nucleic acid. In some embodiments, the dose comprises between 0.01 to 0.05 mg/kg of mRNA.

The dosage of the compounds and/or of their pharmaceutically acceptable salts or the LNPs comprising the compounds and/or of their pharmaceutically acceptable salts may vary within wide limits and should naturally be adjusted, in each particular case, to the individual conditions and to the pathogenic agent to be controlled.

In some embodiments, ionizable cationic lipids (ICLs) are provided. Cationic lipids are engineered with improved stability to oxidative degradation while in storage, while retaining high transfection activity or potency in cells. Aspects of the disclosure are based in part on the discovery that LNP compositions comprising mRNA and certain ionizable cationic lipids (ICL) enhanced expression of the mRNA in human dendritic cells.

In some embodiments, LNP compositions comprise a targeting ligand directed against cell surface receptors to target lipid nanoparticles in a highly specific manner, including to dendritic cells. In some embodiments, the LNP composition comprises a phosphatidyl-L-serine compound as a targeting ligand, such as dipalmitoylphosphatidyl-L-serine (DPPS), or distearoylphosphatidyl-L-serine (DSPS). In some embodiments, the LNP composition comprises a phosphatidyl-L-serine compound as a targeting ligand and an anionic phospholipid. In some embodiments, the LNP composition comprises a phosphatidylglycerol-containing compound as a targeting ligand such as distearoylphosphatidylglycerol (DSPG) or dipalmitoyphosphatidylglycerol (DPPG), for enhancing expression in human dendritic cells. In some embodiments, LNP compositions comprise both a phosphatidyl-L-serine compound as a targeting ligand, and distearoylphosphatidylcholine (DSPC) as the second phospholipid. In some embodiments, LNP compositions comprise both a phosphatidyl-L-serine compound as a targeting ligand, and distearoylphosphatidylcholine (DSPC) as the second phospholipid without dipalmitoylphosphatidylcholine (DPPC).

Aspects of the disclosure are based in part on the discovery that selection of certain cationic ionizable lipids can enhance the transfection of human dendritic cells. For example, the KC3 cationic ionic lipids were more active in transfecting human dendritic cells in LNP compositions than either the KC2 or diacyl ionizable lipids (UO series). Among the LNP compositions comprising KC3 ionizable cationic lipids, those LNP compositions with ionizable cationic lipids having monounsaturated alkyl chains were unexpectedly both more active and more stable to oxidative degradation than those containing those with the dilinoleyl alkyl chains. In addition, we observed reduced transfection in human dendritic cells activity in LNP compositions comprising the monounsaturated lipids, such as for the diacyl ionizable lipids (UO-series).

In some embodiments, certain salts of the phosphatidylserine targeting lipids are provided. For example, in some embodiments, the phosphatidylserine targeting lipids can be provided as an ammonium salt of DPPS having improved biophysical properties and higher solubility in the presence of ethanol, a preferred solvent for preparation of LNPs. The sodium salts of DSPS or DSPS were insoluble in ethanol and required both the presence of methanol and heating to allow for their formation, as did the ammonium salt of DSPS. It is contemplated that the other ammonium salts of phosphatidylserine will give rise to the same advantages in solubility and biophysical properties.

In some embodiments, ionizable cationic lipid compositions useful in the preparation of liposomal nanoparticle (LNP) compositions are provided. In some embodiments, liposomal compositions are provided comprising an ionizable cationic lipid having (a) a pair of linear C16 or C18 hydrocarbon chains each comprising a single unsaturated alkenyl double bond within each polyene hydrocarbon chain, covalently bound to a head group comprising a dialkyl amino alkyl group. In some embodiments, the head group of the ionizable cationic lipid has a dialkyl amino group having a pKa of about 6.3-7.5. In some embodiments, the head group of the ionizable cationic lipid comprises a heterocyclyl or alkyl portion covalently bound to the dialkyl amino group. In some embodiments, the head group of the ionizable cationic lipid optionally further comprises a phosphate group. In some embodiments, each lipid tail of the ionizable cationic lipid compound is identical, and each lipid tail has a total of one olefin with a total length of 15, 16, 17 or 18 carbons.

In some embodiments, a lipid nanoparticle (LNP) composition comprises an ionizable cationic lipid having the chemical structure of Formula (I):

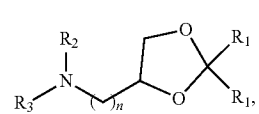

(I)

wherein $R_1$ is

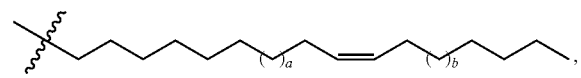

wherein a is 0 or 1; b is 1, 2, 3 or 4, provided the sum a+b is 1, 2, 3 or 4;

$R_2$ and $R_3$ are each independently $(C_1$-$C_4)$ alkyl optionally substituted with hydroxyl; and n is an integer equal to 2, 3 or 4.

In some embodiments, ionizable cationic lipid compositions are provided. In some embodiments, a lipid nanoparticle (LNP) composition comprises an ionizable cationic lipid having the chemical structure of Formula (I) wherein a is 0 or 1; b is 1, 2, 3 or 4, provided the sum a+b is 1, 2, 3 or 4; $R_2$ and $R_3$ are each methyl; and n is an integer equal to 3.

In some embodiments, ionizable cationic lipid compositions are provided. In some embodiments, a lipid nanoparticle (LNP) composition comprises an ionizable cationic lipid having the chemical structure of Formula (I-A):

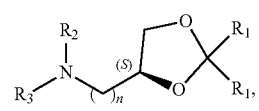

(I-A)

wherein $R_1$ is

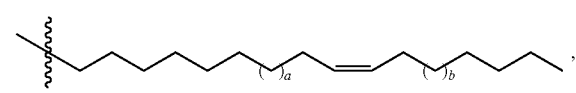

wherein a is 0 or 1; b is 1, 2, 3 or 4, provided the sum a+b is 1, 2, 3 or 4;

$R_2$ and $R_3$ are each methyl; and n is an integer equal to 3.

In some embodiments, a LNP composition comprises an ionizable cationic lipid comprises a pair of identical, lipid hydrocarbon tails having a total of 15, 16, 17 or 18 carbons and comprising a single olefin group, or a pair of olefin groups. In some embodiments, a LNP composition comprises an ionizable cationic lipid selected from the group consisting of:

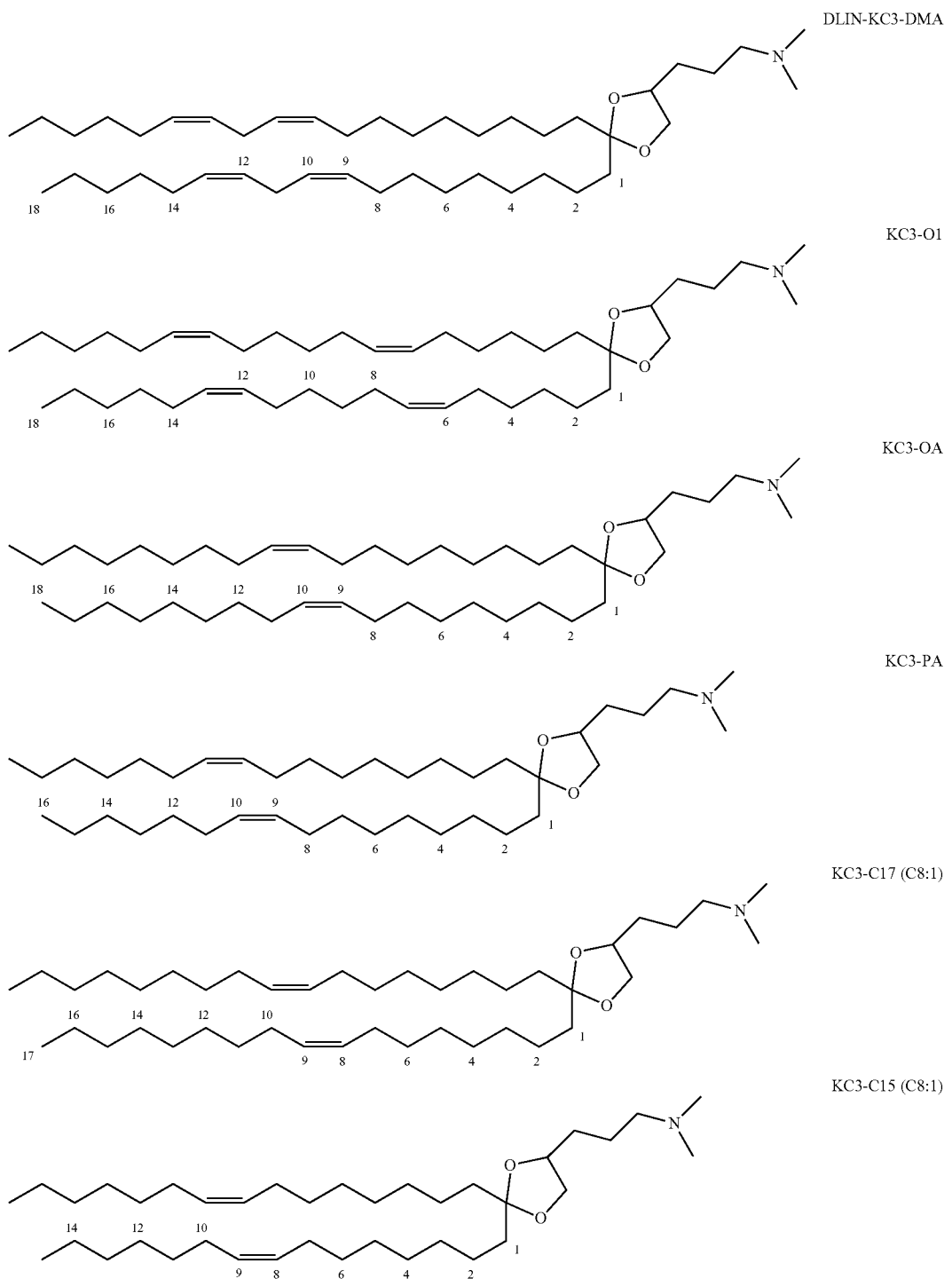

In some embodiments, the ionizable cationic lipid is KC3-PA. In some embodiments, the ionizable cationic lipid is KC3-C15 (C8:1). In some embodiments, the ionizable cationic lipid is KC3-C16 (C8:1). In some embodiments, the ionizable cationic lipid is KC3-C17 (C8:1). In some embodiments, the ionizable cationic lipid is KC3-C18 (C8:1).

In some embodiments, the ionizable cationic lipid is KC3-15. In some embodiments, the ionizable cationic lipid is KC3-16. In some embodiments, the ionizable cationic lipid is KC3-17. In some embodiments, the ionizable cationic lipid is KC3-18.

The salt form of the targeting lipid can influence it's solubility in alcohol containing solvents used in the preparation of lipid nanoparticles. In some embodiments, ionizable cationic lipid compositions are provided. In some embodiments, a lipid nanoparticle (LNP) composition comprises a nucleic acid; an ionizable lipid disclosed herein; a sterol; one or more phospholipids comprising a phosphatidylserine (PS) lipid; and optionally further comprising a conjugated lipid. In some embodiments, a lipid nanoparticle (LNP) composition comprises a mRNA nucleic acid; an ionizable lipid disclosed herein; cholesterol; one or more phospholipids selected from the group consisting of: DSPC, DPPC and DOPC; and a PS lipid selected from the group consisting of: DPPS, DSPS and DOPS; and optionally further comprising a conjugated lipid comprising PEG.

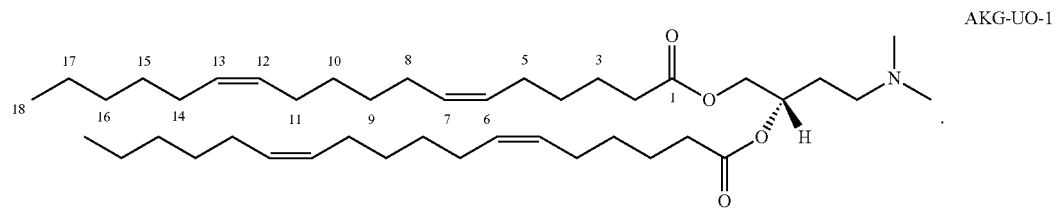 [SMILES: CCCCC/C=C\CCCC/C=C\CCCCC(=O)OC[C@H](CCN(C)C)OC(=O)CCCC/C=C\CCCC/C=C\CCCCC]

AKG-UO-1

In some embodiments, the ionizable lipid is AKG-UO-1A:

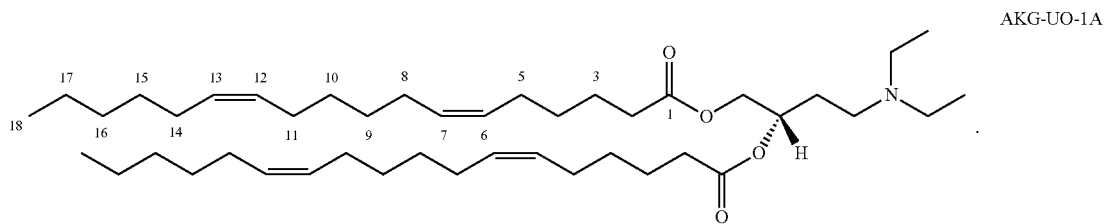 [SMILES: CCCCC/C=C\CCCC/C=C\CCCCC(=O)OC[C@H](CCN(CC)CC)OC(=O)CCCC/C=C\CCCC/C=C\CCCCC]

AKG-UO-1A

In some embodiments, the ionizable lipid is AKG-UO-1B:

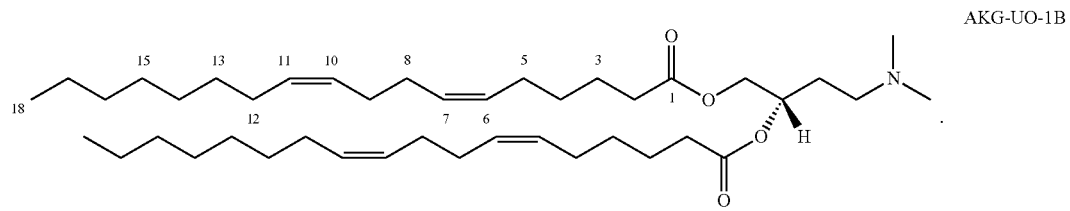 [SMILES: CCCCCCC/C=C\CC/C=C\CCCCC(=O)OC[C@H](CCN(C)C)OC(=O)CCCC/C=C\CC/C=C\CCCCCCC]

AKG-UO-1B

In some embodiments, the ionizable lipid is AKG-UO-2

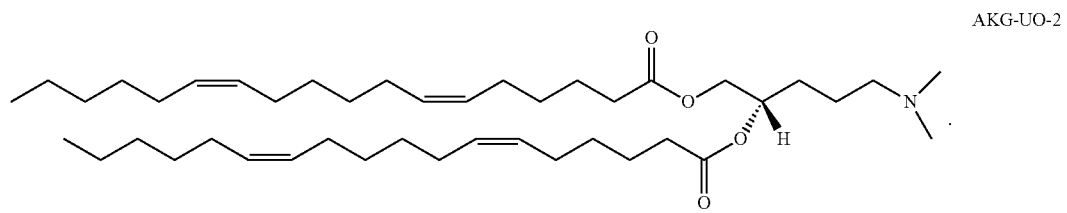 [SMILES: CCCCC/C=C\CCCC/C=C\CCCCC(=O)OC[C@H](CCCN(C)C)OC(=O)CCCC/C=C\CCCC/C=C\CCCCC]

AKG-UO-2

In some embodiments, the ionizable lipid is AKG-UO-4:

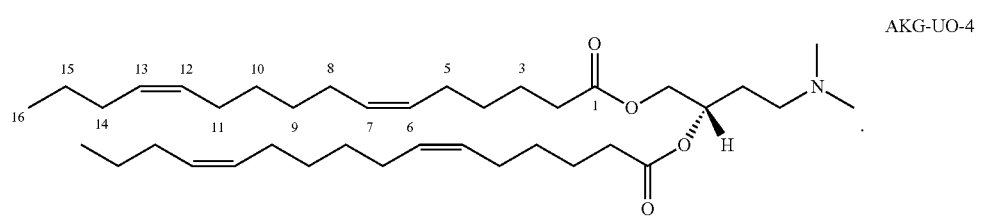 [SMILES: CCC/C=C\CCCC/C=C\CCCCC(=O)OC[C@H](CCN(C)C)OC(=O)CCCC/C=C\CCCC/C=C\CCC]

AKG-UO-4

In some embodiments, the ionizable lipid is AKG-UO-4A:
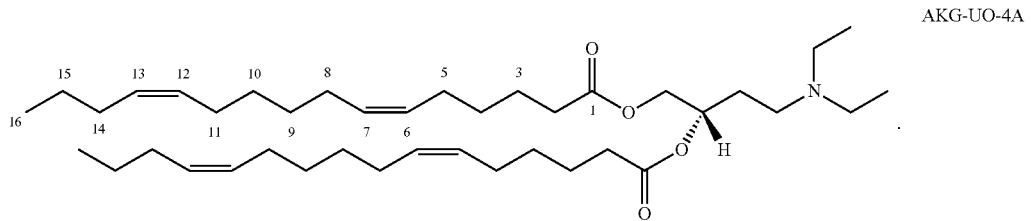 [SMILES: CCC/C=C\CCCC/C=C\CCCCC(=O)OC[C@H](CCN(CC)CC)OC(=O)CCCC/C=C\CCCC/C=C\CCC]
AKG-UO-4A
In some embodiments, the ionizable lipid is AKG-UO-5:
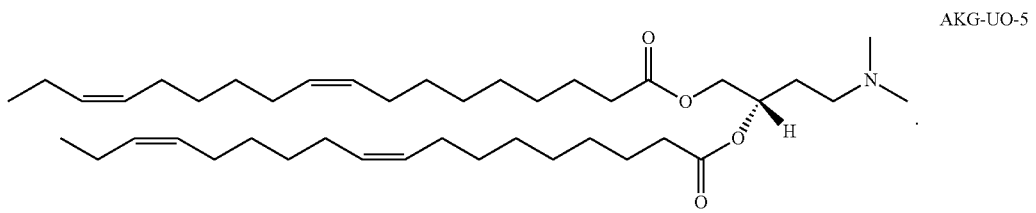 [SMILES: CC/C=C\CCCC/C=C\CCCCCCCC(=O)OC[C@H](CCN(C)C)OC(=O)CCCCCCC/C=C\CCCC/C=C\CC]
AKG-UO-5
In some embodiments, the ionizable lipid is AKG-UO-6, AKG-UO-7, AKG-UO-7, AKG-UO-8, AKG-UO-9, or AKG-UO-10:
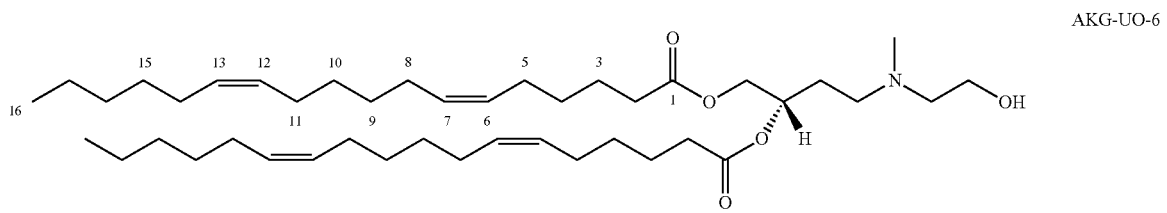
AKG-UO-6
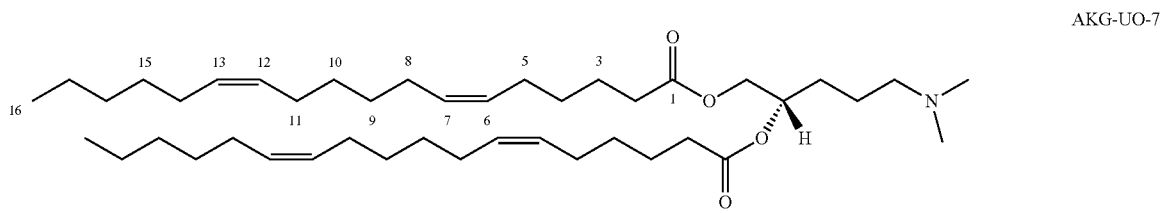
AKG-UO-7
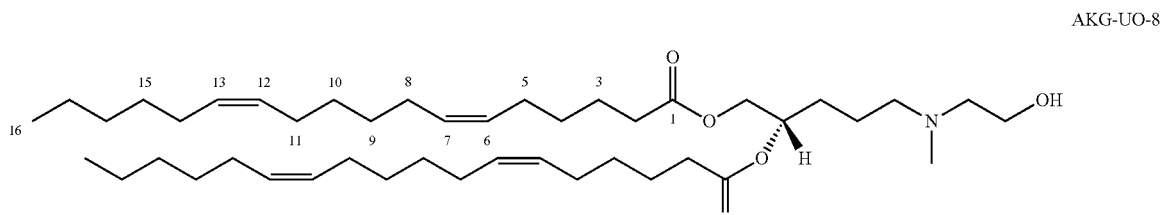
AKG-UO-8
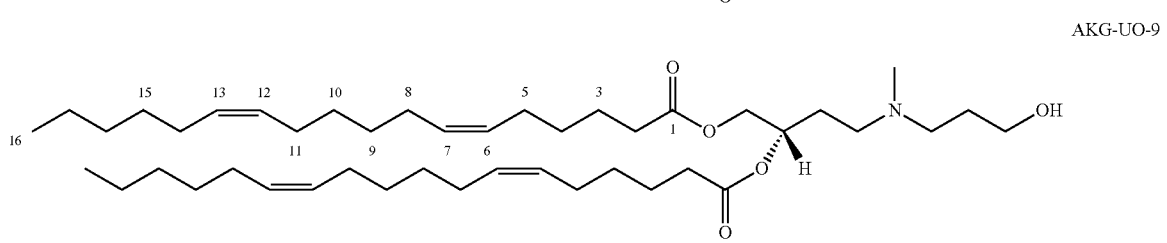
AKG-UO-9

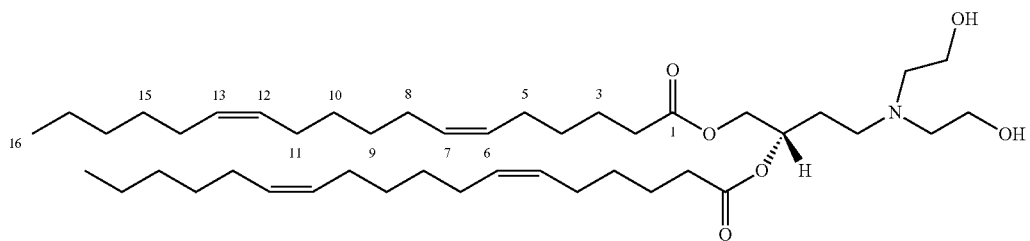

AKG-UO-10

In some embodiments, a LNP composition can comprise an anionic phospholipid. In some embodiments, a LNP composition is prepared using a sodium or ammonium salt of an anionic phospholipid. In some embodiments, the anionic phospholipid salt is a compound of Formula (V-A-1), having the chemical structure:

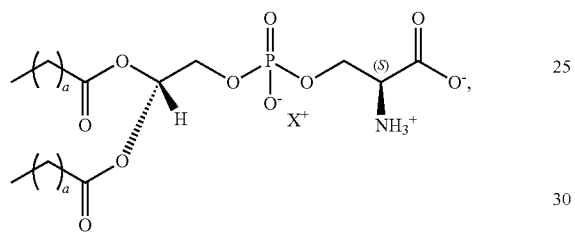

Formula (V-A-1)

wherein
$X^+$ is an ammonium ($NH_4^+$) or sodium ($Na^+$) cation; and
a is 14, 15 or 16.

In some embodiments, the anionic phospholipid salt is selected from the group consisting of:

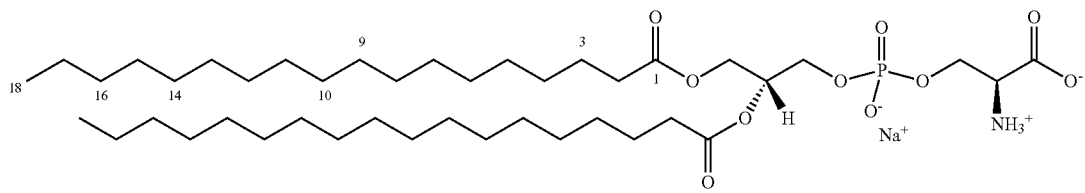

DPSP (L-isomer) - sodium salt

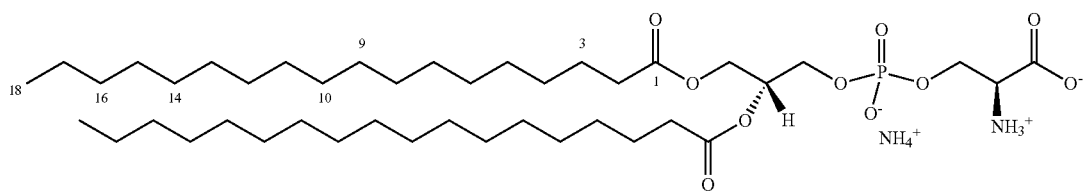

DPSP (L-isomer) - ammonium salt

-continued

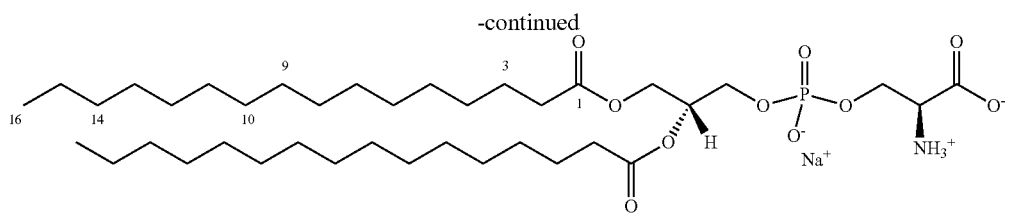

DPPS (L-isomer) - sodium salt

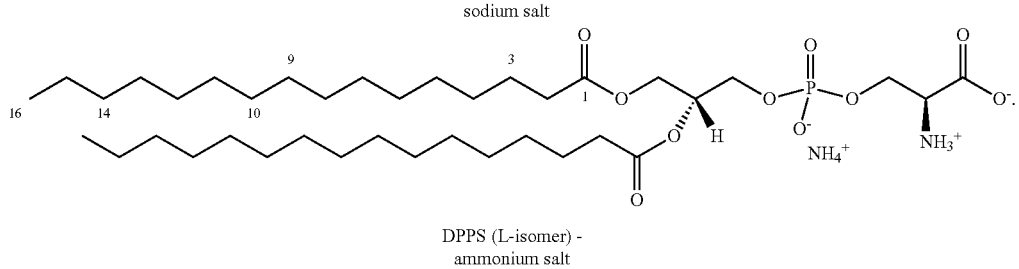

DPPS (L-isomer) - ammonium salt

In some embodiments, the anionic phospholipid salt is DSPS (L-isomer) sodium salt. In some embodiments, the anionic phospholipid salt is DSPS (L-isomer) ammonium salt. In some embodiments, the anionic phospholipid salt is DPPS (L-isomer) sodium salt. In some embodiments, the anionic phospholipid salt is DPPS (L-isomer) ammonium salt. In some embodiments the targeting lipid is a sodium or ammonium salt of dipalmitoylphosphatidyl-L-serine (DPPS) or distearoylphosphatidyl-L-serine (DSPS). In some embodiments the targeting lipid is a sodium or ammonium salt of dipalmitoylphosphatidyl-L-serine (DPPS) or distearoylphosphatidyl-L-serine (DSPS).

In some embodiments, a LNP composition can comprise an anionic phospholipid selected from the group consisting of:

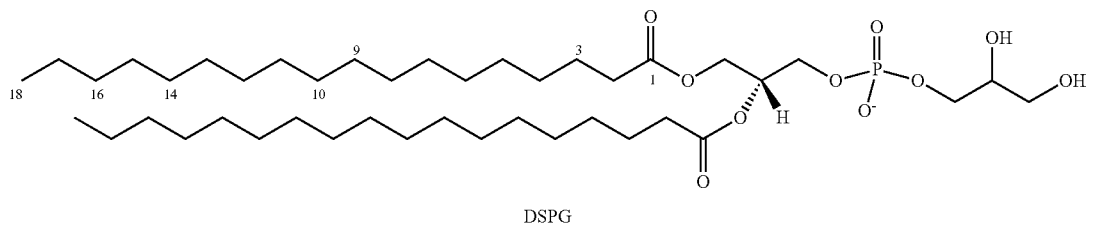

DSPG

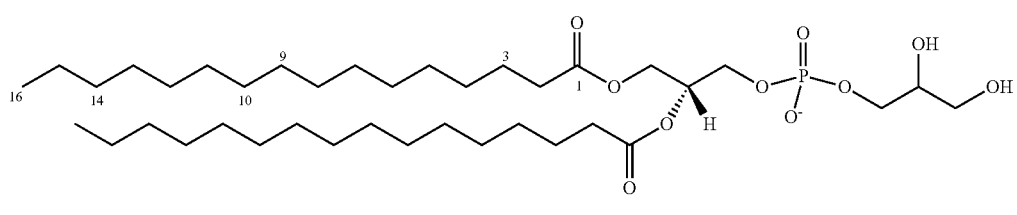

DPPG

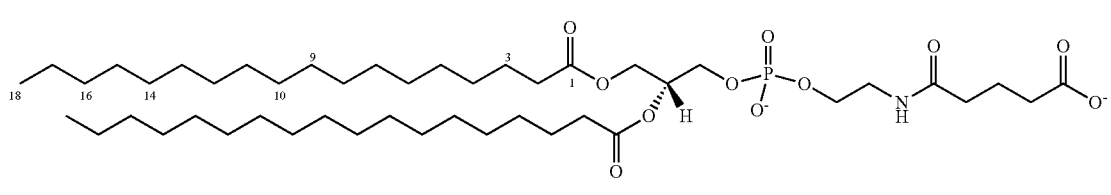

N-Glu-DSPE

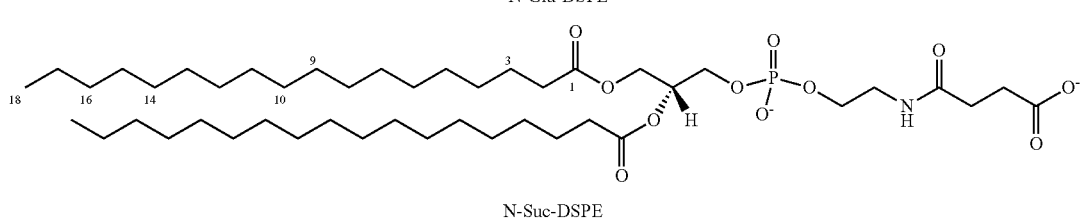

N-Suc-DSPE

-continued

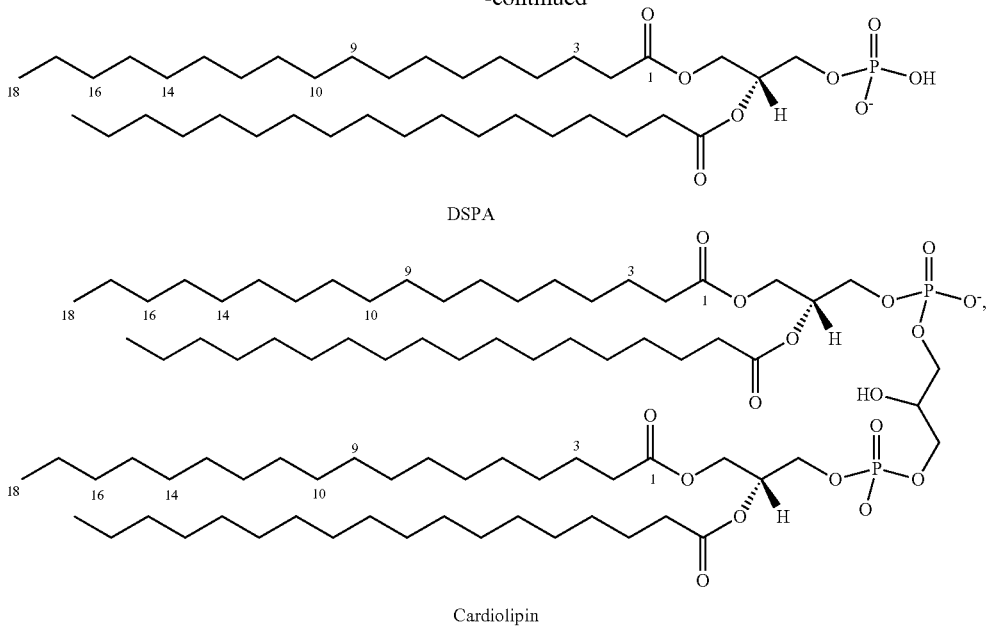

DSPA

Cardiolipin or an ammonium or sodium salt thereof.

In some embodiments, the salt form of phosphatidylserine is highly soluble in ethanol. In some embodiments it is soluble at greater than 0.5 mg/ml, greater than 1 mg/mL, greater than 5 mg/mL, greater than 10 mg/mL, or greater than 20 mg/mL. In some embodiments, the salt is an ammonium salt. In some embodiments, the salt is ammonium itself, an alkylammonium, a dialkylammonium, or a trialkylammonium salt. In some embodiments, the amine is chosen from ammonia, dimethylamine, diethylamine, triethylamine, trimethylamine, 2-(dimethyamino)ethanol, diethanolamine, 2-(diethyamino)ethanol, ethanolamine, ethylenediamine, N-methyl-glucamine, imidazole, histidine, lysine, arginine, 4-(2-hydroxyethyl)-morpholine, piperazine, 1-(2-hydroxyethyl)-pyrrolidine, triethanolamine, and tromethamine (tris(hydroxymethyl)aminomethane), In some embodiments, this targeting lipid is an ammonium salt of DPPS.

Anionic phospholipids, separate from phosphatidyl-L-serine, were also considered as targeting lipids for LNPs. These include phosphatidylglycerol (PG), phosphatidic acid (PA), N-glutaryl-phosphatidylethanolamine (N-Glu-PE), N-succinyl-phosphatidylethanolamine (N-Suc-PE), and cardiolipin. In some embodiments, a LNP comprises anionic phospholipids, separate from phosphatidyl-L-serine, useful as targeting lipids for LNPs. In some embodiments, a LNP comprises anionic phospholipids selected from the group consisting of: phosphatidylglycerol (PG), phosphatidic acid (PA), N-glutaryl-phosphatidylethanolamine (N-Glu-PE), N-succinyl-phosphatidylethanolamine (N-Suc-PE), and cardiolipin. Distearoylphosphatidylglycerol (DSPG), dipalmitoyphosphatidylglycerol (DPPG), N-succinyl-distearoylphosphatidylethanolamine (N-Suc-DSPE), N-glutaryl-distearoylphosphatidylethanolamine (N-glu-DSPE), distearoylphosphatidic acid (DSPA), and cardiolipin are also provided as anionic phospholipids.

In some embodiments, lipid nanoparticle (LNP) compositions comprising an ionizable cationic lipid compositions are provided. In some embodiments, lipid nanoparticle (LNP) compositions comprising an ionizable cationic lipid are provided. In some embodiments, the LNP composition comprises a mRNA nucleic acid. In some embodiments, a lipid nanoparticle (LNP) composition further comprises the PS lipid in a total amount of 2.5-10 mol % of the total lipid in the composition of the LNP. In some embodiments, a lipid nanoparticle (LNP) composition further comprises a PS lipid selected from the group consisting of: DSPS (L-isomer) and DPPS.

In some embodiments, a lipid nanoparticle (LNP) composition comprises a conjugated lipid in a total amount of 0.5-2.0 mol % of the total lipid content of the LNP composition. In some embodiments, a lipid nanoparticle (LNP) composition comprises the conjugated lipid in a total amount of less than 2 mol % of the total lipid content of the LNP composition, and the conjugated lipid is PEG-DMG.

In some embodiments, a lipid nanoparticle (LNP) composition comprises a nucleic acid; an ionizable lipid disclosed herein; a sterol; one or more phospholipids comprising a phosphatidylserine (PS) lipid; and optionally further comprising a conjugated lipid. In some embodiments, a lipid nanoparticle (LNP) composition comprises a mRNA nucleic acid; an ionizable lipid disclosed herein; cholesterol; one or more phospholipids selected from the group consisting of: SM, DSPC, HSPC, DPPC and DOPC; and a PS lipid selected from the group consisting of: DPPS and DSPS; and optionally further comprising a conjugated lipid comprising PEG. In some embodiments, a nucleic acid lipid nanoparticle (LNP) composition comprises: a nucleic acid; an ionizable cationic lipid in a total amount of 40-65 mol % of the total lipid content of the LNP composition; a sterol in a total amount of 25-45 mol % of the total lipid content of the LNP composition; and one or more phospholipids in a total amount of phospholipids of 5-25 mol % of the total lipid content of the LNP composition, and comprising a phosphatidylserine (PS) in a total amount of 2.5-10 mol % of the total lipid content of the LNP composition; and optionally further comprising a conjugated lipid in a total amount of 0.5-2.5 mol % of the total lipid content of the LNP composition.

In some embodiments, the LNP composition further comprises an anionic lipid selected from the group consisting of: DSPS (L-isomer), DPPS (L-isomer), DMPS (L-isomer), DOPS (L-isomer), and DSPS (D-isomer).

Aspects of the disclosure relate to a lipid nanoparticle (LNP) composition comprising an ionizable lipid having the chemical structure:

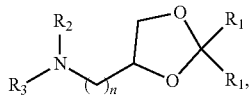

wherein $R_1$ is

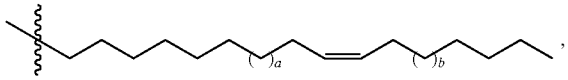

wherein a is 0 or 1; b is 1, 2, 3 or 4, provided the sum a+b is 1, 2, 3 or 4;
$R_2$ and $R_3$ are each independently $(C_1-C_4)$ alkyl optionally substituted with hydroxyl; and
n is an integer equal to 2, 3 or 4.

In some embodiments, n is 2 or 3. In some embodiments, a is 0. In some embodiments, b is 1, 2 or 3. In some embodiments, a is 1. In some embodiments, b is 1, 2 or 3. In some embodiments, $R_2$ and $R_3$ are each methyl.

In some embodiments, $R_1$ is

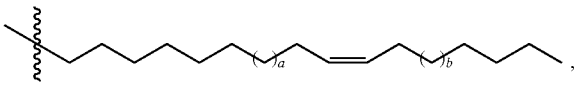

a is 0 or 1 and b is 1 or 3; $R_2$ and $R_3$ are each methyl; and n is 2 or 3. In some embodiments, n is 3.

In some embodiments, the LNP composition comprises a nucleic acid; the ionizable lipid described herein, a sterol; one or more phospholipids comprising a phosphatidylserine (PS) lipid; and optionally a conjugated lipid.

In some embodiments, the nucleic acid is mRNA.
In some embodiments, the sterol is cholesterol.
In some embodiments, the one or more phospholipids consist of: one or more phospholipids selected from the group consisting of: SM, DSPC, HSPC, DPPC and DOPC; and a PS lipid selected from the group consisting of: DPPS, and DSPS.

In some embodiments, the one or more phospholipids consist of: DSPC; and one or more PS lipids selected from the group consisting of (L-Serine) DPPS and (L-Serine) DSPS.

In some embodiments, the composition comprises the PS lipid in a total amount of 2.5-10 mol % of the total lipid in the composition.

In some embodiments, the conjugated lipid comprises PEG.

Aspects of the disclosure relate to a nucleic acid lipid nanoparticle (LNP) composition comprising: a nucleic acid; an ionizable cationic lipid in a total amount of 40-65 mol % of the total lipid content of the LNP composition; a sterol in a total amount of 25-45 mol % of the total lipid content of the LNP composition; and one or more phospholipids in a total amount of phospholipids of 5-25 mol % of the total lipid content of the LNP composition, and comprising a phosphatidylserine (PS) in a total amount of 2.5-10 mol % of the total lipid content of the LNP composition; and optionally a conjugated lipid in a total amount of 0.5-2.5 mol % of the total lipid content of the LNP composition.

In some embodiments, the nucleic acid is mRNA.
In some embodiments, the sterol is cholesterol.
In some embodiments, the one or more phospholipids consist of: DSPC and a L-serine PS.
In some embodiments, the composition comprises the PS in a total amount of 2.5-7.5 mol % of the total lipid in the composition.
In some embodiments, the conjugated lipid comprises PEG. In some embodiments, conjugated lipid is PEG-DMG.
In some embodiments, the LNP comprises the conjugated lipid in a total amount of 0.5-2.0 mol % of the total lipid content of the LNP composition. In some embodiments, the conjugated lipid in a total amount of less than 2 mol % of the total lipid content of the LNP composition.

In some embodiments, the nucleic acid is a mRNA, the ionizable cationic lipid in a total amount of 45-55 mol % of the total lipid content of the LNP composition; a sterol is cholesterol in a total amount of 35-45 mol % of the total lipid content of the LNP composition; the total amount of phospholipid of 7-15 mol % of the total lipid content of the LNP composition; the one or more phospholipids consist of DSPC and the PS lipid is one or more lipids selected from the group consisting of the L-serine configuration of DPPS and DSPS; and the total amount of the PS lipid is about 5 mol % of the total lipid content of the LNP composition.

In some embodiments, the composition comprises the PS lipid in a total amount selected from 1.25 mol %, 2.5 mol %, 5 mol %, 7.5 mol %, and 10 mol % of the total lipid content of the LNP composition.

Aspects of the disclosure relate to a nucleic acid lipid nanoparticle (LNP) composition comprising: a nucleic acid, wherein the nucleic acid is mRNA; an ionizable cationic lipid, the ionizable cationic lipid in a total amount of 45-55 mol % of the total lipid content of the LNP composition; a sterol, wherein the sterol is cholesterol in a total amount of 35-45 mol % of the total lipid content of the LNP composition; one or more phospholipids, wherein the one or more phospholipids in a total amount of phospholipids of 10 mol % of the total lipid content of the LNP composition, and comprising a phosphatidylserine (PS) in a total amount of 3-9 mol % of the total lipid content of the LNP composition; and a conjugated lipid, the conjugated lipid in a total amount of 0.5-2.0 mol % of the total lipid content of the LNP composition.

In some embodiments, the one or more phospholipid is selected from the group consisting of: DSPS (L-isomer), DPPS (L-isomer), DMPS (L-isomer), DOPS (L-isomer), and DSPS (D-isomer).

In some embodiments, the conjugated lipid is PEG-DMG; and the PS lipid is selected from the group consisting of: DSPS (L-isomer) and DPPS.

In some embodiments, the ionizable cationic lipid is one or more compounds selected from the group consisting of: KC3-OA, KC3-PA, KC3-C17 (8:1), and KC3-C15 (C8:1). In some embodiments, the ionizable cationic lipid is KC3-PA. In some embodiments, the ionizable cationic lipid is KC3-OA. In some embodiments, the ionizable cationic lipid is KC3-C17 (C8:1).

In some embodiments, the LNP comprises a nucleic acid; an ionizable cationic lipid in a total amount of 50 mol % of the total lipid content of the LNP composition; cholesterol in a total amount of 38.5 mol % of the total lipid content of the LNP composition; one or more phospholipids in a total amount of 7-15 mol % of the total lipid content of the LNP composition, and comprising a phosphatidylserine (PS) lipid in a total amount of 3-9 mol % of the total lipid content of the LNP composition; and a PEG-containing lipid in a total amount of 0.5-2.0 mol % of the total lipid content of the LNP composition.

In some embodiments, the phospholipids consist of one or more phospholipids selected from the group consisting of: DSPC, DOPC, DPPC, HSPC, and SM.

In some embodiments, the PS lipid is one or more L-serine lipids selected from the group consisting of DPPS and DSPS.

In some embodiments, the one or more phospholipids comprise at least two (L-Serine) PS lipids having mismatched acyl chain lengths.

In some embodiments, the phospholipids are DSPC and DPPS. In some embodiments, the DSPC and DPPS are each present in the LNP at a total amount of 5 mol % each, based on the total lipid content of the LNP composition.

Aspects of the disclosure relate to a nucleic acid lipid nanoparticle (LNP) composition comprising: a nucleic acid, ionizable cationic lipid KC3-PA or KC3-OA, and a (L-Serine) PS lipid in a total amount of 2.5-10 mol % of the total lipid content of the LNP composition.

In some embodiments, the nucleic acid is mRNA, the PS lipid is (L-Serine) DSPS, (L-Serine) DPPS, or a mixture thereof, and the LNP composition further comprises cholesterol and a second phospholipid selected from the group consisting of: DSPC, DPPC, HSPC, and SM.

In some embodiments, the LNP composition further comprises 0.5-2.0 mol % PEG-DMG or PEG-DSG, based on the total lipid content in the LNP composition.

In some embodiments, the ionizable cationic lipid is KC3-PA. In some embodiments, the ionizable cationic lipid KC3-OA.

Aspects of the disclosure relate to a nucleic acid lipid nanoparticle (LNP) composition comprising: a nucleic acid, a KC3-C17 (C8:1) ionizable cationic lipid; and a (L-Serine) PS lipid in a total amount of 2.5-10 mol % of the total lipid content of the LNP composition.

In some embodiments, the LNP composition has a N/P ratio 4 to 7. In some embodiments, the composition has a N/P ratio of 5 to 6. In some embodiments, the composition has a N/P ratio of 5.3.

Aspects of the disclosure relate to a nucleic acid lipid nanoparticle (LNP) composition comprising: a nucleic acid, ionizable cationic lipid KC3-PA, and a (L-Serine) PS lipid in a total amount of 2.5-10 mol % of the total lipid content of the LNP composition.

In some embodiments, the nucleic acid is mRNA, the PS lipid is (L-Serine) DSPS, (L-Serine) DPPS, or a mixture thereof, and the LNP composition further comprises cholesterol and a second phospholipid selected from the group consisting of: DSPC, DOPC, DPPC, HSPC, and SM.

In some embodiments, the LNP composition further comprises 0.5-2.0 mol % PEG-DMG or PEG-DSG, based on the total lipid content in the LNP composition.

Aspects of the disclosure relate to a nucleic acid lipid nanoparticle (LNP) composition comprising: a nucleic acid, an ionizable cationic lipid selected from KC3-C17 (C8:1); and a (L-Serine) PS lipid in a total amount of 2.5-10 mol % of the total lipid content of the LNP composition.

In some embodiments, the N/P ratio is 4 to 7. In some embodiments, the N/P ratio is 5 to 6. In some embodiments, the N/P ratio is 3. In some embodiments, the N/P ratio is 7.

In some embodiments, the nucleic acid is mRNA encoding SARS-CoV-2 spike protein.

Aspects of the disclosure relate to a nucleic acid lipid nanoparticle (LNP) vaccine composition comprising: a mRNA nucleic acid with a N/P ratio of 4 to 7; an KC3-PA ionizable cationic lipid in a total amount of 40-65 mol % of the total lipid content of the LNP composition; cholesterol in a total amount of 25-40 mol % of the total lipid content of the LNP composition; a (L-Serine) PS lipid in a total amount of 2.5-10 mol % of the total lipid content of the LNP composition; DSPC phospholipid in a total amount of 5-25 mol % of the total lipid content of the LNP composition; and PEG-DMG in a total amount of 0-2.5 mol % of the total lipid content of the LNP composition.

Aspects of the disclosure relate to a nucleic acid lipid nanoparticle (LNP) vaccine composition comprising: a mRNA nucleic acid with a N/P ratio of 3 to 8; a KC3-C17 (C8:1) ionizable cationic lipid in a total amount of 40-65 mol % of the total lipid content of the LNP composition; cholesterol in a total amount of 25-40 mol % of the total lipid content of the LNP composition; a (L-Serine) PS lipid in a total amount of 2.5-10 mol % of the total lipid content of the LNP composition; DSPC phospholipid in a total amount of 5-25 mol % of the total lipid content of the LNP composition; and PEG-DMG in a total amount of 0-2.5 mol % of the total lipid content of the LNP composition.

Aspects of the disclosure relate to a nucleic acid lipid nanoparticle (LNP) vaccine composition comprising: a mRNA nucleic acid with a N/P ratio of 4 to 7; a KC3-C15 (C8:1) ionizable cationic lipid in a total amount of 40-65 mol % of the total lipid content of the LNP composition; cholesterol in a total amount of 25-40 mol % of the total lipid content of the LNP composition; a (L-Serine) PS lipid in a total amount of 2.5-10 mol % of the total lipid content of the LNP composition; DSPC phospholipid in a total amount of 5-25 mol % of the total lipid content of the LNP composition; and PEG-DMG in a total amount of 0-2.5 mol % of the total lipid content of the LNP composition.

Aspects of the disclosure relate to a nucleic acid lipid nanoparticle (LNP) vaccine composition comprising: a mRNA nucleic acid with a N/P ratio of 3 to 8; a KC3-C18 ionizable cationic lipid in a total amount of 40-65 mol % of the total lipid content of the LNP composition; cholesterol in a total amount of 25-40 mol % of the total lipid content of the LNP composition; a (L-Serine) PS lipid in a total amount of 2.5-10 mol % of the total lipid content of the LNP composition; DSPC phospholipid in a total amount of 5-25 mol % of the total lipid content of the LNP composition; and PEG-DMG in a total amount of 0-2.5 mol % of the total lipid content of the LNP composition.

In some embodiments, the nucleic acid is a mRNA of SEQ ID NO: 2.

Aspects of the disclosure relate to the use of a (L-Serine) PS lipid in combination with an ionizable cationic lipid described herein in the LNP for targeting of the LNP to dendritic cells. In some embodiments, the LNP comprises mRNA. In some embodiments, the LNP further comprises cholesterol. In some embodiments, the total amount of (L-Serine) PS lipid in the LNP is 2.5-10 mol % of the total lipid content of the LNP composition. In some embodiments, the LNP further comprises one or more additional phospholipids including DSPC. In some embodiments, the LNP further comprises a conjugated lipid. In some embodiments, the LNP comprises: a mRNA nucleic acid with a N/P ratio of 3 to 8; a KC3-PA or KC3-C17 (C8:1) ionizable cationic lipid (ICL), in a total amount of 40-65 mol % of the total lipid content of the LNP composition; cholesterol in a total amount of 25-40 mol % of the total lipid content of the LNP composition; a (L-Serine) PS lipid in a total amount of 2.5-10 mol % of the total lipid content of the LNP composition; DSPC phospholipid in a total amount of 5-25 mol % of the total lipid content of the LNP composition; and a conjugated lipid in a total amount of 0-2.5 mol % of the total lipid content of the LNP composition. In some embodiments, the ICL is KC3-PA. In some embodiments, the ICL is KC3-C17 (C8:1).

Some aspects of the disclosure relate to a lipid nanoparticle (LNP) composition comprising an ionizable lipid having the chemical structure:

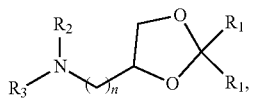

wherein $R_1$ is

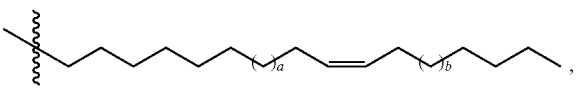

wherein a is 0 or 1; b is 1, 2, 3 or 4, provided the sum a+b is 1, 2, 3 or 4;

$R_2$ and $R_3$ are each independently methyl; and n is an integer equal to 2 or 3.

In some embodiments, a is 0. In some embodiments, b is 1. In some embodiments, b is 3.

In some embodiments, a is 1. In some embodiments, b is 1. In some embodiments, b is 3.

In some embodiments, n is 2. In some embodiments, n is 3.

In some embodiments, the composition comprises an anionic lipid selected from the group consisting of: phosphatidylglycerol (PG), phosphatidic acid (PA), N-glutaryl-phosphatidylethanolamine (N-Glu-PE), N-succinyl-phosphatidylethanolamine (N-Suc-PE), and cardiolipin. Distearoylphosphatidylglycerol (DSPG), dipalmitoyphosphatidylglycerol (DPPG), N-succinyl-distearoylphosphatidylethanolamine (N-Suc-DSPE), N-glutaryl-distearoylphosphatidylethanolamine (N-glu-DSPE), distearoylphosphatidic acid (DSPA), and cardiolipin.

In some embodiments, the composition comprises an anionic targeting phospholipid other than phosphatidyl-L-serine.

In some embodiments, the composition comprises an anionic phospholipid selected from the group consisting of: DSPG and DPPG.

In some embodiments, the composition comprises an anionic phospholipid selected from the group consisting of: N-Glu-DSPE and N-Suc-DSPE.

In some embodiments, the composition comprises a DSPA anionic phospholipid.

In some embodiments, the composition comprises a Cardiolipin anionic phospholipid.

In some embodiments, the ionizable lipid has the chemical structure:

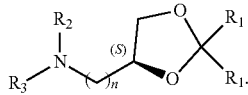

In some embodiments, the ionizable lipid has the chemical structure:

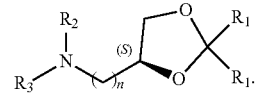

Aspects of the disclosure relates to a sodium or ammonia salt of a composition of an anionic phospholipid of Formula (V-A-1), having the chemical structure:

Formula (V-A-1)

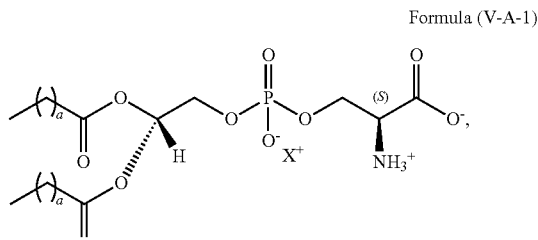

wherein $X^+$ is an ammonium cation or a sodium ($Na^+$) cation; and a is 14, 15 or 16.

In some embodiments, a is 14 or 16. In some embodiments, $X^+$ is ammonium cation ($NH_4^+$).

In some embodiments, $X^+$ is sodium cation ($Na^+$)

In some embodiments, X is an ammonium cation selected from the group consisting of: ammonium ($NH_4^+$), an alkylammonium, a dialkylammonium, and a trialkylammonium salt. In some embodiments, X is X is an ammonium cation selected from the group consisting of: ammonium, dimethylamine, diethylamine, triethylamine, trimethylamine, 2-(dimethyamino)ethanol, diethanolamine, 2-(diethyamino)ethanol, ethanolamine, ethylenediamine, N-methyl-glucamine, imidazole, histidine, lysine, arginine, 4-(2-hydroxyethyl)-morpholine, piperazine, 1-(2-hydroxyethyl)-pyrrolidine, triethanolamine, and tromethamine (tris(hydroxymethyl)aminomethane).

In some embodiments, the anionic phospholipid of Formula (V-A-1) is a sodium salt of distearoylphosphatidyl-L-serine (DSPS L-isomer). In some embodiments, the anionic phospholipid of Formula (V-A-1) is an ammonium salt of distearoylphosphatidyl-L-serine (DSPS L-isomer). In some embodiments, the anionic phospholipid of Formula (V-A-1) is a sodium salt of DPPS (L-isomer). In some embodiments, the anionic phospholipid of Formula (V-A-1) is an ammonium salt of DPPS (L-isomer). Some embodiments relate to the use of the salt form composition in the preparation of a liposomal nanoparticle (LNP) composition. In some embodiments, the use is in combination with one or more of the following LNP components during the preparation of the LNP composition: a mRNA nucleic acid; an ionizable cationic lipid (ICL); cholesterol; a (L-Serine) PS lipid; one or more phospholipids; and a conjugated lipid. In some embodiments, the use comprises the step of combining the ammonium or salt form of a compound of Formula (V-A-1) with one or more of the following LNP components during the preparation of the LNP composition: a mRNA nucleic acid; an ionizable cationic lipid (ICL); cholesterol; a (L-Serine) PS lipid; one or more phospholipids; and a conjugated lipid.

In some embodiments, the LNP is a nucleic acid lipid nanoparticle vaccine composition comprising: a mRNA nucleic acid with a N/P ratio of 4 to 7; an ionizable cationic lipid in a total amount of 40-65 mol % of the total lipid content of the LNP composition; cholesterol in a total amount of 25-40 mol % of the total lipid content of the LNP composition; a (L-Serine) PS lipid in a total amount of 2.5-10 mol % of the total lipid content of the LNP composition; DSPC phospholipid in a total amount of 5-25 mol % of the total lipid content of the LNP composition; and PEG-DMG in a total amount of 0-2.5 mol % of the total lipid content of the LNP composition.

In some embodiments, the nucleic acid is mRNA of SEQ ID NO: 2'.

In some embodiments, the LNP composition comprises the ionizable cationic lipid in a total amount of 46-65 mol % of the total lipid content of the LNP composition. In some embodiments, the LNP composition comprises the PS in a total amount of about 5 mol % of the total lipid in the composition. In some embodiments, the LNP composition comprises the conjugated lipid in a total amount of about 1.5 mol % of the total lipid content of the LNP composition.

In some embodiments, the conjugated lipid is PEG-DMG; and the PS lipid is selected from the group consisting of: DSPS (L-isomer) and DPPS.

In some embodiments, the ionizable cationic lipid is one or more compounds selected from the group consisting of: KC3-OA, KC3-PA, KC3-C17 (C8:1), and KC3-C15 (C8:1). In some embodiments, the ionizable cationic lipid is KC3-PA. In some embodiments, the ionizable cationic lipid is KC3-OA. In some embodiments, the ionizable cationic lipid is KC3-C17 (C8:1).

Some embodiments relate to the use of a (L-Serine) PS lipid in combination with an ionizable cationic lipid described herein in the LNP for targeting of the LNP to dendritic cells.

In some embodiments, the LNP comprises mRNA. In some embodiments, the LNP further comprises cholesterol. In some embodiments, the total amount of (L-Serine) PS lipid in the LNP is 2.5-10 mol % of the total lipid content of the LNP composition. In some embodiments, the LNP further comprises one or more additional phospholipids including DSPC. In some embodiments, the LNP further comprises a conjugated lipid.

In some embodiments, the LNP comprises: a mRNA nucleic acid with a N/P ratio of 3 to 8; a KC3-PA or KC3-C17 (C8:1) ionizable cationic lipid (ICL), in a total amount of 40-65 mol % of the total lipid content of the LNP composition; cholesterol in a total amount of 25-40 mol % of the total lipid content of the LNP composition; a (L-Serine) PS lipid in a total amount of 2.5-10 mol % of the total lipid content of the LNP composition; DSPC phospholipid in a total amount of 5-25 mol % of the total lipid content of the LNP composition; and a conjugated lipid in a total amount of 0-2.5 mol % of the total lipid content of the LNP composition.

In some embodiments, the ICL is KC3-PA. In some embodiments, the ICL is KC3-C17 (C8:1).

In some embodiments, the composition comprises an anionic phospholipid selected from the group consisting of: DSPG and DPPG, in a total amount of 2.5-7.5% of the total lipid content of the LNP composition. In some embodiments, the composition comprises DSPG anionic phospholipid in a total amount of 2.5-7.5% of the total lipid content of the LNP composition. In some embodiments, the composition comprises DPPG anionic phospholipid in a total amount of 2.5-7.5% of the total lipid content of the LNP composition.

In some embodiments, the LNP further comprises one or more additional phospholipids including DSPC.

Aspects of the disclosure relate to a nucleic acid lipid nanoparticle (LNP) composition comprising: a nucleic acid; a KC3 ionizable cationic lipid in a total amount of 40-65 mol % of the total lipid content of the LNP composition; cholesterol in a total amount of 23.5-43.5 mol % of the total lipid content of the LNP composition; a (L-Serine) PS lipid in a total amount of 2.5-10 mol % of the total lipid content of the LNP composition; DSPC or HSPC phospholipid in a total amount of 5-25 mol % of the total lipid content of the LNP composition; and a PEG-containing conjugated lipid in a total amount of 0.5 mol % to 2.5 mol % of the total lipid content of the LNP composition.

In some embodiments, the nucleic acid is mRNA. In some embodiments, the N/P ratio is 3 to 8.

In some embodiments, the KC3 ionizable cationic lipid is selected from the group consisting of: KC3-OA, KC3-PA, KC3-C17 (8:1), and KC3-C15 (C8:1). In some embodiments, the KC3 ionizable cationic lipid is KC3-OA. In some embodiments, the KC3 ionizable cationic lipid is KC3-PA. In some embodiments, the KC3 ionizable cationic lipid is KC3-C17(C8:1). In some embodiments, the KC3 ionizable cationic lipid is KC3-C15(C8:1).

In some embodiments, the conjugated lipid is PEG-DMG or PEG-DSG.

In some embodiments, the composition comprises the PEG-containing conjugated lipid in a total amount of 0.5-2.0 mol % of the total lipid content of the LNP composition.

In some embodiments, the composition comprises the KC3 ionizable cationic lipid in a total amount of 48 mol % of the total lipid content of the LNP composition.

In some embodiments, the composition comprises DSPC and DSPS in a total amount of 10 mol % of the total lipid content of the LNP composition.

In some embodiments, the composition comprises 5% DSPC or HSPC in a total amount of 5 mol % of the total lipid content of the LNP composition.

In some embodiments, the composition comprises PEG-DMG in a total of 1.5 mol % of the total lipid content of the LNP composition.

In some embodiments, the composition comprises cholesterol in a total amount of 40.5 mol % cholesterol of the total lipid content of the LNP composition.

In some embodiments, the composition comprises the DSPC phospholipid in a total amount of mol % of the total lipid content of the LNP composition.

In some embodiments, the PEG-containing conjugated lipid is $PEG_{2000}$-DMG.

In some embodiments, the composition comprises the cholesterol in a total amount of 23.5 mol % of the total lipid content of the LNP composition. In some embodiments, the composition comprises the cholesterol in a total amount of 33.5 mol % of the total lipid content of the LNP composition. In some embodiments, the composition comprises the cholesterol in a total amount of 38.5 mol % of the total lipid content of the LNP composition. In some embodiments, the composition comprises the cholesterol in a total amount of 40.5 mol % of the total lipid content of the LNP composition. In some embodiments, the composition comprises the cholesterol in a total amount of 42.7 mol % of the total lipid content of the LNP composition. b In some embodiments, the composition comprises the cholesterol in a total amount of 43.5 mol % of the total lipid content of the LNP composition. In some embodiments, the composition comprises the cholesterol in a total amount of 33.5-43.5 mol % of the total lipid content of the LNP composition. In some embodiments, the composition comprises the KC3 ionizable cationic lipid in a total amount of 45-55 mol % of the total lipid content of the LNP composition.

Aspects of the disclosure relate to a nucleic acid lipid nanoparticle (LNP) composition comprising: a mRNA nucleic acid; a KC3 ionizable cationic lipid selected from the group consisting of: KC3-OA, KC3-PA, KC3-C17 (8:1), and KC3-C15 (C8:1), in a total amount of 45-55 mol % of the total lipid content of the LNP composition; cholesterol in a total amount of 33.5-43.5 mol % of the total lipid content of the LNP composition; a (L-Serine) DPPS lipid in a total amount of 5 mol % of the total lipid content of the LNP composition; DSPC or HSPC phospholipid in a total amount of 5 mol % of the total lipid content of the LNP composition; and
 a PEG-DMG conjugated lipid in a total amount of 1.5 mol % of the total lipid content of the LNP composition.

Aspects of the disclosure relate to a lipid nanoparticle (LNP) composition comprising a KC3 ionizable cationic lipid, a (L-Serine) PS lipid, cholesterol, one or more phospholipids comprising at least one anionic phospholipid, and a conjugated lipid, wherein the LNP is obtained by a process comprising the step of dissolving a sodium or ammonium salt of the anionic phospholipid.

In some embodiments, the composition comprises a nucleic acid. In some embodiments, the nucleic acid is mRNA.

In some embodiments, the composition is a vaccine.

In some embodiments, the total amount of phospholipids in the composition is 5-25 mol % of the total lipid content of the LNP composition, and the total amount of the phosphatidylserine (PS) is 2.5-10 mol % of the total lipid content of the LNP composition; and the total amount of the conjugated lipid in the composition is a total amount of 0.5-2.5 mol % of the total lipid content of the LNP composition.

In some embodiments, the composition comprises 48 mol % of the KC3 ionizable cationic lipid, 40.5 mol % cholesterol, and 5 mol % (L-Serine) DPPS lipid, wherein each mol % refers to the mol % of the total lipid content of the LNP composition.

In some embodiments, the composition comprises 48 mol % of the KC3 ionizable cationic lipid, 38.5 mol % cholesterol, and 5 mol % (L-Serine) DPPS lipid, wherein each mol % refers to the mol % of the total lipid content of the LNP composition.

In some embodiments, the composition comprises 46-54 mol % of the KC3 ionizable cationic lipid, and 5 mol % (L-Serine) DPPS lipid, wherein each mol % refers to the mol % of the total lipid content of the LNP composition.

In some embodiments, the composition comprises 45 mol % of the KC3 ionizable cationic lipid, 42.7 mol % cholesterol, and 5 mol % (L-Serine) DPPS lipid, wherein each mol % refers to the mol % of the total lipid content of the LNP composition.

In some embodiments, the composition comprises 50 mol % of the KC3 ionizable cationic lipid, 38.5 mol % cholesterol, 5 mol % (L-Serine) DPPS lipid, and a total of 10 mol % phospholipid concentration; wherein each mol % refers to the mol % of the total lipid content of the LNP composition.

In some embodiments, the composition comprises 48 mol % of the KC3 ionizable cationic lipid, 40.5 mol % cholesterol, 5 mol % (L-Serine) DPPS lipid, and a total of 10 mol % phospholipid concentration; wherein each mol % refers to the mol % of the total lipid content of the LNP composition.

In some embodiments, the composition comprises 48 mol % of the KC3 ionizable cationic lipid, 40.5 mol % cholesterol, 5 mol % (L-Serine) DPPS lipid, 5 mol % DSPC or DPPC; and a total of 10 mol % phospholipid concentration; wherein each mol % refers to the mol % of the total lipid content of the LNP composition.

In some embodiments, the composition comprises 46.5 mol % of the KC3 ionizable cationic lipid, 42 mol % cholesterol, 5 mol % (L-Serine) DPPS lipid, wherein each mol % refers to the mol % of the total lipid content of the LNP composition.

In some embodiments, the composition further comprises a total of 5 mol % DSPC or HSPC of the total lipid content of the LNP composition.

In some embodiments, the composition further comprises a total of 1.5 mol % PEG-DMG of the total lipid content of the LNP composition.

In some embodiments, the composition comprises a total of 10 mol % of DSPC/DPPC phospholipid of the total lipid content of the LNP composition.

Aspects of the disclosure relate to a phosphatidylserine salt selected from the group consisting of DSPS sodium, DPPS sodium, DSPS ammonium and DPPS ammonium.

Aspects of the disclosure relate to the use of a DSPS-Na salt or a DPPS-NH$_4^+$ salt in the preparation of a LNP comprising a (L-Serine) PS lipid, a sterol, a conjugated lipid, a phospholipid for targeting the LNP to dendritic cells.

Aspects of the disclosure relate to a solution comprising ethanol and DSPS or DPPS, the solution obtained by a process comprising the step of dissolving a phosphatidylserine salt in ethanol, wherein the phosphatidylserine salt is selected from the group consisting of DSPS sodium, DPPS sodium, DSPS ammonium and DPPS ammonium.

EMBODIMENTS

Non-limiting embodiments are described below each or which is considered to be within the present disclosure.

Embodiment 1: A lipid nanoparticle (LNP) composition comprising an ionizable lipid having the chemical structure:

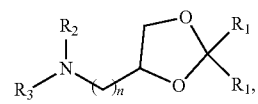

wherein $R_1$ is

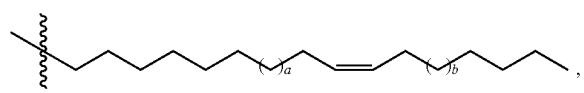

wherein a is 0 or 1; b is 1, 2, 3 or 4, provided the sum a+b is 1, 2, 3 or 4;
$R_2$ and $R_3$ are each independently ($C_1$-$C_4$) alkyl optionally substituted with hydroxyl; and
n is an integer equal to 2, 3 or 4.

Embodiment 2: The composition of embodiment 1, wherein n is 2 or 3.

Embodiment 3: The composition of any one of embodiments 1-2, wherein a is 0.

Embodiment 4: The composition of any one of embodiments 1-3, wherein b is 1, 2 or 3.

Embodiment 5: The composition of any one of embodiments 1-2, wherein a is 1.

Embodiment 6: The composition of any one of embodiments 1-3, wherein b is 1, 2 or 3.

Embodiment 7: The composition of any one of embodiments 1-6, wherein $R_2$ and $R_3$ are each methyl.

Embodiment 8: The composition of embodiment 1, wherein $R_1$ is

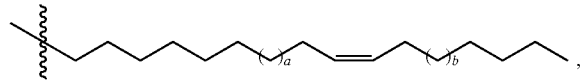

a is 0 or 1 and b is 1 or 3;
$R_2$ and $R_3$ are each methyl; and
n is 2 or 3.

Embodiment 9: The composition of any one of embodiments 1-8, wherein n is 3.

Embodiment 10: A composition of any one of embodiments 1-9, comprising:
a. a nucleic acid;
b. the ionizable lipid of any one of embodiments 1-9;
c. a sterol;
d. one or more phospholipids comprising a phosphatidylserine (PS) lipid; and
e. optionally further comprising a conjugated lipid.

Embodiment 11: The composition of embodiment 10, wherein the nucleic acid is mRNA.

Embodiment 12: The composition of embodiment 11, wherein the sterol is cholesterol.

Embodiment 13: The composition of embodiment 12, wherein the one or more phospholipids consist of:
a. one or more phospholipids selected from the group consisting of: SM, DSPC, HSPC, DPPC and DOPC; and
b. a PS lipid selected from the group consisting of: DPPS, and DSPS.

Embodiment 14: The composition of embodiment 13, wherein the one or more phospholipids consist of:
a. DSPC; and
b. one or more PS lipids selected from the group consisting of (L-Serine) DPPS and (L-Serine) DSPS.

Embodiment 15: The composition of embodiment 13, wherein the composition comprises the PS lipid in a total amount of 2.5-10 mol % of the total lipid in the composition.

Embodiment 16: The composition of any one of embodiments 10-15, wherein the conjugated lipid comprises PEG.

Embodiment 17: A nucleic acid lipid nanoparticle (LNP) composition comprising:
a. a nucleic acid;
b. an ionizable cationic lipid in a total amount of 40-65 mol % of the total lipid content of the LNP composition;
c. a sterol in a total amount of 25-45 mol % of the total lipid content of the LNP composition; and
d. one or more phospholipids in a total amount of phospholipids of 5-25 mol % of the total lipid content of the LNP composition, and comprising a phosphatidylserine (PS) in a total amount of 2.5-10 mol % of the total lipid content of the LNP composition; and
e. optionally further comprising a conjugated lipid in a total amount of 0.5-2.5 mol % of the total lipid content of the LNP composition.

Embodiment 18: The composition of embodiment 17, wherein the nucleic acid is mRNA.

Embodiment 19: The composition of embodiment 18, wherein the sterol is cholesterol.

Embodiment 20: The composition of embodiment 19, wherein the one or more phospholipids consists of: DSPC and a L-serine PS.

Embodiment 21: The composition of embodiment 20, wherein the composition comprises the PS in a total amount of 2.5-7.5 mol % of the total lipid in the composition.

Embodiment 22: The composition of any one of embodiments 17-21, wherein the conjugated lipid comprises PEG.

Embodiment 23: The composition of embodiment 22, wherein the conjugated lipid is PEG-DMG.

Embodiment 24: The composition of embodiment 23, wherein the LNP comprises the conjugated lipid in a total amount of 0.5-2.0 mol % of the total lipid content of the LNP composition.

Embodiment 25: The composition of embodiment 24, wherein the LNP comprises the conjugated lipid in a total amount of less than 2 mol % of the total lipid content of the LNP composition.

Embodiment 26: The composition of embodiment 17, wherein:
a. the nucleic acid is a mRNA,
b. the ionizable cationic lipid in a total amount of 45-55 mol % of the total lipid content of the LNP composition;
c. a sterol is cholesterol in a total amount of 35-45 mol % of the total lipid content of the LNP composition;
d. the total amount of phospholipid of 7-15 mol % of the total lipid content of the LNP composition;
e. the one or more phospholipids consist of DSPC and the PS lipid is one or more lipids selected from the group consisting of the L-serine configuration of DPPS and DSPS; and
f. the total amount of the PS lipid is about 5 mol % of the total lipid content of the LNP composition.

Embodiment 27: The composition of embodiment 26, wherein the composition comprises the PS lipid in a total amount selected from 1.25 mol %, 2.5 mol %, 5 mol %, 7.5 mol %, and 10 mol % of the total lipid content of the LNP composition.

Embodiment 28: A nucleic acid lipid nanoparticle (LNP) composition comprising:
a. a nucleic acid, wherein the nucleic acid is mRNA;
b. an ionizable cationic lipid, the ionizable cationic lipid in a total amount of 45-55 mol % of the total lipid content of the LNP composition;
c. a sterol, wherein the sterol is cholesterol in a total amount of 35-45 mol % of the total lipid content of the LNP composition;
d. one or more phospholipids, wherein the one or more phospholipids in a total amount of phospholipids of 10 mol % of the total lipid content of the LNP composition, and comprising a phosphatidylserine (PS) in a total amount of 3-9 mol % of the total lipid content of the LNP composition; and
e. a conjugated lipid, the conjugated lipid in a total amount of 0.5-2.0 mol % of the total lipid content of the LNP composition.

Embodiment 29: The composition of any one of embodiments 17-28, wherein the one or more phospholipid is selected from the group consisting of: DSPS (L-isomer), DPPS (L-isomer), DMPS (L-isomer), DOPS (L-isomer), and DSPS (D-isomer).

Embodiment 30: The composition of embodiment 29, wherein
a. the conjugated lipid is PEG-DMG; and
b. the PS lipid is selected from the group consisting of: DSPS (L-isomer) and DPPS.

Embodiment 31: The composition of any one of embodiments 17-28, wherein the ionizable cationic lipid is one or more compounds selected from the group consisting of: KC3-OA, KC3-PA, KC3-C17 (8:1), and KC3-C15 (C8:1).

Embodiment 32: The composition of any one of embodiments 17-28, wherein the ionizable cationic lipid is KC3-PA.

Embodiment 33: The composition of any one of embodiments 17-28, wherein the ionizable cationic lipid is KC3-OA.

Embodiment 34: The composition of any one of embodiments 17-28, wherein the ionizable cationic lipid is KC3-C17 (C8:1).

Embodiment 35: The nucleic acid lipid nanoparticle (LNP) composition of embodiment 17, comprising:
a. a nucleic acid;
b. an ionizable cationic lipid in a total amount of 50 mol % of the total lipid content of the LNP composition;
c. cholesterol in a total amount of 38.5 mol % of the total lipid content of the LNP composition;
d. one or more phospholipids in a total amount of 7-15 mol % of the total lipid content of the LNP composition, and comprising a phosphatidylserine (PS) lipid in a total amount of 3-9 mol % of the total lipid content of the LNP composition; and
e. a PEG-containing lipid in a total amount of 0.5-2.0 mol % of the total lipid content of the LNP composition.

Embodiment 36: The composition of embodiment 34, wherein the phospholipids consist of one or more phospholipids selected from the group consisting of: DSPC, DOPC, DPPC, HSPC, and SM.

Embodiment 37: The composition of embodiment 36, wherein the PS lipid is one or more L-serine lipids selected from the group consisting of DPPS and DSPS.

Embodiment 38: The composition of any one of embodiments 17-28, wherein the one or more phospholipids comprise at least two (L-Serine) PS lipids having mismatched acyl chain lengths.

Embodiment 39: The composition of embodiment 38, wherein the phospholipids are DSPC and DPPS.

Embodiment 40: The composition of embodiment 39, wherein the DSPC and DPPS are each present in the LNP at a total amount of 5 mol % each, based on the total lipid content of the LNP composition.

Embodiment 41: A nucleic acid lipid nanoparticle (LNP) composition comprising: a nucleic acid, ionizable cationic lipid KC3-PA or KC3-OA, and a (L-Serine) PS lipid in a total amount of 2.5-10 mol % of the total lipid content of the LNP composition.

Embodiment 42: The composition of embodiment 41, wherein the nucleic acid is mRNA, the PS lipid is (L-Serine) DSPS, (L-Serine) DPPS, or a mixture thereof, and the LNP composition further comprises cholesterol and a second phospholipid selected from the group consisting of: DSPC, DPPC, HSPC, and SM.

Embodiment 43: The composition of embodiment 42, wherein the LNP composition further comprises 0.5-2.0 mol % PEG-DMG or PEG-DSG, based on the total lipid content in the LNP composition.

Embodiment 44: The composition of any one of embodiments 41-43, wherein the ionizable cationic lipid is KC3-PA.

Embodiment 45: The composition of any one of embodiments 41-43, wherein the ionizable cationic lipid KC3-OA.

Embodiment 46: A nucleic acid lipid nanoparticle (LNP) composition comprising: a nucleic acid, a KC3-C17 (C8:1) ionizable cationic lipid; and a (L-Serine) PS lipid in a total amount of 2.5-10 mol % of the total lipid content of the LNP composition.

Embodiment 47: The composition of any one of embodiments 41-46, wherein the LNP composition has a N/P ratio 4 to 7.

Embodiment 48: The composition of embodiment 47, wherein the LNP composition has a N/P ratio of 5 to 6.

Embodiment 49: The composition of embodiment 48, wherein the LNP composition has a N/P ratio of 5.3.

Embodiment 50: A nucleic acid lipid nanoparticle (LNP) composition comprising: a nucleic acid, ionizable cationic lipid KC3-PA, and a (L-Serine) PS lipid in a total amount of 2.5-10 mol % of the total lipid content of the LNP composition.

Embodiment 51: The composition of embodiment 50, wherein the nucleic acid is mRNA, the PS lipid is (L-Serine) DSPS, (L-Serine) DPPS, or a mixture thereof, and the LNP composition further comprises cholesterol and a second phospholipid selected from the group consisting of: DSPC, DOPC, DPPC, HSPC, and SM.

Embodiment 52: The composition of embodiment 51, wherein the LNP composition further comprises 0.5-2.0 mol % PEG-DMG or PEG-DSG, based on the total lipid content in the LNP composition.

Embodiment 53: A nucleic acid lipid nanoparticle (LNP) composition comprising: a nucleic acid, an ionizable cationic lipid selected from KC3-C17 (C8:1); and a (L-Serine) PS lipid in a total amount of 2.5-10 mol % of the total lipid content of the LNP composition.

Embodiment 54: The composition of any one of embodiments 17-21, 26-28, 35-44, or 53, wherein the N/P ratio is 4 to 7.

Embodiment 55: The composition of embodiment 54, wherein the N/P ratio is 5 to 6.

Embodiment 56: The composition of embodiment 55, wherein the N/P ratio is 3.

Embodiment 57: The composition of embodiment 55, wherein the N/P ratio is 7.

Embodiment 58: The composition of any one of embodiments 17-21, 26-28, 35-47, or 53, wherein the nucleic acid is mRNA encoding SARS-CoV-2 spike protein.

Embodiment 59: A nucleic acid lipid nanoparticle (LNP) vaccine composition comprising:
a. a mRNA nucleic acid with a N/P ratio of 4 to 7;
b. an KC3-PA ionizable cationic lipid in a total amount of 40-65 mol % of the total lipid content of the LNP composition;
c. cholesterol in a total amount of 25-40 mol % of the total lipid content of the LNP composition;
d. a (L-Serine) PS lipid in a total amount of 2.5-10 mol % of the total lipid content of the LNP composition;
e. DSPC phospholipid in a total amount of 5-25 mol % of the total lipid content of the LNP composition; and
f. PEG-DMG in a total amount of 0-2.5 mol % of the total lipid content of the LNP composition.

Embodiment 60: A nucleic acid lipid nanoparticle (LNP) vaccine composition comprising:
a. a mRNA nucleic acid with a N/P ratio of 3 to 8;
b. a KC3-C17 (C8:1) ionizable cationic lipid in a total amount of 40-65 mol % of the total lipid content of the LNP composition;
c. cholesterol in a total amount of 25-40 mol % of the total lipid content of the LNP composition;
d. a (L-Serine) PS lipid in a total amount of 2.5-10 mol % of the total lipid content of the LNP composition;
e. DSPC phospholipid in a total amount of 5-25 mol % of the total lipid content of the LNP composition; and
f. PEG-DMG in a total amount of 0-2.5 mol % of the total lipid content of the LNP composition.

Embodiment 61: A nucleic acid lipid nanoparticle (LNP) vaccine composition comprising:
a. a mRNA nucleic acid with a N/P ratio of 4 to 7;
b. a KC3-C15 (C8:1) ionizable cationic lipid in a total amount of 40-65 mol % of the total lipid content of the LNP composition;
c. cholesterol in a total amount of 25-40 mol % of the total lipid content of the LNP composition;
d. a (L-Serine) PS lipid in a total amount of 2.5-10 mol % of the total lipid content of the LNP composition;
e. DSPC phospholipid in a total amount of 5-25 mol % of the total lipid content of the LNP composition; and
f. PEG-DMG in a total amount of 0-2.5 mol % of the total lipid content of the LNP composition.

Embodiment 62: A nucleic acid lipid nanoparticle (LNP) vaccine composition comprising:
a. a mRNA nucleic acid with a N/P ratio of 3 to 8;
b. a KC3-C18 ionizable cationic lipid in a total amount of 40-65 mol % of the total lipid content of the LNP composition;
c. cholesterol in a total amount of 25-40 mol % of the total lipid content of the LNP composition;
d. a (L-Serine) PS lipid in a total amount of 2.5-10 mol % of the total lipid content of the LNP composition;
e. DSPC phospholipid in a total amount of 5-25 mol % of the total lipid content of the LNP composition; and
f. PEG-DMG in a total amount of 0-2.5 mol % of the total lipid content of the LNP composition.

Embodiment 63: The composition of any one of embodiments 59-62, wherein the nucleic acid is a mRNA of SEQ ID NO: 2.

Embodiment 64: Use of a (L-Serine) PS lipid in combination with an ionizable cationic lipid of any one of embodiments 1-9 in the LNP for targeting of the LNP to dendritic cells.

Embodiment 65: The use of embodiment 64, wherein the LNP comprises mRNA.

Embodiment 66: The use of any one of embodiments 64-65, wherein the LNP further comprises cholesterol.

Embodiment 67: The use of embodiment 66, wherein the total amount of (L-Serine) PS lipid in the LNP is 2.5-10 mol % of the total lipid content of the LNP composition.

Embodiment 68: The use of embodiment 67, wherein the LNP further comprises one or more additional phospholipids including DSPC.

Embodiment 69: The use of embodiment 68, wherein the LNP further comprises a conjugated lipid.

Embodiment 70: The use of embodiment 64, wherein the LNP comprises:
a. a mRNA nucleic acid with a N/P ratio of 3 to 8;
b. a KC3-PA or KC3-C17 (C8:1) ionizable cationic lipid (ICL), in a total amount of 40-65 mol % of the total lipid content of the LNP composition;
c. cholesterol in a total amount of 25-40 mol % of the total lipid content of the LNP composition;
d. a (L-Serine) PS lipid in a total amount of 2.5-10 mol % of the total lipid content of the LNP composition;
e. DSPC phospholipid in a total amount of 5-25 mol % of the total lipid content of the LNP composition; and
f. a conjugated lipid in a total amount of 0-2.5 mol % of the total lipid content of the LNP composition.

Embodiment 71: The use of embodiment 70, wherein the ICL is KC3-PA.

Embodiment 72: The use of embodiment 70, wherein the ICL is KC3-C17 (C8:1).

Embodiment 73: A lipid nanoparticle (LNP) composition comprising an ionizable lipid having the chemical structure:

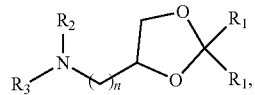

wherein $R_1$ is

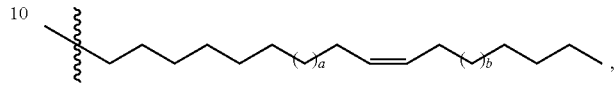

wherein a is 0 or 1; b is 1, 2, 3 or 4, provided the sum a+b is 1, 2, 3 or 4;
$R_2$ and $R_3$ are each independently methyl; and
n is an integer equal to 2 or 3.

Embodiment 74: The composition of embodiment 73, wherein a is 0.

Embodiment 75: The composition of embodiment 74, wherein b is 1.

Embodiment 76: The composition of embodiment 74, wherein b is 3.

Embodiment 77: The composition of embodiment 73, wherein a is 1.

Embodiment 78: The composition of embodiment 77, wherein b is 1.

Embodiment 79: The composition of embodiment 77, wherein b is 3.

Embodiment 80: The composition of any one of embodiments 73-79, wherein n is 2.

Embodiment 81: The composition of any one of embodiments 73-79, wherein n is 3.

Embodiment 82: The composition of any one of embodiments 17-28, wherein the composition comprises an anionic lipid selected from the group consisting of: phosphatidylglycerol (PG), phosphatidic acid (PA), N-glutaryl-phosphatidylethanolamine (N-Glu-PE), N-succinyl-phosphatidylethanolamine (N-Suc-PE), and cardiolipin. Distearoylphosphatidylglycerol (DSPG), dipalmitoyphosphatidylglycerol (DPPG), N-succinyl-distearoylphosphatidylethanolamine (N-Suc-DSPE), N-glutaryl-distearoylphosphatidylethanolamine (N-glu-DSPE), distearoylphosphatidic acid (DSPA), and cardiolipin.

Embodiment 83: The composition of any one of embodiments 17-28 or 82, wherein the composition comprises an anionic targeting phospholipid other than phosphatidyl-L-serine.

Embodiment 84: The composition of any one of embodiments 17-28 or 82-83, wherein the composition comprises an anionic phospholipid selected from the group consisting of: DSPG and DPPG.

Embodiment 85: The composition of any one of embodiments 17-28 or 82-83, wherein the composition comprises an anionic phospholipid selected from the group consisting of: N-Glu-DSPE and N-Suc-DSPE.

Embodiment 86: The composition of any one of embodiments 17-28 or 82-83, wherein the composition comprises a DSPA anionic phospholipid.

Embodiment 87: The composition of any one of embodiments 17-28 or 82-83, wherein the composition comprises a Cardiolipin anionic phospholipid.

Embodiment 88: The composition of any one of embodiments 1-63 or 73-87, wherein the ionizable lipid has the chemical structure:

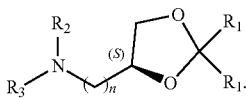

Embodiment 89: The use of any one of embodiments 64-72, wherein the ionizable lipid has the chemical structure:

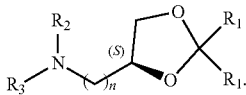

Embodiment 90: A sodium or ammonia salt of a composition of an anionic phospholipid of Formula (V-A-1), having the chemical structure:

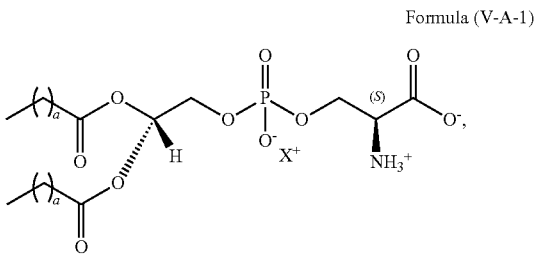

Formula (V-A-1)

wherein
$X^+$ is an ammonium cation or a sodium ($Na^+$) cation; and
a is 14, 15 or 16.

Embodiment 91: The composition of embodiment 90, wherein a is 14 or 16.

Embodiment 92: The composition of any one of embodiments 90 or 91, wherein $X^+$ is ammonium cation ($NH_4^+$).

Embodiment 93: The composition of any one of embodiments 90 or 91, wherein $X^+$ is sodium cation ($Na^+$).

Embodiment 94: The composition of any one of embodiments 90-93, wherein the anionic phospholipid of Formula (V-A-1) is a sodium salt of distearoylphosphatidyl-L-serine (DSPS L-isomer).

Embodiment 95: The composition of any one of embodiments 90-93, wherein the anionic phospholipid of Formula (V-A-1) is an ammonium salt of distearoylphosphatidyl-L-serine (DSPS L-isomer).

Embodiment 96: The composition of any one of embodiments 90-93, wherein the anionic phospholipid of Formula (V-A-1) is a sodium salt of DPPS (L-isomer).

Embodiment 97: The composition of any one of embodiments 90-93, wherein the anionic phospholipid of Formula (V-A-1) is a ammonium salt of DPPS (L-isomer).

Embodiment 98: Use of the salt form composition of any one of embodiments 90-97 in the preparation of a liposomal nanoparticle (LNP) composition.

Embodiment 99: The use of embodiment 98, in combination with one or more of the following LNP components during the preparation of the LNP composition:
a mRNA nucleic acid;
an ionizable cationic lipid (ICL);
cholesterol;
a (L-Serine) PS lipid;
one or more phospholipids; and
a conjugated lipid.

Embodiment 100: The use of embodiment 98, comprising the step of combining the ammonium or salt form of a compound of Formula (V-A-1) with one or more of the following LNP components during the preparation of the LNP composition:
a mRNA nucleic acid;
an ionizable cationic lipid (ICL) of any one of embodiments 1-9 or 73-88;
cholesterol;
a (L-Serine) PS lipid;
one or more phospholipids; and
a conjugated lipid.

Embodiment 101: The use of any one of embodiments 98-100, wherein the LNP is a nucleic acid lipid nanoparticle vaccine composition comprising:
a. a mRNA nucleic acid with a N/P ratio of 4 to 7;
b. an ionizable cationic lipid of any one of embodiments 1-9 or 73-88 in a total amount of 40-65 mol % of the total lipid content of the LNP composition;
c. cholesterol in a total amount of 25-40 mol % of the total lipid content of the LNP composition;
d. a (L-Serine) PS lipid in a total amount of 2.5-10 mol % of the total lipid content of the LNP composition;
e. DSPC phospholipid in a total amount of 5-25 mol % of the total lipid content of the LNP composition; and
f. PEG-DMG in a total amount of 0-2.5 mol % of the total lipid content of the LNP composition.

Embodiment 102: The use of embodiment 101, wherein the nucleic acid is mRNA of SEQ ID NO: 2.

Embodiment 103: The composition of any one of embodiments 17-63, or 73-89, wherein LNP composition comprises the ionizable cationic lipid in a total amount of 46-65 mol % of the total lipid content of the LNP composition.

Embodiment 104: The composition of any one of embodiments 17-63, 73-89, or 103, wherein the LNP composition comprises the PS in a total amount of about 5 mol % of the total lipid in the composition.

Embodiment 105: The composition of any one of embodiments 17-63, 73-89 or 103-104, wherein the LNP composition comprises the conjugated lipid in a total amount of about 1.5 mol % of the total lipid content of the LNP composition.

Embodiment 106: The composition of any one of embodiments 82-87, wherein
the conjugated lipid is PEG-DMG; and
the PS lipid is selected from the group consisting of: DSPS (L-isomer) and DPPS.

Embodiment 107: The composition of any one of embodiments 82-87, wherein the ionizable cationic lipid is one or more compounds selected from the group consisting of: KC3-OA, KC3-PA, KC3-C17 (C8:1), and KC3-C15 (C8:1).

Embodiment 108: The composition of any one of embodiments 82-87, wherein the ionizable cationic lipid is KC3-PA.

Embodiment 109: The composition of any one of embodiments 82-87, wherein the ionizable cationic lipid is KC3-OA.

Embodiment 110: The composition of any one of embodiments 82-87, wherein the ionizable cationic lipid is KC3-C17 (C8:1).

Embodiment 111: Use of a (L-Serine) PS lipid in combination with an ionizable cationic lipid of any one of embodiments 73-87 in the LNP for targeting of the LNP to dendritic cells.

Embodiment 112: The use of embodiment 111, wherein the LNP comprises mRNA.

Embodiment 113: The use of any one of embodiments 111-112, wherein the LNP further comprises cholesterol.

Embodiment 114: The use of embodiment 113, wherein the total amount of (L-Serine) PS lipid in the LNP is 2.5-10 mol % of the total lipid content of the LNP composition.

Embodiment 115: The use of embodiment 114, wherein the LNP further comprises one or more additional phospholipids including DSPC.

Embodiment 116: The use of embodiment 115, wherein the LNP further comprises a conjugated lipid.

Embodiment 117: The use of embodiment 111, wherein the LNP comprises:
  a. a mRNA nucleic acid with a N/P ratio of 3 to 8;
  b. a KC3-PA or KC3-C17 (C8:1) ionizable cationic lipid (ICL), in a total amount of 40-65 mol % of the total lipid content of the LNP composition;
  c. cholesterol in a total amount of 25-40 mol % of the total lipid content of the LNP composition;
  d. a (L-Serine) PS lipid in a total amount of 2.5-10 mol % of the total lipid content of the LNP composition;
  e. DSPC phospholipid in a total amount of 5-25 mol % of the total lipid content of the LNP composition; and
  f. a conjugated lipid in a total amount of 0-2.5 mol % of the total lipid content of the LNP composition.

Embodiment 118: The use of embodiment 117, wherein the ICL is KC3-PA.

Embodiment 119: The use of embodiment 117, wherein the ICL is KC3-C17 (C8:1).

Embodiment 120: The composition of any one of embodiments 90-97, wherein X is an ammonium cation selected from the group consisting of: ammonium ($NH_4^+$), an alkylammonium, a dialkylammonium, and a trialkylammonium salt.

Embodiment 121: The composition of embodiment 120, wherein X is X is an ammonium cation selected from the group consisting of: ammonium, dimethylamine, diethylamine, triethylamine, trimethylamine, 2-(dimethyamino)ethanol, diethanolamine, 2-(diethyamino)ethanol, ethanolamine, ethylenediamine, N-methyl-glucamine, imidazole, histidine, lysine, arginine, 4-(2-hydroxyethyl)-morpholine, piperazine, 1-(2-hydroxyethyl)-pyrrolidine, triethanolamine, and tromethamine (tris(hydroxymethyl)aminomethane).

Embodiment 122: The composition of any one of embodiments 17-28 or 82-83, wherein the composition comprises an anionic phospholipid selected from the group consisting of: DSPG and DPPG, in a total amount of 2.5-7.5% of the total lipid content of the LNP composition.

Embodiment 123: The composition of embodiment 122, wherein the composition comprises DSPG anionic phospholipid in a total amount of 2.5-7.5% of the total lipid content of the LNP composition.

Embodiment 124: The composition of embodiment 122, wherein the composition comprises DPPG anionic phospholipid in a total amount of 2.5-7.5% of the total lipid content of the LNP composition.

Embodiment 125: The use of embodiment 114, wherein the LNP further comprises one or more additional phospholipids including DSPC.

Embodiment 126: A nucleic acid lipid nanoparticle (LNP) composition comprising:
  a. a nucleic acid;
  b. a KC3 ionizable cationic lipid in a total amount of 40-65 mol % of the total lipid content of the LNP composition;
  c. cholesterol in a total amount of 23.5-43.5 mol % of the total lipid content of the LNP composition;
  d. a (L-Serine) PS lipid in a total amount of 2.5-10 mol % of the total lipid content of the LNP composition;
  e. DSPC or HSPC phospholipid in a total amount of 5-25 mol % of the total lipid content of the LNP composition; and
  f. a PEG-containing conjugated lipid in a total amount of 0.5 mol % to 2.5 mol % of the total lipid content of the LNP composition.

Embodiment 127: The composition of embodiment 126, wherein the nucleic acid is mRNA.

Embodiment 128: The composition of any one of v 126-127, wherein the N/P ratio is 3 to 8.

Embodiment 129: The composition of any one of embodiments 126-127, wherein the KC3 ionizable cationic lipid is selected from the group consisting of: KC3-OA, KC3-PA, KC3-C17 (8:1), and KC3-C15 (C8:1).

Embodiment 130: The composition of embodiment 129, wherein the KC3 ionizable cationic lipid is KC3-OA.

Embodiment 131: The composition of embodiment 129, wherein the KC3 ionizable cationic lipid is KC3-PA.

Embodiment 132: The composition of embodiment 129, wherein the KC3 ionizable cationic lipid is KC3-C17(C8:1).

Embodiment 133: The composition of embodiment 129, wherein the KC3 ionizable cationic lipid is KC3-C15(C8:1).

Embodiment 134: The composition of any one of embodiments 126-133, wherein the conjugated lipid is PEG-DMG or PEG-DSG.

Embodiment 135: The composition of embodiment 134, wherein the composition comprises the PEG-containing conjugated lipid in a total amount of 0.5-2.0 mol % of the total lipid content of the LNP composition.

Embodiment 136: The composition of any one of embodiments 126-135, wherein the composition comprises the KC3 ionizable cationic lipid in a total amount of 48 mol % of the total lipid content of the LNP composition.

Embodiment 137: The composition of any one of embodiments 126-136, wherein the composition comprises DSPC and DSPS in a total amount of 10 mol % of the total lipid content of the LNP composition.

Embodiment 138: The composition of any one of embodiments 126-137, wherein the composition comprises 5% DSPC or HSPC in a total amount of 5 mol % of the total lipid content of the LNP composition.

Embodiment 139: The composition of any one of embodiments 126-137, wherein the composition comprises PEG-DMG in a total of 1.5 mol % of the total lipid content of the LNP composition.

Embodiment 140: The composition of any one of embodiments 126-137, wherein the composition comprises cholesterol in a total amount of 40.5 mol % cholesterol of the total lipid content of the LNP composition.

Embodiment 141: The composition of any one of embodiments 126-137, wherein the composition comprises the DSPC phospholipid in a total amount of 10 mol % of the total lipid content of the LNP composition.

Embodiment 142: The composition of any one of embodiments 126-141 wherein the PEG-containing conjugated lipid is $PEG_{2000}$-DMG.

Embodiment 143: The composition of any one of embodiments 126-139, wherein the composition comprises the cholesterol in a total amount of 23.5 mol % of the total lipid content of the LNP composition.

Embodiment 144: The composition of any one of embodiments 126-139, wherein the composition comprises the cholesterol in a total amount of 33.5 mol % of the total lipid content of the LNP composition.

Embodiment 145: The composition of any one of embodiments 126-139, wherein the composition comprises the cholesterol in a total amount of 38.5 mol % of the total lipid content of the LNP composition.

Embodiment 146: The composition of any one of embodiments 126-139, wherein the composition comprises the cholesterol in a total amount of 40.5 mol % of the total lipid content of the LNP composition.

Embodiment 147: The composition of any one of embodiments 126-139, wherein the composition comprises the cholesterol in a total amount of 42.7 mol % of the total lipid content of the LNP composition.

Embodiment 148: The composition of any one of embodiments 126-139, wherein the composition comprises the cholesterol in a total amount of 43.5 mol % of the total lipid content of the LNP composition.

Embodiment 149: The composition of any one of embodiments 126-139, wherein the composition comprises the cholesterol in a total amount of 33.5-43.5 mol % of the total lipid content of the LNP composition.

Embodiment 150: The composition of any one of embodiments 126-149, wherein the composition comprises the KC3 ionizable cationic lipid in a total amount of 45-55 mol % of the total lipid content of the LNP composition.

Embodiment 151: A nucleic acid lipid nanoparticle (LNP) composition comprising:
a. a mRNA nucleic acid;
b. a KC3 ionizable cationic lipid selected from the group consisting of: KC3-OA, KC3-PA, KC3-C17 (8:1), and KC3-C15 (C8:1), in a total amount of 45-55 mol % of the total lipid content of the LNP composition;
c. cholesterol in a total amount of 33.5-43.5 mol % of the total lipid content of the LNP composition;
d. a (L-Serine) DPPS lipid in a total amount of 5 mol % of the total lipid content of the LNP composition;
e. DSPC or HSPC phospholipid in a total amount of 5 mol % of the total lipid content of the LNP composition; and
f. a PEG-DMG conjugated lipid in a total amount of 1.5 mol % of the total lipid content of the LNP composition.

Embodiment 152: A lipid nanoparticle (LNP) composition comprising a KC3 ionizable cationic lipid, a (L-Serine) PS lipid, cholesterol, one or more phospholipids comprising at least one anionic phospholipid, and a conjugated lipid, wherein the LNP is obtained by a process comprising the step of dissolving a sodium or ammonium salt of the anionic phospholipid.

Embodiment 153: The composition of embodiment 152, wherein the anionic phospholipid is the salt of any one of embodiments 90-97.

Embodiment 154: The composition of any one of embodiments 152-153, wherein the composition comprises a nucleic acid.

Embodiment 155: The composition of embodiment 154, wherein the nucleic acid is mRNA.

Embodiment 156: The composition of embodiment 155, wherein the composition is a vaccine.

Embodiment 157: The composition of any one of embodiments 152-156, wherein the total amount of phospholipids in the composition is 5-25 mol % of the total lipid content of the LNP composition, and the total amount of the phosphatidylserine (PS) is 2.5-10 mol % of the total lipid content of the LNP composition; and the total amount of the conjugated lipid in the composition is a total amount of 0.5-2.5 mol % of the total lipid content of the LNP composition.

Embodiment 158: The composition of any one of embodiments 152-156, wherein the composition comprises
48 mol % of the KC3 ionizable cationic lipid,
40.5 mol % cholesterol, and
5 mol % (L-Serine) DPPS lipid,
wherein each mol % refers to the mol % of the total lipid content of the LNP composition.

Embodiment 159: The composition of any one of embodiments 152-156, wherein the composition comprises
48 mol % of the KC3 ionizable cationic lipid,
38.5 mol % cholesterol, and
5 mol % (L-Serine) DPPS lipid,
wherein each mol % refers to the mol % of the total lipid content of the LNP composition.

Embodiment 160: The composition of any one of embodiments 152-156, wherein the composition comprises
46-54 mol % of the KC3 ionizable cationic lipid, and
5 mol % (L-Serine) DPPS lipid,
wherein each mol % refers to the mol % of the total lipid content of the LNP composition.

Embodiment 161: The composition of any one of embodiments 152-156, wherein the composition comprises
45 mol % of the KC3 ionizable cationic lipid,
42.7 mol % cholesterol, and
5 mol % (L-Serine) DPPS lipid,
wherein each mol % refers to the mol % of the total lipid content of the LNP composition.

Embodiment 162: The composition of any one of embodiments 152-156, wherein the composition comprises
50 mol % of the KC3 ionizable cationic lipid,
38.5 mol % cholesterol,
5 mol % (L-Serine) DPPS lipid, and
a total of 10 mol % phospholipid concentration;
wherein each mol % refers to the mol % of the total lipid content of the LNP composition.

Embodiment 163: The composition of any one of embodiments 152-156, wherein the composition comprises
48 mol % of the KC3 ionizable cationic lipid,
40.5 mol % cholesterol,
5 mol % (L-Serine) DPPS lipid, and
a total of 10 mol % phospholipid concentration;
wherein each mol % refers to the mol % of the total lipid content of the LNP composition.

Embodiment 164: The composition of any one of embodiments 152-156, wherein the composition comprises
48 mol % of the KC3 ionizable cationic lipid,
40.5 mol % cholesterol,
5 mol % (L-Serine) DPPS lipid,
5 mol % DSPC or DPPC; and
a total of 10 mol % phospholipid concentration;
wherein each mol % refers to the mol % of the total lipid content of the LNP composition.

Embodiment 165: The composition of any one of embodiments 152-156, wherein the composition comprises
46.5 mol % of the KC3 ionizable cationic lipid,
42 mol % cholesterol,
5 mol % (L-Serine) DPPS lipid,
wherein each mol % refers to the mol % of the total lipid content of the LNP composition.

Embodiment 166: The composition of any one of embodiments 158-165, wherein the composition further comprises a total of 5 mol % DSPC or HSPC of the total lipid content of the LNP composition.

Embodiment 167: The composition of any one of embodiments 158-166, wherein the composition further comprises a total of 1.5 mol % PEG-DMG of the total lipid content of the LNP composition.

Embodiment 168: The composition of any one of embodiments 158-163, wherein the composition comprises a total of 10 mol % of DSPC/DPPC phospholipid of the total lipid content of the LNP composition.

Embodiment 169: A phosphatidylserine salt selected from the group consisting of DSPS sodium, DPPS sodium, DSPS ammonium and DPPS ammonium.

Embodiment 170: Use of a DSPS-Na salt or a DPPS-NH$_4^+$ salt in the preparation of a LNP comprising a (L-Serine) PS lipid, a sterol, a conjugated lipid, a phospholipid for targeting the LNP to dendritic cells.

Embodiment 171: A solution comprising ethanol and DSPS or DPPS, the solution obtained by a process comprising the step of dissolving a phosphatidylserine salt in ethanol, wherein the phosphatidylserine salt is selected from the group consisting of DSPS sodium, DPPS sodium, DSPS ammonium and DPPS ammonium.

disclosure includes any combination of the features, terms, or elements of the various illustrative components and examples.

Unless explicitly indicated otherwise, the isomer form of the phosphatidylserine lipids used in the Examples is phosphatidyl-L-serine.

Certain examples are provided below to illustrate various embodiments of the embodiments disclosed herein. One of ordinary skill in the art will recognize that the various embodiments disclosed herein are not limited to these specific illustrative examples.

Example 1A: Synthesis of Ionizable Lipids

Scheme 1 Synthesis of acid intermediate for AKG-UO-1 to AKG-UO-3. See FIGs. 47A-47B.

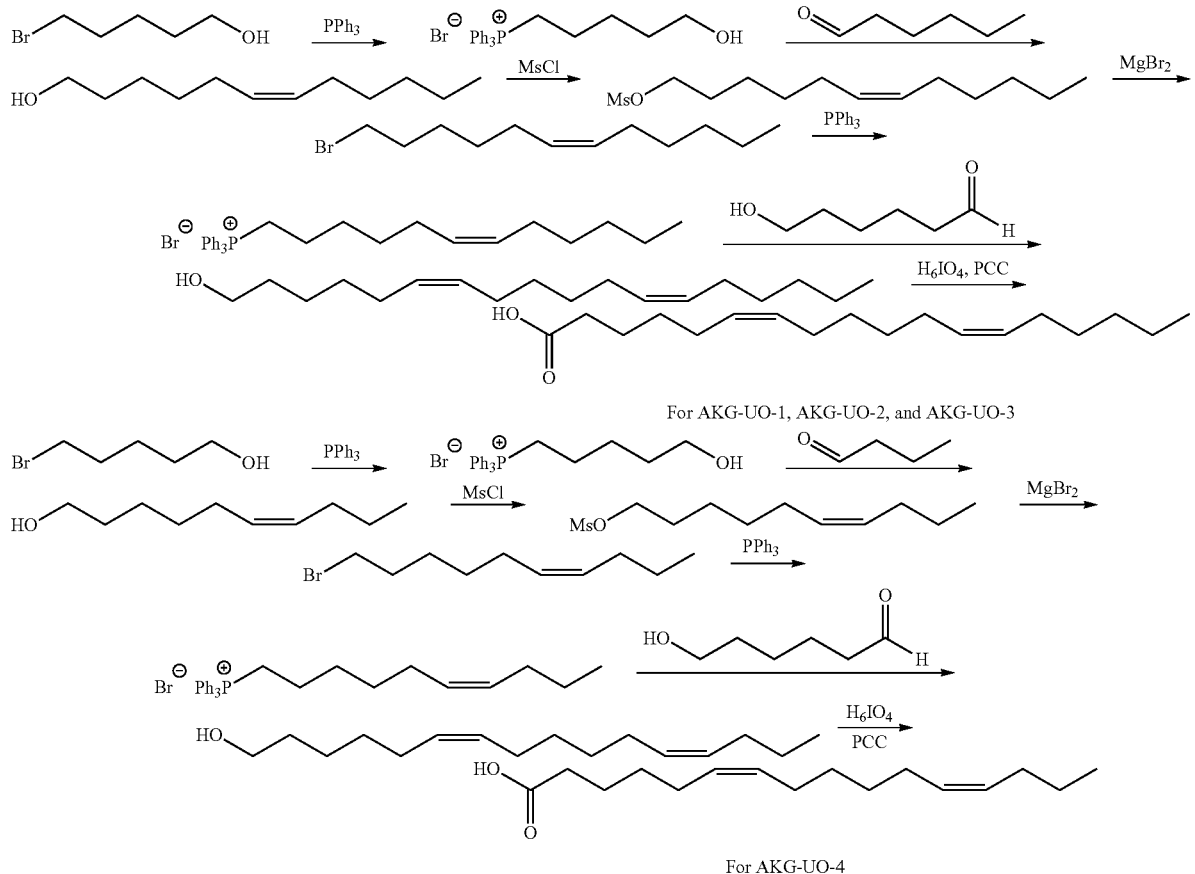

For AKG-UO-1, AKG-UO-2, and AKG-UO-3

For AKG-UO-4

Examples

While this disclosure has been described in relation to certain embodiments, and many details have been set forth for purposes of illustration, it will be apparent to those skilled in the art that this disclosure includes additional embodiments, and that some of the details described herein may be varied considerably without departing from this disclosure. This disclosure includes such additional embodiments, modifications and equivalents. In particular, this The acid intermediates (6Z,12Z)-6,12-octadecadienoic acid and (6Z,12Z)-6,12-hexadecadienoic acid were prepared by a general synthesis, shown in Scheme 1, involving i) an initial Witting reaction of triphenyl phosphonium ylide, prepared from 5-bromo pentanol, and the corresponding aldehyde, ii) conversion of the terminal alcohol to bromide by mesylation and substitution, iii) repeating the sequence of ylide synthesis and Witting reaction, and finally iv) periodic acid oxidation of the terminal alcohol. The resulting acid intermediates were utilized in the synthesis of AKG-UO-1 to AKG-UO-4, vide infra.

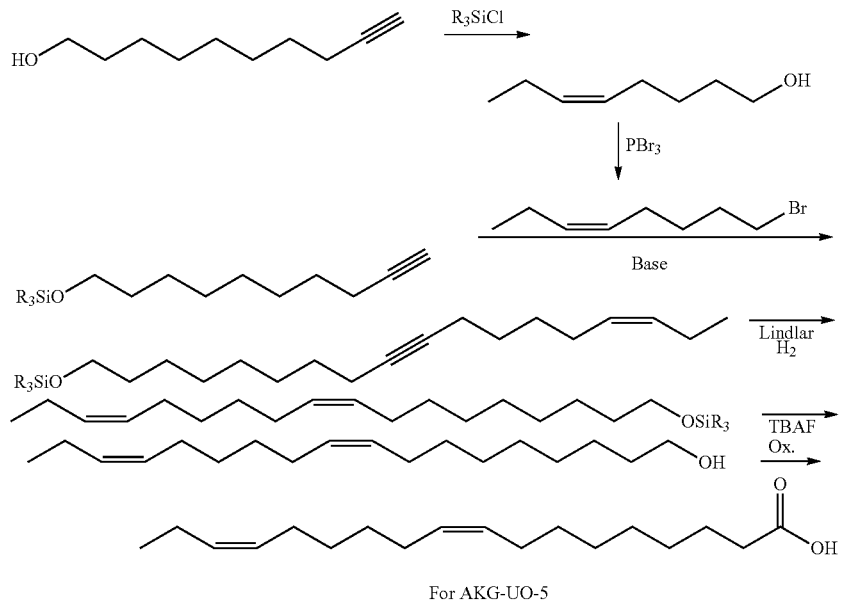

Scheme 2 Synthesis of acid intermediate for AKG-UO-5

The acid intermediate (9Z,15Z)-9,15-octadecadienoic acid used in the synthesis of AKG-UO-5 was prepared by a general synthesis shown in Scheme 2, involving i) alkylation of silyl protected 10-hydroxy-1-decyne with (5Z)-1-bromo-5-octene, ii) catalytic hydrogenation of the alkyne to a cis-alkene, iii) removal of silyl protection on the alcohol, and finally iv) oxidation of the terminal alcohol to the desired acid.

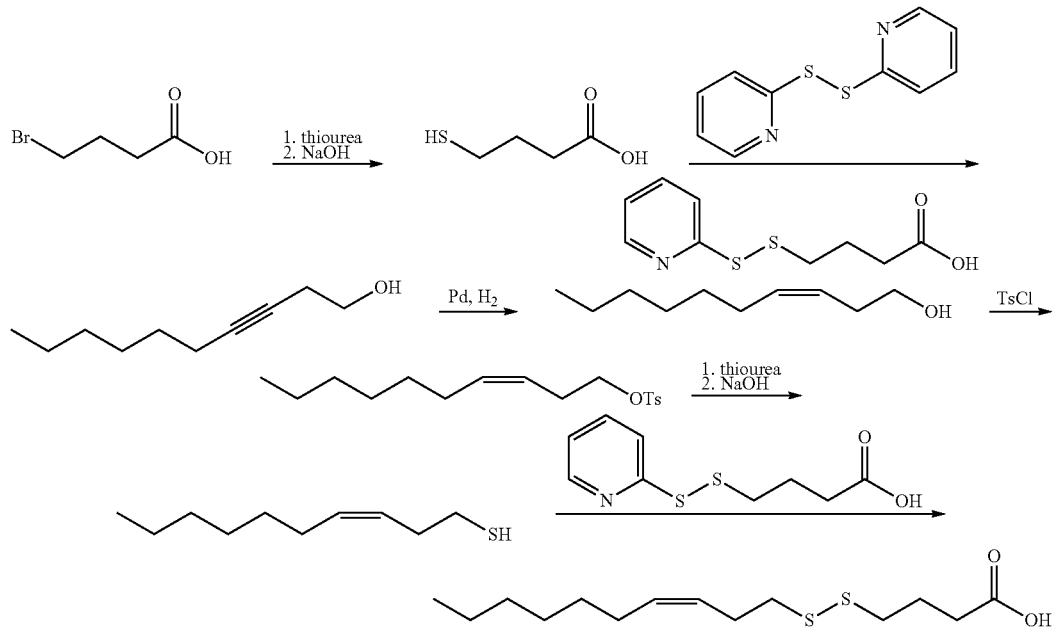

Scheme 3 Synthesis of acid intermediates for AKG-BDG-01 and AKG-BDG-02

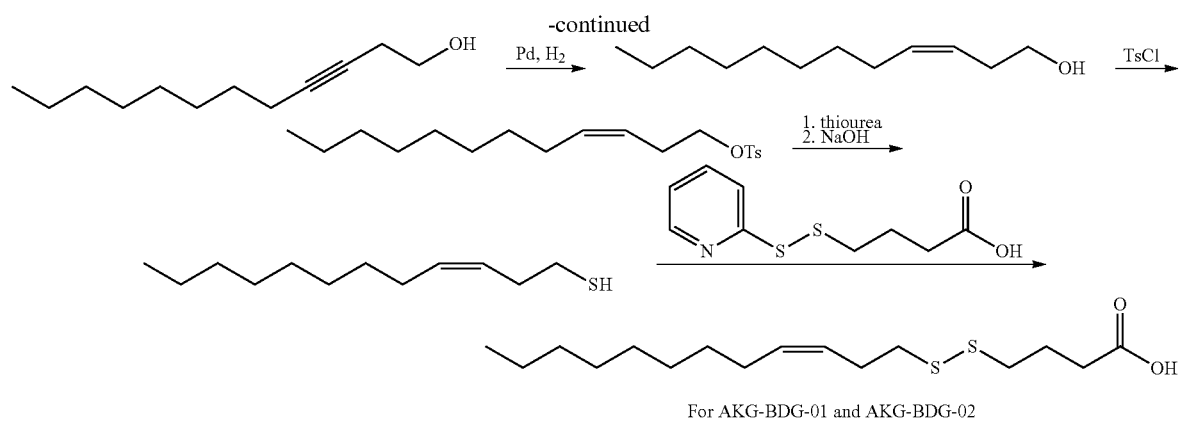

For AKG-BDG-01 and AKG-BDG-02

Synthesis of two disulfide acid intermediates used in the synthesis of AKG-BDG-1 and AKG-BDG-2 is shown in Scheme 4.

A general synthesis of acid intermediate for AKG-BDG-1 involves i) synthesis of 4-mercapto butyric acid from 4-bromo butyric acid, ii) reaction of 4-mercapto butyric acid with DPS resulting in 4-(2-pyridinyldisulfanyl)butanoic acid iii) catalytic hydrogenation of 3-decyn-1-ol to a cis-alkene, iv) tosylation of the primary alcohol, v) displacement of the tosyl group using thiourea resulting in a terminal thiol, and finally vi) coupling of the terminal thiol with 4-(2-pyridinyldisulfanyl)butanoic acid prepared in step ii above, resulting in the disulfide containing acid intermediate. Following a similar synthetic sequence starting from 3-dodecyn-1-ol yielded the second acid intermediate used in the synthesis of AKG-BDG-2.

Scheme 4 Synthesis of AKG-UO-1, AKG-UO-4, AKG-UO-5, AKG-BDG-1 and AKG-BDG-2

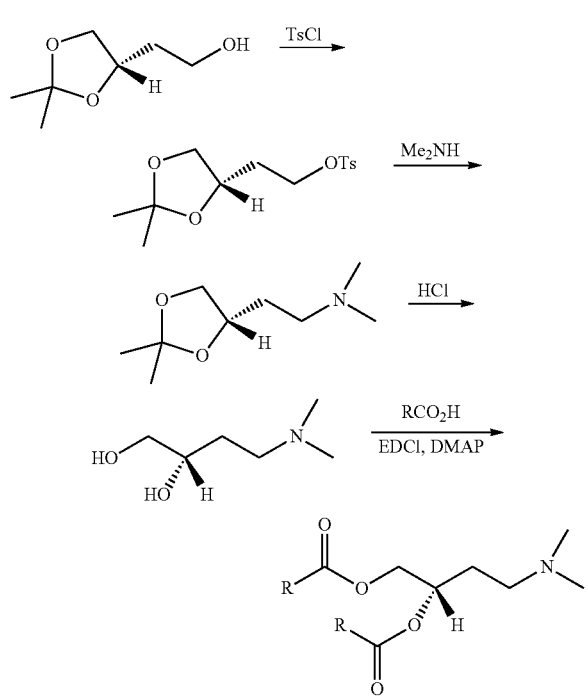

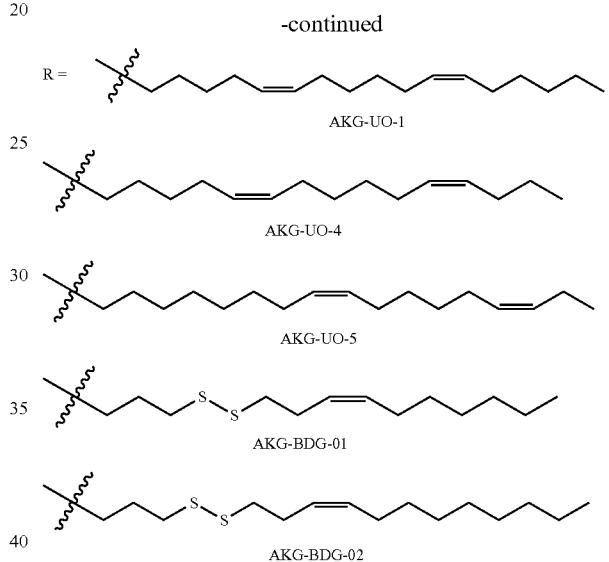

A general synthesis of lipids AKG-UO-1, AKG-UO-4, AKG-UO-5, AKG-BDG-1 and AKG-BDG-2 shown in Scheme 4, involves the following steps: i) tosylation of the primary alcohol of the commercially available chiral dioxolane ii) displacement of the tosyl group using dimethylamine resulting in a tertiary amine, iii) acid catalyzed deprotection of the diol, and finally iv) esterification of the diol with the corresponding acid intermediates synthesized according to Schemes 1-3. AKG-UO-2 is prepared following a similar synthetic sequence starting from a different dioxolane and a corresponding acid intermediate, as shown in Scheme 5 below.

Scheme 5 Synthesis of AKG-UO-2

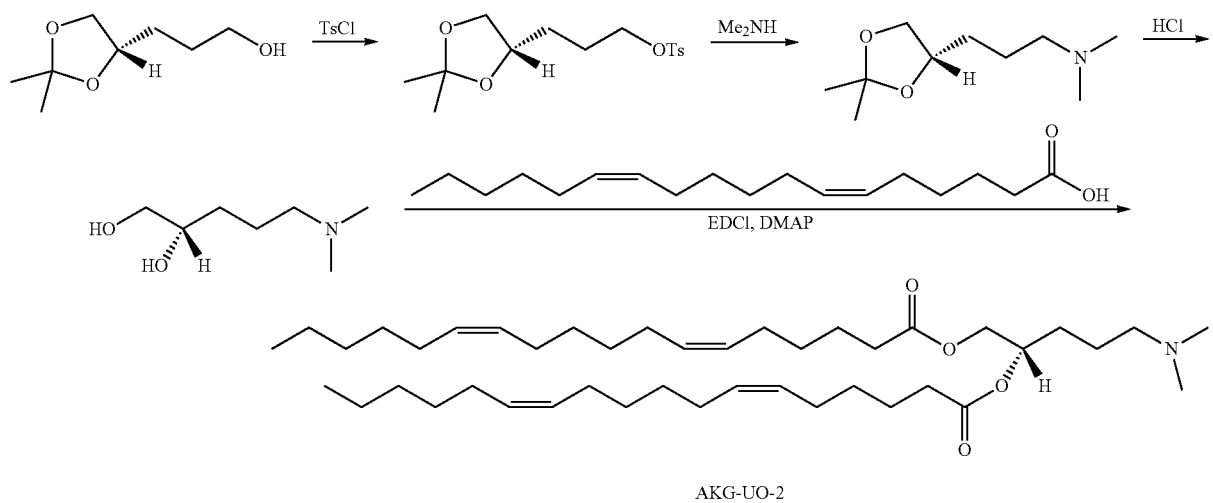

A general synthesis of trialkyl phosphate containing lipid AKG-UO-3 shown in Scheme 6, involves the following steps: i) reaction of primary alcohol of a commercially available chiral dioxolane with methyl dichlorophosphite resulting in the corresponding dialkyl chlorophosphite ii) displacement of the chloride in dialkyl chlorophosphite by treating it with 3-bromo propanol, resulting in the corresponding trialkyl phosphite iii) acid catalyzed deprotection of the diol iv) esterification of the diol with the corresponding acid intermediate synthesized according to Scheme 1, and finally v) displacement of the bromide group using dimethylamine resulting in a tertiary amine.

Scheme 6 Synthesis of AKG-UO-3

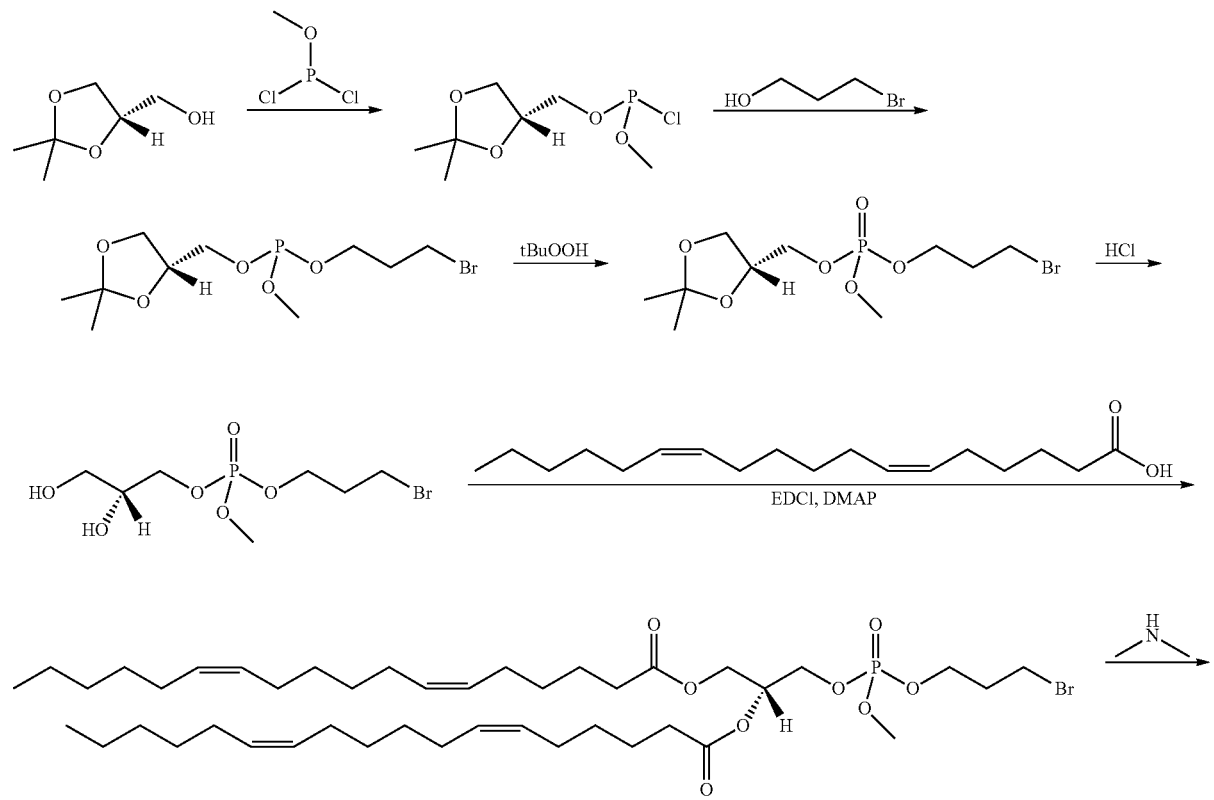

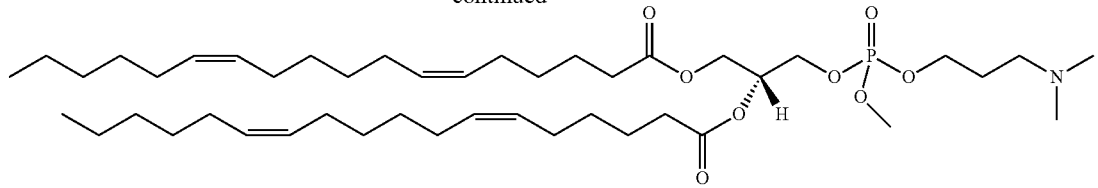

AKG-UO-3

Alternatively, acid intermediates having two methylene groups between double bond positions in the hydrocarbon chain are synthesized as described in Caballeira et al., Chem. Phys. Lipids, vol. 100, p. 33-40, 1999, or as described by D'yakonov et al. (D'yakonov et al., Med. Chem. Res., 2016, vol. 25, p. 30-39; D'yakonov et al., Chem. Commun. 2013, vol. 49, p 8401-8403; D'yakonov et al., 2020, Phytochem. Rev.).

Example 1B. Synthesis of Ionizable Lipids—see FIG. 48

1. 2-((S)-2,2-di((6Z,12Z)-octadeca-6,12-dien-1-yl)-1,3-dioxolan-4-yl)-N,N-dimethylethan-1-amine (AKG-KC2-01, O-12095)
2. 3-((S)-2,2-di((6Z,12Z)-octadeca-6,12-dien-1-yl)-1,3-dioxolan-4-yl)-N,N-dimethylpropan-1-amine (AKG-KC3-01, O-12096)
3. 2-((S)-2,2-di((Z)-octadec-9-en-1-yl)-1,3-dioxolan-4-yl)-N,N-dimethylethan-1-amine (AKG-KC2-OA, O-11880)
4. 2-((S)-2,2-di((Z)-hexadec-9-en-1-yl)-1,3-dioxolan-4-yl)-N,N-dimethylethan-1-amine (AKG-KC2-PA, O-11879)
5. 3-((S)-2,2-di((Z)-octadec-9-en-1-yl)-1,3-dioxolan-4-yl)-N,N-dimethylpropan-1-amine (AKG-KC3-OA, O-11957)
6. 3-((S)-2,2-di((Z)-hexadec-9-en-1-yl)-1,3-dioxolan-4-yl)-N,N-dimethylpropan-1-amine (AKG-KC3-PA, O-12418)
7. 3-((S)-2,2-di((Z)-heptadec-8-en-1-yl)-1,3-dioxolan-4-yl)-N,N-dimethylpropan-1-amine (AKG-KC3-C17(C8:1))
8. (S)-3-(2,2-diheptadecyl-1,3-dioxolan-4-yl)-N,N-dimethylpropan-1-amine (AKG-KC3-C17)

Synthesis of 2-((S)-2,2-di((6Z,12Z)-octadeca-6,12-dien-1-yl)-1,3-dioxolan-4-yl)-N,N-dimethylethan-1-amine (AKG-KC2-01, O-12095)

3-((S)-2,2-di((6Z,12Z)-octadeca-6,12-dien-1-yl)-1,3-dioxolan-4-yl)-N,N-dimethylpropan-1-amine (AKG-KC3-01, O-12096)

See. FIG. 48.

Experimental Procedure

Synthesis of (6Z,12Z)-1-bromooctadeca-6,12-diene, 2

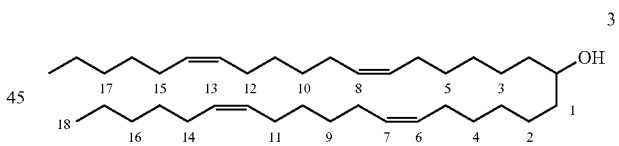

2

To a solution of (6Z,12Z)-octadeca-6,12-dien-1-ol, 1 (3.6 g, 13.7 mmol) in dichloromethane (50 mL) at 0° C. was added methane sulfonyl chloride (1.26 mL, 16.4 mmol) and triethylamine (3.6 mL, 20.5 mmol). The resulting solution was warmed to room temperature and stirred for 2 hours. The mixture was quenched with water and extracted with dichloromethane (2×100 mL). The combined organics were washed with brine then dried over magnesium sulfate then filtered. The filtrate was concentrated under vacuum to give a crude oil. The resulting oil was dissolved in diethyl ether (50 mL), added to a stirring slurry of magnesium bromide ethyl etherate (7 g, 27.4 mmol) in diethyl ether (50 mL) at OC. The mixture was warmed to room temperature and stirred for 2 hours. The reaction mixture was quenched with water and extracted with ethyl acetate (2×100 mL). The combined organics were washed with brine then dried over magnesium sulfate then filtered. The filtrate was concentrated under vacuum to give a crude oil. The crude oil was purified by chromatography on silica using 5-10% ethyl acetate in n-hexane as eluant to give (6Z,12Z)-1-bromooctadeca-6,12-diene, 3 (2.9 g, 8.89 mmol, 65%) as a yellow oil.

$^1$H NMR (300 MHz, CDCl$_3$): 5.36-5.33 (m, 4H), 3.42-3.37 (t, J=7.5 Hz, 2H), 2.04-1.97 (m, 8H), 1.83-1.83 (m, 2H), 1.37-1.28 (m, 14H), 0.90-0.86 (t, J=6.6 Hz, 3H).

Synthesis of (6Z,12Z,25Z,31Z)-heptatriaconta-6,12,25,31-tetraen-19-ol, 3

A solution of (6Z,12Z)-1-bromooctadeca-6,12-diene, 2 (2 g, 6.08 mmol) in ether (10 mL) was added to a mixture of magnesium turnings (162 mg, 6.69 mmol) and iodine in ether (2 mL) under argon at room temperature. The mixture stirred at room temperature for 90 minutes (magnesium turnings consumed) whereupon ethyl formate (0.24 mL, 3.04 mmol) was added. After stirring for one hour at room temperature, the reaction was quenched with 1N HCl solution. The mixture was extracted with ethyl acetate (2×100 mL) and the combined organics washed with water then brine. The organics were dried under magnesium sulfate, filtered, and the filtrate concentrated under vacuum to give a crude oil. The resulting oil was dissolved in ethanol (10 mL) and added to a solution of potassium hydroxide (260 mg) in water (3 mL). After stirring for 12 hours, the mixture pH was adjusted 4 with 2N HCl. The aqueous solution was extracted with dichloromethane (2×) and combined. The organics were washed with brine then dried under magnesium sulfate and filtered. The filtrate was concentrated under vacuum to give a crude oil. Purification of the crude oil on silica using 10-30% ethyl acetate in n-hexane as eluant to give (6Z,12Z,25Z,31Z)-heptatriaconta-6,12,25,31-tetraen-19-ol, 3 (0.29 g, 0.55 mmol, 18%) as a clear oil.

¹H NMR (300 MHz, CDCl₃): 5.36-5.32 (m, 8H), 3.57 (bs, 1H), 3.33-3.32, (m, 2H), 2.13-1.97 (m, 16H), 1.36-1.29 (m, 34H), 0.90-0.86 (t, J=6.6 Hz, 6H).

Synthesis of (6Z,12Z,25Z,31Z)-heptatriaconta-6,12,25,31-tetraen-19-one, 4

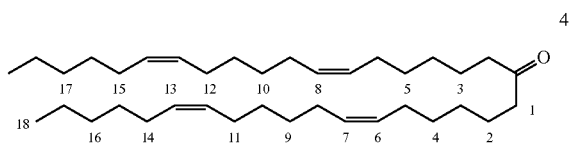

To a mixture of (6Z,12Z,25Z,31Z)-heptatriaconta-6,12,25,31-tetraen-19-ol, 3 (0.29 g, 0.55 mmol) and sodium carbonate (3 mg, 0.03 mmol) in dichloromethane was added pyridinium chlorochromate (236 mg, 1.1 mmol) at 0° C. The mixture was warmed to room temperature and stirred for one hour. After one hour, silica gel (1 g) was added to reaction and the mixture filtered. The filtrate was concentrated, and the resulted oil purified on silica using 10-20% ethyl acetate in n-hexane as eluant to give (6Z,12Z,25Z,31Z)-heptatriaconta-6,12,25,31-tetraen-19-one, 4 (0.12 g, 0.23 mmol, 42%) as a clear oil.

¹H NMR (300 MHz, CDCl₃): 5.36-5.32 (m, 8H), 3.36-3.32, (m, 1H), 2.40-2.35 (t, J=6.6 Hz, 3H), 2.14-2.00 (m, 16H), 1.58-1.54 (m, 4H), 1.34-1.29 (m, 28H), 0.90-0.86 (t, J=6.6 Hz, 6H).

Synthesis of 2-((S)-2,2-di((9Z,12Z)-octadeca-9,12-dien-1-yl)-1,3-dioxolan-4-yl) ethan-1-ol, 7

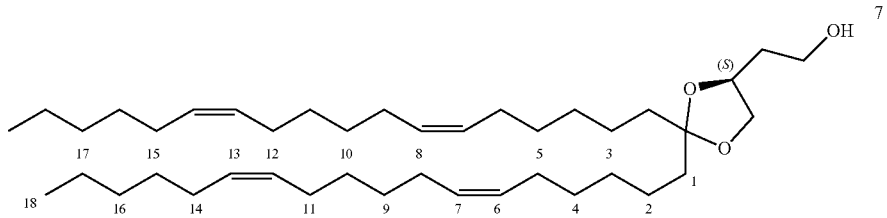

A mixture of (6Z,12Z,25Z,31Z)-heptatriaconta-6,12,25,31-tetraen-19-one, 4 (0.12 g, 0.23 mmol), (4S)-(+)-4-(2-hydroxyethyl)-2,2-dimethyl-1,3-dioxolane 5 (0.20 g, 1.38 mmol), and pyridinium p-toluene sulfonate (9 mg) in toluene (10 mL) was heated at reflux under nitrogen positive pressure. After 12 hours, the mixture was concentrated under vacuum to give a crude oil. The resulting crude oil was purified by chromatography on silica using 20-40% ethyl acetate in n-hexane as eluant to give 2-((S)-2,2-di((9Z,12Z)-octadeca-9,12-dien-1-yl)-1,3-dioxolan-4-yl) ethan-1-ol, 7 (0.11 g, 0.17 mmol, 77%) as a clear oil.

¹H NMR (300 MHz, CDCl₃): 5.36-5.32 (m, 8H), 4.25-4.20 (m, 1H), 4.10-4.06 (m, 1H), 3.82-3.77 (m, 1H), 3.54-3.49 (m, 1H), 2.23-2.19 (t, J=6.6 Hz, 3H), 2.14-2.00 (m, 16H), 1.84-1.78 (m, 2H), 1.62-1.51 (m, 6H), 1.34-1.29 (m, 28H), 0.90-0.86 (t, J=6.6 Hz, 6H).

Synthesis of 3-((S)-2,2-di((9Z,12Z)-octadeca-9,12-dien-1-yl)-1,3-dioxolan-4-yl)propan-1-ol, 8

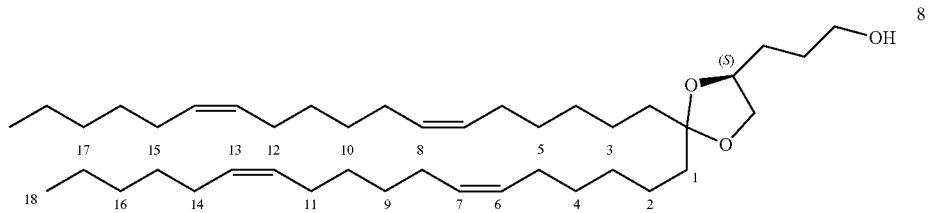

A mixture of (6Z,12Z,25Z,31Z)-heptatriaconta-6,12,25,31-tetraen-19-one, 4 (0.50 g, 0.95 mmol), (S)-(3)-(2,2-Dimethyl-1,3-dioxolane-4-yl)propanol 6 (0.76 g, 4.75 mmol), and pyridinium p-toluene sulfonate (36 mg) in toluene (10 mL) was heated at reflux under nitrogen positive pressure. After 12 hours, the mixture was concentrated under vacuum to give a crude oil. The resulting crude oil was purified by chromatography on silica using 20-40% ethyl acetate in n-hexane as eluant to 3-((S)-2,2-di((9Z,12Z)-octadeca-9,12-dien-1-yl)-1,3-dioxolan-4-yl)propan-1-ol, 8 (0.48 g, 0.76 mmol, 80%) as a clear oil.

$^1$H NMR (300 MHz, CDCl$_3$): 5.34-5.29 (m, 8H), 4.06-4.02 (m, 2H), 3.67-3.47 (m, 2H), 3.45-3.43 (m, 1H), 2.12-2.01 (m, 16H), 1.65-1.62 (m, 8H), 1.34-1.29 (m, 32H), 0.89-0.85 (t, J=6.6 Hz, 6H).

Synthesis of 2-((S)-2,2-di((9Z,12Z)-octadeca-9,12-dien-1-yl)-1,3-dioxolan-4-yl)-N,N-dimethylethan-1-amine, (AKG-KC2-01, O-12095)

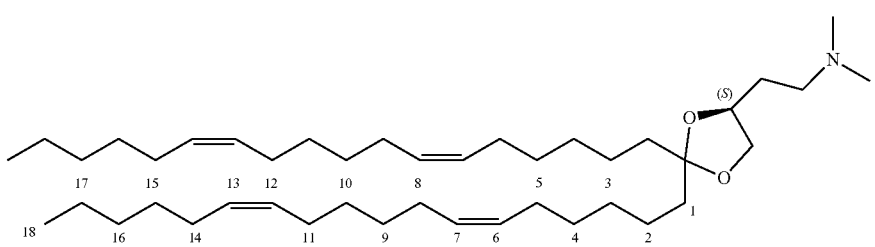

To a solution of 2-((S)-2,2-di((9Z,12Z)-octadeca-9,12-dien-1-yl)-1,3-dioxolan-4-yl) ethan-1-ol, 7 (0.49 g, 0.79 mmol) in dichloromethane (10 mL) at 0° C. was added methanesulfonyl chloride (73 μL, 0.95 mmol) and triethylamine (0.26 mL, 1.2 mmol). The solution was warmed to room temperature and stirred for an addition hour. The reaction was quenched with water and extracted with dichloromethane (2×100 mL). The organics were washed with brine then dried over magnesium sulfate and filtered. The filtrate was concentrated under vacuum to give a crude oil. A solution of 2M dimethylamine (10 mL) was added to the resulting crude oil and allowed to stir for 24 hours. The mixture was then quenched with water and extracted with dichloromethane (2×100 mL). The combined organics were washed with brine then dried over magnesium sulfate then filtered. The filtrate was concentrated under vacuum to give a crude oil. The crude oil was purified by chromatography on silica using 5-100% ethyl acetate in n-hexane as eluant to give 2-((S)-2,2-di((9Z,12Z)-octadeca-9,12-dien-1-yl)-1,3-dioxolan-4-yl)-N,N-dimethylethan-1-amine, (AKG-KC2-01, O-12095), (206 mg, 0.32 mmol, 41%) as a clear oil.

$^1$H NMR (300 MHz, CDCl$_3$): 5.35-5.32 (m, 8H), 4.08-4.03 (m, 2H), 3.47 (t, J=6.8 Hz, 1H), 2.36-2.27 (m, 2H), 2.21 (s, 6H), 2.01-1.99 (m, 16H), 1.88-1.77 (m, 2H), 1.68-1.53 (m, 6H), 1.42-1.19 (m, 34H), 0.96-0.86 (t, J=3.7 Hz, 6H).

MS(APCI) for C$_{43}$H$_{79}$NO$_2$: 642.6

Synthesis of 3-((S)-2,2-di((6Z, 12Z)-octadeca-6-12-dien-4-yl)-1,3-dioxolan-4-yl)-N,N-dimethylpropan-1-amine, AKG-KC3-01, O-12096)

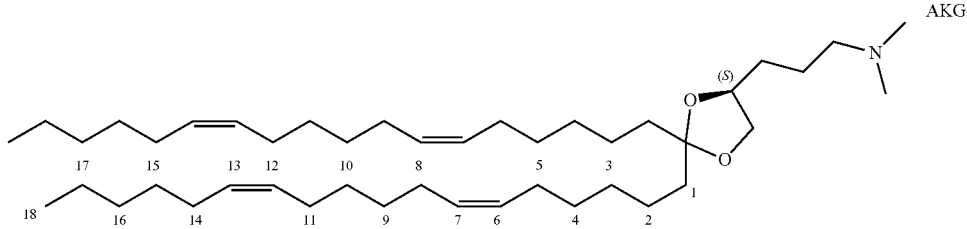

The procedure was previously described. 3-((S)-2,2-di((6Z, 12Z)-octadeca-6-12-dien-4-yl)-1,3-dioxolan-4-yl)-N,N-dimethylpropan-1-amine, (AKG-KC3-01, O-12096), (255 mg, 0.39 mmol, 51%) as a clear oil.
$^1$H NMR (300 MHz, CDCl$_3$): 5.39-5.32 (m, 8H), 4.06-4.02 (m, 211), 3.48-3.44 (m, 1H), 2.35-2.30 (m, 2H), 2.25 (s, 6H), 2.01-1.98 (m, 16H), 1.70-1.51 (m, 12H), 1.35-1.25 (m, 32H), 0.90-0.85 (t, J=6.6 Hz, 6H).
MS(APCI) for C$_{44}$H$_{81}$NO$_2$: 656.6

Synthesis of 2-((S)-2,2-di((Z)-octadec-9-en-1-yl)-1,3-dioxolan-4-yl)-N,N-dimethylethan-1-amine (AKG-KC2-OA, O-11880)

2-((S)-2,2-di((Z)-hexadec-9-en-1-yl)-1,3-dioxolan-4-yl)-N,N-dimethylethan-1-amine (AKG-KC2-PA, O-11879)

3-((S)-2,2-di((Z)-octadec-9-en-1-yl)-1,3-dioxolan-4-yl)-N,N-dimethylpropan-1-amine (AKG-KC3-OA, O-11957)

3-((S)-2,2-di((Z)-hexadec-9-en-1-yl)-1,3-dioxolan-4-yl)-N,N-dimethylpropan-1-amine, (AKG-KC3-PA, O-12418)

See FIG. 49.

Experimental Procedure (Refer to Previously Described Synthesis of AKG-KC2-01)

Synthesis of (Z)-1-bromooctadec-9-ene 3

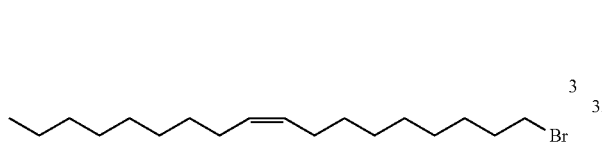

The procedure was previously described.
(Z)-1-bromooctadec-9-ene, (6.4 g, 19.33 mmol) as a clear oil.
$^1$H NMR (300 MHz, CDCl$_3$): 5.36-5.32 (m, 2H), 3.41 (t, J=7.5 Hz, 2H), 2.01-1.99 (m, 4H), 1.87-1.82 (m, 2H), 1.44-1.26 (m, 22H), 0.87 (t, J=6.6 Hz, 3H).

(Z)-16-bromohexadec-7-ene 4

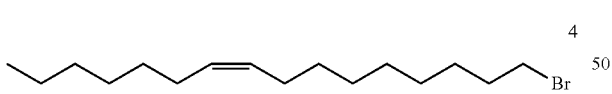

$^1$H NMR (300 MHz, CDCl$_3$): 5.36-5.32 (m, 2H), 3.42 (t, J=7.5 Hz, 2H), 2.01-1.99 (m, 4H), 1.87-1.82 (m, 2H), 1.44-1.26 (m, 18H), 0.89 (t, J=6.6 Hz, 3H).

Synthesis of (9Z,28Z)-heptatriaconta-9,28-dien-19-ol 5

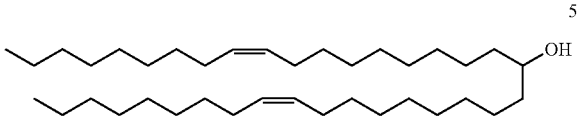 [SMILES: CCCCCCCC/C=C\CCCCCCCCC(O)CCCCCCCC/C=C\CCCCCCCC]

The procedure was previously described.
(9Z,28Z)-heptatriaconta-9,28-dien-19-ol (1.2 g, 2.25 mmol, 47%) as a solid.
$^1$H NMR (300 MHz, CDCl$_3$): 5.36-5.29 (m, 4H), 3.57 (bs, 1H), 2.01-1.97 (m, 8H), 1.42-1.26 (m, 53H), 0.89 (t, J=6.6 Hz, 6H).

(7Z,26Z)-tritriaconta-7,26-dien-17-ol 6

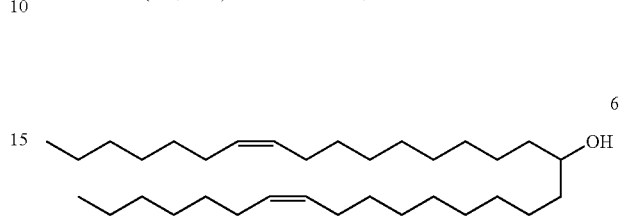

$^1$H NMR (300 MHz, CDCl$_3$): 5.36-5.29 (m, 4H), 3.57 (bs, 1H), 2.01-1.97 (m, 8H), 1.42-1.26 (m, 45H), 0.89 (t, J=6.6 Hz, 6H).

Synthesis of (9Z,28Z)-heptatriaconta-9,28-dien-19-one 7

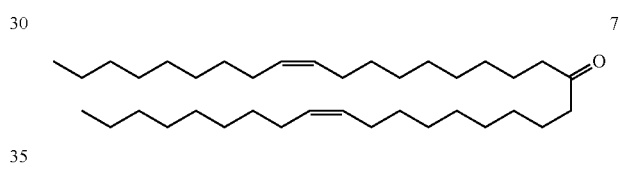

The procedure was previously described.
(9Z,28Z)-heptatriaconta-9,28-dien-19-one (0.89 g, 1.67 mmol, 74%) as a clear oil.
$^1$H NMR (300 MHz, CDCl$_3$): 5.36-5.29 (m, 4H), 2.03-1.98 (m, 8H), 1.42-1.26 (m, 52H), 0.90-0.89 (t, J=6.6 Hz, 6H).

(7Z,26Z)-tritriaconta-7,26-dien-17-one

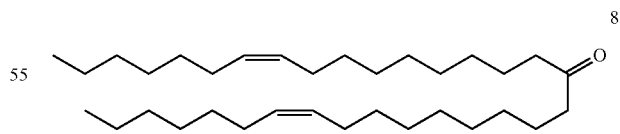

$^1$H NMR (300 MHz, CDCl$_3$): 5.36-5.29 (m, 4H), 2.03-1.98 (m, 8H), 1.42-1.26 (m, 44H), 0.90-0.89 (t, J=6.6 Hz, 6H).

Synthesis of 2-((S)-2,2-di((Z)-octadec-9-en-1-yl)-1,
3-dioxolan-4-yl) ethan-1-ol 9

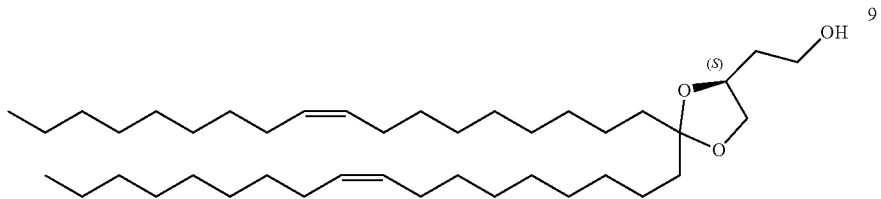

The procedure was previously described. 2-((S)-2,2-di
((Z)-octadec-9-en-1-yl)-1,3-dioxolan-4-yl) ethan-1-ol (0.39
g, 0.63 mmol, 74%) as a clear oil.
¹H NMR (300 MHz, CDCl₃): 5.36-5.28 (m, 4H), 4.22-
4.10 (m, 1H), 4.08-4.05 (m, 1H), 3.82-3.79 (m, 2H), 3.48 (t,
J=6.8 Hz, 1H), 2.24-2.21 (m, 1H), 2.01-1.99 (m, 8H),
1.81-1.80 (m, 2H), 1.59-1.54 (m, 6H), 1.34-1.26 (m, 45H),
0.87 (t, J=6.3 Hz, 6H).

Synthesis of 2-((S)-2,2-di((Z)-hexadec-9-en-1-yl)-1,
3-dioxolan-4-yl)ethan-1-ol, 10

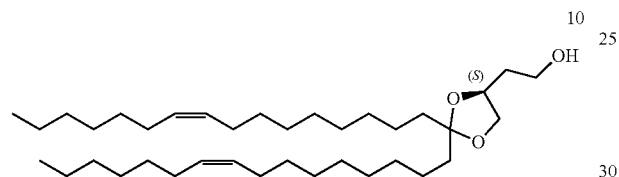

The procedure was previously described. 2-((S)-2,2-di
((Z)-hexadec-9-en-1-yl)-1,3-dioxolan-4-yl)ethan-1-ol (1.02
g, 1.65 mmol, 51%) as a clear oil.
¹H NMR (300 MHz, CDCl₃): 5.36-5.29 (m, 4H), 4.23-
4.10 (m, 1H), 4.07-4.05 (m, 1H), 3.82-3.79 (m, 2H), 3.48 (t,
J=6.6 Hz, 1H), 2.24-2.12 (m, 1H), 2.01-1.97 (m, 8H),
1.84-1.78 (m, 2H), 1.57-1.55 (m, 8H), 1.34-1.29 (m, 35H),
0.87 (t, J=6.3 Hz, 6H).

Synthesis of 3-((S)-2,2-di((Z)-octadec-9-en-1-yl)-1,
3-dioxolan-4-yl)propan-1-ol, 11

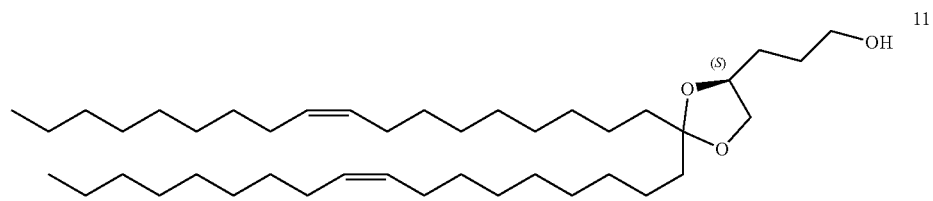

The procedure was previously described.
3-((S)-2,2-di((Z)-octadec-9-en-1-yl)-1,3-dioxolan-4-yl)
propan-1-ol (0.41 g, 0.65 mmol, 76%) as a clear oil
¹H NMR (300 MHz, CDCl₃): 5.39-5.32 (m, 4H), 4.06-
4.03 (m, 2H), 3.71-3.67 (m, 2H), 3.47-3.46 (m, 1H), 2.01-
1.99 (m, 10H), 1.66-1.59 (m, 4H), 1.56-1.54 (m, 6H),
1.34-1.26 (m, 44H), 0.87 (t, J=6.3 Hz, 6H).

Synthesis of 3-((S)-2,2-di((Z)-hexadec-9-en-1-yl)-1,
3-dioxolan-4-yl)propan-1-ol

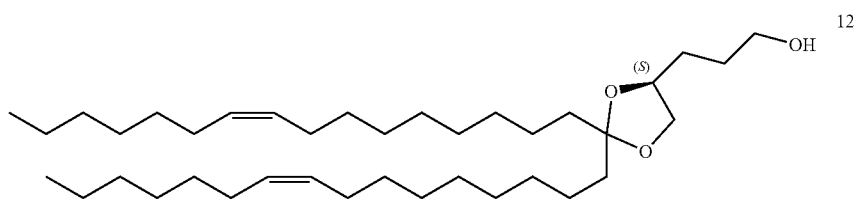

The procedure was previously described.
3-((S)-2,2-di((Z)-hexadec-9-en-1-yl)-1,3-dioxolan-4-yl)
propan-1-ol, (0.9 g, 1.56 mmol, 80%) as a clear oil.

1H NMR (300 MHz, CDCl$_3$): 5.39-5.28 (m, 4H), 4.06-4.01 (m, 2H), 3.71-3.67 (m, 2H), 3.47-3.46 (m, 1H), 2.01-1.99 (m, 10H), 1.66-1.59 (m, 4H), 1.56-1.54 (m, 6H), 1.34-1.26 (m, 37H), 0.87 (t, J=6.3 Hz, 6H).

Synthesis of 2-((S)-2,2-di((Z)-octadec-9-en-1-yl)-1,3-dioxolan-4-yl)-N,N-dimethylethan-1-amine, (AKG-KC2-OA, O-11880)

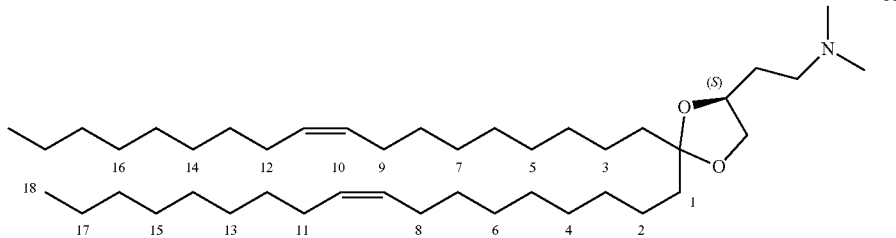

AKG-KC2-OA

The procedure was previously described.

2-((S)-2,2-di((Z)-hexadec-9-en-1-yl)-1,3-dioxolan-4-yl)-N,N-dimethylethan-1-amine, (AKG-KC2-OA, O-11880), (200 mg, 0.31 mmol, 49%) as a clear oil.

$^1$H NMR (300 MHz, CDCl$_3$): 5.38-5.28 (m, 4H), 4.08-4.01 (m, 2H), 3.48 (t, J=6.8 Hz, 1H), 2.39-2.24 (m, 2H), 2.21 (s, 6H), 2.01-1.97 (m, 8H), 1.82-1.77 (m, 2H), 1.68-1.52 (m, 6H), 1.34-1.26 (m, 46H), 0.87 (t, J=6.3 Hz, 6H).

MS(APCI) for C$_{43}$H$_{83}$NO$_2$: 646.7

Synthesis of 2-((S)-2,2-di((Z)-hexadec-9-en-1-yl)-1,3-dioxolan-4-yl)-N,N-dimethylethan-1-amine, (AKG-KC2-PA, O-11879)

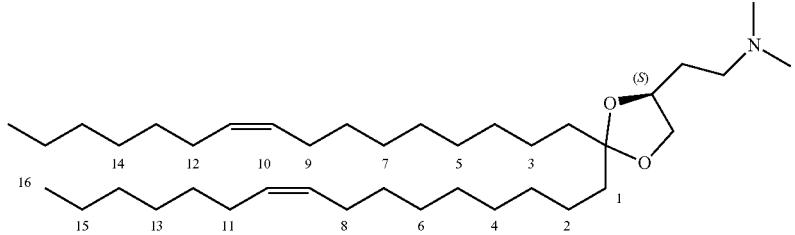

AKG-KC2-PA

The procedure was previously described.

2-((S)-2,2-di((Z)-hexadec-9-en-1-yl)-1,3-dioxolan-4-yl)-N,N-dimethylethan-1-amine, (AKG-KC2-PA, O-11879), (195 mg, 0.33 mmol, 18%) as a clear oil.

$^1$H NMR (300 MHz, CDCl$_3$): 5.35-5.28 (m, 4H), 4.08-4.02 (m, 2H), 3.48 (t, J=6.6 Hz, 1H), 2.38-2.27 (m, 2H), 2.20 (s, 6H), 2.01-1.99 (m, 8H), 1.97-1.80 (m, 2H), 1.77-1.52 (m, 6H), 1.34-1.29 (m, 38H), 0.87 (t, J=6.3 Hz, 6H).

MS(APCI) for C$_{39}$H$_{75}$NO$_2$: 590.6

Synthesis of 3-((S)-2,2-di((Z)-octadec-9-en-1-yl)-1,3-dioxolan-4-yl)-N,N-dimethylpropan-1-amine, (AKG-KC3-OA, O-11957)

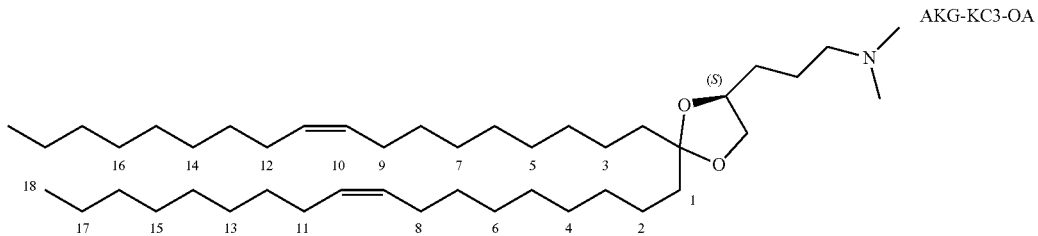

The procedure was previously described.

3-((S)-2,2-di((Z)-octadec-9-en-1-yl)-1,3-dioxolan-4-yl)-N,N-dimethylpropan-1-amine, (AKG-KC3-OA, O-11957), (160 mg, 0.24 mmol, 37%) as a clear oil.

$^1$H NMR (300 MHz, CDCl$_3$): 5.39-5.28 (m, 4H), 4.06-4.01 (m, 2H), 3.44 (t, J=6.8 Hz, 1H), 2.26 (t, J=6.8 Hz, 2H), 2.20 (s, 6H), 2.01-1.97 (m, 8H), 1.82-1.77 (m, 2H), 1.60-1.43 (m, 8H), 1.34-1.26 (m, 46H), 0.87 (t, J=6.3 Hz, 6H).

MS(APCI) for C$_{44}$H$_{85}$NO$_2$: 660.6

Synthesis of 3-((S)-2,2-di((Z)-hexadec-9-en-1-yl)-1,3-dioxolan-4-yl)-N,N-dimethylpropan-1-amine, (AKG-KC3-PA, O-12418)

The procedure was previously described.

3-((S)-2,2-di((Z)-hexadec-9-en-1-yl)-1,3-dioxolan-4-yl)-N,N-dimethylpropan-1-amine, (AKG-KC3-PA, O-12418) (300 mg, 0.49 mmol, 32%) as a clear oil.

$^1$H NMR (300 MHz, CDCl$_3$): 5.39-5.28 (m, 4H), 4.06-4.01 (m, 2H), 3.47-3.42 (m, 1H), 2.43-2.41 (m, 2H), 2.31 (s, 6H), 2.01-1.97 (m, 8H), 1.70-1.52 (m, 6H), 1.27-1.18 (m, 42H), 0.87 (t, J=6.6 Hz, 6H).

MS(APCI) for C$_{44}$H$_{85}$NO$_2$: 604.6

Synthesis of 3-((S)-2,2-di((Z)-heptadec-8-en-1-yl)-1,3-dioxolan-4-yl)-N,N-dimethylpropan-1-amine, AKG-KC3-C17(C8:1)

Synthesis of (S)-3-(2,2-diheptadecyl-1,3-dioxolan-4-yl)-N,N-dimethylpropan-1-amine, AKG-KC3-C17

See FIG. 50.

Experimental Procedure

Synthesis of (9Z,26Z)-pentatriaconta-9,26-dien-18-one, 2

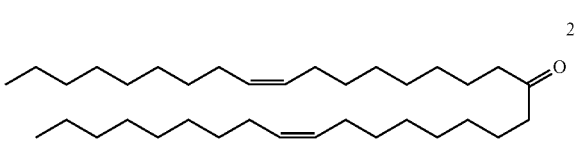 [SMILES: CCCCCCCC/C=C\CCCCCCCC(=O)CCCCCCC/C=C\CCCCCCCC]

To a stirring solution of oleoyl chloride (10 g, 33.3 mmol) in toluene (50 mL) at 0° C. was added triethylamine (5.8 mL, 33.3 mmol). A heavy precipitate formed, and the mixture was allowed to stir at room temperature for 8 hours. The mixture was quenched with 2% sulfuric acid solution and then extracted with ethyl acetate. The organics were washed with brine then dried over magnesium sulfate and filtered. The filtrate was concentrated under vacuum to give a crude oil. The resulting oil was diluted with ethanol (20 mL) and [2N NaOH] (30 mL) was added. The mixture was heated at 100° C. for 12 hours then cooled. The mixture was diluted with 2N HCl solution until a pH 4 was obtained. The mixture was extracted with ethyl acetate. The combined organics were washed with brine then dried over magnesium sulfate and filtered. The filtrate was concentrated under vacuum to give a crude oil. Purification of the oil on silica using 10-20% ethyl acetate in n-hexane as eluant gave (9Z,26Z)-pentatriaconta-9,26-dien-18-one, 2 (3.8 g, 44%) as a yellow oil.

$^1$H NMR (300 MHz, CDCl$_3$): δ ppm 5.35-5.31 (m, 4H), 2.39-2.34 (m, 4H), 2.0-1.85 (m, 8H), 1.57-1.52 (m, 4H), 1.27-1.25 (m, 40H), 0.88 (t, J=6.6 Hz, 3H).

Synthesis of 3-((S)-2,2-di((Z)-heptadec-8-en-1-yl)-1,3-dioxolan-4-yl)propan-1-ol, 3

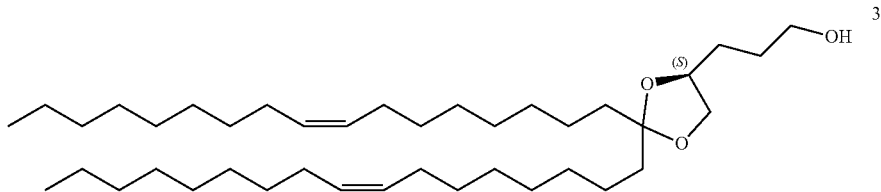

Procedure previously described synthesis of AKG-KC2-01

3-((S)-2,2-di((Z)-heptadec-8-en-1-yl)-1,3-dioxolan-4-yl) propan-1-ol, 3 (0.7 g, 1.15 mmol, 65%) as a clear oil.

$^1$H NMR (300 MHz, CDCl$_3$): δ ppm 5.38-5.31 (m, 4H), 4.08-4.02 (m, 2H), 3.67-3.66 (m, 2H), 3.48-3.43 (m, 1H), 2.15-2.13 (m, 1H), 2.00-1.98 (m, 8H), 1.65-1.56 (m, 8H), 1.27-1.25 (m, 44H), 0.88 (t, J=6.6 Hz, 6H).

Synthesis of (S)-3-(2,2-diheptadecyl-1,3-dioxolan-4-yl)propan-1-ol, 4

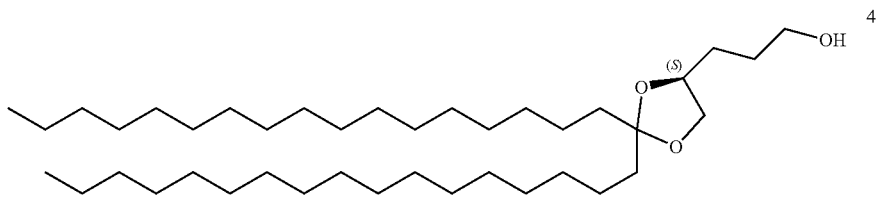

A solution of 3-((S)-2,2-di((Z)-heptadec-8-en-1-yl)-1,3-dioxolan-4-yl) propan-1-ol (1.3 g, 2.15 mmol) in methanol/ethyl acetate (20 mL, 1:1/v:v) was hydrogenated at 1 atm (hydrogen balloon) over 10% palladium on carbon (100 mg) for 2 hours. The mixture was evacuated of hydrogen and flowed with nitrogen. The mixture was filtered over celite, and the filtrate concentrated under vacuum to give (S)-3-(2, 2-diheptadecyl-1,3-dioxolan-4-yl) propan-1-ol, 4 (1.3 g, quant.) as a clear oil.

$^1$H NMR (300 MHz, CDCl$_3$): δ ppm 4.10-4.01 (m, 2H), 3.71-3.64 (m, 1H), 3.47-3.43 (m, 2H), 2.05-2.01 (m, 1H), 1.63-1.51 (m, 8H), 1.42-1.22 (m, 58H), 0.87 (t, J=6.6 Hz, 6H).

Synthesis of 3-((S)-2,2-di((Z)-heptadec-8-en-1-yl)-1,3-dioxolan-4-yl)-N,N-dimethylpropan-1-amine, AKG-KC3-C17(C8:1) (O-12620)

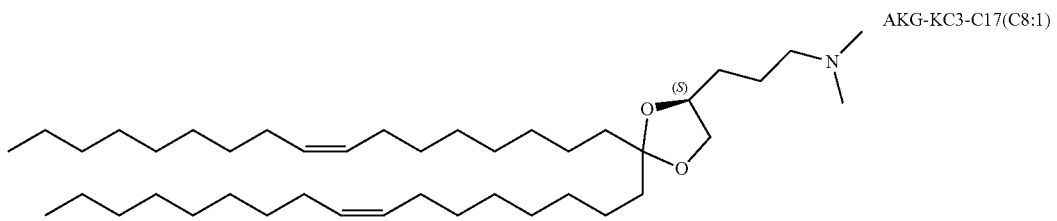

Procedure previously described synthesis of AKG-KC2-01 3-((S)-2,2-di((Z)-heptadec-8-en-1-yl)-1,3-dioxolan-4-yl)-N, N-dimethylpropan-1-amine, (AKG-KC3-C17 (C8:1), O-12620), (290 mg, 0.46 mmol, 40%) a clear oil.

MS (APCI+) for $C_{42}H_{81}NO_2$: 632.6

$^1$H NMR (300 MHz, CDCl$_3$): δ ppm 5.38-5.28 (m, 4H), 4.09-3.99 (m, 2H), 3.48-3.41 (m, 1H), 2.77-2.71 (m, 1H), 2.55 (s, 6H), 2.01-1.95 (m, 8H), 1.88-1.78 (m, 2H), 1.62-1.50 (m, 6H), 1.27-1.24 (m, 44H), 0.88 (t, J=6.8 Hz, 6H).

Synthesis of (S)-3-(2,2-diheptadecyl-1,3-dioxolan-4-yl)-N,N-dimethylpropan-1-amine, AKG-KC3-C17 (O-12637)

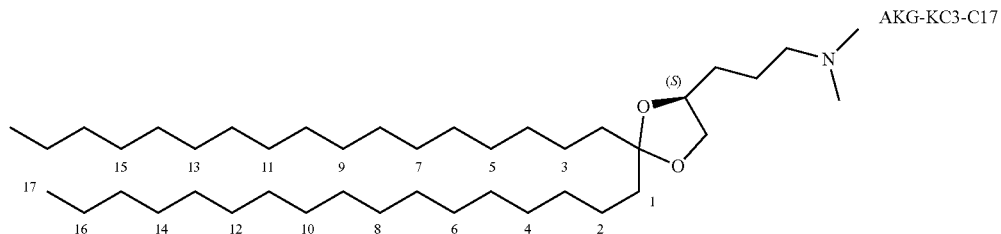

AKG-KC3-C17

Procedure previously described synthesis of AKG-KC2-01

(S)-3-(2,2-diheptadecyl-1,3-dioxolan-4-yl)-N, N-dimethylpropan-1-amine, (AKG-KC3-C17, O-12637), (275 mg, 0.43 mmol, 22%) as a solid.

MS (APCI$^+$) for $C_{42}H_{85}NO_2$: 636.6

$^1$H NMR (300 MHz, CDCl$_3$): δ ppm 4.06-4.00 (m, 2H), 3.47-3.43 (m, 1H), 2.29-2.25 (m, 2H), 2.21 (s, 6H), 1.60-1.48 (m, 8H), 1.29-1.24 (m, 60H), 0.87 (t, J=6.6 Hz, 6H).

Example 1C. Synthesis of Dilauroyl-(S)-glycerol-mPEG2000 (PEG(2000)-DL)

Experimental Procedure

Synthesis of mPEG2000 tosylate 2

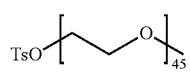

To a solution of Poly (ethylene glycol) methyl ether 1 (7 g, 3.5 mmol) in dichloromethane (30 mL) at 0° C. was added p-toluenesulfonyl chloride (0.9 g, 7 mmol) and triethylamine (1.8 mL, 10.5 mmol). The resulting mixture was stirred at room temperature for 12 hours then quenched with water. The mixture was extracted with dichloromethane and the organics washed with brine then dried over magnesium sulfate and filtered. The filtrate was concentrated under vacuum to give a crude oil. Purification of the oil on silica using 10% methanol in dichloromethane as eluant gave mPEG2000 tosylate (5.2 g, 70%) as a white solid.

1H NMR (300 MHz, CDCl3): δ ppm 7.79-7.76 (d, 2H), 7.34-7.25 (d, 2H), 5.28 (s, 6H), 4.15-4.12 (22H), 3.87-3.81 (m, 11H), 3.71-3.43 (m, 188H). 3.47-3.36 (m, 5H).

Synthesis of (S)-(+)-1,2-Isopropylidene glycerol mPEG2000 4

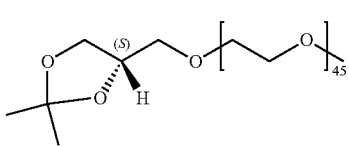

Sodium hydride (133 mg, 3.33 mmol) was added to a solution of (S)-(+)-1,2-Isopropylidene glycerol (440 mg, 3.33 mmol) in tetrahydrofuran (20 mL) at 0° C. After stirring for 30 minutes, Poly (ethylene glycol) methyl tosylate (5.2 g, 2.41 mmol) was added. The mixture was heated at 70° C. for 18 hours then cooled. The reaction was quenched with water and extracted with dichloromethane. The organics were washed with water, dried over magnesium sulfate then filtered. The filtrate was concentrated under vacuum to give a crude oil. Purification of the oil on silica using 1% methanol in dichloromethane as eluant gave (S)-(+)-1,2-Isopropylidene glycerol mPEG 2000 (3.3 g, 56%) as a clear oil.

1H NMR (300 MHz, CDCl3): δ ppm 4.32 (dd, J=11.8, 6.3 Hz, 1H), 3.99 (dd, J=8.2, 6.3 Hz, 1H), 3.85-3.74 (m, 1H), 3.68-3.51 (m, 190H), 3.39-3.36 (m, 5H), 1.35 (s, 3H), 1.28 (s, 311).

Synthesis of (R)-3-(mPEG2000)-propane-1,2-diol 5

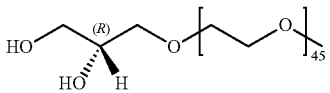

A mixture of (S)-(+)-1,2-Isopropylidene glycerol mPEG 2000 (3.3 g, 1.56 mmol) and 15 mL of [1N HCl] in THF (10 mL) was stirred at room temperature for one hour. After one hour, the mixture was concentrated under vacuum to give (R)-3-(mPEG2000)-propane-1,2-diol (3.4 g, quant) as a white solid. Proceeded without further purification.

1H NMR (300 MHz, CDCl3): δ ppm 4.1-4.12 (m, 1H), 3.68-3.51 (m, 180H), 3.39-3.36 (m, 4H).

Synthesis of Dilauroyl-(S)-glycerol-mPEG2000

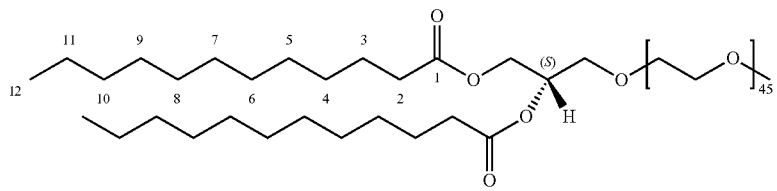

mPEG$_{2000}$-DLG (C12:0)

To a solution of (R)-3-(mPEG2000)-propane-1,2-diol (1.56 mmol) in dichloromethane (10 mL) at 0° C. was added lauroyl chloride (0.75 g, 3.43 mmol), N, N-Diisopropylethylamine (1.2 mL, 6.8 mmol), and 4-dimethylaminopyridine (0.42 g, 3.43 mmol). The resulting mixture was stirred at room temperature for 12 hours then quenched with water. The mixture was extracted with dichloromethane and the organics washed with brine then dried over magnesium sulfate and filtered. The filtrate was concentrated under vacuum to give a crude oil. Purification of the oil on silica using 5-100% diethyl ether in hexane as eluant Dilauroyl-(S)-glycerol-mPEG2000 (0.66 g, 18%) as a white solid.

MS (MALDI): CHCA matrix: 2431.57

1H NMR (300 MHz, CDCl3): δ ppm 5.23-5.18 (m, 1H), 4.32 (dd, J=11.8, 3.6 Hz, 1H), 4.13 (dd, J=11.8, 6.3 Hz, 1H), 3.85-3.74 (m, 1H), 3.68-3.51 (m, 190H), 3.39-3.36 (m, 4H), 2.32-2.25 (m, 4H), 1.66-1.51 (m, 4H), 1.47-1.46 (m, 32H), 0.88-0.85 (m, 6H).

4-nitrophenyl-2,5,8,11,14,17,20,23,26,29,32,35,38, 41,44,47,50,53,56,59,62,65,68, 71,74,77,80,83,86, 89,92,95,98,101,104,107,110,113,116,119,122,125, 128,131-tetratetracontaoxatritriaconta-hectan-133-yl) carbonate, 2

To a solution of poly(ethylene glycol) methyl ether (4 g, 2 mmol) in dichloromethane (20 mL) at 0° C. was added 4-nitrophenyl chloroformate (603 mg, 3 mmol), and pyridine (0.5 mL, 6 mmol). The resulting mixture was stirred at room temperature for 3 hours then quenched with water. The mixture was extracted with dichloromethane and the organics washed with brine then dried over magnesium sulfate and filtered. The filtrate was concentrated under vacuum to give a crude oil. Purification of the oil on silica using 5-10% methanol in dichloromethane as eluant to give 4-nitrophenyl(2,5,8,11,14,17,20,23,26,29,32,35,38,41,44, 47,50,53,56,59,62,65,68,71,74, 77,80,83,86,89,92,95,98, 101,104,107,110,113,116,119,122,125,128,131tetratetracontaoxatritriaconta-hectan-133-yl) carbonate (3.4 g, 82%) as a white solid.

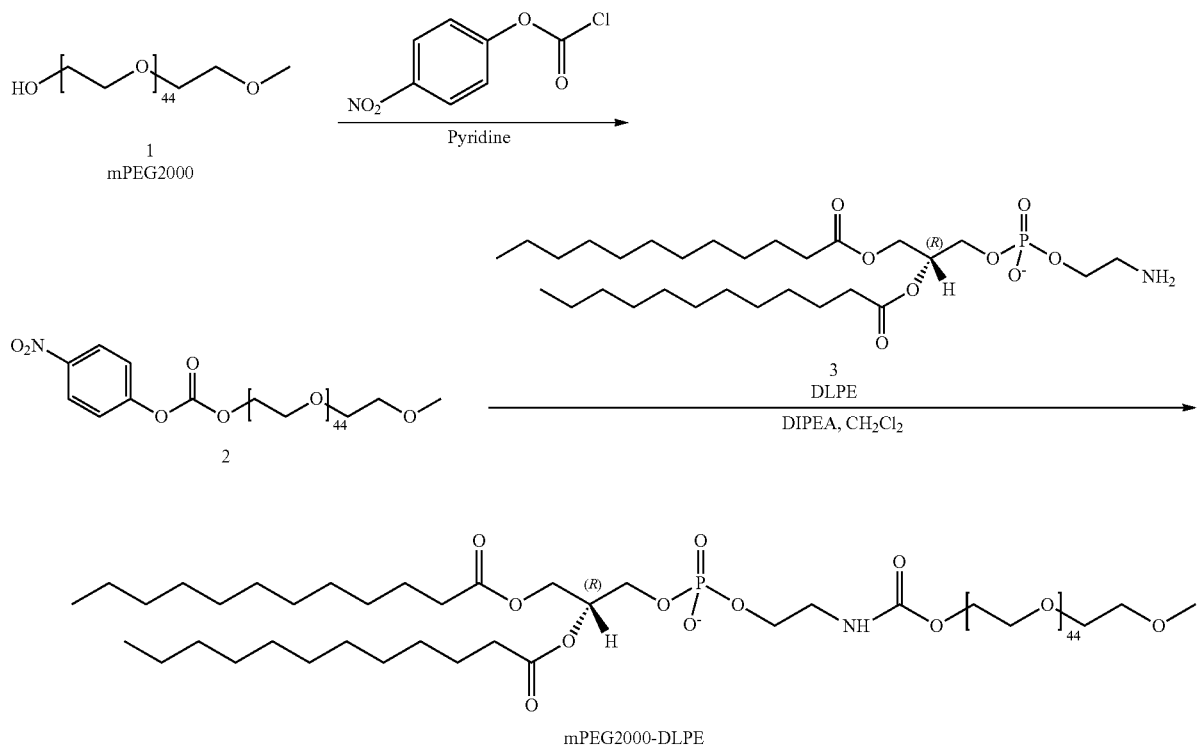

mPEG2000-DLPE

1H NMR (300 MHz, CDCl3): δ ppm 8.28-8.25 (d, 2H), 7.39-7.38 (m, 2H), 4.43-4.41 (m, 1H), 4.00-3.90 (m, 2H), 4.00-3.80 (m, 5H), 3.68-3.36 (m, 188H), 2.03 (s, 3H).

(2R)-3-((hydroxy((135-oxo-2,5,8,11,14,17,20,23,26, 29,32,35,38,41,44,47,50,53,56,59, 62,65,68,71,74, 77,80,83,86,89,92,95,98,101,104,107,110,113,116, 119,122,125,128,131,134-pentatetracontaoxa-136-azaoctatriacontahectan-138-yl)oxy)phosphoryl)oxy) propane-1,2-diyl didodecanoate, mPEG2000-DLPE A mixture of 4-nitrophenyl(2,5,8,11,14,17,20,23,26,29, 32,35,38,41,44,47,50,53,56,59, 62,65,68,71,74,77,80,83,86, 89,92,95,98,101,104,107,110,113,116,119,122,125,128, 131-tetratetra-contaoxatritriacontahectan-133-yl) carbonate 2 (3.4 g, 1.65 mmol), 1,2-dilauroyl-sn-glycero-3-phosphoethanol amine (1 g, 1.72 mmol), and triethylamine (0.32 mL, 2.28 mmol) in dichloromethane (30 mL) was stirred at room temperature for 12 hours. After 12 hours, the mixture was quenched with water and extracted with dichloromethane. The combined organics were washed with brine then dried over magnesium sulfate and filtered. The filtrate was concentrated under vacuum to give a crude oil. Purification of the oil on silica using 1-5% methanol in dichloromethane as eluant gave (2R)-3-((hydroxy((135-oxo-2,5,8,11,14,17,20, 23,26, 29,32,35,38,41,44,47,50,53,56,59,62,65,68,71,74,77, 80,83,86,89,92,95,98,101,104,107,110,113,116,119,122, 125,128,131,134-pentatetracontaoxa-136-azaoctatriacontahectan-138-yl)oxy)phosphoryl)oxy) propane-1,2-diyl didodecanoate mPEG2000-DLPE (2 g, 46%) as a semi solid.

1H NMR (300 MHz, CDCl3): δ ppm 5.17-5.15 (m, 1H), 4.35-4.31 (m, 1H), 4.16-4.10 (m, 3H), 4.00-3.80 (m, 5H), 3.65-3.37 (m, 188H), 3.34 (s, 3H), 3.05-3.01 (m, 11H), 2.26-2.23 (m, 6H), 1.54-1.52 (m, 4H), 1.32-1.17 (m, 33H), 0.86-0.82 (t, J=1.3 Hz, 6H).

Example 1E. Synthesis of Distearoylphosphatidyl-D-serine (O-12153)—See FIG. 51

Benzyl ((benzyloxy)carbonyl)-D-serinate, 2

To a solution of Z-(D)-Serine-OH (2.4 g, 10 mmol) in DMF (10 mLs) was added benzyl bromide (1.2 mL, 10 mmol), and cesium carbonate (3.2 g, 10 mmol). The resulting mixture was stirred at room temperature for 12 hours then quenched with water. The mixture was extracted with dichloromethane and the organics washed with brine then dried over magnesium sulfate and filtered. The filtrate was concentrated under vacuum to give a crude oil. Purification of the oil on silica using 20-40% ethyl acetate in hexane as eluant to give benzyl ((benzyloxy)carbonyl)-D-serinate (2.5 g, 76%) as a white solid.

Benzyl O-((benzyloxy)(diisopropylamino)phosphaneyl)-N-((benzyloxy)carbonyl)-D-serinate, 4

A mixture of 1-(benzyloxy)-N,N,N',N'-tetraisopropylphosphanediamine, 3 (2.8 g, 8.4 mmol), ((benzyloxy)carbonyl)-D-serinate 4 (2.5 g, 7.6 mmol), and tetrazole (16.8 mL, 8.4 mmol) in THF (20 mL) was stirred for 12 hours at room temperature. After 12 hours, the reaction was concentrated under vacuum and the resulting oil was purified on silica (pre-treated with 0.1% Et3N/n-hexane solution) using 10% ethyl acetate in n-hexane as eluant to give benzyl O-((benzyloxy)(diisopropylamino)phosphaneyl)-N-((benzyloxy)carbonyl)-D-serinate 4 (2.0 g, 47%) as a clear oil.

MS (APCI+): 567.2 (M+1); 1H NMR (300 MHz, CDCl3): δ ppm 7.33-7.30 (m, 15H), 5.81-5.61 (dd, J=11.8, 3.6 Hz, 1H), 5.12-5.09 (m, 3H), 4.61-4.58 (m, 2H), 4.13-4.11 (m, 2H), 3.58-3.55 (m, 2H), 1.16-1.12 (m, 12H).

(2R)-3-(((benzyloxy)((R)-3-(benzyloxy)-2-(((benzyloxy)carbonyl)amino)-3-oxopropoxy) phosphoryl) oxy)propane-1,2-diyl distearate, 6

A mixture of 1.2 Distearoyl-sn-glycerol, 5 (1.0 g, 1.6 mmol), benzyl O-((benzyloxy)(diisopropylamino)phosphaneyl)-N-((benzyloxy)carbonyl)-D-serinate 4 (0.94 g, 1.6 mmol), and tetrazole (4.3 mL, 1.9 mmol) in THF (25 mL) was stirred for 6 hours at room temperature. After 6 hours, a solution of tert-butyl hydroperoxide [70% solution in water] in THF (3 mL) was added. The resulting mixture was stirred at room temperature for 1 hour then quenched with saturated sodium thiosulfate. The mixture was extracted with ethyl acetate and the organics washed with brine then dried over magnesium sulfate and filtered. The filtrate was concentrated under vacuum to give a crude oil. Purification of the oil on silica using 10-20% ethyl acetate in hexane as eluant to give (2R)-3-(((benzyloxy)((R)-3-(benzyloxy)-2-(((benzyloxy)carbonyl) amino)-3-oxopropoxy)phosphoryl) oxy)propane-1,2-diyl distearate 6 (1.4 g, 80%) as a white solid.

1H NMR (300 MHz, CDCl$_3$): δ ppm 7.33-7.25 (m, 15H), 5.91-5.79 (dd, J=11.8, 3.6 Hz, 1H), 5.21-5.11 (m, 6H), 5.06-4.95 (m, 3H), 4.60-4.57 (m, 1H), 4.48-4.43 (m, 2H), 4.29-4.20 (m, 2H), 4.05-4.01 (m, 3H), 2.26-2.04 (m, 4H), 1.58-1.48 (m, 8H), 1.29-1.26 (m, 45H), 0.89-0.85 (t, J=1.3 Hz, 6H).

O—(((R)-2,3-bis(stearoyloxy)propoxy)(hydroxy) phosphoryl)-D-serine bis triethylamine salt Hydrogenated a solution of (2R)-3-(((benzyloxy)((R)-3-(benzyloxy)-2-(((benzyloxy)carbonyl)amino)-3-oxopropoxy)phosphoryl)oxy)propane-1,2-diyl distearate 6 (800 mg, 0.72 mmol) in methanol, acetic acid, THF mixture (10:2:4, v:v:v, 10 mL) over 10% palladium on carbon (40 mg) at 1 atmosphere at room temperature. After 3 hours, the mixture was degassed, flooded with nitrogen, and filtered over celite. Triethylamine (0.5 mL) was added to the filtrate, and then concentrate under vacuum to give an oil. The oil was purified on a C18 column using methanol (0.5% triethylamine) as eluant to give O—(((R)-2,3-bis(stearoyloxy) propoxy)(hydroxy)phosphoryl)-D-serine bis triethylamine salt (360 mg, 50%) as a white solid.

MS (APCI+): 567.2 (M+1); 1H NMR (300 MHz, CDCl3): δ ppm 5.30-5.20 (m, 1H), 4.38-4.17 (m, 4H), 3.94-3.84 (m, 4H), 3.12-3.07 (m, 4H), 2.32-2.02 (m, 14H), 1.58-1.57 (m, 4H), 1.24-0.89 (m, 66H), 0.87-0.85 (m, (dd, J=0.6 Hz, 6H).

Example 2. Assay for In Vitro Cytotoxicity in Human Hepatocyte or Cancer Cells

LNPs can be tested in vitro over a series of 10 dilutions to determine IC50 in human hepatocyte/liver (HepG2; ATCC #HB8065) cells. As these formulations are generally expected to be nontoxic, a positive control of Lipofectamine™ 3000 (ThermoFisher #L3000015)-complexed mRNA (2 μl reagent/1 μg mRNA) is included in all studies. The mRNA used is CleanCap FLuc, EGFP, or MCherry reporter gene mRNA (5moU; Trilink #L-7202, #L-7201, or #L-7203). Data is reported out as the full cell viability curve, as well as a calculation of the actual IC50 value for each compound.

Adherent cells are grown to ~80% confluency. The cells are trypsinized by adding 0.25% trypsin-EDTA (Gibco #25200-072) and the cells subsequently spun down, and 5 ml of growth medium (MEM media; Corning #10010 CM) added to disperse the cells. The cell density is determined using a hemocytometer. Growth medium (MEM media containing 10% FBS; Corning #35015 CV) is added to the cells to adjust to an appropriate concentration of cells. Then, 200 µl of the cells (5,000 cells/well) is added to a 96-well clear flat-bottom plate (Costar #9804) and incubated in the plate at 37° C. in a humidified incubator with 5% $CO_2$ for 24 h.

Serial dilutions of LNP formulations using growth medium as solvent are prepared. These compounds are provided as sterile aqueous with a concentration of 1 mg/ml mRNA. For making dilutions, each LNP stock was warmed to room temperature. These were further diluted to 4× in the growth media to the highest mRNA concentration tested of 250 ug/ml.

LNPs are added to the wells at a series of 1:3 dilutions from the initial 250 µg/ml concentration for each LNP by aspirating out the old media and replacing it with 200 µl of the LNP containing media. The plates were incubated at 37° C. in a humidified incubator with 5% $CO_2$ for 72 h. At the end of the LNP incubation period, replace the media in each well with 100 µl of 1× PrestoBlue Cell Viability Reagent (ThermoFisher Cat #A13261). Incubate the plate at 37° C. in a humidified incubator with 5% $CO_2$ 30 min to 2 h. Take readings at 30, 60, and 120 min. Read fluorescence with 560 nm excitation and 590 nm emission using SpectraMax M5 plate reader (Molecular Devices). Correct background by subtracting the RFU of the control containing only the culture medium (background control well) from all sample readings. Calculate the percentage of cytotoxicity using the formula below:

% Cytotoxicity=[(RFU$_{-Medium}$-RFU$_{Treatment}$)/RFU$_{-Medium}$]×100%

The IC50 was determined using GraphPad Prism using the following formula:

$Y = 100/(1+10^{((Log\ IC50-X)*HillSlope)})$

The cytotoxicity of Lipofectamine™ 3000 (ThermoFisher #L3000015)-complexed mRNA (2 µl reagent/1 µg mRNA) positive control can in some embodiments be 5-100-fold more toxic than compounds disclosed here. This shows that disclosed compounds are less toxic than commercial transfection reagents in an in vitro hepatocytotoxicity assay. In some embodiments, the compounds described herein form less toxic LNPs in vivo than commercially available transfection reagents.

Example 3. Determination of pKa of Ionizable Lipid

The pKa of an ionizable cationic lipid can be calculated several ways. For lipids this is sometimes difficult because membrane structure and neighboring lipids in the membrane can influence the dissociation properties of the amino group, potentially giving inaccurate values. An in-situ measurement is ideal, where the apparent pKa of the ionizable lipid is measured while the lipid is within its intended environment, in this case as part of an LNP (Jayaraman 2012, Sabins 2018).

For each LNP formulation, amino lipid pKa values are determined by measuring the fluorescence of 2-(p-toluidino)-6-napthalene sulfonic acid (TNS) during titration from pH 3 to 12. TNS is an anionic molecule that does not fluoresce in solution but increases fluorescence when associated with a positive lipid membrane, and this property has been used in the past to probe membrane surface charge. A master buffer stock is prepared (10 mM sodium phosphate, 10 mM sodium borate, 10 mM sodium citrate, 150 mM sodium chloride) which are used to prepare buffers at various pH values for determining apparent pKa. Using 1 M sodium hydroxide and 1 M hydrochloric acid, ~20 unique buffers from the master buffer stock are prepared at different pH values between about 3 and 12. 300 mM 6-(p-Toluidino)-2-naphthalenesulfonic acid sodium salt (TNS reagent) solubilized in dimethyl sulfoxide (DMSO) is used as a stock. LNP are prepared and purified into the desired pH buffer with a final mRNA concentration of 0.04 mg/mL. Using a 96-well plate, preloaded with desired buffers, mRNA containing LNP are added to so that the final concentration of mRNA is 0.7 µg/mL. To each well, TNS is added so that the DMSO concentration is 1% (v/v). After mixing, the fluorescence of TNS in each well is measured (Ex/Em 331 nm/445 nm) and a sigmoidal best fit analysis is applied to the fluorescence data. The pKa is determined as the pH giving rise to half-maximal fluorescence intensity. The apparent pKa measured for compounds 1-36 is within the pH range 6.0-7.0.

Example 4. Measurement of Cell Uptake of LNPs

Measurement of LNP cellular uptake is achieved by fluorescent imaging and/or fluorescent quantification. There are many suitable fluorescent tracers available, such as 1,1'-Dioctadecyl-3,3,3',3'-Tetramethylindocarbocyanine Perchlorate (DiI), 3,3'-Dilinoleyloxacarbocyanine Perchlorate (DiO), 1,1'-Dioctadecyl-3,3,3',3'-Tetramethylindodicarbocyanine Perchlorate (DiD) and 1,1'-Dioctadecyl-3,3,3',3'-Tetramethylindotricarbocyanine Iodide (DiR) (Thermo). These lipids are weakly fluorescent in water but exhibit high fluorescence when incorporated into lipid membranes such as those present in LNPs. It is important that the lipids chosen are photostable and have high extinction coefficients.

LNPs containing these types of lipids are visualized under a fluorescent microscope. In one method, LNP lipid formulation contains a fluorescent lipid tracer such as 1,1'-Dioctadecyl-3,3,3',3'-Tetramethylindodicarbocyanine-5,5'-Disulfonic Acid (DiI5-DS) at 0.1-0.5 mol % total lipid. Cells of interest are grown in a suitable cell culture dish, such as a 24-well plate (Corning). The cells are seeded the day prior to the uptake study at 50% confluency and grown overnight under appropriate conditions, for example 37° C., 5% CO2, 90-100% humidity. LNPs are added to cell culture medium at 0.1-100 ug/mL mRNA, allowed to interact with the cells for some time (4-24 h), then the cells are washed with media three times to remove non-internalized LNPs before viewing. The cells are viewed with a microscope with fluorescent detection capabilities. The relative extent of LNP cellular uptake is determined from the fluorescent intensity signal from the cells, using non-treated cells as a background control. Alternatively, quantitative measurement of cellular fluorescent lipid may be achieved by pelleting cells, solubilizing them with a detergent such as Triton-X100, and quantifying fluorescence by a spectrofluorometer or quantifying fluorescent lipid tracer by HPLC.

In a similar manner, the quantitation of fluorescently labeled mRNA is achieved. For example, dye-labeled enhanced green fluorescent protein (EGFP) and Firefly luciferase (FLuc) mRNAs, both transcribed with Cyanine 5-UTP:5-Methoxy-UTP at a ratio of 1:3 is currently available from Trilink Biotechnologies. Cyanine 5 has an excitation maximum of 650 nm and an emission maximum of 670 nm. Substitution in this ratio results in mRNA that is easily visualized and that can still be translated in cell culture. By entrapping fluorescently labeled mRNA one can visualize the intracellular delivery of mRNA by methods described above.

LNP uptake in cells may be achieved by endogenous methods such as ApoE mediated, or through exogenous methods such as active targeting. It was found that the LNP systems containing ionizable cationic lipids take advantage of a "natural" targeting process where they adsorb apolipoprotein E (ApoE) in the blood (Cullis et al 2017) and are then actively taken up in hepatocytes by a number of receptors that contain ApoE binding ligands (Williams et al. 2010). By using non-overlapping fluorophores it is possible to independently track mRNA and LNP intracellular distribution and organelle accumulation kinetics.

mRNA cellular expression levels may be quantified by using reporter systems such as EGFP, FLuc or mCherry, available from Trilink Biotechnologies. In one embodiment, EGFP mRNA is encapsulated in LNPs, and added to cells of interest at 0.1-100 ug/mL mRNA. The cells may be washed free of non-internalized LNP by replacing the media after 4-24 h. At 24 h, GFP signal is quantified by fluorescence microscopy or flow cytometry. In this way it is possible to differentiate between a panel of LNP formulations based upon reporter protein expression levels.

Example 5. Transfection Selectivity Index

A Transfection selectivity Index (TSI) is calculated to determine the relative transfection efficiency in mammalian cells, compared to the relative toxicity in those same cells. The selectivity index was calculated using the formula below:

$$TSI=EF_{mammalian}/IC_{50,mammalian}$$

where $EF_{mammalian}$ is the transfection efficiency expressed in terms of ng protein/million cells and $IC_{50,mammalian}$ relates to the cell viability of the same formulation in terms of half maximal inhibitory concentration.

The LNPs using compounds described here (1-36) have a 50% higher TSI than LNPs made using otherwise identical LNPs made with control molecule DLin-MC3-DMA as the ICL Example 6. An Assay for Lipid Peroxidation The extent of oxidation can be determined using a forced degradation assay where LNP samples are treated with 3% $H_2O_2$ at 25° C., and sampled on days 0, 1, 3, and 5 for lipid oxidation products (Blessy et al. (2014) Journal of Pharmaceutical Analysis 4, 159-165). The oxidation reaction can be quenched by addition of 0.1 M butylated hydroxytoluene (BHT) in ethanol and stored frozen at −80° C. until measurement. Lipid oxidation products can be measured using a 2-thiobarbituric acid (TBA) reactivity assay (Gutteridge (1982) FEBS Letters 150, 454-458) to detect malondialdehyde (MDA), an end product of lipid peroxidation or by detection using an HPLC assay with evaporative light scattering detection (ELSD) or charged aerosol detection (CAD). Lipid oxidation and isomerization impurity structures can be assigned based on known literature precedent and are expected to be mixtures of isomers.

Generally, it is known in the art that lipids with multiple unsaturations in the acyl chain are more sensitive to oxidation (see Reis and Spickett (2012) Biochim Biophys Acta 1818, 2374-2387).

It is anticipated that compounds 1-36 described herein will have less susceptibility to oxidative damage or degradation when compared to a control LNPs containing the DLin-KC2-DMA lipid or when compared to a control LNPs containing DLin-MC3-DMA. In some embodiments, the compounds provided herein have greater than 30%, greater 50%, greater 75%, greater 90%, and greater 95% reduction in oxidation byproducts when compared to the control LNP.

Example 7. Preparing Ligand-Targeted LNPs

Figure 2:
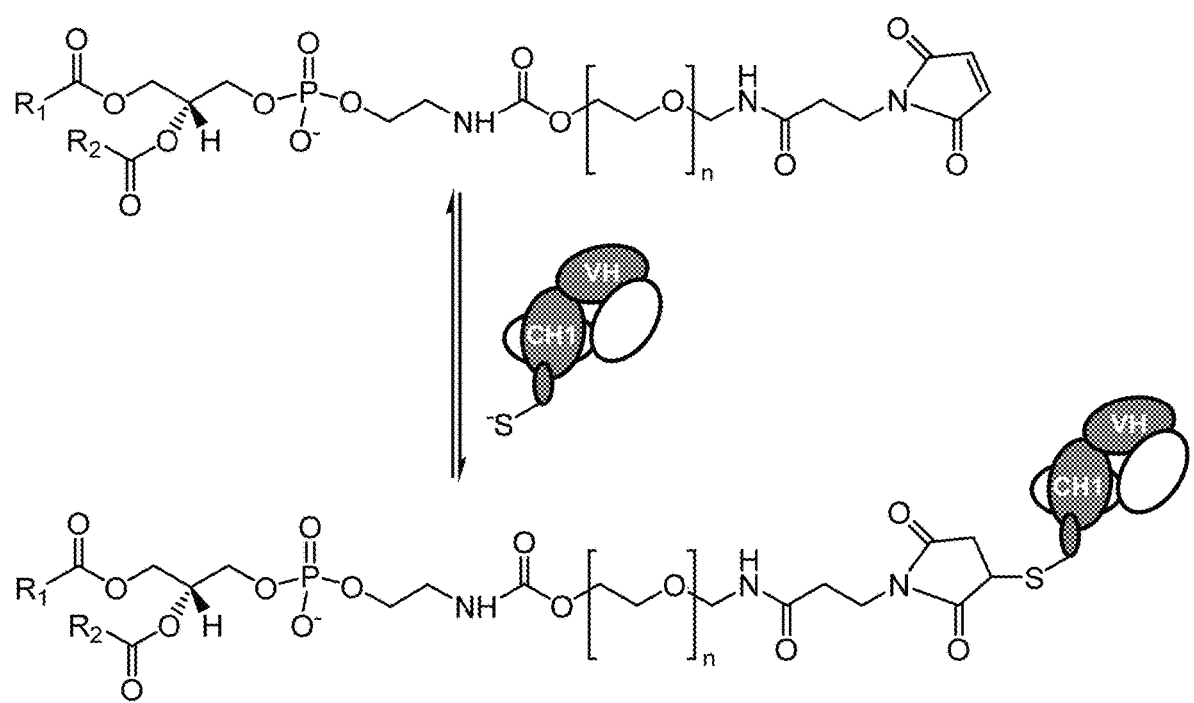
FIG. 2 shows the reaction of the reduced c-terminal cysteine of a Fab' antibody fragment with a maleimide terminated-poly(ethylene glycol) 2000 derivatized distearoylphosphatidylethanolamine. R1 and R2 are stearic acid. The final antibody lipopolymer conjugate is an intermediate that is subsequently inserted into the outer lipid layer of lipidic nanoparticle to make it actively targeted.

Antibody ligands providing for specific uptake of LNPs into the cells of interest, such as, immune cells, in the form of antibody Fab' fragments or single chain Fv fragments are prepared by any method known in the art (for example, as described in Drummond et al. U.S. Pat. Appl. 20180271998; Zhou et al. U.S. Pat. No. 10,406,225; Marks et al. U.S. Pat. No. 8,974,792, which are incorporated herein by reference in their entireties). To provide for conjugation of the ligands to LNPs, the ligands are constructed with a C-terminal sequence having a Cysteine residue, such as CAA, or GGSGGC, and subsequently conjugated to a maleimide-terminated PEG-DSPE anchor as per FIG. 2. The ligands are expressed in bacterial or eukaryotic cells and isolated from the cellular mass or growth medium using standard methods such as protein affinity chromatography or metal chelation chromatography. To activate the thiol group of a terminal Cysteine residue, the ligands are incubated in the presence of 15 mM Cysteine in a 10 mM citrate buffer, pH 6.0-6.2, containing 140 mM NaCl, for 1 hour, and purified by gel-chromatography on a Sephadex G-25 or similar column, eluent 10 mM citrate buffer, pH 6.0-6.2, containing 140 mM NaCl. The protein concentration in the purified, cysteine-activated ligand solution is determined using UV spectrophotometry at 280 nm. The antibody ligand, at 1-10 mg/ml in the above named buffer, is mixed with the aqueous solution of a maleimide-terminated PEG-DSPE derivative (mal-PEG(2000)-DSPE, cat. No. 880126, Avanti Polar Lipids, AL, USA, or Sunbright® DSPE-020MA, NOF corporation, Japan) at the protein/lipid molar ratio of 4:1. Mal-PEG-lipids having PEG spacer with molecular weight or 3,400 (Sunbright® DSPE-034MA) or 5,000, available from NOF Corporation (Sunbright® DSPE-050MA), can be used where longer distance between the LNP surface and the ligand moiety is desirable. The solution is incubated at ambient temperature for 2 hours, adjusted to 0.5 mM Cysteine to block unreacted maleimide groups, and the micellar ligand-PEG-DSPE conjugate is purified by gel chromatography on Ultrogel AcA 34 (if the ligand is a Fab) or Ultrogel AcA 44 (if the ligand is a scFv), eluent—144 mM NaCl buffered with 10 mM HEPES, pH 7.0-7.4. The conjugated protein is quantified by UV spectrophotometry, and the purity is confirmed by SDS gel-electrophoresis.

Ligand is appended to the surface of LNPs by one of the following methods.

Method 1. Preformed LNPs (obtained as described in Hope et al. U.S. Pat. No. 10,653,780 incorporated herein by reference in its entirety) are mixed with the micellar solution of the ligand-PEG-DSPE conjugate in a HEPES-buffered saline (10 mM HEPES, 140 mM NaCl, pH 7.0-7.2) to achieve the required ligand/lipid ratio in the range of 5-100

(typically 15-30) ligands per LNP particle. The mixture is incubated with slow agitation 2 hours at 37-40° C., or overnight at 2-8° C., during which time the conjugate is incorporated into the outer lipid layer of the LNPs. The ligand-conjugated LNPs are purified from unincorporated ligand-PEG-DSPE by gel chromatography on Sepharose CL-2B or CL-4B (hydrophilic size exclusion media with the same molecular weight cutoff can be also used); the LNP fraction appearing near the void volume is collected. The amount of ligand conjugated to the particles is determined by SDS gel-electrophoresis with Coomassie Blue or fluorescent staining and concurrently run ligand standards.

Method 2. A solution of the ligand-PEG-DSPE conjugate in 10 mM Na-citrate buffer pH 4.0 containing also the nucleic acid component of the LNP is mixed with the ethanolic solution of the LNP lipids to the final ethanol concentration of 40% by volume as described by Semple et al., U.S. Pat. No. 8,021,686, incorporated herein by reference in its entirety. Alternatively, a LNP-preparation protocol of Hope et al. U.S. Pat. No. 10,653,780 (incorporated herein by reference in its entirety) is employed. The amount of ligand-PEG-DSPE is 0.1-1 mol % of the lipid. The mixture is dialyzed against HEPES-buffered saline (10 mM HEPES, 140 mM NaCl, pH 7.0) to remove ethanol. Ligand-PEG-DSPE is incorporated in the resulting LNPs. Any residual ligand-PEG-DSPE is removed by gel chromatography using Sepharose CL-4B or CL-2B, eluent HEPES-buffered saline, or by buffer exchange for HEPES-buffered saline by tangential flow filtration on a polysulfone membrane (flat or hollow fiber cartridge) having 500 KD molecular weight cutoff.

Method 3. Mal-PEG-DSPE is combined with preformed LNPs in a citrate-buffered saline (10 mM Na-citrate buffer pH 6.0-6.2, 140 mM NaCl) in the amount of 0.1-1 mol % relative to the LNP lipid in the same manner as ligand-PEG-DSPE of Method 1. LNPs with incorporated mal-PE-DSPE are purified from unincorporated mal-PEG-DSPE by gel chromatography on Sepharose CL-4B in the same buffer, and incubated with thiol-activated antibody ligand (5-100 ligands pre LNP particle) for 2-24 hours. Ligand-conjugated LNP so obtained are purified from unconjugated ligand by Sepharose CL-4B gel chromatography using HEPES-buffered saline pH 7.0 as eluent.

Method 4. Mal-PEG-DSPE is incorporated into the LNPs at 0.1-1 mol % of the LNP lipid in the same manner as ligand-PEG-DSPE according to Method 2. The resulting Mal-PEG-conjugated LNPs are incubated with the thiol-activated ligand and purified as described in Method 3.

Method 5. The protocol of Method 4 is performed with the difference that instead of mal-PEG-DSPE a maleimide-conjugated lipid without a PEG spacer (mal-DSPE, Coatsome® FE-808MA3, NOF corporation, Japan) is added to the lipid solution. The resulting maleimide-LNPs are conjugated to thiol-activated ligand as per Method 3.

Method 6. A low-molecular ligand (e.g., mannose) is conjugated to LNP by the Methods 1 or 2 wherein a mannose-PEG-DSPE (Biochempeg Scientific, MA, USA, cat. No. 12169) is substituted for an antibody ligand-PEG-DSPE.

Example 8. Determining Optimal Ligand Density of the Ligand-Targeted LNPs

A panel of LNPs are prepared with the increasing ligand density in a given range (2-200 ligands per LNP particle, or 5-100 ligands per LNP particle) using any of the methods of Example 7. The LNPs are fluorescently labeled by incorporation of a fluorescently labeled lipid or fluorescently labeled nucleic acid as described in Example 4. The labeled ligand-conjugated LNPs are tested for the cell uptake according to Example 4, and the ligand content corresponding to the maximum of the ligand-specific cell uptake of the LNPs is determined. The nucleic acid intracellular function (such as mRNA expression) can be used as an assay output (Example 4), in which case the presence of a lipid or nucleic acid detectable label is not necessary.

Example 9. Preparation of Lipidic Nanoparticles (LNPs)

mRNA modified with 5-methoxyuridine (5moU) and coding for mCherry (Cat #L-7203) was obtained from Trilink Biotechnologies (San Diego, CA). All uridine nucleosides were substituted with N1-methyl-pseudouridine. To produce the mRNA, a synthetic gene encoding the mRNA sequence was cloned into a DNA plasmid. The synthetic gene was comprised of an RNA promoter, a 5' untranslated region, mCherry protein coding sequence, a 3' untranslated region, and a poly(A) tail region of approximately 120 As. The open reading frame sequence for the mCherry mRNA from Tri-Link (Cat #L-7203) corresponds to SEQ ID NO: 1:

AUGGUGAGCAAGGGCGAGGAGGACAACAUGGCCAUCAUCAAGGAGUUCAU

GCGGUUCAAGGUGCACAUGGAGGGCAGCGUGAACGGCCACGAGUUCGAGA

UCGAGGGCGAGGGCGAGGGCCGGCCCUACGAGGGCACCCAGACCGCCAAG

CUGAAGGUGACCAAGGGCGGCCCCCUGCCCUUCGCCUGGGACAUCCUGAG

CCCCCAGUUCAUGUACGGCCAGCAAGGCCUACGUGAAGCACCCCGCCGACA

UCCCCGACUACCUGAAGCUGAGCUUCCCCGAGGGCUUCAAGUGGGAGCGG

GUGAUGAACUUCGAGGACGGCGGCGUGGUGACCGUGACCCAGGACAGCAG

CCUGCAGGACGGCGAGUUCAUCUACAAGGUGAAGCUGCGGGGCACCAACU

UCCCCAGCGACGGCCCCGUGAUGCAGAAGAAGACCAUGGGCUGGGAGGCC

AGCAGCGAGCGGAUGUACCCCGAGGACGGCGCCCUGAAGGGCGAGAUCAA

GCAGCGGCUGAAGCUGAAGGACGGCGGCCACUACGACGCCGAGGUGAAGA

CCACCUACAAGGCCAAGAAGCCCGUGCAGCUGCCCGGCGCCUACAACGUG

AACAUCAAGCUGGACAUCACCAGCCACAACGAGGACUACACCAUCGUGGA

GCAGUACGAGCGGGCCGAGGGCCGGCACAGCACCGGCGGCAUGGACGAGC

UGUACAAGAGCGGCAACUGA

Stock solutions of each lipid were prepared. Ionizable lipids were weighed out in 4 mL glass vials (Thermo B7999-2) and dissolved in ethanol (Sigma-Aldrich 200 proof, RNase free) to a final concentration of 10 mM. Other lipids such as DSPC, DPPC-NH$_4$, Cholesterol and PEG-DMG were weighed out and dissolved in ethanol to a concentration of 1 mM. DSPS-Na was dissolved in methanol (Sulpelco, Omnisolve) at a concentration of 1 mM and briefly heated to 70° C. to complete its dissolution.

Lipid mixtures for each individual LNP were prepared by adding the desired volume of each lipid stock solution to a new vial, adding ethanol if needed to achieve a final volume of 1.2 mL. For example, an LNP formulation of AKG-UO-1/DSPC/DSPS/Chol/PEG-DMG (50/2.5/7.5/38.5/1.5 mol %), with an N/P of 5 contained 1500 nmol AKG-UO-1, 75 nmol DSPC, 225 nmol DSPS, 1155 nmol Chol and 45 nmol PEG-DMG for every 100 μg of mRNA used.

mRNA solutions were prepared by thawing frozen mRNA (mCherry mRNA, Trilink) vials and diluting mRNA in 6.25 mM sodium acetate (pH 5.0) to a final concentration of 0.033 mg/mL. To prepare LNPs, a NanoAssemblr Benchtop microfluidic device (from Precision Nanosystems) was used. If LNPs contained the sodium or ammonium salts of DSPS, or sodium salt of DPPS the heating block accessory set to 70° C. was used, otherwise LNPs were mixed at room temperature. 3 mL of mRNA solution was loaded into a 3 mL disposable syringe (BD 309656) and 1 ml of lipid mixture in a 1 ml syringe (BD309659) and placed in the NanoAssemblr heating block for 4 min prior to mixing. LNP formation was achieved by pumping the liquid streams through a disposable microfluidics cassette at 3:1 aqueous: alcohol volume ratio at 6 mL/min mixing speed. After mixing, 3.6 mL of LNP mixture was collected, while the initial mixed volume of 0.35 mL and last 0.05 mL of mix was discarded. Ethanol was removed by buffer exchange using SpectraPor dialysis tubing (12-14k MWCO) in PBS (Cytivia, SH30256.01) or by sequential concentration and dilution using Amicon Ultra-4 centrifugal concentrators (10k MWCO, at 500 g).

LNPs were typically exchanged into PBS, pH 7.4 and then 15 mM Tris, pH 7.4, 20% sucrose, concentrated to 20-50 ug/mL mRNA using an Amicon-Ultra 4 (100,000 MWCO) spin column, sterile filtered (Thermo Nalgene 0.2 um #720-1320) prior to freezing by immersion in liquid nitrogen for 5 min and long-term storage at −80° C.

Example 10. LNP Characterization

A. mRNA Concentration and Relative Encapsulation Efficiency Determination by Fluorescent Binding Dye Materials: Ribogreen reagent (Thermo #11491), 3×96-well plates with lids, PBS, dissociation buffer (PBS with 10% DMSO and 1% (wt/wt) Zwittergent 3-14 (Sigma-Aldrich #693017), mRNA, general pipette tips & repeater pipette tips.
  1. 5 mL of 2 µg/mL mRNA stock were prepared in DPBS or PBS
  2. Diluted standards were prepared as follows in single wells in a 96-well plate (Plate A);

| Final [mRNA] ng/mL | Vol. stock 2 µg/mL (µL) | Vol. PBS (µL) |
|---|---|---|
| 2000 | 400 | 0 |
| 1500 | 300 | 100 |
| 1000 | 200 | 200 |
| 500 | 100 | 300 |
| 0 | 0 | 400 |

3. Using different wells in Plate A, sample mRNA concentration was estimated and were diluted to be within the standard curve. For example, if the approximate mRNA concentration should be ~30 ug/mL in the sample, a 20× dilution was performed (Dilution Factor). (20 uL sample added to 380 µL PBS in a well). No lid was used on plate A. Samples were mixed by gentle pipetting up & down.

Example of Plate A

| | | | | | | | | |
|---|---|---|---|---|---|---|---|---|
| A | 0 | 500 | 1000 | 1500 | 2000 | | | |
| B | | | | | | | | |
| C | S 1 | S 2 | S 3 | S 4 | S 5 | S 6 | S 7 S 8 | Etc. |
| D | | | | | | | | |
| E | | | | | | | | |
| F | | | | | | | | |
| G | | | | | | | | |
| H | | | | | | | | |

4. Two more plates, plates B & C were used. Using a multichannel pipettor, 60 µL of each standard 2 were pipetted into wells each (duplicate), and sample into 3 wells each (triplicate)

Example of Plate B and C

| | | | | | | | | |
|---|---|---|---|---|---|---|---|---|
| A | 0 | 500 | 1000 | 1500 | 2000 | | | |
| B | 0 | 500 | 1000 | 1500 | 2000 | | | |
| C | S 1 | S 2 | S 3 | S 4 | S 5 | S 6 | S 7 S 8 | Etc. |
| D | S 1 | S 2 | S 3 | S 4 | S 5 | S 6 | S 7 S 8 | Etc. |
| E | S 1 | S 2 | S 3 | S 4 | S 5 | S 6 | S 7 S 8 | Etc. |
| F | | | | | | | | |
| G | | | | | | | | |
| H | | | | | | | | |

5. The number of wells used on each plate was counted and 4 was added to this number. For plate B, PBS was prepared with Ribogreen diluted 1:100. For example, for 40 wells, 44 was used as the number. 44×60 µL=2.64 mL Ribogreen solution needed, so that would be 2.61 mL PBS with 26.4 µL Ribogreen.
  6. For plate C, 2.61 mL Dissociation buffer and 26.4 uL Ribogreen was pipetted.
  7. Using a repeater pipette set for 60 µL, PBS+RiboGreen was added to each well on plate B and 60 µL Dissociation Buffer+Ribogreen to plate C. Both plates B and C were mixed on an orbital mixer (120 rpm) for 1 min. Plate B was placed in the dark for 15 min. Plate C was incubated at 37° C. in the dark for 10 min, followed by 5 min at RT.
  8. Both plates were read one after the other, using Ex. 465, Em. 530 nm
  9. Using the standard curve, the slope and intercept were calculated and by extrapolation the mRNA concentrations of the samples on plate B & C were calculated (average and std. dev)
  10. Percent encapsulation efficiency (% EE) by [mRNA] plate B/[mRNA] plate C×100 was calculated
  11. Total [mRNA] by taking [mRNA] plate C X dilution factor was calculated.

B. LNP Particle Size
  1. 30 µL of LNP was mixed with 1.5 mL PBS in a polystyrene cuvette (Sarstedt, #67.754) and analyzed for size using a ZetaSizer Pro (Malvern) using ZS Xplorer software, version number 1.4.0.105. The Z-average size and polydispersity index value were recorded. Typically, size measurements of LNPs were taken post LNP mixing, post buffer exchange and post sterile filtering.

C. LNP Zeta Potential
  1. 30 µL of LNP was mixed with 1.5 mL PBS and injected into a disposable folded capillary cell (Malvern Nanoseries DTS1070) and zeta potential measured on a ZetaSizer Pro at 25° C.

Example 11. Determination of Transfection Efficiency in Murine Dendritic Cells of LNPs Using mCherry mRNA A. Cell Propagation, Transfection, Harvesting and Staining Protocol
1. MutuDC1940 cells (Applied Biological Materials, T0528) were grown according to supplier's instructions in T75 flasks. They were plated at 180,000 cells/well into 24-well plate one day prior to transfection.
2. LNPs were added in triplicate to each well at the desired mRNA concentration (e.g. 1 μg/mL) in 1 mL media and after 24 h the cells were washed once with DPBS (VWR 02-0119-1000).
3. 0.2 mL of DPBS (plus 5 mM EDTA, pH 7.4) was then added to facilitate detachment.
4. The cells were placed at 37° C. for 3 min, until detached.
5. 0.5 ml DPBS added to each well and the liquid transferred to a flow cytometry tube (Falcon 5 mL #352054).
6. The tube was centrifuged at 1100 rpm for 3-5 min and the liquid poured off.
7. 100 μL of Zombie Violet (Biolegend) (diluted 1:500 in PBS) was added to each tube.
8. The tubes were gently tapped to resuspend cells and placed in the dark for 15 min at RT.
9. To the cells 0.5 mL of (paraformaldehyde 4% in PBS:DPBS 1:1) was added and the cells flicked gently to resuspend and put on ice for 30 min. Another 2 ml PBS was added.
10. The cells were pelleted as above and resuspended in 0.5 mL DPBS with 5% BSA and placed in the fridge until needed.

B. Cell Analysis

Cells suspensions were analyzed by an Attune NxT flow cytometer using the VL1 and YL2 for live/dead and mCherry fluorescence signals respectively. Gating analysis was performed on FloJo software.

Example 12. Impact of DSPS on Transfection Efficiency of Dendritic Cells Using LNPs with KC2 as Ionizable Cationic Lipid The aim of this study was to explore the effect of phosphatidylserine targeting using DSPS on transfection efficiency in murine dendritic cells. LNPs were prepared as described in Example 9, characterized for particle size and zeta potential as described in Example 10, and evaluated for transfection efficiency in murine dendritic cells as described in Example 11. The LNPs all had DLin-KC2-DMA constant at an N/P ratio of 5 and 50 mol % of total lipid, the PS lipid was varied initially from 0-2.5 mol % and the DSPC phospholipid varied from 0-7.5 mol % (Total mol % of DSPC and DSPS was constant at 10 mol %), and the cholesterol constant at 38.5 mol % (all mol % of total lipid). The particle size, Polydispersity Index (PDI), and entrapment efficiency for all formulations is shown below in Tables 5 and 6.

TABLE 5

Physicochemical properties of KC2-containing LNPs used in Example 12 varying from 0-2.5 mol % used in Example 12 and FIG. 3A.

| Mol % DSPS | Particle Size (nm) | PDI | % Encapsulation ± SD |
|---|---|---|---|
| 0 | 77.6 | 0.075 | 86.4 ± 2.8 |
| 0.1 | 82.0 | 0.171 | 87.0 ± 4.7 |
| 0.5 | 89.2 | 0.285 | 86.3 ± 3.2 |
| 2.5 | 72.2 | 0.263 | 87.1 ± 6.8 |

TABLE 6

Physicochemical properties of KC2-containing LNPs varying from 0-7.5 mol % used in Example 12 and FIG. 3B, FIG. 3C, and FIG. 3D.

| Mol % DSPS | Particle Size (nm) | PDI | % Encapsulation ± SD |
|---|---|---|---|
| 0 | 73.9 | 0.14 | 92.6 ± 6.2 |
| 1.25 | 80.3 | 0.13 | 90.9 ± 5.6 |
| 2.5 | 70.7 | 0.25 | 89.0 ± 7.4 |
| 5 | 78.7 | 0.12 | 85.1 ± 6.8 |
| 7.5 | 76.4 | 0.14 | 85.4 ± 3.6 |

An initial set of LNPs containing DLin-KC2-DMA and varying phosphatidylserine in the form of DSPS from 0-2.5 mol %, showed little transfection at 0 or 0.5 mol % DSPS, but increase by 18-fold when DSPS was incorporated at 2.5 mol % (FIG. 3A). A second series of LNPs prepared with DSPS from 0-7.5 mol % was evaluated at 0.1, 0.3, and 1 μg/mL mRNA concentrations (FIG. 3B, FIG. 3C and FIG. 3D). The transfection efficiency increased as the mol % of DSPS was increased above 2.5 mol %, with a maximum at 7.5 mol % at 1 μg/mL mRNA, and 5 mol % at both 0.1 and 0.3 μg/mL mRNA. These data demonstrate that the inclusion of phosphatidyl-L-serine can dramatically increase the transfection efficiency of mRNA-containing LNPs, and that maximal uptake occurs between 5-7.5 mol % of DSPS (as % of total lipid).

Example 13. Impact of ICL and Anionic Phospholipid Targeting Ligand on mRNA Transfection of Dendritic Cells The aim of this study was to see if other anionic phospholipids could also enhance the transfection efficiency of LNPs and how LNPs prepared with varying ICLs and PS targeting would transfect dendritic cells. LNPs were prepared as described in Example 9, characterized for particle size and zeta potential as described in Example 10, and evaluated for transfection efficiency in murine dendritic cells as described in Example 11. The LNPs had various ICLs (DLin-KC2-DMA, KC2-OA, KC3-OA, or SM-102) constant at an N/P ratio of 5 and 50 mol % of total lipid, the PS lipid was kept constant at 5 mol % and the DSPC at 5 mol %, and the cholesterol constant at 38.5 mol % (all mol % of total lipid). The particle size, PDI, and entrapment efficiency for all formulations is shown below in Table 7.

TABLE 7

Physicochemical properties of LNPs varying in ICL used and with anionic phospholipid at 5 mol %.

| Ionizable Cationic Lipid (ICL) | Anionic lipid | Particle Size (nm) | PDI | % Encapsulation ± SD |
|---|---|---|---|---|
| KC2 | 5% DSPS | 90.9 | 0.13 | 91.0 ± 5.8 |
| KC2-OA | 5% DSPS | 74.8 | 0.13 | 92.8 ± 8.0 |

TABLE 7-continued

Physicochemical properties of LNPs varying in ICL
used and with anionic phospholipid at 5 mol %.

| Ionizable Cationic Lipid (ICL) | Anionic lipid | Particle Size (nm) | PDI | % Encapsulation ± SD |
|---|---|---|---|---|
| KC3-OA | 5% DSPS | 95.5 | 0.09 | 96.6 ± 18.3 |
| SM-102 | None | 77.5 | 0.05 | 92.6 ± 5.0 |
| SM-102 | 5% DSPS | 65.9 | 0.13 | 84.5 ± 7.7 |
| KC2 | 5% Glu-DSPE | 52.1 | 0.23 | 87.9 ± 6.8 |
| KC2 | 5% Suc-DSPE | 64.6 | 0.19 | 86.6 ± 3.6 |

The transfection results are shown in FIG. 4 show high transfection rates with three different KC-series ICLs (KC2, KC2-OA, and KC3-OA), and also with LNPs prepared with the branched ICL, SM-102. The encapsulation efficiency was high and the particle size below 100 nm for all formulations, including those prepared with alternate anionic phospholipids (Suc-DSPE or Glu-DSPE). The data demonstrate that DSPS (L-serine) can not be substituted with either N-glutaryl-distearoylphosphatidylethanolamine (Glu-DSPE) or N-succinyl-distearoylphosphatidylethanolamine (Suc-DSPE) and provide the same high level of mRNA transfection despite both phospholipids also containing two negative charges and both containing the same distearoyl (C18:0) fully saturated acyl chains. These studies also clearly show that the addition of DSPS can give rise to high transfection efficiencies for other ionizable cationic lipids, including those with a single unsaturated acyl gain (KC2-OA or KC3-OA) and those including a branched ICL, like SM-102. The addition of DSPS to SM-102 containing LNPs gave rise to a 22-fold increase in mCherry expression, for example.

Example 14. Dependence of PS Targeting on ICL and PS Structure

The aim of this study was to compare PS-targeted LNPs with KC2 and KC3 series ionizable cationic lipids of varying acyl chain composition. KC2 series lipids having a structure of dimethylaminoethyl headgroup structure were compared to the KC3 series containing a dimethylaminopropyl-derivatized head group. The LNPs contained various ICLs (KC2, KC2-01, KC2-OA, KC2-PA, KC3-OA, and KC3-01) as the ICL at an N/P ratio of 5 and 50 mol % ICL, and a constant 0.1.5 mol % PEG-DMG. The cholesterol content was held constant at 38.5 mol % and the DSPC content varied inversely with the mol % of DSPS at either 0 or 5 mol % (all lipid concentrations were used as mol % of total lipid). Transfection efficiency was evaluated in murine dendritic cells as described in Example 11.

TABLE 8

Physicochemical properties of LNPs varying in ICL
used and with anionic phospholipid at 5 mol %.

| Ionizable Cationic Lipid (ICL) | PS content | Particle Size (nm) | PDI | % Encapsulation ± SD |
|---|---|---|---|---|
| KC2 | None | 95.6 | 0.08 | 91.7 ± 2.0 |
| KC2 | 5% DSPS | 82.5 | 0.09 | 87.1 ± 3.8 |
| KC2-01 | None | 82.4 | 0.08 | 91.6 ± 3.9 |
| KC2-01 | 5% DSPS | 76.0 | 0.10 | 90.5 ± 3.5 |
| KC2-OA | None | 89.5 | 0.08 | 88.6 ± 4.2 |
| KC2-OA | 5% DSPS | 85.9 | 0.10 | 92.4 ± 4.5 |
| KC2-PA | None/10% DPPC | 92.3 | 0.11 | 92.4 ± 4.4 |
| KC2-PA | 5% DSPS/5% DPPC | 85.2 | 0.10 | 95.5 ± 3.4 |
| KC3-01 | None | 88.2 | 0.10 | 94.3 ± 7.1 |
| KC3-01 | 5% DSPS | 101.2 | 0.16 | 95.2 ± 4.4 |
| KC3-OA | None | 105.9 | 0.08 | 86.6 ± 1.6 |
| KC3-OA | 5% DSPS | 103.0 | 0.13 | 93.8 ± 3.2 |
| KC2-PA | 5% DPPS/5% DPPC | 77.1 | 0.06 | 93.8 ± 3.7 |

The transfection results are shown in FIG. 5 and clearly show a positive impact of PS targeting on multiple KC-series ICLs. Here, the data show that ICLs containing both unsaturated C16 and C18 ICLs could be targeted with phosphatidyl-L-serine and give rise to high transfection rates for dendritic cells. The highest rate of transfection came when the PS and PC contained a mismatched acyl chain composition, with 5 mol % DPPC and 5 mol % DSPS, and combined with a C16 ICL (KC2-PA).

Example 15. Impact of Phosphatidylserine Structure on Transfection Efficiency of LNPs The aim of this study was to explore the effect of different anionic phospholipid structures on transfection efficiency in dendritic cells. LNPs were prepared as described in Example 9, characterized for particle size and zeta potential as described in Example 10, and evaluated for transfection efficiency in murine dendritic cells as described in Example 11. The LNPs all had AKG-UO-1 constant at an N/P ratio of 5 and 50 mol % of total lipid, the anionic lipid was varied depending on the formulation and inversely to the DSPC phospholipid, and the cholesterol constant at 38.5 mol % except for the 20 mol % DSPS LNP (all mol % of total lipid). For samples that contained up to 10% phosphatidylserine component, the phosphatidylcholine composition was reduced accordingly from 10 mol %. For example, an LNP with 5 mol % DSPS, contained 5 mol % DSPS and 5 mol % DSPC, and those that contained 10 mol % DSPS had no DSPC. However, for the sample that contained 20 mol % DSPS, there was no DSPC in the formulation and the mol % cholesterol was reduced by 10 mol % to 28.5 mol %.

The entrapment efficiency for all formulations was between 84 and 90%, indicating highly efficiency mRNA entrapment in the LNP.

TABLE 9

Physicochemical properties and encapsulation for LNPs prepared
with AKG-UO-1 as the ICL and varying anionic phospholipids.

| LNP Formulation (anionic lipid) | Particle Size (nm) | PDI | Zeta Potential at pH 5 (mV) | Zeta Potential at pH 7 (mV) | % Encapsulation |
|---|---|---|---|---|---|
| No Anionic lipid | 98.1 | 0.03 | 13.01 | −0.2 | 84.2 ± 4.2 |
| 2.5% L-DSPS | 96.8 | 0.03 | 3.4 | −1.7 | 86.1 ± 5.0 |
| 5% L-DSPS | 95.7 | 0.05 | 14.9 | −2.9 | 88.3 ± 3.2 |
| 7.5% L-DSPS | 95.1 | 0.10 | 17.0 | −4.2 | 89.1 ± 3.6 |
| 10% L-DSPS | 100.5 | 0.08 | 15.2 | −5.1 | 89.6 ± 3.1 |
| 7.5% L-DPPS | 96.3 | 0.07 | 17.8 | −7.6 | 88.1 ± 2.7 |
| 7.5% D-DSPS | 100.1 | 0.14 | 19.5 | −9.6 | 87.4 ± 4.4 |
| 7.5% L-DOPS | 110.4 | 0.07 | 15.1 | −3.5 | 89.5 ± 3.5 |
| 7.5% L-DMPS | 97.6 | 0.08 | 12.7 | −3.8 | 88.4 ± 1.3 |
| 20% L-DSPS | 97.7 | 0.07 | 7.0 | −7.0 | 88.5 ± 1.9 |
| 5% DSPG | 86.6 | 0.04 | 17.5 | −4.7 | 87.1 ± 3.1 |
| 7.5% DSPG | 85.0 | 0.08 | 16.6 | −4.1 | 90.1 ± 0.9 |
| 7.5% Glu-DSPE | 94.0 | 0.07 | 16.9 | −6.4 | 89.6 ± 9.1 |
| 7.5% Suc-DSPE | 96.9 | 0.05 | 14.3 | −5.6 | 88.4 ± 9.0 |

The effect of different phosphatidylserine chemical forms was evaluated in FIG. 6A showing the importance of saturation, acyl chain length, and serine stereochemistry on LNP transfection activity in murine dendritic cells. PS analogs with oleic acid acyl chains (DOPS) or where the stereochemistry as (D-serine) rather than L-serine gave rise to LNPs with transfection activity similar to that of LNPs prepared without any phosphatidylserine. However, LNPs prepared with PS containing the L-isomer of serine and saturated acyl chains are significantly better at transfecting dendritic cells compared to LNPs without any PS. Of the saturated series, those with C16 (DPPS) or C18 (DSPS), showed the highest activity, while those with C14 (DMPS) was lower, although still improved compared to dendritic cells treated with LNPs without any PS. In FIG. 6B the impact of other anionic phospholipids were evaluated with DSPG-containing formulations (5 or 7.5 mol %) showing activity similar to background, and N-glutaryl- or N-succinyl-distearoylphosphatidylethanolamine (Glu-DSPE or Suc-DSPE) showing a more modest 3-5-fold enhancement of activity when included in these AKG-UO1 containing LNPs. This example shows that LNPs prepared with saturated phosphatidyl-L-serines transfect dendritic cells significantly better than those containing the unsaturated dioleoylphosphatidyl-L-serine (DOPS) or the D-isomer of DSPS. LNPs containing the L-isomers of DSPS and DPPS showed the highest level of transfection compared to other forms of PS, anionic N-glutaryl or N-succinyl DSPE analogs, or distearoylphosphatidylglycerol (DSPG) at either 5 or 7.5 mol %.

Example 16. Optimizing the DSPS Density on AKG-UO-1 Containing LNPs

The aim of this study was to explore the impact of DSPS density on transfection efficiency of LNPs. LNPs were prepared as described in Example 9. The LNPs contained AKG-UO-1 as the ICL at an N/P ratio of 5 with between 0 and 20 mol % DSPS and a constant 1.5 mol % PEG-DMG. The cholesterol content was held constant at 38.5 mol % and the DSPC content varied inversely with the mol % of DSPS between 0-10 mol % (all lipid concentrations were used as mol % of total lipid). In the 20 mol % DSPS formulation, there was no DSPC and the cholesterol content decreased in the total by 10 mol % (from 38.5 to 28.5 mol %). Transfection efficiency was evaluated in murine dendritic cells as described in Example 11.

TABLE 10

Physicochemical properties and encapsulation for LNPs prepared
with AKG-UO-1 as the ICL and varying anionic phospholipids.

| LNP Formulation | Particle Size (nm) | PDI | Zeta Potential at pH 5 (mV) | Zeta Potential at pH 7 (mV) | % Encapsulation |
|---|---|---|---|---|---|
| UO1 + 0% DSPS | 98.1 | 0.03 | 13.0 | −0.2 | 84.2 ± 4.2 |
| UO1 + 2.5% DSPS | 96.8 | 0.03 | 3.4 | −1.7 | 86.1 ± 5.0 |
| UO1 + 5% DSPS | 95.7 | 0.05 | 14.9 | −2.9 | 88.3 ± 3.2 |
| UO1 + 7.5% DSPS | 95.1 | 0.10 | 17.0 | −4.2 | 89.1 ± 3.6 |
| UO1 + 10% DSPS | 100.5 | 0.08 | 15.2 | −5.1 | 89.6 ± 3.1 |
| UO1 + 20% DSPS | 97.7 | 0.07 | 7.0 | −7.0 | 88.5 ± 1.9 |

The dependence of the LNP composition on DSPS concentration is shown in FIG. 7 for the AKG-UO1 containing LNPs. This study suggests that the presence of DSPS in the formulation allows for a high level of transfection of dendritic cells between 2.5 and 10 mol % DSPS, and an apparent peak around 5-7.5 mol % DSPS for AKG-UO-1 containing LNPs.

Example 17. Impact of PEG on Transfection Efficiency of AKG-UO-1 Containing LNPs The aim of this study was to explore the impact of PEG-lipid density on transfection efficiency of nontargeted and phosphatidyl-L-serine targeted LNPs. LNPs were prepared as described in Example 9. The LNPs contained AKG-UO-1 as the ICL at an N/P ratio of 5 with either 0 or 5 mol % DSPS and between 0.5-4.5 mol % PEG-DMG. The cholesterol content was held constant at 38.5 mol % and the DSPC content was 10 mol % for the formulations with no DSPS and 5 mol % for those with 5 mol % DSPS. At PEG-DMG content above 1.5 mol %, the total cholesterol content was reduced by the amount of PEG-DMG added, for example with a PEG-DMG content of 3.5 mol %, the cholesterol content was reduced to 36.5 mol % from 38.5 mol %. The particles with 0.5% PEG-DMG showed a negative zeta potential at pH 7.4, and a significant shift to a positive zeta potential at pH 5. The LNPs with 1.5-3.5 mol % PEG-DMG were essentially neutral at pH 7.

TABLE 11

Physicochemical properties of LNPs used in Example 17 and containing AKG-UO-1, 0 or 5 mol % DSPS

| % DSPS | % PEG-DMG | Particle Size (nm) | Zeta Potential at pH 7 (mV) | Zeta Potential at pH 5 (mV) |
|---|---|---|---|---|
| 0 | 0.5 | 98.9 | 0.27 | 25.92 |
| 0 | 1.5 | 75.0 | −0.87 | 12.07 |
| 0 | 2.5 | 73.8 | −0.51 | 11.86 |
| 0 | 3.5 | 81.0 | −0.30 | 6.34 |
| 0 | 4.5 | 143 | −1.47 | 14.51 |
| 5 | 0.5 | 106.1 | −1.35 | 9.30 |
| 5 | 1.5 | 73.7 | −0.21 | 3.23 |
| 5 | 2.5 | 70.7 | −0.20 | 4.75 |
| 5 | 3.5 | 65.6 | −0.10 | 7.54 |
| 5 | 4.5 | 63.1 | −1.12 | 3.73 |

The impact of PEG-DMG on transfection of dendritic cells by DSPS-targeted LNPs containing the AKG-UO-1 ICL is shown in FIG. 8. The formulation with 0.5% PEG-DMG showed a transfection efficiency in the presence of 5% DSPS that was between 6-7 fold higher than observed at 1.5-2.5% PEG-DMG. Transfection at 1.5 and 2.5% PEG-DMG was similar, but decreased dramatically at 3.5 and 4.5 mol % PEG-DMG. The ratio of targeted to nontargeted transfection at each PEG-density varied, and was 12-fold at 0.5% PEG, 7-fold at 1.5% PEG, 37-fold at 2.5% PEG, and below 5-fold at 3.5 and 4.5% PEG, likely because of high PEG-shielding of the PS targeting moiety. The combination of these data show that the optimum range of PEG-densities is between 0.5-2.5% PEG-DMG, with the lower end of the range being optimum for overall transfection efficiency, while the 2.5% being optimal for target specificity.

Example 18. Oxidative Stability of ICLs

The aim of this studies was to compare stability of ionizable cationic lipids with conjugated olefins (such as KC2, KC3 and O-11769) and those with conjugated olefins (such as KC2-01, KC3-01 and UO-1) under accelerated oxidation.

Individual lipid stocks (10 mM) were prepared in ethanol and stored at −20° C. Prior to the experiment, 5 mM suspensions (KC2, KC2-01, KC3, KC3-01, O-11769 and UO-1) were prepared by mixing 45 µl of 10 mM lipid stock in ethanol (Sigma-Aldrich, cat #459836) with 45 µl of ultra-pure water (Rx Biosciences, cat #P01-UPW02-1000). Liposomal formulations based on AKG-UO-1 and O-11769 ionizable cationic lipids (Table 12) were prepared by combining lipid mixtures of desired composition in 1 mL ethanol with 3 mL 6.25 mM sodium acetate, pH 5.0 at 6 mL/min on a NanoAssemblr (Precision Nanosystems). 3.6 mL of the mixture was retained, while the initial 0.35 mL of the mixture and final 0.05 mL were discarded. Ethanol was removed by buffer exchange into PBS, pH 7.4 by concentrating each liposome preparation using an Aminon-Ultra 4 centrifugal concentrator at 500 g for 10 min at 4° C. and diluting back to the original volume with PBS. This cycle was repeated multiple times until the ethanol concentration was <1%. Finally, liposomes were sterile filtered through 0.2 µm PES (Nalgene) syringe filters and size measured by a ZetaSizer (Malvern). The AKG-UO-1 containing formulation (Lot #102021-6) had an average size of 81.8 nm and a PDI of 0.09, whereas the O-11769 containing formulation had an average size of 86.6 nm and a PDI of 0.10.

TABLE 12

LNP formulations used in the accelerated oxidation study.

| Lot# | Composition | MW | mol % | Estimated total lipid [mM] |
|---|---|---|---|---|
| 102021-6 | AKG-UO-1 | 658.1 | 50 | 1.5 |
| | DSPC | 790 | 10 | |
| | Cholesterol | 387 | 38.5 | |
| | PEG$_{2000}$-DMG | 2500 | 1.5 | |
| 102021-7 | O-11769 | 658.1 | 50 | 1.5 |
| | DSPC | 790 | 10 | |
| | Cholesterol | 387 | 38.5 | |
| | PEG$_{2000}$-DMG | 2500 | 1.5 | |

Aliquots of the liposomal formulations were stored at −80° C. and thawed before the experiment. A combined stock in water of 10% $H_2O_2$ (Sigma-Aldrich, cat #H1009) and 1 mM of Fe(III)Cl (Sigma-Aldrich, cat #372870) was freshly prepared prior to the treatment. To make 1% final concentration of $H_2O_2$ and 100 µM Fe(III)Cl, 10 µl of 10% $H_2O_2$/1 mM Fe(III)Cl stock was added to 90 µl of both liposomal formulations and individual lipids The liposomes and individual lipids were incubated with $H_2O_2$/Fe(III)Cl at 37° C. and then 5 µl from each sample was taken at different time points (0, 3, 24, 48 and 72 hours) and dissolved in 90 µl of MeOH for HPLC analysis. Degradation of the main lipid peak was analyzed using Thermo Scientific Vanquish Flex UHPLC occupied with Charged Aerosol Detector (CAD) and Thermo Scientific Accucore™ C18+ UHPLC column (L=50 mm, D=2.1 mm, Particle Size=1.5 µm). The UHPLC operating conditions are listed in Table 13.

TABLE 13

Chromatographic Conditions

| | |
|---|---|
| HPLC Instrument | Thermo Scientific Vanquish Flex UHPLC |
| HPLC Column | Accucore ™ Vanquish ™ C18+ UHPLC column |
| Column Temperature | 55° C. |
| Flow Rate | 0.5 mL/min |
| Injection Volume | 5 µL |
| Absorbance detection | 210 nm |
| CAD | 10 Hz |
| Run Time | 15 min |
| Sample Temperature | 21° C. |
| Sample Solvent | MeOH |
| Mobile Phase Mobile phase | Mobile Phase A: 5 mM ammonium acetate in water (pH 4) Mobile Phase B: Methanol |

| | Mobile | Mobile |
|---|---|---|
| Time, min | Phase A, % | Phase B, % |
| Mobile phase program: −0.5 | 15 | 85 |
| 0 | 15 | 85 |
| 2 | 10 | 90 |
| 4 | 2 | 98 |

TABLE 13-continued

Chromatographic Conditions

| | | |
|---|---|---|
| 8 | 2 | 98 |
| 12 | 2 | 100 |
| 14 | 15 | 85 |
| 15 | 15 | 85 |

The data are presented as a percentage of the main lipid pea measure at different time points relative to the lipid peak measured at time zero.

TABLE 14

Degradation of ICLs with two olefins separated by one (KC2, KC3, or O-11769) or more (KC2-01, KC3-01, UO-1, UO-6, and UO-7) methylenes.

| Lipid/Formulation | % of parent lipid peak at time 0 | | |
|---|---|---|---|
| | 24 h | 48 h | 72 h |
| ICL Lipid Suspensions | | | |
| KC2 | 35 ± 0.7 | 6 ± 1.9 | 0 ± 0.0 |
| KC2-01 | 91 ± 0.3 | 87 ± 0.9 | 83 ± 0.3 |
| KC3 | 46 ± 1.8 | 1 ± 0.2 | 0 ± 0.0 |
| KC3-01 | 83 ± 4.3 | 80 ± 0.4 | 74 ± 2.2 |
| O-11769 | 31 ± 0.9 | 1 ± 0.2 | 0.3 ± 0.1 |
| UO-1 | 78 ± 0.6 | 74 ± 0.1 | 65 ± 2.5 |
| UO-6 | 58 ± 0.8 | 32 ± 1.3 | 22 ± 1.8 |
| UO-7 | 80 ± 1.7 | 71 ± 0.8 | 62 ± 1.0 |
| Liposome preparations | | | |
| UO-1 (102021-6) | 86 ± 6.2 | 85 ± 4.2 | 73 ± 0.1 |
| O-11769 (102021-7) | 27 ± 2.2 | 8 ± 1.4 | 4 ± 0.1 |

As shown in FIG. 9A and FIG. 9B, all ICLs with olefins that had four methylenes between the two olefins (KC2-01, KC3-01 and UO-1) demonstrate dramatically superior stability under accelerated oxidation with hydrogen peroxide comparing to their counterparts with a single methylene separating the two olefins (KC2, KC3 and O-11769 respectively). Even after 72 h treatment with hydrogen peroxide, the main peaks of KC2-01, KC3-01 and UO-1 stay above 70% relative to the start of the treatment, while KC2, KC3 and O-11769 are fully degraded after 48 hours of incubation with hydrogen peroxide. Two other polyunsaturated ICLs (UO-6 and UO-7) similarly showed good stability to oxidation, although the UO-7 with a hydroxyethyl substituent in the head group degraded more rapidly than then dimethylamino ICLs (Table 14).

The stability of ICLs with olefins separated by more than one methylene were studied as part of mRNA-free liposomal formulations using the structurally related UO-1 and O-11769 ICLs. Other ionizable cationic lipids (KC2, KC2-01, KC3 and KC3-01) were excluded from this study since their chromatographic peaks overleap with the peak of DSPC which compromises the data interpretation. The stability data of UO-1 and O-11769 based liposomal formulations are shown in FIG. 9A. UO-1 formulated in liposomes has 73±0.05% of main UO-1 peak after 72 hours of incubation in the presence of 1% hydrogen peroxide. In contrast, O-11769 based liposomes show only 3.9 t 0.06% of the O-11769 peak after 72 hours of the treatment.

The totality of this data suggests that in addition to the improved transfection efficiency demonstrated in Examples 14 and 20 or the ICLs with more than one methylene between their olefins, these lipids also display significantly improved stability to oxidative degradation.

Example 19. Impact of N/P Ratio on Transfection Efficiency of mCherry mRNA Containing LNPs The aim of this study was to explore the effect of different N/P ratios on transfection efficiency in dendritic cells. LNPs were prepared as described in Example 9, characterized for particle size and zeta potential as described in Example 10, and evaluated for transfection efficiency in murine dendritic cells as described in Example 11. The LNPs all used KC2-01 as the ICL but varied the cationic lipid-to-mRNA phosphate (N/P) ratio from 4-7, the PS lipid was constant at 5 mol % and the DSPC phospholipid constant at 5 mol %, and the cholesterol constant at 38.5 mol %. The entrapment efficiency for all formulations was between 84 and 90%, indicating highly efficiency mRNA entrapment in the LNP. Transfection efficiency was evaluated in murine dendritic cells as described in Example 11.

TABLE 15

Physicochemical properties of LNPs used in Example 19

| % DSPS | N/P | Particle Size (nm) | Zeta Potential at pH 7 (mV) | Zeta Potential at pH 5 (mV) |
|---|---|---|---|---|
| 0 | 4 | 85.4 | −10.8 | 16.3 |
| 0 | 5 | 84.9 | −6.9 | 20.9 |
| 0 | 6 | 81.1 | −7.0 | 21.6 |
| 0 | 7 | 75.7 | −6.1 | 21.5 |
| 5 | 4 | 84.1 | −17.5 | 13.8 |
| 5 | 5 | 80.9 | −17.2 | 20.4 |
| 5 | 6 | 82.2 | −15.5 | 15.8 |
| 5 | 7 | 79.5 | −13.9 | 16.6 |

Transfection activity was evaluated for both DSPS-targeted and nontargeted KC-01 LNP formulations at both 1 ug/ml (FIG. 10A) and 0.33 ug/ml (FIG. 10B). These data show high DSPS-mediated transfection efficiency for KC2-01 containing LNPs over a broad range of N/P ratios with the greatest transfection efficiency being observed at an N/P of 7.

Example 20. Impact of Ionizable Lipid Structure on Transfection Efficiency Containing LNPs The aim of this study was to explore the effect of different ICLs on transfection efficiency in dendritic cells. LNPs were prepared as described in Example 9, characterized for particle size and zeta potential as described in Example 10, and evaluated for transfection efficiency in murine dendritic cells as described in Example 11. The LNPs used the ionizable lipids in Table 16 in the ICL with a constant N/P ratio of 5, the PS lipid was either 0 or 7.5 mol % and the DSPC phospholipid constant at 10 or 2.5 mol % (total of DSPC and DSPC was 10 mol %), and the cholesterol constant at 38.5 mol %.

TABLE 16

Physicochemical properties of LNPs used in Example 20.

| ICL | % DSPS | Particle Size (nm) | Particle Size (nm) Post-Freeze/Thaw | Encapsulation Efficiency (%) |
|---|---|---|---|---|
| AKG-UO1 | 0 | 98.0 | 122.6 | 75.4 ± 2.2 |
| AKG-UO1 | 7.5 | 93.9 | 94.2 | 91.6 ± 2.9 |
| AKG-UO1A | 0 | 84.4 | 103.2 | 77.5 ± 0.9 |
| AKG-UO1A | 7.5 | 89.2 | 91.1 | 88.7 ± 4.1 |
| O-11769 | 0 | 83.0 | 89.6 | 87.5 ± 2.7 |
| O-11769 | 7.5 | 130.8 | 126.4 | 91.5 ± 6.2 |

TABLE 16-continued

Physicochemical properties of LNPs used in Example 20.

| ICL | % DSPS | Particle Size (nm) | Particle Size (nm) Post-Freeze/Thaw | Encapsulation Efficiency (%) |
|---|---|---|---|---|
| AKG-UO4 | 0 | 102.3 | 169.4 | 46.5 ± 1.8 |
| AKG-UO4 | 7.5 | 89.9 | 91.3 | 89.0 ± 7.6 |
| AKG-UO4A | 0 | 112.1 | 123.4 | 73.1 ± 4.1 |
| AKG-UO4A | 7.5 | 92.4 | 91.81 | 85.8 ± 4.3 |
| AKG-DM2-OA | 0 | 77.6 | 111.5 | 64.9 ± 3.4 |
| AKG-DM2-OA | 7.5 | 106.5 | 123.0 | 86.2 ± 5.5 |
| DODAP | 0 | 69.8 | 68.2 | 83.4 ± 7.7 |
| DODAP | 7.5 | 90.1 | 88.0 | 84.1 ± 2.3 |

The effect of targeting and ICL choice on transfection activity was evaluated using both nontargeted and 7.5 mol % DSPS-targeted LNPs (FIG. 11). All ICLs used in this study had a related diacyl structure that varied either in the degree and position of unsaturations in the acyl chains or the specific ionizable amine used, and thus it's apparent pKa. This data shows that the AKG-UO1 lipid with the two olefins separated by four methylenes (C18 total length) showed the highest activity when incorporated into LNPs. The O-11769 lipid (dilinoleic acid) showed activity that was approximately half of the AKG-UO-1 containing LNP, the latter having similar activity to the AKG-UO4 lipid with C16 acyl chains and the ICL with the same head group but oleic acid (single olefin) at both acyl chains (AKG-OA-DM2). However, the largest reductions in activity came from changing the dimethyl amine substituent in AKG-UO-1 to diethylamino in UO-1A, or in decreasing the number of methylenes between the two esters and dimethylamino group (DODAP). These two changes gave rise to large reductions in transfection activity, the latter even in the presence of DSPS targeting.

It is also worth noting that among this series, those LNPs that contained 7.5 mol % DSPS were less susceptible to adverse changes in particle size after they underwent a freeze-thaw process than those that did not contain DSPS. On average, those LNPs that did not contain DSPS changed 28.4 nm in diameter, whereas those that contained DSPS changed 3.9 nm. Since, storage stability is of major concern for mRNA vaccines, the addition of DSPS provides an important stabilizing effect to these LNPs.

Example 21. Measuring the Effect of Adding 10 and 25 Mol % DOPS on LNP Particle Formation and Activity in MutuDC1940 Dendritic Cell Line The aim of this study was to explore the impact of including DOPS into mRNA LNP formulations at compositions at or below the mol % previously shown in the literature (Gaitonde et al. (2011) Clin Immunol 138, 135-145; Rodriquez-Fernandez (2018) Front Immunol 9, 253) to enhance liposome (with) uptake into dendritic cells. LNPs were prepared as described in Example 9 at 25° C. and analyzed as in Example 10. The LNPs contained KC2 as the ICL at an N/P ratio of 5 with between 0, 10 and 25 mol % DOPS and a constant 1.5 mol % PEG-DMG. The cholesterol content was held constant at 38.5 mol % for the 0% and 10% DOPS formulations and the DSPC content varied inversely with the mol % of DOPS between 0-10 mol % (all lipid concentrations were used as mol % of total lipid). In the 25 mol % DOPS formulation, there was no DSPC and the cholesterol content decreased in the total by 15 mol % (from 38.5 to 23.5 mol %). Transfection efficiency was evaluated in murine dendritic cells as described in Example 11.

TABLE 17

Physicochemical properties of DOPS containing LNP formulations

| LNP Formulation | Particle Size (nm) | PDI | Encapsulation Efficiency (%) |
|---|---|---|---|
| KC2/DSPC/DOPS/Chol/PEG-DMG (50/10/0/38.5/1.5) | 68.8 | 0.136 | 90.0 ± 3.5 |
| KC2/DSPC/DOPS/Chol/PEG-DMG (50/0/10/38.5/1.5) | 80.8 | 0.163 | 90.9 ± 3.5 |
| KC2/DSPC/DOPS/Chol/PEG-DMG (50/0/25/23.5/1.5) | Peak 1 = 62.6, Peak 2 = 416.3 | 0.398 | 77.3 ± 3.5 |

The impact of 10-25 mol % DOPS on targeting of LNPs to dendritic cells was evaluated in FIG. 12. This study shows that including 10 mol % DOPS in a KC2-based LNP formulation had a positive effect on mCherry expression levels in MutuDC1940 cells, while not adversely affecting either particle size or encapsulation of mRNA. However, when the DOPS content was increased to 25 mol % the expression of mCherry was lower than the formulation that had no DOPS and the size distribution widened as demonstrated by an increase in the PDI and gave rise to a distribution that contained particles >400 nm. Taken together, 25 mol % may have been shown in the literature to enhance liposome uptake into dendritic cells, while in an LNP formulation with mRNA it had a deleterious effect on both particle size and transfection activity. Importantly, the DOPS used here and in the literature contained unsaturated acyl chains, in this case oleic acid. This is similar to what is typical in many cells, where the phosphatidylserine acyl chains are often unsaturated in the sn-2 position, in many instances with multiple olefins (2-4). Although there is a small enhancement with a lower concentration of DOPS, this enhancement was shown in Example 15 to be significantly higher when the PS was comprised of saturated acyl chains, most preferably dipalmitoyl (C16) or distearoyl (C18).

Example 22. Impact of Pegylation and Phosphatidylserine Targeting on Immunogenicity of SARS-CoV-2 Spike Protein mRNA Vaccine Constructs Mice and study design. The in vivo study was carried out. Female BALB/c mice were purchased from Jackson Labs, allowed to acclimate in the vivarium for at least 7 days, and were 6-8 weeks at the start of the study. On study day 0 mice were injected intramuscularly in the right quadricep with 1 ug of vaccine candidate (quantity refers to mRNA) in a volume of 50 µL. Study groups consisted of 5 mice and included vehicle control, comparator vaccines, and experimental vaccine candidates. Mice were given a second injection of the same vaccine candidate 21 days later. Blood was collected and serum was isolated from 5 randomly selected control mice at the start of the study and from all mice on study day 21 and 34. Serum was stored at −80° C. until analysis for antibody titers. On study day 34, mice were euthanized and spleens were harvested.

Design and preparation of mRNA. mRNA encoding the SARS-CoV-2 full length spike protein and flanked with the same UTRs used in the BNT162b2 (Comirnaty) vaccine was purchased from Vernal Biosciences. All uridine nucleosides were substituted with N1-methyl-pseudouridine. To produce the mRNA, a synthetic gene encoding the mRNA sequence (VRN029; SEQ ID NO: 2, FIG. 13A) was cloned into a DNA plasmid. The synthetic gene was comprised of an RNA promoter, a 5' untranslated region, the SARS-COV2 Spike protein receptor binding domain, a 3' untranslated region, and a poly(A) tail region of approximately 120 As. The plasmid was propagated and expanded in a culture of E. coli and then isolated from the clarified E. coli lysate via anion exchange chromatography. The purified plasmid was linearized using a type IIs restriction enzyme that cut at a site at the end of the poly(A) tail encoding region. That plasmid was then incubated in a buffer with nucleotide triphosphates, RNA polymerase, and RNase inhibitor. To stop the reaction, DNase I was added to digest the linear plasmid template. The uncapped RNA was then purified using chromatography and then incubated in another buffer with GTP, S-adenosylmethionine, a guanalyltransferase, 2'-O-methyltransferase, and RNase inhibitor. The capped mRNA was then purified using chromatography, buffer exchanged into water, and filled into vials.

Generation of lipid nanoparticles (LNP) containing mRNA. Stock solutions of each lipid were prepared. Ionizable lipids were weighed out in 4 mL glass vials (Thermo B7999-2) and dissolved in ethanol (Sigma-Aldrich 200 proof, RNase free) to a final concentration of 10 mM. Other lipids such as DSPC (Avanti Polar Lipids), Cholesterol (Dishman) and PEG-DMG (NOF) were weighed out and dissolved in ethanol to a concentration of 1 mM. DSPS-Na (NOF) was dissolved in methanol (Sulpelco, Omnisolve) at a concentration of 1 mM and briefly heated to 70° C. to complete its dissolution.

Lipid mixtures for each individual LNP were prepared by adding the desired volume of each lipid stock solution to a new vial, adding ethanol if needed to achieve a final volume of 1.2 mL. For example, a LNP formulation of AKG-UO-1/DSPC/DSPS/Chol/PEG-DMG (50/2.5/7.5/38.5/1.5 mol %), with an N/P of 5 contained 1500 nmol AKG-UO-1, 75 nmol DSPC, 225 nmol DSPS, 1155 nmol Chol and 45 nmol PEG-DMG for every 100 µg of mRNA used. mRNA solutions were prepared by thawing frozen mRNA (SARS-CoV-2 spike mRNA, Vernal) vials and diluting mRNA in 6.25 mM sodium acetate (pH 5.0) to a final concentration of 0.033 mg/mL, where the concentration is confirmed by absorbance on a Nanodrop.

To prepare LNPs, a NanoAssemblr Benchtop microfluidic device (from Precision Nanosystems) was used. If LNPs contained DSPS, the heating block accessory set to 70° C. was used, otherwise LNPs were mixed at room temperature. 3 mL of mRNA solution was loaded into a 3 mL disposable syringe (BD 309656) and 1 ml of lipid mixture in a 1 ml syringe (BD309659) and placed in the NanoAssemblr heating block for 4 min prior to mixing. LNP formation was achieved by pumping the liquid streams through a disposable microfluidics cassette at 3:1 aqueous:alcohol volume ratio at 6 mL/min mixing speed. After mixing, 3.6 mL of LNP mixture was collected, while the initial mixed volume of 0.35 mL and last 0.05 mL of mix was discarded. Ethanol was removed by buffer exchange using SpectraPor dialysis tubing (12-14k MWCO) in PBS (Cytivia, SH30256.01). LNPs were typically exchanged into PBS, pH 7.4 and then 15 mM Tris, pH 7.4, 20% sucrose, concentrated to 20-50 ug/mL mRNA, sterile filtered (Thermo Nalgene 0.2 um #720-1320) prior to freezing by immersion in liquid nitrogen for 5 min and long-term storage at −20° C. For this study, samples were concentrated to >40 µg/mL mRNA, and diluted with varying volumes of 15 mM Tris, 20% Sucrose, pH 7.4 to a target concentration of 40 µg mRNA and then frozen on LN2. Characterization of LNPs was undertaken after an aliquot of the LNPs were thawed and diluted 1:1 (vol:vol) with 15 mM Tris, pH 7.4 such that the final concentration was 20 µg/mL mRNA in 15 mM Tris, 10% sucrose, pH 7.4. This simulated the conditions of sample preparation that were performed prior to dosing the animals with an injection of 1 µg mRNA in 50 µL volume via IM injection into a hind limb.

LNP Characterization. mRNA encapsulation and mRNA concentration within the LNPs was measured using a Ribogreen assay. Nanoparticle size and zeta potential were measured by a zetasizer (Malvern).

SARS-CoV-2 anti-spike antibody titers. A standard indirect ELISA was performed to analyze serum samples for total IgG binding antibodies to the SARS-CoV-2 spike protein. For this assay, Nunc MaxiSorp 96-well plates were coated with 100 µL of SARS-CoV-2 spike protein (Sino Biological, cat. no. 40589-V08B1) diluted to 2 µg/mL in 1×PBS, pH 7.4. Plates were incubated statically for 12 hrs at 37° C. Unbound coating antigen was removed by washing plates 3× with 100 µL PBS+0.05% Tween-20. Plates were then blocked in PBS+5% skim milk for 1 hr at 37° C. Test and positive control samples were diluted in assay diluent (PBS, Tween-20, 1% skim milk) to starting point dilution 1:20 followed by four-fold serial dilutions using U-bottom dilution plates. Once blocking was completed, blocking buffer was removed by inversion and each sample was plated in duplicates. Plates were statically incubated for 2 hr at 37° C., followed by washing 3× with 100 µL of PBS+ 0.05% Tween-20 to remove unbound sera. 100 µL of secondary detection antibody (goat anti-mouse-HRP IgG, Abcam) was added to each well at a dilution of 1:10,000. Plates were incubated statically for 30 min at RT, and unbound antibodies were subsequently removed and plates were washed as described above. To develop, 100 µL of 1-Step Ultra TMB substrate was added to each well and the reaction was stopped after ~10 min with 50 µL of TMB stop solution (SeraCare, cat. no. 5150-0019). The plates were read within 30 min at 450 nm with a Thermo LabSystems Multiskan spectrophotometer. Titers were defined as the reciprocal of the dilutions that generated a specific cut-off value for OD 450 on the linear part of the titration curve.

Ex vivo T cell responses. On study day 34, spleens were mechanically dissociated to single-cell suspensions. Cells were resuspended in cell-stimulation media (RPMI with L-Glutamine and HEPES buffer, heat-inactivated fetal bovine serum, and Pen/Strep) and $2 \times 10^6$ cells were aliquoted in a volume of 100 µL into 96-well plates. Splenocytes from each mouse were stimulated for approximately 18 hrs at 37° C. with 100 µL of media alone, treated with positive control Cell Stimulation Cocktail (ThermoFisher, cat. #00-4970-93) containing PMA and ionomycin, or 1 µg/mL of a peptide pool covering the SARS-CoV-2 spike protein (JPT, cat. #PM-WCPV-S-2). After 1 hr of stimulation, Golgi Stop (BD Biosciences, cat. #554724) was added to each well.

Flow cytometry. After the stimulation, cells were washed with PBS and transferred to 96-well deep-well plates. Cells were stained with LIVE/DEAD near IR viability dye (ThermoFisher, cat. #L10119) diluted in PBS for 20 min at 4° C. Cells were washed with FBS staining buffer (BD Biosciences, cat. #554656) and incubated with Fc Block (BD Biosciences, cat. 553142) for 10 min at 4° C. Cells were then stained for 40 min at 4° C. with a cell surface antibody cocktail consisting of CD3 BV605 (BD, cat. #564009), CD4 BV421 (BD, cat. #562891), and CD8 APC (BD, cat. #553035). BD Brilliant Stain Buffer (cat. #563794) was included in the staining buffer. Cells were washed with FBS staining buffer and then fixed for 20 min at room temperature with Fix/Perm buffer (ThermoFisher, cat. #00-5523-00). Cells were washed with 1× Perm buffer, incubated with Fc Block, and then stained for 40 min at 4° C. with an intracellular cytokine antibody cocktail consisting of IFN-g PE/Cy7 (BD, cat. #557649), IL-2 PE (BioLegend, cat. #503808) and TNF-α FITC (BD, cat. #554418). Cells were then washed, resuspended in FBS stain buffer and acquired on a MACSQuant 16 flow cytometer (Miltenyi Biotec). Flow data was analyzed using FlowJo v10.8.1 (BD Biosciences).

0315 negatively impacted total IgG anti-spike antibody levels (FIG. 13F). DSPS had the opposite effect on LNPs containing the ionizable lipids UO1 and KC20A and significantly increased geometric mean antibody levels 36- and 46-fold, respectively. DSPS also had an effect on CD4 T cell responses, with responses trending higher for LNPs containing UO1 and KC20A, and significantly higher for SM-102. Taken together, inclusion of DSPS in lipid nanoparticles can substantially influence the immunogenicity of mRNA vaccines, and that the impact of DSPS is influenced by the type of ionizable cationic lipid.

TABLE 18

Physicochemical properties of LNPs used in evaluating the immunogenicity of SARS-CoV-2 spike protein mRNA vaccine construct

| LNP Formulation | Particle Size (nm) | Zeta Potential (mV) pH 5 | Zeta Potential (mV) pH 7 | Encapsulation Efficiency (%) |
|---|---|---|---|---|
| 7.5% DSPS_UO1_PEG-DMG 1.5% | 80.3 | 5.3 | −2.6 | 90.7 ± 7.1 |
| 7.5% DSPS_UO1_PEG-DMG 2.5% | 71.0 | 5.5 | −1.0 | 89.1 ± 9.3 |
| 7.5% DSPS_UO1_PEG-DMG 3.5% | 61.9 | 6.6 | −3.6 | 89.3 ± 10.0 |
| 7.5% DSPS_UO1_PEG-DPPE 1.5% | 80.7 | 7.9 | −5.1 | 90.7 ± 14.2 |
| 7.5% DSPS_UO1_PEG-DPPE 2.5% | 68.4 | 2.7 | −2.4 | 91.0 ± 6.9 |
| 7.5% DSPS_UO1_PEG-DSG 1.5% | 100.7 | 9.6 | −6.7 | 88.8 ± 5.1 |
| 7.5% DPPS_UO1_PEG-DMG 1.5% | 89.8 | 14.4 | −1.4 | 93.8 ± 9.2 |
| UO1_PEG-DMG 1.5% | 116.0 | 20.2 | 2.5 | 86.5 ± 9.3 |
| 7.5% DSPS_KC2OA_PEG-DMG 1.5% | 80.0 | 11.7 | −3.5 | 90.9 ± 5.5 |
| 7.5% DSPS_KC2OA_PEG-DSG 1.5% | 88.5 | 9.0 | −3.9 | 92.2 ± 9.7 |
| ALC0315_1.5% PEG-DMG | 79.5 | 2.0 | −2.4 | 86.7 ± 9.3 |
| SM102_1.5% PEG-DMG | 92.6 | 11.8 | −0.1 | 92.0 ± 7.1 |

To evaluate the impact of PEG-lipid concentration on vaccine immunogenicity, BALB/c mice were immunized with mRNA-LNPs containing increasing amounts of PEG-lipid (PEG-DMG or PEG-DPPE). Blood serum was collected on day 21 post prime and on day 13 post boost (day 34 of study) for antibody analysis. Splenocytes were stimulated with Spike peptide pools and the percent of CD4 T cells producing IL-2 was quantified using flow cytometry (FIG. 13B and FIG. 13C). Both forms of PEG, PEG-DMG (FIG. 13B) or PEG-DPPE (FIG. 13C), inversely impacted mRNA-LNPA vaccine immunogenicity, with lower concentrations of PEG-lipid showing higher levels of both B-cell and T-cell responses.

To evaluate the impact of PEG-lipid acyl chain composition on mRNA-LNP immunogenicity, BALB/c mice were immunized with mRNA-LNPs containing different PEG formats (PEG-DMG or PEG-DSG). Blood serum was collected on day 21 post prime and on day 13 post boost (day 34 of study). Splenocytes were stimulated with Spike peptide pools and the percent of CD4 T cells producing IL-2 was quantified using flow cytometry. Antibody titer data were log-transformed prior to statistical analysis. Groups were compared using an unpaired t test. For LNPs made with the ionizable lipid KC20A, either PEG format performed similarly (FIG. 13D). In contrast, LNPs using the ionizable lipid UO1 and PEG-DMG induced a superior antibody response than LNPs containing PEG-DSG (FIG. 13E).

To assess how the incorporation of phosphatidylserine influences mRNA-LNP immunogenicity, BALB/c mice were immunized with mRNA-LNPs containing various ionizable lipids with or without DSPS. On Day 34 (13 days post-boost), serum was collected for quantification of total IgG anti-spike antibodies by ELISA. Splenocytes were stimulated with peptide and the percent of CD4 T cells producing IL-2 was quantified using flow cytometry. The inclusion of DSPS with comparator ionizable lipid ALC- The effects of different phosphatidylserine acyl chain composition on serum antibody titers (FIG. 13G, panel A) and the magnitude of the spike-specific CD4 T cell response in the spleen (FIG. 13G, panel B) was evaluated. Mice were immunized with LNPs using the ionizable lipid UO1 and either the DSPS or DPPS forms of phosphatidyl serine. On Day 34 (13 days post-boost), serum was collected for quantification of total IgG anti-spike antibodies by ELISA. Splenocytes were stimulated with peptide and the percent of CD4 T cells producing IL-2 was quantified using flow cytometry.

With regards to the impact of the PS acyl chain composition, both forms of PS comparably increased antibody levels over the base formulation lacking PS (FIG. 13G, Panel A). Both forms of PS also had a positive effect on the CD4 T cell response (FIG. 13G, Panel B), although only the formulation containing DPPS was significantly higher than the based formulation without PS. Taken together, both forms of PS included in our LNPs, DPPS or DSPS, had a similar positive effect on increasing the immunogenicity of mRNA-LNP vaccines.

Example 23. Measuring the Effect of Adding Either DSPS D-Isomer or L-Isomer at 7.5 Mol % in KC2-01 Based LNPs by Particle Characteristics and Activity in MutuDC1940 Dendritic Cell Line The aim of this study was to compare the impact of including the D and the L-isomers of DSPS into mRNA LNP formulations at 7.5 mol %. LNPs were prepared as described in Example 9 at 25° C. and analyzed as in Example 10. The LNPs contained KC2-01 as the ICL at an N/P ratio of 5 with 2.5 mol % DSPC, 7.5 mol % DSPS (D or L) and a constant 1.5 mol % PEG-DMG. Transfection efficiency was evaluated in murine dendritic cells as described in Example 11.

TABLE 19

Physicochemical properties of KC2-01 LNPs with mCherry mRNA and distearoylphosphatidyl-L-serine or distearoylphosphatidyl-D-serine.

| LNP Formulation | DSPS (serine isomer) | Particle Size (nm) | PDI | Zeta Potential mV, pH 5 | Potential Zeta mV, pH 7 | Encapsulation Efficiency (%) |
|---|---|---|---|---|---|---|
| KC2-01/DSPC/Chol/PEG-DMG (50/10/38.5/1.5) | N/A | 83.92 | 0.03 | 7.7 | −0.47 | 89.2 ± 5.7 |
| KC2-01/DSPC/DSPS/Chol/PEG-DMG (50/2.5/7.5/38.5/1.5) | D | 85.4 | 0.09 | 7.8 | −4.8 | 88.7 ± 3.5 |
| KC2-01/DSPC/DSPS/Chol/PEG-DMG (50/2.5/7.5/38.5/1.5) | L | 87.4 | 0.04 | 7.7 | −2.7 | 90.9 ± 6.0 |

This study shows that including 7.5 mol % DSPS (either isomer) in a KC2-01 based LNP formulation had no effect on the particle size or mRNA encapsulation. The zeta potential values are similar at pH 5, but the DSPS containing formulation have more negative values at pH 7 than the non-DSPS containing formulation, likely a result of the additional negative charge added by the DSPS. The impact of the stereochemistry on transfection was evaluated in FIG. 14A and FIG. 14B. An 8-fold increase in mCherry expression was observed when the D-isomer of DSPS was used compared to the L isomer at 1 µg/mL mRNA (and 4.7-fold at 0.33 µg/mL mRNA), indicating that the uptake or expression mechanism(s) of DSPS containing LNPs is likely stereo-specific.

Example 24. Measuring the Effect of Inclusion of DSPS in KC2-Based LNPs at 25° C. and 65° C. on Particle Characteristics and Activity in MutuDC1940 Dendritic Cell Line The aim of this study was to compare the impact of including the D-isomer of DSPS in KC2 based LNPs produced at two different temperatures. LNPs were prepared as described in Example 9 where those that contained DSPS were made at 65° C. at those that did not include DSPS were made at 25° C. and all LNPs were analyzed as in Example 10.

All LNPs contained ICL at an N/P ratio of 5 with a constant 1.5 mol % PEG-DMG. The cholesterol content was held constant at 38.5 mol % and the DSPC content varied inversely with the mol % of DSPS at 5 and 7.5 mol % (all lipid concentrations were used as mol % of total lipid). These mRNA LNPs all contained mCherry mRNA and the composition of comparator formulations using SM-102 based lipid formulation, the same lipid composition as that used in mRNA-1273 and that using ALC-0315, similar to that used in BNT162b2 were taken from their respective prescribing information. Note, the BNT162b2 comparator using ALC-0315 was made with an N/P of 5.0 in keeping with the other formulations in this study, which is different than the approved Covid vaccine Comirnaty.

TABLE 20

Physicochemical properties of KC2 containing LNPs with 5 or 7.5% DSPS to similar LNPs prepared with SM102 or ALC-0315 ionizable cationic lipid.

| LNP Formulation | Mixing Temp ° C. | Particle Size (nm) | PDI | Zeta Potential mV, pH 5 | Zeta Potential mV, pH 7 | Encapsulation Efficiency (%) |
|---|---|---|---|---|---|---|
| KC2 | 25 | 70.4 | 0.21 | 4.5 | −1.1 | 87.3 ± 3.2 |
| KC2 with 5% DSPS | 25 | 78.3 | 0.12 | 2.5 | −2.2 | 87.0 ± 2.2 |
| KC2 with 5% DSPS | 65 | 88.2 | 0.11 | 7.4 | −4.2 | 87.0 ± 3.8 |
| KC2 with 7.5% DSPS | 25 | 73.5 | 0.11 | 1.0 | −2.3 | 86.9 ± 3.8 |
| KC2 with 7.5% DSPS | 65 | 74.3 | 0.07 | 0.5 | −8.2 | 87.8 ± 2.2 |
| SM102 | 25 | 84.0 | 0.17 | 6.3 | −0.7 | 81.9 ± 3.9 |
| ALC-0315 | 25 | 72.1 | 0.08 | 3.3 | −3.0 | 80.7 ± 2.2 |

This study shows that heating the lipid solution and mRNA solution in a heating block set to 65° C. had no deleterious effect on particle diameter or, zeta potential or mRNA encapsulation readings at either 5 or 7.5 mol % DSPS content. The impact of temperature on transfection of DSPS-targeted KC2 LNPs, and the comparison to SM102 and ALC-0315 containing LNPs is shown in FIG. 15. The 5 mol % DSPS formulation had a 2-fold higher mCherry expression than the exact same formulation made at 25° C. ($p<0.05$, T-Test). A comparison of the formulations with 7.5 mol % DSPS made at either temperature showed no significant difference. The 5 mol % DSPS containing LNP, made at 65° C. gave a 6.5-fold increase in mCherry expression over the SM102 formulation. It is likely that higher temperatures increase the solubility of DSPS in alcohol and allow better incorporation of the lipid in the particle, which allows for enhanced uptake in this in vitro study, while nor adversely affecting many of the LNP crucial particle characteristics such as size, encapsulation or mRNA expression.

Example 25. Comparing UO1, UO6 & 7 in LNPs with and without DSPS

The aim of this study was to evaluate AKG-UO-6 ("UO-6") and AKG-UO-7 ("UO-7") in LNPs with and without 7.5 mol % DSPS. Previously, it was found that 7.5 mol % DSPS produced the most optimal LNPs from a UO-1 series. Here 7.5 mol % DSPS was chosen as an initial amount of DSPS to include to compare the structurally similar UO-6 and 7 LNPs were prepared as described in Example 9 and analyzed as in Example 10.

The LNPs contained either UO-1, UO-6 or UO-7 as the ICL at 50 mol %. The formulations also contained 38.5 mol % cholesterol, and 1.5 mol % PEG-DMG. The non DSPS containing samples have 10 mol % DSPC, and to the 7.5 mol % DSPS containing LNPs, DSPS was added at 7.5 mol % and DSPC was included at 2.5 mol %. The N/P in all formulations was 5. Transfection efficiency was evaluated in murine dendritic cells as described in Example 11.

TABLE 21

Physicochemical properties and encapsulation efficiency of UO-1, UO-6, and UO-7 LNPs with and without DSPS-targeting.

| LNP Formulation | Particle Size (nm) | PDI | Zeta Potential mV, pH 5 | Zeta Potential mV, pH 7 | Encapsulation Efficiency (%) |
|---|---|---|---|---|---|
| UO1 | 72.8 | 0.11 | 14.5 | 5.6 | 89.6 ± 4.8 |
| UO1_7.5%_DSPS | 80.5 | 0.03 | 13.9 | −2.4 | 91.4 ± 4.2 |
| UO6 | 72.0 | 0.22 | 14.9 | 4.2 | 90.5 ± 11.1 |
| UOUO6_7.5%_DSPS | 86.1 | 0.13 | 14.3 | 1.7 | 92.8 ± 11.1 |
| UO7 | 79.3 | 0.16 | 18.2 | −2.6 | 91.4 ± 2.5 |
| UO7_7.5%_DSPS | 94.3 | 0.13 | 16.9 | −5.3 | 92.3 ± 5.0 |

This study shows that including DSPS in LNPs based on UO1, UO6 and UO7 caused an increase in expression of mCherry, without adverse changes in particle size or mRNA entrapment. The impact of 7.5% DSPS incorporation into LNPs on dendritic cell transfection activity was shown for formulations prepared with three different ICLs (UO-1, UO-6, and UO-7) (FIG. 16). For UO-1 with 7.5 mol % DSPS, the mCherry expression was 11-fold higher than UO6 with 7.5 mol % DSPS and 7-fold higher than UO7 with 7.5 mol % DSPS. UO-7 with DSPS had 1.5-fold more mCherry expression than UO6 with DSPS. Of the non DSPS containing formulations, UO7 was 2.2-fold more active than UO1 and 1.9-fold more active than UO6. However, LNPs prepared with all three ICLs maintained good encapsulation efficiencies, particle size, and zeta potential, while benefiting from targeting with DSPS inclusion in the formulation.

Example 26. Evaluating the Effect of Adding DSPS to UO1, SM102 and ALC-0315 Based LNPs by Comparing Particle Characteristics and Activity in MutuDC1940 Dendritic Cell Line The aim of this study was to evaluate the effect of including the L-isomers of DSPC into mRNA LNP formulations at 0, 5% and 7.5 mol %. LNPs were prepared as described in Example 9 at 25° C. and analyzed as in Example 10.

The LNPs contained either AKG-UO-1 ("UO-1") or SM102 as the ICL at 50 mol %. For UO1 and SM102 the formulations contained 38.5 mol % cholesterol, and 1.5 mol % PEG-DMG. The non DSPS containing samples have 10 mol % DSPC, and to the DSPS containing LNPs, DSPS was added at 5 or 7.5 mol % with a concomitant reduction in DSPC by the same mol %. For the ALC-0315 formulation, the ICL was 46.3 mol %, DSPC 9.4 mol %, cholesterol 42.7 mol % and PEG-DMG 1.5 mol %. DSPS was a-dded with concomitant reduction in the DSPC mol % as above. The N/P in all formulations was 5. Transfection efficiency was evaluated in murine dendritic cells as described in Example 11.

TABLE 22

Physicochemical properties and encapsulation efficiency of PS-targeted formulations of UO1, SM102, and ALC-0315 containing LNPs

| LNP Formulation | Particle Size (nm) | PDI | Zeta Potential mV, pH 5 | Zeta Potential mV, pH 7 | Encapsulation Efficiency (%) |
|---|---|---|---|---|---|
| UO1 | 72.8 | 0.11 | 10.2 | 3.6 | 89.6 ± 4.8 |
| UO1_5%_DSPS | 83.0 | 0.11 | 9.9 | -2.7 | 91.4 ± 4.2 |
| UO1_7.5%_DSPS | 80.5 | 0.03 | 11.0 | 1.4 | 91.1 ± 6.3 |
| SM102 | 80.7 | 0.04 | 13.0 | 1.6 | 90.1 ± 5.6 |
| SM102_5%_DSPS | 81.0 | 0.02 | 13.1 | -6.1 | 90.5 ± 1.4 |
| SM102_7.5%_DSPS | 80.1 | 0.05 | 13.0 | -4.0 | 90.1 ± 2.7 |
| ALC0315 | 74.6 | 0.06 | 6.2 | -0.9 | 72.3 ± 0.9 |
| ALC0315_5%_DSPS | 68.1 | 0.10 | 8.0 | -8.8 | 84.2 ± 1.3 |
| ALC0315_7.5%_DSPS | 75.0 | 0.02 | 7.9 | -11.8 | 84.9 ± 3.8 |

This study shows that including DSPS in LNPs based on UO1, SM102 and ALC-0315 caused an increase in expression of mCherry (FIG. 17), without adverse changes in particle size or mRNA entrapment. For UO-1 and SM102, 5 mol % DSPS looked maximal, while 7.5 mol % DSPS was maximal for the ALC-0315 formulation. For UO-1 and SM102 the increase in expression was 18.1 and 58.7-fold respectively for the 5 mol % DSPS samples. The increase was 80.9-fold for the ALC-0315 based sample for 7.5 mol % DSPS.

Example 27. Additional Exemplary Phosphatidyl-L-Serine Targeted LNP Formulations Additional formulations shown below could also be prepared using the methods described in the Examples above.

All lipid concentrations are shown as mol % as a percentage of the total lipid in the LNP. The below compositions vary in conjugated lipid content from 0.5 to 2.5 mol %, in sterol content from 25-45 mol %, in ICL content from 40-65 mol %, in saturated phosphatidyl-L-serine content from 2-10 mol %, and in total noncationic phospholipid content from 5-20 mol %. Most compositions would contain two phospholipids, typically phosphatidyl-L-serine (DSPS or DPPS being preferred) and phosphatidylcholine, although some exemplary formulations may contain more than two phospholipids, including phosphatidylethanolamines, like dioleoylphosphatidylethanolamine (DOPE).

TABLE 23

Exemplary phosphatidyl-L-serine containing LNP formulations

| Formulation (#) | Ionizable Cationic Lipid (mol %) | PS (mol %) | Additional Phospholipid(s) (mol %) | Sterol (mol %) | Conjugated lipid (mol %) |
|---|---|---|---|---|---|
| 1 | AKG-UO-1 (47.5) | DSPS (7.5) | DSPC (3.5) | Chol (40) | PEG-DMG (1.5) |
| 2 | AKG-UO-1 (45) | DSPS (8) | DSPC (4) | Chol (42) | PEG-DMG (1) |
| 3 | AKG-KC2-01 (40) | DSPS (5) | DSPC (5) DOPE (5) | Chol (44) | PEG-DMG (1) |
| 4 | AKG-KC2-01 (42.5) | DSPS (7.5) | DSPC (6.5) | Chol (42) | PEG-DMG (1.5) |
| 5 | AKG-KC2-01 (65) | DSPS (7.5) | DSPC (2.5) | Chol (24.5) | PEG-DMG (0.5) |
| 6 | AKG-KC2-01 (60) | DSPS (6) | DSPC (4) | Chol (29) | PEG-DMG (1) |
| 7 | AKG-KC2-01 (55) | DSPS (7) | DSPC (3) | Chol (34) | PEG-DMG (1) |
| 8 | AKG-KC2-01 (57) | DSPS (6.5) | DSPC (3.5) | Chol (28) | PEG-DMG (1) |
| 9 | AKG-KC2-01 (60) | DSPS (7.5) | DSPC (2.5) DOPE (4) | Chol (28.5) | PEG-DMG (1.5) |
| 10 | AKG-KC2-01 (48) | DSPS (6) | DSPC (4) | Chol (41.5) | PEG-DMG (0.5) |
| 11 | AKG-KC2-01 (48) | DPPS (6) | DSPC (4) | Chol (41.5) | PEG-DMG (0.5) |
| 12 | AKG-KC2-01 (48) | DSPS (6) | DPPC (4) | Chol (41.5) | PEG-DMG (0.5) |
| 13 | AKG-KC2-PA (47.5) | DSPS (6) | DSPC (4) | Chol (41.5) | PEG-DMG (1) |
| 14 | AKG-KC2-PA (47.5) | DPPS (6) | DSPC (4) | Chol (41.5) | PEG-DMG (1) |
| 15 | AKG-KC2-PA (47.5) | DSPS (6) | DPPC (4) | Chol (41.5) | PEG-DMG (1) |
| 16 | AKG-UO-04 (48) | DSPS (7.5) | DSPC (2.5) | Chol (41.5) | PEG-DMG (0.5) |
| 17 | AKG-UO-04 (48) | DPPS (7.5) | DSPC (2.5) | Chol (41.5) | PEG-DMG (0.5) |
| 18 | AKG-UO-04 (48) | DSPS (7.5) | DPPC (2.5) | Chol (41.5) | PEG-DMG (0.5) |
| 19 | AKG-UO-1 (47.5) | DSPS (7.5) | DSPC (4.5) | Chol (39) | PEG-DMG (1.5) |
| 20 | AKG-UO-1 (47.5) | DPPS (7.5) | DSPC (4.5) | Chol (39) | PEG-DMG (1.5) |
| 21 | AKG-UO-1 (47.5) | DSPS (7.5) | DSPC (2.5) | β-sitosterol (42) | PEG-DMG (0.5) |
| 22 | AKG-UO-1 (50) | DSPS (7.5) | DSPC (2.5) | β-sitosterol (39) | PEG-DMG (1) |
| 23 | AKG-UO-1 (52.5) | DSPS (7.5) | DSPC (2.5) | β-sitosterol (39) | PEG-DMG (1) |
| 24 | AKG-UO-1 (55) | DSPS (7.5) | DSPC (2.5) | β-sitosterol (39) | PEG-DMG (1) |
| 25 | AKG-UO-1 (55) | DSPS (7.5) | DSPC (2.5) | Chol (34) | PEG-DMG (1) |
| 26 | AKG-UO-1 (57) | DSPS (6.5) | DSPC (3.5) DOPE (4) | Chol (28) | PEG-DMG (1) |
| 27 | AKG-UO-1 (52.5) | DSPS (7.5) | DSPC (6.5) DOPE (4) | Chol (28) | PEG-DMG (1.5) |
| 28 | AKG-UO-1a (48) | DSPS (8) | DSPC (2) | Chol (41.5) | PEG-DMG (0.5) |
| 29 | AKG-UO-7 (48) | DSPS (7) | DSPC (3) | Chol (41) | PEG-DMG (1) |

TABLE 23

Exemplary phosphatidyl-L-serine containing LNP formulations

| Formulation (#) | Ionizable Cationic Lipid (mol %) | PS (mol %) | Additional Phospholipid(s) (mol %) | Sterol (mol %) | Conjugated lipid (mol %) |
|---|---|---|---|---|---|
| 30 | AKG-KC3-01 (45) | DSPS (6) | DSPC (4) | Chol (44) | PEG-DMG (1) |
| 31 | AKG-KC2-01 (42.5) | DSPS (7.5) | DSPC (6.5) | Chol (42) | PEG-DMG (1.5) |
| 32 | AKG-UO-2 (48) | DPPS (8) | DSPC (2) | Chol (41.5) | PEG-DMG (0.5) |
| 33 | Compound 29 (48) | DSPS (5) | DSPC (5) | Chol (41.5) | PEG-DMG (0.5) |
| 34 | Compound 33 (48) | DSPS (7.5) | DSPC (2.5) | Chol (41) | PEG-DMG (1) |
| 35 | Compound 29 (50) | DSPS (5) | DSPC (5) | Chol (39) | PEG-DMG (1) |
| 36 | Compound 33 (50) | DSPS (7.5) | DSPC (2.5) | Chol (39) | PEG-DMG (1) |
| 37 | KC3-OA (48) | DSPS (5) | DSPC (5) | Chol (41.5) | PEG-DMG (0.5) |
| 38 | ALC-0315 (46) | DSPS (5) | DSPC (5) | Chol (43) | PEG-DMG (1) |
| 39 | ALC-0315 (48) | DSPS (5) | DSPC (5) | Chol (41) | PEG-DMG (1) |
| 40 | SM-102 (50) | DSPS (5) | DSPC (5) | Chol (39.5) | PEG-DMG (0.5) |
| 41 | SM-102 (50) | DSPS (7.5) | DSPC (2.5) | Chol (39) | PEG-DMG (1) |
| 42 | SM-102 (48) | DSPS (5) | DSPC (5) | Chol (41) | PEG-DMG (1) |
| 43 | AKG-UO-1 (48) | DSPS (7.5) | — | Chol (43.5) | PEG-DMG (1) |
| 44 | AKG-UO-1 (48) | DSPS (7.5) | — | Chol (43.5) | PEG-DMG (1) |
| 45 | AKG-KC3-01 (48) | DSPS (5) | DSPC (5) DOPE (15) | Chol (26) | PEG-DMG (1) |
| 46 | AKG-KC3-01 (48) | DSPS (5) | DSPC (5) DOPE (10) | Chol (31) | PEG-DMG (1) |
| 47 | AKG-KC3-01 (48) | DSPS (6) | DSPC (4) | Chol (40) | PEG-DMG (2) |
| 48 | AKG-KC3-01 (48) | DSPS (6) | DSPC (4) | Chol (39.5) | PEG-DMG (2.5) |
| 49 | AKG-UO-1 (46) | DSPS (7) | DSPE (5) | Chol (41.5) | PEG-DMG (0.5) |
| 50 | AKG-UO-1 (48) | DSPS (7.5) | eggSM (2.5) | Chol (41.5) | PEG-DMG (0.5) |
| 51 | AKG-KC3-01 (48) | DSPS (5) | HSPC (5) | Chol (41.5) | PEG-DMG (0.5) |
| 52 | AKG-UO-1 (47.5) | DSPS (7.5) | DSPC (2.5) | Chol (42) | PEG-DPG (0.5) |
| 53 | AKG-UO-1 (47) | DSPS (7.5) | DSPC (2.5) | Chol (42) | PEG-DPG (1) |

Example 28. Determination of Transfection Efficiency in Human Dendritic Cells of LNPs Using mCherry mRNA Four days prior to transfection, monocytes were isolated using CD14 isolation kit (StemCell) from PBMCs of healthy donors. Purity CD14=90.3%, viability=93.2%. The monocytes were cultured with IL-4 (R&D 1000 IU/mL) and GM-CSF (R&D, 800 IU/mL) in a 6 well dish at $1\times10^6$ cells/mL at 37° C., 5% CO2. After 4 days the immature DCs were harvested and seeded in a 96 well round bottom plate at 50,000 cells/well. LNPs were thawed by placing the vials in a 37° C. water bath for 30 seconds, or until the sample had almost fully melted. The vials were immediately placed on ice until use. The LNPs were added to final concentrations of 1 µg/ml and 0.1 µg/mL mRNA. For 1 µg/mL treatment, LNPs were added directly to each well then wells were mixed by pipetting. For 0.1 µg/mL treatment, LNPs were diluted 1:10 in complete media then added to each well and mixed by pipetting. After 4 h a maturation cytokine cocktail was added directly to each well consisting of TNF-a (R&D, 10 ng/mL), IL-1b (R&D, 2 ng/mL), IL-6 (R&D, 1000 IU/mL), and PGE1 (R&D, 1 µg/mL). After 24 h, the cells were centrifuged, washed in PBS and analyzed by flow cytometry for mCherry fluorescence. Gating analysis was performed using CytExpert software.

Example 29. Stability of Ionizable Cationic Lipids Under Accelerated Oxidation Conditions The aim of this studies was to compare stability of ionizable cationic lipids under accelerated oxidation.

Ethanol (Sigma-Aldrich, cat #459836) stocks of 1 mM cationic lipids (KC3, KC3-OA, KC3-PA, KC3-C17 and KC3-C17(C8:1)) were prepared and stored at −20° C. Prior to the experiment, 75 µl of a lipid stock was mixed with 75 µl of ultra-pure water (Rx Biosciences, cat #P01-UPW02-1000) to make 0.5 mM of cationic lipids and 5 mM of linoleic acid respectively. A combined stock in water of 10% $H_2O_2$ (Sigma-Aldrich, cat #H1009) and 1 mM of Fe(III)Cl (Sigma-Aldrich, cat #372870) was freshly by prepared prior to the experiment. To make 1% final concentration of $H_2O_2$ and 100 µM Fe(III)Cl, 15 µl of 10% $H_2O_2$/1 mM Fe(III)Cl stock was added to 135 µl of individual lipids The liposomes and individual lipids were incubated with $H_2O_2$/Fe(III)Cl at 37° C. and then 5 µl from each sample was taken at different time points (0, 24, 48, 72 and 96 hours) and dissolved in 90 µl of MeOH for HPLC analysis. Degradation of the main lipid peak was analyzed using Thermo Scientific Vanquish Flex UHPLC occupied with Charged Aerosol Detector (CAD) and Phenomenex™ Kinetex C8 column (L=150 mm, D=2.1 mm, Particle Size=1.7 µm, 100 A). The UHPLC operating conditions are listed in Table 24.

TABLE 24

Chromatographic Conditions

| | |
|---|---|
| HPLC Instrument | Thermo Scientific Vanquish Flex UHPLC |
| HPLC Instrument | Thermo Scientific Vanquish Flex UHPLC |
| HPLC Column | PhenomenexTM Kinetex C8 column (L = 150 mm, D = 2.1 mm, Particle Size = 1.7 µm, 100 A) |
| Column Temperature | 50° C. |
| Flow Rate | 0.5 mL/min |
| Injection Volume | 5 µL |
| CAD | 10 Hz |
| Run Time | 11 min |
| Sample Temperature | 21° C. |
| Sample Solvent | MeOH |
| Mobile Phase | Mobile Phase A: 100 mM ammonium acetate in water (pH 4) Mobile Phase B: Methanol |

| | Time, min | Mobile Phase A, % | Mobile Phase B, % |
|---|---|---|---|
| Mobile phase program: | −0.5 | 18 | 82 |
| | 0 | 18 | 82 |
| | 1 | 16 | 84 |
| | 4 | 10 | 90 |
| | 6 | 0 | 100 |
| | 9 | 0 | 100 |
| | 10 | 18 | 82 |
| | 11 | 18 | 82 |

The data are presented as a percentage of the main lipid peak measured at different time points relative to the lipid peak measured at time zero.

As shown in FIG. 18 and Table 25, KC3 demonstrated the fastest degradation relative to other cationic lipids under the forced oxidation with $H_2O_2$.

TABLE 25

Effect of hydrogen peroxide on the stability of individual ionizable cationic lipids

| | % of main lipid peak to $T_o$ | | |
|---|---|---|---|
| Lipid | 24 h. | 48 h. | 72 h. |
| KC3 | 11.2 ± 1.0 | 10.5 ± 0.5 | 0 ± 0 |
| KC3-OA | 88.9 ± 0.5 | 84.6 ± 0.9 | 79.0 ± 0.1 |
| KC3-PA | 62.7 ± 0.1 | 59.2 ± 0.8 | 60.2 ± 0.6 |
| KC3-17 | 92.9 ± 0.3 | 91.8 ± 1.2 | 90.2 ± 1.2 |
| KC3-17 (C8:1) | 66.1 ± 0.6 | 58.4 ± 1.5 | 45.9 ± 4.7 |

Example 30. Comparison of Transfection Efficiency in Human Dendritic Cells of LNPs Prepared Using KC3-OA, UO-1, or UO-1A Lipids The aim of this study was to explore the effect of different ICLs on transfection efficiency in human dendritic cells. LNPs were prepared as described in Example 9, characterized for particle size and zeta potential as described in Example 10, and evaluated for transfection efficiency in human dendritic cells as described in Example 28. The LNPs used the ionizable lipids in Tables 26-28 and the ICL was held at a constant N/P ratio of 5, the PS lipid was either 0 or 7.5 mol %, and DSPC phospholipid was either 10 or 2.5 mol % (total of DSPS and DSPC was 10 mol %), and the cholesterol was held constant at 38.5 mol %.

TABLE 26

Physicochemical properties of LNPs used in Example 30.

| ICL | % DSPS | Particle Size (nm) | Particle Size (nm) Post-Freeze/Thaw | Encapsulation Efficiency (%) |
|---|---|---|---|---|
| AKG-UO1 | 0 | 97.97 | 122.6 | 75.4 ± 2.2 |
| AKG-UO1 | 7.5 | 93.86 | 94.16 | 91.6 ± 2.9 |
| AKG-UO1A | 0 | 84.41 | 103.2 | 77.5 ± 0.9 |
| AKG-UO1A | 7.5 | 89.19 | 91.05 | 88.7 ± 4.1 |
| KC3-OA | 5 | 93.3 | 90.0 | 91.7 ± 3.6 |

TABLE 27 mCherry expression in human dendritic cells for targeted UO-1 or KC3-OA LNPs at 1 ug/mL

| ICL | % DSPS | MFI | T/NT | Vs KC3-OA LNPs (fold) |
|---|---|---|---|---|
| untreated | | 1,456 ± 27 | | |
| AKG-UO1 | 0 | 2,073 ± 180 | | |
| AKG-UO1 | 7.5 | 22,310 ± 3,915 | 33.8 | 16.4 |
| AKG-UO1A | 0 | 1,595 ± 37 | | |
| AKG-UO1A | 7.5 | 16,381 ± 899 | 107.5 | 22.8 |
| KC3-OA | 5 | 342,442 ± 106,704 | | |

TABLE 28 mCherry expression in human dendritic cells for targeted UO-1 or KC3-OA LNPs at 0.1 ug/mL

| ICL | % DSPS | MFI | T/NT | Vs KC3-OA LNPs (fold) |
|---|---|---|---|---|
| untreated | | 1,245 ± 3 | | |
| AKG-UO1 | 0 | 1,385 ± 4 | | |
| AKG-UO1 | 7.5 | 2,716 ± 233 | 10.6 | 25.3 |
| AKG-UO1A | 0 | 1,346 ± 14 | | |
| AKG-UO1A | 7.5 | 1,805 ± 79 | 5.6 | 66.4 |
| KC3-OA | 5 | 38,385 ± 1,705 | | |

The effect of targeting and ICL choice on transfection activity was evaluated using both nontargeted and 7.5 mol % DSPS-targeted LNPs (FIG. 19). The three ICLs used in this study had either a diacyl structure (UO-1 or UO-1A) that varied in the specific ionizable amine used (dimethylaminoethyl or diethylaminoethyl), and thus its apparent pKa. The final ICL used with KC3-OA with dioxalane structure and single olefin. For both UO-1 or UO-1A containing LNPs there was a significant improvement in transfection activity of human dendritic cells when the anionic phospholipid DSPS was included in the formulation, 33.8-107.5 fold at 1 µg/mL of mRNA and 5.6-10.6 fold at 0.1 µg/mL. This illustrated the ability of phosphatidylserine to positively impact transfection activity. In addition, when comparing the DSPS-targeted KC3-OA LNP to either DSPS-targeted UO-1 or UO-1A LNPs, the KC3-OA containing formulation was more than an order of magnitude more active. At 1 ug/mL this difference was 16.4-22.8 fold and at 0.1 µg/mL this increase in transfection activity was 25.3-66.4 fold, suggesting the KC3-OA containing formulations were considerably more active in transfecting human dendritic cells.

Example 31. Comparison of KC2 and KC3-Family Lipids in PS-Targeted LNP Expression Murine Dendritic Cells The aim of this study was to explore the effect of different KC2 and KC3 ICLs on transfection efficiency in murine dendritic cells. The KC2 (DLin-KC2-DMA) and KC3 (DLin-KC3-DMA) lipids both have linoleic chains with two olefins each but differ in the ionizable amine group coming off the dioxolane ring, with KC2 having a dimethylaminoethyl group at this position and KC3 has a dimethylaminopropyl group at this position. Two other variants evaluated have monounsaturated alkyl chains with KC3-OA being 18 carbons in length and KC3C17(8:1) having 17 carbons. LNPs were prepared as described in Example 9, characterized for particle size and zeta potential as described in Example 10, and evaluated for transfection efficiency in murine dendritic cells as described in Example 11. The LNPs used the ionizable lipids in Tables 29-30 in the ICL with a constant N/P ratio of 5.25, the DPPS (NH4+ salt) lipid was either 0 or 5 mol % and the DSPC phospholipid constant at 10 or 5 mol % (total of DPPS and DSPC was 10 mol %), and the cholesterol constant at 38.5 mol %.

TABLE 29

Physicochemical properties of LNPs used in Example 31.

| LNP formulation | Particle Size (nm) | Particle Size (nm) Post-Freeze/ Thaw | Encapsulation Efficiency (%) |
|---|---|---|---|
| KC2/DSPC/DSPS | 87.8 | | 85.6 ± 4.6 |
| KC3/DSPC | 91.2 | 90.1 | 95.1 ± 5.6 |
| KC3/DSPC/DPPS | 90.5 | 90.2 | 95.0 ± 9.8 |
| KC3-OA/DSPC | 88.4 | 84.7 | 96.0 ± 13.1 |
| KC3-OA/DSPC/DPPS | 97.7 | 97.7 | 96.5 ± 7.3 |
| KC3C17(8:1)/DSPC | 85.3 | 83.0 | 94.4 ± 6.2 |
| KC3C17(8:1)/DSPC/DPPS | 100.2 | 96.8 | 94.7 ± 8.4 |
| KC3C17/DSPC | 73.9 | 77.5 | 95.6 ± 5.5 |
| KC3C17/DSPC/DPPS | 85.2 | 81.4 | 97.0 ± 8.4 |

TABLE 30 mCherry expression in murine dendritic cells

| LNP formulation | [mRNA] (µg/mL) | MFI | T/NT | vs KC3 LNP (%) |
|---|---|---|---|---|
| Untreated (UT) | | 234 ± 6 | | |
| KC2/DSPC/DSPS | 1 | 13,570 ± 2,324 | | 17.3% |
| KC3/DSPC | 1 | 14,962 ± 711 | | |
| | 0.3 | 6,656 ± 125 | | |
| KC3/DSPC/DPPS | 1 | 78,539 ± 15,239 | 5.32 | |
| | 0.3 | 30,525 ± 2,946 | 4.72 | |
| KC3-OA/DSPC | 1 | 27,513 ± 10,579 | | 185% |
| | 0.3 | 12,719 ± 1,316 | | 194% |
| KC3-OA/DSPC/DPPS | 1 | 163,844 ± 24,614 | 6.00 | 209% |
| | 0.3 | 85,584 ± 10,863 | 6.84 | 282% |
| KC3C17(8:1)/DSPC | 1 | 16,075 ± 1,956 | | 108% |
| | 0.3 | 6,701 ± 440 | | 101% |
| KC3C17(8:1)/DSPC/DPPS | 1 | 145,159 ± 35,387 | 9.15 | 185% |
| | 0.3 | 61,788 ± 7,404 | 9.52 | 203% |
| KC3C17DSPC | 1 | 344 ± 15 | | 0.8% |
| | 0.3 | 270 ± 8 | | 0.6% |
| KC3C17/DSPC/DPPS | 1 | 428 ± 30 | 1.77 | 0.3% |
| | 0.3 | 330 ± 5 | 2.64 | 0.3% |

The effect of targeting and ICL choice on transfection activity was evaluated using both nontargeted and 5 mol % DSPS-targeted LNPs (FIG. 20). The five ICLs used in this study had either a diacyl structure that varied in the specific ionizable amine used, and thus it's apparent pKa. This data shows that the two KC3 lipids with a single olefin, KC3OA and KC3C17(8:1) showed the highest activity when incorporated into LNPs. These two lipids when incorporated into 5 mol % DPPS-targeted LNPs showed between 185-282% of the activity of the KC3 lipid containing LNP formulation and 1,087-1,227% of the transfection activity of LNPs containing the KC2 lipid. Previously, Semple and colleagues (Semple et al., (2010) Nature Biotech. 28 (2) 172-176) had shown that KC2 was 6-fold more active compared to KC3, and all the lipids were designed with the understanding that linoleyl lipids with two cis double bonds would be significantly less active based on prior work with DLinDMA (Heyes et al., (2005) J Control Release 107, 276-287), and thus monounsaturated lipids were never evaluated. Here, the data clearly show using two different monounsaturated ICLs, KC3-OA and KC3C17(8:1), that the monounsaturated lipids were clearly superior to lipids containing dilioleyl chains and compared to those containing fully saturated alkyl chains (KC3C17), which was completely inactive, even in the presence of DPPS targeting lipid. The data also show these new lipids were significantly more active than the lead, and most active lipid, KC2 (DLin-KC2-DMA) arising from this early work. Finally, LNPs comprised of both DPPS and one of these two monounsaturated ICLs, showed a 6-10 fold targeting effect compared to similar LNPs without DPPS.

Example 32. Comparison of KC2 and KC3-Family Lipids in PS-Targeted LNP Expression Human Dendritic Cells The aim of this study was to explore the effect of different KC2 and KC3 ICLs on transfection efficiency in human dendritic cells. The KC2 (DLin-KC2-DMA) and KC3 (DLin-KC3-DMA) lipids both have linoleic chains with two olefins each but differ in the ionizable amine group coming off the dioxolane ring, with KC2 having a dimethylaminoethyl group at this position and KC3 has a dimethylaminopropyl group at this position. Three other variants evaluated have monounsaturated alkyl chains with KC3-OA being 18 carbons in length, KC3-PA having 16 carbons, and KC3C17 (8:1) having 17 carbons. The aim of this study was also to evaluate the impact of the PC component on transfection by comparing the fully saturated C16 DPPC and the fully saturated DSPC using both KC3-OA and KC3C17(8:1) containing LNPS. LNPs were prepared as described in Example 9, characterized for particle size and zeta potential as described in Example 10, and evaluated for transfection efficiency in murine dendritic cells as described in Example 11. The LNPs used the ionizable lipids in Tables 31-33 with the ICL held constant at an N/P ratio of 5.25 and 48 mol %, the DPPS (NH4+ salt) lipid was included at mol % and the DSPC phospholipid constant at 5 mol % (total of DPPS and DSPC/DPPC was 10 mol %), and the cholesterol constant at 38.5 mol %. The final ALC-0315/DSPC formulation was composed of 46.3 mol % ALC-0315, 9.4 mol % DSPC, 42.7 mol % cholesterol and 1.56 mol % PEG-DMG with a N/P of 6.2. The final SM-102/DSPC formulation was composed of 50 mol % SM-102, 10 mol % DSPC, 38.5 mol % cholesterol and 1.5 mol % PEG-DMG with a N/P of 5.

TABLE 31

Physicochemical properties of LNPs used in Example 32.

| LNP formulation | Particle Size (nm) | Particle Size (nm) Post-Freeze/ Thaw | Encapsulation Efficiency (%) |
|---|---|---|---|
| KC2/DSPC/DSPS | 71.8 | 69.6 | 85.4 ± 1.5 |
| KC3-01/DSPC/DPPS | 67.9 | 71.7 | 84.3 ± 3.6 |

TABLE 31-continued

Physicochemical properties of LNPs used in Example 32.

| LNP formulation | Particle Size (nm) | Particle Size (nm) Post-Freeze/Thaw | Encapsulation Efficiency (%) |
|---|---|---|---|
| KC3/DSPC/DPPS | 103.4 | 100.3 | 91.5 ± 6.2 |
| KC3-OA/DSPC/DPPS | 87.9 | 87.7 | 92.2 ± 8.6 |
| KC3-OA/DPPC/DPPS | 89.8 | 98.2 | 91.7 ± 6.3 |
| KC3-PA/DSPC/DPPS | 104.7 | 98.0 | 90.1 ± 10.3 |
| KC3C17(8:1)/DSPC/DPPS | 91.6 | 92.7 | 91.7 ± 5.3 |
| KC3C17(8:1)/DPPC/DPPS | 86.6 | 88.7 | 92.9 ± 2.6 |
| ALC-0315/DSPC | 69.8 | 71.5 | 88.0 ± 4.1 |
| SM-102/DSPC | 82.1 | 83.4 | 92.4 |

TABLE 32 mCherry expression in human dendritic cells following incubation at 1 µg/ml

| LNP formulation | MFI | vs KC3 LNP (fold) | vs DPPC LNP (fold) |
|---|---|---|---|
| Untreated (UT) | 2,279 ± 129 | | |
| KC2/DSPC/DSPS | 11,150 ± 1,556 | 0.08 | |
| KC3-01/DSPC/DPPS | 1,149,875 ± 111,037 | 10.08 | 2.35 |
| KC3-OA/DSPC/DPPS | 963,929 ± 95,910 | 8.44 | |
| KC3-OA/DPPC/DPPS | 412,204 ± 37,299 | 3.60 | |
| KC3-PA/DSPC/DPPS | 757,849 ± 95,345 | 6.64 | |
| KC3C17(8:1)/DSPC/DPPS | 534,708 ± 80,921 | 4.68 | 3.60 |
| KC3C17(8:1)/DPPC/DPPS | 149,980 ± 34,195 | 1.30 | |
| KC3/DSPC/DPPS | 116,155 ± 30,093 | 1.00 | |
| ALC-0315/DSPC | 10,327 ± 1,916 | 0.07 | |
| SM-102/DSPC | 258,967 ± 16,828 | 2.25 | |

TABLE 33 mCherry expression in human dendritic cells following incubation at 0.1 µg/ml

| LNP formulation | MFI | vs KC3 LNP (fold) | vs DPPC LNP (fold) |
|---|---|---|---|
| Untreated (UT) | 2,502 ± 293 | | |
| KC2/DSPC/DSPS | 3,048 ± 193 | 0.09 | |
| KC3-01/DSPC/DPPS | 46,489 ± 4,173 | 7.45 | |
| KC3-OA/DSPC/DPPS | 44,197 ± 4,407 | 7.06 | 2.61 |
| KC3-OA/DPPC/DPPS | 18,485 ± 1,488 | 2.71 | |
| KC3-PA/DSPC/DPPS | 35,177 ± 3,396 | 5.53 | |
| KC3C17(8:1)/DSPC/DPPS | 25,044 ± 2,144 | 3.82 | 2.82 |
| KC3C17(8:1)/DPPC/DPPS | 10,499 ± 979 | 1.35 | |
| KC3/DSPC/DPPS | 8,409 ± 660 | 1.00 | |
| ALC-0315/DSPC | 3,783 ± 1,090 | 0.22 | |
| SM-102/DSPC | 9,177 ± 1,494 | 1.13 | |

The effect of targeting and ICL choice on transfection activity was evaluated using both nontargeted and 5 mol % DPPS-targeted LNPs (FIG. 21). The five ICLs used in this study had a diacyl structure that varied in the specific ionizable amine used. This data shows that the three KC3 lipids with a single olefin, KC3OA, KC3-PA and KC3C17 (8:1), or the polyunsaturated KC3-01 lipid with four methylenes between the two olefins showed the highest activity when incorporated into LNPs (Tables 32 and 33). The four lipids showed a 4.7-10.8 fold increase in transfection activity compared to KC3-containing LNPs in human dendritic cells at 1 µg/ml and 3.8-7.5 fold increase at 0.1 µg/mL. The increase was a further 10-12 fold higher when compared to targeted LNPs containing KC2. Both KC2 and KC3 containing linoleoyl alkyl chains (two olefins separated by one methylene). Previously, Semple and colleagues (Semple et al., (2010) Nature Biotech. 28 (2) 172-176) had shown that KC2 was 6-fold more active compared to KC3, and all the lipids were designed with the understanding that linoleyl lipids with two cis double bonds would be significantly less active based on prior work with DLinDMA (Heyes et al., (2005) J Control Release 107, 276-287), and thus monounsaturated lipids were never evaluated. Here, the data clearly show using three different monounsaturated ICLs, KC3-OA, KC3-PA, and KC3C17(8:1), that the monounsaturated lipids were clearly superior to lipids containing dilioleyl chains. However, the largest improvement at both concentrations came when using the KC3-01 ICL with four methylenes between two olefins. The data also show these new lipids were significantly more active than the lead, and most active lipid, KC2 (DLin-KC2-DMA) arising from this early work and compared to LNPs containing either ALC-0315 or SM-102. Finally, two of the DPPS-targeted LNPs comprised of both DPPS and either KC3-OA or KC3-C17(8:1) ICLs, were evaluated with either the C16 DPPC or the C18 DSPC as the phosphatidylcholine component. For both sets of formulations, the DSPC-containing formulation showed higher transfection activity in human dendritic cells compared to the DPPC formulation, 2.61-2.82-fold higher 0.1 µg/mL and 2.35-3.60-fold higher at 1 µg/mL. This suggests that the DSPC containing LNPs provide for greater transfection activity when compared to lower phase transition lipids like DPPC.

Example 33. Impact of ICL Concentration in PS-Targeted LNPs on Expression in Human Dendritic Cells The aim of this study was to explore the effect of KC3-OA concentration in DSPS-targeted LNPs on transfection efficiency in human dendritic cells. The concentration of KC3-OA were varied from 46-54 mol %, while keeping the DSPS and DSPC concentrations constant at 5 mol % each and PEG-DMG at 1.5 mol %. The increase in % KC3OA was commensurate with a proportional reduction in the % of cholesterol. ALC-0315 and SM-102 comparator formulations were also evaluated. The final ALC-0315/DSPC formulation was composed of 46.3 mol % ALC-0315, 9.4 mol % DSPC, 42.7 mol % cholesterol and 1.56 mol % PEG-DMG with a N/P of 6.2. The final SM-102/DSPC formulation was composed of 50 mol % SM-102, 10 mol % DSPC, 38.5 mol % cholesterol and 1.5 mol % PEG-DMG with a N/P of 5.

LNPs were prepared as described in Example 9, characterized for particle size and zeta potential as described in Example 10, and evaluated for transfection efficiency in murine dendritic cells as described in Example 28.

TABLE 34

Physicochemical properties and characterization of DSPS-targeted KC3-OA LNPs containing various concentrations of KC3-OA

| LNP formulation | Particle size (nm) | Particle Size (nm) Post-Freeze/Thaw | Encapsulation Efficiency (%) |
|---|---|---|---|
| SM-102/DSPC | 71.0 | 74.1 | 84.1 ± 10.7 |
| ALC-0315/DSPC | 63.0 | 62.3 | 89.0 ± 5.9 |
| KC3-OA (46)/DSPC/DSPS | 101.9 | 110.0 | 94.1 ± 10.0 |

TABLE 34-continued

Physicochemical properties and characterization of DSPS-targeted KC3-OA LNPs containing various concentrations of KC3-OA

| LNP formulation | Particle size (nm) | Particle Size (nm) Post-Freeze/Thaw | Encapsulation Efficiency (%) |
|---|---|---|---|
| KC3-OA(48)/DSPC/DSPS | 96.9 | 110.6 | 93.8 ± 16.8 |
| KC3-OA(50/DSPC/DSPS | 109.0 | 108.0 | 93.1 ± 14.4 |
| KC3-OA(52)/DSPC/DSPS | 108.6 | 110.9 | 93.8 ± 10.0 |
| KC3-OA(54)/DSPC/DSPS | 121.2 | 122.8 | 93.8 ± 17.0 |

All DSPS-targeted KC3-OA formulations showed a particle size around 100-120 nm and greater than 90% encapsulation efficiency. All particles were stable to freezing and thawing at −80° C. There was no apparent impact of the concentration of KC3-OA used in the range of 46-54 mol % on these properties.

TABLE 35 mCherry expression in human dendritic cells following incubation at 1 µg/ml for DSPS-targeted KC3-OA LNPs containing various concentrations of KC3-OA

| LNP formulation | MFI | vs SM-102 (fold) | vs ALC-0315 (fold) |
|---|---|---|---|
| Untreated (UT) | 1,343 ± 104 | | |
| SM-102/DSPC | 4,242 ± 1,942 | | |
| ALC-0315/DSPC | 3,760 ± 1,625 | | |
| KC3-OA (46)/DSPC/DSPS | 100,521 ± 44,930 | 34 | 41 |
| KC3-OA(48)/DSPC/DSPS | 116,994 ± 52, 141 | 40 | 48 |
| KC3-OA(50)/DSPC/DSPS | 107,911 ± 46,614 | 37 | 44 |
| KC3-OA(52)/DSPC/DSPS | 67,845 ± 37,779 | 23 | 28 |
| KC3-OA(54)/DSPC/DSPS | 101,338 ± 46,945 | 34 | 41 |

TABLE 36 mCherry expression in human dendritic cells following incubation at 0.1 µg/ml for DSPS-targeted KC3-OA LNPs containing various concentrations of KC3-OA

| LNP formulation | MFI | vs SM-102 (fold) | vs ALC-0315 (fold) |
|---|---|---|---|
| Untreated (UT) | 1,295 ± 116 | | |
| SM-102/DSPC | 1,492 ± 26 | | |
| ALC-0315/DSPC | 1,405 ± 28 | | |
| KC3-OA (46)/DSPC/DSPS | 6,915 ± 1,659 | 29 | 51 |
| KC3-OA(48)/DSPC/DSPS | 10,491 ± 3,164 | 47 | 84 |
| KC3-OA(50)/DSPC/DSPS | 11,033 ± 3,043 | 49 | 89 |
| KC3-OA(52)/DSPC/DSPS | 8,393 ± 2,447 | 36 | 65 |
| KC3-OA(54)/DSPC/DSPS | 7,496 ± 1,855 | 31 | 57 |

The effect of targeting and ICL choice on transfection activity was evaluated using 5 mol % DSPS-targeted LNPs comprised of KC3-OA at concentrations ranging from 46-54 mol % (FIG. 22). This targeted composition was highly active at all concentrations of KC3-OA at both 0.1 and 1 ug/mL, and only showed a slight peak at 48-50 mol % KC3-OA. However, all variations of this DSPS-targeted KC3-OA LNP formulation were significantly more active than either SM-102/DSPC or ALC-0315/DSPC controls (Tables 34-36).

Example 34. Impact of N/P Ratio in PS-Targeted LNPs on Expression in Human Dendritic Cells The aim of this study was to explore the effect of varying the N/P ratio in DSPS-targeted KC2-01 LNPs on transfection efficiency in human dendritic cells. The N/P ratio was varied from 4-7, while keeping the DSPS and DSPC concentrations constant at 5 mol % each, the concentration of KC2-01 constant at 50 mol %, and PEG-DMG at 1.5 mol %. ALC-0315 and SM-102 comparator formulations were also evaluated. The final ALC-0315/DSPC formulation was composed of 46.3 mol % ALC-0315, 9.4 mol % DSPC, 42.7 mol % cholesterol and 1.56 mol % PEG-DMG with a N/P of 6.2. The final SM-102/DSPC formulation was composed of 50 mol % SM-102, 10 mol % DSPC, 38.5 mol % cholesterol and 1.5 mol % PEG-DMG with a N/P of 5.

LNPs were prepared as described in Example 9, characterized for particle size and zeta potential as described in Example 10, and evaluated for transfection efficiency in murine dendritic cells as described in Example 28.

TABLE 37

Physicochemical properties and characterization of DSPS-targeted KC2-O1 LNPs containing KC2-O1 at various N/P ratios

| LNP formulation | Particle size | Particle Size (nm) Post-Freeze/Thaw | Encapsulation Efficiency (%) |
|---|---|---|---|
| KC2-O1 (N/P = 4) | 85.4 | 91.3 | 83.2 ± 4.7 |
| KC2-O1/DSPS (N/P = 4) | 84.1 | 90.2 | 85.5 ± 3.9 |
| KC2-O1 (N/P = 5) | 84.9 | 87.0 | 88.0 ± 4.7 |
| KC2-O1/DSPS (N/P = 5) | 80.91 | 88.0 | 88.3 ± 4.0 |
| KC2-O1 (N/P = 6) | 81.1 | 84.0 | 88.0 ± 1.3 |
| KC2-O1/DSPS (N/P = 6) | 82.2 | 88.0 | 89.6 ± 2.7 |
| KC2-O1 (N/P = 7) | 75.7 | 84.0 | 89.0 ± 3.1 |
| KC2-O1/DSPS (N/P = 7) | 79.5 | 81.5 | 88.8 ± 4.1 |

All DSPS-targeted KC2-O1 formulations showed a particle size around 76-85 nm and greater than 80% encapsulation efficiency. All particles were stable to freezing and thawing at −80° C. There was no apparent impact of the N/P used in the range of 4-7 on these properties.

TABLE 38 mCherry expression in human dendritic cells following incubation at 0.1 µg/ml for DSPS-targeted KC2-O1 LNPs containing KC2-O1 at various N/P ratios

| LNP formulation | MFI | T/NT | vs N/P = 4 |
|---|---|---|---|
| Untreated (UT) | 1,245 ± 3 | | |
| KC2-O1 (N/P = 4) | 2,077 ± 40 | | |
| KC2-O1/DSPS (N/P = 4) | 12,466 ± 2,359 | 13.5 | 1 |
| KC2-O1 (N/P = 5) | 1,966 ± 163 | | |
| KC2-O1/DSPS (N/P = 5) | 35,574 ± 13,780 | 47.6 | 3.1 |
| KC2-O1 (N/P = 6) | 3,389 ± 1,157 | | |
| KC2-O1/DSPS (N/P = 6) | 29,617 ± 3,345 | 13.2 | 2.5 |
| KC2-O1 (N/P = 7) | 5,852 ± 1,961 | | |
| KC2-O1/DSPS (N/P = 7) | 39,097 ± 6,398 | 8.2 | 3.4 |

The effect of targeting and N/P ratio on transfection activity was evaluated using 5 mol % DSPS-targeted LNPs comprised of KC2-01 at ratios of 4-7 (FIG. 23). This targeted composition was highly active at all N/P ratios, but did display an approximately 3-fold drop off going from N/P of 5 to N/P of 4. The targeted to nontargeted (T/NT) ratio displayed a clear peak at N/P=5 (Table 38).

Example 35. Impact of Ionizable Lipid on Immunogenicity of SARS-CoV-2 Spike Protein mRNA Vaccine Constructs Mice and study design. Female BALB/c mice were purchased from Charles River Laboratories, allowed to acclimate in the vivarium for at least 4 days, and were 6-8 weeks old at the start of the study. On study day (SD) 0 mice were injected intramuscularly in the left rear thigh with 1 μg of vaccine candidate (quantity refers to mRNA) in a volume of 50 μL. Study groups consisted of 5 mice and included vehicle control, comparator vaccines, and experimental vaccine candidates. Mice were given a second injection of the same vaccine candidate 21 days later. Blood was collected via submandibular puncture or terminally via cardiac puncture and serum or plasma was isolated from mice on SD 21 and 34 (+13 days post boost). Samples were stored at −80° C. until analysis for antibody titers.

Design and preparation of mRNA. mRNA encoding the SARS-CoV-2 full length spike protein and flanked with the same UTRs used in the BNT162b2 (Comirnaty) vaccine was purchased from Vernal Biosciences. All uridine nucleosides were substituted with N1-methyl-pseudouridine. To produce the mRNA, a synthetic gene encoding the mRNA sequence (VRN029; SEQ ID NO: 2, FIG. 13A) was cloned into a DNA plasmid. The synthetic gene was comprised of an RNA promoter, a 5' untranslated region, the SARS-COV2 Spike protein receptor binding domain, a 3' untranslated region, and a poly(A) tail region of approximately 120 As. The plasmid was propagated and expanded in a culture of $E.\ coli$ and then isolated from the clarified $E.\ coli$ lysate via anion exchange chromatography. The purified plasmid was linearized using a type IIs restriction enzyme that cut at a site at the end of the poly(A) tail encoding region. That plasmid was then incubated in a buffer with nucleotide triphosphates, RNA polymerase, and RNase inhibitor. To stop the reaction, DNase I was added to digest the linear plasmid template. The uncapped RNA was then purified using chromatography and then incubated in another buffer with GTP, S-adenosyl-methionine, a guanalyltransferase, 2'-O-methyltransferase, and RNase inhibitor. The capped mRNA was then purified using chromatography, buffer exchanged into water, and filled into vials.

Generation of lipid nanoparticles (LNP) containing mRNA. Stock solutions of each lipid were prepared. Ionizable lipids were weighed out in 4 mL glass vials (Thermo B7999-2) and dissolved in ethanol (Sigma-Aldrich 200 proof, RNase free) to a final concentration of 10 mM. Other lipids such as DSPC (Avanti Polar Lipids), Cholesterol (Dishman) and PEG-DMG (NOF) were weighed out and dissolved in ethanol to a concentration of 1 mM. DSPS-Na (NOF) was dissolved in methanol (Sulpelco, Omnisolve) at a concentration of 1 mM and briefly heated to 70° C. to complete its dissolution. DPPS-NH$_4$ (Avanti Polar Lipids) was dissolved directly in ethanol and incorporated at room temperature along with the other lipid components.

Lipid mixtures for each individual LNP were prepared by adding the desired volume of each lipid stock solution to a new vial, adding ethanol if needed to achieve a final volume of 1.2 mL. All formulations had 5 mol % of the PC and PS component, 40.5 mol % of cholesterol, 1.5 mol % of PEG-DMG, 48 mol % of the ICL, and a constant N/P ratio of 5.25. For example, a LNP formulation of KC3-PA/DPPC/DPPS/Chol/PEG-DMG (48/5/5/40.5/1.5 mol %), with an N/P of 5.25 contained 1575 nmol KC3-PA, 164.1 nmol DPPC, 164.1 nmol DPPS, 1296.1 nmol Chol and 82 nmol PEG-DMG for every 100 μg of mRNA used. mRNA solutions were prepared by thawing frozen mRNA (SARS-CoV-2 spike mRNA, Vernal) vials and diluting mRNA in 6.25 mM sodium acetate (pH 5.0) to a final concentration of 0.033 mg/mL, where the concentration is confirmed by absorbance on a Nanodrop.

To prepare LNPs, a NanoAssemblr Benchtop microfluidic device (from Precision Nanosystems) was used. If LNPs contained DSPS, the heating block accessory set to 70° C. was used, otherwise LNPs were mixed at room temperature. 3 mL of mRNA solution was loaded into a 3 mL disposable syringe (BD 309656) and 1 ml of lipid mixture in a 1 ml syringe (BD309659) and placed in the NanoAssemblr heating block for 4 min prior to mixing. LNP formation was achieved by pumping the liquid streams through a disposable microfluidics cassette at 3:1 aqueous:alcohol volume ratio at 6 mL/min mixing speed. After mixing, 3.6 mL of LNP mixture was collected, while the initial mixed volume of 0.35 mL and last 0.05 mL of mix was discarded. Ethanol was removed by buffer exchange using SpectraPor dialysis tubing (12-14k MWCO) in PBS (Cytivia, SH30256.01). LNPs were typically exchanged into PBS, pH 7.4 and then 15 mM Tris, pH 7.4, 20% sucrose, concentrated to 20-50 ug/mL mRNA, sterile filtered (Thermo Nalgene 0.2 um #720-1320) prior to freezing by immersion in liquid nitrogen for 5 min and long-term storage at −20° C. For this study, samples were concentrated to >40 μg/mL mRNA, and diluted with varying volumes of 15 mM Tris, 20% Sucrose, pH 7.4 to a target concentration of 40 μg mRNA and then frozen on LN2. Characterization of LNPs was undertaken after an aliquot of the LNPs were thawed and diluted 1:1 (vol:vol) with 15 mM Tris, pH 7.4 such that the final concentration was 20 μg/mL mRNA in 15 mM Tris, 10% sucrose, pH 7.4. This simulated the conditions of sample preparation that were performed prior to dosing the animals with an injection of 1 μg mRNA in 50 μL volume via IM injection into a hind limb.

LNP Characterization. mRNA encapsulation and mRNA concentration within the LNPs was measured using a Ribogreen assay. Nanoparticle size and zeta potential were measured by a zetasizer (Malvern).

SARS-CoV-2 anti-spike antibody titers. A standard indirect ELISA was performed to analyze serum samples for total IgG binding antibodies to the SARS-CoV-2 spike protein. Nunc MaxiSorp 96-well plates were coated with 75 μL of SARS-CoV-2 (Wuhan-Hu-1) spike protein (Sino Biological, cat. no. 40589-V08B1) diluted to 5 nM in 1×PBS, pH 7.4, covered and incubated statically for 16-18 hrs at 4° C. Unbound coating antigen was removed by washing plates 3× with 300 μL PBS+0.05% Tween-20 using a BioTek 405 TS plate washer. Plates were then blocked in PBS+5% w/v non-fat skim milk (Research Products International, cat. no. M17200-1000.0) for 1 hr at 37° C. Test and positive control samples were diluted in assay diluent (PBS, 0.05% Tween-20, 1% w/v non-fat skim milk) to a starting dilution of 1:20 or 1:40 followed by four-fold serial dilutions using U-bottom dilution plates. Once blocking was completed, blocking buffer was removed by inversion, plates were blotted on paper towels, and each sample was plated in duplicates. Plates were statically incubated for 2 hr at 37° C., followed by washing 3× with 300 μL. 100 μL of secondary detection antibody (goat anti-mouse-HRP IgG, Abeam, cat. no. ab6789) in assay diluent was added to each well at a dilution of 1:10,000 (1.33 nM concentration). Plates were incubated statically for 30 min at room temperature, and unbound antibodies were subsequently removed by plate inversion then washed 3×300 uL. To develop, 100 μL of room temperature 1-Step Ultra TMB substrate (ThermoFisher, cat. no. 34028) was added to each well and the reaction was stopped after 10 min with 50 μL of TMB stop solution (ThermoFisher cat. no. SS04). The plates were read within 30 min at 450 nm with a BioTek Synergy Neo 2 spectrophotometer.

Titers were defined as the reciprocal of the dilution that generated an absorbance signal on the linear part of the titration curve.

TABLE 39

Physicochemical properties of LNPs used in evaluating the immunogenicity of SARS-CoV-2 spike protein mRNA vaccine construct

| LNP Formulation | Particle Size (nm) | Zeta Potential (mV) pH 5 | Zeta Potential (mV) pH 7 | Encapsulation Efficiency (%) |
|---|---|---|---|---|
| KC3/DPPS-NH4/DPPC/PEG-DMG | 98.2 | 5.2 | −3.2 | 87.4 ± 7.4 |
| KC3-OA/DPPS-NH4/DPPC/PEG-DMG | 73.7 | 11.8 | −2.6 | 91.2 ± 5.5 |
| KC3-OA/DSPS/DSPC/PEG-DMG | 97.3 | 7.4 | −3.7 | 87.7 ± 5.9 |
| KC3-PA/DPPS-NH4/DPPC/PEG-DMG | 89.7 | 8.4 | −1.0 | 88.0 ± 4.3 |
| KC3-PA/DSPS/DSPC/PEG-DMG | 87.8 | 9.0 | −2.9 | 91.8 ± 8.2 |

To evaluate the impact of ionizable lipid composition on mRNA-LNP immunogenicity, BALB/c mice were immunized with mRNA-LNPs containing different ionizable lipids (KC3, KC3-OA, and KC3-PA). Blood plasma was collected on day 21 post prime and on day 13 post boost (day 34 of study). Total anti-spike binding IgG antibody titers were determined via ELISA. Reciprocal antibody titer data were log-transformed prior to statistical analysis. Groups were compared using one-way ANOVA with a Dunnett's multiple comparisons post-test. LNPs prepared using the ionizable lipid KC3-OA or KC3-PA induced a superior antibody response than LNPs containing the dilinoleoyl KC3 (DLin-KC3-DMA or just KC3) at both day 21 post prime (FIG. 24A) and day 13 post boost (study day 34) (FIG. 24B).

Example 36. Preparation of Ammonium Salts of DPPS and DSPS

Dissolve 1.5 g PS sodium salt (DPPS-Na or DSPS-Na) in 500 ml of CHCl$_3$:Methanol:Water (CMW) 1:3:1 by volume. with 1M NH$_4$Cl in the water, to make a single-phase solution in a separatory funnel. Swirl 3-5 minutes, apply minimal heat if PS is not completely dissolved. Add CHCl3 and distilled water (approximately 200 mL each) and shake the funnel 2-3 minutes until a clear two-phase partition is achieved. Collect the bottom layer and re-partition with CMW 1:1:1 (by volume) with 1M NH$_4$Cl in the water. Collect the bottom layer and wash it 2× with fresh methanol-water (the volume of methanol is 50% of the volume of CHCl$_3$ and the volume of water is 20% of the total volume of chloroform and methanol) until a clear two-phase partition is achieved. Remove solvents under vacuum and freeze-dry from cyclohexane. Yield 1.2 g.

Example 37. Apparent Solubility of Phosphatidylserine Salts in Ethanol

Apparent solubilities of phosphatidylserine salts in ethanol were determined by shake flask technique. Sodium and ammonium salts of phosphatidylserines in the powder form were obtained from Avanti Polar Lipids (Alabama, USA). Aliquots of phosphatidylserine salt powder were placed in 12×75 borosilicate glass tubes in triplicate. Three mL of 200 proof ethanol (catalog number E-7023, MilliporeSigma, USA) were added, the tubes were closed with polyethylene snap caps, agitated using vortex mixer for 10-15 s to obtain uniform suspensions, and placed in a horizontal position on a rocking platform at room temperature (20-22° C.) overnight. The ambient temperature at the end of incubation was 20.4-20.9° C. After 24 hours incubation, the suspensions were visually checked for the presence of a solid phase, allowed to settle under gravity, and the supernatant solutions were passed through a 0.2-µm PTFE syringe membrane filters. The first 0.5 ml of the filtrate was discarded, the next 1 ml was collected, and phosphatidylserine in the filtrates was quantified by phospholipid phosphate assay as follows: 20 µL aliquots of the filtrate were taken in triplicate into glass tubes, ethanol was evaporated in a stream of argon at 70° C., and the residue was digested in a mixture of 60 µL concentrated sulfuric acid and 20 µL 30% hydrogen peroxide for 10 min at 180-190° C. The digested samples were diluted with 1 mL of deionized water, 20 µL of 10% sodium sulfite was added to destroy any residual peroxide, and the samples were incubated on a boiling water bath for 15 min to hydrolyze any condensed phosphate species. The samples were chilled down to room temperature, mixed with 0.2 mL of 2% (w/w) ammonium molybdate solution and 20 µL of 10% (w/w) ascorbic acid solution, incubated on a boiling water bath for 10 min, and chilled down in a water bath at room temperature. The phosphate concentration was determined from the optical density of the formed blue phosphomolybdic acid at 825 nm using five-point standard curve from concurrently run standards prepared from the NIST-traceable commercial phosphate standard solution diluted to cover the range of 0-2 mM phosphate (coefficient of determination $R^2>0.9999$). Solubility of phosphatidylserine salts was expressed in molarity units of phosphatidylserine (Table 40). The data are average f SD (N=3).

TABLE 40

Solubility of phosphatidylserine salts in 100% ethanol at room temperature.

| Phosphatidylserine salt | Solubility, mM phosphatidylserine |
|---|---|
| DSPS sodium | 0.111 ± 0.009 |
| DPPS sodium | 0.201 ± 0.004 |
| DSPS ammonium | 0.034 ± 0.004 |
| DPPS ammonium | 0.865 ± 0.060 |

Ammonium salt of dipalmitoylphosphatidylserine (DPPS) unexpectedly showed several-fold higher ethanol solubility than ammonium salt of distearoylphosphatidylserine (DSPS) or sodium salts of any of these compounds.

Example 38. Impact of PEG-Stearic Acid, N/P, and ICL on Transfection Efficiency in Human Dendritic Cells The aim of this study was to explore the effect of varying the KC3-OA concentration and N/P ratio in DSPS-targeted LNPs on transfection efficiency in human dendritic cells. In addition, the effect of replacing PEG-DMG with PEG-stearic acid (PEG-SA) (BroadPharm, BP-26262) at 1 and 3 mol % total lipid was compared.

The concentration of KC3-OA was varied from 45-48 mol %, while keeping the DSPS and DSPC concentrations constant at 5 mol % each and PEG-DMG at 1.5 mol. The increase in % KC3OA was commensurate with a proportional reduction in the % of cholesterol. The N/P was varied from 5-6.5 in 0.5 increments while keeping 45 mol % KC3OA constant. In certain cases, PEG-DMG was replaced with PEG-stearic acid. ALC-0315 and SM-102 comparator formulations were also evaluated. The final ALC-0315/DSPC formulation was composed of 46.3 mol % ALC-0315, 9.4 mol % DSPC, 42.7 mol % cholesterol and 1.56 mol % PEG-DMG with a N/P of 6.2. The final SM-102/DSPC formulation was composed of 50 mol % SM-102, 10 mol % DSPC, 38.5 mol % cholesterol and 1.5 mol % PEG-DMG with a N/P of 5.

LNPs were prepared as described in Example 9, characterized for particle size and zeta potential as described in Example 10, and evaluated for transfection efficiency in human dendritic cells as described in Example 28.

TABLE 41

Physicochemical properties and characterization of DSPS-targeted KC3-OA LNPs at various N/P ratios, various ICL concentrations, and PEG-SA concentrations used in Example 38

| LNP formulation | Particle size (nm) | Zeta Potential (mV) pH 5 | Zeta Potential (mV) pH 7 | Encapsulation Efficiency (%) |
|---|---|---|---|---|
| KC3-OA, 5% DSPS | 85.2 | 13.9 | −1.9 | 90.3 ± 6.4 |
| SM102 | 71.0 | 6.0 | −3.5 | 84.1 ± 10.7 |
| ALC-0315 | 63.0 | 5.2 | −5.2 | 89.0 ± 5.9 |
| 45 mol % KC3-OA, 5 % DSPS (N/P = 5) | 90.9 | 15.4 | −2.0 | 93.9 ± 2.4 |
| 45 mol % KC3-OA, 5 % DSPS (N/P = 5.5) | 91.1 | 14.4 | −0.48 | 92.9 ± 1.7 |
| 45 mol % KC3-OA, 5 % DSPS (N/P = 6) | 81.2 | 12.5 | −1.9 | 92.8 ± 6.3 |
| 45 mol % KC3-OA, 5 % DSPS (N/P = 6.5) | 73.0 | 16.9 | −1.6 | 92.8 ± 7.6 |
| 43% KC3-OA, 5% DSPS (N/P = 5) | 84.3 | 20.8 | −0.2 | 93.0 ± 4.2 |
| 48% KC3-OA, 5% DSPS (N/P = 5) | 102.6 | 19.6 | −2.1 | 94.4 ± 4.5 |
| 45% KC3-OA, 5% DSPS, 1% PEG-SA (N/P = 5) | 141.7 | 19.6 | −1.6 | 93.8 ± 2.9 |
| 45% KC3-OA, 5% DSPS, 3% PEG-SA (N/P = 5) | 123.1 | 17.0 | −3.3 | 91.7 ± 4.8 |
| 45% KC3-OA, 5% DSPS, 1% PEG-SA (N/P = 6) | 163 | 23.3 | −1.5 | 92.9 ± 1.7 |
| 45% KC3-OA, 5% DSPS, 3% PEG-SA (N/P = 6) | 142.2 | 17.2 | −2.3 | 92.6 ± 3.6 |

All DSPS-targeted KC3-OA formulations showed a particle size about 90 nm and greater than 90% encapsulation efficiency when formulated with 1.5 mol % PEG-DMG. However, the sized increased significantly to about 140 nm when substituting 1.5 mol % PEG-DMG for either 1 or 3 mol % of PEG200-stearic acid (PEG-SA). All particles showed a slightly negative zeta potential at pH 7.4, and a zeta potential between 12.5 and 23 mV at pH 5.

TABLE 42 mCherry expression in human dendritic cells following incubation at 1 μg/ml

| LNP formulation | MFI |
|---|---|
| UT | 1,343 ± 263 |
| KC3-OA, 5% DSPS | 74,561 ± 8,663 |
| SM102 | 4,242 ± 1,942 |
| ALC-0315 | 3,760 ± 1,625 |
| 45 mol % KC3-OA, 5% DSPS (N/P = 5) | 70,437 ± 26,182 |

TABLE 42-continued mCherry expression in human dendritic cells following incubation at 1 μg/ml

| LNP formulation | MFI |
|---|---|
| 45 mol % KC3-OA, 5% DSPS (N/P = 5.5) | 71,757 ± 25,238 |
| 45 mol % KC3-OA, 5% DSPS (N/P = 6) | 29,810 ± 11,956 |
| 45 mol % KC3-OA, 5% DSPS (N/P = 6.5) | 17,921 ± 8,100 |
| 43% KC3-OA, 5% DSPS (N/P = 5) | 39,229 ± 13,743 |
| 48% KC3-OA, 5% DSPS (N/P = 5) | 117,973 ± 42,550 |
| 45% KC3-OA, 5% DSPS, 1% PEG-SA (N/P = 5) | 76,331 ± 26,839 |
| 45% KC3-OA, 5% DSPS, 3% PEG-SA (N/P = 5) | 38,667 ± 21,077 |
| 45% KC3-OA, 5% DSPS, 1% PEG-SA (N/P = 6) | 74,019 ± 46,480 |
| 45% KC3-OA, 5% DSPS, 3% PEG-SA (N/P = 6) | 49,934 ± 24,738 |

TABLE 43 mCherry expression in human dendritic cells following incubation at 0.1 μg/ml

| LNP formulation | MFI |
|---|---|
| UT | 1,295 ± 116 |
| KC3-OA, 5% DSPS | 5,670 ± 886 |
| SM102 | 1,492 ± 26 |
| ALC-0315 | 1,405 ± 28 |
| 45 mol % KC3-OA, 5% DSPS (N/P = 5) | 10,035 ± 2,773 |
| 45 mol % KC3-OA, 5% DSPS (N/P = 5.5) | 11,461 ± 3,826 |
| 45 mol % KC3-OA, 5% DSPS (N/P = 6) | 9,014 ± 1,673 |
| 45 mol % KC3-OA, 5% DSPS (N/P = 6.5) | 5,214 ± 1,678 |
| 43% KC3-OA, 5% DSPS (N/P = 5) | 8,403 ± 2,185 |
| 48% KC3-OA, 5% DSPS (N/P = 5) | 13,434 ± 5,292 |
| 45% KC3-OA, 5% DSPS, 1% PEG-SA (N/P = 5) | 7,943 ± 2,848 |
| 45% KC3-OA, 5% DSPS, 3% PEG-SA (N/P = 5) | 6,362 ± 1,502 |
| 45% KC3-OA, 5% DSPS, 1% PEG-SA (N/P = 6) | 7,197 ± 1,495 |
| 45% KC3-OA, 5% DSPS, 3% PEG-SA (N/P = 6) | 6,601 ± 1,756 |

The effect of targeting and ICL choice on transfection activity was evaluated using 5 mol % DSPS-targeted LNPs comprised of KC3-OA at concentrations ranging from 43-48 mol % (FIGS. 25A-25B) and N/P from 5-6.5. LNP formulations at N/P 5 and 6, and 45 mol % KC3-OA were also prepared with PEG-SA at both 1 and 3 mol % and compared to similar formulation with 1.5 mol % PEG-DMG. All formulations were highly active, although formulations with PEG-DMG did display about 30-40% higher transfection than those with PEG-SA. The formulations did trend over the range to have higher transfection going from 43 to 48

An increase in DSPS content was commensurate with a proportional reduction in the % of DSPS and inclusion of anionic lipids was in conjunction with a proportional reduction in DSPC.

LNPs were prepared as described in Example 9, characterized for particle size and zeta potential as described in Example 10, and evaluated for transfection efficiency in human dendritic cells as described in Example 28.

TABLE 44

Physicochemical properties and characterization of LNPs used in Example 39

| LNP formulation | Particle size (nm) | Zeta Potential (mV) pH 5 | Zeta Potential (mV) pH 7 | Encapsulation Efficiency (%) |
| --- | --- | --- | --- | --- |
| KC30A/5 mol % DSPS-Na | 73.4 | 13.8 | −1.8 | 90.3 ± 6.4 |
| AKG-UO1 | 108 | 13.1 | −0.2 | 84.2 ± 4.2 |
| AKG-UO1/2.5 mol % DSPS-Na | 120.6 | 3.4 | −1.7 | 86.1 ± 5.0 |
| AKG-UO1/5 mol % DSPS-Na | 101.3 | 14.9 | −2.9 | 88.3 ± 3.2 |
| AKG-UO1/7.5 mol % DSPS-Na | 107 | 17.0 | −4.2 | 89.1 ± 3.6 |
| AKG-UO1/10 mol % DSPS-Na | 110.1 | 15.2 | −5.1 | 88.1 ± 2.7 |
| AKG-UO1/7.5 mol % DPPS-Na | 99.37 | 17.8 | −7.6 | 87.4 ± 4.4 |
| AKG-UO1/7.5 mol % DOPS-Na | 120.6 | 15.1 | −3.5 | 89.5 ± 3.5 |
| AKG-UO1/7.5 mol % DMPS-Na | 101.8 | 12.7 | −3.8 | 88.4 ± 1.3 |
| AKG-UO1/20 mol % DSPS-Na | 130.7 | 7.0 | −7.0 | 88.5 ± 1.9 |
| AKG-UO1/5 mol % DSPG-Na | 101.1 | 17.5 | −4.7 | 87.1 ± 0.9 |
| AKG-UO1/10 mol % DSPG-Na | 86.23 | 16.5 | −4.1 | 90.1 ± 3.1 |
| AKG-UO1/7.5 mol % DSPE-Glut | 98.31 | 16.9 | −6.5 | 89.6 ± 9.1 |
| AKG-UO1/7.5 mol % DSPE-SA | 98.6 | 14.3 | −5.6 | 88.4 ± 9.0 | mol % KC3-OA. All LNP variations of this DSPS-targeted KC3-OA LNP formulation were significantly more active than either SM-102/DSPC or ALC-0315/DSPC controls at both concentrations evaluated (Tables 42 and 43).

Example 39. Targeting of Human Dendritic Cells with Anionic Phospholipids

The aim of this study was to explore the effect of targeting AKG-UO-1 based LNPs with increasing amounts of DSPS to determine if an optimal composition can be defined. In addition, while keeping the phosphatidyl serine composition constant, a comparison between the sodium salts of L-DSPS, L-DPPS, L-DOPS, L-DMPG and the D isomer of DSPS were compared. Additionally, the targeting effect of phosphatidylserine was compared to the potential targeting effect of other anionic lipids by preparing AKG-UO-1 LNPs containing the sodium salts of DSPG (Avanti Polar Lipids #840465), DSPE-gluraric acid (BroadPharm, BP-26158) and DSPE-succinyl (Avanti Polar Lipids) and determining their transfection efficiency in human dendritic cells.

The concentration of KC3-OA was kept constant at 50 mol %, the total phospholipid concentration was kept constant at 10 mol %, the cholesterol composition was kept constant at 38.5 mol % and the PEG-DMG concentration kept constant at 1.5 mol %. N/P ratio was 5 for all samples.

The expression data for these UO-1 containing LNPs targeted with various anionic phospholipids in human dendritic cells are shown in FIG. 26A for a 1 µg/mL mRNA concentration and FIG. 26B for a 0.1 µg/mL concentration. These studies show that LNPs incorporating DPPS or DSPS demonstrated a markedly higher expression compared to those without any phosphatidylserine, and that these two saturated PS analogs were superior to LNPs containing either the C14 saturated DMPS and the C18 monounsaturated DOPS. Surprisingly, the incorporation of DSPG into LNPs increased expression at both 0.1 and 1 ug/mL equally as well as DSPS or DPPS, while neither Glu-DSPE or Suc-DSPE showed any improvement in expression. Surprisingly, while it was shown that there was no advantage of using phophatidylglycerol (PG) in LNPs with murine dendritic cells (Example 15), the results provided in this Example show that PG, when incorporated into LNPs can dramatically improve transfection of human dendritic cells and thus be a useful component of human LNP vaccines.

Example 40. Targeting of Human Dendritic Cells with Phosphatidylglycerol

The aim of this study was to explore the effect of targeting LNPs containing UO-1 or KC3-01 ICLs with various densities of distearoylphosphatidylglycerol (DSPG) on transfection efficiency in human dendritic cells. DSPG was incorporated in the LNPs at densities ranging from 0-10 mol % of the total lipid content. Control LNPs included KC3-OA LNPs with the previously established, mol % of DSPS as the targeting lipid, and nontargeted SM-102 or ALC-0315 containing LNPs. LNPs were prepared as described in Example 9, characterized for particle size and zeta potential as described in Example 10, and evaluated for transfection efficiency in human dendritic cells as described in Example 28. The LNPs used the ionizable lipids in Table 45 in the ICL with a constant N/P ratio of 5.25 and 48 mol %, the DSPG (Na$^+$ salt) lipid was included at 0-mol % and the DSPC phospholipid constant at 10 mol %-mol % incorporated of DSPG (total of DSPG and DSPC was 10 mol %), and the cholesterol constant at 40.5 mol %. PEG-DMG was held constant in all formulations at 1.5 mol %. The final ALC-0315/DSPC formulation was composed of 46.3 mol % ALC-0315, 10 mol % DSPC, 42.7 mol % cholesterol and 1.5 mol % PEG-DMG. The SM-102/DSPC formulation was composed of 50 mol % SM102, 10 mol % DSPC, 38.5 mol % cholesterol and 1.5 mol % PEG-DMG.

TABLE 45

Physicochemical properties and characterization of LNPs used in Example 40

| LNP formulation | Particle size (nm) | Zeta Potential (mV) pH 5 | Zeta Potential (mV) pH 7 | Encapsulation Efficiency (%) |
|---|---|---|---|---|
| KC3-OA, 5% DSPS | 85.2 | 13.9 | −1.9 | 90.3 ± 6.4 |
| SM102 | 71.0 | 6.0 | −3.5 | 84.1 ± 10.7 |
| ALC-0315 | 63.0 | 5.2 | −5.2 | 89.0 ± 5.9 |
| UO1 | 99.2 | 25.4 | 2.9 | 86.9 ± 2.5 |
| UO1, 1.25% DSPG | 101.2 | 17.7 | 0.4 | 85.3 ± 2.4 |
| UO1, 2.5% DSPG | 89.7 | 13.5 | −2.3 | 83.8 ± 8.4 |
| UO1, 5.0% DSPG | 81.2 | 17.3 | −0.7 | 90.9 ± 2.7 |
| UO1, 7.5% DSPG | 65.9 | 15.9 | −1.8 | 91.0 ± 8.1 |
| UO1, 10% DSPG | 67.7 | 16.7 | −2.9 | 90.5 ± 6.6 |
| KC3-01 | 95.0 | 26.4 | 1.5 | 90.3 ± 11.5 |
| KC3-01, 1.25% DSPG | 98.4 | 27.4 | 0.0 | 90.7 ± 3.1 |
| KC3-01, 2.5% DSPG | 82.1 | 18.5 | −0.8 | 90.6 ± 3.2 |
| KC3-01, 5.0% DSPG | 72.4 | 18.1 | −2.1 | 89.9 ± 3.8 |
| KC3-01, 7.5% DSPG | 71.0 | 14.8 | −2.2 | 89.4 ± 3.6 |
| KC3-01, 10% DSPG | 74.6 | 13.0 | −2.3 | 89.5 ± 13.5 |

TABLE 46 mCherry expression in human dendritic cells following incubation at 1 µg/ml

| LNP formulation | MFI | T/NT | vs ALC-0315 LNP (fold) | vs SM-102 LNP (fold) |
|---|---|---|---|---|
| Untreated (UT) | 1,453 ± 263 | | | |
| KC3-OA, 5% DSPS | 89,815 ± 16,603 | | 76.8 | 8.4 |
| SM102 | 11,924 ± 1,089 | | | |
| ALC-0315 | 2,604 ± 376 | | | |
| UO1 | 2,049 ± 297 | | 0.5 | 0.1 |
| UO1, 1.25% DSPG | 2,728 ± 950 | 2.1 | 1.1 | 0.1 |
| UO1, 2.5% DSPG | 8,134 ± 3,763 | 11.2 | 5.8 | 0.6 |
| UO1, 5.0% DSPG | 22,206 ± 3,488 | 34.8 | 18.0 | 2.0 |
| UO1, 7.5% DSPG | 12,424 ± 1,939 | 18.4 | 9.5 | 1.0 |
| UO1, 10% DSPG | 5,561 ± 639 | 6.9 | 3.6 | 0.4 |
| KC3-01 | 49,931 ± 14,344 | | 42.1 | 4.6 |
| KC3-01, 1.25% DSPG | 119,467 ± 21,513 | 2.4 | 102.6 | 11.3 |
| KC3-01, 2.5% DSPG | 112,191 ± 12,156 | 2.3 | 96.2 | 10.6 |
| KC3-01, 5.0% DSPG | 86,696 ± 10,231 | 1.8 | 74.1 | 8.1 |
| KC3-01, 7.5% DSPG | 25,230 ± 2,061 | 0.5 | 20.7 | 2.3 |
| KC3-01, 10% DSPG | 8,250 ± 2,442 | 0.1 | 5.9 | 0.6 |

TABLE 47 mCherry expression in human dendritic cells following incubation at 0.1 µg/ml

| LNP formulation | MFI | T/NT | vs ALC-0315 LNP (fold) | vs SM-102 LNP (fold) |
|---|---|---|---|---|
| Untreated (UT) | 1,403 ± 190 | | | |
| KC3-OA, 5% DSPS | 10,347 ± 3,118 | | 308.6 | 48.0 |
| SM102 | 1,590 ± 243 | | | |
| ALC-0315 | 1,432 ± 198 | | | |
| UO1 | 1,393 ± 237 | | | |
| UO1, 1.25% DSPG | 1,409 ± 262 | 0.5 | 0.2 | 0 |
| UO1, 2.5% DSPG | 1,474 ± 280 | 6.7 | 2.4 | 0.4 |
| UO1, 5.0% DSPG | 2,253 ± 1,089 | 81.0 | 29.3 | 4.6 |
| UO1, 7.5% DSPG | 1,887 ± 400 | 46.2 | 16.7 | 2.6 |
| UO1, 10% DSPG | 1,515 ± 252 | 10.7 | 3.9 | 0.6 |
| KC3-01 | 1,976 ± 112 | | 19.8 | 3.1 |
| KC3-01, 1.25% DSPG | 2,377 ± 329 | 1.7 | 33.6 | 5.2 |
| KC3-01, 2.5% DSPG | 3,801 ± 485 | 4.2 | 82.7 | 12.9 |
| KC3-01, 5.0% DSPG | 8,580 ± 786 | 12.5 | 247.6 | 38.5 |
| KC3-01, 7.5% DSPG | 3,075 ± 279 | 2.9 | 57.7 | 9.0 |
| KC3-01, 10% DSPG | 1,619 ± 146 | 0.4 | 7.4 | 1.2 |

The effect of targeting two different LNPs with DSPG on transfection activity was evaluated using 0-10 mol % DSPG-targeted LNPs (FIGS. 27A-27B). For UO-1 containing LNPs the optimum DSPG concentration was 5 mol % at both 1 and 0.1 ug/ml, resulting in a 34.8 folding targeting effect at 1 ug/ml and 81-fold improvement over nontargeted LNPs at 0.1 ug/ml. For KC3-01 containing LNPs the optimum DSPG concentration was also at 5 mol % for the 0.1 ug/mL, but showed a broader peak of 1.25-5 mol % at the higher concentration of 1 ug/mL with a targeting effect of 2.4-fold at 1 ug/mL and 12.5-fold at the lower concentration of 0.1 ug/mL. Both of the peak targeted LNPs showed increased transfection activity compared to nontargeted ALC-0315 and SM-102 LNPs (Tables 46 and 47), with an up to 102.6% increase compared to ALC-0315 for DSPG-targeted KC3-01 LNPs at 1 ug/mL and an up to 247.6 fold increase at 0.1 ug/mL. The improvement over SM-102 LNPs was as high as 38.50-fold for the 5 mol % DSPG targeted KC3-01 LNP and 48-fold for the DSPS-targeted targeted KC3-OA LNP control. This data shows that DSPG can be a potent targeting anionic lipid to increase transfection efficiency in human dendritic cells and thus for inclusion in human lipid nanoparticle-based vaccines. The data show that PG-targeting of LNPs is highly effective when combined with the KC3-family of ICLs. These results were unexpected in light of the use of a highly negatively charged anionic phospholipid with LNPs that also incorporate a negatively charged nucleic acid to compete with. These results were also surprising in light of the lack of impact of including DSPG in LNPs on uptake in murine dendritic cells (Example 15).

Example 41. Comparison of DSPC and DPPC as Helper Lipids in a KC3-PA-Based LNP Formulation The aim of this study was to explore comparing DSPC and DPPC in KC3-PA DPPS-targeted and non-targeted LNPs. The concentration of KC3-OA was 48 mol %, cholesterol 40.5 mol %, PEG-DMG 1.5 mol %. The phospholipid composition was kept constant at 10 mol %, but for those that were targeted with DPPS, the DPPS concentration was 5 mol % and either DSPC or DPPC at 5 mol %. All formulations had an N/P of 5.25.

LNPs were prepared as described in Example 9, and were characterized for particle size, mRNA concentration and % mRNA entrapment after ethanol removal by dialysis and after sterile filtration as described in Example 10.

TABLE 48

Physicochemical properties and characterization of KC3-PA-targeted and non-targeted LNPs

| LNP formulation | Particle Size (nm) after filtration | Encapsulation Efficiency (%) | % mRNA Loss upon filtration |
|---|---|---|---|
| KC3-PA/DPPC | 108.5 | 82.2 ± 2.4 | 35.5 |
| KC3-PA/DPPC/DPPS-NH[4] | 107.7 | 90.6 ± 6.1 | 10.6 |
| KC3-PA/DSPC | 114.0 | 86.4 ± 5.7 | 12.5 |
| KC3-PA/DSPC/DPPS-NH[4] | 91.6 | 91.3 ± 6.7 | 4.4 |

Once the LNPs have been prepared and the ethanol removed by dialysis, the measurement of mRNA concentration before and after filtration provides another metric to evaluate the formulations. It is advantageous if LNPs have a high efficiency of sterile filtration, where mRNA loss is minimized and eliminates membrane fouling and poor product yields. In the non-targeted group, we found a 2.8-fold improvement in mRNA recovery with the DSPC sample compared to DPPC and in the targeted group we found a 2.4-fold increase in mRNA recovery. This suggests that DSPC is a more compatible helper lipid in formulations with KC3-PA than DPPC with and without 5 mol % DPPS.

Example 42. Comparison of UO-1, UO-6, UO-7 in PS-Targeted LNPs on Expression in Murine Dendritic Cells The aim of this study was to compare the transfection activities in murine dendritic cells of a series of ionizable lipid analogs when formulated into LNPs with and without DSPS-targeting. AKG-UO-1, AKG-UO-6 and AKG-UO-7 were formulated into LNPs at 50 mol % containing 10% phospholipid, 38.5 mol % cholesterol, 1.5 mol % PEG-DMG within N/P of 5 using mCherry encoded mRNA. If DSPS was added there was a proportional reduction in the mol % of DSPC included in the formulation.

LNPs were prepared as described in Example 9, characterized for particle size and zeta potential as described in Example 10, and evaluated for transfection efficiency in murine dendritic cells as described in Example 11.

TABLE 49

Physicochemical properties and characterization of DSPS-targeted LNPs containing either UO-1, UO-6, or UO-7

| LNP formulation | Particle size (nm) | Zeta Potential (mV) pH 5 | Zeta Potential (mV) pH 7 | Encapsulation Efficiency (%) |
|---|---|---|---|---|
| UO-1 | 72.8 | 10.2 | 3.6 | 89.6 ± 4.8 |
| UO-1/7.5% DSPS | 80.5 | 9.2 | -2.7 | 91.1 ± 4.2 |
| UO-6 | 80.0 | 14.5 | 5.6 | 90.5 ± 11.1 |
| UO-6/7.5% DSPS | 86.1 | 13.9 | -2.4 | 92.8 ± 11.3 |
| UO-7 | 79.3 | 14.9 | 4.3 | 91.4 ± 2.5 |
| UO-7/7.5% DSPS | 94.3 | 14.3 | -2.6 | 92.3 ± 5.0 |

LNPs prepared with or without 7.5% DSPS and three different ICLs, UO-1, UO-6, and UO-7 all displayed a small size of 72-95 nm and greater than approximately 90% encapsulation efficiency. All of the LNPs had a positive zeta potential at pH 5, while the DSPS containing formulations showed a slightly anionic zeta potential at neutral pH.

TABLE 50 mCherry expression in murine dendritic cells following incubation at 1 μg/ml for DSPS-targeted LNPs containing either UO-1, UO-6, or UO-7

| LNP formulation | MFI | T/NT | vs UO-1 (fold) |
|---|---|---|---|
| Untreated (UT) | 233 ± 9 | | |
| UO-1 | 2,234 ± 204 | | |
| UO-1/7.5% DSPS | 31,928 ± 3,992 | 15.8 | |
| UO-6 | 433 ± 70 | | |
| UO-6/7.5% DSPS | 2,894 ± 255 | 13.3 | 0.08 |
| UO-7 | 510 ± 18 | | |
| UO-7/7.5% DSPS | 4,486 ± 1,042 | 15.4 | 0.13 |

The expression data for LNPs comprised of each of the three different ICLs showed a 13.3-15.4 fold targeting effect (T/NT) compared to those LNPs not including 7.5 mol % DSPS (FIG. 28). However, LNPs including UO-1 were clearly superior in transfecting murine dendritic cells compared to both UO-6 and UO-7. This was surprising given that we had previously showed with the dioxolane series lipids that the dimethylaminopropyl head group (e.g. KC3-01) was clearly superior to LNPs prepared with KC2-01, where the headgroup was dimethylaminoethyl, and thus contained an ethyl group (two carbons) between the titratable amine group and the dioxolane backbone. However, with the UO-series of lipids, the UO-7 lipid that contains the same dimethylaminopropyl group used in KC3 is clearly inferior to the UO-1 lipid, with the dimethylaminoethyl group containing the two carbon ethyl group between the amine and now the glycerol backbone. In fact, LNPs containing UO-7 showed only 13% of the activity seen with LNPs containing UO-1.

Example 43. Impact of Ionizable Lipid and ICL Density on Immunogenicity of SARS-CoV-2 Spike Protein mRNA LNPs LNPs were prepared as described in Example 9, characterized for particle size and zeta potential as described in Example 10, and evaluated for transfection efficiency in human dendritic cells as described in Example 28. The LNPs used the ionizable lipids in Table 51 in the ICL with a constant N/P ratio of 5.25. The concentration of ICL used in a particular formulation is displayed in the graph. For example, 46.5% KC3-OA %/5% DSPC/5% DSPS formulation contains, 46.5 mol % KC3-OA, 5 mol % DSPC, 5 mol % DSPS, 42 mol % cholesterol and 1.5 mol % PEG-DMG, or 1575 nmol KC3-OA, 169.4 nmol DSPC, 169.4 nmol DSPS, 1422.6 nmol cholesterol and 50.8 nmol PEG-DMG per 100 μg mRNA. The PEG-DMG concentration was held constant at 1.5 mol % for all samples. If the ICL concentration is increased, there is a proportional decrease in the cholesterol concentration. For formulations with KC-like ICLs, they were targeted with 5 mol % DSPS and for UO-like ICLs, they were targeted with 7.5 mol % DSPS.

The ALC-0315 formulation was composed of 46.3 mol % ALC-0315, 10 mol % DSPC, 42.7 mol % cholesterol and 1.56 mol % PEG-DMG.

TABLE 51

Physicochemical properties and characterization of LNPs containing either ALC-0315, KC2, KC3-OA, UO-1 and UO-9 containing SARS-CoV-2 spike protein mRNA

| LNP formulation | Particle Size (nm) | Zeta Potential (mV) pH 5 | Zeta Potential (mV) pH 7 | Encapsulation Efficiency (%) |
| --- | --- | --- | --- | --- |
| ALC-0315 | 99.2 | 25.4 | 2.9 | 81.1 ± 3.7 |
| 46.5% KC2/5% DSPC/5% DSPS | 89.7 | 13.5 | −2.3 | 92.1 ± 3.8 |
| 46.5% KC3-01/5% DSPC/5% DSPS | 81.2 | 17.3 | −0.7 | 92.3 ± 6.4 |
| 46.5% KC3-OA/5% DSPC/5% DSPS | 65.9 | 15.9 | −1.8 | 91.3 ± 7.7 |
| 48% KC3-OA/5% DSPC/5% DSPS | 67.8 | 16.7 | −2.9 | 89.9 ± 7.2 |
| 46.5 KC3-OA/5% DPPC/5% DSPS | 95.0 | 26.4 | 1.5 | 91.5 ± 3.8 |
| 48% UO-1/5% DSPC/7.5% DSPS | 82.1 | 18.5 | −0.8 | 91.9 ± 7.8 |
| 48% UO-9/5% DSPC/7.5% DSPS | 72.4 | 18.1 | −2.1 | 92.8 ± 6.5 |

However, it was not clear if lowering the mol % of the ionizable lipid would negatively impact in vivo immunogenicity. Using the same methods outlined in Example 35, BALB/c mice were immunized intramuscularly with 1 μg of vaccine candidates and blood was collected 21 days later.

Serum was assayed for total anti-spike IgG antibodies by ELISA. The geometric mean titers were similar between mice immunized with LNPs containing either 46.5 or 48 mol % KC3-OA. LNPs containing 46.5 mol % of the ionizable lipid KC3-01 were similarly immunogenic (FIG. 29). All KC3-01 or KC3-OA LNPs showed significantly higher titers when compared to ALC-0315 or KC2 LNP controls.

Mice were also immunized with vaccine candidates containing the ionizable lipids AKG-UO1 and AKG-UO9. AKG-UO1 induced antibody titers similar to KC3-OA, but LNPs containing AKG-UO9 were poorly immunogenic.

Example 44. Impact of PG and PS Targeting of KC3-OA Containing LNPs on mRNA Expression in Human Dendritic Cells The aim of this study was to explore the effect of targeting LNPs containing KC3-OA ICLs with various forms of phosphatidylglycerol (PG), including distearoylphosphatidylglycerol (DSPG), dipalmitoylphosphatidylglycerol (DPPG), dioleoylphosphatidylglycerol (DOPG), and dimyristoylphosphatidylglycerol (DMPG) on transfection efficiency in human dendritic cells. A second aim was to compare these targeted LNPs to those containing DSPS, and finally to compare formulations that incorporated two anionic phospholipids (DSPG and DSPS).

PG in various forms was incorporated in the LNPs at densities ranging from 0-5 mol % of the total lipid content. Control LNPs included KC3-OA LNPs with the previously established 5 mol % of DSPS as the targeting lipid. LNPs were prepared as described in Example 9, characterized for particle size and zeta potential as described in Example 10, and evaluated for transfection efficiency in human dendritic cells as described in Example 28. The LNPs used the ionizable lipids in Table 52 in the ICL with a constant N/P ratio of 5.25 and 48 mol %, the DSPG (Nat salt) lipid was included at 0-10 mol % and the DSPC phospholipid was also varied from 0-10 mol %, and the cholesterol constant at 40.5 mol %. Some formulations included DSPS and DSPG, with or without DSPC. PEG-DMG was held constant in all formulations at 1.5 mol %.

TABLE 52

Physicochemical properties and characterization of LNPs used in Example 44.

| LNP formulation | Particle size (nm) | Zeta Potential (mV) pH 5 | Zeta Potential (mV) pH 7 | Encapsulation Efficiency (%) |
|---|---|---|---|---|
| 10% DSPC | 91.9 | 22.19 | 1.712 | 92.7 ± 3.1 |
| 5% DSPG/5% DSPC | 94.0 | 15.01 | −6.99 | 90.3 ± 2.1 |
| 5% DOPG/5% DSPC | 77.0 | 15.64 | 2.303 | 92.0 ± 7.5 |
| 5% DPPG/5% DSPC | 93.6 | 14.7 | −0.2016 | 90.6 ± 2.7 |
| 5% DMPG/5% DSPC | 66.0 | 19.29 | 0.8961 | 92.8 ± 8.0 |
| 5% DSPS/5% DSPC | 87.9 | 23.18 | −1.219 | 92.7 ± 4.5 |
| 5% DSPG/5% DSPS | 69.9 | 25.61 | −1.651 | 93.3 ± 6.1 |
| 2.5% DSPG/5% DSPS/2.5% DSPC | 72.2 | 19.36 | −1.596 | 92.7 ± 6.0 |
| 5% DSPG/5% DSPS/2.5% DSPC | 66.6 | 16.72 | −5.128 | 92.6 ± 2.0 |
| 5% DSPG/5% DSPS/5% DSPC | 69.1 | 17.75 | −4.506 | 93.5 ± 3.3 |
| 5% DSPG/5% DSPS/7.5% DSPC | 66.9 | 11.11 | −5.389 | 93.4 ± 9.0 |
| 5% DSPG/5% DSPS/10% DSPC | 64.6 | 15.43 | −6.708 | 93.2 ± 4.2 |

All formulations showed particle sizes between 65-100 nm with a slightly negative charge at pH 7.4 and a clearly positive zeta potential of 10-25 mV at pH 5. All particles had greater than 90% encapsulation efficiency, despite the presence of anionic phospholipids that could compete for binding with the negative charged phosphates on mRNA.

TABLE 53 mCherry expression in human dendritic cells following incubation at 1 µg/ml

| LNP formulation | MFI (donor 1) | T/NT (donor 1) | MFI (donor 2) | T/NT (donor 2) |
|---|---|---|---|---|
| Untreated (UT) | 2,735 ± 56 | | 1,354 ± 19 | |
| 10% DSPC | 14,152 ± 661 | | 14,034 ± 5,257 | |
| 5% DSPG/5% DSPC | 43,413 ± 5,029 | 3.56 | 53,670 ± 1,974 | 4.13 |
| 5% DOPG/5% DSPC | 16,783 ± 1,375 | 1.23 | 62,404 ± 2,841 | 4.81 |
| 5% DPPG/5% DSPC | 39,042 ± 6,957 | 3.18 | 58,557 ± 3,456 | 4.51 |
| 5% DMPG/5% DSPC | 70,516 ± 1,584 | 1.79 | 51,862 ± 5,953 | 3.98 |
| 5% DSPS/5% DSPC | 70,516 ± 1,584 | 5.94 | 225,546 ± 11,751 | 17.68 |
| 5% DSPG/5% DSPS | 10,148 ± 313 | 0.65 | 15,158 ± 289 | 1.09 |
| 2.5% DSPG/5% DSPS/2.5% DSPC | 35,797 ± 2,364 | 2.90 | 85,066 ± 8,576 | 6.60 |
| 5% DSPG/5% DSPS/2.5% DSPC | 27,349 ± 4,520 | 2.16 | 59,403 ± 4,237 | 4.58 |
| 5% DSPG/5% DSPS/5% DSPC | 52,500 ± 1,351 | 4.36 | 98,242 ± 1,421 | 7.64 |
| 5% DSPG/5% DSPS/7.5% DSPC | 49,439 ± 3,660 | 4.09 | 80,055 ± 7,036 | 6.21 |
| 5% DSPG/5% DSPS/10% DSPC | 32,566 ± 4,525 | 2.61 | 47,190 ± 9,456 | 3.61 |

TABLE 54 mCherry expression in human dendritic cells following incubation at 0.1 µg/ml

| LNP formulation | MFI (donor 1) | T/NT (donor 1) | MFI (donor 2) | T/NT (donor 2) |
|---|---|---|---|---|
| Untreated (UT) | 2,687 ± 27 | | 1,390 ± 11 | |
| 10% DSPC | 3,330 ± 216 | | 1,721 ± 36 | |
| 5% DSPG/5% DSPC | 6,292 ± 155 | 5.61 | 4,289 ± 19 | 8.76 |
| 5% DOPG/5% DSPC | 4,288 ± 52 | 2.49 | 5,951 ± 370 | 13.78 |
| 5% DPPG/5% DSPC | 6,754 ± 312 | 6.32 | 5,243 ± 535 | 11.64 |
| 5% DMPG/5% DSPC | 4,912 ± 647 | 3.46 | 4,202 ± 199 | 8.49 |
| 5% DSPS/5% DSPC | 10,776 ± 161 | 12.58 | 21,283 ± 1,303 | 60.10 |
| 5% DSPG/5% DSPS | 3,379 ± 112 | 1.08 | 3,574 ± 178 | 6.60 |
| 2.5% DSPG/5% DSPS/2.5% DSPC | 6,190 ± 184 | 5.45 | 11,379 ± 133 | 30.18 |
| 5% DSPG/5% DSPS/2.5% DSPC | 4,967 ± 291 | 3.55 | 6,028 ± 65 | 14.01 |

TABLE 54-continued mCherry expression in human dendritic cells following incubation at 0.1 µg/ml

| LNP formulation | MFI (donor 1) | T/NT (donor 1) | MFI (donor 2) | T/NT (donor 2) |
|---|---|---|---|---|
| 5% DSPG/5% DSPS/5% DSPC | 8,353 ± 153 | 8.81 | 9,758 ± 214 | 25.28 |
| 5% DSPG/5% DSPS/7.5% DSPC | 10,604 ± 126 | 12.31 | 10,602 ± 1,620 | 27.83 |
| 5% DSPG/5% DSPS/10% DSPC | 11,761 ± 502 | 14.11 | 10,139 ± 339 | 26.43 |

The effect of targeting two different LNPs with DSPG on transfection activity was evaluated using PG-targeted LNPs of various compositions (FIGS. 30A-30B). For KC3-OA containing LNPs, all forms of PG showed some level of increased expression relatively to 10% DSPC controls, and although there was small preference for the saturated DPPG or DSPG forms of PG with one donor, in a separate donor DOPG and DMPG showed similar activity. The highest increase over DSPC control came from the 5% DSPS targeted LNP, and combining DSPS with DSPG did not improve transfection activity further, and in most instances was antagonistic when compared to those formulations containing DSPS as the sole anionic phospholipid. In fact, those LNP formulations where all the phospholipids were either DSPG or DSPS (e.g. no DSPC) showed the lowest transfection activity of the targeted LNP formulations. This data shows that both PG and DSPS can be potent targeting anionic lipids to increase transfection efficiency in human dendritic cells, although combining the two does not appear to further improve activity.

Example 45. Use of Ethanol Soluble DPPS-NH4 as Opposed to the Less Soluble DSPS-Na Allows for Room Temperature Preparation of Phosphatidylserine-Targeted KC3OA-Based LNPs The aim of this study was to compare DSPS-Na and DPPS-NH$_4$ as targeting ligands in LNPs by measuring their transfection efficiency in murine DC cells. LNPs were prepared as in Example 10. Prior to LNP preparation stock solutions of each lipid were made in ethanol before use, except DSPS-Na, which because of its low solubility in ethanol (see Example 37) was dissolved in methanol at elevated temperatures (70 C) to ensure complete dissolution. Once cooled to room temperature, the methanol solution will maintain DSPS-Na solubility for a short period of time (<1 hour). Therefore, after addition of KC3OA, DSPC, Chol and PEG-DMG and DSPS-Na from their respective lipid stocks, the resulting mixture contains about 16% methanol by volume in ethanol. To make DSPS-targeted LNPs, and to ensure complete solubility of DSPS-Na, the ethanol/methanol solution is incubated at 70 C in a syringe holder heating block prior to mixing with pre-warmed mRNA. Care must be taken to maintain elevated temperature control prior to LNP formation, otherwise DSPS aggregation or LNP aggregation can occur. Once the LNPs were formed, the suspension was allowed to cool naturally to room temperature before solvent removal by dialysis. KC3OA was kept constant at 48 mol %, the DSPC concentration was 5 mol % with either 5 mol % DSPS-Na or DPPS-NH$_4$, 38.5 mol % cholesterol and 1.5 mol % PEG-DMG. The N/P was 5.25. The KC3OA/DSPS sample contained 1575 nmol KC3OA, 164.1 nmol DSPC, 164.1 nmol DSPS-Na, 1328.9 nmol cholesterol and 49.2 nmol PEG-DMG per 100 µg mRNA. In contrast, because of the higher solubility of DPPS-NH$_4$, LNPs can be prepared from all ethanol stock solutions, thereby eliminating the need for high temperature incubation before mixing and eliminates methanol from the process, which are both advantageous from a scale-up and residual solvent perspective. The KC3OA/DPPS sample contained 1575 nmol KC3OA, 164.1 nmol DSPC, 164.1 nmol DPPS-NH$_4$, 1328.9 nmol cholesterol and 49.2 nmol PEG-DMG per 100 µg mRNA and was mixed at room temperature. The final ALC-0315/DSPC formulation was composed of 46.3 mol % ALC-0315, 10 mol % DSPC, 42.7 mol % cholesterol and 1.5 mol % PEG-DMG. The SM-102/DSPC formulation was composed of 50 mol % SM102, 10 mol % DSPC, 38.5 mol % cholesterol and 1.5 mol % PEG-DMG, both controls prepared at room temperature.

LNPs were exchanged into PBS, pH 7.4 and then 15 mM Tris, pH 7.4, 20% sucrose, concentrated to 20-50 ug/mL mRNA using an Amicon-Ultra 4 (100,000 MWCO) spin column, sterile filtered (Thermo Nalgene 0.2 um #720-1320) prior to freezing by immersion in liquid nitrogen for 5 min and long-term storage at −80° C. LNPs were analyzed as described in Example 10, and were tested in murine DC cells as described in Example 11.

TABLE 55A

| LNP formulation | Particle Size (nm) | Zeta Potential (mV) pH 5 | Zeta Potential (mV) pH 7 | Encapsulation Efficiency (%) |
|---|---|---|---|---|
| ALC-0315 | 71.0 | 6.0 | −3.5 | 84.1 ± 10.7 |
| SM102 | 63.0 | 5.2 | −5.2 | 89.0 ± 5.9 |
| KC3-OA/DSPS-Na | 83.9 | 19.04 | −0.8 | 92.6 ± 8.7 |
| KC3-OA/DSPS-NH$_4$ | 78.3 | 11.91 | −0.1 | 93.3 ± 1.2 |

TABLE 55B

| LNP formulation | mCherry MFI | vs ALC-0315 LNP (fold) | vs SM-102 LNP (fold) |
|---|---|---|---|
| Untreated (UT) | 282.7 ± 3.8 | | |
| ALC-0315 | 1336.3 ± 91.6 | | |
| SM-102 | 6978.3 ± 1388 | | |
| KC3-OA/DSPS-Na | 16039.3 ± 4046.4 | 12.0 | 2.3 |
| KC3-OA/DSPS-Na | 32326.3 ± 735.9 | 24.2 | 4.6 |

The KC3-OA/DPPS-NH$_4$ LNP was comparable to the DSPS-targeted LNP from a biophysical point of view, all measured characteristics were very similar. In addition, it was found that inclusion of DPPS induced an approximately 2-fold increase in mCherry expression (FIG. 31). The comparable biophysical LNP characteristics combined with the comparable and slightly improved mRNA expression, suggests that DPPS-NH$_4$ is an attractive PS-targeting ligand targeting for KC3-OA LNPs.

Example 46: Synthesis of Cationic Lipids with Asymmetric Chains and Also where One Chain is Saturated Alkyl and Another is Monounsaturated, C15 or C17

Synthesis of (7Z, 24Z)-tritriaconta-7,24-dien-16-one (asymmetric C$_{15}$(8:1)-C$_{17}$(8:1) ketone). An equimolar mixture of oleoyl chloride and palmitoleoyl chloride is processed essentially as described above for the synthesis of (9Z,26Z)-pentatriaconta-9,26-dien-18-one (2). The products (C$_{15}$(8:1)-C$_{15}$(8:1), C$_{17}$(8:1)-C$_{17}$(8:1), and C$_{15}$(8:1)-C$_{17}$(8:1) ketones) are separated using column chromatography to isolate the asymmetric C$_{15}$(8:1)-C$_{17}$(8:1) ketone. The structure is confirmed by NMR.

Synthesis of 3-(S)-2-(8Z)-pentadec-8-en-1-yl-2'-(8Z)-heptadec-8-en-1-yl-1,3-dioxolan-4-yl)-N.N-dimethylpropan-1-amine The procedure for the synthesis of 3-((S)-2,2-di((Z)-heptadec-8-en-1-yl)-1,3-dioxolan-4-yl)-N,N-dimethylpropan-1-amine, AKG-KC3-C17(C8:1)), described above, is essentially followed using (7Z, 24Z)-tritriaconta-7,24-dien-16-one as a starting material. A cationic lipid having general structure I-A with one C17 monounsaturated and one C15 monounsaturated R$_1$ hydrocarbon chain is obtained.

Synthesis of (9Z)-pentatriacont-9-en-18-one (asymmetric C$_{17}$(8:1)-C$_{17}$ ketone) An equimolar mixture of oleoyl chloride and stearoyl chloride is processed essentially as described above for the synthesis of (9Z,26Z)-pentatriaconta-9,26-dien-18-one (2). The products (C$_{17}$(8:1)-C$_{17}$(8:1), C$_{17}$(8:1)-C$_{17}$, and C$_{17}$-C$_{17}$ketones) are separated using column chromatography to isolate the asymmetric C$_{17}$(8:1)-C$_{17}$ ketone. The structure is confirmed by NMR.

Synthesis of 3-(S)-2-(8Z)-heptadec-8-en-1-yl-2'-heptadec-1-yl-1,3-dioxolan-4-yl)-N.N-dimethylpropan-1-amine The procedure for the synthesis of 3-((S)-2,2-di((Z)-heptadec-8-en-1-yl)-1,3-dioxolan-4-yl)-N,N-dimethylpropan-1-amine, AKG-KC3-C17(C8:1)), described above, is essentially followed using (9Z)-pentatriacont-9-en-18-one as a starting material. A cationic lipid having general structure I-A with one C17 monounsaturated and one C17 saturated (alkyl) R$_1$ hydrocarbon chain is obtained.

Synthesis of (24Z)-tritriacont-24-en-16-one (asymmetric C$_{15}$-C$_{17}$(8:1) ketone) An equimolar mixture of oleoyl chloride and palmitoyl chloride is processed essentially as described above for the synthesis of (9Z,26Z)-pentatriaconta-9,26-dien-18-one (2). The products (C$_{17}$(8:1)-C$_{17}$(8:1), C$_{15}$-C$_{15}$, and C$_{15}$-C$_{17}$(8:1) ketones) are separated using column chromatography to isolate the asymmetric C$_{15}$-C$_{17}$(8:1) ketone. The structure is confirmed by NMR.

Synthesis of 3-(S)-2-(8Z)-pentadec-8-en-1-yl-2'-heptadec-1-yl-1,3-dioxolan-4-yl)-N.N-dimethylpropan-1-amine The procedure for the synthesis of 3-((S)-2,2-di((Z)-heptadec-8-en-1-yl)-1,3-dioxolan-4-yl)-N,N-dimethylpropan-1-amine, AKG-KC3-C17(C8:1)), described above, is essentially followed using (24Z)-tritriacont-24-en-16-one as a starting material. A cationic lipid having general structure I-A with one C17 monounsaturated and one C15 saturated (alkyl) R$_1$ hydrocarbon chain is obtained.

Example 47. Impact of Targeting KC3OA Based LNPs Using Phosphatidylserine on Murine DC Cells In Vitro and Comparison to ALC-0315 and SM-102 LNP Formulations LNP lipid formulations corresponding to Comirnaty® ("ALC-0315") and Spikevax® ("SM102") containing reporter mRNA mCherry (Trilink Biotechnologies, San Diego, CA, #7203) were prepared and characterized as described in Examples 9 and 10 and compared to KC3OA (KC3OA-PS) and KC3OA/5 mol % DPPS (KC3OA+PS) formulations. Specifically, the formulations consisted of ALC-0315/DSPC/Chol/ALC-0159 (46.3/9.4/42.7/1.56 mol %, "ALC-0315"); SM102/DSPC/Chol/PEG-DMG (50/10/38.5/1.5 mol %, "SM102"); KC3OA/DSPC/Chol/PEG-DMG (48/10/40.5/1.5 mol %, "KC3OA-PS"); and KC3OA/DSPC/DPPS/Chol/PEG-DMG (48/5/5/40.5/1.5 mol %, "KC3OA+PS"). The fluorescent lipid marker 1,1'-Dioctadecyl-3,3,3',3'-Tetramethylindodicarbocyanine-5,5'-Disulfonic Acid (DiIC18(5)-DS, ATT Bioquest, cat #22054) was added to each at 0.025 mol %. SM-102 was purchased from Organix, Inc (O-11182) and ALC-0315 (BP-25498) and ALC-0159 (BP-25711) were purchased from BroadPharm, Inc. The analytics of these formulations are shown in Table 56. (Abbreviations: F/T, freeze/thaw cycle. % EE, mRNA encapsulation efficiency. %. Stdev—EE standard deviation. Zeta, zeta-potential (mV). C/F, concentrating and 0.2-μm sterile filtration step. Z-Ave, Z-average particle size by DLS, nm. PDI, polydispersity index by DLS)

TABLE 56

Analysis of LNPs formulations described in Example 47.

| | Post C/F | | Post F/T | | zeta | | Post C/F | | Post F/T | |
|---|---|---|---|---|---|---|---|---|---|---|
| LNP | Z-Ave | PDI | Z-Ave | PDI | pH 5 | pH 7 | % EE | stdev | % EE | stdev |
| ALC-0315 | 78.88 | 0.12 | 80.11 | 0.13 | 3.7 | −6.77 | 77.7 | 3.5 | 77.6 | 4.8 |
| SM102 | 90.00 | 0.00 | 90.67 | 0.04 | 10.8 | −3.48 | 88.4 | 5.1 | 88.8 | 2.7 |
| KC3OA − PS | 113.00 | 0.06 | 110.7 | 0.07 | 17.8 | −4.44 | 92.4 | 7.8 | 91.9 | 3.8 |
| KC3OA + PS | 98.70 | 0.07 | 97.74 | 0.12 | 15.4 | −1.61 | 92.3 | 9.5 | 91.6 | 8.1 |

F/T, freeze/thaw cycle. EE, encapsulation efficiency.

Figure 32:
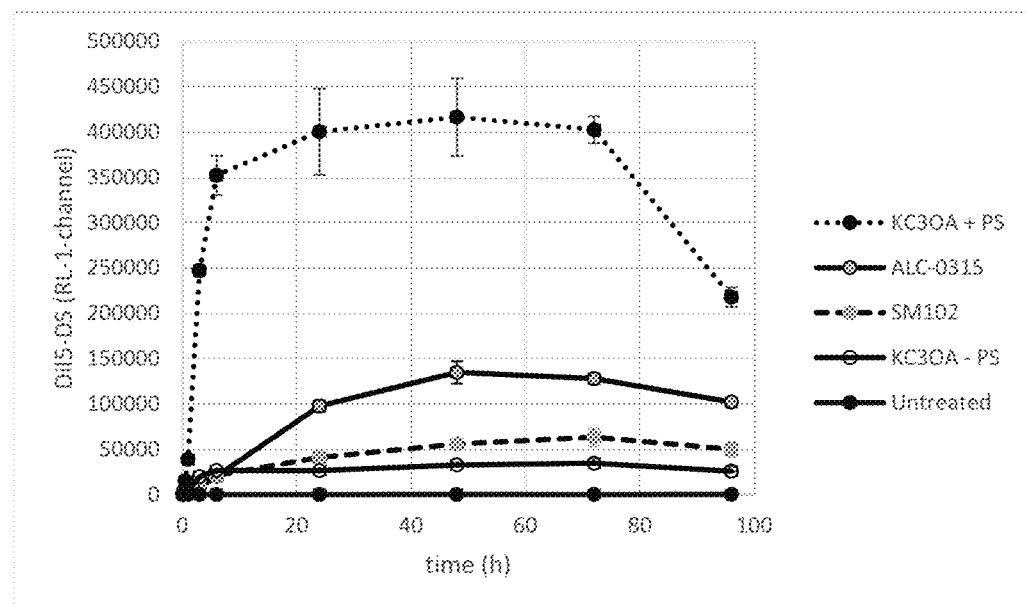
FIG. 32. Graph of LNP uptake over time in MutDC1940 cells incubated with various LNP formulations of mCherry mRNA (0.2 μg/mL) labeled with a fluorescent lipid label DiIC18(5)-DS (DiI5-DS) (Example 47). At indicated times LNP uptake was quantified by flow cytometry of the label (RL-1 fluorescence channel) and plotted as median cell fluorescence intensity. Data are the average of triplicate runs. Error bars, standard deviation. Formulations: AKG+PS, KC3OA+PS; AKG-PS, KC3OA-PS; SM102; ALC-0315. Untreated refers to the cells without LNP treatment.
Figure 33:
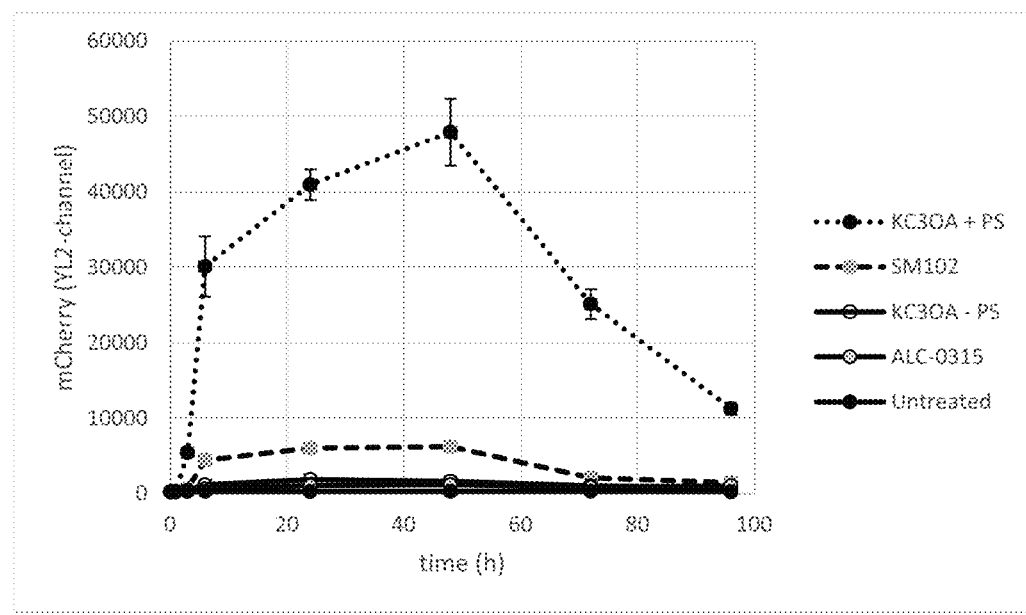
FIG. 33. Graph of LNP mRNA expression over time in MutuDC1940 cells incubated with various LNP formulations of mCherry mRNA (0.2 μg/mL) labeled with a fluorescent lipid label DiIC18(5)-DS (DiI5-DS) (Example 47). At indicated times mCherry protein expression was quantified by flow cytometry by the protein fluorescence (YL-2 fluorescence channel) and plotted as median cell fluorescence intensity. Data are the average of triplicate runs. Error bars, standard deviation. Formulations: AKG+PS, KC3OA+PS; AKG-PS, KC3OA-PS; SM102; ALC-0315. Untreated refers to the cells without LNP treatment.

The LNPs exhibited little change in mRNA encapsulation over freezing and thawing (<1%) and less than 2% change in size. The LNPs exhibited the expected change in zeta potential when they were suspended in pH 5.0 or pH 7.0 buffers (they went from cationic to neutral surface charge). The formulations were added to MutuDC1940 cells at a concentration of 0.2 μg mRNA/ml and incubated at 37° C. At various incubation times, the cells were washed, harvested, stained with a live/dead dye, fixed and analyzed for either DiIC18(5)-DS content or mCherry protein content by flow cytometry as described in Example 11. The results are shown in FIG. 32 and FIG. 33 and in Table 57.

We observed rapid cellular accumulation of the PS-targeted KC3OA LNPs compared to the base formulation KC3OA-PS, as observed by the increase in DiIC18(5)-DS signal over time, which plateaued at approximately 24 h and decreased after 72 h. The DiIC18(5)-DS signal for KC3OA+PS was 15.1-fold higher at 24 h compared to KC3OA-PS. The DiIC18(5)-DS signal was also higher for the targeted formulation as compared to the ALC-0135 or SM102 formulations (4.1 and 9.7-fold higher respectively) at 24 h. Indeed, the increased cellular accumulation led to enhanced mCherry expression; the PS-targeted KC3OA formulation had a 22-fold higher mCherry signal compared to the non-targeted KC3OA formulation and was 38.5 and 6.8-fold higher than ALC-0315 and SM102 LNPs, respectively. The decrease in cellular signal for both DiIC18(5)-DS and mCherry after 72 h may be due to signal dilution from MutuDC1940 cell division.

0315"); SM102/DSPC/Chol/PEG-DMG (50/10/38.5/1.5 mol %, "SM102"); KC3OA/DSPC/Chol/PEG-DMG (48/10/40.5/1.5 mol %, "KC3OA-PS"); and KC3OA/DSPC/DPPS/Chol/PEG-DMG (48/5/5/40.5/1.5 mol %, "KC3OA+PS"). The fluorescent marker DiIC18(5)-DS was added to each at 0.025 mol %. LNPs were made and characterized as described in Examples 9 and 10.

Liposome Preparation. Several design elements were contemplated in preparing the blocking liposomes. First, the majority lipid should be similar to KC3OA by its bilayer-forming properties. We therefore chose 1,2-dioleoyl-sn-glycero-3-phosphocholine (DOPC) as it has the same alkyl chains as KC3OA, and we used it in the same proportion as our KC3OA-LNPs at 48 mol %. Second, the cholesterol and PEG-DMG contents were kept at 40.5 and 1.5 mol %, consistent with our typical KC3OA-based LNP. For non-PS containing liposomes we used 10 mol % DSPC. For PS-containing liposomes we replaced DSPC with a PS-variant: either L-DPPS, L-DOPS, L-DSPC (Avanti Polar Lipids) or D-DSPC (as described in Example 1E).

TABLE 57

Median fluorescence intensity (MedFI) of DiIC18(5)-DS lipid label and mCherry protein in MutuDC1940 cells at various incubation times in the presence of mCherry mRNA-LNP formulations.

| Time, h | ALC-0315 | SM102 | AKG – PS | AKG + PS |
|---|---|---|---|---|
| DiIC18(5)-DS Uptake | | | | |
| 0.08 | 227.3 ± 6.8 | 382.7 ± 23.2 | 677.3 ± 75.2 | 726 ± 118.9 |
| 0.25 | 257.7 ± 10.1 | 443.7 ± 45.5 | 775 ± 208.1 | 3848 ± 320 |
| 0.5 | 383.7 ± 28.6 | 571 ± 65.9 | 1,573.7 ± 123.7 | 15,579.3 ± 3,688.8 |
| 1 | 803.3 ± 23.1 | 863.7 ± 26 | 3,546 ± 156.5 | 38,914.3 ± 2,170.4 |
| 3 | 7,861.7 ± 575.7 | 1,1493 ± 1030.2 | 19,864.7 ± 622.9 | 247,097.3 ± 6,530.3 |
| 6 | 20,506.7 ± 2381.1 | 21,278.7 ± 1787.7 | 26,716 ± 1094.6 | 352,339 ± 21,625.6 |
| 24 | 97,906 ± 6553 | 41,135.3 ± 585 | 26,575.7 ± 2772.5 | 400,445 ± 476,77.6 |
| 48 | 134,970.3 ± 12277.7 | 55,837.7 ± 3247.6 | 32,861 ± 3080.6 | 416,549 ± 42829 |
| 72 | 128,059 ± 5843.2 | 63,535 ± 9808 | 34,736 ± 4999.8 | 402,600 ± 14,855.3 |
| 96 | 102,199.3 ± 3865.9 | 50,093.3 ± 8009.1 | 25,992 ± 5200.1 | 218,035 ± 10,560 |
| mCherry Expression | | | | |
| 0.08 | 220.7 ± 1.2 | 214 ± 3.5 | 218.3 ± 7.2 | 176.1 ± 75.2 |
| 0.25 | 218.7 ± 5.1 | 218.3 ± 3.5 | 216.3 ± 4.5 | 218.7 ± 1.5 |
| 0.5 | 233.7 ± 4.9 | 234 ± 3.6 | 233 ± 5 | 239.3 ± 4.7 |
| 1 | 246 ± 4.4 | 228.7 ± 2.5 | 240.7 ± 2.9 | 273.7 ± 2.9 |
| 3 | 335.7 ± 21.7 | 665 ± 11.5 | 425.3 ± 24.2 | 5,422 ± 489.5 |
| 6 | 628 ± 34 | 4,415.3 ± 601.3 | 1,154.3 ± 87.5 | 30,103.7 ± 4,000.4 |
| 24 | 1,062 ± 82.9 | 6,014.3 ± 676.4 | 1,848.7 ± 93.9 | 40,977.7 ± 2,040.9 |
| 48 | 1,171.3 ± 159.9 | 6,230 ± 444.9 | 1,606 ± 115.5 | 47,934.7 ± 4,430.3 |
| 72 | 840 ± 35 | 2,072.7 ± 190.4 | 1,016.7 ± 86.1 | 25,137.3 ± 1,973.9 |
| 96 | 1,019 ± 99.7 | 1,446.7 ± 75.4 | 803 ± 47.1 | 11,256.3 ± 794.6 |

Example 48. Impact of Co-Incubation of Phosphatidylserine-Containing Liposomes with LNPs on DC Uptake of mRNA-LNPs The aim of this experiment was to determine if phosphatidylcholine/cholesterol/PEG-DMG liposomes containing PS variants competed for cellular uptake of different LNP formulations in vitro. We hypothesized that if PS-containing liposomes and LNPs are internalized through Tim4/Tim1 and other PS-specific dendritic cell surface receptors, then the similarly sized, non-LNP, neutral liposomes containing PS (the "blocking liposomes") would specifically block the uptake of PS-targeted LNPs and liposomes devoid of PS would have less efficient blocking, therefore demonstrating that the enhanced uptake mechanism of PS-containing LNPs is PS-specific. The LNPs used in this study were ALC-0315/DSPC/Chol/ALC-0159 (46.3/9.4/42.7/1.56 mol %, "ALC- The liposomes were prepared as follows:
1. Lipid stock solutions were prepared in ethanol (DNAse, RNAse free, Sigma E7023) (except DPPS was in ethanol-methanol mix) were combined in a 25-ml glass pear-shaped flasks (based on 72 umol DOPC).
2. The lipid solutions were rotoevaporated at 50° C. to visible dryness and re-dissolved in 0.5 ml ethanol at 65° C.
3. To the lipid ethanolic solution, 4.5 ml of 25 mM Tris, 145 mM NaCl, pH 7.5 (TBS-25-7.5) was added and swirled at 65° C. for 2 min to form multilamellar vesicles (MLV).
4. The MLVs were passed five times through a stack of polycarbonate track-etched membranes (PCTE, Whatman Nuclepore) with the pore size (top to bottom) 200 nm (1), 100 nm (1), and 50 nm (1) using a 10-ml thermobarrel extruder (Lipex, Northern Lipids) at 65° C., 34-350 psi, and chilled in refrigerator overnight.

5. The liposomes were dialyzed against 2 changes of 150 ml TBS-25-7.5 for 2 hours each at room temperature using SpectraPor 12-14 MWCO 25 mm tubing.
6. The liposomes were aseptically filtered through 0.2-μm 13-mm sterile PES filters (Nalgene) and characterized by phospholipid content (as described in Example 37, except an aliquot of diluted liposomes or standards was 5 ul, and the standards were in the range of 2.5-10 mM phosphate), and by the particle size using DLS. The results are shown below in Table 58.

TABLE 58

Characteristics of the liposome lots for the LNP co-incubation study

| Lot | Ls-391 | Ls-388 | Ls-394 | Ls-392 | Ls-393 |
|---|---|---|---|---|---|
| Phospholipid, | DSPC | DPPS | DOPS | D-DSPS | L-DSPS |
| PhL, mM, | 14.2 | 13.70 | 12.8 | 14.2 | 14.2 |
| Z-Ave, nm, | 81.0 | 83.0 | 80.3 | 82.0 | 82.0 |
| PDI, SD | 0.0149 | 0.0409 | 0.0502 | 0.0454 | 0.0653 |

Figure 34:
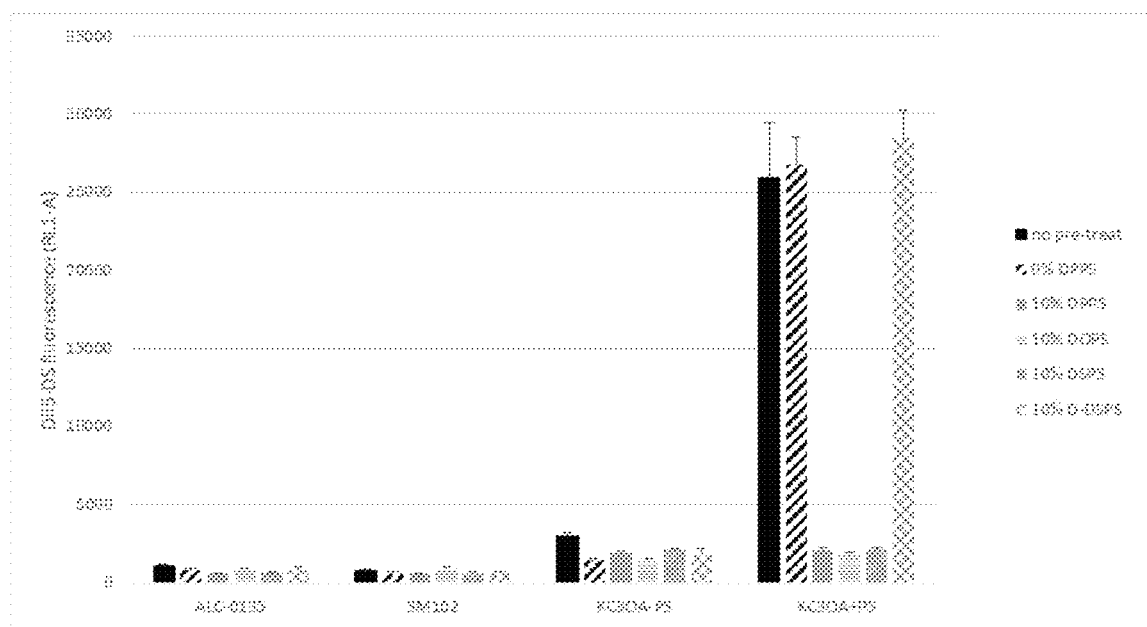
FIG. 34. The effect of cell pre-treatment with "blocking liposomes" at 10× the LNP lipid concentration on the uptake of DiI5-DS-labeled LNPs by MutuDC1940 cells (Example 48). The liposomes were added 15 min prior to the LNPs. After 1 h of LNP exposure the uptake of LNPs was measured as DiI5-DS fluorescence by flow cytometry (RL1-A channel) and plotted as median cellular fluorescence intensity. Data are the average of quadruplicate runs. Error bars, standard deviation. LNP type is shown at the horizontal axis. The legend indicates the amount and nature of the PS component in the "blocking liposomes" The "%" indicates mol % of PS in the blocking liposome formulation related to the total lipid.
Figure 35:
FIG. 35. The effect of PS targeting agents on mCherry expression in MutuDC1940 cell after 3 hours incubation with mCherry mRNA-LNP constructs (0.3 μg/mL mRNA) prepared with various ICL (Example 49). The expression was quantified by flow cytometry by the mCherry protein fluorescence (YL2-A fluorescence channel) and plotted as median cell fluorescence intensity. Data are the average of quadruplicate runs. Error bars, standard deviation. ICL: UO1, KC2, KC3OA. Targeting PS: DPPS, DSPS, D-DSPS, no targeting (NT). UT refers to the cells without LNP treatment.
Figure 36:
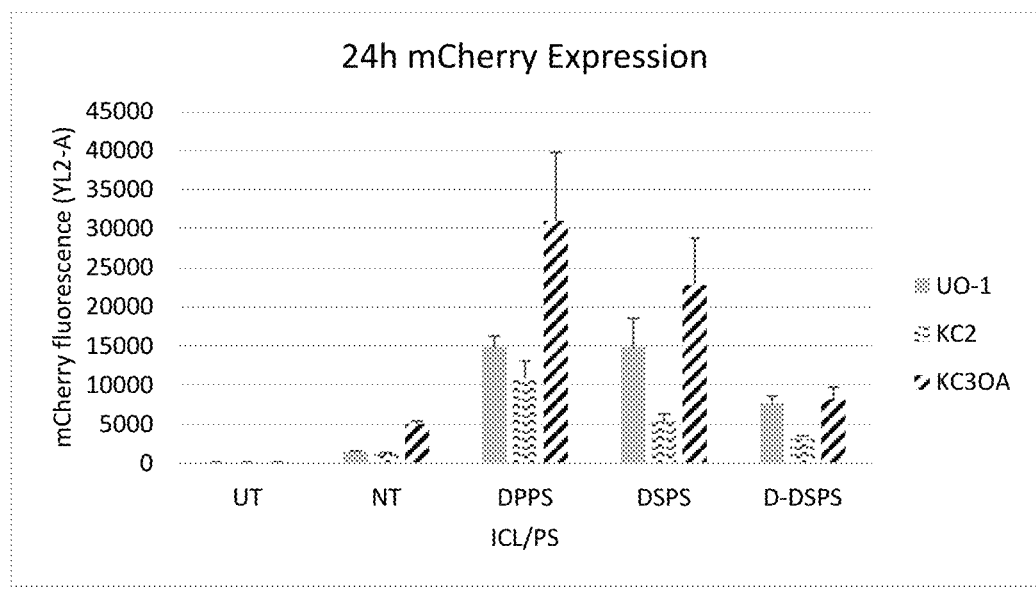
FIG. 36. The effect of PS targeting agents on mCherry expression in MutuDC1940 cell after 24 hours incubation with mCherry mRNA-LNP constructs (0.3 μg/mL mRNA) prepared with various ICL (Example 49). The expression was quantified by flow cytometry by the mCherry protein fluorescence (YL2-A fluorescence channel) and plotted as median cell fluorescence intensity. Data are the average of quadruplicate runs. Error bars, standard deviation. ICL: UO1, KC2, KC3OA. Targeting PS: DPPS, DSPS, D-DSPS, no targeting (NT). UT refers to the cells without LNP treatment.
Figure 37:
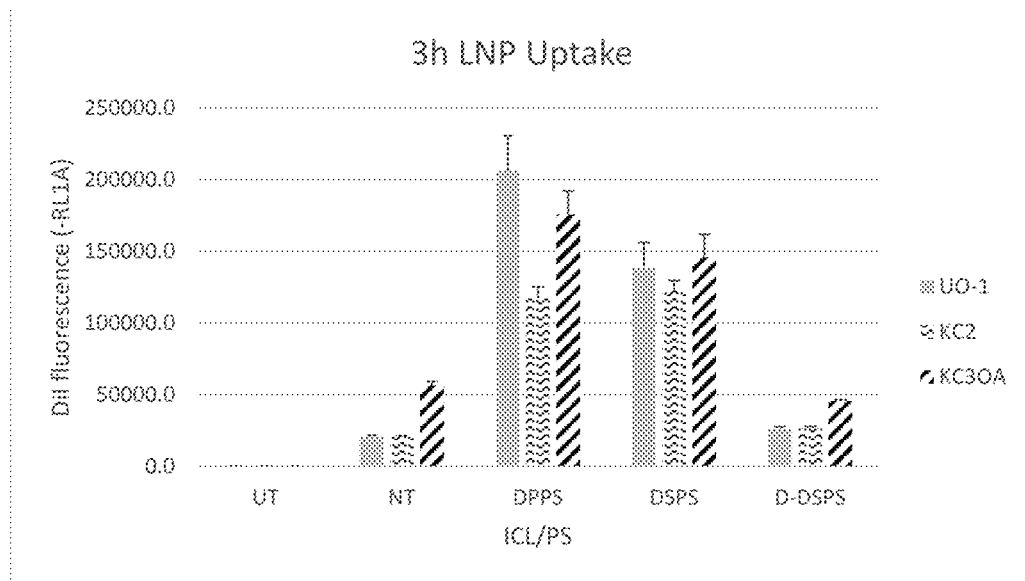
FIG. 37. The effect of PS targeting agents on the LNP uptake in MutuDC1940 cell after 3 hours incubation with mCherry mRNA-LNP constructs (0.3 μg/mL mRNA) prepared with various ICL (Example 49). The expression was quantified by flow cytometry by the DiI5-DS (DiI) lipid label fluorescence (RL1A fluorescence channel) and plotted as median cell fluorescence intensity. Data are the average of quadruplicate runs. Error bars, standard deviation. ICL: UO1, KC2, KC3OA. Targeting PS: DPPS, DSPS, D-DSPS, no targeting (NT). UT refers to the cells without LNP treatment.
Figure 38:
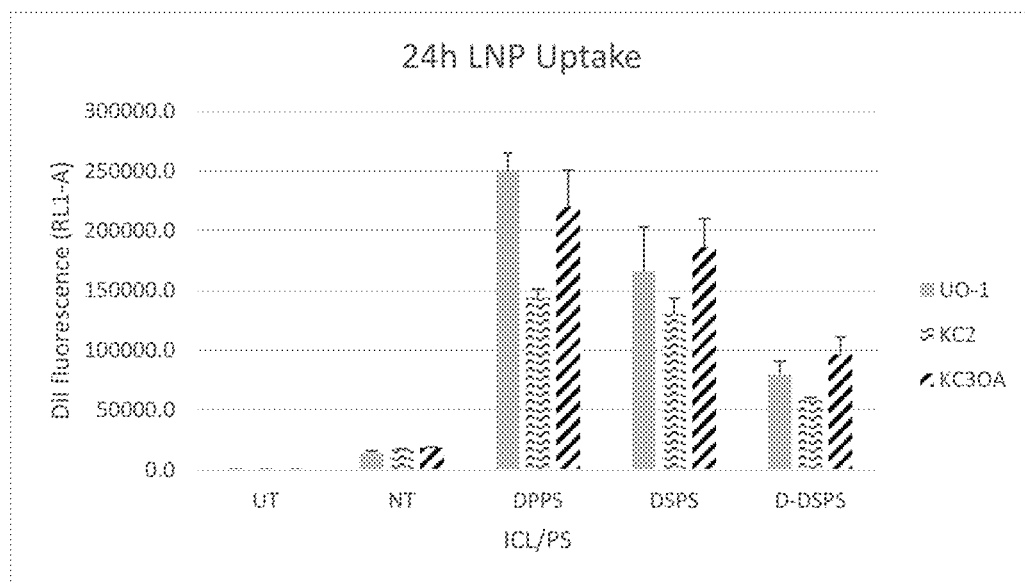
FIG. 38. The effect of PS targeting agents on the LNP uptake in MutuDC1940 cell after 24 hours incubation with mCherry mRNA-LNP constructs (0.3 μg/mL mRNA) prepared with various ICL (Example 49). The expression was quantified by flow cytometry by the DiI5-DS (DiI) lipid label fluorescence (RL1A fluorescence channel) and plotted as median cell fluorescence intensity. Data are the average of quadruplicate runs. Error bars, standard deviation. ICL: UO1, KC2, KC3OA. Targeting PS: DPPS, DSPS, D-DSPS, no targeting (NT). UT refers to the cells without LNP treatment.

MutuDC1940 cells were plated as described in Example 11, except 96-well plates were used and cells were plated at 35,000 cells/well. 15 min prior to adding LNPs (n=4), liposomes were added at a total lipid concentration of ~32 μM. LNPs were added at 0.1 μg/ml mRNA or 3.2 μM total lipid and after incubation at 37 C for 1 h, the cells washed and analyzed by flow cytometry for DiIC18(5)-DS signal. The results are shown in FIG. 34 and Table 59. "Cells only" sample MedFI was 319 f 56.6 fluorescence units.

TABLE 59

DiIC18(5)-DS median fluorescence intensity (medFI, mean ± standard deviation (SD)) of cells treated with LNPs and liposomal blocking agents.

| Liposomes\LNP | ALC-0135 | SM102 | KC30A − PS | KC30A + PS |
|---|---|---|---|---|
| No pretreat | 1105 ± 33 | 783 ± 92.5 | 2999.3 ± 224.5 | 25932.7 ± 3529.4 |
| Ls-388 (DPPS) | 579.3 ± 30.3 | 543.5 ± 81.4 | 1917.3 ± 104.6 | 2098.5 ± 137.5 |
| Ls-391 (DSPC, no PS) | 791.5 ± 92.2 | 595.3 ± 77.8 | 1448.5 ± 74 | 26752.5 ± 1798.9 |
| Ls-392 (D-DSPS) | 837.8 ± 187.1 | 583.8 ± 67 | 1775 ± 380.4 | 28463.5 ± 1829.5 |
| Ls-393 (L-DSPS) | 638.8 ± 76.2 | 592.5 ± 84.4 | 2109 ± 96.1 | 2147.3 ± 142.5 |
| Ls-394 (DOPS) | 814 ± 138.1 | 915 ± 101.4 | 1342.3 ± 191.5 | 1744 ± 205.1 |

We observed that none of the liposomes had any significant effect on the uptake of either the ALC-0315 or SM102 formulations. However, pretreatment with certain liposomes had dramatic effects on the uptake of PS-targeted KC3OA LNPs. For example, liposomes containing L-DPPS, L-DOPS or L-DSPS extensively blocked targeted KC3OA+PS LNP uptake, reducing it to similar levels of the non-targeted formulation KC3OA-PS. In contrast, liposomes without PS had no effect on the LNP uptake. Importantly, liposomes containing D-DSPS had no effect, demonstrating the specificity of the uptake related to the L-isomer of PS. These data support the hypothesis that PS-targeted LNPs are internalized by DCs via an L-isomer-specific PS-dependent mechanism.

Example 49. Impact of D- or L-Isomer on the Targeting Ability of Phosphatidylserine-Containing LNP Formulations on Murine DC Cells In Vitro The aim of this study was to evaluate the impact of serine group chirality on the phosphatidylserine-containing LNP uptake and functional mRNA delivery. LNPs containing mCherry mRNA (Trilink, Cat #L-7203) were prepared with UO-1, KC2 or KC3OA ICLs at a N/P 15=5.25 and formulated into 15 mM Tris, 20% sucrose, pH 7.4 buffer for storage at −80° C. The phosphatidylserine (PS) lipids L-DSPS-Na, D-DSPS-Na or L-DPPS-NH$_4$ were included in the preparations at 7.5 mol % for UO-1 containing LNPs and 5.0 mol % for KC-series ICLs, which we found in previous experiments to be the optimal mol % for each ICL. LNPs devoid of PS were also prepared. PS lipids were titrated into the formulation with a proportional reduction in the mol % of DSPC. The PS+DSPC composition was 10 mol % in all formulations and for those devoid of PS, DSPC was 10 mol %. The ICL content was 48 mol %, the cholesterol content was 38.5 mol % and the PEG-DMG content was 1.5 mol % relative to the total LNP lipid. DSPS-Na and DPPS-NH$_4$ were obtained from Avanti Polar Lipids and D-DSPS synthesized and purified as described in Examples 9 and 10. A fluorescent non-exchangeable lipid marker DiIC18(5)-DS at 0.025 mol % total lipid was also included. The formulations were freeze-thawed to simulate conditions of sample preparation that were performed prior to transfection as described in Example 51. LNP characterization data is shown below in Table 60 (For abbreviations see Example 47, Table 56).

TABLE 60

Analysis of LNP formulations described in Example 47.

| LNP | Post C/F Z-Ave | PDI | Post F/T Z-Ave | PDI | Zeta pH 5 | pH 7 | Post C/F % E.E | stdev | Post F/T % E.E | stdev |
|---|---|---|---|---|---|---|---|---|---|---|
| UO-1/DPPS | 91.80 | 0.09 | 91.62 | 0.10 | 16.77 | −4.63 | 87.48 | 5.45 | 88.77 | 5.76 |
| UO-1/DSPS | 101.20 | 0.04 | 100.40 | 0.04 | 16.68 | −2.47 | 89.60 | 5.85 | 89.86 | 8.07 |
| UO-1/D-DSPS | 104.30 | 0.08 | 102.70 | 0.08 | 18.40 | −3.51 | 90.33 | 5.24 | 87.27 | 4.61 |
| KC2/DPPS | 81.44 | 0.04 | 79.25 | 0.04 | 12.74 | −1.32 | 85.93 | 2.09 | 87.27 | 8.34 |
| KC2/DSPS | 85.32 | 0.02 | 83.28 | 0.03 | 9.78 | −4.57 | 87.36 | 4.52 | 88.75 | 7.68 |
| KC2/D-DSPS | 84.88 | 0.07 | 85.35 | 0.03 | 10.70 | −4.85 | 89.33 | 5.32 | 88.75 | 7.68 |
| KC3OA/DPPS | 104.60 | 0.12 | 103.90 | 0.12 | 15.69 | −1.31 | 91.65 | 3.70 | 92.42 | 2.75 |
| KC3OA/DSPS | 111.80 | 0.08 | 110.50 | 0.12 | 16.31 | −2.36 | 92.26 | 6.51 | 92.40 | 3.99 |
| KC3OA/D-DSPS | 115.10 | 0.12 | 114.20 | 0.10 | 14.47 | −1.65 | 90.55 | 7.00 | 91.19 | 9.45 |
| UO-1 | 96.92 | 0.09 | 124.80 | 0.13 | 11.04 | 1.32 | 88.33 | 8.65 | 82.35 | 5.97 |
| KC2 | 106.00 | 0.09 | 106.60 | 0.12 | 17.17 | −0.63 | 87.26 | 7.13 | 86.60 | 8.14 |
| KC3OA | 104.30 | 0.15 | 105.80 | 0.13 | 15.54 | 3.10 | 91.84 | 9.12 | 91.83 | 3.62 |

We found less than 2.8% change in LNP size upon F/T, with the exception of UO-1 (no PS) where the LNPs increased from 97 nm to 125 nm. The LNPs exhibited little change in mRNA encapsulation over freezing and thawing (<3.5%), with the exception of UO-1 (no PS) which saw a reduction from 88% to 82% (6% reduction). The LNPs exhibited the expected change in zeta potential when they were suspended in pH 5.0 or pH 7.0 buffers (they went from cationic to neutral surface charge). LNPs were added to MutuDC1940 cells as described in Example 11 at 0.3 µg mRNA/ml (n=4) and at 3 h and 24 h cells washed, stained for live/dead, fixed and analyzed by flow cytometry for mCherry and DiIC18(5)-DS signal using an AttuneNxT cytometer. Targeting with the L-isomer of DSPS improved the uptake by MutuDC1940 cells over non-targeted samples and those containing the non-natural D-isomer version of DSPS. LNP uptake and mCherry expression were time dependent (FIGS. 35-38) and data shown in Table 61A.

TABLE 61A mCherry median fluorescent intensity values in MutuDC1940 cells after treatment with LNPs of Example 49 for 3 h or 24 h.

| LNP Formulation | mCherry Expression (3 h) medFI | stdev | mCherry Expression (24 h) medFI | stdev |
|---|---|---|---|---|
| UT | 169 | 3 | 149 | 4 |
| UO1 | 283 | 28 | 1,514 | 70 |
| UO1/DPPS | 2,366 | 949 | 14,823 | 1,435 |
| UO1/DSPS | 1,972 | 873 | 14,809 | 3,717 |
| UO1/D-DSPS | 264 | 29 | 7,664 | 938 |
| KC2 | 301 | 27 | 1,283 | 90 |
| KC2/DPPS | 1,678 | 432 | 10,883 | 2,185 |
| KC2/DSPS | 898 | 383 | 5,381 | 923 |
| KC2/D-DSPS | 233 | 25 | 3,114 | 378 |
| KC3OA | 525 | 59 | 4,999 | 386 |
| KC3OA/DPPS | 1,965 | 357 | 30,996 | 8,747 |
| KC3OA/DSPS | 1,484 | 215 | 22,768 | 6,034 |
| KC3OA/D-DSPS | 274 | 10 | 8,158 | 1,577 |

TABLE 61B

DiIC18(5)-DS median fluorescent intensity values of MutuDC1940 cells treated with LNPs (0.3 µg mRNA dose) for 3 h or 24 h

| LNP Formulation | Cell Uptake (DiIC18(5)-DS) - 3 h medFI | stdev | Cell Uptake (DiIC18(5)-DS) - 24 h medFI | stdev |
|---|---|---|---|---|
| UT | 247.8 | 38.0 | 279.0 | 227.4 |
| UO1 | 21,032.5 | 803.6 | 14,119.5 | 1,701.2 |
| UO1/DPPS | 206,581.8 | 24,173.8 | 250,388.8 | 14,557.6 |
| UO1/DSPS | 138,715.8 | 17,472.5 | 166,328.3 | 36,956.2 |
| UO1/D-DSPS | 26,353.3 | 1,421.6 | 79,878.0 | 10,846.4 |
| KC2 | 20,716.8 | 762.0 | 16,844.0 | 763.6 |
| KC2/DPPS | 117,301.5 | 7,956.7 | 144,347.8 | 6,911.8 |
| KC2/DSPS | 12,3615.0 | 6,040.3 | 130,389.8 | 12,992.5 |
| KC2/D-DSPS | 26,675.3 | 1,282.8 | 58,229.5 | 2,232.9 |
| KC3OA | 56,610.0 | 2,856.1 | 18,451.8 | 630.3 |
| KC3OA/DPPS | 175,661.0 | 16,507.1 | 220,166.8 | 30,492.5 |
| KC3OA/DSPS | 145,807.8 | 16,163.0 | 186,204.8 | 23,922.1 |
| KC3OA/D-DSPS | 45,704.3 | 922.4 | 96,361.5 | 14,802.3 |

TABLE 62

The comparative ratio of mCherry expression or DiIC18(5)-DS uptake of L-DPPS, L-DSPS or D-DSPS targeted LNPs at 3 and 24 h in MutuDC1940 cells. Ratios are expressed as the fold difference in medFI mCherry or DiIC18(5)-DS signal of cells treated with L-DPPS-containing LNPs versus cells treated with either non-targeted LNPs (DPPS/NT), LNPs containing L-DSPS (DPPS/DSPS) or the D isomer of DSPS (DPPS/D-DSPS).

| ICL | DPPS/NT | DPPS/DSPS | DPPS/D-DSPS | DPPS/NT | DPPS/DSPS | DPPS/D-DSPS |
|---|---|---|---|---|---|---|
| | 24 h mCherry Expression (MedFI) | | | 24 h DiIC18(5)-DS Uptake (MedFI) | | |
| UO-1 | 9.8 | 1.0 | 1.9 | 17.7 | 1.5 | 3.1 |
| KC2 | 8.5 | 2.0 | 3.5 | 8.6 | 1.1 | 2.5 |
| KC3OA | 6.2 | 1.4 | 3.8 | 11.9 | 1.2 | 2.3 |
| | 3 h mCherry Expression (MedFI) | | | 3 h DiI Uptake (MedFI) | | |
| UO-1 | 8.4 | 1.2 | 9.0 | 9.8 | 1.5 | 1.5 |
| KC2 | 5.6 | 1.9 | 7.2 | 5.7 | 2.4 | 5.8 |
| KC3OA | 3.7 | 1.3 | 7.2 | 3.1 | 1.4 | 5.5 |

We observed a 6.2-9.8-fold increase in mutuDC 1940 mCherry expression at 24 h with the L-DPPS targeted LNPs, the largest fold increase coming from LNP formulations containing the UO-1 ICL shown in Table 62. We observed a corresponding 11.9-17.7-fold increase in LNP uptake (DiIC18(5)-DS signal) at 24 h over the non-targeted LNP by inclusion of DPPS. In general, DPPS had a slight advantage over DSPS in targeting capability, but the L-isomer of DSPS was 7.2-9-fold better than the D-isomer lipid, indicating that the L isomer form of PS is important for optimal LNP targeting to DCs. We propose that the PS-targeted LNPs in this example are taking advantage of the natural PS/receptor internalization and cell uptake mechanisms to improve intracellular delivery and translation of mRNA.

Example 50. Impact of PEG-DLG on LNP Biophysical Properties and Transfection Efficiency of Human Monocyte Derived Dendritic Cells Due to increased dissociation from the lipid bilayers, conjugated lipids with double hydrocarbon chains of less than 14 carbon atoms are generally not considered for generating size-stable LNPs with effective cellular delivery of their nucleic acid payload. Nonetheless, we explored whether our LNP formulations would allow the use of di-C12-PEG-conjugated lipid (PEG-dilauroylglycerol, PEG-PLG) as an LNP stabilizing agent how increasing the mol % of PEG-DLG in LNPs affects the biophysical properties and transfection efficiency. To this end, various amounts of PEG-DLG were incorporated into KC3OA+PS LNPs. KC3OA+PS LNPs containing 1.5 mol % of a di-C14-PEG-conjugated Lipid PEG DMG were also prepared for comparison. The protocols of Examples 9 and 10 were used for LNP preparation and characterization, and the base lipid composition for these LNPs was KC3OA/DSPC/DPPS-NH$_4$/Chol/PEG-lipid at the molar ratios of 48/5/5/(42−X)/X where X=0.5, 1.0, 1.5, 2.0, or 2.5, with mRNA at N/P of 5.25. The LNP particle size and mRNA encapsulation efficiency are shown in Table 63.

TABLE 63

Physicochemical properties of KC3OA + PS LNPs used in Example 50

| Lot # | PEG-Lipid | PEG lipid mol % | Particle Size (nm) | PDI | % E.E ± SD |
|---|---|---|---|---|---|
| 032922-1 | PEG-DMG | 1.5 | 98.7 | 0.14 | 92.0 ± 8.6 |
| 032922-2 | PEG-DLG | 0.5 | 94.4 | 0.13 | 92.5 ± 7.6 |
| 032922-3 | PEG-DLG | 1.0 | 90.3 | 0.19 | 92.6 ± 3.0 |
| 032922-4 | PEG-DLG | 1.5 | 93.3 | 0.14 | 91.9 ± 4.4 |
| 032922-5 | PEG-DLG | 2.0 | 85.2 | 0.12 | 92.1 ± 3.9 |
| 032922-6 | PEG-DLG | 2.5 | 81.5 | 0.13 | 91.6 ± 3.6 |

Within the series of LNPs with increasing amounts of PEG-DLG we observed an inverse relationship between LNP size and PEG-DLG content (lots #032922-2 through 032922-6), while encapsulation efficiency remained similar at ~ 92%, also similar to the 1.5 mol % PEG-DMG sample (92%). The similar size and mRNA entrapment features of lots 032922-1 and 032922-4 suggests that LNPs containing PEG-DLG closely resemble those containing PEG-DMG.

Four days prior to transfection, monocytes were isolated using CD14 isolation kit (StemCell) from PBMCs of healthy donors as described in Example 28. CD14 purity of donor 1 and donor 2 monocytes was 95% and 98%, respectively; overall viability >92%. The monocytes were cultured with IL-4 (R&D 1000 IU/mL) and GM-CSF (R&D, 800 IU/mL) in a 6 well dish at 1×10$^6$ cells/mL at 37° C., 5% CO2. After 4 days the immature DCs were harvested and seeded in a 96 well round bottom plate at 50,000 cells/well. LNPs were thawed by placing the vials in a 37° C. water bath for 30 seconds, or until the sample had almost fully melted. The vials were immediately placed on ice until use. The LNPs were added to final concentrations of 1 µg/ml and 0.1 µg/mL mRNA. For 1 µg/mL treatment, LNPs were added directly to each well then wells were mixed by pipetting. For 0.1 µg/mL treatment, LNPs were diluted 1:10 in complete media then added to each well and mixed by pipetting. After 4 h a maturation cytokine cocktail was added directly to each well consisting of TNF-α (R&D, 10 ng/mL), IL-1b (R&D, 2 ng/mL), IL-6 (R&D, 1000 IU/mL), and PGE1 (R&D, 1 µg/mL). After 24 h, the cells were centrifuged, washed in PBS and analyzed by flow cytometry for mCherry fluorescence. Gating analysis was performed using CytExpert software.

Figure 39:
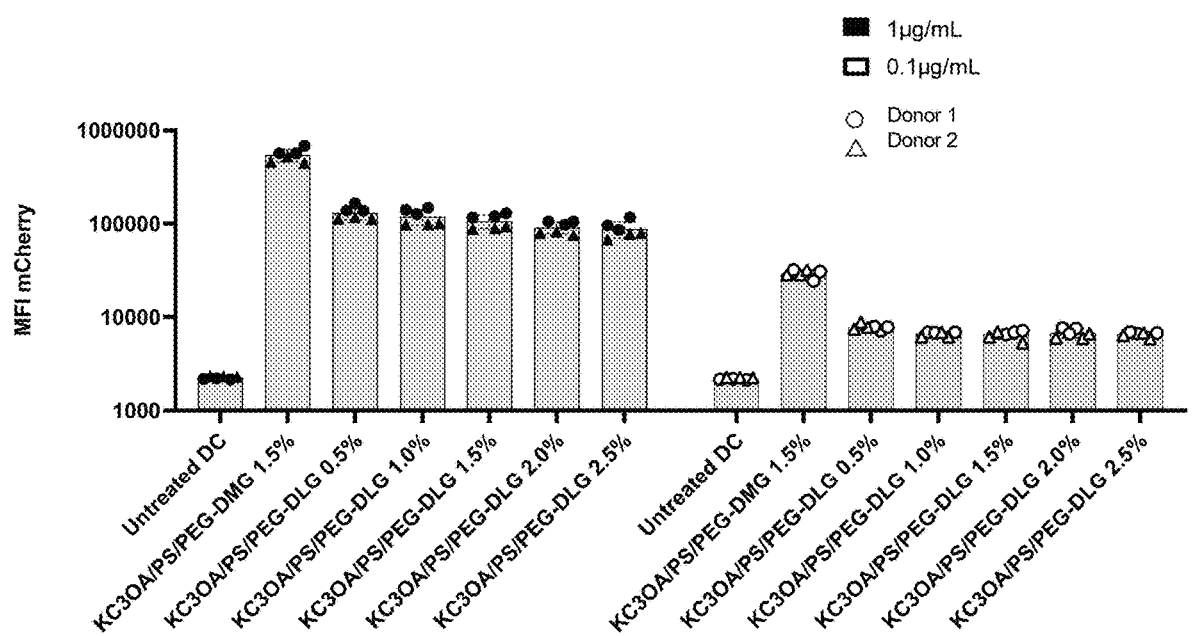
FIG. 39. Expression of mCherry mRNA delivered to MutuDC1940 cells by LNP formulations of mCherry mRNA (0.3 μg/mL) formulated in KC3OA/DPPS LNPs prepared with PEG-DMG and various amounts of PEG-DLG (Example 50). The expression was quantified by flow cytometry of mCherry fluorescence 24 hours after transfection with LNPs at 1.0 and 0.1 μg/mL mRNA. PBMCs were taken from two donors and each was run in triplicate. The bars are average across the combined donor replicate data. LNP compositions are indicated at the X-axis. "%" refers to the mol % of the PEG-lipid component relative to the total LNP lipid.

The mCherry expression (FIG. 39) demonstrated an inverse relationship between mCherry expression and PEG-DLG content. LNPs 032911-1 through 6 contain varying amounts of PEG-DLG ranging from 0.5-2.5 mol % in 0.5 mol % increments. Within this series, the increasing PEG-DLG content correlated with reduced mCherry expression. If a direct comparison is made between LNPs made with PEG-DMG or PEG-DLG (lot 032922-1 v 032922-4) at 1.5 mol % each, the mCherry expression for the PEG-DMG LNP was ~5.2-fold (1 µg/ml) or 4.5-fold (0.1 µg/ml) higher than for the PEG-DLG LNP while LNP size and mRNA encapsulation efficiency were similar for both.

Example 51. A Comparison of PEG-DMG and PEG-DLG in KC3-PA-Based LNP Formulations of Covid Spike mRNA for their Ability to Produce Anti-Spike Antibodies In Vivo The aim of this study was to compare PEG-DMG and PEG-DLG in LNP formulations containing mRNA encoding the SARS-COV2 Spike protein for their capability to induce antibody titers against SARS-COV2 spike protein in mice.

Design and preparation of mRNA. mRNA encoding the SARS-CoV-2 full length spike protein and flanked with the same UTRs used in the BNT162b2 (Comirnaty®) vaccine was prepared by Vernal Biosciences as described in Example 35.

LNP Preparation

LNPs were prepared as described in Example 9 using KC3-PA as the ionizable lipid at 48 mol %, DPPC as the phospholipid at 5 mol %, 5 mol % DPPS-$NH_4$ and varying the amount of PEG-DLG from 1.5 mol % to 2.5 mol % using mRNA VRN029 at a N/P ratio of 5.25. Increasing the PEG-lipid content was made at the expense of cholesterol content similarly to Example 50. A comparator formulation 031822-9 composed of KC3-PA/DSPC/DPPS/Chol/PEG-DMG (48/5/5/40.5/1.5 mol %) from Example 35 was also used.

Freeze/Thaw Protocol

Freezing LNP is accomplished by partial immersion of sample vial in liquid nitrogen (LN2) for 5 min, followed by storage at −80 C. Before dosing, a vial of each LNP is placed in a floater and put in a 37° C. water bath for ~30 seconds until the ice has almost fully melted inside the vials. For this study, samples were concentrated to >40 μg/mL mRNA, and diluted with varying volumes of 15 mM Tris, 20% Sucrose, pH 7.4 to a target concentration of 40 μg mRNA and then frozen on LN2. Characterization of LNPs was undertaken after an aliquot of the LNPs were thawed and diluted 1:1 (vol:vol) with 15 mM Tris, pH 7.4 such that the final concentration was 20 μg/mL mRNA in 15 mM Tris, 10% sucrose, pH 7.4. This simulated the conditions of sample preparation used prior to dosing animals with an i.m. injection of 1 μg LNP formulated mRNA in 50 μL volume into a hind limb thigh area. The LNPs were characterized by particle size and mRNA encapsulation efficiency (Table 64).

TABLE 64

Composition and characterization of LNPs used in a Covid Spike mRNA immunogenicity study of Example 51.

| Lot # | ICL | PEG-Lipid | Mol % | % Chol | Particle Size (nm) | PDI | % E.E ± SD |
|---|---|---|---|---|---|---|---|
| 031822-9 | KC3-PA | PEG-DMG | 1.5 | 40.5 | 89.7 | 0.26 | 87.4 ± 10.3 |
| 031822-10 | KC3-PA | PEG-DLG | 1.5 | 40.5 | 114.7 | 0.020 | 84.2 ± 5.7 |
| 031822-11 | KC3-PA | PEG-DLG | 2.0 | 40.0 | 101.2 | 0.020 | 88.8 ± 5.6 |
| 031822-12 | KC3-PA | PEG-DLG | 2.5 | 39.5 | 105.5 | 0.09 | 84.9 ± 3.9 |

Immunization and SARS-CoV-2 anti-spike antibody titers. The mice were immunized with the LNPs and a standard indirect ELISA was performed to analyze serum samples for total IgG binding antibodies to the SARS-CoV-2 spike protein as described in Example 35.

FIG. 40 displays the titers of anti-spike antibodies in the blood of the mice at 2 weeks post boost dose with KC3-PA based LNPs (SD35). Surprisingly, in spite of the differences in the in vitro mRNA expression (see Example 50), these PEG-DMG and PEG-DLG containing LNPs performed very similarly in vivo. As the mol % of PEG-DLG increases above 1.5 mol % to 2.0 and 2.5 mol % of the total lipid the average antibody titers obtained with the corresponding LNPs were not statistically different using one-way ANOVA with a Dunnett's multiple comparisons post-test. This indicates that PEG-DLG can be used as an alternative to PEG-DMG. In some embodiments, the range of PEG-DLG concentration is about 0.5-2.5 mol %.

Example 52. Comparative Immunogenicity of PEG-DMG and PEG-DLG-Containing SARS-COV-2 Spike mRNA LNP Formulations of KC3-OA Effect of the DPPS Content (3.5-6.5 Mol %)

The aim of this study was to compare PEG-DMG and PEG-DLG-containing KC3-OA based LNP formulations containing mRNA encoding the SARS-COV2 Spike protein for their capability to induce antibodies against SARS-COV2 spike protein. LNPs were prepared using mRNA encoding the SARS-CoV-2 full length spike protein using KC3-OA as the ionizable lipid, 5 mol % DPPS as a targeting ligand and differed in the type of PEG-lipid used to stabilize the LNP. LNPs having KC3OA, DSPC, DPPS-$NH_4$, cholesterol, and PEG-lipid at the molar ratio of 48/(10−X)/X/40.5/1.5, X=3.5, 5.0, or 6.5, were prepared as described in Example 9. Their composition and characterization are shown in Table 65.

TABLE 65

Composition and characterization of KC3-OA-containing LNPs used in Example 52.

| Lot # | PEG-Lipid | DPPS, mol % | Z-average size (nm) | PDI | % E.E | ZP pH 7 | ZP pH 5 |
|---|---|---|---|---|---|---|---|
| 051722-8 | PEG-DMG | 5.0 | 114.3 | 0.13 | 93.8 ± 5.6 | 7.12 | −0.22 |
| 051722-11 | PEG-DLG | 5.0 | 107.6 | 0.15 | 94.7 ± 5.4 | 7.33 | −0.47 |
| 051722-9 | PEG-DMG | 3.5 | 103.8 | 0.13 | 94.3 ± 5.0 | 5.00 | −0.03 |
| 051722-10 | PEG-DMG | 6.5 | 105.9 | 0.19 | 94.6 ± 5.4 | 11.82 | −0.56 |

ZP, zeta potential (mV). % EE, encapsulation efficiency, % (mean ± standard deviation).

Balb/C mice (n=5) were dosed with an injection of 1 μg LNP formulated mRNA in 50 μL volume via IM injection into a hind limb. At 3 weeks post dosing, serum was collected and analyzed for anti-spike antibodies via ELISA as described in Example 35, data shown in FIG. 41A.

Again, contrary to the in vitro results, inclusion of PEG-DLG instead of PEG-DMG showed even a slight improvement in immunogenicity while other particle characteristics were similar. This indicates that PEG-DLG has potential to be used in LNP formulations that yield similar biophysical characteristics and can have similar or better activity in vivo. When titers were measured at 2 weeks post boost, we observed similar titers between KC3-OA LNPs targeted with mol % DPPS containing either PEG-DLG or PEG-DMG (FIG. 41B), with at least two orders of magnitude higher titers than 3 weeks after prime dose FIG. 41A. Also shown in FIG. 41B are formulations with 3.5-6.5 mol % DPPS, and also containing 1.5 mol % PEG-DMG. The three 1.5 mol % PEG-DMG LNP formulations across the range of 3.5-6.5 mol % DPPS were similar to one another and to the 5 mol % DPPS formulation with 1.5 mol % PEG-DLG in their capacity to elicit immune response to the mRNA-encoded antigen in vivo (FIG. 41B). The formulation size and mRNA encapsulation efficiencies of these formulations were similar, indicating the range of DPPS concentrations that can be included into LNPs without substantial changes in their biophysical characteristics and/or immunogenicity.

Example 53. Biophysical Characterization and In Vitro Comparison of LNPs Containing PEG-DMG and PEG-DLPE at Various Mol %

The aim of this study was to compare the effects of replacing PEG-DMG with a different di-C12-PEG lipid, a phosphatidylethanolamine lipid derivative 1,2-dilauroyl-sn-glycero-3-phosphoethanolamine-N-[methoxy(polyethylene glycol)-2000] (PEG-DLPE) at various concentrations (0.5-2.5 mol %) on the biophysical characteristics of LNP particle size, % mRNA encapsulation and freeze-thaw stability. The LNPs containing KC3OA/DSPC/DPPS-NH$_4$/cholesterol//PEG-lipid in the molar ratio 48/5/5/(42−X)/X, where X=0.5, 1.0, 1.5, 2.0, or 2.5, and mRNA at N/P=5.25 were prepared, analyzed and frozen as described above in Examples 9 and 10. Analytical data of the LNPs are in Tables 66 and 67 (Abbreviations: % EE, mRNA encapsulation efficiency, %; stdev, % EE standard deviation; post-mix, after mixing of the lipids and mRNA solutions; post spin+filter, after buffer exchange by centrifugal concentrators and 0.2-μm filtration; post FT, after freeze-thaw cycle; Z-Ave, z-average particle size by DLS, nm; PDI, size polydispersity index).

TABLE 66 mRNA concentration and encapsulation efficiency of KC3-OA-containing LNPs as measured from a fluorometric Ribogreen ® assay described above in Example 10.

| Lot # | Process Stage | PEG-lipid | PEG-lipid mol % (X) | mRNA μg/mL | % E.E | stdev |
|---|---|---|---|---|---|---|
| 082322-1 | pre-freeze/thaw | PEG-DMG | 0.5 | 45.7 | 92.0 | 1.8 |
| 082322-1 | post-freeze/thaw | PEG-DMG | 0.5 | 46.2 | 86.1 | 8.8 |
| 082322-2 | pre-freeze/thaw | PEG-DMG | 1.0 | 60.3 | 92.2 | 8.7 |
| 082322-2 | post-freeze/thaw | PEG-DMG | 1.0 | 59.0 | 93.5 | 7.8 |
| 082322-3 | pre-freeze/thaw | PEG-DMG | 1.5 | 59.8 | 90.9 | 2.6 |
| 082322-3 | post-freeze/thaw | PEG-DMG | 1.5 | 58.0 | 92.4 | 9.2 |
| 082322-4 | pre-freeze/thaw | PEG-DMG | 2.0 | 52.3 | 90.3 | 7.9 |
| 082322-4 | post-freeze/thaw | PEG-DMG | 2.0 | 51.9 | 89.9 | 6.7 |
| 082322-5 | pre-freeze/thaw | PEG-DMG | 2.5 | 56.6 | 89.5 | 7.8 |
| 082322-5 | post-freeze/thaw | PEG-DMG | 2.5 | 56.6 | 90.9 | 4.0 |
| 082322-11 | pre-freeze/thaw | PEG-DLPE | 0.5 | 30.2 | 87.7 | 4.0 |
| 082322-11 | post-freeze/thaw | PEG-DLPE | 0.5 | 28.7 | 77.5 | 5.5 |
| 082322-12 | pre-freeze/thaw | PEG-DLPE | 1.0 | 60.4 | 89.4 | 9.1 |
| 082322-12 | post-freeze/thaw | PEG-DLPE | 1.0 | 58.5 | 93.2 | 8.4 |
| 082322-13 | pre-freeze/thaw | PEG-DLPE | 1.5 | 50.3 | 90.7 | 10.0 |
| 082322-13 | post-freeze/thaw | PEG-DLPE | 1.5 | 51.0 | 90.3 | 7.0 |
| 082322-14 | pre-freeze/thaw | PEG-DLPE | 2.0 | 65.4 | 90.0 | 6.2 |
| 082322-14 | post-freeze/thaw | PEG-DLPE | 2.0 | 63.3 | 89.9 | 7.9 |
| 082322-15 | pre-freeze/thaw | PEG-DLPE | 2.5 | 63.7 | 90.0 | 5.6 |
| 082322-15 | post-freeze/thaw | PEG-DLPE | 2.5 | 64.2 | 89.6 | 6.0 |

In general, it was observed that there was little variance between the mRNA encapsulation efficiency prior to and after freezing/thawing (less than 1.2% for LNPs with 1 mol % or more PEG-lipid). However, in the case of 0.5 mol %

PEG-DLPE the encapsulation decreased 11.7% respectively after thawing, indicating the importance of PEG-lipid concentration on freeze/thaw stability for this PEG-lipid variant.

TABLE 67

Particle size properties of KC3-OA-containing LNPs of Example 53 at various preparation process steps.

| Lot# | PEG-lipid | Post-mix Z-Ave | Post-mix PDI | Post spin + filter Z-Ave | Post spin + filter PDI | Post F/T Z-Ave | Post F/T PDI |
|---|---|---|---|---|---|---|---|
| 082322-1 | 0.5 PEG-DMG | 78.34 | 0.10 | 123.10 | 0.05 | 124.30 | 0.07 |
| 082322-2 | 1.0 PEG-DMG | 67.84 | 0.16 | 107.80 | 0.06 | 106.10 | 0.04 |
| 082322-3 | 1.5 PEG-DMG | 59.43 | 0.14 | 89.48 | 0.07 | 92.96 | 0.07 |
| 082322-4 | 2.0 PEG-DMG | 55.14 | 0.09 | 85.39 | 0.10 | 83.35 | 0.13 |
| 082322-5 | 2.5 PEG-DMG | 53.24 | 0.15 | 74.84 | 0.11 | 74.43 | 0.15 |
| 082322-11 | 0.5 PEG-DLPE | 102.90 | 0.10 | 154.10 | 0.12 | 156.80 | 0.13 |
| 082322-12 | 1.0 PEG-DLPE | 91.21 | 0.28 | 129.10 | 0.19 | 129.20 | 0.17 |
| 082322-13 | 1.5 PEG-DLPE | 82.43 | 0.34 | 122.40 | 0.22 | 120.90 | 0.25 |
| 082322-14 | 2.0 PEG-DLPE | 81.70 | 0.28 | 114.90 | 0.22 | 112.70 | 0.20 |
| 082322-15 | 2.5 PEG-DLPE | 92.6 | 0.32 | 101.0 | 0.20 | 102.5 | 0.21 |

It was observed that for both PEG-DMG and PEG-DLPE the lower the PEG-lipid concentration within the formulation, the larger the LNP sizes. This is most likely a consequence of the well-known concentration dependent stabilizing effect of PEG-lipid in LNP formulations (Mui B L, et al. Mol Ther Nucleic Acids. 2013 Dec. 17; 2(12):e139. doi: 10.1038/mtna.2013.66. PMID: 24345865; PMCID: PMC3894582). In general, the sizes of LNPs with PEG-DMG were smaller than those with the corresponding content of PEG-DLPE ranging from 19.8-27.0% lower in diameter. However, the change in size upon freezing and thawing compared to the original samples was less than 1.5% in all cases.

In vitro expression of mCherry protein mRNA in the LNPs of Example 53 was studied in a murine DC cell line MutuDC1940 after 24 h incubation with 0.3 μg/mL LNP-formulated mCherry mRNA was measured by flow cytometry (Table 68, FIG. 42) with experiment details and cellular sample preparation described in Example 11.

TABLE 68 mCherry median fluorescent intensity (MedFI) values in MutuDC1940 cells treated with LNPs of Example 53.

| Lot # | PEG-lipid | X | MedFI | stdev |
|---|---|---|---|---|
| Untreated | | | 281.7 | 5.7 |
| 082322-1 | PEG-DMG | 0.5 | 183,442.3 | 27,278.5 |
| 082322-2 | PEG-DMG | 1.0 | 145,519.0 | 4,167.8 |
| 082322-3 | PEG-DMG | 1.5 | 81,032.7 | 4,320.6 |
| 082322-4 | PEG-DMG | 2.0 | 30,000.0 | 1,817.3 |
| 082322-5 | PEG-DMG | 2.5 | 12,835.0 | 564.3 |
| 082322-11 | PEG-DLPE | 0.5 | 61,306.7 | 2,682.7 |
| 082322-12 | PEG-DLPE | 1.0 | 48,264.7 | 5,298.1 |
| 082322-13 | PEG-DLPE | 1.5 | 31,809.3 | 2,376.0 |
| 082322-14 | PEG-DLPE | 2.0 | 34,627.0 | 2,546.0 |
| 082322-15 | PEG-DLPE | 2.5 | 27,116.7 | 2,789.8 |

It was found that within each group, lower PEG-lipid concentration led to higher transfection rates. The LNPs containing PEG-DMG performed best at lower PEG-lipid content (1.5 mol % or less), while PEG-DLPE performed better than PEG-DMG at PEG-lipid greater than 2 mol %. In selected ranges, mCherry expression was reduced in a linear manner ($r^2$=0.99) for LNPs with PEG-DMG (0.5-2 mol %) and LNPs containing 0.5-1.5 mol % PEG-DLPE ($r^2$=0.99). The data suggest that another di-C12-PEG-lipid conjugate, PEG-DLPE was as effective as PEG-DMG in the LNP formulations. It provided for the LNPs with high mRNA trapping efficiencies, had a concentration dependent effect on LNP size, prevented LNP structural instabilities upon freezing and thawing, provided LNPs with mRNA transfection activities similar to PEG-DMG, and at higher PEG densities may be more efficient than PEG-DMG.

Example 54. In Vivo Immunogenicity Comparison of LNPs with a Range of PS Concentrations, a Comparison Between PEG-DMG and PEG-DLG at a Single PS Concentration and a Comparison of DSPS and DPPS as a Targeting Ligand The first aim of this study was to ascertain if there was a specific amount of PS-targeting lipid that could be incorporated into KC3OA-based LNPs that could achieve the highest antibody titers in mice. This was tested by producing PEG-DMG containing LNPs with 0, 2, 3.5, 5, 6.5 or 9 mol % DPPS (the balance being DSPC to the sum of DPPS+DSPC equal 10 mol % of the total lipid) encapsulating mRNA VRN029 (N/P=5.25), dosing mice at 0.3 μg LNP formulated mRNA (n=5) and at Day 20, collecting serum and analyzing for anti-spike antibody titers. LNPs were made and characterized as described in Example 9, the mice were immunized and the anti-spike antibody titers determined as in Example 35. The Day 20 titer data is shown in FIG. 43A. A striking dependence on DPPS-NH$_4$ content was observed with the range 2.0-5.0 mol % found as optimal for activity. The ratios of geomean titers of each of the formulations relative to the LNP without DPPS (non-targeted) is shown in Table 69. Lipid composition and biophysical characterization of LNPs used in Example 54 are described in Tables 70 and 71 respectively.

TABLE 69

Fold-difference between a given formulation and the non-targeted variant (KC3OA with no DPPS targeting lipid included) in serum anti-spike antibody titers at Day 20.

| Formulation | Fold difference in geomean relative to untargeted KC3-OA |
|---|---|
| KC3-OA, 9 DPPS, 1.5 PEG-DMG | 0.66 |
| KC3-OA, 6.5 DPPS, 1.5 PEG-DMG | 1.78 |
| KC3-OA, 5 DPPS, 1.5 PEG-DMG | 6.48 |
| KC3-OA, 3.5 DPPS, 1.5 PEG-DMG | 5.96 |
| KC3-OA, 2 DPPS, 1.5 PEG-DMG | 4.63 |

From the data above, the optimal DPPS mol % was found to be within 2-5 mol %. A set of LNPs containing 3.5 mol % DPPS but differing in the amount of PEG-DLG or PEG-DMG were prepared, characterized and mice immunized at 0.3 µg LNP formulated mRNA. An ALC-0315 LNP was prepared as a control. Different amounts of PEG-DMG or PEG-DLG were included in the KC3-OA LNPs (KC3OA/DSPC/DPPS/Chol/PEG lipid 48/6.5/3.5/42-X/X molar parts, X=0.5, 1.0, 1.5, 2.0) by reducing the proportional mol % of Chol content. The anti-spike titers were measured at Day 35 (FIG. 43B), 2 weeks after initial prime dose. In the case of PEG-DMG (formulations 16, 15 and 5 at 0.5, 1.0 and 1.5 mol % PEG-DMG respectively, Table 70), no significant change in antibody titers was observed. The average LNP sizes were 145, 125 and 103 nm respectively where the size was found to be inversely proportional to the PEG-lipid content (Table 71). In addition, no significant change in titers was observed for the formulations with 1.0, 1.5 or 2.0 mol % PEG-DLG was detected and from an immunogenicity readout these formulations were indistinguishable. LNP Z-average particle sizes for these formulations also inversely correlated with the PEG-DLG content at 113, 94 and 88 nm for the 1.0, 1.5 and 2.0 mol % respectively. The similarity of the data borne from KC3-OA LNPs targeted with 3.5 mol % DPPS, across multiple different concentrations of PEG-DMG and PEG-DLG demonstrated that PEG-DLG can be used as an alternative to PEG-DMG in LNP formulations. All DPPS targeted KC3-OA formulations, regardless of PEG-lipid identity or concentration were substantially more active than the ALC-0315 control formulation or the non-targeted KC3-OA LNP.

Additionally, a comparison of KC3-OA-based LNP formulations using DSPS-Na as the targeting component (5 mol %) with either 1.5 mol % PEG-DMG or PEG-DLG was completed and the SD35 titer data shown in FIG. 43C. A comparator formulation of KC3OA with 5 mol % DPPS, with 1.5 mol % PEG-DMG was also tested. The data show that the formulations had similar immunogenicity, suggesting that DSPS and DPPS are equivalent for dendritic cell targeting purposes and that PEG-DLG could be used as an effective alternative to PEG-DMG in LNP formulations potentially less prone to eliciting undesirable anti-PEG antibody response.

All lipid compositions of the formulations used in Example 54 are presented in Table 70, while the biophysical characteristics such as size, zeta potential and mRNA entrapment are displayed in Table 71. The total phospholipid in all LNPs is 10 mol % with DSPC making up the difference following inclusion of variable amounts of phosphatidylserines.

TABLE 70

LNP formulation details used in Example 54.

| LNP # | ICL | mol % | PtdSer | mol % | Chol, mol % | PEG | mol % |
|---|---|---|---|---|---|---|---|
| 1 | ALC-0315 | 46.3 | none | 0 | 42.7 | ALC-0159 | 1.5 |
| 2 | KC3-OA | 48 | DPPS-NH4 | 9 | 40.5 | PEG-DMG | 1.5 |
| 3 | KC3-OA | 48 | DPPS-NH4 | 6.5 | 40.5 | PEG-DMG | 1.5 |
| 4 | KC3-OA | 48 | DPPS-NH4 | 5 | 40.5 | PEG-DMG | 1.5 |
| 5 | KC3-OA | 48 | DPPS-NH4 | 3.5 | 40.5 | PEG-DMG | 1.5 |
| 6 | KC3-OA | 48 | DPPS-NH4 | 2 | 40.5 | PEG-DMG | 1.5 |
| 7 | KC3-OA | 48 | none | 0 | 40.5 | PEG-DMG | 1.5 |
| 8 | KC3-OA | 48 | DPPS-NH4 | 3.5 | 40.5 | PEG-DLG | 1.5 |
| 9 | KC3-OA | 48 | none | 0 | 40.5 | PEG-DLG | 1.5 |
| 10 | KC3-OA | 48 | DSPS-Na | 5 | 40.5 | PEG-DMG | 1.5 |
| 11 | KC3-OA | 48 | DSPS-Na | 5 | 40.5 | PEG-DLG | 1.5 |
| 12 | KC3-OA | 48 | DPPS-NH4 | 3.5 | 41 | PEG-DMG | 1 |
| 13 | KC3-OA | 48 | DPPS-NH4 | 3.5 | 41.5 | PEG-DMG | 0.5 |
| 14 | KC3-OA | 48 | DPPS-NH4 | 3.5 | 40 | PEG-DLG | 2 |
| 15 | KC3-OA | 48 | DPPS-NH4 | 3.5 | 41 | PEG-DLG | 1 |

TABLE 71

% E.E refers to the mRNA encapsulation efficiency.

| | C/F | | post F/T | | C/F | | post F/T | |
|---|---|---|---|---|---|---|---|---|
| LNP# | Size | PDI | Size | PDI | % E.E | stdev | % E.E | stdev |
| 1 | 84.21 | 0.12 | 80.88 | 0.10 | 79.2 | 2.5 | 79.8 | 2.1 |
| 2 | 94.88 | 0.08 | 95.44 | 0.12 | 89.9 | 5.7 | 91.0 | 1.2 |
| 3 | 97.22 | 0.09 | 96.31 | 0.09 | 90.0 | 6.1 | 91.0 | 1.2 |
| 4 | 99.84 | 0.06 | 98.44 | 0.09 | 89.8 | 5.6 | 90.6 | 4.9 |
| 5 | 103.90 | 0.08 | 103.40 | 0.08 | 89.1 | 5.4 | 89.1 | 4.0 |
| 6 | 109.30 | 0.07 | 106.20 | 0.10 | 90.1 | 5.6 | 90.0 | 7.7 |
| 7 | 103.50 | 0.03 | 102.70 | 0.07 | 90.0 | 3.4 | 89.8 | 4.2 |
| 8 | 93.51 | 0.11 | 93.98 | 0.11 | 89.9 | 4.5 | 90.8 | 6.4 |
| 9 | 100.70 | 0.10 | 98.92 | 0.10 | 89.8 | 6.1 | 89.3 | 4.6 |
| 10 | 101.60 | 0.04 | 99.64 | 0.05 | 90.2 | 4.2 | 91.3 | 5.9 |
| 11 | 101.00 | 0.04 | 104.40 | 0.01 | 89.7 | 3.6 | 90.9 | 5.3 |
| 12 | 122.70 | 0.04 | 124.80 | 0.07 | 91.6 | 5.8 | 92.2 | 5.1 |
| 13 | 143.60 | 0.04 | 145.30 | 0.02 | 91.2 | 4.6 | 91.7 | 5.0 |
| 4 | 88.72 | 0.11 | 89.88 | 0.09 | 89.7 | 6.3 | 90.2 | 8.9 |
| 15 | 112.90 | 0.06 | 107.60 | 0.07 | 90.1 | 2.6 | 90.2 | 8.9 |

F/T refers to freeze/thaw.

The LNP formulations and characterization data are shown in Table 69 and 70 respectively. The % E.E of the LNPs ranged from 79.2 to 91.6% among formulations and varied to less than 2.5% as a result of freeze-thawing. The LNP particle size after buffer exchange and sterile filtering ranged from 80.9 to 145.3 nm between different formulations, with less than a 5% change in size upon freezing and thawing.

TABLE 72

Log-transformed reciprocal serum titers of anti-SARS-COV-2 spike protein antibodies in mice treated with 0.3 µg mRNA in LNPs at Day 0 and Day 21: bleed time Day 35 (boost). The log titers are shown as mean ± standard deviation (median).

| Formulation | Composition | Day 35 Log titer |
|---|---|---|
| 1 | ALC-0315, ALC-0159 | 5.16 ± 0.15 (5.15) |
| 2 | KC3-OA, 9 DPPS, 1.5 PEG-DMG | 5.28 ± 0.49 (5.55) |
| 3 | KC3-OA, 6.5 DPPS, 1.5 PEG-DMG | 5.85 ± 0.20 (5.75) |
| 4 | KC3-OA, 5 DPPS, 1.5 PEG-DMG | 5.88 ± 0.33 (5.70) |
| 5 | KC3-OA, 3.5 DPPS, 1.5 PEG-DMG | 5.84 ± 0.17 (5.78) |
| 6 | KC3-OA, 2 DPPS, 1.5 PEG-DMG | 5.73 ± 0.20 (5.73) |
| 7 | KC3-OA, 0 DPPS, 1.5 PEG-DMG | 5.53 ± 0.25 (5.64) |
| 8 | KC3-OA, 3.5 DPPS, 1.5 PEG-DLG | 5.66 ± 0.07 (5.64) |
| 9 | KC3-OA, 0 DPPS, 1.5 PEG-DLG | 5.17 ± 0.05 (5.16) |
| 10 | KC3-OA, 5 DSPS, 1.5 PEG-DMG | 6.07 ± 0.51 (6.03) |
| 11 | KC3-OA, 5 DSPS, 1.5 PEG-DLG | 5.77 ± 0.09 (5.76) |
| 12 | KC3-OA, 3.5 DPPS, 1.5 PEG-DMG | 5.84 ± 0.27 (5.79) |
| 13 | KC3-OA, 3.5 DPPS, 0.5 PEG-DMG | 5.67 ± 0.07 (5.65) |
| 14 | KC3-OA, 3.5 DPPS, 2 PEG-DLG | 5.72 ± 0.23 (5.75) |
| 15 | KC3-OA, 3.5 DPPS, 1 PEG-DLG | 5.67 ± 0.24 (5.70) |

This study suggests that potentially less immunogenic conjugated lipids containing dilauroyl alkyl chains can be successfully used in LNP compositions developed for local administration, such as is the case for intramuscularly delivered LNP vaccines.

Example 55. A Comparison of LNPs Encapsulating Different SARS-CoV-2 Full Length Spike Protein Encoded mRNAs The purpose of this study was to compare the mRNA encoding the SARS-CoV-2 full length spike protein, flanked with the same UTRs used in the BNT162b2 (Comeirnaty) vaccine (VRN029), to two other mRNAs containing the same endogenous 5' signal sequence and polyA tails but differing in their ORF codon optimization and UTR optimization and sequence. The two mRNA variants are VRN118 (Akagera (AKG) optimized, HBB UTRs, SEQ ID: NO 3) and VRN119 (AKG optimized, Vernal UTRs, SEQ ID: NO 4). Our hypothesis was that sequence optimization of the mRNA contained in the Comirnaty® vaccine drug product, may lead to enhanced immunogenicity.

```
The sequence of VRN 118 (SEQ ID NO: 3) is listed below.
ACATTTGCTTCTGACACAACTGTGTTCACTAGCAACCTCAAACAGCCACCATGTTCGTGTTCCTGGTGCTGCTGCCC

CTGGTGAGCAGCCAGTGCGTGAACCTGACCACCAGGACCCAGCTGCCCCCCGCCTACACCAACAGCTTCACCAGGGG

CGTGTACTACCCCGACAAGGTGTTCAGGAGCAGCGTGCTGCACAGCACCCAGGACCTGTTCCTGCCCTTCTTCAGCA

ACGTGACCTGGTTCCACGCCATCCACGTGAGCGGCACCAACGGCACCAAGAGGTTCGACAACCCCGTGCTGCCCTTC

AACGACGGCGTGTACTTCGCCAGCACCGAGAAGAGCAACATCATCAGGGGCTGGATCTTCGGCACCACCCTGGACAG

CAAGACCCAGAGCCTGCTGATCGTGAACAACGCCACCAACGTGGTGATCAAGGTGTGCGAGTTCCAGTTCTGCAACG

ACCCCTTCCTGGGCGTGTACTACCACAAGAACAACAAGAGCTGGATGGAGAGCGAGTTCAGGGTGTACAGCAGCGCC

AACAACTGCACCTTCGAGTACGTGAGCCAGCCCTTCCTGATGGACCTGGAGGGCAAGCAGGGCAACTTCAAGAACCT

GAGGGAGTTCGTGTTCAAGAACATCGACGGCTACTTCAAGATCTACAGCAAGCACACCCCCATCAACCTGGTGAGGG

ACCTGCCCCAGGGCTTCAGCGCCCTGGAGCCCCTGGTGGACCTGCCCATCGGCATCAACATCACCAGGTTCCAGACC

CTGCTGGCCCTGCACAGGAGCTACCTGACCCCCGGCGACAGCAGCAGCGGCTGGACCGCCGGCGCCGCCGCCTACTA

CGTGGGCTACCTGCAGCCCAGGACCTTCCTGCTGAAGTACAACGAGAACGGCACCATCACCGACGCCGTGGACTGCG

CCCTGGACCCCCTGAGCGAGACCAAGTGCACCCTGAAGAGCTTCACCGTGGAGAAGGGCATCTACCAGACCAGCAAC

TTCAGGGTGCAGCCCACCGAGAGCATCGTGAGGTTCCCCAACATCACCAACCTGTGCCCCTTCGGCGAGGTGTTCAA

CGCCACCAGGTTCGCCAGCGTGTACGCCTGGAACAGGAAGAGGATCAGCAACTGCGTGGCCGACTACAGCGTGCTGT

ACAACAGCGCCAGCTTCAGCACCTTCAAGTGCTACGGCGTGAGCCCCACCAAGCTGAACGACCTGTGCTTCACCAAC

GTGTACGCCGACAGCTTCGTGATCAGGGGCGACGAGGTGAGGCAGATCGCCCCCGGCCAGACCGGCAAGATCGCCGA

CTACAACTACAAGCTGCCCGACGACTTCACCGGCTGCGTGATCGCCTGGAACAGCAACAACCTGGACAGCAAGGTGG

GCGGCAACTACAACTACCTGTACAGGCTGTTCAGGAAGAGCAACCTGAAGCCCTTCGAGAGGGACATCAGCACCGAG

ATCTACCAGGCCGGCAGCACCCCCTGCAACGGCGTGGAGGGCTTCAACTGCTACTTCCCCCTGCAGAGCTACGGCTT

CCAGCCCACCAACGGCGTGGGCTACCAGCCCTACAGGGTGGTGGTGCTGAGCTTCGAGCTGCTGCACGCCCCCGCCA

CCGTGTGCGGCCCCAAGAAGAGCACCAACCTGGTGAAGAACAAGTGCGTGAACTTCAACTTCAACGGCCTGACCGGC

ACCGGCGTGCTGACCGAGAGCAACAAGAAGTTCCTGCCCTTCCAGCAGTTCGGCAGGGACATCGCCGACACCACCGA

CGCCGTGAGGGACCCCCAGACCCTGGAGATCCTGGACATCACCCCCTGCAGCTTCGGCGGCGTGAGCGTGATCACCC

CCGGCACCAACACCAGCAACCAGGTGGCCGTGCTGTACCAGGACGTGAACTGCACCGAGGTGCCCGTGGCCATCCAC

GCCGACCAGCTGACCCCCACCTGGAGGGTGTACAGCACCGGCAGCAACGTGTTCCAGACCAGGGCCGGCTGCCTGAT

CGGCGCCGAGCACGTGAACAACAGCTACGAGTGCGACATCCCCATCGGCGCCGGCATCTGCGCCAGCTACCAGACCC

AGACCAACAGCCCCAGGAGGGCCAGGAGCGTGGCCAGCCAGAGCATCATCGCCTACACCATGAGCCTGGGCGCCGAG

AACAGCGTGGCCTACAGCAACAACAGCATCGCCATCCCCACCAACTTCACCATCAGCGTGACCACCGAGATCCTGCC

CGTGAGCATGACCAAGACCAGCGTGGACTGCACCATGTACATCTGCGGCGACAGCACCGAGTGCAGCAACCTGCTGC

TGCAGTACGGCAGCTTCTGCACCCAGCTGAACAGGGCCCTGACCGGCATCGCCGTGGAGCAGGACAAGAACACCCAG

GAGGTGTTCGCCCAGGTGAAGCAGATCTACAAGACCCCCCCCATCAAGGACTTCGGCGGCTTCAACTTCAGCCAGAT

CCTGCCCGACCCCAGCAAGCCCAGCAAGAGGAGCTTCATCGAGGACCTGCTGTTCAACAAGGTGACCCTGGCCGACG

CCGGCTTCATCAAGCAGTACGGCGACTGCCTGGGCGACATCGCCGCCAGGGACCTGATCTGCGCCCAGAAGTTCAAC
```

-continued

```
GGCCTGACCGTGCTGCCCCCCCTGCTGACCGACGAGATGATCGCCCAGTACACCAGCGCCCTGCTGGCCGGCACCAT
CACCAGCGGCTGGACCTTCGGCGCCGGCGCCGCCCTGCAGATCCCCTTCGCCATGCAGATGGCCTACAGGTTCAACG
GCATCGGCGTGACCCAGAACGTGCTGTACGAGAACCAGAAGCTGATCGCCAACCAGTTCAACAGCGCCATCGGCAAG
ATCCAGGACAGCCTGAGCAGCACCGCCAGCGCCCTGGGCAAGCTGCAGGACGTGGTGAACCAGAACGCCCAGGCCCT
GAACACCCTGGTGAAGCAGCTGAGCAGCAACTTCGGCGCCATCAGCAGCGTGCTGAACGACATCCTGAGCAGGCTGG
ACCCCCCCGAGGCCGAGGTGCAGATCGACAGGCTGATCACCGGCAGGCTGCAGAGCCTGCAGACCTACGTGACCCAG
CAGCTGATCAGGGCCGCCGAGATCAGGGCCAGCGCCAACCTGGCCGCCACCAAGATGAGCGAGTGCGTGCTGGGCCA
GAGCAAGAGGGTGGACTTCTGCGGCAAGGGCTACCACCTGATGAGCTTCCCCCAGAGCGCCCCCCACGGCGTGGTGT
TCCTGCACGTGACCTACGTGCCCGCCCAGGAGAAGAACTTCACCACCGCCCCCGCCATCTGCCACGACGGCAAGGCC
CACTTCCCCAGGGAGGGCGTGTTCGTGAGCAACGGCACCCACTGGTTCGTGACCCAGAGGAACTTCTACGAGCCCCA
GATCATCACCACCGACAACACCTTCGTGAGCGGCAACTGCGACGTGGTGATCGGCATCGTGAACAACACCGTGTACG
ACCCCCTGCAGCCCGAGCTGGACAGCTTCAAGGAGGAGCTGGACAAGTACTTCAAGAACCACACCAGCCCCGACGTG
GACCTGGGCGACATCAGCGGCATCAACGCCAGCGTGGTGAACATCCAGAAGGAGATCGACAGGCTGAACGAGGTGGC
CAAGAACCTGAACGAGAGCCTGATCGACCTGCAGGAGCTGGGCAAGTACGAGCAGTACATCAAGTGGCCCCTGGTACA
TCTGGCTGGGCTTCATCGCCGGCCTGATCGCCATCGTGATGGTGACCATCATGCTGTGCTGCATGACCAGCTGCTGC
AGCTGCCTGAAGGGCTGCTGCAGCTGCGGCAGCTGCTGCAAGTTCGACGAGGACGACAGCGAGCCCGTGCTGAAGGG
CGTGAAGCTGCACTACACCTGATAATAGGCTCGCTTTCTTGCTGTCCAATTTCTATTAAAGGTTCCTTTGTTCCCTA
AGTCCAACTACTAAACTGGGGGATATTATGAAGGGCCTTGAGCATCTGGATTCTGCCTAATAAAAAACATTTATTTT
CATTGCAA
```

The sequence of VRN 119 (SEQ ID NO: 4) is listed below.
```
GGGAAATAAGAGAGAAAAGAAGAGTAAGAAGAAATATAAGACCCCGGCGCCACCATGTTCGTGTTCCTGGTGCTGCT
GCCCCTGGTGAGCAGCCAGTGCGTGAACCTGACCACCAGGACCCAGCTGCCCCCGCCTACACCAACAGCTTCACCA
GGGGCGTGTACTACCCCGACAAGGTGTTCAGGAGCAGCGTGCTGCACAGCACCCAGGACCTGTTCCTGCCCTTCTTC
AGCAACGTGACCTGGTTCCACGCCATCCACGTGAGCGGCACCAACGGCACCAAGAGGTTCGACAACCCCGTGCTGCC
CTTCAACGACGGCGTGTACTTCGCCAGCACCGAGAAGAGCAACATCATCAGGGGCTGGATCTTCGGCACCACCCTGG
ACAGCAAGACCCAGAGCCTGCTGATCGTGAACAACGCCACCAACGTGGTGATCAAGGTGTGCGAGTTCCAGTTCTGC
AACGACCCCTTCCTGGGCGTGTACTACCACAAGAACAACAAGAGCTGGATGGAGAGCGAGTTCAGGGTGTACAGCAG
CGCCAACAACTGCACCTTCGAGTACGTGAGCCAGCCCTTCCTGATGGACCTGGAGGGCAAGCAGGGCAACTTCAAGA
ACCTGAGGGAGTTCGTGTTCAAGAACATCGACGGCTACTTCAAGATCTACAGCAAGCACACCCCCATCAACCTGGTG
AGGGACCTGCCCCAGGGCTTCAGCGCCCTGGAGCCCCTGGTGGACCTGCCCATCGGCATCAACATCACCAGGTTCCA
GACCCTGCTGGCCCTGCACAGGAGCTACCTGACCCCCGGCGACAGCAGCAGCGGCTGGACCGCCGGCGCCGCCGCCT
ACTACGTGGGCTACCTGCAGCCCAGGACCTTCCTGCTGAAGTACAACGAGAACGGCACCATCACCGACGCCGTGGAC
TGCGCCCTGGACCCCCTGAGCGAGACCAAGTGCACCCTGAAGAGCTTCACCGTGGAGAAGGGCATCTACCAGACCAG
CAACTTCAGGGTGCAGCCCACCGAGAGCATCGTGAGGTTCCCCAACATCACCAACCTGTGCCCCTTCGGCGAGGTGT
TCAACGCCACCAGGTTCGCCAGCGTGTACGCCTGGAACAGGAAGAGGATCAGCAACTGCGTGGCCGACTACAGCGTG
CTGTACAACAGCGCCAGCTTCAGCACCTTCAAGTGCTACGGCGTGAGCCCCACCAAGCTGAACGACCTGTGCTTCAC
CAACGTGTACGCCGACAGCTTCGTGATCAGGGGCGACGAGGTGAGGCAGATCGCCCCCGGCCAGACCGGCAAGATCG
CCGACTACAACTACAAGCTGCCCGACGACTTCACCGGCTGCGTGATCGCCTGGAACAGCAACAACCTGGACAGCAAG
GTGGGCGGCAACTACAACTACCTGTACAGGCTGTTCAGGAAGAGCAACCTGAAGCCCTTCGAGAGGGACATCAGCAC
CGAGATCTACCAGGCCGGCAGCACCCCCTGCAACGGCGTGGAGGGCTTCAACTGCTACTTCCCCCTGCAGAGCTACG
GCTTCCAGCCCACCAACGGCGTGGGCTACCAGCCCTACAGGGTGGTGGTGCTGAGCTTCGAGCTGCTGCACGCCCCC
```

-continued

GCCACCGTGTGCGGCCCCAAGAAGAGCACCAACCTGGTGAAGAACAAGTGCGTGAACTTCAACTTCAACGGCCTGAC

CGGCACCGGCGTGCTGACCGAGAGCAACAAGAAGTTCCTGCCCTTCCAGCAGTTCGGCAGGGACATCGCCGACACCA

CCGACGCCGTGAGGGACCCCCAGACCCTGGAGATCCTGGACATCACCCCCTGCAGCTTCGGCGGCGTGAGCGTGATC

ACCCCCGGCACCAACACCAGCAACCAGGTGGCCGTGCTGTACCAGGACGTGAACTGCACCGAGGTGCCCGTGGCCAT

CCACGCCGACCAGCTGACCCCCACCTGGAGGGTGTACAGCACCGGCAGCAACGTGTTCCAGACCAGGGCCGGCTGCC

TGATCGGCGCCGAGCACGTGAACAACAGCTACGAGTGCGACATCCCCATCGGCGCCGGCATCTGCGCCAGCTACCAG

ACCCAGACCAACAGCCCCAGGAGGGCCAGGAGCGTGGCCAGCCAGAGCATCATCGCCTACACCATGAGCCTGGGCGC

CGAGAACAGCGTGGCCTACAGCAACAACAGCATCGCCATCCCCACCAACTTCACCATCAGCGTGACCACCGAGATCC

TGCCCGTGAGCATGACCAAGACCAGCGTGGACTGCACCATGTACATCTGCGGCGACAGCACCGAGTGCAGCAACCTG

CTGCTGCAGTACGGCAGCTTCTGCACCCAGCTGAACAGGGCCCTGACCGGCATCGCCGTGGAGCAGGACAAGAACAC

CCAGGAGGTGTTCGCCCAGGTGAAGCAGATCTACAAGACCCCCCCCATCAAGGACTTCGGCGGCTTCAACTTCAGCC

AGATCCTGCCCGACCCCAGCAAGCCCAGCAAGAGGAGCTTCATCGAGGACCTGCTGTTCAACAAGGTGACCCTGGCC

GACGCCGGCTTCATCAAGCAGTACGGCGACTGCCTGGGCGACATCGCCGCCAGGGACCTGATCTGCGCCCAGAAGTT

CAACGGCCTGACCGTGCTGCCCCCCCTGCTGACCGACGAGATGATCGCCCAGTACACCAGCGCCCTGCTGGCCGGCA

CCATCACCAGCGGCTGGACCTTCGGCGCCGGCGCCGCCCTGCAGATCCCCTTCGCCATGCAGATGGCCTACAGGTTC

AACGGCATCGGCGTGACCCAGAACGTGCTGTACGAGAACCAGAAGCTGATCGCCAACCAGTTCAACAGCGCCATCGG

CAAGATCCAGGACAGCCTGAGCAGCACCGCCAGCGCCCTGGGCAAGCTGCAGGACGTGGTGAACCAGAACGCCCAGG

CCCTGAACACCCTGGTGAAGCAGCTGAGCAGCAACTTCGGCGCCATCAGCAGCGTGCTGAACGACATCCTGAGCAGG

CTGGACCCCCCGAGGCCGAGGTGCAGATCGACAGGCTGATCACCGGCAGGCTGCAGAGCCTGCAGACCTACGTGAC

CCAGCAGCTGATCAGGGCCGCCGAGATCAGGGCCAGCGCCAACCTGGCCGCCACCAAGATGAGCGAGTGCGTGCTGG

GCCAGAGCAAGAGGGTGGACTTCTGCGGCAAGGGCTACCACCTGATGAGCTTCCCCCAGAGCGCCCCCCACGGCGTG

GTGTTCCTGCACGTGACCTACGTGCCCGCCCAGGAGAAGAACTTCACCACCGCCCCCGCCATCTGCCACGACGGCAA

GGCCCACTTCCCCAGGGAGGGCGTGTTCGTGAGCAACGGCACCCACTGGTTCGTGACCCAGAGGAACTTCTACGAGC

CCCAGATCATCACCACCGACAACACCTTCGTGAGCGGCAACTGCGACGTGGTGATCGGCATCGTGAACAACACCGTG

TACGACCCCCTGCAGCCCGAGCTGGACAGCTTCAAGGAGGAGCTGGACAAGTACTTCAAGAACCACACCAGCCCCGA

CGTGGACCTGGGCGACATCAGCGGCATCAACGCCAGCGTGGTGAACATCCAGAAGGAGATCGACAGGCTGAACGAGG

TGGCCAAGAACCTGAACGAGAGCCTGATCGACCTGCAGGAGCTGGGCAAGTACGAGCAGTACATCAAGTGGCCCTGG

TACATCTGGCTGGGCTTCATCGCCGGCCTGATCGCCATCGTGATGGTGACCATCATGCTGTGCTGCATGACCAGCTG

CTGCAGCTGCCTGAAGGGCTGCTGCAGCTGCGGCAGCTGCTGCAAGTTCGACGAGGACGACAGCGAGCCCGTGCTGA

-continued

```
AGGGCGTGAAGCTGCACTACACCTGATAATAGCTAGTGACTGACTAGGATCTGGTTACCACTAAACCAGCCTCAAGA

ACACCCGAATGGAGTCTCTAAGCTACATAATACCAACTTACACTTACAAAATGTTGTCCCCCAAAATGTAGCCATTC

GTATCTGCTCCTAATAAAAAGAAAGTTTCTTCACAT
```

The LNPs were prepared and analyzed following the procedures of Examples 9 and 10, with the lipid compositions of KC3OA/DSPC/DPPS/Chol/PEG-DMG at the molar ratio of 48/6.5/3.5/40.5/1.5, mRNA N/P=5.25 (KC3OA), and ALC-0315/DSPC/Chol/ALC-0159 at the molar ratio of 46.3/9.4/42.7/1.5, mRNA N/P=6.2 (ALC-0315). The analytical data are in Table 73 (for abbreviations, see Example 47, Table 56).

TABLE 73

Analysis of LNP formulations of Example 55 The KC3OA formulations

| | | post C/F | | post F/T | | post C/F | | post FT | |
|---|---|---|---|---|---|---|---|---|---|
| ICL | mRNA | Z-Ave | PDI | Z-Ave | PDI | % EE | stdev | % EE | stdev |
| ALC-0315 | VRN029 | 84.21 | 0.12 | 80.88 | 0.10 | 79.2 | 2.5 | 79.8 | 2.1 |
| KC3-OA | VRN029 | 99.84 | 0.06 | 98.44 | 0.09 | 89.8 | 5.6 | 90.6 | 4.9 |
| KC3-OA | VRN118 | 95.48 | 0.09 | 97.38 | 0.09 | 90.5 | 7.0 | 91.5 | 3.6 |
| KC3-OA | VRN119 | 93.94 | 0.08 | 95.73 | 0.10 | 90.8 | 7.8 | 91.9 | 5.6 |

The LNPs used in this study were <100 nm in diameter and displayed good mRNA entrapment 80-91% and showed little change in these characteristics after a freeze-thaw cycle. Immunogenicity of these LNPs was studied in Balb/C mice as in Example 35, except the does was 0.3 μg mRNA. At Day 20 (prime) and Day 35 (boost) post injection, serum was collected and evaluated for anti-spike titers and the data presented in FIG. 44.

ALC-0315 based formulation at SD20 (3 weeks after initial immunization), using an additional two different SARS-CoV2 mRNA sequences (VRN118 and VRN119). Taken together, these data suggests that the enhanced immunogenicity observed from KC3-OA/PS based LNPs over ALC-0315 based formulation is due to the lipid carrier, not the mRNA.

TABLE 74

Log-transformed reciprocal serum titers of anti-SARS-COV-2 spike protein antibodies in mice treated with LNPs containing various spike-coding mRNAs. The log titers are shown as mean ± standard deviation (median).

| Composition | Day 20 | Day 35 |
|---|---|---|
| ALC-0315, ALC-0159, VRN029 mRNA | 2.39 ± 0.12 (2.44) | 5.16 ± 0.15 (5.15) |
| KC3-OA, 5 DPPS, 1.5 PEG-DMG, VRN029 mRNA | 3.85 ± 0.33 (3.79) | 5.88 ± 0.33 (5.70) |
| KC3-OA, 5 DPPS, 1.5 PEG-DMG, VRN118 mRNA | 4.13 ± 0.13 (4.15) | 5.82 ± 0.05 (5.81) |
| KC3-OA, 5 DPPS, 1.5 PEG-DMG, VRN119 mRNA | 4.10 ± 0.28 (4.07) | 5.74 ± 0.13 (5.80) |

We found that mRNA formulated in the same LNP formulation (KC3OA/DSPC/DPPS/Chol/PEG-DMG 48.5/5/5/40.5/1.5 mol %) at the same N/P=5.25 ratio, both mRNA VRN118 and VRN119 resulted in superior titers to VRN029 (~1.5-fold higher on average), while the KC3OA/5% PS formulation of VRN029 was ~35-fold higher than the ALC-0315 formulation.

Example 32 shows that KC3-OA PS targeted LNPs have a larger mCherry signal than an ALC-0315 formulation in human monocyte derived dendritic cells in vitro, where both formulations contained the same mRNA. In Example 45, a similarly superior mCherry signal was observed in MutuDC1940 murine DC cells in vitro over an ALC-0315 formulation using the same mRNA. Examples 54 and 55 show that PS-targeted LNPs have an advantage over ALC-0315-based LNPs, both using a SARS-CoV2 mRNA sequence (VRN029) for producing anti-spike titers in mice. In this example, it was determined that DPPS-targeted KC3-OA LNPs also have superior immunogenicity over the Example 56. Impact of LNP Formulation and Dose on Immunogenicity of SARS-COV-2 Spike mRNA in Mice A goal of this study was to compare the immunogenicity of the LNP lipid formulations present in Comirnaty® and Spikevax® known mRNA-LNP vaccines to KC3OA/5% DPPS at 1, 0.3 and 0.1 μg mRNA VRN029 doses in mice. The compositions for formulations corresponding to the published information for Comirnaty®, Spikevax® were prepared and their lipid composition shown below in Table 75. Also shown is the composition for KC3OA/5% DPPS. All formulations were made using a NanoAssemblr as described earlier (Example 35) at N/P=6.25, 5.0 and 5.25 respectively and purified into 15 mM Tris, 20% sucrose, pH 7.4 for storage at −80 C.

TABLE 75

Lipid composition of formulations used in Example 56 and FIG. 45A

| LNP # | ICL | ICL mol % | Targeting PtdSer | mol % | PC | mol % | Chol, mol % | PEG-lipid | PEG-lipid, mol % |
|---|---|---|---|---|---|---|---|---|---|
| 1 | ALC-0315 | 46.3 | none | 0 | DSPC | 9.4 | 42.7 | ALC-0159 | 1.5 |
| 2 | SM-102 | 50 | none | 0 | DSPC | 10 | 38.5 | PEG-DMG | 1.5 |
| 3 | KC3-OA | 48 | DPPS-NH4 | 5 | DSPC | 5 | 40.5 | PEG-DMG | 1.5 |

The formulation biophysical characteristics are shown below in Table 76. For abbreviations, see Example 47, Table 56)

TABLE 76

Characterization of ALC-0315, SM102 and KC3OA/5% DPPS LNP formulations used in Example 56 and FIG. 45A.

| LNP | Post C/F Z-Ave | Post C/F PDI | Post F/T Z-Ave | Post F/T PDI | Zeta potential pH 5 | Zeta potential pH 7 | Post C/F % EE | Post C/F stdev | Post F/T % EE | Post F/T stdev |
|---|---|---|---|---|---|---|---|---|---|---|
| ALC-0135 | 84.34 | 0.09 | 83.75 | 0.11 | 7.98 | −3.63 | 87.5 | 3.7 | 87.1 | 3.1 |
| SM102 | 91.92 | 0.04 | 92.20 | 0.07 | 14.64 | −0.41 | 90.9 | 7.7 | 90.3 | 4.6 |
| KC3OA/5% DPPS | 100.60 | 0.13 | 98.22 | 0.12 | 13.92 | −1.74 | 93.2 | 9.2 | 93.6 | 2.3 |

The formulations were freeze-thawed to simulate conditions of sample preparation that were performed prior to dosing the animals. After freezing and thawing % E.E size changed less than 1% and size less than 2.5%. The LNPs exhibited the expected change in zeta potential when they were suspended in pH 5.0 (10 mM MES, 15 mM NaCl) or pH 7.0 (10 mM HEPES, 15 mM NaCl) buffers (they went from cationic to neutral surface charge). Balb/C mice were dosed with an injection of 1 µg, 0.3 µg or 0.1 µg LNP formulated mRNA in 50 µL volume via IM injection into a hind limb and again at 3 weeks, and the serum antibody titers were measured at Day 20 and as described in Example 35 (FIG. 45A, Table 77).

An antibody titer dose dependence was observed for all formulations. While ALC-0315 and SM-102 had similar titers at the higher doses, a non-linear dependence was found for ALC-0315 formulation, which was less productive at 0.1 µg dose compared to SM-102. In contrast, we found that KC3OA/5% DPPS formulation produced higher titers than comparators ALC-0135 and SM-102 at all doses tested, (2.7-fold and 3.7-fold at 1 µg and 4.1-fold and 3.1-fold at 0.3 µg dose respectively) and the difference strongly increased at the lower dose, (0.1 µg, 80-fold and 6.1-fold higher respectively, P=0.009 by Mann-Whitney U test). Not being bound by a theory, we hypothesize that this strong increase in immunogenicity is most likely a result of the increased specificity of LNP uptake into dendritic cells afforded to this formulation by inclusion of DPPS.

TABLE 77

Log-transformed reciprocal serum titers of anti-SARS-COV-2 spike protein antibodies in mice treated with ALC-0315, SM-102 and KC3OA/5% DPPS LNPs at three spike mRNA dose levels at Day 0 (prime) and Day 21 (boost); bleed time Day 20 (prime) and Day 35 (prime-boost). The log titers are shown as mean ± standard deviation (median).

| Formulation | Dose (µg/mouse) | Day 20 | Day 35 |
|---|---|---|---|
| ALC-0315 | 1 | 4.14 ± 0.20 (4.18) | 5.99 ± 0.21 (5.93) |
| ALC-0315 | 0.3 | 3.13 ± 0.64 (3.32) | 5.40 ± 0.30 (5.30) |
| ALC-0315 | 0.1 | 1.72 ± 0.46 (1.72) | 3.85 ± 0.44 (3.98) |
| SM102 | 1 | 3.98 ± 0.54 (4.16) | 5.85 ± 0.20 (5.78) |
| SM102 | 0.3 | 3.62 ± 0.58 (3.85) | 5.52 ± 0.57 (5.61) |
| SM102 | 0.1 | 2.45 ± 0.82 (2.43) | 4.96 ± 0.40 (5.15) |
| KC3OA/5 DPPS | 1 | 4.30 ± 0.22 (4.25) | 6.42 ± 0.11 (6.41) |
| KC3OA/5 DPPS | 0.3 | 3.90 ± 0.36 (3.78) | 6.01 ± 0.23 (6.03) |
| KC3OA/5 DPPS | 0.1 | 2.96 ± 0.61 (3.03) | 5.75 ± 0.10 (5.73) |

In addition, the dose dependence of the anti-spike antibody response elicited by a SARS-COV-2 spike mRNA formulated in KC3-OA LNPs containing varying amounts of PEG-DMG was determined. The formulations containing KC3-OA/DPPS/DSPC/Chol/PEG-DMG at the molar ratio 48/5/5/(42-X)/X, X=0.5, 1.0, 1.5 were prepared according to Example 9. The LNP analytical data are Table 78, and the immunogenicity results are in Table 79 and FIG. 45B.

TABLE 78

The biophysical characteristics of KC3-OA formulation used in Example 56, FIG. 45B.

| ICL | DPPS, mol % | PEG-DMG, mol % | Post filter | | Zeta potential | | % E.E Post Filter | stdev |
|---|---|---|---|---|---|---|---|---|
| | | | Z-Ave | PDI | ph 5 | ph 7 | | |
| KC3OA | 5 | 1.5 | 98.2 | 0.12 | 7.98 | −3.63 | 93.2 | 9.2 |
| KC3OA | 5 | 1.0 | 107.7 | 0.09 | 14.64 | −0.41 | 93.6 | 11.6 |
| KC3OA | 5 | 0.5 | 130.6 | 0.08 | 13.92 | −1.74 | 94.7 | 11.2 |

TABLE 79

Log-transformed reciprocal serum titers of anti-SARS-COV-2 spike protein antibodies in mice treated with KC3OA/5% DPPS LNPs with different amount of PEG-DMG at three spike mRNA dose levels at Day 0 (prime) and Day 21 (boost); bleed time Day 20 (prime) and Day 35 (prime-boost). The log titers are shown as mean ± standard deviation (median).

| Formulation | Dose (µg/mouse) | Log titer D20 | Log titer D35 |
|---|---|---|---|
| KC3-OA, 1.5 mol % PEG-DMG | 1 | 4.30 ± 0.22 (4.25) | 6.42 ± 0.11 (6.41) |
| KC3-OA, 1.5 mol % PEG-DMG | 0.3 | 3.90 ± 0.36 (3.78) | 6.01 ± 0.23 (6.03) |
| KC3-OA, 1.5 mol % PEG-DMG | 0.1 | 2.96 ± 0.61 (3.03) | 5.75 ± 0.10 (5.73) |
| KC3-OA, 1.0 mol % PEG-DMG | 1 | 4.28 ± 0.24 (4.36) | 6.57 ± 0.24 (6.50) |
| KC3-OA, 1.0 mol % PEG-DMG | 0.3 | 3.91 ± 0.48 (4.15) | 6.14 ± 0.41 (6.04) |
| KC3-OA, 1.0 mol % PEG-DMG | 0.1 | 2.63 ± 0.98 (3.06) | 5.31 ± 0.46 (5.40) |
| KC3-OA, 0.5 mol % PEG-DMG | 1 | 4.25 ± 0.32 (4.19) | 6.35 ± 0.17 (6.26) |
| KC3-OA, 0.5 mol % PEG-DMG | 0.3 | 3.74 ± 0.30 (3.59) | 6.01 ± 0.23 (6.02) |
| KC3-OA, 0.5 mol % PEG-DMG | 0.1 | 3.20 ± 0.69 (3.41) | 5.72 ± 0.04 (5.73) |

In the range of 0.5-1.5 mol % PEG-DMG the antibody titers in each dose group were similar.

Example 57. Impact of PS-Targeting on LNP Formulation Immunogenicity of SARS-CoV2 Spike mRNA in Mice at Low Doses The data of Example 56 (FIG. 45A) suggested that the immunogenicity advantage of KC3-OA formulations was more prominent at the lower administered doses of LNP-formulated mRNA. We examined if active targeting to DC afforded by inclusion of PS may be more specific at lower doses because there is a limited amount of target receptors responsible for LNP uptake in vivo and at higher doses the target receptors may be saturated. This leads to a greater proportion of the dose going to off-target tissues and being ineffective. To LNPs prepared using ALS-0135 ICL, KC3-OA ICL, and KC3-OA ICL with 5 mol % DPPS as a targeting agent, encapsulating SARS-COV-2 spike mRNA VRN029 were prepared according to Example 9 with the following lipid compositions: ALC-0315/DSPC/Chol/ALC-0159 molar ratio 46.3/9.4/42.7/1.5 (ALC-0315); KC3-OA/DPPS-NH$_4$/DSPC/Chol/PEG-DMG molar ratio 48/5/5/40.5/1.5 (Targeted KC3-OA), and KC3-OA/DSPC/Chol/PEG-DMG molar ratio 48/10/40.5/1.5(KC3-OA). mRNA was added at N/P 5.25. The formulations were characterized by particle size and encapsulation efficiency (Table 80), and administered to mice at the mRNA dose of 0.1 µg at Day 0 and Day 21 as described in Example 56. The blood was sampled at Day 20 and Day 35 and the anti-spike antibody titers were determined as in Example 35. The results (FIGS. 46A, 46B) indicated that at the low dose of 0.1 g mRNA the effect of PS targeting was the highest, leading to 12.7-fold (Day 20, P=0.028 by Mann-Whitney U_test) and 7-fold (Day 35, P=0.009 by Mann-Whitney U test) increase in the antibody titer compared to the matched formulation without PS targeting. A published comparator LNP formulation (ALC-0315) produced a detectable titer signal in only one of the five mice in that group.

TABLE 80

Characterization of ALC-0315, KC3OA/5% DPPS, and non-targeted LNP formulations used in Example 57

| LNP | Post filter | | Post F/T | | Zeta potential | | % E.E | | % E.E | |
|---|---|---|---|---|---|---|---|---|---|---|
| | Z-Ave | PDI | Z-Ave | PDI | ph 5 | ph 7 | 0.2 um | stdev | post F/T | stdev |
| ALC-0135 | 84.34 | 0.09 | 83.75 | 0.11 | 7.98 | −3.63 | 87.5 | 3.7 | 87.1 | 3.1 |
| KC3OA/5 % DPPS | 100.60 | 0.13 | 98.22 | 0.12 | 13.92 | −1.74 | 93.2 | 9.2 | 93.6 | 2.3 |
| KC3-OA | 97.74 | 0.06 | 97.12 | 0.07 | 18.4 | 0.11 | 93.1 | 7.0 | 93.9 | 6.5 |

Example 58. Comparing the Shorter Alkyl-Chain PEG-DLG and PEG-DLPE in LNP Formulations Composed of the Ionizable Lipids ALC-0315, SM-102 and AKG UO-1

Examples 52 and 53 demonstrated that di-C12-PEG-lipids PEG-DLG and PEG-DLPE were viable options for the stabilizing PEG-lipid PEG-DMG in KC3-OA based LNP formulations. The goal of this study was to prepare and characterize a series of PEG-DLG or PEG-DLPE-containing LNPs based on other ionizable cationic lipids. other ionizable lipids. Branched ester containing ICLs family (ALC-0315 and SM-102) and a dialkyl-ionizable cationic lipid containing olefins in the lipid tails separated by two methylene groups (AKG-UO-1) were used. ALC-0315, SM-102 and KC3-OA/PS LNPs were prepared as described in Example 9, with N/P ratios of 6.2, 5.0 and 5.25 respectively, using mCherry encoded mRNA with final buffer exchange into PBS, pH 7.4. The LNPs were characterized for particle size, mRNA encapsulation and surface charge as described in Example 10. The LNP lipid formulation and characterization data is shown in Table 81. (For abbreviations see Example 47, Table 56).

TABLE 81

Lipid composition and characterization of LNPs utilizing either PEG-DLG or PEG-DLPE.

| Formulation, lipids (molar ratios) | Post C/F Z-Ave | PDI | zeta pH 5 | pH 7 | % E.E ± stdev |
|---|---|---|---|---|---|
| ALC-0315/DSPC/Chol/PEG-DLG (46.5/9.4/42.7/1.5) | 69.11 | 0.10 | 6.24 | −1.93 | 86.4 ± 11.1 |
| ALC-0315/DSPC/Chol/PEG-DLPE (46.5/9.4/42.7/1.5) | 70.12 | 0.13 | 4.17 | −4.78 | 83.9 ± 8.2 |
| SM-102/DSPC/Chol/PEG-DLG (50/10/38.5/1.5) | 69.80 | 0.02 | 9.28 | 0 | 89.3 ± 7.4 |
| SM-102/DSPC/Chol/PEG-DLPE (50/10/38.5/1.5) | 82.97 | 0.18 | 8.92 | −2.18 | 89.4 ± 5.6 |
| AKG-UO-1/DSPC/DPPS/Chol/PEG-DLG (48/5/5/40.5/1.5) | 80.08 | 0.08 | 8.52 | −1.19 | 91.3± 2.8 |
| AKG-UO-1/DSPC/DPPS/Chol/PEG-DLPE (48/5/5/40.5/1.5) | 100.70 | 0.13 | 7.28 | −2.03 | 90.9 ± 7.9 |

The LNP formulations shown in Table 81 displayed small sizes with goo size homogeneity (PDI<0.2) and mRNA trapping efficiencies. The ALC-0315, SM-102 and AKG UO-1 formulations described in Table 81 have similar biophysical characteristics to similar formulations which instead use PEG-DMG at the same mol %, displayed in other Examples (see Example 24, Table 20 for ALC-0315 and SM-102 comparisons and Example 15, Table 9 for UO-1 comparison). Thus, PEG-DLG and PEG-DLPE are viable substitutes for to PEG-DMG as the stabilizing PEG-lipid for use in LNP formulations based on various ICL structures.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

All publications, patents and patent applications referenced in this specification are incorporated herein by reference in their entirety for all purposes to the same extent as if each individual publication, patent or patent application were specifically indicated to be so incorporated by reference.

What is claimed is:

1. A nucleic acid lipid nanoparticle (LNP) composition comprising:
   a. a nucleic acid;
   b. an ionizable cationic lipid at a N/P ratio of 3 to 8 relative to the nucleic acid in a total amount of 40-65 mol % of the total lipid content of the LNP composition;
   c. a sterol in a total amount of 25-45 mol % of the total lipid content of the LNP composition;
   d. one or more phospholipids in a total amount of phospholipids of 5-25 mol % of the total lipid content of the LNP composition, and comprising a phosphatidyl-L-serine lipid in a total amount of 2.5-10 mol % of the total lipid content of the LNP composition; and
   e. a conjugated lipid in a total amount of 0.5-2.5 mol % of the total lipid content of the LNP composition.

2. The composition of claim 1, wherein the sterol is cholesterol.

3. The composition of claim 2, wherein the one or more phospholipids comprise phospholipids having mismatched acyl chain lengths.

4. The composition of claim 3, wherein the phosphatidyl-L-serine lipid is dipalmitoylphosphatidyl-L-serine ((L-serine)DPPS).

5. The composition of claim 4, wherein the one or more phospholipids comprise a phospholipid selected from the group consisting of: distearoylphosphatidylcholine (DSPC) and hydrogenated soy phosphatidylcholine (HSPC).

6. The composition of claim 5, wherein the one or more phospholipids comprise distearoylphosphatidylcholine (DSPC) and the phosphatidyl-L-serine.

7. The composition of claim 3, wherein the ionizable cationic lipid is 3-((S)-2,2-di((Z)-octadec-9-en-1-yl)-1,3-dioxolan-4-yl)-N,N-dimethylpropan-1-amine (KC3-OA).

8. The composition of claim 6, wherein the ionizable cationic lipid is 3-((S)-2,2-di((Z)-octadec-9-en-1-yl)-1,3-dioxolan-4-yl)-N,N-dimethylpropan-1-amine (KC3-OA).

9. The composition of claim 8, wherein the one or more phospholipids consist of distearoylphosphatidylcholine (DSPC) and dipalmitoylphosphatidyl-L-serine ((L-serine)DPPS).

10. The composition of claim 1, wherein the conjugated lipid is a PEG-containing conjugated lipid, and wherein the PEG-containing conjugated lipid is selected from the group consisting of: PEG(2000)-dimyristoylglycerol (PEG-DMG), 1,2-dilauroyl-sn-glycero-3-phosphoethanolamine-N-[methoxy(polyethylene glycol)-2000] (PEG-DLPE), and PEG(2000)-dilauroylglycerol (PEG-DLG).

11. The composition of claim 2, wherein:
   a. the nucleic acid is mRNA;
   b. the one or more phospholipids comprise dipalmitoylphosphatidyl-L-serine ((L-serine)DPPS) and one or more phospholipids selected from the group consisting of: distearoylphosphatidylcholine (DSPC), and hydrogenated soy phosphatidylcholine (HSPC); and
   c. the conjugated lipid comprises a polyethylene glycol (PEG).

12. The composition of claim 11, wherein the conjugated lipid is PEG(2000)-dimyristoylglycerol (PEG-DMG).

13. The composition of claim 12, wherein the ionizable cationic lipid is 3-((S)-2,2-di((Z)-octadec-9-en-1-yl)-1,3-dioxolan-4-yl)-N,N-dimethylpropan-1-amine (KC3-OA).

14. The composition of claim 13, wherein the one or more phospholipids consist of distearoylphosphatidylcholine (DSPC) and dipalmitoylphosphatidyl-L-serine ((L-serine) DPPS).

15. The composition of claim 4, wherein the dipalmitoylphosphatidyl-L-serine ((L-serine)DPPS) is an ammonium salt of (L-Serine)DPPS.

16. The composition of claim 1, wherein
   a. the nucleic acid is mRNA;
   b. the sterol is a cholesterol sterol in a total amount of 25-45 mol % of the total lipid content of the LNP composition;
   c. the ionizable cationic lipid is at a N/P ratio of 3 to 8 relative to the nucleic acid in a total amount of 40-65 mol % of the total lipid content of the LNP composition;
   d. the one or more phospholipids is in a total amount of phospholipids of 5-25 mol % of the total lipid content of the LNP composition, the one or more phospholipids consisting of:
      i. dipalmitoylphosphatidyl-L-serine ((L-serine)DPPS) lipid in a total amount of 2.5-10 mol % of the total lipid content of the LNP composition; and
      ii. a distearoylphosphatidylcholine (DSPC) phospholipid in a total amount of 5-mol % of the total lipid content of the LNP composition; and
   e. the conjugated lipid is a PEG-containing conjugated lipid in a total amount of 0.5-2.5 mol % of the total lipid content of the LNP composition.

17. The composition of claim 16, wherein the PEG-containing conjugated lipid is selected from the group consisting of: PEG(2000)-dimyristoylglycerol (PEG-DMG), 1,2-dilauroyl-sn-glycero-3-phosphoethanolamine-N-[methoxy(polyethylene glycol)-2000](PEG-DLPE), and PEG(2000)-dilauroylglycerol (PEG-DLG).

18. A nucleic acid lipid nanoparticle (LNP) human vaccine composition comprising:
   a. a nucleic acid;
   b. an ionizable cationic lipid at a N/P ratio of 3 to 8 relative to the nucleic acid in a total amount of 40-65 mol % of the total lipid content of the LNP composition;

c. a sterol in a total amount of 25-45 mol % of the total lipid content of the LNP composition; and
d. one or more phospholipids in a total amount of phospholipids of 5-25 mol % of the total lipid content of the LNP composition, and comprising a phosphatidylglycerol (PG) in a total amount of 1.0-10 mol % of the total lipid content of the LNP composition; and
e. a conjugated lipid in a total amount of 0.5-2.5 mol % of the total lipid content of the LNP composition.

19. A nucleic acid lipid nanoparticle (LNP) composition comprising an ionizable cationic lipid in a total amount of 40-65 mol % of the total lipid content of the LNP composition, wherein the ionizable cationic lipid is selected from the group consisting of: KC3-PA, KC3-C17 (8:1), and KC3-C15 (C8:1), KC3-OA, and KC3-01 the lipid nanoparticle (LNP) composition comprises:
a. the nucleic acid;
b. the ionizable cationic lipid at a N/P ratio of 5 to 6 relative to the nucleic acid in a total amount of 45-55 mol % of the total lipid content of the LNP composition;
c. cholesterol in a total amount of 30-40 mol % of the total lipid content of the LNP composition;
d. the one or more phospholipids in a total amount of phospholipids of 10-20 mol % of the total lipid content of the LNP composition, the one or more phospholipids consisting of:
  i. dipalmitoylphosphatidyl-L-serine ((L-serine)DPPS) lipid in a total amount of 2.5-7.5 mol % of the total lipid content of the LNP composition; and

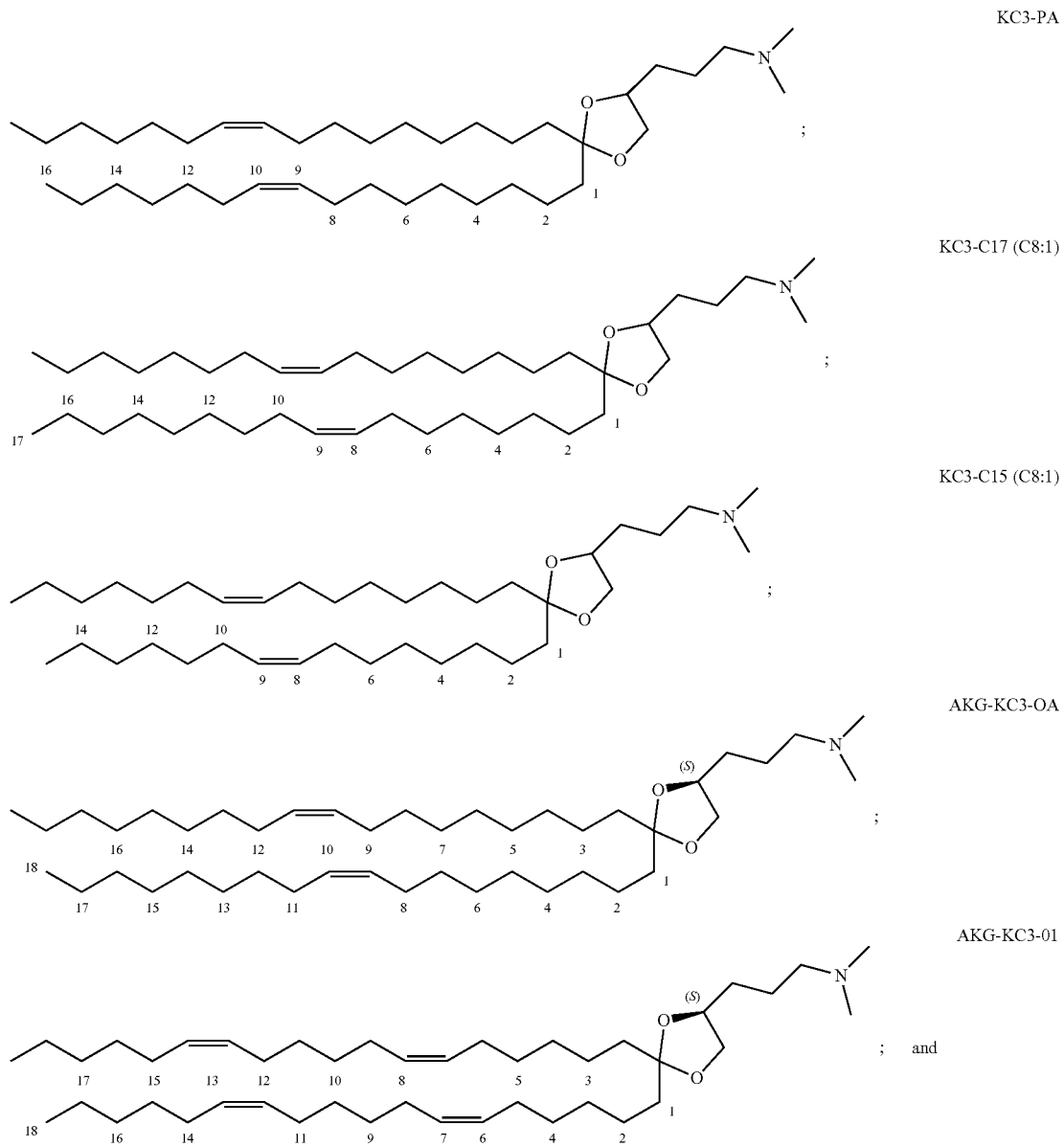

20. The composition of claim 1, wherein the ionizable cationic lipid is 3-((S)-2,2-di((Z)-octadec-9-en-1-yl)-1,3-dioxolan-4-yl)-N,N-dimethylpropan-1-amine (KC3-OA); and ii. a distearoylphosphatidylcholine (DSPC) phospholipid in a total amount of 5-mol % of the total lipid content of the LNP composition; and e. the conjugated lipid in a total amount of 0.5-2.5 mol % of the total lipid content of the LNP composition.

21. The composition of claim 20, wherein
a. the nucleic acid is mRNA; and
b. the conjugated lipid is a PEG-containing conjugated lipid, and wherein the PEG-containing conjugated lipid is selected from the group consisting of: PEG(2000)-dimyristoylglycerol (PEG-DMG), and PEG(2000)-dilauroylglycerol (PEG-DLG).

22. The composition of claim 21, wherein the conjugated lipid is PEG(2000)-dilauroylglycerol (PEG-DLG).

23. The composition of claim 21, wherein the conjugated lipid is PEG(2000)-dimyristoylglycerol (PEG-DMG).

24. A nucleic acid lipid nanoparticle (LNP) composition comprising a nucleic acid, a KC3 ionizable cationic lipid and one or more targeting phospholipids selected from the group consisting of: a phosphatidyl-L-serine lipid and a phosphatidylglycerol lipid, wherein the KC-3 ionizable cationic lipid has the chemical structure:

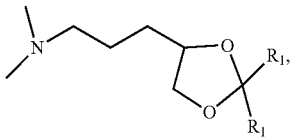

and $R_1$ is alkyl group of $C_{15}$-$C_{19}$ containing one or two olefins.

25. The composition of claim 24, wherein the nucleic acid is mRNA encoding a coronavirus or portion thereof.

26. The composition of claim 19, wherein the ionizable cationic lipid is KC3-OA.

27. The composition of claim 1, wherein the LNP composition consists of:
a. KC3-OA ionizable cationic lipid;
b. an antigen generating mRNA nucleic acid;
c. cholesterol;
d. one or more phospholipids comprising one or more targeting phospholipids selected from the group consisting of: a phosphatidyl-L-serine lipid, and a phosphatidylglycerol lipid; and
e. a conjugated PEG lipid.

28. The composition of claim 27, wherein the composition is a LNP vaccine composition further comprising the LNP composition in an aqueous buffer.

* * * * *

UNITED STATES PATENT AND TRADEMARK OFFICE
CERTIFICATE OF CORRECTION

PATENT NO. : 12,064,479 B2
APPLICATION NO. : 18/324097
DATED : August 20, 2024
INVENTOR(S) : Daryl C. Drummond et al.

It is certified that error appears in the above-identified patent and that said Letters Patent is hereby corrected as shown below:

On the Title Page

Column 2, bottom of page: Please replace "28 Claims" with -- 27 Claims --

In the Claims

In Claim 16, Column 240, Line 49: Replace "5-mol%" with -- 5-25 mol% --

In Claim 20, Column 242, Line 66: Replace "5-mol%" with -- 5-15 mol% --

Column 244, Line 3-4: Claim 25 (cancelled)

Column 244, Line 6: Please renumber Claim 26 as Claim 25

Column 244, Line 8: Please renumber Claim 27 as Claim 26

Signed and Sealed this
Twelfth Day of November, 2024

Katherine Kelly Vidal
*Director of the United States Patent and Trademark Office*

SEQUENCE LISTING

```
Sequence total quantity: 4
SEQ ID NO: 1            moltype = RNA   length = 720
FEATURE                 Location/Qualifiers
source                  1..720
                        mol_type = other RNA
                        organism = Synthetic construct
SEQUENCE: 1
atggtgagca agggcgagga ggacaacatg gccatcatca aggagttcat gcggttcaag  60
gtgcacatgg agggcagcgt gaacggccac gagttcgaga tcgagggcga gggcgagggc 120
cggccctacg agggcaccca gaccgccaag ctgaaggtga ccaagggcgg ccccctgccc 180
ttcgcctggg acatcctgag cccccagttc atgtacggca gcaaggccta cgtgaagcac 240
cccgccgaca tccccgacta cctgaagctg agcttccccg agggcttcaa gtgggagcgg 300
gtgatgaact tcgaggacgg cggcgtggtg accgtgaccc aggacagcag cctgcaggac 360
ggcgagttca tctacaaggt gaagctgcgg ggcaccaact tccccagcga cggccccgtg 420
atgcagaaga gaccatggg ctgggaggcc agcagcgagc ggatgtaccc cgaggacggc 480
gccctgaagg gcgagatcaa gcagcggctg aagctgaagg acggcggcca ctacgacgcc 540
gaggtgaaga ccacctacaa ggccaagaag cccgtgcagc tgcccggcgc ctacaacgtg 600
aacatcaagc tggacatcac cagccacaac gaggactaca ccatcgtgga gcagtacgag 660
cgggccgagg gccggcacag caccggcggc atggacgagc tgtacaagag cggcaactga 720

SEQ ID NO: 2            moltype = RNA   length = 4319
FEATURE                 Location/Qualifiers
source                  1..4319
                        mol_type = other RNA
                        organism = Synthetic construct
SEQUENCE: 2
gggaataaac tagtattctt ctggtcccca cagactcaga gagaacccgc caccatgttc  60
gtgttcctgg tgctgctgcc tctggtgtcc agccagtgtg tgaacctgac caccagaaca 120
cagctgcctc cagcctacac caacagcttt accagaggcg tgtactaccc cgacaaggtg 180
ttcagatcca gcgtgctgca ctctacccag gacctgttcc tgcctttctt cagcaacgtg 240
acctggttcc acgccatcca cgtgtccggc accaatggca ccaagagatt cgacaacccc 300
gtgctgccct tcaacgacgg ggtgtacttt gccagcaccg agaagtccaa catcatcaga 360
ggctggatct tcggcaccac actggacagc aagacccaga gcctgctgat cgtgaacaac 420
gccaccaacg tggtcatcaa agtgtgcgag ttccagttct gcaacgaccc cttcctgggc 480
gtctactacc acaagaacaa caagagctgg atggaaagcg agttccgggt gtacagcagc 540
gccaacaact gcaccttcga gtacgtgtcc cagcctttcc tgatggacct ggaaggcaag 600
cagggcaact tcaagaacct gcgcgagttc gtgtttaaga acatcgacgg ctacttcaag 660
atctacagca agcacacccc tatcaacctc gtgcgggatc tgcctcaggg cttctctgct 720
ctggaacccc tggtggatct gcccatcggc atcaacatca cccggtttca gactactgtg 780
gccctgcaca gaagctacct gacacctggc gatagcagca gctggtgc 840
gccgcttact atgtgggcta cctgcagcct agaaccttcc tgctgaagta caacgagaac 900
ggcaccatca ccgacgccgt ggattgtgct ctggatcctc tgagcgagac aaagtgcacc 960
ctgaagtcct tcaccgtgga aaagggcatc taccagacca gcaacttccg ggtgcagccc 1020
accgaatcca tcgtgcggtt ccccaatatc accaatctgt gccccttcgg cgaggtgttc 1080
aatgccacca gattcgcctc tgtgtacgcc tggaaccgga gcggatcag caattgcgtg 1140
gccgactact ccgtgctgta caactccgcc agcttcagca ccttcaagtg ctacggcgtg 1200
tcccctacca gctgaacga cctgtgcttc acaaacgtgt acgccgacag cttcgtgatc 1260
cggggagatg aagtgcggca gattgcccct ggacagacga gcaagatgc cgactacaac 1320
tacaagctgc ccgacgactt caccggctgt gtgattgcct ggaacagcaa caacctggac 1380
tccaaagtcg gcggcaacta caattacctg taccggctgt tccggaagtc caatctgaag 1440
cccttcgagc gggacatctc caccgagatc tatcaggccg gcagcacccc ttgtaacggc 1500
gtggaaggct tcaactgcta cttcccactg cagtcctacg gctttcagcc cacaaatggc 1560
gtgggctatc agccctacag agtggtggtg ctgagcttcg aactgctgca tgccccctgcc 1620
acagtgtgcg ccctaagaa aagcaccaat ctcgtgaaga caaatgcgt gaacttcaac 1680
ttcaacggcc tgaccggcac cggcgtgctg acagagagca caagaagtt cctgccattc 1740
cagcagtttg gccgggatat cgccgatacc acagacgccg ttagagatcc ccagacactg 1800
gaaatcctgg acatcacccc ttgcagcttc ggcggagtgc tgtgatcac ccctggcacc 1860
aacaccagca tcaggtggc agtgctgtac caggacgtga actgtaccga agtgcccgtg 1920
gccattcacg ccgatcagct gacacctaca tggcggggtgt actccaccgg cagcaatgtg 1980
tttcagacca gagccggctg tctgatcgga gccgagcacg tgaacaatag ctacgagtgc 2040
gacatcccca tcggcgctgg aatctgcgcc agctaccaga cacagacaaa cagccctcgg 2100
agagccagaa gcgtggccag ccagagcatc attgcctaca caatgtctct gggcgccgag 2160
aacagcgtgg cctactccaa caactctatc gctatcccca ccaacttcac catcagcgtg 2220
accacagaga tcctgcctgt gtccatgacc aagaccagct ggactgcac catgtacatc 2280
tgcggcgatt ccaccgagtg ctccaacctg ctgctgcagt acggcagctt ctgcacccag 2340
ctgaatagag ccctgacagg gatcgccgtg gaacaggaca gaacaccca agaggtgttc 2400
gcccaagtga gcagatcta caagacccct cctatcaagg acttcggcgg cttcaatttc 2460
agccagattc tgcccgatcc tagcaagccc agcaagcgga gcttcatcga ggacctgctg 2520
ttcaacaaag tgacactggc cgacgccggc ttcatcaagc agtatggca ttgtctgggc 2580
gacattgccg ccagggatct gatttgcgcc cagaagttta acggactgac agtgctgcct 2640
cctctgctga ccgatgagat gatcgcccag tacacactg ccctgctggc cggcacaatc 2700
acaagcggct ggacatttgg agcaggcgcc gctctgcaga tccccttgc tatgcagatg 2760
gcctaccgtt tcaacggcat cggagtgacc cagaatgtgc tgtacgagaa ccagaagctg 2820
atcgccaacc agttcaacag cgccatcggc aagatccagg acagcctgag cagcacagca 2880
agcgccctgg gaaagctgca ggacgtggtc aaccagaatg cccaggcact gaacaccctg 2940
gtcaagcagc tgtcctccaa cttcggcgcc atcagctctg tgctgaacga tatcctgagc 3000
agactggacc ctcctgaggc cgaggtgcag atcgacagac tgatcacagg cagactgcag 3060
agcctccaga catacgtgac ccagcagctg atcagagccg ccgagattag agcctctgcc 3120
```

```
aatctggccg ccaccaagat gtctgagtgt gtgctgggcc agagcaagag agtggacttt   3180
tgcggcaagg gctaccacct gatgagcttc cctcagtctg cccctcacgg cgtggtgttt   3240
ctgcacgtga catatgtgcc cgctcaagag aagaatttca ccaccgctcc agccatctgc   3300
cacgacggca agcccacttt cctagagaa ggcgtgttcg tgtccaacgg cacccattgg    3360
ttcgtgacac agcggaactt ctacgagccc cagatcatca ccaccgacaa caccttcgtg   3420
tctggcaact gcgacgtcgt gatcggcatt gtgaacaata ccgtgtacga ccctctgcag   3480
cccgagctgg acagcttcaa agaggaactg gacaagtact ttaagaacca cacaagcccc   3540
gacgtggacc tgggcgatat cagcggaatc aatgccagcg tcgtgaacat ccagaaagag   3600
atcgaccggc tgaacgaggt ggccaagaat ctgaacgaga gcctgatcga cctgcaagaa   3660
ctggggaagt acagcagta catcaagtgg ccctggtaca tctggctggg ctttatcgcc    3720
ggactgattg ccatcgtgat ggtcacaatc atgctgtgtt gcatgaccag ctgctgtagc   3780
tgcctgaagg gctgttgtag ctgtggcagc tgctgcaagt cgacgagga cgattctgag    3840
cccgtgctga agggcgtgaa actgcactac acatgatgac tcgacgtggt actgcatgca   3900
cgcaatgcta gctgcccctt tcccgtcctg ggtacccga gtctcccccg acctcgggtc    3960
ccaggtatgc tcccacctcc acctgcccca ctcaccacct ctgctagttc agacacctc    4020
ccaagcacgc agcaatgcag ctcaaaacgc ttagcctagc cacacccca cgggaaacag    4080
cagtgattaa cctttagcaa taaacgaaag tttaactaag ctatactaac cccagggttg   4140
gtcaatttcg tgccagccac accctggagc tagcagcggc cgcggccgca aaaaaaaaa   4200
aaaaaaaaaa aaaaaaaaaa aaaaaaaaaa aaaaaaaaaa aaaaaaaaaa aaaaaaaaaa   4260
aaaaaaaaaa aaaaaaaaaa aaaaaaaaaa aaaaaaaaaa aaaaaaaaaa aaaaaaaa     4319

SEQ ID NO: 3           moltype = RNA   length = 4012
FEATURE                Location/Qualifiers
source                 1..4012
                       mol_type = other RNA
                       organism = Synthetic construct
SEQUENCE: 3
acatttgctt ctgacacaac tgtgttcact agcaacctca aacagccacc atgttcgtgt   60
tcctggtgct gctgccctg gtgagcagcc agtgcgtgaa cctgaccacc aggacccagc    120
tgcccccgc ctacaccaac agcttcacca ggggcgtgta ctaccccgca aaggtgttca    180
ggagcagcgt gctgcacagc acccaggacc tgttcctgcc cttcttcagc aacgtgacct   240
ggttccacgc catccacgtg agcggcacca acggcaccaa gaggttcgac aaccccgtgc   300
tgcccttcaa cgacggcgtg tacttcgcca gcaccgagaa gagcaacatc atcaggggct   360
ggatcttcgg caccacctg gacagcaaga cccagagcct gctgatcgtg aacaacgca    420
ccaacgtggt gatcaaggtg tgcgagttcc agttctgcaa cgaccccttc ctgggcgtga   480
actaccacaa gaacaacaag agctggatgg agagcgagtt cagggtgtac agcagcgcca   540
acaactgcac cttcgagtac gtgagccagc ccttcctgat ggacctggag ggcaagcagg   600
gcaacttcaa gaacctgagg gagttcgtgt tcaagaacat cgacggctac ttcaagatct   660
acagcaagca caccccatc aacctggtga gggacctgcc ccagggcttc agcgccctg    720
agccctggt ggacctgccc atcggcatca acatcaccag gttccagacc ctgctggccc    780
tgcacaggag ctacctgacc cccggcgaca gcagcagcgg ctggaccgcc ggcgccgcg    840
cctactacgt gggctacctg cagcccagga ccttcctgct gaagtacaac agaacggca    900
ccatcaccga cgccgtggac tgcgccctgg acccccgga cgagacaag tgcacccga    960
agagcttcac cgtggagaag ggcatctacc agaccagcaa cttcagggtg cagcccaccg   1020
agagcatcgt gaggttcccc aacatcacca acctgtgccc cttcggcgag gtgttcaacg   1080
ccaccagtt cgccagcgtg tacgcctgga acaggaagag gatcagcaac tgcgtggccg   1140
actacagcgt gctgtacaac agcgccagct tcagcacctt caagtgctac ggcgtgagcc   1200
ccaccaagct gaacgacctg tgcttcacca acgtgtacgc cgacagcttc gtgatcaggg   1260
gcgacgaggt gaggcagatc gcccccgggc agaccggcaa gatcgccgac tacaactaca   1320
agctgcccga cgacttcacc ggctgcgtga tcgcctggaa cagcaacaac ctggacagca   1380
aggtgggcgg caactacaac tacctgtaca ggctgttcag gaagagcaac ctgaagcctt   1440
tcgagaggga catcagcacc gagatctacc aggccggcag cacccccctgc aacggcgtgg   1500
agggcttcaa ctgctacttc ccctgcaga gctacggctt ccagcccacc aacggcgtgg   1560
gctaccagcc ctacagggtg gtggtgctga gcttcgagct gctgcacgcc cccgccaccg   1620
tgtgcggccc caagaagagc accaacctgg tgaagaacaa gtgcgtgaac ttcaacttca   1680
acggcctgac cggcaccggc gtgctgaccg agagcaacaa gaagttcctg ccccttccagc   1740
agttcggcag ggacatcgcc gacaccaccg acgccgtgag gaccccccag accctggaga   1800
tcctggacat caccccctgc agcttcggcg gcgtgagcgt gatcaccccc ggcaccaaca   1860
ccagcaacca ggtggccgtg ctgtaccagg acgtgaactg caccgaggtg cccgtggcca   1920
tccacgccga ccagctgacc cccacctgga gggtgtacag caccggcagc aacgtgttcc   1980
agaccagggc cggctgcctg atcggcgccg agcacgtgaa caacagctac gagtgcgaca   2040
tccccatcgg cgcggcatc tgcgccagct accagcccca gccaacagc cccaggaggg    2100
ccaggagcgt ggccagccag agcatcatcg cctacaccat gagcctgggc gccgagaaca   2160
gcgtggccta cagcaacaac agcatcgcca tccccaccaa cttcaccatc agcgtgacca   2220
ccgagatcct gcccgtgagc atgaccaaga ccagcgtgga ctgcaccatg tacatctgcg   2280
gcgacagcac cgagtgcagc aacctgctgc tgcagtacgg cagcttctgc acccagctga   2340
acagggccct gaccggcatc gccgtggagc aggacaagaa cacccaggag gtgttcgccc   2400
aggtgaagca gatctacaag accccccca tcaaggactt cggcggcttc aacttcagcc   2460
agatcctgcc cgaccccagc aagcccagca gaggagcct catcgaggac ctgctgttca   2520
acaaggtgac cctggccgac gccggcttca tcaagcagta cggcgactgc ctgggcgaca   2580
tcgccgccag gaccctgatc tgcgcccaga agttcaacgg cctgaccgtg ctgccccccc   2640
tgctgaccga cgagatgatc gcccagtaca ccagcgccct gctggccggc accatcacca   2700
gcggctggac cttcggcgcc ggcgccgcc tgcagatccc cttcgccatg cagatggcct   2760
acaggttcaa cggcatcggc gtgacccaga acgtgctgta cgagaaccag aagctgatcg   2820
ccaaccagtt caacagcgcc atcggcaaga tccaggacgt cctgagcagc accgccagcg   2880
ccctgggcaa gctgcaggac gtggtgaacc agaacgccca ggccctgaac accctggtga   2940
agcagctgag cagcaacttc ggcgccatca gcagcgtgct gaacgacatc ctgagcaggc   3000
tggaccccc cgaggccgag gtgcagatcg acaggctgat caccggcagg ctgcagagcc   3060
tgcagaccta cgtgacccag cagctgatca ggaccgcgca gatcagggcc agcgccaacc   3120
```

```
tggccgccac caagatgagc gagtgcgtgc tgggccagag caagagggtg gacttctgcg   3180
gcaagggcta ccacctgatg agcttccccc agagcgcccc ccacggcgtg gtgttcctgc   3240
acgtgaccta cgtgcccgcc caggagaaga acttcaccac cgcccccgcc atctgccacg   3300
acggcaaggc ccacttcccc agggagggcg tgttcgtgag caacggcacc cactggttcg   3360
tgacccagag gaacttctac gagccccaga tcatcaccac cgacaacacc ttcgtgagcg   3420
gcaactgcga cgtggtgatc ggcatcgtga acaacaccgt gtacgacccc ctgcagcccg   3480
agctggacag cttcaaggag gagctggaca agtacttcaa gaaccacacc agccccgacg   3540
tggacctggg cgacatcagc ggcatcaacg ccagcgtggt gaacatccag aaggagatcg   3600
acaggctgaa cgaggtggcc aagaacctga acgagagcct gatcgacctg caggagctgg   3660
gcaagtacga gcagtacatc aagtggccct ggtacatctg gctgggcttc atcgccggcc   3720
tgatcgccat cgtgatggtg accatcatgc tgtgctgcat gaccagctgc tgcagctgcc   3780
tgaagggctg ctgcagctgc ggcagctgct gcaagttcga cgaggacgac agcgagcccg   3840
tgctgaaggg cgtgaagctg cactcacct gataataggc tcgctttctt gctgtccaat   3900
ttctattaaa ggttccttg ttccctaagt ccaaactacta aactggggga tattatgaag   3960
ggccttgagc atctggattc tgcctaataa aaaacattta ttttcattgc aa            4012

SEQ ID NO: 4           moltype = RNA  length = 4040
FEATURE                Location/Qualifiers
source                 1..4040
                       mol_type = other RNA
                       organism = Synthetic construct
SEQUENCE: 4
gggaaataag agagaaaaga agagtaagaa gaaatataag accccggcgc caccatgttc   60
gtgttcctgg tgctgctgcc cctggtgagc agccagtgcg tgaacctgac caccaggacc   120
cagctgcccc ccgcctacac caacagcttc accaggggcg tgtactaccc cgacaaggtg   180
ttcaggagca gcgtgctgca cagcacccag gacctgttcc tgcccttctt cagcaacgtg   240
acctggttcc acgccatcca cgtgagcggc accaacggca ccaagaggtt cgacaacccc   300
gtgctgccct tcaacgacgg cgtgtacttc gccagcaccg agaagagcaa catcatcagg   360
ggctggatct tcggcaccac cctggacagc aagacccaga gcctgctgat cgtgaacaac   420
gccaccaacg tggtgatcaa ggtgtgcgag ttccagttct gcaacgaccc cttcctgggc   480
gtgtactacc acaagaacaa caagagctgg atggagagcg agttcagggt gtacagcagc   540
gccaacaact gcaccttcga gtacgtgagc cagcccttcc tgatggacct ggagggcaag   600
cagggcaact tcaagaacct gagggagttc gtgttcaaga acatcgacgg ctacttcaag   660
atctacagca agcacacccc catcaacctg gtgagggacc tgccccaggg cttcagcgcc   720
ctggagcccc tggtggacct gcccatcggc atcaacatca ccaggttcca gacctgctg   780
gccctgcaca ggagctacct gacccccggc gacagcagca gcggctggac cgccggcgcc   840
gccgcctact acgtgggcta cctgcagccc aggaccttcc tgctgaagta caacgagaac   900
ggcaccatca ccgacgccgt ggactgcgcc ctggaccccc tgagcgagac caagtgcacc   960
ctgaagagct tcaccgtgga aagggcatc taccagacca gcaacttcag ggtgcagccc   1020
accgagagca tcgtgaggtt ccccaacatc accaacctgt gcccctttcgg cgaggtgttc   1080
aacgccacca ggttcgccag cgtgtacgcc tggaacagga gaggatcag caactgcgtg   1140
gccgactaca gcgtgctgta caacagcgcc agcttcagca ccttcaagtg ctacggcgtg   1200
agcccaccca agctgaacga cctgtgcttc accaacgtgt acgccgacag cttcgtgatc   1260
agggcgacg aggtgaggca gatcgccccc ggccagaccg gcaagatcgc cgactacaac   1320
tacaagctgc ccgacgactt caccggctgc gtgatcgcct ggaacagcaa caacctggac   1380
agcaaggtgg gcggcaacta caactacctg tacaggctgt tcaggaagag caacctgaag   1440
cccttcgaga gggacatcag caccgagatc taccaggcg gcaccacccc ctgcaacggc   1500
gtggagggct tcaactgcta cttcccctg cagagctacg gcttccagcc caccaacggc   1560
gtgggctacc agccctacag ggtggtggtg ctgagcttcg agctgctgca cgcccccgcc   1620
accgtgtgcg gccccaagaa gagcaccaac ctggtgaaga caagtgcgt gaacttcaac   1680
ttcaacggcc tgaccggcac cggcgtgctg accgagagca acaagaagtt cctgccctc   1740
cagcagttcg gcagggacat cgccgacacc accgacgccg tgagggaccc ccagaccctg   1800
gagatcctgg acatcacccc ctgcagcttc ggcggcgtga gcgtgatcac ccccggcacc   1860
aacaccagca accaggtggc cgtgctgtac caggacgtga actgcaccga ggtgcccgtg   1920
gccatccacg ccgaccagct gacccccacc tggagggtgt acagcaccgg cagcaacgtg   1980
ttccagacca gggccggctg cctgatcggc gccgagcacg tgaacaacag ctacgagtgc   2040
gacatcccca tcggcgccgg catctgcgcc agctaccaga cccagaccaa cagccccagg   2100
agggccagga gcgtggccag ccagagcatc atcgcctaca ccatgagcct gggcgccgag   2160
aacagcgtgg cctacagcaa caacagcatc gccatcccca ccaacttcac catcagcgtg   2220
accaccgaga tcctgcccgt gagcatgacc aagaccagcg tggactgcac catgtacatc   2280
tgcggcgaca gcaccgagtg cagcaacctg ctgctgcagt acggcagctt ctgcacccag   2340
ctgaacaggg ccctgaccgg catcgccgtg agcaggaca gaacaccca ggaggtgttc   2400
gcccaggtga agcagatcta caagaccccc cccatcaagg acttcggcgg cttcaacttc   2460
agccagatcc tgcccgaccc cagcaagccc agcaagagga gcttcatcga ggacctgctg   2520
ttcaacaagg tgaccctggc cgacgccggc ttcatcaagc agtacggcga ctgcctgggc   2580
gacatcgccg ccaggacct gatctgcgcc cagaagttca acggcctgac cgtgctgccc   2640
cccctgctga ccgacgagat gatcgcccag tacaccagcg ccctgctggc cggcaccatc   2700
accagcggct ggaccttcgg cgccggcgcc gccctgcaga tccccttcgc catgcagatg   2760
gcctacaggt tcaacggcat cggcgtgacc cagaacgtgc tgtacgagaa ccagaagctg   2820
atcgccaacc agttcaacag cgccatcggc aagatccagg acagcctgag cagcaccgcc   2880
agcgccctgg gcaagctgca ggacgtggtg aaccagaacg cccaggccct gaacaccctg   2940
gtgaagcagc tgagcagcaa cttcggcgcc atcagcagcg tgctgaacga catcctgagc   3000
aggctggacc cccccgaggc cgaggtgcag atcgacaggc tgatcaccgg caggctgcag   3060
agcctgcaga cctacgtgac ccagcagctg atcagggcc ccgagatgga ggccagcgcc   3120
aacctggcc ccaccaagat gagcgagtgc gtgctgggcc agagcaagag ggtggacttc   3180
tgcggcaagg gctaccacct gatgagcttc ccccagagcg ccccccacgg cgtggtgttc   3240
ctgcacgtga cctacgtgcc cgccaggag aagaacttca ccaccgcccc cgccatctgc   3300
cacgacggca aggcccactt ccccagggag ggcgtgttcg tgagcaacgg cacccactgg   3360
ttcgtgaccc agaggaactt ctacgagccc cagatcatca ccaccgacaa caccttcgtg   3420
```

-continued

```
agcggcaact gcgacgtggt gatcggcatc gtgaacaaca ccgtgtacga cccctgcag    3480
cccgagctgg acagcttcaa ggaggagctg gacaagtact tcaagaacca caccagcccc   3540
gacgtggacc tgggcgacat cagcggcatc aacgccagcg tggtgaacat ccagaaggag   3600
atcgacaggc tgaacgaggt ggccaagaac ctgaacgaga gcctgatcga cctgcaggag   3660
ctgggcaagt acgagcagta catcaagtgg ccctggtaca tctggctggg cttcatcgcc   3720
ggcctgatcg ccatcgtgat ggtgaccatc atgctgtgct gcatgaccag ctgctgcagc   3780
tgcctgaagg gctgctgcag ctgcggcagc tgctgcaagt tcgacgagga cgacagcgag   3840
cccgtgctga agggcgtgaa gctgcactac acctgataat agctagtgac tgactaggat   3900
ctggttacca ctaaaccagc ctcaagaaca cccgaattgga gtctctaagc tacataatac   3960
caacttacac ttacaaaatg ttgtcccca aatgtagcc attcgtatct gctcctaata    4020
aaaagaaagt ttcttcacat                                               4040
```